United States Patent [19]
Attardo et al.

[11] Patent Number: 5,606,037
[45] Date of Patent: Feb. 25, 1997

[54] PROCESSES ANTINEOPLASTIC HETERONAPHTHOQUINONES

[75] Inventors: Giorgio Attardo, Laval; Tibor Breining, St. Laurent; Marc Courchesne, Laval-des-Rapides; Serge Lamothe, Boisbriand; Jean-François Lavallée, Laval; Dieu Nguyen, Chomedey; Rabindra Rej; Yves St-Denis, both of Montreal; Wuyi Wang, St- Laurent, all of Canada; Yao-Chang Xu, Indianapolis, Ind.; France Barbeau, St-Thérèse; Elaine Lebeau, Kamloops, both of Canada; Jean L. Kraus, Marseille, France

[73] Assignee: BioChem Pharma Inc., Laval, Canada

[21] Appl. No.: 401,492

[22] Filed: Mar. 10, 1995

Related U.S. Application Data

[63] Continuation-in-part of Ser. No. 148,251, Nov. 5, 1993, which is a continuation-in-part of Ser. No. 973,233, Nov. 9, 1992, abandoned.

[51] Int. Cl.$^6$ .............................. C07H 1/00; C07C 50/22
[52] U.S. Cl. ........................... 536/6.4; 552/201; 552/202; 549/363; 536/18.1
[58] Field of Search ..................................... 536/6.4, 18.5; 552/201, 202; 549/363

[56] References Cited

FOREIGN PATENT DOCUMENTS

| | | |
|---|---|---|
| 0475473A2 | 3/1992 | European Pat. Off. . |
| WO-A-9119725 | 12/1991 | WIPO . |

OTHER PUBLICATIONS

LoRusso, P. et al. "Antitumor efficacy of PD115934 . . ." Cancer Res., 50, (1990), pp. 4900–4905.
Schabel, F. M. et al. "Establishment of cross–resistance . . ." Cancer Treat. Rep, 67 (1983) pp. 905–922.
Weiss, R. B. et al. "Anthracycline analogs . . . " Cancer Chemother Pharmacol. 18, (1986), pp. 185–197.
Olson, R. D. et al. "Doxorubicin cardiotoxicity . . . " Proc. Natl. Acad. Sci. USA, 85, (1988), pp. 3585–3589.
Mimnaugh, E. G. et al. "Differential oxygen radical . . . " Cancer Research, 49(1989), pp. 8–15.
McGrath, T. et al. "Multiple mechanisms of adriamycin . . ." Biochemical Pharmacol., 38(3), (1989) pp. 497–501.
Brown, J. R. et al. "5 Recent studies on doxorubicin . . . " Prog. Med. Chem. 21 (1984), pp. 170–236.
Brown, J. R. "3 Adriamycin and related . . . " Prog. Med. Chem., 15, (1978), pp. 125–164.
Moore, H. W. et al. "Naturally occuring quinones . . . " Medicinal Research Reviews, edition J. Wiley & Sons, Inc. vol 1(3)(1981), pp. 249–280.
Dufat–Trinh Van, H. et al. "Chiral pool synthesis . . . " Heterocycles 26(2), (1987), pp. 341–345.
Dufat–Trinh Van, H. et al. "Total synthesis of 7–hydroxy–. . . " Heterocycles 26(4), (1987), pp. 879–882.
Plumb, J. A. et al. "Effects of the pH dependencies . . . " Cancer Research, 49 (1989), pp. 4435–4440.
Krohn, K. et al. "Konvergente synthese . . . " Liebigs Ann–Chem., (1988), pp. 943–948.
Arcamone, F. "Properties of antitumor anthracyclines . . . " Cancer Research, 45(1985), pp. 5995–5999.
Acton, E. M. et al. "Intensely potent morpholinyl . . . " J. Med. Chem. 27(5) (1984), pp. 638–645.
Singh, S. B. et al. "Structure and stereochemistry . . . " Tetrahedron Letters 32(36) (1991), pp. 5279–5282.
Alderseley, M. F. et al. "Pyridinium ylides in syntheses . . ." Jour. of Chem. Soc., Perkin Transactions, 1(1990), pp. 2163–2174.
Hoeksema, H. et al. "Kalafungin II Chemical . . . " Jour. of Antibiotics, 29(7) (1976), pp. 704–709.
Parisot, D. et al. "6–0 demethyl–5–deoxyfusabarin . . . " Jour. of Antibiotics, 44(1), (1991), pp. 103–107.
Chorn, T. A. et al. "Synthese of napthol[2,3–c]pyran . . . " Jour. of the chem. Soc., Chemical Communications, (1981), pp. 534–535.
Mitsher, L. A. et al. "Total chemical synthesis . . . " J. Med. Chem., 29(1986), pp. 1277–1281.
Chemical Abstracts 94(5)(2 Feb. 1981)#24828t & Euro. J. Pharmacol. 67(1980), pp. 2–3.
Chemical Abstracts 108(21)(23 May 1988),#186527d, & Synthesis 1987(9), pp. 824–827.
Giles, R. G. F. et al. "An investigation into the formation of benzo–. . . " Chem. Soc. Perkin Trans. 1, (1984), p. 2389.
Chemical Abstracts 97(5)(2 Aug. 1982)#38804t & Synth. Commun. 1982, 12(4), pp.279–285.

*Primary Examiner*—Elli Peselev
*Attorney, Agent, or Firm*—Nixon & Vanderhye

[57] ABSTRACT

This invention relates to a naphthoquinone derivatives, to processes and to intermediates for preparing these derivatives, to pharmaceutical composition and to the use of these derivatives as antitumor agents in mammals.

53 Claims, No Drawings

PROCESSES ANTINEOPLASTIC HETERONAPHTHOQUINONES

This application is a continuation in part of U.S. patent application 08/148,251 (enclosed herein by reference) which is a continuation in part of U.S. application 07/973,233, now abandoned.

This invention relates to a naphthoquinone derivatives, to processes and to intermediates for preparing these derivatives, to pharmaceutical composition and to the use of these derivatives as antitumor agents in mammals.

BACKGROUND OF THE INVENTION

Anthracycline antibiotics including doxorubicin and daunorubicin are important chemotherapeutic agents in the treatment of a broad spectrum of neoplastic conditions. While daunorubicin (1) is clinically used mainly against acute childhood and adult leukemias, doxorubicin (2), also known as adriamycin, has the widest spectrum of antitumor activity of all chemotherapeutic agents (Weiss, R. B., Sarosy, G., Clagett-Carr, K., Russo, M. and Leyland-Jones, B., Cancer Chemother. Pharmacol., 18, 185–197, 1986; Arcamone, F., Doxorubicin, Academic Press, New York, 1980).

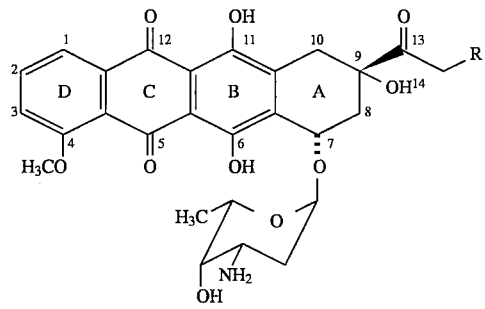

(A) daunorubicin R = H
(B) doxorubicin R = OH

The usefulness of known anthracycline antibiotics is compromised by dose limiting toxicities such as myelosuppression (Crooke, S. K., Anthracyclines; Current Status and New Developments, Academic Press, N.Y. 1980) and cardiotoxicity (Olson, R. D. et al, Proc. Natl. Acad. Sci., USA 85 3585–3589, 1988 and references therein) as well as the resistance from treated tumors (Mimnaugh, E. G. et al, Cancer Research, 49, 8–15, 1989; McGrath, T. et al, Biochemical Pharmacology, 38 497–501, 1989). In view of the proven effectiveness of known anthracyclines in the treatment of cancer, efforts have been undertaken to develop anthracycline analogs with either an improved therapeutic index or with reduced cross-resistance.

Several thousand anthracycline derivatives have been obtained either from streptomyces biosynthesis or via the semisynthetic modification of known natural anthracycline antibiotics (Arcamone, F., Doxorubicin, Academic Press, N.Y. 1980; Thomson, R. H., Naturally Occurring Quinones III: Recent Advances, Chapman and Hall, New York 1987; Anthracyclines: Current Status and New Developments, Academic Press, New York, 1980; Brown, J. R. and Iman, S. H., Recent Studies on Doxorubicin and its Analogues, Prog. Med. Chem. 21 170–236, 1984; Brown, J. R. Adriamycin and Related Anthracycline Antibiotics, Prog. Med. Chem., 15, 125–164, 1978). The majority of known anthracyclines show two types of structural differences: (i) the substitution pattern of the aglycone tetracyclic ring system, and (ii) the structure and number of glycosides attached at C-7 or C-10 (doxorubicin numbering). Some examples of the structural diversity of anthracycline antibiotics are:

FIG. 1

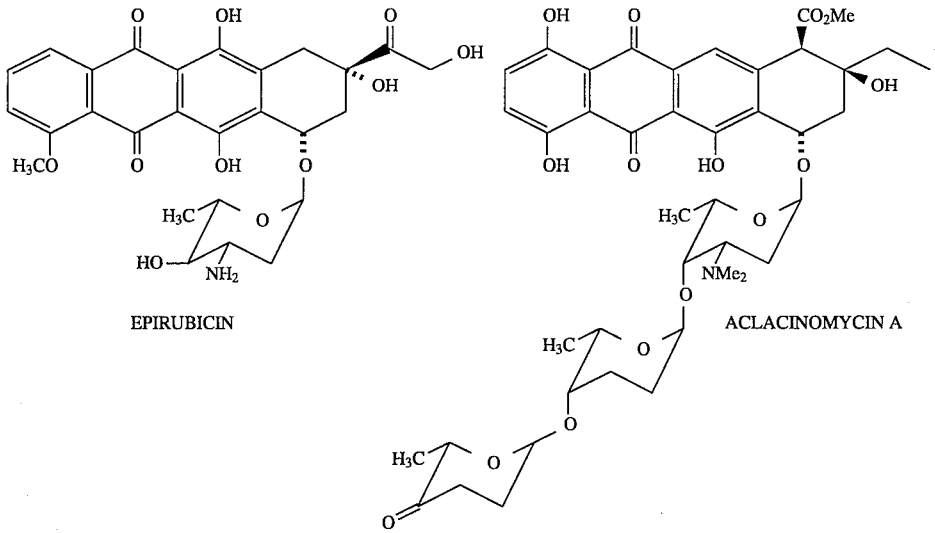

EPIRUBICIN                ACLACINOMYCIN A

-continued
FIG. 1

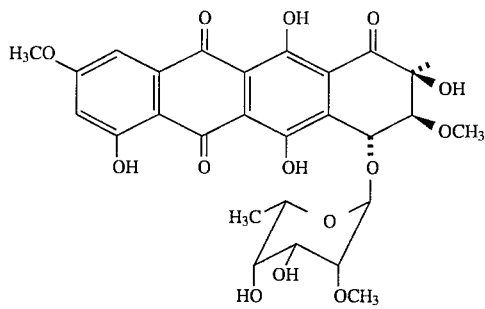

STEFFIMYCIN B

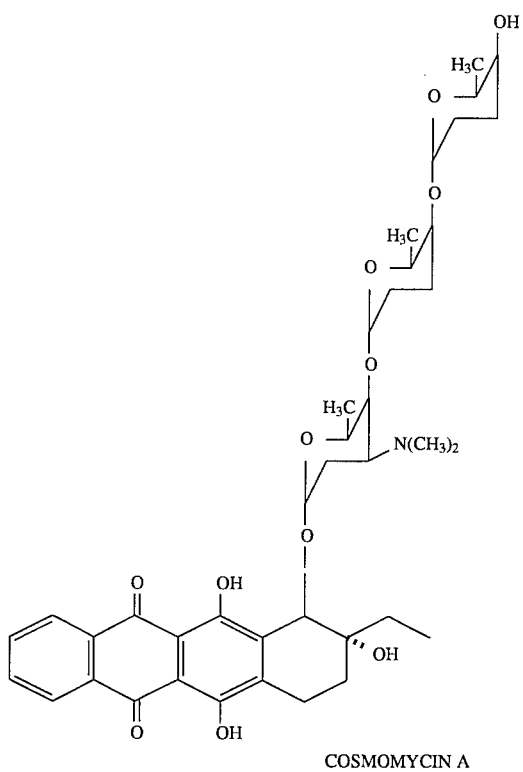

COSMOMYCIN A

Tricyclic variants (C) of daunorubicin have been reported to possess antitumor activity (EPA 91202015.3)

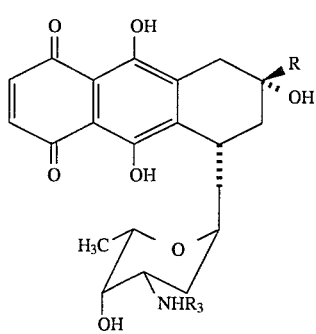

C wherein R is $COCH_3$ or C—CH or C—C—$Si(CH_3)_3$, and $R_3$ is H or $COCF_3$.

Pyranonaphthoquinones such as nanaomycin A (D) and kalafungin (E) occur naturally and show potent antibacterial as well as antifungal activity (Moore, H. W. and Czerniak, R., Medicinal Research Reviews, 1(3), 249–280, 1981 and references therein).

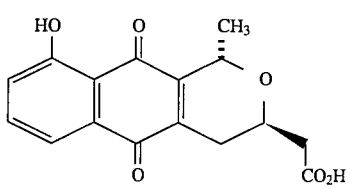

D

-continued

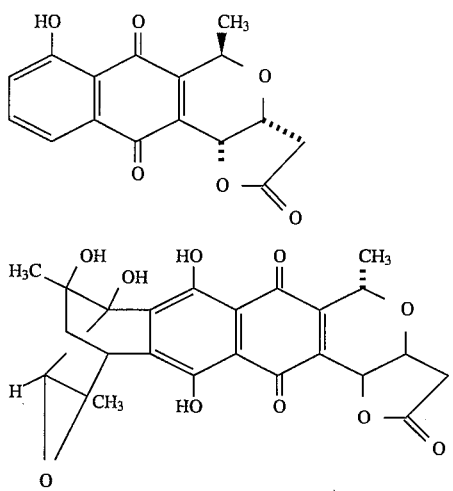

E

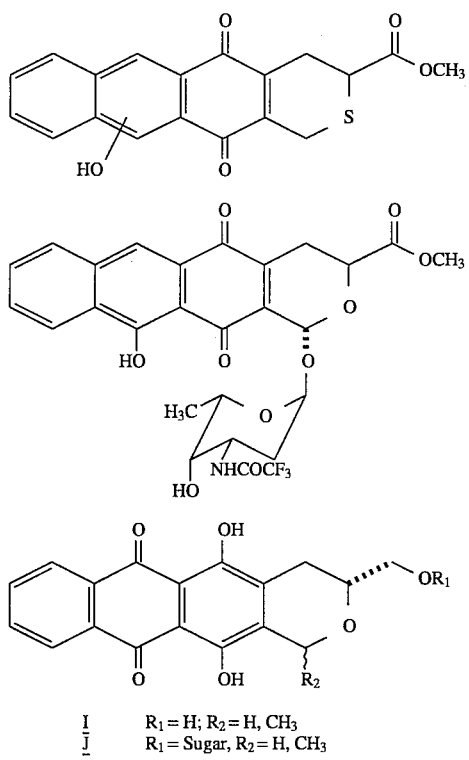

F

Granaticin (F) has been reported to show antitumor activity (Chang, C. J., Floss, H. G., Soong, P. 1 and Chang, C. T., J. Antibiot., 28, 156, 1975). More recently thiopyranoanthraquinone (G) and pyranoanthraquinone (H) were found to possess antitumor activity (PCT, CA9100208). In contrast antitumor activity of other 9-oxa-heteroanthracylines such as (I), (J), and (K) was not significant (Heterocycles, 26 (2), 341-5, 1987; Heterocycles 26 (4), 879–82, 1987).

G

H

I  $R_1 = H; R_2 = H, CH_3$
J  $R_1 = Sugar, R_2 = H, CH_3$

-continued

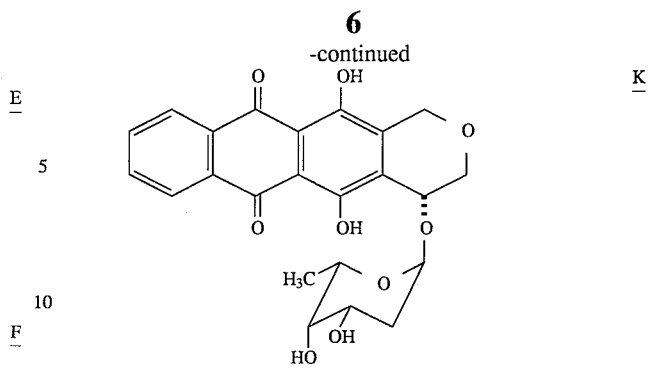

K

SUMMARY OF THE INVENTION

There is provided a novel tricyclic compound of formula (1), geometric isomers and optical isomers, thereof mixtures of those isomers, and pharmaceutically acceptable acid addition salts thereof,

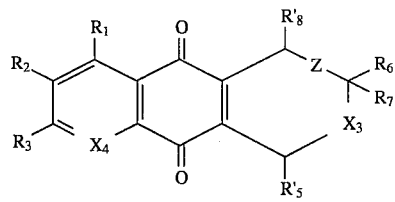

1 wherein;

$X_3$ is selected from the group consisting of O; S; and $SO_2$;

$X_4$ is selected from the group consisting of C—Q; nitrogen; and NO;

z is a single or a double bond with the proviso that if z is a double bond only one of $R_6$ or $R_7$ is present;

$R_1, R_2, R_3$ and Q are each independently selected from the group consisting of hydrogen; hydroxy; CN; $NO_2$; $C_{1-16}$ alkyl; $C_{2-16}$ alkenyl; $C_{2-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amino; amido; sulfono; $C_{2-16}$ acyloxy; and halogen;

$R_6$ is selected from the group consisting of hydrogen; CN; $NO_2$; $C_{1-16}$ alkyl; $C_{2-16}$ alkenyl; $C_{2-16}$ alkynyl; $C_{1-16}$ alkoxy; $C_{6-16}$ aryl; $C_{7-16}$ aralkyl; $C_{6-16}$ aryloxy; $C_{1-16}$ acyl; amino; sulfono; $C_{2-16}$ ester; phosphono; and halogen;

$R_7$ is selected from the group consisting of hydrogen; hydroxy; CN; $NO_2$; $C_{1-16}$ alkyl; $C_{1-16}$ alkoxy; $C_{1-16}$ acyl; amine; sulfono; $C_{2-16}$ ester; thiol; and halogen;

$R'_5$ is selected from the group consisting of hydrogen; hydroxy; $C_{1-16}$ alkyl; $C_{1-16}$ alkoxy; $C_{1-16}$ acyl; amino; amido; sulfono; $C_{2-16}$ ester; azole; phosphono; halogen; morpholino; and a saccharide W;

$R'_8$ is selected from the group consisting of hydrogen; hydroxy; $C_{1-16}$ alkyl; $C_{1-16}$ alkoxy; $C_{1-16}$ acyl; amino; amido; sulfono; $C_{2-16}$ ester; azole; phosphono; halogen; and morpholino;

with the provisos that:

1) when z is a single bond; $X_3$ is not O; $R_1, R_2, R_3, Q; R_7$, and $R'_8$, are not H; $R'_5$ is not OH or $OCH_3$; $R_6$ is not $CH_3$;

2) when z is a single bond; $X_3$ is not O; $R_1, R_3, R'_5$, and $R'_8$, are not H; $R_2$ is not OH or $OCH_3$; Q is not OH; $R_6$ is not OH; $R_7$ is not $CH_3$;

3) when z is a double bond; $X_3$ is not O; $R_1$, $R_3$, $R'_5$, $R_7$, and $R'_8$, are not H; $R_2$ is not OH or $OCH_3$; Q is not OH or $OCH_3$; $R_6$ is not $CH_3$; and 4) when z is a single bond; $X_3$ is not O; $R_1$, $R_2$, $R_3$, Q, $R_7$, and $R'_8$, are not H; $R'_5$ is not OH or $OCH_3$; $R_6$ is not $CH_3$.

In a preferred embodiment the saccharide W is a saccharide of formula (30):

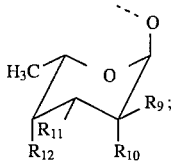

wherein;

$R_9$ and $R_{10}$ are independently selected from the group consisting of hydrogen; hydroxy; —$NH_2$; $C_{1-16}$ alkyl; $C_{1-16}$ alkoxy; amino; amido; $C_{2-16}$ ester; and halogen;

$R_{11}$ is selected from the group consisting of hydrogen; hydroxy; —$NH_2$; $C_{1-16}$ alkoxy; amino; amido; $C_{2-16}$ ester; sulfono;thiol; azido; and halogen; and $R_{12}$ selected from the group consisting of hydrogen; hydroxy; —$NH_2$; $C_{1-16}$ alkoxy; amino; amido; $C_{1-16}$ acyl; $C_{6-16}$ aryl; $C_{2-16}$ ester; sulfono; saccharide; and halogen.

In a further aspect of the present invention, there is provided a new process for producing a tricyclic compound of formula (1) and pharmaceutically acceptable acid addition salts thereof,

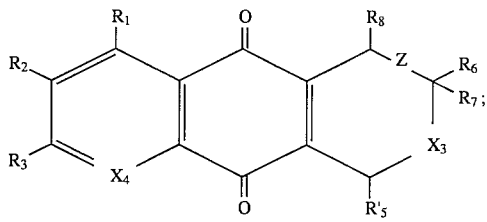

wherein;

$X_3$ is selected from the group consisting of O; S; and $SO_2$;

$X_4$ is selected from the group consisting of C—Q; nitrogen; and NO;

z is a single or a double bond with the proviso that if z is a double bond only one of $R_6$ or $R_7$ is present;

$R_1$, $R_2$, $R_3$ and Q are each independently selected from the group consisting of hydrogen; hydroxy; CN; $NO_2$; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amine; amido; sulfono; $C_{2-16}$ acyloxy; and halogen;

$R_6$ is selected from the group consisting of hydrogen; CN; $NO_2$; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ acyl; amine; sulfono; $C_{2-16}$ ester; phosphono; and halogen;

$R_7$ is selected from the group consisting of hydrogen; hydroxy; CN; $NO_2$; $C_{1-16}$ alkyl; $C_{1-16}$ alkoxy; $C_{1-16}$ acyl; amine; sulfono; $C_{2-16}$ ester; thiol; and halogen;

$R'_5$ is independently selected from the group consisting of hydrogen; hydroxy; $C_{1-16}$ alkyl; $C_{1-16}$ alkoxy; $C_{1-16}$ acyl; amino; amido; sulfono; $C_{2-16}$ ester; azole; phosphono; halogen; morpholino; and a saccharide of formula W;

$R_8$ is independently selected from the group consisting of hydrogen; $C_{1-16}$ alkyl; $C_{1-16}$ alkoxy; $C_{1-16}$ acyl; amino; amido; sulfono; $C_{2-16}$ ester; azole; phosphono; halogen; and morpholino wherein when z is a single bond, said tricyclic of formula (1) is produced by a process comprising the step of:

step 1) cycloadding a quinone of formula (2)

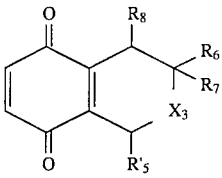

wherein, $X_3$, $R'_5$ $R_6$, $R_7$ and $R_8$ are as defined above; with a diene of formula (3a) or (3b)

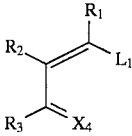

or

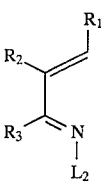

wherein $R_1$, $R_2$, $R_3$ and $X_4$ are as defined above;

each one of $L_1$; and $L_2$ is independently a leaving group; to yield said tricyclic compound of formula (1);

optionally, if z is a double bond, said process comprising the further step of:

step 2) air-oxydizing the compound obtained in step (1) with an appropriate organic or inorganic base or a fluoride salt (h) to yield to a tricyclic compound of formula (1).

In a preferred embodiment, the saccharide W is a saccharide of formula (30):

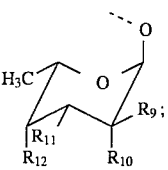

wherein;

$R_9$ and $R_{10}$ are independently selected from the group consisting of hydrogen; hydroxy; —$NH_2$; $C_{1-16}$ alkyl; $C_{1-16}$ alkoxy; amino; amido; $C_{2-16}$ ester; and halogen;

$R_{11}$ is selected from the group consisting of hydrogen; hydroxy; —$NH_2$; $C_{1-16}$ alkoxy; amino; amido; $C_{2-16}$ ester; sulfono; thiol; azido; and halogen; and $R_{12}$ selected from the group consisting of hydrogen; hydroxy; —$NH_2$; $C_{1-16}$ alkoxy; amino; amido; $C_{1-16}$ acyl; $C_{6-16}$ aryl; $C_{2-16}$ ester; sulfono; sahharide; and halogen.

DETAILED DESCRIPTION OF THE INVENTION

In a first aspect of the present invention, there is provided an heteronaphtoquinone of formula (4) the geometric isomers and opticals isomers, the mixtures of those isomers, and pharmaceutically acceptable acid addition salts thereof,

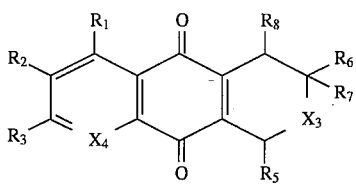

wherein;

X₃ is selected from the group consisting of O; S; and SO₂.
X₃ is preferably O or S.
X₃ is more preferably O.
X₄ is selected from the group consisting of C—Q; nitrogen; and NO.
X₄ is preferably C—Q.
$R_1$, $R_2$, $R_3$ and Q are each independently selected from the group consisting of hydrogen; hydroxy; CN; NO₂; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amino; amido; sulfono; $C_{2-16}$ ester; and halogen.
$R_1$, $R_2$, $R_3$ and Q are each independently preferably selected from the group consisting of hydrogen; hydroxy; $C_{1-16}$ alkyl; $C_{1-16}$ alkoxy; $C_{6-16}$ aryl; and halogen.
$R_1$, $R_2$, $R_3$ and Q are each independently more preferably selected from the group consisting of hydrogen; hydroxy; $C_{1-6}$ alkyl; $C_{1-6}$ alkoxy; $C_{6-12}$ aryl; and halogen.
$R_1$, $R_2$, $R_3$ and Q are most preferably hydrogen.
$R_5$ is selected from the group consisting of hydrogen; hydroxy; CN; NO₂; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amino; amido; sulfono; $C_{2-16}$ ester; thiol; azole; phosphono; morpholino; and halogen.
$R_5$ is preferably selected from the group consisting of hydrogen; hydroxy; amino; amido; and morpholino.
$R_5$ is more preferably selected from the group consisting of hydrogen; hydroxy; prolyl; seryl; leucyl; serylleucine methyl ester;

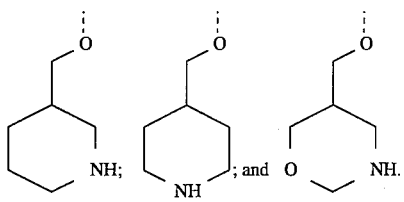

$R_6$ is selected from the group consisting of hydrogen; hydroxy; CN; NO₂; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amino; amido; sulfono; $C_{2-16}$ ester; thiol; azole; phosphono; and halogen.
$R_6$ is preferably selected from the group consisting of $C_{1-6}$ alkyl; $C_{1-6}$ alkenyl; $C_{1-6}$ alkynyl; $C_{1-16}$ alkoxy; $C_{1-16}$ acyl; amido; thiol; azole and $C_{2-16}$ ester.
$R_6$ is more preferably selected from the group consisting of $C_{1-6}$ acyl; amido; and $C_{2-6}$ ester.
$R_6$ is most preferably acetyl.
$R_7$ is selected from the group consisting of hydrogen; hydroxy; CN; NO₂; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amino; amido; sulfono; $C_{2-16}$ ester; thiol; azole; phosphono; and halogen.
$R_7$ is preferably selected from the group consisting of hydrogen; hydroxy; $C_{1-6}$ alkyl; $C_{1-6}$ alkoxy; and $C_{2-6}$ ester.
$R_7$ is more preferably hydrogen.
$R_8$ is selected from the group consisting of hydrogen; hydroxy; $C_{1-16}$ alkyl; $C_{1-16}$ alkenyl; $C_{1-16}$ alkynyl; $C_{1-16}$ alkoxy; $C_{1-16}$ acyl; halogen; and $C_{2-16}$ ester.

$R_8$ is preferably selected from the group consisting of hydrogen; hydroxy; $C_{1-6}$ alkyl; $C_{1-6}$ alkoxy; and halogen.
$R_8$ is more preferably selected from the group consisting of hydrogen; hydroxy;and $C_{1-6}$ alkyl.
$R_8$ is most preferably hydrogen.

In a further preferred embodiment, the heteronaphtoquinone of formula (4) is selected from the group consisting of:

Methyl (5,10-dioxo-3,4,5,10-tetrahydronaphtho[2,3-C]pyran-3-yl) ketone BCH-1125 Methyl (7-hydroxy-5,10-dioxo-3,4,5,10-tetrahydronaphtho[2,3-C]pyran-3-yl) ketone BCH-1129;
Methyl (1-hydroxy-5,10-dioxo-3,4,5,10-tetrahydronaphtho[2,3-C]pyran-3-yl) ketone BCH-1148;
(trans)-5,10-dioxo-3-isopropenyl-1-methoxy-3,4,5,10-tetrahydro-1H-naphtho-[2,3-c]-pyran (BCH-2148);
3-ethylthiocarbonyl-1,3,4,5,10-pentahydro-5,10-dioxo-naphtho-[2,3-c]pyran (BCH-2003);
3-(5'-tosyloxazolyl)-1,3,4,5,10-pentahydro-5,10-dioxo-naphtho-[2,3-c]pyran (BCH-2155);
(1,3-trans)-anline-(1-methoxy-5,10-dioxo-3,4,5,10-tetrahydro-1H-naphtho-[2,3-c]-pyran)-3-carboxamide (BCH-2041);
(1,3-cis)-anline-(1-methoxy-5,10-dioxo-3,4,5,10-tetrahydro-1H-naphtho-[2,3-c]-pyran)-3-carboxamide (BCH-2042);
(1,3-trans)-1-methoxy-3-(3'-aminothiazolyl)-5,10-dioxo-3,4,5,10-tetrahydro-1H-naphtho[2,3-c]pyran (BCH-1616);
1-methoxy-3-dimethyl phosphonoacetyl-5,10-dioxo-3,4,5,10-tetrahydro-1H-naphtho-[2,3-c]-pyran (BCH-1674);
3-(3'-aminothiazolyl)-5,10-dioxo-1,3,4,5,10-pentahydro-naphtho-[2,3-c]-pyran (BCH);
(1S,2'S,3S,5'S)-Methyl-(1-O-[N-BOC-Serine-Leucine-Me ester]-5,10-dioxo-3,4,5,10-tetrahydro-1-H-naphtho[2,3-c]pyran-3-yl) ketone(BCH-1998);
(1S, 2'S, 3R) and (1R, 2'S, 3S)-methyl-(1-[O-serine methyl ester]-5,10-dioxo-3,4,5,10-tetrahydronaphtaleno[2,3-C]pyran-3-yl) ketone hydrochloride (BCH-1654);
Trans-5,10-dioxo-1-acetamido-3-ethyl-3,4,5,10-tetrahydro-1H-naphtho-[2,3-c]-pyran (BCH-2027);
3-ethyl-5,10-dioxo-3,4,5,10-tetrahydro-1H-naphtho-[2,3-c]pyran (BCH-2154);
(1,3-trans)-1-methoxy-3-carboxyl-5,10-dioxo-3,4,5,10-tetrahydro-1H-naphtho-[2,3-c]-pyran, (BCH-2045);
(1S,2'S,3S,5'S)-Methyl-(1-O-[Serine-Leucine-Me ester]-5,10-dioxo-3,4,5,10-tetrahydro-1-H-naphtho[2,3-c]pyran-3-yl) ketone hydrochloride BCH-2000;
(1S, 2'S, 3R) and (1R, 2'S, 3S)-methyl-(1-[O-N-BOC-prolinol]-5,10-dioxo-3,4,5,10-tetrahydro-1-H-naphtho[2,3-C]pyran-3-yl) ketone BCH-2067;
Methyl-(1-O-[2'-piperidinemethanol]-5,10-dioxo-3,4,5,10-tetrahydronaphthaleno-[2,3-c]pyran-3-yl) ketone, racemic, hydrochloride (BCH-2069);
Methyl-(1-O-[N-BOC-4-piperidine-methanol]-5,10-dioxo-3,4,5,10-tetrahydronaphthaleno-[2,3-c]pyran-3-yl) ketone, racemic, hydrochloride(BCH-2068);
Methyl-(1-O-[N-BOC-3-piperidinemethanol]-5,6-dioxo-3,4,5,10-tetrahydronaphthaleno-[2,3-c]pyran-3-yl) ketone, mixture of isomers (BCH-2060);
Methyl-(1-O-[3-piperidinemethanol]-5,10-dioxo-3,4,5,10-tetrahydronaphthaleno-[2,3-c]pyran-3-yl) ketone hydrochloride salt, mixture of isomers (BCH-2061); and
(1S, 2'S, 3R) and (1R, 2'S, 3S)-methyl-(1-[O-prolinol]-3,4,5,12-tetrahydronaphtho-[2,3-C]pyran-3-yl) ketone hydrochloride salt (BCH-1658).

In a second aspect of the present invention, there is provided a coupled heteronaphtoquinone of formula (8) the geometric isomers and opticals isomers, the mixtures of those isomers, and pharmaceutically acceptable acid addition salts thereof,

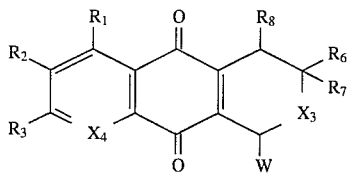
(8)

$X_3$ is selected from the group consisting of O; S; and $SO_2$.

$X_3$ is preferably O or S.

$X_3$ is more preferably O.

$X_4$ is selected from the group consisting of C—Q; nitrogen; and NO.

$X_4$ is preferably CQ.

$R_1$, $R_2$, $R_3$ and Q are each independently selected from the group consisting of hydrogen; hydroxy; CN; $NO_2$; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amino; amido; sulfono; $C_{2-16}$ ester; and halogen.

$R_1$, $R_2$, $R_3$ and Q are each independently preferably selected from the group consisting of hydrogen; hydroxy; $C_{1-16}$ alkyl; $C_{1-16}$ alkoxy; $C_{6-16}$ aryl; and halogen.

$R_1$, $R_2$, $R_3$ and Q are each independently more preferably selected from the group consisting of hydrogen; hydroxy; $C_{1-6}$ alkyl; $C_{1-6}$ alkoxy; $C_{6-12}$ aryl; and halogen.

$R_1$, $R_2$, $R_3$ and Q are most preferably hydrogen.

$R_6$ is selected from the group consisting of hydrogen; hydroxy; CN; $NO_2$; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amino; amido; sulfono; $C_{2-16}$ ester; thiol; azole; phosphono; and halogen.

$R_6$ is preferably selected from the group consisting of hydrogen; $C_{1-16}$ alkyl; $C_{1-16}$ alkenyl; $C_{1-16}$ alkynyl; $C_{1-16}$ alkoxy; $C_{1-16}$ acyl; $C_{1-16}$ acyl; $C_{6-16}$ aryl; $C_{6-16}$ aryloxy; amino; thiol; halogen; azole; phosphono; and $C_{2-6}$ ester.

$R_6$ is more preferably selected from the group consisting of hydrogen; $C_{1-16}$ alkyl; $C_{1-16}$ alkenyl; $C_{1-16}$ alkynyl; $C_{1-16}$ alkoxy; $C_{1-16}$ acyl; $C_{6-12}$ aryl; $C_{6-12}$ aryloxy; amino; halogen;azole; phosphono; and $C_{2-6}$ ester.

$R_6$ is most preferably selected from the group consisting of hydrogen; $C_{1-6}$ acyl; amido; and $C_{2-6}$ ester.

In a further preferred embodiment, $R_6$ is acetyl.

$R_7$ is selected from the group consisting of hydrogen; hydroxy; CN; $NO_2$; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amino; amido; sulfono; $C_{2-16}$ ester; thiol; azole; phosphono; and halogen.

$R_7$ is preferably selected from the group consisting of hydrogen; $C_{1-16}$ alkyl; and $C_{1-16}$ alkoxy.

$R_7$ is more preferably selected from the group consisting of hydrogen; $C_{1-6}$ alkyl; and $C_{1-6}$ alkoxy.

$R_7$ is most preferably hydrogen.

$R_8$ is selected from the group consisting of hydrogen; hydroxy; $C_{1-16}$ alkyl; $C_{1-16}$ alkenyl; $C_{1-16}$ alkynyl; $C_{1-16}$ alkoxy; $C_{1-16}$ acyl; halogen; and $C_{2-16}$ ester.

$R_8$ is preferably selected from the group consisting of hydrogen; hydroxy;and $C_{1-16}$ alkyl.

$R_8$ is more preferably selected from the group consisting of hydrogen; hydroxy;and $C_{1-6}$ alkyl.

$R_8$ is most preferably selected from the group consisting of hydrogen; hydroxy;and $C_{1-6}$ alkyl.

In a further preferred embodiment, $R_8$ is hydrogen.

W is a saccharide.

W is preferably a saccharide of formula (30) or (50):

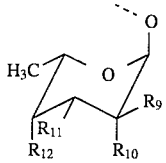
30 or

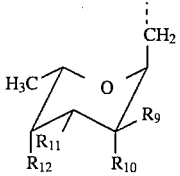
50 wherein;

$R_9$; $R_{10}$; $R_{11}$; and $R_{12}$ are independently selected from the group consisting of hydrogen; hydroxy; CN; $C_{1-16}$ alkyl; $C_{1-16}$ alkenyl; $C_{1-16}$ alkynyl; $C_{1-16}$ alkoxy; $C_{1-16}$ acyl; amino; amido; $C_{2-16}$ ester; azido; saccharide, $NH_2$; sulfono; morpholino; and halogen.

$R_9$; $R_{10}$; $R_{11}$; and $R_{12}$ are preferably independently selected from the group consisting of hydrogen; hydroxy; $C_{1-6}$ alkyl; $C_{1-6}$ alkenyl; $C_{1-6}$ alkynyl; $C_{1-6}$ alkoxy; $C_{1-6}$ acyl; $C_{2-6}$ ester; amino; amido; and halogen.

$R_9$ is more preferably selected from the group consisting of hydrogen; hydroxy;and $C_{1-6}$ alkyl.

$R_9$ is most preferably hydrogen.

$R_{10}$ is preferably selected from the group consisting of hydrogen; $C_{1-6}$ alkyl; $C_{1-6}$ acyl; amino; halogen; and hydroxy.

$R_{10}$ is more preferably selected from the group consisting of hydrogen; $C_{1-6}$ alkyl; $C_{1-6}$ acyl; halogen; and hydroxy.

$R_{10}$ is most preferably selected from the group consisting of hydrogen; $C_{1-6}$ acyl; halogen; and hydroxy.

$R_{11}$ and $R_{12}$ are independently more preferably selected from the group consisting of hydrogen; $C_{1-6}$ alkyl; $C_{1-6}$ acyl; $C_{2-6}$ ester; halogen; hydroxy; and amino.

$R_{11}$ is most preferably selected from the group consisting of hydrogen; $C_{1-6}$ alkyl; $C_{1-6}$ acyl; hydroxy; and amino.

$R_{12}$ is most preferably selected from the group consisting of $C_{1-6}$ acyl; $C_{2-6}$ ester; halogen; hydroxy; and amino.

In a further preferred embodiment, the coupled heteronaphtoquinone of formula (8) is selected from the group consisting of (1'S,1R,3S)-Methyl (5,10-dioxo-1-(2',3',6'-trideoxy-3'-trifluoroacetamido-4'-hydroxy-L-lyxohexopyranose)-3,4,5, 10-tetrahydronaphtho [2,3-C]pyran-3-yl) ketone BCH-1184;

(1'S,1S,3R)-Methyl (5,10-dioxo-1-(2',3',6'-trideoxy-3'-trifluoroacetamido-4'-hydroxy-L-lyxohexopyranose)-3,4,5, 10-tetrahydronaphtho [2,3-C]pyran-3-yl) ketone BCH-1146;

(1'S,1R,3S)-Methyl (5,10-dioxo-1-(2',3',6'-trideoxy-3'-trifluoroacetamido-L-lyxohexopyranose)-7-hydroxy-3,4,5, 10-tetrahydro[2,3-C]pyran-3-yl) ketone BCH-1181;

(1'S,1S,3R)-Methyl (5,10-dioxo-1-(2',3',6'-trideoxy-3'-trifluoroacetamido-L-lyxohexopyranose)-7-hydroxy-3,4,5, 10-tetrahydro[2,3-C]pyran-3-yl) ketone BCH-1180;

(1'-S, 1-R, 3-S) and (1'-S, 1-S, 3-R)-3-cyano-1-[2',3',6'-trideoxy-3'-trifluoroacetamido-4'-hydroxy-L-lyxohexopyranose)-5,10-dioxo-3,4,5,10-tetrahydronaphtho-[2,3C]pyran-3-yl BCH-1688;

(1'-S, 1-S, 3-R) and (1'-S, 1-R, 3-S)-methyl-(1-[2',3',4',6' tetradeoxy-3'-trifluoroacetamido-4'-O-methane-sulfonyl-L- lyxohexopyranose)-5,10-dioxo-3,4,5,10 tetrahydronaphtho-[2,3-c]pyran-3-yl) ketone BCH-2095;

(1'-S, 1-S, 3-R)-methyl-(1-[2',3',4',6' tetradeoxy-3'-trifluoroacetamido-4'-O-(2-bromo-acetyl)-L-lyxopyranose]-5,10-dioxo-3,4,5,10 tetrahydronaphto-[2,3-c]pyran-3-yl) ketone BCH-2105;

(1'-S, 1-R, 3-S)-methyl-(1-[2',3',4',6' tetradeoxy-3'-methoxy-4'-O-methanesulfonyl-L-lyxohexopyranose)-5,10-dioxo-3,4,5,10 tetrahydronaphtho-[2,3-c]pyran-3-yl) ketone BCH-2070;

(1'-S, 1'S, 3-R)-methyl-(1-[2',3',4',6' tetradeoxy-3'-methoxy-4'-O-methanesulfonyl-L-lyxohexopyranose)-5,10-dioxo-3,4,5,10 tetrahydronaphtho-[2,3-c]pyran-3-yl) ketone BCH-2072;

(1-S, 3-R) and (1-R, 3-S)-methyl-(1-(1-methoxy-4-oxocyclohexyloxy)-5,10-dioxo-3,4,5,10 tetrahydronaphtho-[2,3-c]pyran-3-yl) ketone BCH-2096;

(1'-S, 1-S, 3-R) and (1'-S, 1-R, 3-S)-1-(6-hydroxy-1-(2',3',6'-trideoxy-3'-trifluoroacetamido, 4-hydroxy-L-lyxopyranose)-5,10-dioxo-3,4,5,10 tetrahydronaphtho-[2,3-c]pyran-3-yl) propane-2-one BCH-2098;

3,3-bis-(methoxycarbonyl)-5,10-dioxo-3,4,5,10-tetrahydro-1H-naphtho-[2,3-c]-pyran (BCH-1665);

(1'S, 1R, 3S)-5,10-dioxo-3-methoxymethyl-1-(2',3',6'-trideoxy-3'-trifluoroacetamido-L-lyxchexopyranose)-3,4,5,10-tetrahydro-1H-naphtho-[2,3-c]-pyran (BCH-1691);

(1'S, 1S, 3R)-5,10-dioxo-3-methoxymethyl-1-(2',3',6'-trideoxy-3'-trifluoroacetamido-L-lyxohexopyranose)-3,4,5,10-tetrahydro-1H-naphtho[2,3-c]pyran (BCH-1693);

(1'S, 1R, 3R)-5,10-dioxo-3-ethyl-1-(2',3',6'-trideoxy-3'-trifluoroacetamido-L-lyxohexopyranose)-3,4,5,10-tetrahydro-1H-naphtho-[2,3-c]pyran (BCR-2026);

(1'S, 1S, 3S)-5,10-dioxo-3-ethyl-1-(2',3',6'-trideoxy-3'-trifluoroacetamido-L-lyxohexopyranose)-3,4,5,10-tetrahydro-1H-naphtho-[2,3-c]-pyran (BCH-2020);

(1–S, 1S, 3S)-5,10-dioxo-3-ethyl-1- (2',3',6'-trideoxy-3'-amino-L-lyxohexopyranose)-3,4,5,10-tetrahydro-1H-naphtho-[2,3-c]-pyran (BCH-2021);

(1'S, 1R, 3S)-5,10-dioxo-3-isopropyl-1-(2',3',6'-trideoxy-3'-trifluoroacetamido-L-lyxohexopyranose)-3,4,5,10-tetrahydro-1H-naphtho-[2,3-c]-pyran (BCH-2053);

(1'S, 1S, 3R)-5,10-dioxo-3-isopropyl-1-(2',3',6'-trideoxy-3'-trifluoroacetamido-L-lyxohexopyranose)-3,4,5,10-tetrahydro-1H-naphtho-[2,3-c]-pyran (BCH-2052);

(1'S, 1R, 3S)-5,10-dioxo-3-isopropenyl-1-(2',3',6'-trideoxy-3'-trifluoroacetamido-L-lyxohexopyranose)-3,4,5,10-tetrahydro-1H-naphtho-[2,3-c]-pyran (BCH-2153);

(1'S, 1S, 3R)-5,10-dioxo-3-isopropenyl-1-(2',3',6'-trideoxy-3'-trifluoroacetamido-L-lyxohexopyranose)-3,4,5,10-tetrahydro-1H-naphtho-[2,3-c]-pyran (BCH-21-52);

(1'S, 1R, 3S)-5,10-dioxo-3-methoxycarbonyl-1-(2',3',6'-trideoxy-3'-trifluoroacetamido-L-lyxohexopyranose)-3,4,5,10-tetrahydro-1H-naphtho-[2,3-c]-pyrano (BCH-2128);

(1'S, 1R, 3S)-isopropyl-[1-(2',3',6'-trideoxy-3'-trifluoroacetamido-L-lyxohexopyranose)-5,10-dioxo-3,4,5,10-tetrahydro-1H-naphtho-[2,3-c]-pyranyl]-ketone (BCH-2112);

(1'S, 1R, 3S)-5,10-dioxo-3-isopropoxycarbonyl-1-(2',3',6'-trideoxy-3'-trifluoroacetamido-L-lyxohexopyranose)-3,4,5,10-tetrahydro-1H-naphtho-[2,3-c]-pyran (BCH-2122);

(1'S, 1S)-5,10-dioxo-3,3-dimethoxymethyl-1-(2',3',6'-trideoxy-3'-trifluoroacetamido-4'-O-p-nitrobenzoyl-L-lyxohexo-pyranose)-isochroman (BCH-1697);

(1'S, 1R, 4R)-5,10-dioxo-4-ethyl-1-(2',3',6'-trideoxy-3'-trifluoroacetamido-L-lyxohexopyranose)-3,4,5,10-tetrahydro-1H-naphtho-[2,3-c]pyran (BCH-2091);

(1'S, 1R, 3S)-5,10-dioxo-3-phenyloxymethyl-1-(2',3',6'-trideoxy-3'-trifluoroacetamido-L-lyxohexopyranose)-3,4,5,10-tetrahydro-1H-naphtho-[2,3-c]pyran (BCH-2032);

(1'S,1S,3S) and (1'S,1-R,3-R)-3-([2',3',6'-trideoxy-3'-trifluoroacetamido-4'-hydroxy-L-lyhohexopyranose]-5,10-dioxo-3,4,5,10-tetrahydronaphtho-[2,3-c]-pyran-3-yl)-propene (BCH-2031);

(1'-S,1-R,3-S)-methyl-(1-[2',3',6'-trideoxy-3'-trifluoroacetamido-4'-iodo-L-lyxohexopyranose]-5,10-dioxo-3,4,5,10-tetrahydronaphtho-[2,3-c]-pyran-3-yl)-ketone (BCH-1620);

(1'-S,1-R,3-S)-3-([2',3',6'-trideoxy-3'-trifluoroacetamido-4'-hydroxy-L-lyhohexopyranose]-5,10-dioxo-3,4,5,10-tetrahydronaphtho-[2,3-c]-pyran-3-yl)-propene (BCH-1649);

(1'-S,1-R,3-S,4a-S,10a-S)-methyl-(1-[2',3',4',6'-tetradeoxy-3'-methoxy-4'-O-methanesulfonyl-L-lyxohexopyranose)-4a,10a-epoxy-5,10-dioxo-3,4,5,10-tetrahydronaphtho-[2,3-c]pyran-3-yl) ketone (BCH-2141);

(1S,3R,1'S,5'S,6'S) and (1R,3S,1'S,5'S,6'S)-methyl-(1-[4'trifluoroacetamido-5'-methyltetrahydropyranyl]-5,10-dioxo-3,4,5,10-tetrahydronaphthaleno-[2,3-c]pyran-3-yl) ketone (BCH-1673);

(1'S,1S,3R)-3 (oximoethyl)-5,10-dioxo-1 (2,3,6-trideoxy-3-trifluoroacetamido-L-lyxohexopyranose)-3,4,5,10-tetrahydro-1H-naphtho-[2,3-c]pyran (BCH-2101);

(1'S, 1R, 3S)-3 (oximoethyl)-5,10-dioxo-1 (2,3,6-trideoxy-3-trifluoroacetamido-L-lyxohexopyranose)-3,4,5,10-tetrahydro-1H-naphtho-(2,3-c)-pyran (BCH-2115);

(1'S,1S,3R)-3-(trifluoroacetamidoethyl)-5,10-dioxo-1-(2',3',6'-trideoxy-3',4'-dihydroxy-L-lyxohexopyranose)-3,4,5,10-tetrahydro-1H-naphtho-[2,3-c]-pyran (BCH-2018);

(1'R, 1R, 3S)-3-aceto-5,10-dioxo-1-(2-deoxy-2-chloroethylnitrosoureido-D-glucopyranose)-3,4,5,10-tetrahydro-1H-naphtho-[2,3-C]pyran (BCH-2038) (1R,3S) and (1S,3R)-3-aceto-5,10-dioxo-1 (4-chloroethylnitrosoureido cyclohexyloxy)-3,4,5,10-tetrahydro-1H-naphtho-(2,3-c)-pyran (BCH-2114);

(1'S,1S,3R)-1-(3'-trifluoroacetamido-2',3',6'-trideoxy-lyxo-L-hexopyranose)-3-methoxycarbonyl-3-methyl-3,4,5,10-tetrahydro-5,10-dioxo-naphtho-[2,3-c]pyran (BCH-2076);

(1'S, 1R, 3S)-2',3',6'-trideoxy-3'-trifluoroacetamido-L-lyxohexopyranose-3-[5'-tosyloxazolyl]-5,10-dioxo-3,4,5,10-tetrahydro-1H-naphtho-[2,3-c]-pyran (BCH-2150);

(1'S, 1S, 3R)-2',3',6'-trideoxy-3'-trifluoroacetamido-L-lyxohexopyranose-3-[5'-tosyloxazolyl)]-5,10-dioxo-3,4,5,10-tetrahydro-1H-naphtho-[2,3-C]-pyran (BCH-2151);

(1'S, 1R, 3S)-1-(3'-trifluoroacetamido-2',3',6'-trideoxy-L-lyxohexopyranose)-5,10-dioxo-4,5,10-trihydro-1H-naphtho-[2,3-c]-pyran (BCH-2077);

(1'S, 1S, 3R)-1-(3'-trifluoroacetamido-2',3',6'-trideoxy-L-lyxohexopyranose)-3-acetyl-3-methyl-5,10-dioxo-4,5,10-trihydro-1H-naphtho-[2,3-c]-pyran (BCH-2082);

(1'S,1S,3R)-1-(2',3',6'-trideoxy-3'-trifluoroacetamido-L-lyxohexopyranose)-3-dimethylphosphonoacetyl-5,10-dioxo-3,4,5-10-tetrahydro-1H-naphtho-[2,3-c]-pyran (BCH-1690);

(1'S, 1S, 3S)-1-(3'-trifluoroacetamido-2',3',6'-trideoxy-lyxohexopyranose)-3-methoxycarbonyl-3-methyl-5,10-dioxo-4,5,10-trihydro-1H-naphtho-[2,3-c]-pyran (BCH-2081);

(1'S,1S,3S)-1-(3'-trifluoroacetamido-2',3',6'-trideoxy-L-lyxohexopyranose)-5,10-dioxo-3,4,5,10-tetrahydro-1H-naphtho-[2,3-c]-thiopyran (BCH-2037.001);

(1'S,1R,3R)-1-(3'trifluoroacetamido-2',3',6'-trideoxy-lyxo-L-hexopyranose)-3-dimethoxphosphonoacetyl-3,4,5,10-tetrahydro-5,10-dioxo-naphtho-[2,3-c]pyran (BCH-2127);

(1'S,1S,3S)-1-(3'-trifluoroacetamido-2',3',6'-trideoxy-lyxo-L-hexopyranose)-3-acetyl-3-methyl-3,4,5,10-tetrahydro-5,10-dioxo-1H-naphtho-[2,3-c]pyran (BCH-2090);

(1'S,1R,3S)-1-(3'-trifluoroacetamido-2',3',6'-trideoxy-lyxo-L-hexopyranose)-3-dimethoxyphosphonoacetyl-3,4,5,10- tetrahydro-5,10-dioxo-naphtho-[2,3-c]pyran (BCH-1689);
(1'S,1R,3S)-methyl-(1-[2',6'-dideoxy-3',4'-dihydroxy-2'-iodo-L-lyxohexopyranose]-5,10-dioxo-3,4,5,10-tetrahydronaphtho[2,3-c]-pyran-3-yl) ketone (BCH-2015) ;
(1'S,1R,3S)-methyl-(1-[2',6'-dideoxy-3'-4'-diacetoxy-2'-iodo-L-lyxohexopyranose]-5,10-dioxo-3,4,5,10-tetrahydronaphtho[2,3-c]-pyran-3-yl) ketone (BCH-1666);
(1'S,1S,3R)-methyl-(1-[2',6'-dideoxy-3',4'-diacetoxy-2'-iodo-L-lyxohexopyranose]-5,10-dioxo-3,4,5,10-tetrahydronaphtho[2,3-c]-pyran-3-yl) ketone (BCH-1667);
(1'S,1S,3R)-methyl-(1-[2',6'-dideoxy-3',4'-dihydroxy-2'-iodo-L-lyxohexopyranose]-5,10-dioxo-3,4,5,10-tetrahydronaphtho[2,3-c]-pyran-3-yl)-ketone (BCH-2014);
(1'S,1R,3S)-methyl-(1-[2',6'-dideoxy-3',4'-diacetoxy-2'-bromo-L-lyxohexopyranose]-5,10-dioxo-3,4,5,10-tetrahydronaphtho-[2,3-c]-pyran-3-yl) ketone (BCH-2100);
(1'S,1R,3S)-methyl-(1-[2',3',6'-trideoxy-2'-iodo-3'-trifluoroacetamido-4'-hydroxy-L-lyxohexopyranose]-5,10-dioxo-3,4,5,10-tetrahydronaphtho-[2,3-c]-pyran-3-yl) ketone (BCH-2023);
(1'S,1S,3R)-methyl-(1-[2',3',6'-trideoxy-2'-iodo-3 '-trifluoroacetamido-4'-hydroxy-L-lyxohexopyranose]-5,10-dioxo-3,4,5,10-tetrahydronaphtho-[2,3-c]-pyran-3-yl) ketone (BCH-2022);
(1'S,1R,1S) and (1'S ,1S,3R)-methyl-(1-[2',6'-dideoxy-3',4'-diacetoxy-2'-iodo-L-arabino-hexopyranose]-5,10-dioxo-3,4,5,10-tetrahydronaphtho-[2,3-c]-pyran-3-yl) ketone (BCH-2065);
(1'S,1S,3R) and (1'S,1R,3S)-methyl-(1-[dideoxy-2',6'-dihydroxy-3',4'-L-lyxohexopyranose]-5,10-dioxo-3,4,5,10-tetrahydronaphtho-[2,3-c]-pyran-3-yl) ketone (BCH-2117);
(1'S,1S,3R) and (1'S,1R,3S)-methyl-(1-[dideoxy-2',6'-diacetoxy-3',4'-L-lyxohexopyranose]-5,10-dioxo-3,4,5,10-tetrahydronaphtho-[2,3-c]-pyran-3-yl) ketone (BCH-2118);
Methyl-(6-hydroxy-5,10-dioxo-3,4,5,10-tetrahydronaphtho-[2,3-c]-pyran-3-yl) ketone and methyl-(9-hydroxy-5,10-dioxo-3,4,5,10-tetrahydronaphtho-[2,3-c]-pyran-3-yl) ketone (BCH-2062);
(1'S,1S,3R)-methyl-(6 and 9-hydroxy-1-[2',3',6'-trideoxy-3'-trifluoroacetamido-4'-hydroxy-L-lyxohexopyranose]-5,10-dioxo-3,4,5,10-tetrahydronaphtho-[2,3-c]-pyran-3-yl-ketone (BCH-2078);
(1R,3S,1'S) and (1S,3R,1'S)-Methyl-(1-[2',3',4',6'-tetradeoxy-3',4'-bis-trifluoroacetamido-L-arabinohexopyranose]-5,10-dioxo-3,4,5,10-tetrahydronaphthaleno-[2,3-c] pyran-3-yl) ketone (BCH-2104 and BCH-2102);
(1S,3R,1'S)-Methyl-(1-[2',3',4',6'-tetradeoxy-3'-trifluoroacetamido-4'-bromo-L-lyxohexopyranose]-5,10-dioxo-3,4,5,10-tetrahydronaphthaleno-[2,3-c]pyran-3-yl) ketone (BCH-2047);
(1'-S,1-S,3-R)-1-(2',3',6'-trideoxy-3'-trifluoroacetamido-L-lyxohexopyranose)-3-(2-aza-3-acetamido-thiazolyl)-5,10-dioxo-3,4,5,10-tetrahydro-1H-naphtho-[2,3-c]-pyran (BCH-1198);
(1'S, 1S, 3S) and (1'S, 1R, 3R)-5,10-dioxo-3-ethyl-1-(2',3',4',6'-tetradeoxy-3',4'-diacetoxy-L-lyxohexo-pyranose)-3,4,5,10-tetrahydro-1H-naphtho[2,3-C]pyran (BCH-1607);
(1'S,1S,3R)-methyl-(1-[2',6'-dideoxy-3',4'-diacetoxy-2'-bromo-L-lyxohexopyranose]-5,10-dioxo-3,4,5,10-tetrahydronaphtho-[2,3-c]-pyran-3-yl) ketone (BCH-2099);
(1'S, 2'R, 3'S, 5'R, 1S, 3R)-1-(3-trifluoroacetamido-2-hydroxy-1-methyl tetrahydropyran-5-yl)-methyl-3-ethyl-5,10-dioxo-3,4,5,10-tetrahydro-1H-naphtho[2,3-C]pyran (BCH-2818);
(1'S, 2'R, 3'S, 5'R, 1R, 3S)-1-(3-trifluoroacetamido-2-hydroxy-1-methyl tetrahydropyran-5-yl)-methyl-3-ethyl-5, 10-dioxo-3,4,5,10-tetrahydro-1H-naphtho[2,3-C]pyran (BCH-2819);
(1'S,2'R,3'S,5'R,1R,3R)-3-(3-trifluoroacetamido-2-hydroxy-1-methyl tetrahydropyran-5-yl)methyl-3-methylketone-5,10-dioxo-3,4,5,10-tetrahydro-1H-naphtho[2,3-C]pyran. (BCH-2821); and
(1'S,2'R,3'S,5'R,1S,3S )-1-(3-trifluoroacetamido-2-hydroxy-1-methyl tetrahydropyran-5-yl)methyl-3-methylketone-5,10-dioxo-3,4,5,10-tetrahydro-1H-naphtho[2,3-C]pyran. (BCH-2820).

There is provided in a third aspect of the present invention, an insaturated heteronaphtoquinone of formula (50a) the geometric isomers and opticals isomers, the mixtures of those isomers, and pharmaceutically acceptable acid addition salts thereof,

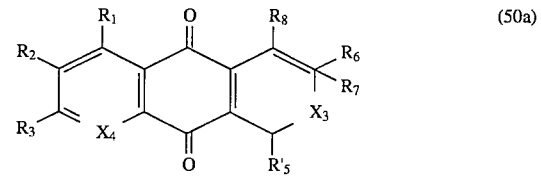

(50a)

$X_3$ is preferably selected from the group consisting of O; and S.

$X_3$ is more preferably O.

$X_4$ is selected from the group consisting of C—Q; nitrogen; and NO.

$X_4$ is more preferably CQ.

$R_1$, $R_2$, $R_3$ and Q are each preferably independently selected from the group consisting of hydrogen; hydroxy; $C_{1-16}$ alkyl; $C_{1-16}$ alkenyl; $C_{1-16}$ alkynyl; $C_{1-16}$ alkoxy; $C_{6-16}$ aryl; $C_{1-16}$ acyl; amino; amido; and halogen.

$R_1$, $R_2$, $R_3$ and Q are each more preferably independently selected from the group consisting of hydrogen; hydroxy; $C_{1-6}$ alkyl; $C_{1-6}$ alkenyl; $C_{1-6}$ alkynyl; $C_{1-6}$ alkoxy; amino; amido; $C_{6-12}$ aryl; and halogen.

$R_1$, $R_2$, $R_3$ and Q are each most preferably independently selected from the group consisting of hydrogen; hydroxy; and $C_{1-6}$ alkyl.

In a further preferred embodiment $R_1$, $R_2$, $R_3$ and Q are each hydrogen.

$R'_5$ preferably is selected from the group consisting of hydrogen; hydroxy; $C_{1-16}$ alkyl; $C_{1-16}$ alkenyl; $C_{1-16}$ alkynyl; $C_{1-16}$ alkoxy; $C_{6-16}$ aryl; $C_{1-16}$ acyl; amino; amido; sulfono; $C_{2-16}$ ester; thiol; azole; morpholino; halogen; and a saccharide W, wherein, W is a saccharide of formula (30) or (50):

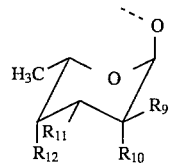

30 or

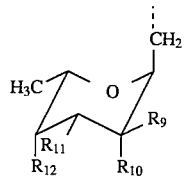

50 wherein;

$R_9$; $R_{10}$; $R_{11}$; and $R_{12}$ are independently selected from the group consisting of hydrogen; hydroxy; CN; $C_{1-16}$ alkyl; $C_{1-16}$ alkenyl; $C_{1-16}$ alkynyl; $C_{1-16}$ alkoxy; $C_{1-16}$ acyl; amino; amido; $C_{2-16}$ ester; azido; saccharide, $NH_2$; sulfono; morpholino; and halogen.

$R_9$; $R_{10}$; $R_{11}$; and $R_{12}$ are preferably independently selected from the group consisting of hydrogen; hydroxy; $C_{1-6}$ alkyl; $C_{1-6}$ alkenyl; $C_{1-6}$ alkynyl; $C_{1-6}$ alkoxy; $C_{1-6}$ acyl; $C_{2-6}$ ester; amino; amido; and halogen.

$R_9$ is more preferably selected from the group consisting of hydrogen; hydroxy;and $C_{1-6}$ alkyl.

$R_9$ is most preferably hydrogen.

$R_{10}$ is more preferably selected from the group consisting of hydrogen; $C_{1-6}$ alkyl; $C_{1-6}$ acyl; amino; halogen; and hydroxy.

$R_{10}$ is most preferably selected from the group consisting of hydrogen; $C_{1-6}$ acyl; halogen; and hydroxy.

$R_{11}$ and $R_{12}$ are preferably independently selected from the group consisting of hydrogen; $C_{1-6}$ alkyl; $C_{1-6}$ acyl; $C_{2-6}$ ester; halogen; hydroxy; and; amino.

$R_{11}$ is more preferably selected from the group consisting of hydrogen; $C_{1-6}$ alkyl; $C_{1-6}$ acyl; hydroxy and; amino.

$R_{12}$ is more preferably selected from the group consisting of $C_{1-6}$ acyl; $C_{2-6}$ ester; halogen; hydroxy; and amino.

$R'_5$ is more preferably selected from the group consisting of hydrogen; $C_{1-6}$ alkyl; $C_{1-6}$ alkoxy; amino; amido; $C_{2-16}$ ester; azole; and morpholino.

$R'_5$ is most preferably selected from the group consisting of hydrogen; and $C_{1-6}$ alkyl; $C_{1-6}$ alkoxy.

$R_6$ is selected from the group consisting of hydrogen; hydroxy; $C_{1-16}$ alkyl; $C_{1-16}$ alkenyl; $C_{1-16}$ alkynyl; $C_{1-16}$ alkoxy; $C_{6-16}$ aryl; $C_{1-16}$ acyl; amino; amido; sulfono; $C_{2-16}$ ester; thiol; azole; and halogen.

$R_6$ is preferably selected from the group consisting of hydrogen; $C_{1-6}$ alkyl; $C_{1-6}$ alkenyl; $C_{1-6}$ alkynyl; $C_{1-6}$ alkoxy; $C_{1-6}$ acyl; $C_{6-12}$ aryl; amino; amido; thiol; halogen; azole; and $C_{2-6}$ ester.

$R_6$ is more preferably selected from the group consisting of hydrogen; $C_{1-6}$ alkyl; $C_{1-6}$ alkoxy; $C_{1-6}$ acyl; amido;azole; thiol; and $C_{2-6}$ ester.

$R_6$ is most preferably selected from the group consisting of $C_{1-6}$ acyl; amido; and $C_{2-6}$ ester.

$R_8$ is preferably selected from the group consisting of hydrogen; hydroxy; $C_{1-16}$ alkyl; $C_{1-16}$ alkenyl; $C_{1-16}$ alkynyl; $C_{1-16}$ alkoxy; $C_{1-16}$ acyl; halogen; and $C_{2-16}$ ester.

$R_8$ is more preferably selected from the group consisting of hydrogen; hydroxy;and $C_{1-6}$ alkyl.

$R_8$ is most preferably hydrogen.

In a further preferred embodiemnt, the insaturated heteronaphtoquinone of formula (50a) according are selected from the group consisting of
1-Methoxy-5,10-dioxo-5,10-dihydro-1H-naphtho[2,3-c]pyran-3-[N-(3-dimethylamino-propyl)carboxamide]hydrochloride monohydrate (BCH-2051);
3-Aceto-5,10-dioxo-1-methoxy-5,10-dihydro-1H-naphtho-(2,3-c)-pyran (BCH-2129); 1-methoxy-3-N-anilinylcarbonyl-5,10-dioxo-5,10-dihydro-1H-naphtho-[2,3-c]-pyran (BCH-2044).
1-methoxy-3-(3-N-pyrrolidinomylpropylaminocarbonyl)-5,10-dioxo-5,10-dihydro-1H-naphtho-[2,3-c]-pyran (BCH-2166);
(3-N-hydrochloroimidazolylpropyl)-1-methoxy-5,10-dioxo-5,10-dihydro-1H-naphtho-[2,3-c]-pyran-3-carboxamide (BCH-2157);
2-hydrochloro-(N-pyrrolidinyl)ethyl-(1-propyl-5,10-dioxo-5,10-dihydro-1H-naphtho-[2,3-c]-pyran-3)-carboxamide (BCH-2875);
3-N-oxo-dimethylaminopropyl-(1-methoxy-5,10-dioxo-5,10-dihydro-1H-naphtho-[2,3-c]-pyran-3)-carboxamide (BCH-2877);
2-(2-N-methyl pyrrolyl)-ethyl-(1-propyl-5,10-dioxo-5,10-dihydro-1H-naphtho-[2,3-c]-pyran-3)-carboxamide (BCH-2876);
1-methoxy-3-[2-(N-morpholino) ethyl amino carbonyl]-5,10-dioxo-5,10-dihydro-1H-naphtho-[2,3-c]-pyran (BCH-2170);
1-methoxy-3-[2-(N-morpholine) ethyl amino carbonyl]-5,10-dioxo-5,10-dihydro-1H-naphtho-[2,3-c]-pyran (BCH-2171);
1-methoxy-3-[2-(2-pyridinyl) ethyl amino carbonyl]-5,10-dioxo-5,10-dihydro-1H-naphtho-[2,3-c]-pyran hydrochloride (BCH-2835);
1-methoxy-3-[(2-pyridinyl) methyl amino carbonyl]-3-methoxy-5,10-dioxo-5,10-dihydro-1H-naphtho-[2,3-c]-pyran (BCH-2840);
1-methoxy-3-[(2-pyridinyl) methyl amino carbonyl]-3-methoxy-5,10-dioxo-5,10-dihydro-1H-naphtho-[2,3-c]-pyran hydrochloride salt (BCH-2841);
1-methoxy-3-[2-(N-pyrrolidinyl) ethyl amino carbonyl]-5,10-dioxo-5,10-dihydro-1H-naphtho-[2,3-c]-pyran hydrochloride salt (BCH-2839);
1-methoxy-3-[(4-diethoxy) butyl amino carbonyl]-5,10-dioxo-5,10-dihydro-1H-naphtho-[2,3-c]-pyran (BCH-2848);
1-methoxy-3-(3-hydroxy) propyl amino carbonyl-5,10-dioxo-5,10-dihydro-1H-naphtho-[2,3-c]-pyran (BCH-2849);
1-methoxy-3-methoxy carbonyl-5,10-dioxo-5,10-dihydro-1H-naphtho-[2,3-c]-pyran (BCH-2160);
1-propyl-3-(3-dimethyl amino propyl amino carbonyl)-5,10-dihydro-5,10-dioxo-1H-naphtho-[2,3-c]-pyran (BCH-2168);
3-methoxy carbonyl-5,10-dioxo-5,10-dihydro-1H-naphtho-[2,3-c]-pyran (BCH-2830);
1-methoxy-3-(2-trimethyl ammonium ethyl amino carbonyl)-5,10-dioxo-5,10-dihydro-1H-naphtho-[2,3-c]-pyran chloride salt (BCH-2837);
1-methoxy-3-(2-pyrrolidinoethylcarbonyl)-5,10-dioxo-5,10-dihydro-1H-naphtho-[2,3-c]pyran hydrochloride (BCH-2854);
1-Methoxy-3[2-(N-pyrrolidinylethoxylcarbonyl)]-5,10-dioxo-5,10-dihydro-1H-naphtho-[2,3-c]-pyran (BCH-2861);
1-methoxy-5,10-dioxo-5,10-dihydro-1H-naphtho[2,3-c]thiine-3-[N-(3-dimethylaminopropyl) carboxamide] (BCH-2878);
(1'S) Methyl (5,10-dioxo-1-(2',3',4',6'-tetradeoxy-3',4'-diacetoxy-L-lyxohexopyranose-5,10-dihydro-1H-naphtho[2,3-c]thiopyran-3-yl) ketone (BCH-2879); and
N-Boc-N-{1-methoxy-5,10-dihydro-5,10-dioxo-1H-naphtho-[2,3-c]-pyran-3-carbonyl}-propyldiamine (BCH-2881).

The coupled heteronaphtoquinone of formula (8); heteronaphtoquinone of formula (4) and insaturated heteronaphtoquinone of formula (50a) ("the compound(s) of the invention") possess antitumor and anticancer activity. While it is possible to administer one or more of the compounds of the invention as a raw chemical, it is preferred to administer the active ingredient(s) as a pharmaceutical composition.

In another aspect, the invention therefore provides pharmaceutical compositions primarily suitable for use as antitumor and anticancer agents, comprising an effective amount of at least one compound of the invention or a pharmaceutically acceptable derivative thereof in association with one or more pharmaceutically acceptable carriers and optionally other therapeutic and/or prophylactic ingredients. All the pharmaceutically acceptable salts for example the HCl and tartaric acid salts of the compounds useful as antitumor agents in mammals, including humans, are included in this invention.

It will be appreciated by those familiar with the art of clinical oncology that the compound(s) of this invention can be used in combination with other therapeutic agents, including chemotherapeutic agents (Cancer: Principles and Practices of Oncology, 3rd Edition, V. T. DeVito Jr., S. Hellman and S. A. Rosenberg; Antineoplastic Agents edited by W. A. Remers, John Wiley and Sons, N.Y., 1984). Thus, it will be understood that the compounds or pharmaceutical compositions of the invention may be formulated with the therapeutic agent to form a composition and administered to the patient or the compounds or compositions and the therapeutic agent may be administered separately, as appropriate for the medical condition being treated.

Therefore, for therapeutic purposes, a compound or composition of this invention can be used in association with one or more of the therapeutic agents belonging to any of the following groups:

1) Alkylating agents such as:
2-haloalkylamines (e.g. melphalan and chlorambucil);
2-haloalkylsulfides;
N-alkyl-N-nitrosoureas (e.g. carmustine, lomustine or semustine);
aryltriazines (e.g. decarbazine);
mitomycins (e.g. mitomycin C);
methylhydrazines (e.g. procarbazine);
bifunctional alkylating agents (e.g. mechlorethamine);
carbinolamines (e.g. sibiromycin);
streptozotocins and chlorozotocins;
phosphoramide mustards (e.g. cyclophosphamide);
urethane and hydantoin mustards
2) Antimetabolites such as:
mercaptopurines (e.g. 6-thioguanine and 6-[methylthio] purine);
azapyrimidines and pyrimidines;
hydroxyureas;
5-fluorouracil;
folic acid antagonists (e.g. amethopterin);
cytarabines;
prednisones;
diglycoaldehydes;
methotrexate;
3) Intercalators such as:
bleomycins and related glycoproteins;
anthracylines (e.g. doxorubicin, daunorubicin, epirubicin, esorubicin, idarubicin, aclacinomycin A);
acridines (e.g. m-AMSA);
hycanthones;
ellipticines (e.g. 9-hydroxyellipticine);
actinomycins (e.g. actinocin);
anthraquinones (e.g. 1,4-bis[(aminoalkyl)amino]-9,10-anthracenediones);
anthracene derivatives (e.g. pseudourea and bisanthrene);
phleomycins;
aureolic acids (e.g. mithramycin and olivomycin);
Camptothecins (e.g. topotecan);
4) Mitotic inhibitors such as:
dimeric catharanthus alkaloids (e.g. vincristine, vinblastine and vindesine);
colchicine derivatives (e.g. trimethylcolchicinic acid)
epipodophyllotoxins and podophylotoxins (e.g. etoposide and teniposide);
maytansinoids (e.g. maytansine and colubrinol);
terpenes (e.g. helenalin, tripdiolide and taxol);
steroids (e.g. 4β-hyroxywithanolide E);
quassinioids (e.g. bruceantin);
pipobroman;
methylglyoxals (e.g. methylglyoxalbis-(thiosemicarbazone);
5) Hormones (e.g. estrogens, androgens, tamoxifen, nafoxidine, progesterone, glucocorticoids, mitotane, prolactin);
6) Immunostimulants
(e.g. human interferons, levamisole and tilorane);
7) Monoclonal and polyclonal antibodies;
8) Radiosensitizing and radioprotecting compounds (e.g. netronidazole and misonidazole);
9) Other miscellaneous cytotoxic agents such as:
camptothecins;
quinolinequinones (e.g. streptonigrin and isopropylidene azastreptonigrin);
cisplatin, cisrhodium and related platinum series complexes;
tricothecenes (e.g. trichodermol or vermicarin A);
cephalotoxines (e.g. harringtonine);
10) Cardioprotecting compounds, such as (±)-1,2-bis(3, 5-dioxopiperazin-1-yl) propane, commonly known as ICRF-187, and ICRF-198;
11) Drug-resistance reversal compounds such as P-glycoprotein inhibitors, for example Verapamil, cyclosporin-c, fujimycin;
12) Cytotoxic cells such as lymphokine activated killer -cells or T-cells,
13) Other Immunostimulants such as interleukin factors or antigens.
14) Polynucleotides of sence or antisensing nature.
15) Polynucleotides capable of forming triple helices with DNA or RNA.
16) Polyethers
17) Distamycin and analogs.
18) Taxanes such as taxol and taxotere.

The above list of possible therapeutic agents is not intended to limit this invention in any way.

The pharmaceutical compositions of the invention can be in forms suitable for oral, rectal, nasal, topical (including buccal and sublingual), vaginal or parenteral (including intraarterial, intraperitoneal, intramuscular, subcutaneous and intravenous administration), by inhalation or by insufflation. Where appropriate, the formulations may be conveniently presented in discrete dosage units and may be prepared by any method well known in the art of pharmacy. All methods include the step of bringing into association the active compound with liquid carriers or finely divided solid carriers or both and then, if necessary, shaping the product into the desired formulation.

For injectable use, the pharmaceutical composition forms include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol for example, chremophor-EL, tween 80[1], glycerol, dimethyl sulfoxide (DMSO), propylene glycol, and liquid polyethylene glycol, and the like suitable mixtures thereof, and vegetable oils. The proper fluidity can be maintained for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

[1] denotes trademark

Sterile injectable solutions are prepared by incorporating the active ingredient or ingredients in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique. These methods yield a powder of the active ingredient plus any additional desired ingredient from a previously sterile-filtered solution thereof.

Pharmaceutical formulations suitable for oral administration may conveniently be presented as discrete units such as capsules, sachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

As used herein, the expression "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except isofar as any conventional media or agent is incompatible with the active ingredient, its use in the present compositions is contemplated. Supplementary active ingredients can be incorporated into the inventive compositions.

It is especially advantageous to formulate compositions in dosage unit form for ease of administration and uniformity of dosage. Dosage unit form as used in the specification and claims herein refers to physically discrete units suited as unitary dosages for the animal subjects to be treated, each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding such an active material for the treatment of disease in living subjects having a diseased condition in which bodily health is impaired as disclosed in detail in this specification.

The dosage of the principal active ingredient for the treatment of the indicated conditions depends upon the age, weight and condition of the subject being treated the particular condition and its severity; the particular form of the active ingredient, the potency of the active ingredient, and the route of administration. A daily dose of from about 0.001 to about 100 mg/kg of body weight given singly or in divided doses of up to 5 times a day or by continuous infusion embraces the effective range for the treatment of most conditions for which the novel compounds are effective. For a 75 kg subject, this translates into between about 0.075 and about 7500 mg/day. If the dosage is divided for example, into three individual dosages, these will range from about 0.25 to about 2500 mg. of the active ingredient. The preferred range is from about 0.1 to about 50 mg/kg of body weight/day with about 0.2 to about 30 mg/kg of body weight/day being more preferred.

The principal active ingredient is compounded for convenient and effective administration in effective amounts with a suitable pharmaceutically acceptable carrier in dosage unit form as hereinbefore disclosed. A unit dosage form can, for example, contain the principal active ingredient in amounts ranging from about 0.1 to about 1000 mg., with from about 1.0 to about 500 mg. being preferred. Expressed in proportions, the active ingredient is generally present in from about 0.1 to about 500 mg/ml of carrier. In the case of compositions containing supplementary active ingredients, the dosages are determined by reference to the usual dose and manner of administration of the said ingredients.

Antitumor treatment comprises the administration of any of the compounds of this invention in an acceptable pharmaceutical formulation at the effective therapeutic dosage. It is understood that chemotherapy can require the use of any of the compounds of this invention bound to an agent which facilitates targeting the compound to the tumor cells. The agent may be chosen from, for example, monoclonal or polyclonal antibodies, proteins and liposomes. The compounds of this invention could also be administered as monomeric, dimeric, trimeric or oligomeric metal chelate complexes with, for example iron, magnesium or calcium.

The compounds of the invention exhibit antitumor activity, most notably, antitumor activity with human breast cancer, leukemia, colon cancer, ovarian cancer, and melanoma. This list of conditions is however not exclusive, and it is believed that the compounds of the invention will exhibit activity against other tumors and cancers, such as for example pancreatic cancer, bladder cancer, lung cancer, and central nervous system (CNS) cancer. Most notably the compounds of this invention are more potent than doxorubicin against P-170 mediated multidrug resistant cancers.

There is provided, in a fourth aspect of this invention, a process for the preparation of an heteronaphtoquinone of formula (4) or a coupled heteronaphtoquinone of formula (8) and pharmaceutically acceptable acid addition salts thereof

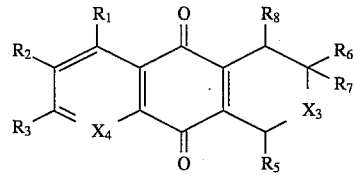

4 or

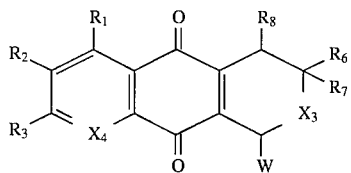

wherein;

$X_3$ is selected from the group consisting of O; S; and $SO_2$.

$X_4$ is selected from the group consisting of C—Q; nitrogen; and NO.

$R_1$, $R_2$, $R_3$ and Q are each independently selected from the group consisting of hydrogen; hydroxy; CN; $NO_2$; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amino; amido; sulfono; $C_{2-16}$ ester; and halogen.

$R_6$ is selected from the group consisting of hydrogen; hydroxy; CN; $NO_2$; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amino; amido; sulfono; $C_{2-16}$ ester; thiol; azole; phosphono; and halogen.

$R_7$ is selected from the group consisting of hydrogen; hydroxy; CN; $NO_2$; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ alkoxyalkyl; $C_{1-16}$ acyl; amine; amido; sulfono; $C_{2-16}$ ester; thiol; azole; phosphono; and halogen.

$R_5$ is selected from the group consisting of hydrogen; hydroxy; CN; $NO_2$; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{7-16}$ aryloxy; $C_{1-16}$ alkoxyalkyl; $C_{1-16}$ acyl; amino; amido; sulfono; $C_{2-16}$ ester; thiol; azole; phosphono; morpholino; and halogen.

$R_8$ is selected from the group consisting of hydrogen; hydroxy; $C_{1-16}$ alkyl; $C_{1-16}$ alkenyl; $C_{1-16}$ alkynyl; $C_{1-16}$ alkoxy; $C_{1-16}$ acyl; halogen; and $C_{2-16}$ ester.

W is a saccharide.

said process comprising the steps of step 1) oxidyzing a protected isochroman of formula (5) with an oxidant (a)

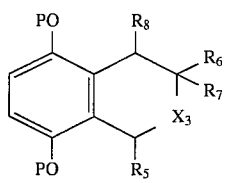

wherein

P is an oxygen protecting group; and $R_5$, $R_6$, $R_7$, $R_8$, and $X_3$ are as defined above;

to yield a dioxoisochroman compound of formula (6)

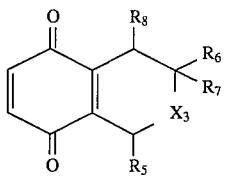

wherein $R_5$, $R_6$, $R_7$, $R_8$, and $X_3$ are as defined above;

step 2) cyclo-adding said dioxoisochroman of formula (6) with a diene of formula (3a) or (3b)

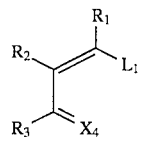

or

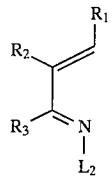

wherein $R_1$, $R_2$, $R_3$ and $X_4$ are as defined above;

each one of $L_1$; and $L_2$ is independently a leaving group;

to yield a heteronaphthoquinone of formula (4)

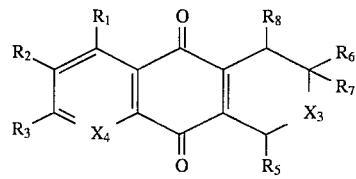

wherein $R_1$, $R_2$, $R_3$, $R_5$, $R_6$, $R_7$, $R_8$, $X_3$, and $X_4$ are as defined above;

step 3) optionally coupling said heteronaphthoquinone of formula (4) at position $R_5$, wherein $R_5$ is —OH, with W' wherein W' is an activated precursor of W; and W is as defined above;

in the presence of a coupling agent (b) to yield a coupled heteronaphtoquinone of formula (8)

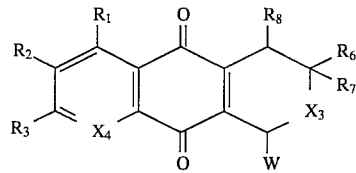

wherein; $R_1$, $R_2$, $R_3$, $R_6$, $R_7$, $R_8$, $X_3$, $X_4$, and W are as defined above;

if z is a double bond; said process further comprising the step of step 4) optionally converting the coupled heteronaphtoquinone of formula (8) or the heteronaphthoquinone of formula (4) to an insaturated coupled heteronaphtoquinone of formula (8a) or an insaturated heteronaphthoquinone of formula (4a)

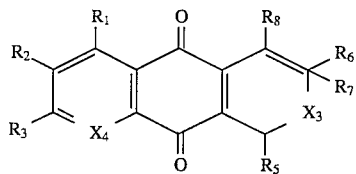

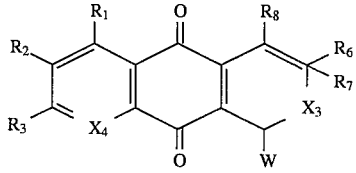

wherein;

$R_1$, $R_2$, $R_3$, $R_5$, $R_6$, $R_7$, $R_8$, $X_3$, $X_4$, and W are as defined above, with the proviso that only one of $R_6$ or $R_7$ is present; by air-oxydizing said coupled heteronaphtoquinone of formula (8) or the heteronaphthoquinone of formula (4) with an appropriate organic or inorganic base or a fluoride salt (h) to yield to said insaturated coupled heteronaphtoquinone of formula (8a) or insaturated heteronaphtoquinone of formula (4a).

Preferably, the organic or inorganic (h) is a non-nucleophilic base like sodium hydroxide or triethylamine.

More preferably, the organic or inorganic (h) is sodium hydroxide.

In a preferred embodiment of the fourth aspect of the invention there is provided a process wherein;
$X_3$ is preferably O or S.
$X_3$ is more preferably O.
$X_4$ is preferably CQ or N.
$X_4$ is more preferably CQ.
$R_1$, $R_2$, $R_3$ and Q are preferably each independently selected from the group consisting of hydrogen; hydroxy; $C_{1-16}$ alkyl; $C_{1-16}$ alkoxy; $C_{6-16}$ aryl; and halogen.
$R_1$, $R_2$, $R_3$ and Q are more preferably each independently selected from the group consisting of hydrogen; hydroxy; $C_{1-6}$ alkyl; $C_{1-6}$ alkoxy; $C_{6-12}$ aryl; and halogen.
$R_1$, $R_2$, $R_3$ and Q are most preferably hydrogen.
$R_5$ is preferably selected from the group consisting of hydrogen; hydroxy; amino; amido; and morpholino. $R_5$ is more preferably selected from the group consisting of hydrogen; hydroxy; prolyl; seryl; leucyl;

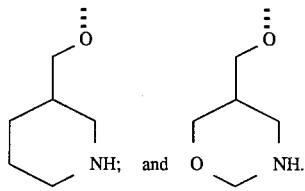

W is preferably a saccharide of formula (30):

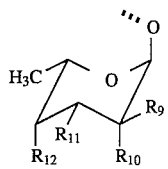

wherein;

$R_9$; $R_{10}$; $R_{11}$; and $R_{12}$ are independently selected from the group consisting of hydrogen; hydroxy; CN; $C_{1-16}$ alkyl; $C_{1-16}$ alkenyl; $C_{1-16}$ alkynyl; $C_{1-16}$ alkoxy; $C_{1-16}$ acyl; amino; amido; $C_{2-16}$ ester; and halogen.

$R_6$ is preferably selected from the group consisting of hydrogen; hydroxy; CN; $C_{1-16}$ alkyl; $C_{1-16}$ alkenyl; $C_{1-16}$ alkynyl; $C_{1-16}$ alkoxy; $C_{6-16}$ aryl; $C_{7-16}$ aralkyl; $C_{6-16}$ aryloxy; $C_{1-16}$ acyl; amino; amido; $C_{2-16}$ ester; azole; and halogen.

$R_6$ is more preferably selected from the group consisting of $C_{1-6}$ alkyl; $C_{1-6}$ alkenyl; $C_{1-6}$ alkynyl; $C_{1-6}$ alkoxy; $C_{1-6}$ acyl; amido; thiol; azole and $C_{2-6}$ ester.

$R_6$ is most preferably selected from the group consisting of $C_{1-6}$ acyl; amido; and $C_{2-6}$ ester.

In a further preferred embodiment, $R_6$ is acetyl.

$R_7$ is preferably selected from the group consisting of hydrogen; hydroxy; $C_{1-16}$ alkyl; $C_{1-16}$ alkenyl; $C_{1-16}$ alkynyl; $C_{1-16}$ alkoxy; and $C_{2-16}$ ester.

$R_7$ is more preferably selected from the group consisting of hydrogen; hydroxy; $C_{1-6}$ alkyl; $C_{1-6}$ alkoxy; and $C_{2-6}$ ester.

$R_7$ is most preferably hydrogen.

$R_8$ is preferably selected from the group consisting of hydrogen; hydroxy; $C_{1-16}$ alkyl; $C_{1-16}$ alkenyl; $C_{1-16}$ alkynyl; $C_{1-16}$ alkoxy; and halogen.

$R_8$ is more preferably selected from the group consisting of hydrogen; hydroxy; $C_{1-6}$ alkyl; $C_{1-6}$ alkoxy; and halogen.

$R_8$ is most preferably selected from the group consisting of hydrogen; hydroxy; and $C_{1-6}$ alkyl.

In a further prefered embodiment, $R_8$ is hydrogen or hydroxy.

$L_1$ is preferably a $C_{1-6}$ acyl.
$L_2$ is preferably $N(C_{1-6}alkyl)_2$.

In a fifth aspect of the present invention, there is provided a process comprising:

step 1) coupling the protected isochroman of formula (5), wherein $R_5$ is H, with W' wherein W' is as defined above;

in the presence of a coupling agent (c) to yield a coupled protected isochroman of formula (11)

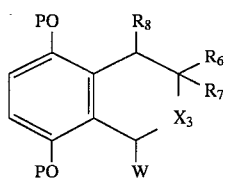

wherein P, $R_6$, $R_7$, $R_8$, W, and $X_3$ are as defined above;

step 2) oxidating the coupled protected isochroman of formula (11) with an oxydating agent (a) to yield a coupled dioxoisochroman of formula (12)

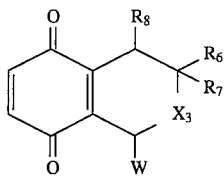

wherein; $R_6$, $R_7$, $R_8$, W, and $X_3$ are as defined above;

step 3) cyclo-adding coupled dioxoisochroman of formula (12) with a diene of formula (3a) or (3b)

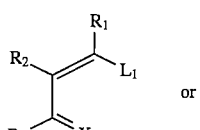

or

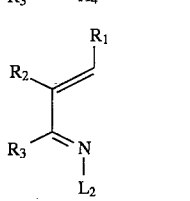

wherein $R_1$, $R_2$, $R_3$, $X_4$, $L_1$, and $L_2$ are as defined above; to yield the coupled napthoquinone of formula (8)

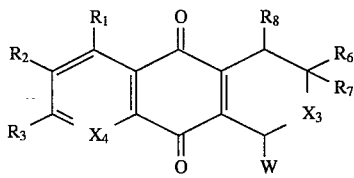

wherein; $R_1$, $R_2$, $R_3$, $R_6$, $R_7$, $R_8$, W, $X_3$, and $X_4$ are as defined above.

In a preferred embodiment of the fifth aspect of the invention there is provided a process wherein;

W' is preferably a saccharide precursor of formula (33)

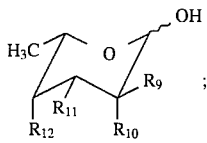

W is preferably a saccharide of formula (30):

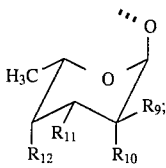

wherein;

$R_9$; $R_{10}$; $R_{11}$; and $R_{12}$ are independently selected from the group consisting of hydrogen; hydroxy; CN; $C_{1-16}$ alkyl; $C_{1-16}$ alkenyl; $C_{1-16}$ alkynyl; $C_{1-16}$ alkoxy; $C_{1-16}$ acyl; amino; amido; $C_{2-16}$ ester; and halogen.

$R_9$; $R_{10}$; $R_{11}$; and $R_{12}$ are preferably independently selected from the group consisting of hydrogen; hydroxy; $C_{1-6}$ alkyl; $C_{1-6}$ alkenyl; $C_{1-6}$ alkynyl; $C_{1-6}$ alkoxy; $C_{1-6}$ acyl; $C_{2-6}$ ester; amino; amido; and halogen.

$R_9$ is more preferably selected from the group consisting of hydrogen; hydroxy; and $C_{1-6}$ alkyl.

$R_9$ is most preferably hydrogen.

$R_{10}$ is more preferably selected from the group consisting of hydrogen; $C_{1-6}$ alkyl; $C_{1-6}$ acyl; amino; halogen; and hydroxy.

$R_{10}$ is most preferably selected from the group consisting of hydrogen; $C_{1-6}$ acyl; halogen; and hydroxy.

$R_{11}$ and $R_{12}$ are more preferably independently selected from the group consisting of hydrogen; $C_{1-6}$ alkyl; $C_{1-6}$ acyl; $C_{2-6}$ ester; halogen; hydroxy; and amino.

$R_{11}$ is most preferably selected from the group consisting of hydrogen; $C_{1-6}$ alkyl; $C_{1-6}$ acyl; hydroxy; and amino.

$R_{12}$ is most preferably selected from the group consisting of $C_{1-6}$ acyl; $C_{2-6}$ ester; halogen; hydroxy; and amino.

$R_6$ is preferably selected from the group consisting of hydrogen; $C_{1-16}$ alkyl; $C_{1-16}$ alkenyl; $C_{1-16}$ alkynyl; $C_{1-16}$ alkoxy; $C_{1-16}$ acyl; $C_{6-16}$ aryl; $C_{6-16}$ aryloxy; amino; halogen; azole; phosphono; thiol; and $C_{2-6}$ ester.

$R_6$ is more preferably selected from the group consisting of hydrogen; $C_{1-6}$ alkyl; $C_{1-6}$ alkenyl; $C_{1-6}$ alkynyl; $C_{1-6}$ alkoxy; $C_{1-6}$ acyl; amido; $C_{6-12}$ aryl; $C_{6-12}$ aryloxy; halogen; phosphono; azole; and $C_{2-6}$ ester.

$R_6$ is most preferably selected from the group consisting of hydrogen; $C_{1-6}$ acyl; amido; and $C_{2-6}$ ester.

In a further preferred embodiment, $R_6$ is acetyl.

$R_7$ is preferably selected from the group consisting of hydrogen; $C_{1-16}$ alkyl; and $C_{1-16}$ alkoxy.

$R_7$ is more preferably selected from the group consisting of hydrogen; $C_{1-6}$ alkyl; and $C_{1-6}$ alkoxy.

$R_7$ is most preferably hydrogen.

$R_8$ is preferably selected from the group consisting of hydrogen; hydroxy; and $C_{1-16}$ alkyl.

$R_8$ is more preferably selected from the group consisting of hydrogen; hydroxy; and $C_{1-6}$ alkyl.

$R_8$ is most preferably hydrogen or hydroxy.

$R_1$, $R_2$, $R_3$ and Q are preferably hydrogen.

$X_3$ is preferably O or S.

$X_3$ is more preferably O.

Each oxygen protecting group P is preferably independently a $C_{1-6}$ alkyl.

Each oxygen protecting group P is more preferably $CH_3$.

Said coupling agent (c) is preferably 2,3 dichloro-5,6-dicyano-1,4-benzoquinone.

Said oxydating agent (a) is preferably ceric ammonium nitrate or silver oxide.

Said oxydating agent (a) is more preferably ceric ammonium nitrate.

In a sixth aspect of this invention, there is provided a a process comprising the steps of step 1) coupling the dioxoisochroman of formula (6),

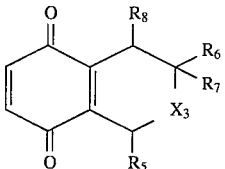

wherein $R_5$ is —OH, with W' wherein W' is as defined above, in the presence of a coupling agent (b) to yield a coupled dioxoisochroman of the formula (12)

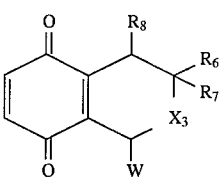

wherein $R_6$, $R_7$, $R_8$, W, and $X_3$ are as defined above step 2) cycloadding said a coupled dioxoisochroman of formula (12) with a diene of formula (3a) or (3b) in a solvent (b)

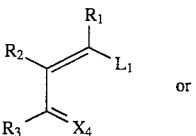

or

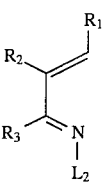

wherein $R_1$, $R_2$, $R_3$, $X_4$, $L_1$; and $L_2$ are as defined above, to yield a coupled napthoquinone of formula (8)

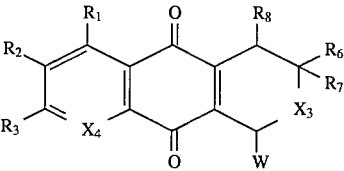

wherein; $R_1$, $R_2$, $R_3$, $R_6$, $R_7$, $R_8$, W, $X_3$, and $X_4$ are as defined above.

In a preferred embodiment of the sixth aspect of this invention, there is provided a process wherein;

W' is a saccharide precursor of formula (34a) or (34b)

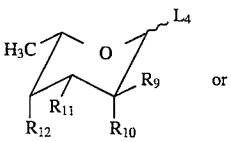

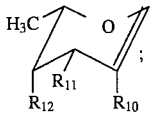

W is a saccharide of formula (30):

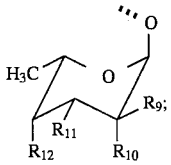

wherein;

$R_9$; $R_{10}$; $R_{11}$; and $R_{12}$ are independently selected from the group consisting of hydrogen; hydroxy; CN; $C_{1-16}$ alkyl; $C_{1-16}$ alkenyl; $C_{1-16}$ alkynyl; $C_{1-16}$ alkoxy; $C_{1-16}$ acyl; amino; amido; $C_{2-16}$ ester; and halogen.

$R_9$; $R_{10}$; $R_{11}$; and $R_{12}$ are preferably independently selected from the group consisting of hydrogen; hydroxy; $C_{1-6}$ alkyl; $C_{1-6}$ alkenyl; $C_{1-6}$ alkynyl; $C_{1-6}$ alkoxy; $C_{1-6}$ acyl; $C_{2-6}$ ester; amino; amido; and halogen.

$R_9$ is more preferably selected from the group consisting of hydrogen; hydroxy; and $C_{1-6}$ alkyl.

$R_9$ is most preferably hydrogen.

$R_{10}$ is more preferably selected from the group consisting of hydrogen; $C_{1-6}$ alkyl; $C_{1-6}$ acyl; amino; halogen; and hydroxy.

$R_{10}$ is most preferably selected from the group consisting of hydrogen; $C_{1-6}$ acyl; halogen; and hydroxy.

In a more prefered embodiment, $R_{11}$ and $R_{12}$ are independently selected from the group consisting of hydrogen; $C_{1-6}$ alkyl; $C_{1-6}$ acyl; $C_{2-6}$ ester; halogen; hydroxy; and; amino.

$R_{11}$ is most preferably selected from the group consisting of hydrogen; $C_{1-6}$ alkyl; $C_{1-6}$ acyl; hydroxy and; amino.

$R_{12}$ is most preferably selected from the group consisting of $C_{1-6}$ acyl; $C_{2-6}$ ester; halogen; hydroxy; and amino.

$R_6$ is preferably selected from the group consisting of hydrogen; $C_{1-6}$ acyl; $C_{1-16}$ alkyl; $C_{1-16}$ alkenyl; $C_{1-16}$ alkynyl; $C_{1-16}$ alkoxy; $C_{1-16}$ acyl; $C_{6-16}$ aryl; $C_{6-16}$ aryloxy; amino; halogen;azole; phosphono; thiol; and $C_{2-6}$ ester.

$R_6$ is more preferably selected from the group consisting of hydrogen; $C_{1-6}$ alkyl; $C_{1-6}$ alkenyl; $C_{1-6}$ alkynyl; $C_{1-6}$ alkoxy; $C_{1-6}$ acyl; $C_{6-12}$ aryl; $C_{6-12}$ aryloxy; amido; halogen; azole; phosphono; and $C_{2-6}$ ester.

$R_6$ is most preferably selected from the group consisting of hydrogen; $C_{1-6}$ acyl; amido; and $C_{2-6}$ ester.

In a further most preferred embodiemnt, $R_6$ is acetyl.

$R_7$ is preferably selected from the group consisting of hydrogen; $C_{1-16}$ alkyl; and $C_{1-16}$ alkoxy.

$R_7$ is more preferably selected from the group consisting of hydrogen; $C_{1-6}$ alkyl; and $C_{1-6}$ alkoxy.

$R_7$ is most preferably hydrogen.

$R_8$ is preferably selected from the group consisting of hydrogen; hydroxy;and $C_{1-16}$ alkyl.

$R_8$ is more preferably selected from the group consisting of hydrogen; hydroxy;and $C_{1-6}$ alkyl.

$R_8$ is most preferably hydrogen or hydroxy.

$R_1$, $R_2$, $R_3$ and Q are preferably hydrogen.

$X_3$ is preferably O or S.

$X_3$ is more preferably O.

$L_4$ is preferably selected from the group consisting of I; Cl; Br; tosyl; benzoyl; p-nitrobenzyl; $O(C_{1-6}$ alkyl); and $O(C_{1-6}$ acyl).

$L_4$ is more preferably selected from the group consisting of I; Cl; and Br.

Said coupling agent (b) is preferably a Lewis acid.

Said coupling agent (b) is more preferably trimethyl silyl triflate.

The tricyclic compounds of formula (1) coupled heteronaphtoquinone of formula (8); heteronaphthoquinone of formula (4); insaturated coupled heteronaphtoquinone of formula (8a); and insaturated heteronaphthoquinone of formula (4a) produced by the process oh this invention include:

Monofluoromethyl (5,10-dioxo-3,4,5,10-tetrahydronaphtho [2,3-C]pyran-3-yl) ketone;

(1'S,1S,3R)-Methyl (5,10-dioxo-1-(2',3',6'-trideoxy-3'-trifluoroacetamido-4'-O-p-nitrobenzoyl-L-lyxohexo-pyranose)-3,4,5,10-tetrahydronaphtho[2,3-C]pyran-3-yl) ketone;

(1'S,1R,3S)-Methyl (5,10-dioxo-1-(2',3',6'-trideoxy-3'-trifluoroacetamido-4'-O-p-nitrobenzoyl-L-lyxohexo-pyranose)-7-hydroxy-3,4,5,10-tetrahydronaphtho[2,3-C]pyran-3-yl) ketone;

(1'S,1S,3R)-Methyl (5,10-dioxo-1-(2',3',6'-trideoxy-3'-trifluoroacetamido-4'-O-p-nitrobenzoyl-L-lyxohexo-pyranose)-7-hydroxy-3,4,5,10-tetrahydronaphtho[2,3-C]pyran-3-yl) ketone;

2-[4,-Hydroxy-1',2'-dioxo-3'-cyclobutenoxy]methyl-(5,10-dioxo-3,4,5,10-tetrahydronaphtho[2,3-C]pyran-3-yl) ketone;

Bromomethyl (5,10-dioxo-5,10-dihydronaphtho[2,3-C]pyran-3 -yl) Ketone;

2-[4'-Hydroxy-1',2'-dioxo-3'-cyclobutenoxy]methyl (5,10-dioxo-3,4,5,10-tetrahydro[2,3-C]pyran-3-yl) ketone;

(1'S,1R,3S) and (1'S,1S,3R)-Bromomethyl (5,10-dioxo-1-(2',3',6'-trideoxy-4'-O-P-nitrobenzoyl-3'-trifluoro acetamido-L-lyxohexopyranose)-(3,4,5,10-tetrahydronaphtho[2, 3-C]pyran-3-yl) ketone;

(1'S,1R,3S) and (1'S,1S,3R)-2-[4'-hydroxy-1',2'-dioxo-3'-cyclobutenoxy]methyl (5,10-dioxo-1-[2",3",6"-trideoxy-4"-O-p-nitrobenzoyl-3"-trifluoroacetamido-L-lyxohexopyranose]-3,4,5,10-tetrahydronaphtho[2,3,c]pyran-3-yl) ketone;

(1'-S, 1-R, 3-S)-1-(2'-3'-6'-trideoxy-4'-p-nitrobenzoyl-3'-trifluoroacetamido-L-lyxohexopyranose)-3-(2-bromo-acetyl)-5,10-dioxo-3,4,5,10-tetrahydro-1H-naphtho-(2,3-c)-pyran;

(1'S,1-R,3-S)-1-(2',3',6'-trideoxy-4'-p-nitrobenzoyl-3'-trifluoroacetamido-L-lyxohexopyranose)-3-(2-aza-3-aminothiazolyl)-5,10-dioxo-3,4,5,10-tetrahydro-1H-naphtho-(2,3-c)pyran;

(1'S,1-R,3-S)-1-(2',3',6'-trideoxy-3'-trifluoroacetamido-4'-p-nitrobenzoyl-L-lyxohexopyranose)-3-(2-aza-3-acetamidothiazolyl)-5,10-dioxo-3,4,5,10-tetrahydro-1H-naphtho-[2,3-c]-pyran;

(1'-S,1-R,3-S)-1-(2',3',6'-trideoxy-3'-trifluoro acetamido-L-lyxohexopyranose)-3-(2-aza-3-acetamido thiazolyl)-5,10-dioxo-3,4,5,10-tetrahydro-1H-naphtho-[2,3-c]-pyran;

(1'-S,1-R,3-S)-1-(2',3',6'-trideoxy-3'-trifluoro acetamido-L-lyxohexopyranose)-3-(2-aza-3-aminothiazolyl)-5, 0-dioxo-3,4,5,10-tetrahydro-1H-naphtho-[2,3-C]pyran;

(1'-S,1-S,3-R)-1-(2',3'-6'-trideoxy-4'-p-nitrobenzoyl-3'-trifluoro-acetamido-L-lyxohexopyranose)-3-(2-bromoacetyl)-5,10-dioxo-3,4,5,10-tetrahydro-1H-naphtho-[2,3-c]-pyran;

(1'-S,1-S,3-R)-1-(2',3'-6'-trideoxy-4'-O-p-nitrobenzoyl-3'-trifluoroacetamido-L-lyxohexopyranose)-3-(2-aza-3-acetamido)-5,10-dioxo-3,4,5,10-tetrahydro-1H-naphtho-[2,3-c]-pyran;

(1'S,1S,3R) and (1'S,1R,3S) methyl (1-[2',3',6'-trideoxy-3'-trifluoroacetamido-4'-O-p-nitrobenzoyl-L-lyxohexo-pyranose]-5,10-dioxo-3,4,5,10-tetrahydro-7-methyl-9-aza naphtho[2,3-c]pyran-3-yl ketone;

(1'S,1S,3R) and (1'S,1R,3S) methyl-1-(2',3',6'-trideoxy-3'-trifluoroacetamido-4'-hydroxy-L-lyxohexopyranose)-5,10- dioxo-3,4,5,10-tetrahydro-7-methyl-O-azanaphtho[2,3-c]pyran-3-yl ketone;

Trans-3-aceto-1-methoxy-1,2,3,4-tetrahydro-(2-sulfur)anthracene-5,10-dione and cis-3-aceto-1-methoxy-1,2,3,4-tetrahydro-(2-sulfur)anthracene-5,10-dione;

cis-3-aceto-1-methoxy-1,2,3,4-tetrahydro-(2-sulfur) anthracene-5,10-dione and trans-3-aceto-1-methoxy-1,2,3,4-tetrahydro-(2-sulfur) anthracene-5,10-dione;

Methyl (1-methoxy-5,10-dioxo-3,4,5,10-tetrahydro-1H-naphtho[2,3-c]pyran-3-yl) formate;

Methyl (1-methoxy-5,10-dioxo-5,10-dihydro-1H-naphtho [2,3-c]pyran-3-yl) formate;

Methyl (1-methoxy-5,10-dioxo-5,10-dihydro-1H-naphtho [2,3-c]pyran-3-yl) formate.;

1-Methoxy-5,10-dioxo-5,10-dihydro-1H-naphtho[2,3-c]pyran-3-carboxylic acid;

1-Methoxy-5,10-dioxo-5,10-dihydro-1H-naphtho[2,3-c]pyran-3-[N-(3-dimethylamino-propyl)carboxamide];

(1S, 2'S, 3R) and (1R, 2'S, 3S)-methyl-(1-[O-N-BOC-serine methyl ester]-5,10-dioxo-3,4,5,10-tetrahydro-1-H-naphtho [2,3-C]pyran-3-yl) ketone.;

(1'S, 1S, 3R) and (1'S, 1R, 3S)-5,10-dioxo-3-cyano-1-(2',3',6',-trideoxy-3'-trifluoroacetamido-4'-O-p-nitrobenzoyl-L-lyxohexopyranose)-3,4,5,10-tetrahydro-1-H-naphtho-[2,3-c]pyran;

5,10-Dioxo-3-(propane-2-one)-1-(2',3',6'-trideoxy-3'-trifluoroacetamido-4'-O-p-nitrobenzoyl-L-lyxohexopyranose)-3,4,5,10-tetrahydro-1H-naphtho-[2,3-c]pyran;

(1'S, 1R, 3S)-5,10-dioxo-3-methoxymethyl-1-(2',3',6'-trideoxy-3'-trifluoroacetamido-4'-O-p-nitrobenzoyl-L-lyxohexo-pyranose)-3,4,5,10-tetrahydro-1H-naphtho-[2,3-c]pyran (1'S, 1R, 3R)-5,10-dioxo-3-ethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c]pyran;

(1'S, 1S, 3S)-5,10-dioxo-3-ethyl-1-(2',3',6'-trideoxy-3'-trifluoroacetamido-4'-O-p-nitrobenzoyl-L-lyxohexo-pyranose)-3,4,5,10-tetrahydro-1H-naphtho-[2,3-c]-pyran;

(1'S, 1S, 3R)-5,10-dioxo-3-isopropyl-1-(2',3',6'-trideoxy-3'-trifluoroacetamido-4'-O-p-nitrobenzoyl-L-lyxohexo-pyranose)-3,4,5,10-tetrahydro-1H-naphtho-[2,3-c]-pyran;

(1'S, 1R, 3S)-5,10-dioxo-3-isopropenyl-1-(2',3',6'-trideoxy-3'-trifluoroacetamido-4'-O-p-nitrobenzoyl-L-lyxohexopyranose) 3,4,5,10-tetrahydro-1H-naphtho-[2,3-2]-pyran;

(1'S, 1S, 3R)-5,10-dioxo-3-isopropenyl-1-(2',3',6'-trideoxy-3'-trifluoroacetamido-4"-O-p-nitrobenzoyl-L-lyxohexopyranose) 3,4,5,10-tetrahydro-1H-naphtho-[2,3-c]-pyran;

(1'S, 1R, 3S)-5,10-dioxo-3-methoxycarbonyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c]-pyran;

(1'S, 1R, 3S)-isopropyl-[1-(2',3',6'-trideoxy-3'-trifluoroacetamido-4'-O-p-nitrobenzoyl-L-lyxohexopyranose)-5,10-dioxo-3,4,5,10-tetrahydro-1H-naphtho-[2,3-c]-pyranyl]-ketone;

(1'S, 1R, 3S), and (1'S, 1S, 3R)-5,10-dioxo-3-isopropoxycarbonyl-1-(2',3',6'-trideoxy-3',trifluoroacetamido-4'-O-p-nitrobenzoyl-L-lyxohexopyranose)-3,4,5,10-tetrahydro-1H-naphtho-[2,3-c]-pyran;

(1'S, 1S)-5,10-dioxo-3,3-dimethoxymethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c]pyran;

(1'S, 1R, 4R)-5,10-dioxo-4-ethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c]-pyran;

(1'S, 1R, 3S)-5,10-dioxo-3-phenyloxymethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c]pyran;

(1'S,1S,3S) and (1'-S,1-R,3-R)-3-([2',3',6'-trideoxy-3'-trifluoroacetamidoo-4'-paramitrobenzoyl-L-lyxohexopyranose)-5,10-dioxo-3,4,5,10-tetrahydronaphtho-[2,3-c]-pyran-3-yl)-propene;

(1'R, 1R, 3S)-3-aceto-5,10-dioxo-1-(2-deoxy-2-chloroethylureido-4,6-benzylidene-D-glucopyranose)-3,4,5,10-tetrahydro-1H-naphtho-[2,3-C]pyran;

(1R,3S) and (1S,3R)-3-Aceto-5,10-dioxo-1 (4-chloroethylureido cyclohexyloxy)-3,4,5,10-tetrahydro-1H-naphtho-(2,3-c)-pyran;

(3-N-imidazolylpropyl)-1-methoxy-5,10-dioxo-5,10-dihydro-1H-naphtho-[2,3-c]-pyran-3-carboxamide;

(1'S, 1S, 3R)-1-(4'-p-nitrobenzoyl-3'-trifluoroacetamido-2',3',6'-trideoxy-lyxohexopyranose)-3-methoxy-carbonyl-3-methyl-5,10-dioxo-4,5,10-trihydro-1H-naphtho-[2,3-c]-pyran;

(1'S, 1R, 3S)-1-(4'-p-nitrobenzoyl-3-trifluoroacetamido-2',3',6'-trideoxy-L-lyxohexopyranose)-3-(5"-tosyl-oxazolyl)-5,10-dioxo-3,4,5,10-tetrahydro-1H-naphtho-[2,3-c]-pyran;

(1'S, 1S, 3R)-1-(4'-p-nitrobenzoyl-3-trifluoroacetamido-2',3',6'-trideoxy-L-lyxohexopyranose)-3-(5"-tosyl-oxazolyl)-5,10-dioxo-3,4,5,10-tetrahydro-1H-naphtho-[2,3-c]-pyran;

1-methoxy-3-acetyl-5,10-dioxo-3,4,5,10-tetrahydro-1H-naphtho-[2,3-c]-pyran;

3-bromoacethyl-1-methoxy-5,10-dioxo-3,4,5,10-tetrahydro-1H-naphtho-[2,3-c]-pyran;

(1'S, 1R, 3S)-1-(4'-p-nitrobenzoyl-3'-trifluoroacetamido-2',3',6'-trideoxy-lyxohexopyranose)-3-methoxy-carbonyl-3-methyl-5,10-dioxo-4,5,10-trihydro-1H-naphtho-[2,3-c]-pyran;

(1'S, 1S, 3S)-1-(4'-p-nitrobenzoyl-3'-trifluoroacetamido-2',3',6'-trideoxy-lyxohexopyranose)-3-methoxy-carbonyl-3-methyl-5,10-dioxo-4,5,10-trihydro-1H-naphtho -[2,3-c]-pyran;

(1'S,1S,3S)-1-(4'-p-nitrobenzoyl-3'-trifluoroacetamido-2',3',6'-trideoxy-L-lyxohexopyranose)-3-acetyl-5,10-dioxo-3,4,5,10-tetrahydro-1H-naphtho-[2,3-c]-thiopyran;

(1'S,1S,3S) and (1'S, 1S, 3R)-1-(4'-p-nitrobenzoyl-3'-trifluoroacetamido-2',3',6'-trideoxy-lyxohexopyranose)-3-acetyl-3-methyl-5,10-dioxo-4,5,10-trihydro-1H-naphtho-[2,3-c]-pyran;

(1'S,1R,3S)-1-(2',3',6'-trideoxy-4'-p-niprobenzoyl-3'-trifluoroacetamido-L-lyxohexo pyranose)-3-dimethyl phosphonoacetyl-5,10-dioxo-3,4,5,10-tetrahydro-1H-naphtho[2,3-c] -pyran;

(1'S,1S,3R)-methyl-(6 and 9-hydroxy-1-(2',3',6'-trideoxy-3'-trifluoroacetamido-4'-O-p-nitrobenzoyl-L-lyxohexopyranose)-5,10-dioxo-3,4,5,10-tetrahydro-1H-naphtho-[2,3-c]-pyran-3-yl) ketone;

3-aceto-5,10-dioxo-3,4,5,10-tetrahydro-1H-naphtho-[2,3-c] -pyran;

3-bromoacetyl-5,10-dioxo-3,4,5,10-tetrahydro-1H-naphtho-[2,3-c]-pyran;

Methyl (1-methoxy-5,10-dioxo-3,4,5,10-tetrahydro-1H-naphtho[2,3-c]pyran-3-yl) formate;

Methyl (1-methoxy-5,10-dioxo-5,10-dihydro-1H-naphtho [2,3-c]pyran-3-yl) formate;

Methyl (1-methoxy-5,10-dioxo-5,10-dihydro-1H-naphtho [2,3-c]pyran-3-yl) formate.;

1-Methoxy-5,10-dioxo-5,10-dihydro-1H-naphtho[2,3-c]pyran-3-carboxylic acid;

1-Methoxy-5,10-dioxo-5,10-dihydro-1H-naphtho[2,3-c]pyran-3-[N-(3-dimethylamino-propyl)carboxamide];

1-methoxy-3-methoxy carbonyl-5,10-dioxo-5,10-dihydro-1H-naphtho-[2,3-c]-pyran;

(3-N-imidazolylpropyl)-1-methoxy-5,10-dioxo-5,10-dihydro-1H-naphtho-[2,3-c]-pyran-3-carboxamide;

1-methoxy-3-[2-(N-morpholino) ethyl amino carbonyl]-5,10-dioxo-5,10-dihydro-1H-naphtho-[2,3-c]-pyran;

1-methoxy-3-[2-(N-morpholine) ethyl amino carbonyl]-5,10-dioxo-5,10-dihydro-1H-naphtho-[2,3-c]-pyran;

1-methoxy-3-[2-(2-pyridinyl) ethyl amino carbonyl]-5,10-dioxo-5,10-dihydro-1H-naphtho-[2,3 -c]-pyran;

1-methoxy-3-[2-(2-pyridinyl) ethyl amino carbonyl]-5,10-dioxo-5,10-dihydro-1H-naphtho-[2,3-c]-pyran hydrochloride;

1-methoxy-3-[(2-pyridinyl) methyl amino carbonyl]-3-methoxy-5,10-dioxo-5,10-dihydro-1H-naphtho-[2,3-c]-pyran hydrochloride salt;

1-methoxy-3-[2-(N-pyrrolidinyl) ethyl amino carbonyl]-5,10-dioxo-5,10-dihydro-1H-naphtho-[2,3-c]-pyran;

1-methoxy-3-[2-(N-pyrrolidinyl) ethyl amino carbonyl]-5,10-dioxo-5,10-dihydro-1H-naphtho-[2,3-c]-pyran hydrochloride salt;

1-methoxy-3-[(4-diethoxy) butyl amino carbonyl]-5,10-dioxo-5,10-dihydro-1H-naphtho-[2,3-c]-pyran;

1-methoxy-3-(3-hydroxy) propyl amino carbonyl-5,10-dioxo-5,10-dihydro-1H-naphtho-[2,3-c]-pyran;

1-propyl-3-methoxycarbonyl-5,10-dioxo-5,10-dihydro-1H-naphtho-[2,3-c]-pyran.;

1-propyl-3-carboxyl-5,10-dihydro-5,10-dioxo-1H-naphtho-[2,3-c]-pyran.;

1-propyl-3-(3-dimethyl amino propyl amino carbonyl)-5,10-dihydro-5,10-dioxo-1H-naphtho-[2,3-c]-pyran.;

2-(N-pyrrolidinyl) ethyl-(1-propyl-5,10-dioxo-5,10-dihydro-1H-naphtho-[2,3-c]-pyran-3)-carboxamide;

Methyl-1-methoxy-5,10-dioxo-3,4,5,10-tetrahydro-1H-naphtho[2,3-c]thiine-3-carboxylate;

1-methoxy-5,10-dioxo-5,10-dihydro-1H-naphtho[2,3-c]thiine-3-carboxylic acid;

Methyl (5,10-dioxo-3,4,5,10-tetrahydronaphtho[2,3- C]pyran-3-yl) ketone;

(1'S,1R,3S)-Methyl (5,10-dioxo-1-(2',3',6'-trideoxy-3'-trifluoroacetamido-4'-hydroxy-L-lyxohexopyranose)-3,4,5,10-tetrahydronaphtho[2,3-C]pyran-3-yl) ketone BCH-1184;

(1'S,1S,3R)-Methyl (5,10-dioxo-1-(2',3',6'-trideoxy-3'-trifluoroacetamido-4'-hydroxy-L-lyxohexopyranose)-3,4,5,10-tetrahydronaphtho[2,3-C]pyran-3-yl) ketone BCH-1146;

(1'S,1R,3S)-Methyl (5,10-dioxo-1- (2',3',6'-trideoxy-3'-trifluoroacetamido-L-lyxohexopyranose)-7-hydroxy-3,4,5,10-tetrahydro[2,3-C]pyran-3-yl) ketone BCH-1181;

(1'S,1S,3R)-Methyl (5,10-dioxo-1-(2',3',6'-trideoxy-3'-trifluoroacetamido-L-lyxohexopyranose)-7-hydroxy-3,4,5,10-tetrahydro[2,3-C]pyran-3-yl) ketone BCH-1180;

(1'-S, 1-R, 3-S) and (1'-S, 1-S, 3-R)-3-cyano-1-[2',3',6'-trideoxy-3'-trifluoroacetamido-4'-hydroxy-L-lyxohexopyranose)-5,10-dioxo-3,4,5,10-tetrahydronaphtho-[2,3-C]pyran-3-yl BCH-1688;

(1'-S, 1-S, 3-R) and (1'-S, 1-R, 3-S)-methyl-(1-[2',3',4',6'tetradeoxy-3'-trifluoroacetamido-4'-O-methane-sulfonyl-L-lyxohexopyranose)-5,10-dioxo-3,4,5,10 tetrahydronaphtho-[2,3-c]-pyran-3-yl) ketone BCH-2095;

(1'-S, 1-S, 3-R)-methyl-(1-[2',3',4',6'tetradeoxy-3'-trifluoroacetamido-4'-O-(2-bromo-acetyl)-L-lyxopyranose]-5,10-dioxo-3,4,5,10 tetrahydronaphtho-[2,3-c]pyran-3-yl) ketone BCH-2105;

(1'-S, 1-R, 3-S)-methyl-(1-[2',3',4',6'tetradeoxy-3'-methoxy-4'-O-methanesulfonyl-L-lyxohexopyranose)-5,10-dioxo-3, 4,5,10 tetrahydronaphtho-[2,3-c]pyran-3-yl) ketone BCH-2070;

(1'-S, 1'S, 3-R)-methyl-(1-[2',3',4',6'tetradeoxy-3'-methoxy-4'-O-methanesulfonyl-L-lyxohexopyranose)-5,10-dioxo-3,4,5,10 tetrahydronaphtho-[2,3-c]pyran-3-yl) ketone BCH-2072;

(1-S, 3-R) and (1-R, 3-S)-methyl-(1-(1-methoxy-4-oxocyclohexyloxy)-5,10-dioxo-3,4,5,10 tetrahydronaphtho-[2,3-c]pyran-3-yl) ketone BCH-2096;

(1'-S, 1-S, 3-R) and (1'-S, 1-R, 3-S)-1-(6-hydroxy-1-(2',3',6'-trideoxy-3'-trifluoroacetamido-4-hydroxy-L-lyxopyranose)-5,10-dioxo-3,4,5,10 tetrahydronaphtho-[2,3-c]pyran-3-yl) propane-2-one BCH-2098;

3,3-bis-(methoxycarbonyl)-5,10-dioxo-3,4,5,10-tetrahydro-1H-naphtho-[2,3-c]-pyran (BCH-1665);

(1'S, 1R, 3S)-5,10-dioxo-3-methoxymethyl-1-(2',3',6'-trideoxy-3'-trifluoroacetamido-L-lyxohexopyranose)-3,4,5,10-tetrahydro-1H-naphtho-[2,3-c]-pyran (BCH-1691);

(1'S, 1S, 3R)-5,10-dioxo-3-methoxymethyl-1-(2',3',6'-trideoxy-3'-trifluoroacetamido-L-lyxohexopyranose)-3,4,5,10-tetrahydro-1H-naphtho-[2,3-c]pyran (BCH-1693);

(1'S, 1R, 3R)-5,10-dioxo-3-ethyl-1-(2',3',6'-trideoxy-3'-trifluoroacetamido-L-lyxohexopyranose)-3,4,5,10-tetrahydro-1H-naphtho-[2,3-c]pyran (BCH-2026);

(1'S, 1S, 3S)-5,10-dioxo-3-ethyl-1-(2',3',6'-trideoxy-3'-trifluoroacetamido-L-lyxohexopyranose)-3,4,5,10-tetrahydro-1H-naphtho-[2,3-c]pyran (BCH-2020);

(1'S, 1S, 3S)-5,10-dioxo-3-ethyl-1-(2',3',6'-trideoxy-3'-amino-L-lyxohexopyranose)-3,4,5,10-tetrahydro-1H-naphtho-[2,3-c]-pyran (BCH-2021);

(1'S, 1R, 3S)-5,10-dioxo-3-isopropyl-1-(2',3',6'-trideoxy-3'-trifluoroacetamido-L-lyxohexopyranose)-3,4,5,10-tetrahydro-1H-naphtho-[2,3-c]-pyran (BCH-2053);

(1'S, 1S, 3R)-5,10-dioxo-3-isopropyl-1-(2',3',6'-trideoxy-3'-trifluoroacetamido-L-lyxohexopyranose)-3,4,5,10-tetrahydro-1H-naphtho-[2,3-c]-pyran (BCH-2052);

(1'S, 1R, 3S)-5,10-dioxo-3-isopropenyl-1-(2',3',6'-trideoxy-3'-trifluoroacetamido-L-lyxohexopyranose)-3,4,5,10-tetrahydro-1H-naphtho-[2,3-c]-pyran (BCH-2153);

(1'S, 1S, 3R)-5,10-dioxo-3-isopropenyl-1-(2',3',6'-trideoxy-3'-trifluoroacetamido-L-lyxohexopyranose)-3,4,5,10-tetrahydro-1H-naphtho-[2,3-c]-pyran (BCH-21-52);

(1'S, 1R, 3S)-5,10-dioxo-3-methoxycarbonyl-1-(2',3',6'-trideoxy-3'-trifluoroacetamido-L-lyxohexopyranose)-3,4,5,10-tetrahydro-1H-naphtho-[2,3-c]-pyrano (BCH-2128);

(1'S, 1R, 3S)-isopropyl-[1-(2',3',6'-trideoxy-3'-trifluoroacetamido-L-lyxohexopyranose)-5,10-dioxo-3,4,5,10-tetrahydro-1H-naphtho-[2,3-c]-pyranyl]-ketone (BCH-2112);

(1'S, 1R, 3S)-5,10-dioxo-3-isopropoxycarbonyl-1-(2',3',6'-trideoxy-3'-trifluoroacetamido-L-lyxohexopyranose)-3,4,5,10-tetrahydro-1H-naphtho-[2,3-c]-pyran (BCH-2122);

(1'S, 1S)-5,10-dioxo-3,3-dimethoxymethyl-1-(2',3',6'-trideoxy-3'-trifluoroacetamido-4'-O-p-nitrobenzoyl-L-lyxohexo-pyranose)-isochroman (BCH-1697);

(1'S, 1R, 4R)-5,10-dioxo-4-ethyl-1-(2',3',6'-trideoxy-3'-trifluoroacetamido-L-lyxohexopyranose)-3,4,5,10-tetrahydro-1H-naphtho-[2,3 -c ]pyran (BCH-2091);

(1'S, 1R, 3S)-5,10-dioxo-3-phenyloxymethyl-1-(2',3',6'-trideoxy-3'-trifluoroacetamido-L-lyxohexopyranose)-3,4,5,10-tetrahydro-1H-naphtho-[2,3-c]pyran (BCH-2032);

(1'S,1S,3S) and (1'S,1-R,3-R)-3-([2',3',6'-trideoxy-3'-trifluoroacetamido-4'-hydroxy-L-lyhohexopyranose]-5,10-dioxo-3,4,5,10-tetrahydronaphtho-[2,3-c]-pyran-3-yl)-propene (BCH-2031);

(1'-S,1-R,3-S)-methyl-(1-[2',3',6'-trideoxy-3'-trifluoroacetamido-4'-iodo-L-lyxohexopyranose]-5,10-dioxo-3,4,5,10-tetrahydronaphtho-[2,3-c]-pyran-3-yl)-ketone (BCH-1620);

(1'-S,1-R,3-S)-3-([2',3',6'-trideoxy-3'-trifluoroacetamido-4'-hydroxy-L-lyhohexopyranose]-5,10-dioxo-3,4,5,10-tetrahydronaphtho-[2,3-c]-pyran-3-yl)-propene (BCH-1649);

(1'-S,1-R,3-S,4a-S,10a-S)-methyl-(1-[2',3',4',6'-tetradeoxy-3'-methoxy-4'-O-methanesulfonyl-L-lyxohexopyranose)-

4a,10a-epoxy-5,10-dioxo-3,4,5,10-tetrahydronaphtho-[2,3-c]pyran-3-yl) ketone (BCH-2141);
(1S,3R,1'S,5'S,6'S) and (1R,3S,1'S,5'S,6'S)-methyl-(1-[4'trifluoroacetamido-5'-methyltetrahydropyranyl]-5,10-dioxo-3,4,5,10-tetrahydronaphthaleno-[2,3-c]pyran-3-yl) ketone (BCH-1673);
(1'S,1S,3R)-3(oximoethyl)-5,10-dioxo-1(2,3,6-trideoxy-3-trifluoroacetamido-L-lyxohexopyranose)-3,4,5,10-tetrahydro-1H-naphtho-[2,3-c]pyran (BCH-2101);
(1'S, 1R, 3S)-3(oximoethyl)-5,10-dioxo-1 (2,3,6-trideoxy-3-trifluoroacetamido-L-lyxohexopyranose)-3,4,5,10-tetrahydro-1H-naphtho-(2,3-c)-pyran (BCH-2115);
(1'S ,1S,3R)-3-(trifluoroacetamidoethyl)-5,10-dioxo-1-(2',3',6'-trideoxy-3',4'-dihydroxy-L-lyxohexopyranose)-3,4,5,10-tetrahydro-1H-naphtho-[2,3-c]-pyran (BCH-2018);
(1'R, 1R, 3S)-3-aceto-5,10-dioxo-1-(2-deoxy-2-chloroethylnitrosoureido-D-glucopyranose)-3,4,5,10-tetrahydro-1H-naphtho-[2,3-C]pyran (BCH-2038)
(1R,3S) and (1S,3R)-3-aceto-5,10-dioxo-1 (4-chloroethylnitrosoureido cyclohexyl-oxy)-3,4,5,10-tetrahydro-1H-naphtho-(2,3-c)-pyran (BCH-2114);
(1'S,1S,3R)-1-(3'-trifluoroacetamido-2',3',6'-trideoxy-lyxo-L-hexopyranose)-3-methoxycarbonyl-3-methyl-3,4,5,10-tetrahydro-5,10-dioxo-naphtho-[2,3-c]pyran (BCH-2076);
(1'S, 1R, 3S)-2',3',6'-trideoxy-3'-trifluoroacetamido-L-lyxohexopyranose-3-[5'-tosyloxazolyl]-5,10-dioxo-3,4,5,10-tetrahydro-1H-naphtho-[2,3-c]-pyran (BCH-2150);
(1'S, 1S, 3R)-2',3',6'-trideoxy-3'-trifluoroacetamido-L-lyxohexopyranose-3-[5'-tosyloxazolyl)]-5,10-dioxo-3,4,5,10-tetrahydro-1H-naphtho-[2,3-C]-pyran (BCH-2151);
(1'S, 1R, 3S)-1-(3'-trifluoroacetamido-2',3',6'-trideoxy-L-lyxohexopyranose)-5,10-dioxo-4,5,10-trihydro-1H-naphtho-[2,3-c]-pyran (BCH-2077);
(1'S, 1S, 3R)-1-(3'-trifluoroacetamido-2',3',6'-trideoxy-L-lyxohexopyranose)- 3-acetyl-3-methyl-5,10-dioxo-4,5,10-trihydro-1H-naphtho-[2,3-c]-pyran (BCH-2082);
(1'S,1S,3R)-1-(2',3',6'-trideoxy-3'-trifluoroacetamido-L-lyxohexopyranose)-3-dimethylphosphonoacetyl-5,10-dioxo-3,4,5-10-tetrahydro-1H-naphtho-[2,3-c]-pyran (BCH-1690);
(1'S, 1S, 3S)-1-(3'-trifluoroacetamido-2',3',6'-trideoxy-lyxohexopyranose)-3-methoxycarbonyl-3-methyl-5,10-dioxo-4,5,10-trihydro-1H-naphtho-[2,3-c]-pyran (BCH-2081);
(1'S,1S,3S)-1-(3'-trifluoroacetamido-2',3',6'-trideoxy-L-lyxohexopyranose)-5,10-dioxo-3,4,5,10-tetrahydro-1H-naphtho-[2,3-c]-thiopyran (BCH-2037.001);
(1'S,1R,3R)-1-(3'trifluoroacetamido-2',3',6'-trideoxy-lyxo-L-hexopyranose)-3-dimethoxyphosphonoacetyl-3,4,5,10-tetrahydro-5,10-dioxo-naphtho-[2,3-c]pyran (BCH-2127);
(1'S,1S,3S)-1-(3'-trifluoroacetamido-2',3',6'-trideoxy-lyxo-L-hexopyranose)-3-acetyl-3-methyl-3,4,5,10-tetrahydro-5,10-dioxo-1H-naphtho-[2,3-c]pyran (BCH-2090);
(1'S,1R,3S)-1-(3'-trifluoroacetamido-2',3',6'-trideoxy-lyxo-L-hexopyranose)-3-dimethoxyphosphonoacetyl-3,4,5,10-tetrahydro-5,10-dioxo-naphtho-[2,3-c]pyran (BCH-1689);
(1'S,1R,3S)-methyl-(1-[2',6'-dideoxy-3'-4'-dihydroxy-2'-iodo-L-lyxohexopyranose]-5,10-dioxo-3,4,5,10-tetrahydronaphtho[2,3-c]-pyran-3-yl) ketone (BCH-2015);
(1'S,1R,3S)-methyl-(1-[2',6'-dideoxy-3'-4'-diacetoxy-2'-iodo-L-lyxohexopyranose]-5,10-dioxo-3,4,5,10-tetrahydronaphtho[2,3-c]-pyran-3-yl) ketone (BCH-1666);
(1'S,1S,3R)-methyl-(1-[2',6'-dideoxy-3'-4'-diacetoxy-2'-iodo-L-lyxohexopyranose]-5,10-dioxo-3,4,5,10-tetrahydronaphtho[2,3-c]-pyran-3-yl) ketone (BCH-1667);
(1'S,1S,3R)-methyl-(1-[2',6'-dideoxy-3'-4'-dihydroxy-2'-iodo-L-lyxohexopyranose]-5,10-dioxo-3,4,5,10-tetrahydronaphtho[2,3-c]-pyran-3-yl)-ketone (BCH-2014);

(1'S,1R,3S)-methyl-(1-[2',6'-dideoxy-3',4'-diacetoxy-2'-bromo-L-lyxohexopyranose]-5,10-dioxo-3,4,5,10-tetrahydronaphtho-[2,3-c]-pyran-3-yl) ketone (BCH-2100);
(1'S,1R,3S)-methyl-(1-[2',3',6'-trideoxy-2'-iodo-3'-trifluoroacetamido-4'-hydroxy-L-lyxohexopyranose]-5,10-dioxo-3,4,5,10-tetrahydronaphtho-[2,3-c]-pyran-3-yl) ketone (BCH-2023);
(1'S,1S,3R)-methyl-(1-[2',3',6'-trideoxy-2'-iodo-3'-trifluoroacetamido-4'- hydroxy-L-lyxohexopyranose]-5,10-dioxo-3,4,5,10-tetrahydronaphtho-[2,3-c]-pyran-3-yl) ketone (BCH-2022);
(1'S,1R,1S) and (1'S,1S,3R)-methyl-(1-[2',6'-dideoxy-3',4'-diacetoxy-2'-iodo-L-arabino-hexopyranose]-5,10-dioxo-3,4,5,10-tetrahydronaphtho-[2,3-c]-pyran-3-yl) ketone (BCH-2065);
(1'S,1S,3R) and (1'S,1R,3S)-methyl-(1-[dideoxy-2',6'-dihydroxy-3',4'-L-lyxohexopyranose]-5,10-dioxo-3,4,5,10-tetrahydronaphtho-[2,3-c]-pyran-3-yl) ketone (BCH-2117);
(1'S,1S,3R) and (1'S,1R,3S)-methyl-(1-[dideoxy-2',6'-diacetoxy-3',4'-L-lyxohexopyranose]-5,10-dioxo-3,4,5,10-tetrahydronaphtho-[2,3-c]-pyran-3-yl) ketone (BCH-2118);
Methyl-(6-hydroxy-5,10-dioxo-3,4,5,10-tetrahydronaphtho-[2,3-c]-pyran-3-yl) ketone and methyl-(9-hydroxy-5,10-dioxo-3,4,5,10-tetrahydronaphtho-[2,3-c]-pyran-3-yl) ketone (BCH-2062);
(1'S,1S,3R)-methyl-(6 and 9-hydroxy-1-[2',3',6'-trideoxy-3'-trifluoroacetamido-4'-hydroxy-L-lyxohexopyranose]-5,10-dioxo-3,4,5,10-tetrahydronaphtho-[2,3-c]-pyran-3-yl-ketone (BCH-2078);
(1R,3S,1'S) and (1S,3R,1'S)-Methyl-(1-[2',3',4',6'-tetradeoxy-3',4'-bis-trifluoroacetamido-L-arabinohexopyranose]-5,10-dioxo-3,4,5,10-tetrahydronaphthaleno-[2,3-c] pyran-3-yl) ketone (BCH-2104 and BCH-2102);
(1S,3R,1'S)-Methyl-(1-[2',3',4',6'-tetradeoxy-3'-trifluoroacetamido-4'-bromo-L-lyxohexopyranose]-5,10-dioxo-3,4,5,10-tetrahydronaphthaleno-[2,3-c]pyran-3-yl) ketone (BCH-2047);
(1'-S,1-S,3-R)-1-(2',3',6'-trideoxy-3'-trifluoro acetamido-L-lyxohexopyranose)-3-(2-aza-3-acetamido-thiazolyl)-5,10-dioxo-3,4,5,10-tetrahydro-1H-naphtho-[2,3-c]-pyran (BCH-1198);
(1'S, 1S, 3S) and (1'S, 1R, 3R)-5,10-dioxo-3-ethyl-1-(2',3',4',6'-tetradeoxy-3',4'-diacetoxy-L-lyxohexo-pyranose)-3,4,5,10-tetrahydro-1H-naphto[2,3-C]pyran (BCH-1607);
(1'S,1S,3R)-methyl-(1-[2',6'-dideoxy-3',4'-diacetoxy-2'-bromo-L-lyxohexopyranose]-5,10-dioxo-3,4,5,10-tetrahydronaphtho-[2,3-c]-pyran-3-yl) ketone (BCH-2099);
(1'S, 2'R, 3'S, 5'R, 1S, 3R)-1-(3-trifluoroacetamido-2-hydroxy-1-methyl tetrahydropyran-5-yl)-methyl]-3-ethyl-5,10-dioxo-3,4,5,10-tetrahydro-1H-naphtho[2,3-C]pyran (BCH-2818);
(1'S, 2'R, 3'S, 5'R, 1R, 3S)-1-(3-trifluoroacetamido-2-hydroxy-1-methyl tetrahydropyran-5-yl)-methyl]-3-ethyl-5,10-dioxo-3,4,5,10-tetrahydro-1H-naphtho[2,3-C]pyran (BCH-2819);
(1'S,2'R,3'S,5'R,1R,3R)-1-(3-trifluoroacetamido-2-hydroxy-1-methyl tetrahydropyran-5-yl)methyl-3-methylketone-5,10-dioxo-3,4,5,10-tetrahydro-1H-naphtho[2,3-C]pyran. (BCH-2821);
(1'S,2'R,3'S,5'R,1S,3S)-1-(3-trifluoroacetamido-2-hydroxy-1-methyl tetrahydropyran-5-yl)methyl-3-methylketone-5,10-dioxo-3,4,5,10-tetrahydro-1H-naphtho[2,3-C]pyran. (BCH-2820);
(1'S,1R,3S)-Methyl (5,10-dioxo-1-(2',3',6'-trideoxy-3'-trifluoroacetamido-4'-hydroxy-L-lyxohexopyranose)-3,4,5,10-tetrahydronaphtho[2,3-C]pyran-3-yl) ketone BCH-1184;
(1'S,1S,3R)-Methyl (5,10-dioxo-1-(2',3',6'-trideoxy-3'-trifluoroacetamido-4'-hydroxy-L-lyxohexopyranose)-3,4,5, 10-tetrahydronaphtho[2,3-C]pyran-3-yl) ketone BCH-1146;
(1'S,1R,3S)-Methyl (5,10-dioxo-1-(2',3',6'-trideoxy-3'-trifluoroacetamido-L-lyxohexopyranose)-7-hydroxy-3,4,5,10-tetrahydro[2,3-C]pyran-3-yl) ketone BCH-1181;
(1'S,1S,3R)-Methyl (5,10-dioxo-1-(2',3',6'-trideoxy-3'-trifluoroacetamido-L-lyxohexopyranose)-7-hydroxy-3,4,5,10-tetrahydro[2,3-C]pyran-3-yl) ketone BCH-1180;
(1'-S, 1-R, 3-S) and (1'-S, 1-S, 3-R)-3-cyano-1-[2',3',6'-trideoxy-3'-trifluoroacetamido-4'-hydroxy-L-lyxohexopyranose)-5,10-dioxo-3,4,5,10-tetrahydronaphtho-[2,3-C]pyran-3-yl BCH-1688;
(1'-S, 1-S, 3-R) and (1'-S, 1-R, 3-S)-methyl-(1-[2',3',4',6'tetradeoxy-3'-trifluoroacetamido-4'-O-methane-sulfonyl-L-lyxohexopyranose)-5,10-dioxo-3,4,5,10 tetrahydronaphtho-[2,3-c]pyran-3-yl) ketone BCH-2095;
(1'-S, 1-S, 3-R)-methyl-(1-[2',3',4',6'tetradeoxy-3'-trifluoroacetamido-4'-O-(2-bromo-acetyl)-L-lyxopyranose)-5,10-dioxo-3,4,5,10 tetrahydronaphtho-[2,3-c]pyran-3-yl) ketone BCH-2105;
(1'-S, 1-R, 3-S)-methyl-(1-[2',3',4',6'tetradeoxy-3'-methoxy-4'-O-methanesulfonyl-L-lyxohexopyranose)-5,10-dioxo-3,4,5,10 tetrahydronaphtho-[2,3-c]pyran-3-yl) ketone BCH-2070;
(1'-S, 1'S, 3-R)-methyl-(1-[2',3',4',6'tetradeoxy-3'-methoxy-4'-O-methanesulfonyl-L-lyxohexopyranose)-5,10-dioxo-3,4,5,10 tetrahydronaphtho-[2,3-c]pyran-3-yl) ketone BCH-2072;
(1-S, 3-R) and (1-R, 3-S)-methyl-(1-(1-methoxy-4-oxocyclohexyloxy)-5,10-dioxo-3,4,5,10 tetrahydronaphtho-[2,3-c]pyran-3-yl) ketone BCH-2096;
(1'-S, 1-S, 3-R) and (1'-S, 1-R, 3-S)-1-(6-hydroxy-1-(2',3',6'-trideoxy-3'-trifluoroacetamido,4-hydroxy-L-lyxopyranose)-5,10-dioxo-3,4,5,10 tetrahydronaphtho-[2,3-c]pyran-3-yl) propane-2-one BCH-2098;
3,3-bis-(methoxycarbonyl)-5,10-dioxo-3,4,5,10-tetrahydro-1H-naphtho-[2,3-c]-pyran (BCH-1665);
(1'S, 1R, 3S)-5,10-dioxo-3-methoxymethyl-1-(2',3',6'-trideoxy-3'-trifluoroacetamido-L-lyxohezopyranose)-3,4,5,10-tetrahydro-1H-naphtho-[2,3-c]-pyran (BCH-1691);
(1'S, 1S, 3R)-5,10-dioxo-3-methoxymethyl-1-(2',3',6'-trideoxy-3'-trifluoroacetamido-L-lyxohexopyranose)-3,4,5,10-tetrahydro-1H-naphtho[2,3-c]pyran (BCH-1693);
(1'S, 1R, 3R)-5,10-dioxo-3-ethyl-1-(2',3',6'-trideoxy-3'-trifluoroacetamido-L-lyxohexopyranose)-3,4,5,10-tetrahydro-1H-naphtho-[2,3-c]pyran (BCH-2026);
(1'S, 1S, 3S)-5,10-dioxo-3-ethyl-1-(2',3',6'-trideoxy-3'-trifluoroacetamido-L-lyxohexopyranose)-3,4,5,10-tetrahydro-1H-naphtho-[2,3-c]-pyran (BCH-2020);
(1'S, 1S, 3S)-5,10-dioxo-3-ethyl-1-(2',3',6'-trideoxy-3'-amino-L-lyxohexopyranose)-3,4,5,10-tetrahydro-1H-naphtho-[2,3-c]-pyran (BCH-2021);
(1'S, 1R, 3S)-5,10-dioxo-3-isopropyl-1-(2',3',6'-trideoxy-3'-trifluoroacetamido-L-lyxohexopyranose)-3,4,5,10-tetrahydro-1H-naphtho-[2,3-c]-pyran (BCH-2053);
(1'S, 1S, 3R)-5,10-dioxo-3-isopropyl-1-(2',3',6'-trideoxy-3'-trifluoroacetamido-L-lyxohexopyranose)-3,4,5,10-tetrahydro-1H-naphtho-[2,3-c]-pyran (BCH-2052);
(1'S, 1R, 3S)-5,10-dioxo-3-isopropenyl-1-(2',3',6'-trideoxy-3'-trifluoroacetamido-L-lyxohexopyranose)-3,4,5,10-tetrahydro-1H-naphtho-[2,3-c]-pyran (BCH-2153);
(1'S, 1S, 3R)-5,10-dioxo-3-isopropenyl-1-(2',3',6'-trideoxy-3'-trifluoroacetamido-L-lyxohexopyranose)-3,4,5,10-tetrahydro-1H-naphtho-[2,3-c]-pyran (BCH-21-52);
(1'S, 1R, 3S)-5,10-dioxo-3-methoxycarbonyl-1-(2',3',6',-trideoxy-3'-trifluoroacetamido-L-lyxohexopyranose)-3,4,5,10-tetrahydro-1H-naphtho-[2,3-c]-pyrano (BCH-2128);
(1'S, 1R, 3S)-isopropyl-[1-(2',3',6'-trideoxy-3'-trifluoroacetamido-L-lyxohexopyranose)-5,10-dioxo-3,4,5,10-tetrahydro-1H-naphtho-[2,3-c]-pyranyl]-ketone (BCH-2112);
(1'S, 1R, 3S)-5,10-dioxo-3-isopropoxycarbonyl-1-(2',3',6'-trideoxy-3'-trifluoroacetamido-L-lyxohexopyranose)-3,4,5,10-tetrahydro-1H-naphtho-[2,3-c]-pyran (BCH-2122);
(1'S, 1S)-5,10-dioxo-3,3-dimethoxymethyl-1-(2',3',6'-trideoxy-3'-trifluoroacetamido-4'-O-p-nitrobenzoyl-L-lyxohexo-pyranose)-isochroman (BCH-1697);
(1'S, 1R, 4R)-5,10-dioxo-4-ethyl-1-(2',3',6'-trideoxy-3'-trifluoroacetamido-L-lyxohexopyranose)-3,4,5,10-tetrahydro-1H-naphtho-[2,3-c]pyran (BCH-2091);
(1'S, 1R, 3S)-5,10-dioxo-3-phenyloxymethyl-1-(2',3',6'-trideoxy-3'-trifluoroacetamido-L-lyxohexopyranose)-3,4,5,10-tetrahydro-1H-naphtho-[2,3-c]pyran (BCH-2032);
(1'S,1S,3S) and (1'S,1-R,3-R)-3-([2',3',6'-trideoxy-3'-trifluoroacetamido-4'-hydroxy-L-lyhohexopyranose]-5,10-dioxo-3,4,5,10-tetrahydronaphtho-[2,3-c]-pyran-3-yl)-propene (BCH-2031);
(1'-S,1-R,3-S)-methyl-(1-[2',3',6'-trideoxy-3'-trifluoroacetamido-4'-iodo-L-lyxohexopyranose]-5,10-dioxo-3,4,5,10-tetrahydronaphtho-[2,3-c]-pyran-3-yl)-ketone (BCH-1620);
(1'-S,1-R,3-S)-3-([2',3',6'-trideoxy-3'-trifluoroacetamido-4'-hydroxy-L-lyhohexopyranose]-5,10-dioxo-3,4,5,10-tetrahydronaphtho-[2,3-c]-pyran-3-yl)-propene (BCH-1649);
(1'-S,1-R,3-S,4a-S,10a-S)-methyl-(1-[2',3',4',6'-tetradeoxy-3'-methoxy-4'-O-methanesulfonyl-L-lyxohexopyranose)-4a,10a-epoxy-5,10-dioxo-3,4,5,10-tetrahydronaphtho-[2,3-c]pyran-3-yl) ketone (BCH-2141);
(1S,3R,1'S,5'S,6'S) and (1R,3S,1'S,5'S,6'S)-methyl-(1-[4'trifluoroacetamido-5'-methyltetrahydropyranyl]-5,10-dioxo-3,4,5,10-tetrahydronaphthaleno-[2,3-c]pyran-3-yl) ketone (BCH-1673);
(1'S,1S,3R)-3 (oximoethyl)-5,10-dioxo-1 (2,3,6-trideoxy-3-trifluoroacetamido-L-lyxohexopyranose)-3,4,5,10-tetrahydro-1H-naphtho-[2,3-c]pyran (BCH-2101);
(1'S, 1R, 3S)-3 (oximoethyl)-5,10-dioxo-1 (2,3,6-trideoxy-3-trifluoroacetamido-L-lyxohexopyranose)-3,4,5,10-tetrahydro-1H-naphtho-(2,3-c)-pyran (BCH-2115);
(1'S,1S,3R)-3-(trifluoroacetamidoethyl)-5,10-dioxo-1-(2',3',6'-trideoxy-3',4'-dihydroxy-L-lyxohexopyranose)-3,4,5,10-tetrahydro-1H-naphtho-[2,3-c]pyran (BCH-2018);
(1'R, 1R, 3S)-3-aceto-5,10-dioxo-1-(2-deoxy-2-chloroethylnitrosoureido-D-glucopyranose)-3,4,5,10-tetrahydro-1H-naphtho-[2,3-C]pyran (BCH-2038)
(1R,3S) and (1S,3R)-3-aceto-5,10-dioxo-1 (4-chloroethylnitrosoureido cyclohexyl-oxy)-3,4,5,10-tetrahydro-1H-naphtho-(2,3-c)-pyran (BCH-2114);
(1'S,1S,3R)-1-(3'-trifluoroacetamido-2',3',6'-trideoxy-lyxo-L-hexopyranose)-3-methoxycarbonyl-3-methyl-3,4,5,10-tetrahydro-5,10-dioxo-naphtho-[2,3-c]pyran (BCH-2076);
(1'S, 1R, 3S)-2',3',6'-trideoxy-3'-trifluoroacetamido-L-lyxohexopyranose-3-[5'-tosyloxazolyl]-5,10-dioxo-3,4,5,10-tetrahydro-1H-naphtho-[2,3-c]-pyran (BCH-2150);
(1'S, 1S, 3R)-2',3',6'-trideoxy-3'-trifluoroacetamido-L-lyxohexopyranose-3-[5'-tosyloxazolyl)]-5,10-dioxo-3,4,5,10-tetrahydro-1H-naphtho-[2,3-C]-pyran (BCH-2151);
(1'S, 1R, 3S)-1-(3'-trifluoroacetamido-2',3',6'-trideoxy-L-lyxohexopyranose)-5,10-dioxo-4,5,10-trihydro-1H-naphtho-[2,3-c]-pyran (BCH-2077);
(1'S, 1S, 3R)-1-(3'-trifluoroacetamido-2',3',6'-trideoxy-L-lyxohexopyranose)-3-acetyl-3-methyl-5,10-dioxo-4,5,10-trihydro-1H-naphtho-[2,3-c]-pyran (BCH-2082);
(1'S,1S,3R)-1-(2',3',6'-trideoxy-3'-trifluoroacetamido-L-lyxohexopyranose)-3-dimethylphosphonoacetyl-5,10-dioxo-3,4,5-10-tetrahydro-1H-naphtho-[2,3-c]-pyran (BCH-1690);
(1'S, 1S, 3S)-1-(3'-trifluoroacetamido-2',3',6'-trideoxy-lyxohexopyranose)-3-methoxycarbonyl-3-methyl-5,10-dioxo-4, 5,10-trihydro-1H-naphtho-[2,3-c]-pyran (BCH-2081);
(1'S,1S,3S)-1-(3'-trifluoroacetamido-2',3',6'-trideoxy-L-lyxohexopyranose)-5,10-dioxo-3,4,5,10-tetrahydro-1H-naphtho-[2,3-c]-thiopyran (BCH-2037.001);
(1'S,1R,3R)-1-(3'trifluoroacetamido-2',3',6'-trideoxy-lyxo-L-hexopyranose)-3-dimethoxyphosphonoacetyl-3,4,5,10-tetrahydro-5,10-dioxo-naphtho-[2,3-c]pyran (BCH-2127);
(1'S,1S,3S)-1-(3'-trifluoroacetamido-2',3',6'-trideoxy-lyxo-L-hexopyranose)-3-acetyl-3-methyl-3,4,5,10-tetrahydro-5,10-dioxo-1H-naphtho-[2,3-c]pyran (BCH-2090);
(1'S,1R,3S)-1-(3'-trifluoroacetamido-2',3',6'-trideoxy-lyxo-L-hexopyranose)-3-dimethoxyphosphonoacetyl-3,4,5,10-tetrahydro-5,10-dioxo-naphtho-[2,3-c]pyran (BCH-1689);
(1'S,1R,3S)-methyl-(1-[2',6'-dideoxy-3',4'-dihydroxy-2'-iodo-L-lyxohexopyranose]-5,10-dioxo-3,4,5,10-tetrahydronaphtho[2,3-c]-pyran-3-yl) ketone (BCH-2015);
(1'S,1R,3S)-methyl-(1-[2',6'-dideoxy-3'-4'-diacetoxy-2'-iodo-L-lyxohexopyranose]-5,10-dioxo-3,4,5,10-tetrahydronaphtho[2,3 -c]-pyran-3-yl) ketone (BCH-1666);
(1'S,1S,3R)-methyl-(1-[2',6'-dideoxy-3',4'-diacetoxy-2'-iodo-L-lyxohexopyranose]-5,10-dioxo-3,4,5,10-tetrahydronaphtho[2,3-c]-pyran-3-yl) ketone (BCH-1667);
(1'S,1S,3R)-methyl-(1-[2',6'-dideoxy-3',4'-dihydroxy-2'-iodo-L-lyxohexopyranose]-5,10-dioxo-3,4,5,10-tetrahydronaphtho[2,3-c]-pyran-3-yl)-ketone (BCH-2014);
(1'S,1R,3S)-methyl-(1-[2',6'-dideoxy-3',4'-diacetoxy-2'-bromo-L-lyxohexopyranose]-5,10-dioxo-3,4,5,10-tetrahydronaphtho-[2,3-c]-pyran-3-yl) ketone (BCH-2100);
(1'S,1R,3S)-methyl-(1-[2',3',6'-trideoxy-2'-iodo-3'-trifluoroacetamido-4'-hydroxy-L-lyxohexopyranose]-5,10-dioxo-3,4,5,10-tetrahydronaphtho-[2,3-c]-pyran-3-yl) ketone (BCH-2023);
(1'S,1S,3R)-methyl-(1-[2',3',6'-trideoxy-2'-iodo-3'-trifluoroacetamido-4'-hydroxy-L-lyxohexopyranose]-5,10-dioxo-3,4,5,10-tetrahydronaphtho-[2,3-c]-pyran-3-yl) ketone (BCH-2022);
(1'S,1R,1S) and (1'S,1S,3R)-methyl-(1-[2',6'-dideoxy-3',4'-diacetoxy-2'-iodo-L-arabino-hexopyranose]-5,10-dioxo-3,4,5,10-tetrahydronaphtho-[2,3-c]-pyran-3-yl) ketone (BCH-2065);
(1'S,1S,3R) and (1'S,1R,3S)-methyl-(1-[dideoxy-2',6'-dihydroxy-3',4'-L-lyxohexopyranose]-5,10-dioxo-3,4,5,10-tetrahydronaphtho-[2,3-c]-pyran-3-yl) ketone (BCH-2117);
(1'S,1S,3R) and (1'S,1R,3S)-methyl-(1-[dideoxy-2',6'-diacetoxy-3',4'-L-lyxohexopyranose]-5,10-dioxo-3,4,5,10-tetrahydronaphtho-[2,3-c]-pyran-3-yl) ketone (BCH-2118);
Methyl-(6-hydroxy-5,10-dioxo-3,4,5,10-tetrahydronaphtho-[2,3-c]-pyran-3-yl) ketone and methyl-(9-hydroxy-5,10-dioxo-3,4,5,10-tetrahydronaphtho-[2,3-c]-pyran-3-yl) ketone (BCH-2062);
(1'S,1S,3R)-methyl-(6 and 9-hydroxy-1-[2',3',6'-trideoxy-3'-trifluoroacetamido-4'-hydroxy-L-lyxohexopyranose]-5,10-dioxo-3,4,5,10-tetrahydronaphtho-[2,3-c]-pyran-3-yl-ketone (BCH-2078);
(1R,3S,1'S) and (1S,3R, 1'S)-Methyl-(1-[2',3',4',6'-tetradeoxy-3',4'-bis-trifluoroacetamido-L-arabinohexopyranose]-5,10-dioxo-3,4,5,10-tetrahydronaphthaleno-[2,3-c]pyran-3-yl) ketone (BCH-2104 and BCH-2102);
(1S,3R,1'S)-Methyl-(1-[2',3',4',6'-tetradeoxy-3'-trifluoroacetamido-4'-bromo-L-lyxohexopyranose]-5,10-dioxo-3,4,5,10-tetrahydronaphthaleno-[2,3-c]pyran-3-yl) ketone (BCH-2047);
(1'-S,1-S,3-R)-1-(2',3',6'-trideoxy-3'-trifluoro acetamido-L-lyxohexopyranose)-3-(2-aza-3-acetamido-thiazolyl)-5,10-dioxo-3,4,5,10-tetrahydro-1H-naphtho-[2,3-c]-pyran (BCH-1198);
(1'S, 1S, 3S) and (1'S, 1R, 3R)-5,10-dioxo-3-ethyl-1-(2',3',4',6'-tetradeoxy-3',4'-diacetoxy-L-lyxohexo-pyranose)-3,4,5,10-tetrahydro-1H-naphtho[2,3-C]pyran (BCH-1607);
(1'S,1S,3R)-methyl-(1-[2',6'-dideoxy-3',4'-diacetoxy-2'-bromo-L-lyxohexopyranose]-5,10-dioxo-3,4,5,10-tetrahydronaphtho-[2,3-c]-pyran-3-yl) ketone (BCH-2099);
(1'S, 2'R, 3'S, 5'R, 1S, 3R)-1-(3-trifluoroacetamido-2-hydroxy-1-methyl tetrahydropyran-5-yl)-methyl2-3-ethyl-5,10-dioxo-3,4,5,10-tetrahydro-1H-naphtho[2,3-C]pyran (BCH-2818);
(1'S, 2'R, 3'S, 5'R, 1R, 3S)-1-(3-trifluoroacetamido-2-hydroxy-1-methyl tetrahydropyran-5-yl)-methyl-3-ethyl-5,10-dioxo-3,4,5,10-tetrahydro-1H-naphtho[2,3-C]pyran (BCH-2819);
(1'S,2'R,3'S,5'R,1R,3R)-1-(3-trifluoroacetamido-2-hydroxy-1-methyl tetrahydropyran-5-yl)methyl-3-methylketone-5,10-dioxo-3,4,5,10-tetrahydro-1H-naphtho[2,3-C]pyran. (BCH-2821); and
(1'S,2'R,3'S,5'R,1S,3S)-1-(3-trifluoroacetamido-2-hydroxy-1-methyl tetrahydropyran-5-yl)methyl-3-methylketone-5,10-dioxo-3,4,5,10-tetrahydro-1H-naphtho[2,3-C]pyran. (BCH-2820).

1-Methoxy-5,10-dioxo-5,10-dihydro-1H-naphtho[2,3-c]pyran-3-[N-(3-dimethylamino-propyl)carboxamide]hydrochloride monohydrate (BCH-2051);
3-Aceto-5,10-dioxo-1-methoxy-5,10-dihydro-1H-naphtho-(2,3-c)-pyran (BCH-2129); 1-methoxy-3-N-anilinylcarbonyl-5,10-dioxo-5,10-dihydro-1H-naphtho-[2,3-c]-pyran (BCH-2044);
1-methoxy-3-(3-N-pyrrolidinomylpropylaminocarbonyl)-5,10-dioxo-5,10-dihydro-1H-naphtho-[2,3-c]-pyran (BCH-2166);
(3-N-hydrochloroimidazolylpropyl)-1-methoxy-5,10-dioxo-5,10-dihydro-1H-naphtho-[2,3-c]-pyran-3-carboxamide (BCH-2157);
2-hydrochloro-(N-pyrrolidinyl)ethyl-(1-propyl-5,10-dioxo-5,10-dihydro-1H-naphtho-[2,3-c]-pyran-3)-carboxamide (BCH-2875);
3-N-oxo-dimethylaminopropyl-(1-methoxy-5,10-dioxo-5,10-dihydro-1H-naphtho-[2,3-c]-pyran-3)-carboxamide (BCH-2877);
2-(2-N-methyl pyrrolyl)-ethyl-(1-propyl-5,10-dioxo-5,10-dihydro-1H-naphtho-[2,3-c]-pyran-3)-carboxamide (BCH-2876);
1-methoxy-3-[2-(N-morpholino) ethyl amino carbonyl]-5,10-dioxo-5,10-dihydro-1H-naphtho-[2,3-c]-pyran (BCH-2170);
1-methoxy-3-[2-(N-morpholine) ethyl amino carbonyl]-5,10-dioxo-5,10-dihydro-1H-naphtho-[2,3-c]-pyran (BCH-2171);
1-methoxy-3-[2-(2-pyridinyl) ethyl amino carbonyl]-5,10-dioxo-5,10-dihydro-1H-naphtho-[2,3-c]-pyran hydrochloride (BCH-2835);
1-methoxy-3-[(2-pyridinyl) methyl amino carbonyl]-3-methoxy-5,10-dioxo-5,10-dihydro-1H-naphtho-[2,3-c]-pyran (BCH-2840);
1-methoxy-3-[(2-pyridinyl) methyl amino carbonyl]-3-methoxy-5,10-dioxo-5,10-dihydro-1H-naphtho-[2,3-c]-pyran hydrochloride salt (BCH-2841);
1-methoxy-3-[2-(N-pyrrolidinyl) ethyl amino carbonyl]-5,10-dioxo-5,10-dihydro-1H-naphtho-[2,3-c]-pyran hydrochloride salt (BCH-2839);
1-methoxy-3-[(4-diethoxy) butyl amino carbonyl]-5,10-dioxo-5,10-dihydro-1H-naphtho-[2,3-c]-pyran (BCH-2848);
1-methoxy-3-(3-hydroxy) propyl amino carbonyl-5,10-dioxo-5,10-dihydro-1H-naphtho-[2,3-c]-pyran (BCH-2849);
1-methoxy-3-methoxy carbonyl-5,10-dioxo-5,10-dihydro-1H-naphtho-[2,3-c]-pyran (BCH-2160);

1-propyl-3-(3-dimethyl amino propyl amino carbonyl)-5,10-dihydro-5,10-dioxo-1H-naphtho-[2,3-c]-pyran (BCH-2168);

3-methoxy carbonyl-5,10-dioxo-5,10-dihydro-1H-naphtho-[2,3-c]-pyran (BCH-2830);

1-methoxy-3-(2-trimethyl ammonium ethyl amino carbonyl)-5,10-dioxo-5,10-dihydro-1H-naphtho-[2,3-c]-pyran chloride salt (BCH-2837);

1-methoxy-3-(2-pyrrolidinoethyl carbonyl)-5,10-dioxo-5,10-dihydro-1H-naphtho-[2,3-c]pyran hydrochloride (BCH-2854);

1-Methoxy-3[2-(N-pyrrolidinylethoxylcarbonyl)]-5,10-dioxo-5,10-dihydro-1H-naphtho-[2,3-c]-pyran (BCH-2861);

1-methoxy-5,10-dioxo-5,10-dihydro-1H-naphtho[2,3-c]thiine-3-[N-(3-dimethylaminopropyl) carboxamide] (BCH-2878);

(1'S) Methyl (5,10-dioxo-1-(2',3',4',6'-tetradeoxy-3',4'-diacetoxy-L-lyxohexopyranose-5,10-dihydro-1H-naphtho[2,3-c]thiopyran-3-yl) ketone (BCH-2879); and N-Boc-N-{1-methoxy-5,10-dihydro-5,10-dioxo-1H-naphtho-[2,3-c]-pyran-3-carbonyl}-propyldiamine (BCH-2881).

There is provided in a seventh aspect of the present invention, a process wherein said protected isochroman of formula (5) or said dioxoisochroman of formula (6) is produced by:

step 1) condensing a precursor compound of formula (13)

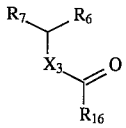

wherein:

$R_6$ is selected from the group consisting of $C_{1-16}$ acyl; $C_{2-16}$ ester; and CN;

$R_7$ is a $C_{2-16}$ ester or a $C_{1-16}$ alkyl;

$X_3$ is O or S;

$R_{16}$ is a $C_{6-12}$ aryl;

with a protected aromatic compound of formula (14);

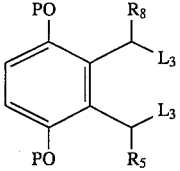

wherein:

P, is an oxygen protecting group; $R_5$ and $R_8$ are as defined on page 34 with the proviso that $R_8$ are not OH; CN or $NO_2$ and each one of $L_3$ is independently a leaving group;
to yield a protected isochroman of formula (5)

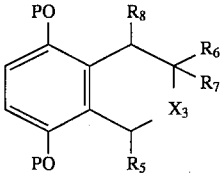

wherein:

$R_5$, $R_6$, $R_7$, $R_8$, and $X_3$ are as defined above;

step 2) oxydating the protected isochroman of formula (5) in the presence of an oxydating agent (a) to yield to a dioxoisochroman of formula (6)

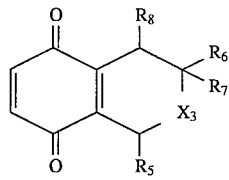

wherein $X_3$, $R_5$, $R_6$, $R_7$, and $R_8$ are as defined above.

In a prefered embodiment of the seventh aspect of this invention there is provided a process wherein;

$X_3$ is more preferably O.

$R_5$ is preferably selected from the group consisting of hydrogen; $C_{1-16}$ alkyl; $C_{6-16}$ aryl; amino; and amido.

$R_5$ is more preferably selected from the group consisting of hydrogen; $C_{1-16}$ alkyl; $C_{6-12}$ aryl; amino; and amido.

$R_6$ is preferably selected from the group consisting of $C_{1-6}$ acyl; $C_{2-6}$ ester; and —CN.

$R_7$ is preferably a $C_{2-6}$ ester or a $C_{1-6}$ alkyl.

$R_8$ is preferably selected from the group consisting of hydrogen; $C_{1-16}$ alkyl; $C_{6-16}$ aryl; and halogen.

P is preferably a $C_{1-6}$ alkyl.

P is more preferably —$CH_3$.

Each of $L_3$ is preferably independently selected from the group consisting of I; Br; and Cl.

Said oxydating agent (a) is preferably ceric ammonium nitrate or silver oxide.

Said oxydating agent (a) is more preferably ceric ammonium nitrate.

There is provided in a eight aspect of the present invention, a process wherein said protected isochroman of formula (5) or said dioxoisochroman of, formula (6) is produced by:

step 1) reacting an intermediate of formula (15)

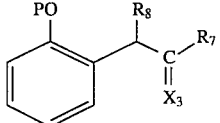

wherein:

$X_3$ is O; and

P is an oxygen protecting group;

$R_7$ is hydrogen; and $R_8$ is hydrogen or a $C_{1-16}$ alkyl;

with a magnesium halide of formula (16)

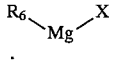

wherein:

$R_6$ is selected from the group consisting of $C_{1-16}$ alkyl; $C_{2-16}$ alkenyl; $C_{2-16}$ alkynyl; and $C_{6-16}$ aryl; and X is an halogen;

to yield product of formula (17)

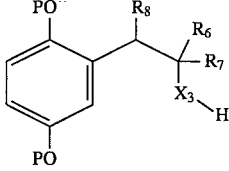

wherein:

$X_3$ is oxygen; and $R_6$, $R_7$, and $R_8$ are as defined above;

step 2) further reacting said product of formula (17): with a compound of formula (18a) or (18b) in the presence of an coupling agent (d);

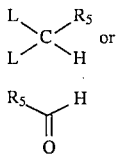   18a

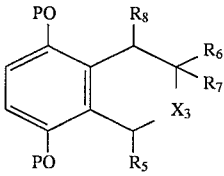   18b wherein:

$R_5$, is as defined page 34, with the proviso that $R_5$ is not alkoxy, and each L is independently a leaving group;

to yield a protected isochroman of formula (5)

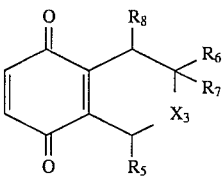   5 wherein:

$X_3$ is O, and P, $R_5$, $R_6$, $R_7$, and $R_8$ are as defined above;

step 3) optionally, oxidating the dimethoxyisochroman of formula (5) in the presence of an oxydating agent (a) to yield to a dioxoisochroman of formula (6);

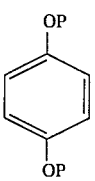   6 wherein:

$X_3$ is O; and $R_5$, $R_6$, $R_7$, and $R_8$ are as defined above.

In a prefered embodiment of the eight aspect of this invention there is provided a process wherein;

$R_5$ is preferably selected from the group consisting of $C_{1-16}$ alkyl; and $C_{6-16}$ aryl.

$R_5$ is more preferably selected from the group consisting of $C_{1-6}$ alkyl; and $C_{6-12}$ aryl.

$R_6$ is preferably selected from the group consisting of hydrogen; $C_{1-16}$ alkyl; and $C_{6-16}$ aryl.

$R_6$ is more preferably selected from the group consisting of hydrogen; $C_{1-6}$ alkyl; and $C_{6-12}$ aryl.

P is preferably a $C_{1-6}$ alkyl.

P is more preferably —$CH_3$.

Said coupling agent (d) is preferably a Lewis acid.

Said coupling agent (d) is more preferably boron trifluoroetherate.

Each of the leaving group L is preferably independently —O[$C_{1-6}$ alkyl].

Each of the leaving group L is more preferably —$OCH_3$.

In a ninth aspect of this invention there is provided a process wherein said protected isochroman of formula (5), wherein $X_3$ is O, or said dioxoisochroman of formula (6), wherein $X_3$ is O, is produced by:

step 1) reacting a protected benzene of formula (19)

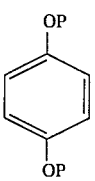   19 wherein:

P is an oxygen protecting group;

in the presence of a coupling agent (e) with an epoxide of formula (20)

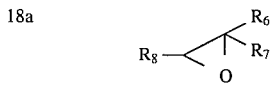   20 wherein:

$R_7$ and $R_8$ are hydrogen; and $R_6$ is selected from the group consisting of $C_{1-16}$ alkyl; $C_{6-16}$ aryl; silyloxy; and hydrogen;

to yield to an intermediate of formula (17)

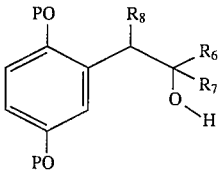   17 wherein:

$R_7$ and $R_8$ are hydrogen; and

P and $R_6$ are as defined above;

step 2) further reacting said intermediate of formula (17) with a compound of formula (18a) or (18b) in the presence of a coupling agent (d);

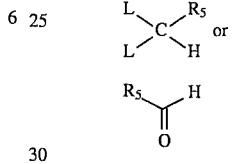

18a

18b wherein:

$R_5$ is as defined on page 34, with the proviso that $R_5$ is not alkoxy, and each L is independently a leaving group;

to yield a protected isochroman of formula (5a)

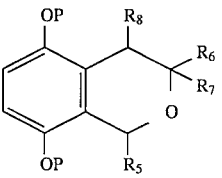   5a wherein:

$R_7$, $R_8$, P, $R_5$, and $R_6$ are as defined above;

step 3) oxidizing the protected isochroman of formula (5a) in the presence of an oxydating agent (a) to yield to a dioxoisochroman of formula (6a)

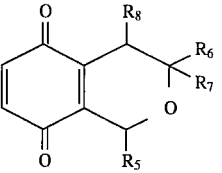   6a wherein:

$R_7$, $R_8$, P, $R_5$, and $R_6$ are as defined above.

In a prefered embodiment of the ninth aspect of this invention there is provided a process wherein;

$R_5$ is preferably selected from the group consisting of hydrogen; $C_{1-16}$ alkyl; and $C_{6-16}$ aryl.

$R_5$ is more preferably selected from the group consisting of hydrogen; $C_{1-6}$ alkyl; and $C_{6-12}$ aryl.

$R_6$ is preferably a $C_{1-16}$ alkyl or hydrogen.

$R_6$ is more preferably a $C_{1-6}$ alkyl or hydrogen.

P i preferably a $C_{1-6}$ alkyl.

P is more preferably —$CH_3$.

Each of L is preferably independently —O[$C_{1-6}$ alkyl].

Said oxydating agent (a) is preferably ceric ammonium nitrate or silver oxide.

Said oxydating agent (a) is more preferably ceric ammonium nitrate.

Said coupling agents (d) and (e) are preferably independently Lewis acids.

Said coupling agents (d) and (e) are more preferably boron trifloroetherate.

In a tenth aspect of this invention there is provided a process wherein said protected isochroman of formula (5), wherein $X_3$ is O, or said dioxoisochroman of formula (6), wherein $X_3$ is O, is produced by:

step 1) reacting a protected intermediate of formula (21);

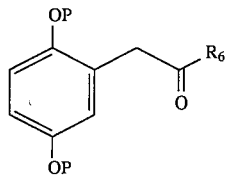

wherein:
P is as defined above and
$R_6$ is hydrogen or a $C_{1-16}$ alkyl;
with an haloalkyl of formula (22)

$$R_8-X$$

wherein:
$R_8$ is a $C_{1-16}$ alkyl; a $C_{1-16}$ acyl or an ester; and X is halogen; to yield to a compound of formula (23):

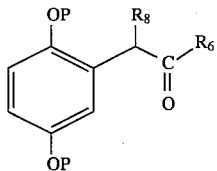

wherein:
P, $R_6$ and $R_8$ are as defined above;

step 2) reducing said compound of formula (23) with a reducing agent (f) to yield to a compound of formula (24)

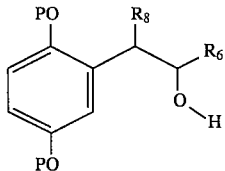

wherein:
$R_6$, P, and $R_8$ are as defined above;

step 3) further reacting said compound of formula (24) with a compound of formula (18a) or (18b) in the presence of a coupling agent (d);

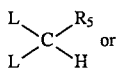

wherein:
L and $R_5$ are as defined on page 70, to yield a protected isochroman of formula (5a)

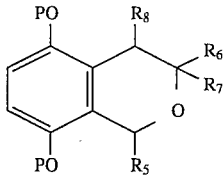

wherein:
$R_7$, P, $R_5$, $R_6$, and $R_8$ are as defined above;

step 4) oxidize the protected isochroman of formula (5a) in the presence of an oxydating agent (a) to yield to a dioxoisochroman of formula (6a)

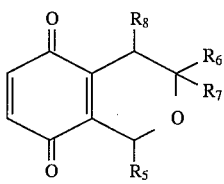

wherein:
$R_7$, $R_5$, $R_6$, and $R_8$ are as defined above.

In a prefered embodiment of the tenth aspect of this invention there is provided a process wherein;

$R_5$ is preferably selected from the group consisting of hydrogen; $C_{1-16}$ alkyl; and $C_{6-16}$ aryl.

$R_5$ is more preferably selected from the group consisting of hydrogen; $C_{1-6}$ alkyl; and $C_{6-12}$ aryl.

$R_6$ is preferably a $C_{1-16}$ alkyl, or a $C_{1-16}$ alkoxy.

$R_6$ is more preferably a $C_{1-6}$ alkyl, or a $C_{1-6}$ alkoxy.

$R_8$ is preferably selected from the group consisting of $C_{1-16}$ alkyl; and $C_{6-16}$ acyl; and $C_{1-16}$ alkoxy.

$R_8$ is more preferably selected from the group consisting of $C_{1-6}$ alkyl; and $C_{1-6}$ acyl; and $C_{1-6}$ alkoxy.

X is preferably I.
P is preferably a $C_{1-6}$ alkyl.
P is more preferably —$CH_3$.
Each of L is preferably independently —O[$C_{1-6}$ alkyl].
Each L is more preferably —$OCH_3$.

Said oxydating agent (a) is preferably ceric ammonium nitrate or silver oxide.

Said oxydating agent (a) is more preferably ceric ammonium nitrate.

Said reducing agent (f) is preferably diisobutylaluminium hydride.

Said coupling agent (d) is preferably a Lewis acid.

Said coupling agent (d) is more preferably boron trifloroetherate.

There is provided, in an eleventh aspect of the present invention a process wherein said a coupled heteronaphtoquinone of formula (8):

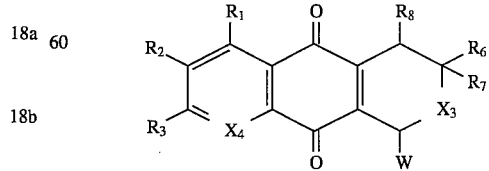

wherein; $R_1$, $R_2$, $R_3$, $R_6$, $R_7$, $R_8$, $X_3$, and $X_4$ are as defined on page 34 and W is defined by formula (50):

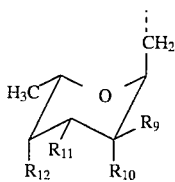

50 wherein;

$R_9$; $R_{10}$; $R_{11}$; and $R_{12}$ are independently selected from the group consisting of hydrogen; hydroxy; CN; $C_{1-16}$ alkyl; $C_{2-16}$ alkenyl; $C_{2-16}$ alkynyl; $C_{1-16}$ alkoxy; $C_{1-16}$ acyl; amino; amido; $C_{2-16}$ ester; and halogen; is produced by:

step 1) coupling a coupled saccharide dioxoisochroman of formula (51);

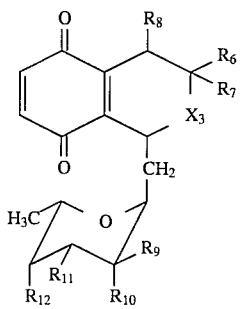

51 wherein; $R_1$, $R_2$, $R_3$, $R_6$, $R_7$, $R_8$, $X_3$, $X_4$, $R_9$, $R_{10}$, $R_{11}$, and $R_{12}$ are as defined above;
with a diene of formula (3a) or (3b)

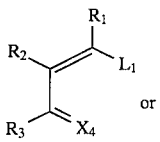

3a or

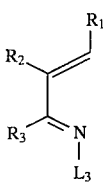

3b wherein $R_1$, $R_2$, $R_3$ and $X_4$ are as defined above; and
each one of $L_1$ and $L_2$ is independently a leaving group to yield to a coupled heteronaphtoquinone of formula (8).

In a prefered embodiment of the eleventh aspect of the present invention, there is provided a process wherein said coupled saccharide dioxoisochroman of formula (51);

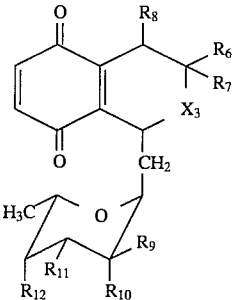

51 wherein;

$X_3$ is O or S;

$R_6$ is selected from the group consisting of $C_{1-16}$ alkyl; $C_{2-16}$ alkenyl; $C_{2-16}$ alkynyl; and $C_{6-16}$ aryl;

$R_7$ is hydrogen;

$R_8$ is hydrogen or a $C_{1-16}$ alkyl; and $R_9$, $R_{10}$, $R_{11}$, and $R_{12}$ are as defined above;
is produced by:

step 1) reacting a compound of formula (17);

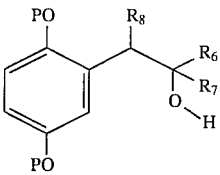

17 wherein:

$X_3$, $R_6$, $R_7$, and $R_8$ are as defined above; and each P is independently a protecting group;
with a saccharide precursor of formula (52a) or (52b) in the presence of a coupling agent (d);

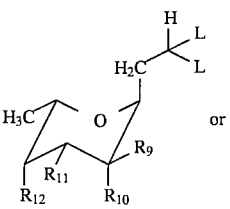

52a or

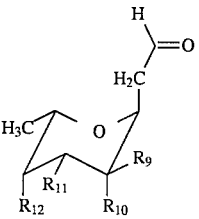

52b wherein;

$R_9$, $R_{10}$, $R_{11}$, and $R_{12}$ are as defined above; and each L is independently a leaving group;
to yield to a coupled saccharide protected isochroman of formula (53);

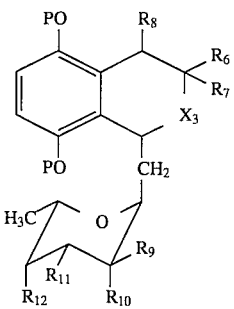

53 wherein; $R_6$, $R_7$, $R_8$, $X_3$, $R_9$, $R_{10}$, $R_{11}$, and $R_{12}$ are as defined above;

step 2) oxidyzing said coupled saccharide protected isochroman of formula (53) in the presence of an oxydating agent (a) to yield to a coupled saccharide dioxoisochroman of formula (51).

In a further prefered embodiment of the eleventh aspect of the present invention, there is provided a process wherein;

$X_3$ is preferably O;

$R_6$ is preferably selected from the group consisting of hydrogen; $C_{1-16}$ alkyl; and $C_{6-16}$ aryl.

$R_6$ is more preferably selected from the group consisting of hydrogen; $C_{1-6}$ alkyl; and $C_{6-12}$ aryl.

P is preferably a $C_{1-6}$ alkyl.

P is more preferably —$CH_3$.

Each of L is preferably independently —O[$C_{1-6}$ alkyl].

Each of the leaving group L is more preferably —OCH$_3$.

$R_9$; $R_{10}$; $R_{11}$; and $R_{12}$ are preferably independently selected from the group consisting of hydrogen; hydroxy; $C_{1-6}$ alkyl; $C_{1-6}$ alkenyl; $C_{1-6}$ alkynyl; $C_{1-6}$ alkoxy; $C_{1-6}$ acyl; $C_{2-6}$ ester; amino; amido; and halogen.

$R_9$ is more preferably selected from the group consisting of hydrogen; hydroxy; and $C_{1-6}$ alkyl.

$R_9$ is most preferably hydrogen.

$R_{10}$ is more preferably selected from the group consisting of hydrogen; $C_{1-6}$ alkyl; $C_{1-6}$ acyl; amino; halogen; and hydroxy.

$R_{10}$ is most preferably selected from the group consisting of hydrogen; $C_{1-6}$ acyl; halogen; amino and hydroxy.

$R_{11}$ and $R_{12}$ are more preferably independently selected from the group consisting of hydrogen; $C_{1-6}$ alkyl; $C_{1-6}$ acyl; $C_{2-6}$ ester; halogen; hydroxy; and amino.

$R_{11}$ is most preferably selected from the group consisting of hydrogen; $C_{1-6}$ alkyl; $C_{1-6}$ acyl; hydroxy; and amino.

$R_{12}$ is most prefeably selected from the group consisting of $C_{1-6}$ acyl; ester; halogen; hydroxy; and amino.

Said oxydating agent (a) is preferably ceric ammonium nitrate or silver oxide.

Said oxydating agent (a) is more preferably ceric ammonium nitrate.

Said coupling agent (d) is preferably a Lewis acid; and

Said coupling agent (d) is more preferably boron trifluoroetherate.

The quinone of formula (2); and coupled dioxoisochroman of formula (12)produce by the process of this invention include:

(1S,1R,3S) and (1'S,1S,3R)-Methyl (5,8-dioxo-1-(2',3',6'-trideoxy-3'-trifluoroacetamido-4'-O-p-nitrobenzoyl-L-lyxohexopyranose)-3,4,5,8-tetrahydrobenzo[2,3-C]pyran-3-yl) ketone;

(1'S,1R,3S)-Methyl (5,10-dioxo-1-(2',3',6'-trideoxy-3'-trifluoroacetamido-4'-O-p-nitrobenzoyl-L-lyxohexo-pyranose)-3,4,5,10-tetrahydronaphtho[2,3-C]pyran-3-yl) ketone;

(1'S,1S,3R) and 1'S,1R,3S)-methyl-1-(2',6'-dideoxy-3',4'-di-O-p-nitrobenzoyl-L-lyxohexopyranose)-5,10-dioxo-3,4,5,10-tetrahydronaphtho[2,3-C]pyran-3-yl) ketone;

(1'S,1R,3S) and (1'S,1S,3R) methyl (5,8-dioxo-1-(2',3',4',6'-tetradeoxy-3',4'-diacetoxy-L-lyxohexo-pyranose)-3,4,5,8-tetrahydrobenzo[2,3-c]thiopyran-3-yl) ketone;

5,8-Dioxo-3-(propane-2-one)-1-(2',3',6'-trideoxy-3'-trifluoroacetamido-4'-O-p-nitrobenzoyl-L-lyxokexopyranose)-isochroman;

(1'S, 1R, 3S)-5,8-dioxo-3-methoxymethyl-1-(2',3',6'-trideoxy-3'-trifluoroacetamido-4'-O-p-nitrobenzoyl-L-lyxohexo-pyranose)-5,8-dihydroisochroman and its (1'S, 1S, 3R) diastereomer;

(1'S, 1R, 3R)-5,8-dioxo-3-ethyl-1-(2',3',6'-trideoxy-3'-trifluoroacetamido-4'-O-p-nitrobenzoyl-L-lyxohexopyranose)-isochroman;

(1'S, 1S, 3S)-5,8-dioxo-3-ethyl-1-(2',3',6'-trideoxy-3'-trifluoroacetamido-4'-O-p-nitrobenzoyl-L-lyxohexo-pyranose)-5,8-dihydro-isochroman;

(1'S, 1S, 3R)-5,8-dioxo-3-isopropyl-1-(2',3',6'-trideoxy-3'-trifluoroacetamido-4'-O-p-nitrobenzoyl-L-lyxohexopyranose)-5,8-dihydro-isochroman;

(1'S, 1R, 3S) and (1'S, 1S, 3R)-5,8dioxo-3-methoxycarbonyl-1-(2',3',6'-trideoxy-3'-trifluoroacetamido-4'-O-p-nitrobenzoyl-L-lyxohexopyranose)-5,8-dihydro-isochroman.;

(1'S, 1S)-5,8-dioxo-3,3-dimethoxymethyl-1-(2',3',6'-trideoxy-3'-trifluoroacetamido-4'-O-p-nitrobenzoyl-L-lyxohexopyranose)-isochroman;

(1'S, 1R, 4R)-5,8-dioxo-4-ethyl-1-(2',3',6'-trideoxy-3'-trifluoroacetamido-4'-O-p-nitrobenzoyl-L-lyxohexopyranose)-isochroman;

(1'S, 1R, 3S)-5,8-dioxo-3-phenyloxymethyl-1-(2',3',6'-trideoxy-3'-trifluoroacetamido-4'-O-p-nitrobenzoyl-L-lyxohexopyranose)-isochroman;

(±)-Methyl ketone hydroxy-1-isochroman quinone;

(1'S, 1S, 3R)-1-(4'-p-nitrobenzoyl-3'-trifluoroacetamido-2',3',6'-trideoxy-lyxohexopyranose)-3-methoxy-carbonyl-3-methyl-5,8-dioxo-4,5,8-trihydro-1H-benzo-[2,3-c]-pyran;

(1'S, 1S, 3R)-1-(4'-p-nitrobenzoyl-2',3',6'-trideoxy-3'-trifluoroacetamido-L-lyxohexopyranose)-3-(5"-tosyloxazolyl)-5,8-dioxo-3,4,5,8-tetrahydrobenzo-[2,3-c]-pyran.;

(1'S, 1S, 3R)-1-(4'-p-nitrobenzoyl-2',3',6'-trideoxy-3'-trifluoroacetamido-L-lyxohexopyranose)-3-(5"-tosyloxazolyl)-5,8-dioxo-3,4,5,8-tetrahydrobenzo-[2,3-c]-pyran;

(1'S, 1R, 3R)-1-(4'-p-nitrobenzoyl-3'-trifluoroacetamido-2',3',6'-trideoxy-lyxohexopyranose)-3-methoxycarbonyl-3-methyl-5,8-dioxo-4,5,8-trihydro-1H-benzo-[2,3-c]-pyran;

(1'S, 1S, 3S)-1-(4'-p-nitrobenzoyl-3'-trifluoroacetamido-2',3',6'-trideoxy-lyxohexopyranose)-3-methoxy-carbonyl-3-methyl-5,8-dioxo-4,5,8-trihydro-1H-benzo-[2,3-c]-pyran.;

(1'S,1S,3S) and (1'S, 1S, 3R)-1-(4'-p-nitrobenzoyl-3'-trifluoroacetamido-2',3',6'-trideoxy-lyxohexopyranose)-3-acetyl-3-methyl-5,8-dioxo-4,5,8-trihydro-1H-benzo-[2,3-c]pyran;

[(1'S,1S,3R) and (1'S,1R,3S)-1-(2',3,6'-trideoxy-3'-trifluoroacetamido-4'-p-nitrobenzoyl-L-lyxohexopyranose)-3-dimethylphosphonoacethyl-3,4,5,8-tetrahydronaphthaleno-[2,3-c]-pyran;

(1'S,1R,3S)-3-aceto-1-(2',6'-dideoxy-2'-iodo-L-lyxohexopyranose)-5,8-dioxo-5,8-dihydroisochroman;

(1'S,1R,3S)-5,8-Dioxo-3-aceto-1-(2',6'-dideoxy-3',4'-diacetoxy-2'-iodo-L-lyxohexopyranose)-5,8-dihydroisochroman;

(1'S,1S,3R)-3-aceto-1-(2',6'-dideoxy-2'-iodo-L-lyxohexopyranose)-5,8-dioxo-5,8-dihydroisochroman;

(1'S,1R,3S)-5,8-dioxo-1-(2',6'-dideoxy-3',4'-diacetoxy-2'-bromo-L-lyxohexopyranose)-5,8-dihydroisochroman;

(1'S,1R,3S)-5,8-dioxo-3-aceto-1-(2',6'-dideoxy-3',4'-diacetoxy-2'-bromo-L-lyxohexopyranose)-5,8-dihydroisochroman;

(1'S,1R,3S)-5,8-Dimethoxy-3-aceto-1-(2',3',6'-trideoxy-3'-trifluoroacetamido-2'-iodo-L-lyxohexopyranose)-isochroman;

(1'S,1R,3S)-3-aceto-1-(2',3',6'-trideoxy-2'-iodo-3'-trifluoroacetamido-L-lyxohexopyranose)-5,8-dioxo-5,8-dihydroisochroman;

(1'S,1S,3R)-3-aceto-1-(2',3',6'-trideoxy-2'-iodo-3'-trifluoroacetamido-L-lyxohexopyranose)-5,8-dioxo-5,8-dihydroisochroman;

(1'S,1R,3S) and (1'S,1S,3R)-3-aceto-1-(2',6'-dideoxy-2'-iodo-L-arabinohexopyranose)-5,8-dioxo-5,8-dihydroisochroman;

(1'S,1S,3R) and (1'S,1R,3S)-5,8-dioxo-3-aceto-1-(2',6'-dideoxy-L-lyxohexopyranose)-5,8-dihydroisochroman;

(1'S,1S,3R) and (1'S,1R,3S)-5,8-dioxo-3-aceto-1-(2',6'-dideoxy-3',4'-diacetoxy-L-lyxohexopyranose) isochroman;

(1R,3S,1'S)-Methyl-(1-[2',3',4',6'-tetradeoxy-3'-trifluoroacetamido-4'-bromo-L-lyxohexopyranose]-5,10-dioxo-3,4,5,10-tetrahydronaphthaleno-[2,3-c]pyran-3-yl) ketone;and (1'S) Methyl (5,8-dioxo-1-(2',3',4',6'-tetradeoxy-3',4'-diacetoxy-L-lyxohexopyranose)-5,8-dihydro-1H-benzo[2,3-c]thiopyran-3-yl) ketone.

The quinone of formula (2); and dioxoisochroman of formula (6) produce by the process of this invention include:

Monofluoromethyl (5,8-dioxo-3,4,5,8-tetrahydrobenzo[2,3-C]pyran-3-yl) ketone;

Bromomethyl (5,8-dioxo-5,8-dihydrobenzo[2,3-C]pyran-3-yl) ketone;
3-Ethyl-1-hydroxy-isochroman-5,8-dione.;
cis-3-aceto-1-methoxy-5,8-dioxoisothiochroman;
Methyl (1-Methoxy-5,8-dioxo-5,8-dihydro-isochroman-3-yl) formate;
(1S,2'S,3R,5'S) and (1R,2'S,3S,5'S)-1-[O-N-BOC-Serine-Leucine-Me ester]-3-aceto-5,8-dimethoxy-isochroman;
1-hydroxy-3-cyano-5,8-dioxo-5,8-dihydroisochroman;
5,8-dioxo-3,3 bis (methoxycarbonyl)-5,8-dihydro-isochroman;
(trans)-1-acetamido-5,8-dioxo-3-ethyl-5,8-dihydro-isochroman;
5,8-dioxo-3-ethyl-5,8-dihydro-isochroman;
3-ethylthiocarbonyl-5,8-dioxo-1,3,4,5,8-penta-1H-benzo-[2,3-c]-pyran;
3-(5'-tosyloxazolyl)-5,8-dioxo-1,3,4,5,8-pentahydrobenzo-[2,3-c]-pyran;
1-methoxy-3-acetyl-5,8-dioxo-3,4,5,8-tetrahydrobenzo-[2,3-c]-pyran;
3-aceto-5,8-dioxo-3,4,5,8-tetrahydro-1H-benzo-[2,3-c]-pyran;
Methyl (1-Methoxy-5,8-dioxo-5,8-dihydro-isochroman-3-yl) formate;
1-propyl-3-methoxycarbonyl-3,4,5,8-tetrahydro-5,8-dioxo-1H-benzo-[2,3-c]-pyran.;
1-methoxy-3-methoxycarbonyl-5,8-dioxo-1H-benzo-[2,3-c]-pyran;
The coupled protected isochroman of formula (11) produce by the process of this invention include:
(1'S,1R,3S) and (1'S,1S,3R) methyl (5,8-dimethoxy-1-(2',3',4',6'-tetradeoxy-3',4'-diacetoxy-L-lyxohexo-pyranose)-3',4'-dihydrobenzo[2,3-c]thiopyran-3-yl) ketone;
5,8-Dimethoxy-3-(propane-2-one)-1-(2',3',6'-trideoxy-3'-trifluoroacetamido-4'-O-p-nitrobenzoyl-L-lyxohexopyranose)-isochroman;
(1'S, 1R, 3R)-5,8-dimethoxy-3-ethyl-1-(2',3',6'-trideoxy-3'-trifluoroacetamido-4'-O-p-nitrobenzoyl-L-lyxohexopyranose)-isochroman;
(1'S, 1S, 3R)-5,8-dimethoxy-3-isopropenyl-1-(2',3',6'-trideoxy-3'-trifluoroacetamido-4'-O-p-nitrobenzoyl-L-lyxohexo-pyranose) isochroman;
(1'S, 1R, 3S) and (1'S, 1S, 3R)-5,8 dimethoxy-3-methoxycarbonyl-1-(2',3',6'-trideoxy-3'-trifloroacetamido-4'-O-p-nitrobenzoyl-L-lyxohexopyranose)-isochroman.;
(1'S, 1S)-5,8-dimethoxy-3,3-dimethoxymethyl-1-(2',3',6'-trideoxy-3'-trifluoroacetamido-4'-O-p-nitrobenzoyl-L-lyxohexopyranose)-isochroman;
(1'S, 1R, 4R)-5,8-dimethoxy-4-ethyl-1-(2',3',6'-trideoxy-3'-trifluoroacetamido-4'-O-p-nitrobenzoyl-L-lyxohexo-pyranose)-isochroman;
(1'S, 1R, 3S)-5,8-dimethoxy-3-phenyloxymethyl-1-(2',3',6'-trideoxy-3'-trifluoroacetamido-4'-O-p-nitrobenzoyl-L-lyxohexopyranose)-isochroman;
(1'S,1S,3S) and (1'S,1-R,3-R)-1-(2',3',6',-trideoxy-3'-trifluoroacetamido-4'-O-paranitrobenzoyl-L-lyxohexopyranose)-5,8-dimethoxy-3-(2-propenyl)-isochroman;
(1S,3R)-3 (oximoethyl)-1 (2,3,6-trideoxy-3-trifluoroacetamido-4-p-nitrobenzoyl-L-lyxohexopyranose)-5,8-dimethoxy-isochroman;
(1R,3S)-3-(oximoethyl)-1 (2,3,6-trideoxy-3-trifluoroaceta-mido-4-p-nitrobenzoyl-L-lyxohexopyranose)-5,8-dimethoxy-isochroman;
(1S',1S,3R)-3-(trifluoroacetamidoethyl)-5,8-dimethoxy-1-(2',3',6'-trideoxy-3',4'-dihydroxy-L-lyxohexopyranose)-isochroman;
(1'R, 1R, 3S)-3-aceto-5,8-dimethoxy-1(2-deoxy-2-chloroethylureido-3,4,6-triacetyl-D-glucopyranose)-isochroman.;
(1'R, 1R, 3S)-3-aceto-5,8-dimethoxy-1(2-deoxy-2-chloroethylureido-4,6-benzylidene-D-glucopyranose)-isochroman;
(1'S, 1S, 3R)-1-(4'-p-nitrobenzoyl-2',3',6'-trideoxy-3'-trifluoroacetamido-L-lyxohexopyranose)-3-(5"-tosyloxazolyl)-5,8-dimethoxy isochroman;
(1'S, 1R, 3S)-1-(4'-p-nitrobenzoyl-3'-trifluoroacetamido-2',3',6'-trideoxy-Llyxohexopyranose)-3-methoxy-carbonhyl-3-methyl-5,8-dimethoxy-isochroman;
(1'S,1S,3S) and (1'S,1R,3R)-1-(3'-trifluoroacetamido-2',3',6'-trideoxy-L-lyxohexopyranose)-3-acetyl-5,8-dimethoxythioisochroman;
(1'S,1S,3S) and (1'S,1S,3R)-1-(4'-p-nitrobenzoyl-3'-trifluoroacetamido-2',3',6'-trideoxy-L-lyxohexopyranose)-3-acetyl-3-methyl-5,8-dimethoxy-isochroman;
(1'S,1S,3R) (1'S,1R,3S)-5,8-dimethoxyl(2',3',6'-trideoxy-3'-trifluoroacetamido-4'-p-nitrobenzoyl-L-lyxohexopyranose)-3-dimethylphosphonoacetyl isochroman;
(1'S,1R,3S) and (1'S,1S,3R)-2,5-Dimethoxy-1-(2',6'-dideoxy-3',4'-diacetoxy-2'-iodo-L-lyxohexopyranose)-3-acetoisochroman;
(1'S,1R,3S)-5,8-Dimethoxy-3-aceto-1-(2',6'-dideoxy-2'-iodo-L-lyxohexopyranose)-isochroman;
(1'S,1R,3S) and (1'S,1S,3R)-2,5-Dimethoxy-1-(2',6'-dideoxy-3',4'-diacetoxy-2'-bromo-L-lyxohexopyranose)-3-acetoisochroman;
(1'S,1R,3S) and (1'S,1S,3R)-2,5-Dimethoxy-3-aceto-1-(2',3',6'-trideoxy-2'-iodo-3'-trifluoroacetamido-4'-O-acetyl-L-lyxohexopyranose)-isochroman;
(1'S,1S,3R)-5,8-dimethoxy-3-aceto-1-(2',3',6'-trideoxy-3'-trifluoroacetamido-2'-iodo-L-lyxohexopyranose) isochroman;
(1'S,1S,3R) and (1'S,1R,3S)-5,8-Dimethoxy-3-aceto-1-(2',6'-dideoxy-34',4'-diacetoxy-2'-iodo-L-arabinohexopyranose) isochroman;
(1'S,1S,3R) and (1'S,1R,3S)-5,8-dimethoxy-3-aceto-1-(2',6'-dideoxy-3',4'-diacetoxy-L-lyxohexopyranose) isochroman;
(1'S,1S,3R) and (1'S,1R,3S)-5,8-dimethoxy-3-aceto-1-(2',6'-dideoxy-L-lyxohexopyranose) isochroman; and
(1'S) Methyl (5,8-dimethoxy-1-(2',3',4',6'-tetradeoxy-3',4'-diacetoxy-L-lyxohexopyranose)-1H-benzo[2,3-c]thiopyran-3-yl) ketone.

The protected isochroman of formula (5) produce by the process of this invention include:
5,8-Dimethoxy-3-ethyl-1-hydroxy-isochroman;
3-Aceto-5,8-dimethoxythioisochroman;
Trans-3-aceto-1,5,8-trimethoxythioisochroman and cis-3-aceto-1,5,8-trimethoxythioisochroman;
Trans-3-aceto-1-methoxy-5,8-dioxoisothiochroman;
Methyl (1,5,8-trimethoxyisochroman-3-yl) formate;
(1S, 2'S, 3R) and (1R, 2'S, 3S)-1-[O-serine methyl ester]-3-aceto-5,8-dimethoxy isochroman.;
(1S, 2'S, 3R) and (1R, 2'S, 3S)-1-[O-N-BOC-prolinol]-3-acetyl-5,8-dimethoxy isochroman;
5,8-dimethoxy-3-phenylsulphone isochroman;
5,8-dimethoxy-3-cyano isochroman;
1-hydroxy-3-cyano-5,8-dimethoxy isochroman;
5,8-Dimethoxy-3- (t-butyl acetoacetato) isochroman;
5,8- Dimethoxy-3-(propane-2-one) isochroman;
5,8-dimethoxy-3,3 bis (methoxycarbonyl)-isochroman;
5,8-dimethoxy-3-hydroxymethyl-isochroman;
5,8-dimethoxy-3-methoxymethylisochroman;
5,8-dimethoxy-3-ethyl-isochroman;
3-isopropyl-5,8-dimethoxy-isochroman;
5,8-dimethoxy-3-isopropenyl-isochroman;
isopropyl-(5,8-dimethoxy-isochroman-3-yl)-ketone;
5,8-dimethoxy-3,3 bis (dihydroxymethyl)-isochroman;
5,8-dimethoxy-3,3 bis (dimethoxymethyl)-isochroman;

5,8-dimethoxy-4-ethyl-isochroman;
5,8-dimethoxy-3-phenoxymethyl-isochroman;
5,8-dimethoxy-3-(2-propenyl)-isochroman;
3-(Trifluoroacetamido-ethyl)-5,8-dimethoxy isochroman;
(1R,3S) and (1S,3R)-3-Aceto-1 (4-chloroethylureido-cyclohexyloxy)-5,8-dimethoxy-isochroman;
3-ethylthiocarbonyl-5,8-dimethoxy-isochroman;
3-(5'-tosyloxazolyl)-5,8-dimethoxy isochroman;
3-methoxycarbonyl-3-methyl-5,8-dimethoxy isochroman;
3-acetyl-3-methyl-5,8-dimethoxy isochroman;
3-bromoacetyl-5,8-dimethoxy-isochroman;
3-dimethoxy phosphinoacetyl-5,8-dimethoxy-isochroman;
1-O-[N-BOC-4-piperidinemethanol]-3-acetyl-5,8-dimethoxy isochroman racemic;
1-O-[N-BOC-3-piperidinemethanol]-3-acetyl-5,8-dimethoxy isochroman;
Methyl (1,5,8-trimethoxyiscchroman-3-yl) formate;
(1,3-trans)-1-allyl-3-methoxy carbonyl-5,8-dimethoxy-isochroman;
1-propyl-3-methoxy carbonyl-5,8-dimethoxy-isochroman;
3-methoxycarbonyl-3,4-didehydro-5,8-dimethoxy isochroman;
1-methoxy-3-methoxycarbonyl-3,4-didehydro-5,8-dimethoxy isochroman; and
1-hydroxy-3-methoxycarbonyl-3,4-didehydro-5,8-dimethoxy isochroman.

As used in this application, the term "L" represents a "leaving group", i.e., an atom or a group which is displaceable upon reaction with a quinone, a protected isochroman, a coupled isochroman, a coupled protected isochroman, a dioxoisochroman, a coupled dioxoisichroman, an heteronaphthoquinone, a coupled heteronaphthoquinone or any intermediate with or without the presence of a Lewis acid. Suitable leaving groups include acyloxy groups, alkoxy groups, e.g., alkoxy carbonyl groups such as ethoxy carbonyl; halogens such as iodine, bromine, chlorine, or fluorine; amido; azido; isocyanato; substituted or unsubstituted, saturated or unsaturated thiolates, such as thiomethyl or thiophenyl; substituted or unsubstituted, saturated or unsaturated seleno, seleninyl, or selenonyl compounds, such as phenyl selenide or alkyl selenide. A suitable leaving group may also be —OR, where R is a substituted or unsubstituted, saturated or unsaturated alkyl group, e.g., $C_{1-6}$ alkyl or alkenyl group; a substituted or unsubstituted aliphatic or aromatic acyl group. e.g., $C_{1-6}$ aliphatic acyl group such as acetyl and a substituted or unsubstituted aromatic acyl group such as benzoyl; a substituted or unsubstituted, saturated or unsaturated alkoxy or aryloxy carbonyl group, such as methyl carbonate and phenyl carbonate; substituted or unsubstituted sulphonyl imidazolide; substituted or unsubstituted aliphatic or aromatic amino carbonyl group, such as phenyl carbamate, substituted or unsubstituted alkyl imidiate group such as trichloroacetamidate; substituted or unsubstituted, saturated or unsaturated phosphonate, such as diethylphosphonate; substituted or unsubstituted aliphatic or aromatic sulphinyl or sulphonyl group, such as tosylate; or hydrogen.

As used in this application, the term "alkyl" represents a substituted (by a halogen, hydroxy, aldehyde, ketone, or $C_{6-20}$ aryl) or unsubstituted, straight chain, branched chain, or cyclic hydrocarbon moiety having 1 to 16 carbon atoms and preferably, from 1 to 6 carbon atoms wherein said straight chain, branched chain, or cyclic hydrocarbon moiety can be interrupted by one or more hetereoatoms (suh as oxygen, nitrogen or sulfur).

The terms "alkenyl" and "alkynyl" represent substituted (by a halogen, aldehyde, ketone ,hydroxy or $C_{6-20}$ aryl) or unsubstituted straight, branched or cyclic hydrocarbon chains having 2 to 16 carbon atoms and preferably form 2 to 6 carbon atoms and containing at least one unsaturated group (e.g., allyl) wherein said straight chain, branched chain, or cyclic hydrocarbon moiety can be interrupted by one or more hetereoatoms (suh as oxygen, nitrogen or sulfur).

The term "alkoxy" represents a substituted or unsubstituted alkyl group containing from 1 to 16 carbon atoms and preferably from 1 to 6 carbon atoms, wherein the alkyl group is covalently bonded to an adjacent element through an oxygen atom (e.g., methoxy and ethoxy).

The term "amino" represents alkyl, acyl, aryl, alkenyl, alkynyl or aralkyl groups containing from 1 to 16 carbon atoms and preferably 1 to 6 carbon atoms wherein said alkyl, acyl, aryl, alkenyl, alkynyl or aralkyl groups is interrupted by at least one nitrogen atom (e.g., pyrrolidine, and piperidyl). They include primary, secondary and tertiary amines and quaternary ammonium salts.

The term "thiol" represents alkyl, acyl, aryl, aralkyl, alkenyl or alkynyl groups containing from 1 to 16 carbon atoms and preferably form 1 to 6 carbon atoms, covalently bonded to an adjacent element through a sulfur atom (e.g., thiomethyl).

The term "aryl" represents a carbocyclic moiety which may be substituted or interrupted by at least one heteroatom (e.g., N, O, or S) and containing at least one benzenoid-type ring and preferably containing from 6 to 16 carbon atoms (e.g., phenyl and naphthyl).

The term "aralkyl" represents an aryl group attached to the adjacent atom by an alkyl (e.g., benzyl).

The term "alkoxyalkyl" represents an alkoxy group attached to the adjacent group by an alkyl group (e.g., methoxymethyl).

The term "aryloxy" represents a substituted (by a halogen, trifluoromethyl or $C_{1-6}$ alkoxy) or unsubstituted aryl moiety covalently bonded through an oxygen atom (e.g., phenoxy).

The term "acyl" refers to a radical derived from a carboxylic acid, substituted (by a halogen (F, Cl, Br, I), $C_{6-20}$ aryl or $C_{1-6}$ alkyl) or unsubstituted, by replacement of the —OH group. Like the acid to which it is related, an acyl radical may be aliphatic or aromatic, substituted (by a halogen, $C_{1-5}$ alkoxyalkyl, nitro or $O_2$) or unsubstituted, and whatever the structure of the rest of the molecule may be, the properties of the functional group remain essentially the same (e.g., acetyl, propionyl, isobutanoyl, pivaloyl, hexanoyl, trifluoroacetyl, chloroacetyl, and cyclohexanoyl).

The term "acyloxy" represents a substituted (by a halogen, trifluoromethyl or $C_{1-6}$ alkoxy) or unsubstituted acyl moiety covalently bonded through an oxygen atom (e.g., acetoxy).

The term "azole" refers to a saturated or unsaturated, substituted (by a halogen, hydroxyl, amino or alkyl) or unsubstituted five membered heterocycle comprising at least two heteroatoms group, said substituted heterocycle containing from 1 to 16 carbon atoms and preferably form 1 to 6 carbon atoms (e.g. aminothiazole and aminodithiazole).

The term "morpholino" refers to a saturated or unsaturated, substituted (by a halogen, hydroxyl, amino or alkyl) or unsubstituted six membered heterocycle comprising at least two heteroatoms group wherein said morpholino group contains from 1 to 30 carbon atoms and preferably from 1 to 6 carbon atoms (e.g. morpholinyl).

The term "amido" represents alkyl, acyl, aryl, aralkyl, alkenyl or alkynyl groups containing from 1 to 30 carbon atoms and preferably from 1 to 6 carbon atoms, covalently bonded to an amide group (e.g.butanamide, methylpropanamide or serylglycine).

The term "sulfono" represents alkyl, acyl, aryl, aralkyl, alkenyl or alkynyl groups containing from 1 to 30 carbon atoms and preferably from 1 to 6 carbon atoms, covalently bonded to an adjacent element through a sulfonyl bond (e.g. methylsulfate or toluene sulfonate).

The term "phosphono" represents alkyl, acyl, aryl, aralkyl, alkenyl or alkynyl groups containing from 1 to 30 carbon atoms and preferably from 1 to 6 carbon atoms, covalently bonded to an adjacent element through a phosphate or a phosphonate bond (e.g. phosphonoformyl).

The term "ester" refers to a radical derived from a carboxylic acid, substituted (by a halogen (F, Cl, Br, I), $C_{6-20}$ aryl or $C_{1-6}$ alkyl) or unsubstituted, by replacement of the —H moiety. Like the acid to which it is related, an ester radical may be aliphatic or aromatic, substituted (by a halogen, $C_{1-5}$ alkoxyalkyl, nitro or $O_2$) or unsubstituted, and whatever the structure of the rest of the molecule may be, the properties of the functional group remain essentially the same (e.g. methoxycarbonyl and ethoxycarbonyl).

The term "saccharide" represents any naturrally occuring saccharide, an analogue or a derivative thereof. By a saccharide analogue or derivative is meant any polyhydroxy aldehyde, ketone or cyclic hemiacetal which has been modified in any of the following or combination of the following ways; acetylation of at least one of the hydroxy; addition of a substitutent or substitution of at least one of the hydroxyl groups by any substituent, including hydrogen; substitution of at least one of the hydrogen moiety by any substituent; and modification of an hydroxyl group by a protecting group (e.g. methoxy). Examples of saccharide analogue or derivative include glucose pentacetate, glucosamine, and gluconolactone. It will be appreciated by those skilled in the art that when $R_1=R_4=$hydroxyl that compounds of formulae (4) and (8) exist in equilibrium with tautomers of formula (4') and (8'). Therefore, the process of this invention can also be used to produce compounds of formulae (4') and (8').

deprotection of functional groups may be effected using conventional means. Thus, for example, amino groups may be protected by a group selected from aralkyl (e.g. benzyl), acyl or aryl (e.g. 2,4-dinitrophenyl), subsequent removal of the protecting group being effected when desired by hydrolysis or hydrogenolysis as appropriate using standard conditions. Hydroxyl groups may be protected using any conventional hydroxyl protecting group, for example, as described in "Protective Groups in Organic Chemistry", Ed. J. F. W. McOmie (Plenum Press, 1973) or "Protective Groups in Organic Synthesis" by Theodora W. Greene (John Wiley and Sons, 1981, 1991). Examples of suitable hydroxy protecting groups include groups selected from alkyl (e.g. methyl, t-butyl or methoxymethyl), aralkyl (e.g. benzyl, diphenylmethyl or triphenylmethyl), heterocyclic groups such as tetrahydropyranyl, acyl (e.g. acetyl or benzoyl), and silyl groups such as trialkylsilyl (e.g. t-butyldimethylsilyl). The hydroxy protecting groups may be removed by conventional techniques. Thus, for example, alkyl, silyl, acyl and heterocyclic groups may be removed by solvolysis, e.g. by hydrolysis under acidic or basic conditions. Aralkyl groups such as triphenylmethyl may be similarly removed by solvolysis, e.g. by hydrolysis under acidic conditions. Aralkyl groups such as benzyl may be cleaved, for example, by treatment with $BF_3$/etherate and acetic anhydride followed by removal of acetate groups.

In the process of this invention, the compounds of formula (1), (4) or (8) are generally obtained as a mixture of diastereoisomers. These isomers may be separated by conventional chromatography or fractional crystallization techniques.

Where the compound of formulae (1), (4) or (8) is desired as a single isomer, it may be obtained either by resolution of the final product or by stereospecific synthesis from isomerically pure starting material or any convenient intermediate.

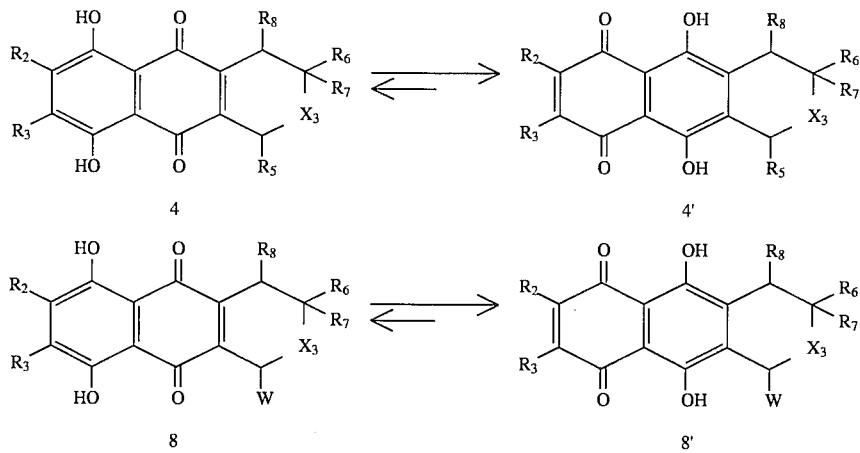

This process of the invention can also be used for producing all the possible isomers and mixtures thereof, including diastereoisomeric mixtures and racemic mixtures, resulting from the possible combination of R or S stereochemical centers, when pertinent, at $C_1$, $C_2$ and $C_3$ as well as in all the other chiral centers.

It will also be appreciated that the process of this invention may require the use of, or conveniently may be applied to, starting materials having protected functional groups, and deprotection might thus be required as an intermediate or final step to yield the desired compound. Protection and Resolution of the final product, or an intermediate or starting material therefor, may be effected by any suitable method known in the art: see for example, "Stereochemistry of Carbon Compounds", by E. L. Eliel (McGraw Hill, 1962) and "Tables of Resolving Agents", by S. H. Wilen.

EXAMPLE 1

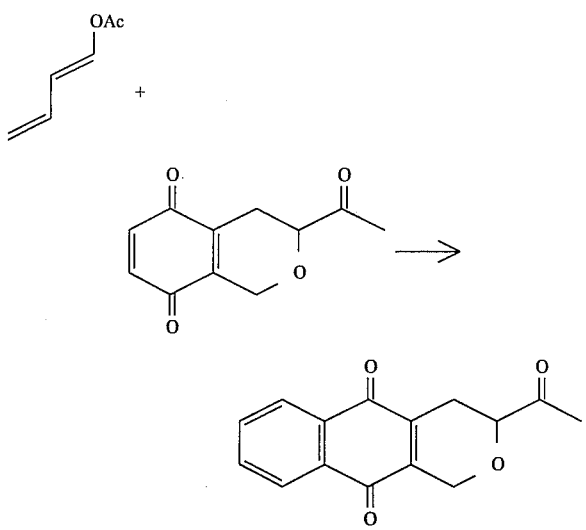

Methyl (5,10-dioxo-3,4,5,10-tetrahydronaphtho
[2,3-C] pyran-3-yl) ketone BCH-1125

A mixture of methyl (5,8-dioxo-3,4,5,8-tetrahydrobenzo [2,3-C] pyran-3-yl) ketone (100 mg, 0.485 mmol) and acetoxybutadiene (75 μl, 0.630 mmol) in dry benzene (5 mL) was heated for 12 hours at 60° C. under argon atmosphere. The solvent was then removed in vacuo and the resulting adduct dried under reduced pressure. The adduct was dissolved in 10 mL of ethanol and to this solution was added 1 mL of 1% $K_2CO_3$ aqueous solution. After stirring for 2 hours at R.T., the reaction mixture was neutralized (pH=6) and extracted with $CH_2Cl_2$ (2×50 mL). The organic layer was then washed with water (3×50 mL) and dried over $MgSO_4$. Flash chromatography (toluene:ethyl acetate; 95%:5%) of the residue gave 69 mg (55% yield) of pure titled compound. (MP: 135°–136° C.).

PMR (CDCl$_3$,250 MHz): 2.31 (s,3H,CH$_3$), 2.54 (dddd, 1H,J=18.0, 10.3,3.6 and 1.8 Hz,HCHa—CH), 2.97 (dm,1H, J=19 and 3.0 Hz,HCHe—CH=), 4.05 (dd, 1H,J=10.3 and 3.9 Hz, CH$_2$—CH), 4.58 (dt,1H,J=18.7 and 3.6 Hz,HC Ha—O), 4.92 (dd,1H,J=18.7 and 1.8 Hz,HCHe—O), 7.72 (m,2H,Ar—H), 8.04 (m,2H,Ar—H). CMR _(CDCl$_3$,75.44 MHz): 24.42 (CH$_2$—CH), 26,57 (COCH$_3$), 63.97(CH$_2$—O—), 78.63 (CH$_2$—CH), 126.70, 127.08, 132.36 and 134.52 (CH aromatic); 132.20, 134.42, 141.30, and 142.41 (C quaternary), 183.51 and 183.63 (C=O quinone), 207.25 (CO—CH$_3$).

EXAMPLE 2

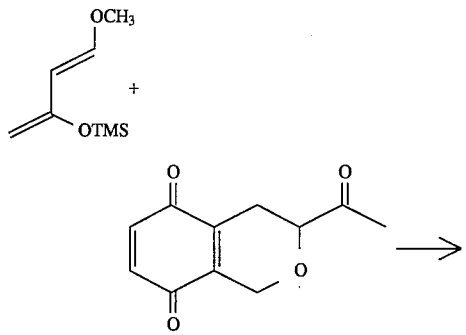

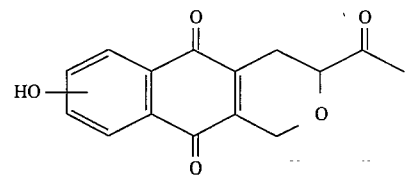

Methyl (7-hydroxy-5,10-dioxo-3,4,5,10-tetrahydronaphtho [2,3-C] pyran-3-yl) ketone BCH-1129

A mixture of 1-methoxy-3-trimethylsilyloxy butadiene (776 mg, 4.51 mmol) and methyl (5,8-dioxo-3,4,5,8-tetrahydrobenzo [2,3-C] pyran-3-yl) ketone (309 mg, 1.50 mmol) in 6 mL of dry toluene was stirred for 90 minutes at room temperature under argon atmosphere. The solvent was then removed in vacuo and the dried residue was dissolved in 10 mL of THF. To this solution was added 2 mL of a 4% aq. HCl solution. The combined organic layers were then washed with water and dried over MgSO$_4$. Flash chromatography (toluene:ethyl acetate; 95%:5%) of the residue gave 180 mg (65% yield) of the titled compound (MP: 169°–170° C.).

PMR (DMSO-d$_6$, 250 MHz): 2.24 (s,3H,CH$_3$), 2.45 (m, 1H,HCHa—CH=), 2.77 (dd,1H,J=19 and 3.0 Hz,HC He—CH),4.20 (dd,1H,J=9.8 and 3.9 Hz,CH$_2$—CH), 4.55 (d overlapped, 1H, J=22 Hz,HCHa—O—), 4.78 (d overlapped, 1H, J=18.0 Hz,HCHe—O), 7.15 (dd,1H,J=8.5 and 2.4 Hz,Ar—H), 7.30 (2d, 1H, J=2.5 Hz,Ar—H), 7.88 (2d,1H, J=9.1 Hz,Ar—H), 10.96 (s,1H,Ar—OH).

EXAMPLE 3

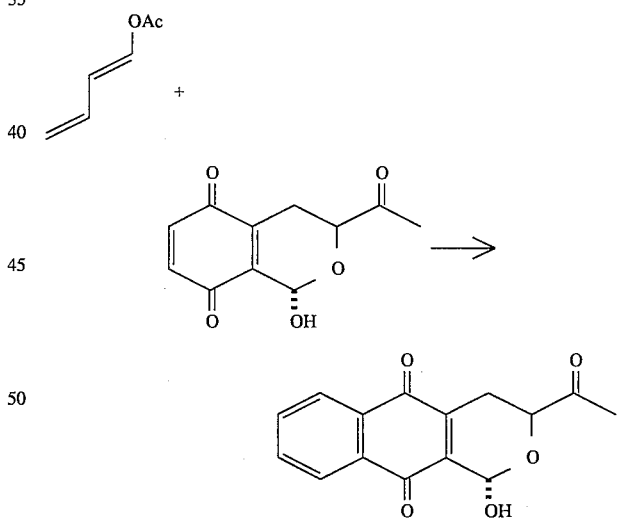

Methyl (1-hydroxy-5,10-dioxo-3,4,5,10-tetrahydronaphtho [2,3-C] pyran-3-yl) ketone BCH-1148

A mixture of methyl (1-methoxy-5,8 dioxo-tetrahydrobenzo [2,3-C] pyran-3-yl) ketone (100 mg, 0.450 mmol) and acetoxy butadiene (80 μg, 0.675 mmol) in dry benzene (5 mL) was heated for 3 hours at 60° C. under argon atmosphere. The solvent was then removed in vacuo and the resultting adduct was dissolved in 10 mL of toluene and then aromatized on silica gel by flash chromatography (toluene- :ethyl acetate; 90%:10% followed by 70%:30%). Evaporation of the solvents gave 37 mg (31% yield) of pure titled compound.

PMR (Acetone $d_6$, 250 MHz): 2.26 (s,3H,COCH$_3$), 2.50 (dd,1H,J=11.6, 19.5 Hz, HCHa—CH), 2.89 (dd,1H, J=4.2, 19.5 Hz,HCHe—CH), 4.71 (dd,1H, J=4.2,11.6 Hz,CH—CH$_2$); 6.12 (broad s,1H,CHOH); 7.87 (m,2H,ArH); 8.07 (m,2H, ArH).

EXAMPLE 4

Monofluoromethyl (5,10-dioxo-3,4,5,10-tetrahydronaphtho [2,3-C] pyran-3-yl) ketone

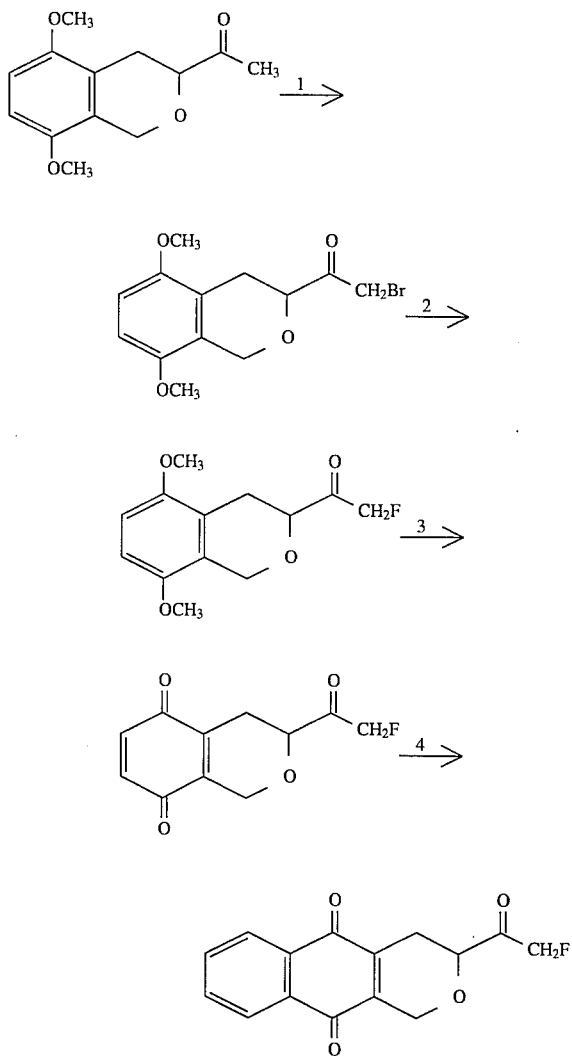

Step 1

Monobromomethyl (5,8-dimethoxy-3,4-dihydrobenzo [2,3-C] pyran-3-yl) ketone

To a stirred solution of methyl (5,8-dimethoxy-3,4-dihydrobenzo[2,3-c] pyran-3-yl) ketone (1.905 g, 8.04 mmol) and trimethylsilyl chloride (1.530 µl, 12.0 mmol) in tetrahydrofuran (48 ml) under nitrogen, at −78° C., was slowly added lithium diisopropyl amide (diisopropyl amine 10.71 mmol, n-butyl lithium 4.26 ml of a 2.5M solution in tetrahydrofuran, and 6.0 ml of tetrahydrofuran). After stirring for 10 minutes the temperature was raised to 0° C., and stirring was continued for 10 more minutes. Solvent was removed and the crude product was dissolved in 48 ml of tetrahydrofuran, N-bromosuccinamide (1,716 mg, 9.66 mmol) was added slowly to the solution. After 10 minutes, the reaction system was worked up with saturated aqueous sodium bicarbonate and washed with brine. The titled compound was obtained following flash chromatography (hexanes:ethyl acetate, 9:1) of the crude product. $^1$H NMR (benzene-$d_6$, 250 MHz) _: 2.68 (dd,1H,HCHa), 3.16 (dd, 1H,HCHe), 3.28 (s,3H,OCH$_3$), 3.32 (s,3H,OCH$_3$), 3.73 (dd, 1H,J=4.0,11.8 Hz,CH), 3.81 (dd,2H,CH$_2$Br), 4.51 (d,1H, J=15.8 Hz, HCHaO), 5.05 (d,1H,J=15.8 Hz,HCHeO), 6.335 (dd,2H,ArH),

Step 2

Monofluoromethyl (5,8-dimethoxy-3,4-dihydrobenzo [2,3-C] pyran-3-yl) ketone

To a solution of 1 equivalent (3.75 mM, 1.18 g) of bromomethyl ketone isochroman from step 1 and 3 equivalents (11.25 mM, 2.160 g) of pTSA in 20 mL of dry THF was added slowly, at R.T., 6 equi. (22.5 mM, 22.5 mL) of a 1M solution in THF of N$^+$(Bu)$_4$F$^-$. After stirring one night at R.T., 15 mL of H$_2$O were added and the mixture was extracted with 3×20 mL of ethyl acetate. After drying with NaSO$_4$ and solvent evaporation, the residue was flash chromatographed (Toluene:Ethyl acetate; 9.5:0.5) to give a 50% yield of pure titled compound.

$^1$H NMR (250 MHz, CDCl$_3$): 2.61 (dd,1H,HCHa), 3.11 (dd,1H,HCHe), 4.27 (dd,1H,CH), 4.63 (d,1H,HCHaO), 4.99 (d,1H,HCHeO), 5.33 (d, 2H, CH$_2$F), 6.67 (dd,2H,ArH).

Step 3

Monofluoromethyl (5,8-dioxo-3,4,5,8-tetrahydrobenzo [2,3-C] pyran-3-yl) ketone

To 1 equivalent (0.220 mM, 56 mg) of the fluoromethylketone isochroman from step 2 dissolved in 3 mL of acetonitrile at 0° C. was added 3 equivalents of ceric ammonium nitrate (0.66 mM). After 10 minutes, the reaction mixture was brought to R.T., stirred for 20 minutes, and then extracted with dichloromethane/THF (1/1). The organic layer was dried over MgSO$_4$. The titled quinone was obtained (67 mg) following evaporation of solvent.

$^1$H NMR (250 MHz, CDCl$_3$): $^1$H NMR (250 MHz, CDCl$_3$) _: 2.46 (dddd,1H,J=3.0,4.0,10.4,18.9 Hz,HCHa), 2.91 (dt, 1H, J=3.5, 18.9 Hz, HCHe), 4.25 (dd,J=3.8,10.4 Hz,CH), 4.445 (dt,J=3.5,18.4 Hz,HCHaO), 4.77 (dd,J=2.2, 18.5 Hz,HCHeO), 5.25 (d,2H,CH$_2$F), 6.75 (dd,2H, HC═CH).

Step 4

Monofluoromethyl (5,10-dioxo-3,4,5,10-tetrahydronaphtho [2,3-C] pyran-3-yl) ketone To 1 equivalent (0.220 mM, 50 mg) of the fluoroquinone from step 3 dissolved in 5 mL of dry toluene was added 1.3 equivalents (0.286 mM, 32.0 mg, 35 µl) of acetoxy butadiene and stirred overnight. The reaction mixture was passed directly on a silica gel column. 20 mg of pure titled compound was isolated after two flash chromatography (2% EtOAc in toluene).

PMR (Acetone-$d_6$, 250 MHz): 2.62 (dddd,1H,HCHa), 2.94 (dt,1H,HCHe), 4.46 (dd,1H,CH), 4.62 (dt,1H,HCHa), 4.84 (dd,1H,HCHe), 5.43 (d, 2H, CH$_2$F), 7.83 (m, 2H,ArH), 8.03 (m,2H,ArH).

EXAMPLE 5

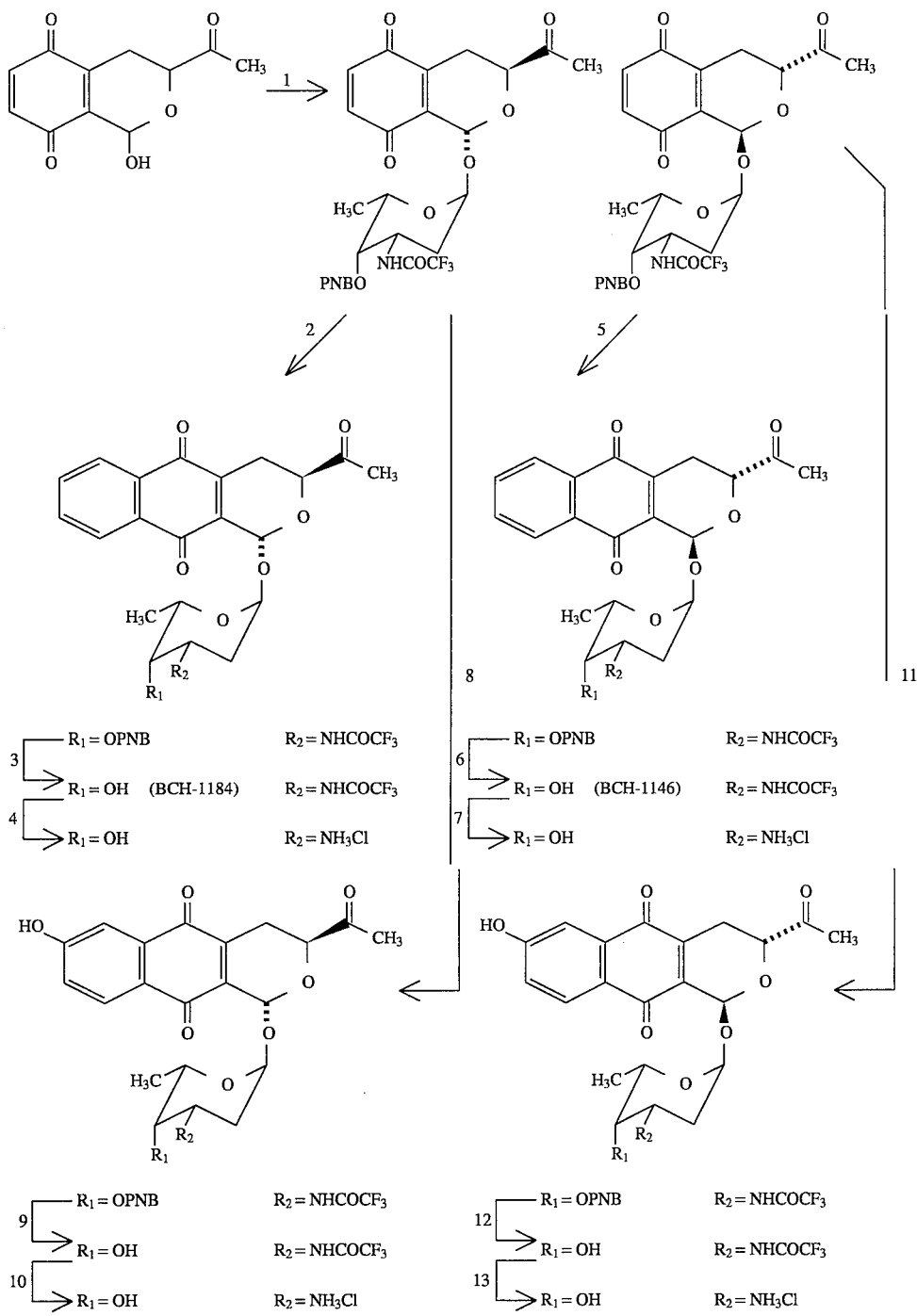

Step 1

(1'S,1R,3S) and (1'S,1S,3R)-Methyl (5,8-dioxo-1-(2',3',6'-trideoxy-3'-trifluoroacetamido-4'-O-p-nitrobenzoyl-L-lyxo-hexopyranose)-3,4,5,8-tetrahydrobenzo [2,3-C] pyran-3-yl) ketone To a stirred solution of 1,4-di-O-p-nitrobenzoyl-N-trifluoroacyl daunosamine (1.584 g, 2.93 mmol) in 160 mL of dry dichloromethane and 40 mL of anhydrous ether, maintained at −35° C. under argon atmosphere, was added dropwise 1.132 mL (5.85 mmol) of trimethyl silyl triflate (TMSOTf).

After stirring for 1.5 hours at 0° C., the temperature was lowered to −15° C. and a cooled (0° C.) solution of methyl (1-hydroxy-5,8-dioxo-3,4,5,8-tetrahydrobenzo [2,3-C] pyran-3-yl) ketone in dry dichloromethane (40 mL) was added. After 5 hours of stirring, the reaction mixture was put into a solution of 150 mL of ethyl acetate and 50 mL of a saturated $NaHCO_3$ solution. The organic layer was washed with water and dried ($Na_2SO_4$). Flash chromatography of the residue gave 917 mg (69% yield) of the mixture of titled stereoisomers. A second flash chromatography seperated the individual diastereomers.

The 1'S,1S,3R titled diastereomer had ¹H NMR (250 MHz, acetone-d₆) _: 1.28 (d,3H,J=6.4 Hz,CH₃), 2.05 (hidden m, 1H,2'-CH₂), 2.30 (s,1H, COCH₃), 2.42–2.49 (m,2H, 2'-CH₂ overlapped with HCHe), 2.84 (dd,1H,HCHe,) 4.53–4.65 (broad m,1H,3'-CH), 4.635 (dd,2H,J=4.2, 11.6 Hz,O—CH—COCH₃), 4.76 (broad q,1H,5'-CH), 5.50 (broad s,1H,4'-CH), 5.69 (broad s,1H,1'-CH), 6.02 (s,1H, O—CH—O), 6.90 (dd,2H,2×C=CH), 8.37 (m,4H,ArH), 8.68 (broad d,1H,NH).

The 1'S,1R,3S titled diastereomer had ¹H NMR (250 MHz, acetone-d₆) _: 1.19 (d,3H,J=6.6 Hz,CH₃), 1.89 (dd, 1H,J=4.6,13.1 Hz,2'-CH₂),2.32 (s, 3H,COCH₃), 2.29–2.47 (m,2H,2'-CH₂ overlapped with HCHa), 2.89 (dd,1H, J=4.1 Hz,HCHe), 4.60 (m,2H,3'-CH overlapped with 5'-CH), 4.71 (dd,1H, J=4.1,11.5 Hz,O—CH—COCH₃), 5.48 (broad s, 1H,4'-CH), 5.64 (broad s, 1H,1'-CH), 5.89 (s,1H,O—CH—O), 6.87 (dd,2H,2×C=CH), 8.37 (dd,4H, ArH), 8.69 (broad d, 1H, NH).

Step 2

(1'S,1R,3S) -Methyl 5,10-dioxo-1-(2',3',6'-trideoxy-3'-trifluoroacetamido-4'-O-p-nitrobenzoyl-L-lyxohexo-pyranose)-3,4,5,10-tetrahydroxtaphtho [2,3-C] pyran-3-yl) ketone To a stirred solution of 1'S, 1R, 1S -diastereomer, from step 1 (Example 5), (0.464 mmol) in dry benzene (10 mL) under argon was added 78 μl (696 mL) of 1-acetoxybutadiene. After stirring for 16 hours at room temperature, the reaction mixture was flash chromatographed (toluene:ethyl acetate; 90%:10%) to give 244 mg (82% yield) of the pure titled compound.

¹H NMR (250 MHz, acetone-d₆): 1.22 (d,3H,J=6.4 Hz,CH₃), 1.94 (dd,1H,J=4.7,13.1 Hz,2'-CH₂), 2.35 (s,3H, COCH₃), 2.42 (m, 1H,2'-CH₂), 2.52 (dd,1H,J=11.6,19.8 Hz,HCHa), 3.04 (dd,1H,J=3.9,19.6 Hz, HCHe), 4.55–4.68 (overlapped m,2H,3'-CH and 5'-CH), 4.79 (dd, 1H,J=4.0, 11.5 Hz,O—CH—COCH₃), 5.49 (broad s,1H,4'-CH), 5.75 (broad s,1H,1'-CH), 6.07 (s,1H,O—CH—O), 7.83–7.93 (m,2H,ArH), 8.06–8.14 (m,2H,ArH), 8.32–8.43 (m,4H, ArH), 8.67 (broad d,1H,NH).

Step 3

(1'S,1R,3S)-Methyl (5,10-dioxo-1-(2',3',6'-trideoxy-3'-trifluoroacetamido-4'-hydroxy-L-lyxohexopyranose)-3,4,5,10-tetrahydronaphto [2,3-C] pyran-3-yl) ketone BCH-1184

To a stirred solution of the glycoside from step 2, (30 mg, 4.65×10⁻⁵ mmol) in 4 mL of dry methanol and 1 mL of anhydrous THF at 0° C. and under argon, was added 11 μl (4.66×10⁻⁵ mmol) of NaOCH₃ (4.37M) solution in methanol. After 5 minutes: of stirring, the reaction was quenched with 1 mL of saturated NH₄Cl solution and extracted with CH₂Cl₂. Following evaporation of solvent, flash chromatography of the residue gave 23 mg (100% yield) of pure titled compound.

¹H NMR (250 MHz, Acetone-d₆): 1.25 (d,3H,J=6.5 Hz,CH₃), 1.76 (dd,1H, J=4.5,12.9 Hz,2'-CH₂), 2.16 (m,1H, 2'-CH₂), 2.32 (s,3H,COCH₃), 2.48(dd, J=11.6,19.5 Hz,HCHa), 2.99 (dd, 1H,J=4.1,19.5 Hz,HCHe), 3.68 (broad s,1H, 4'-CH), 4.17–4.41 (overlapped m,2H,3'-CH and 5'-CH), 4.69 (dd, 1H,J=4.0,11.0 Hz,O—CH—COCH₃), 5.53 (broad s,1H, 1'-CH), 5.97 (s,1H,O—CH—O), 7.82–7.90 (m,2H, ArH), 8.01–8.05 (m,2H,ArH), 8.13 (broad d, 1H,NH).

Step 4

(1'S,1S,3R)-Methyl (5,10-dioxo-1-(2',3',6'-trideoxy-3'-trifluoroacetamido-4'-O-p-nitrobenzoyl-L-lyxohexo-pyranose)-3,4,5,10-tetrahydroxxaphtho [2,3-C] pyran-3-yl) ketone Application of the procedure described in step 2 of the present example on the 1'S, 1S, 3R quinone glycoside from step 1 gave the titled compound which had:

¹H NMR (250 MHz, Acetone-d₆): 1.33 (d,3H,J=6.6 Hz,CH₃), 1.94 to 2.08 (m,1H,2'-CH₂), 2.33 (s,3H, COCH₃), 2.49 (m, 1H,2'-CH₂), 2.58 (dd,1H, J=11.7,19.6 Hz,HCHa), 3.01 (dd,1H,J=4.1,19.7 Hz,HCHe), 4.53–4.65 (m, 1H,3'-CH), 4.71 (dd, 1H,J=4.1,11.5 Hz,O—CH—COCH₃), 4.90 (broad q,1H, 5'-CH), 5.53 (broad s,1H,4'-CH), 5.75 (broad s,1H,1'-CH), 6.21 (s, 1H,O—CH—O), 7.88–7.92 (m,2H, ArH), 8.08–8.16 (m,2H,ArH), 8.34–8.43 (m,4H,ArH), 8.69 (broad d,1H,NH).

Step 5

(1'S,1R,3S) -Methyl (5,10-dioxo-1-(2',3',6'-trideoxy-3'-trifluoroacetamido-4'-O-p-nitrobenzoyl-L-lyxohexo-pyranose)-7-hydroxy-3,4,5,10-tetrahydronaphto [2,3-C] pyran-3-yl) ketone Treatment of the glycoside obtained from step 5 with sodium methoxide as described in step 3 of this example yielded the titled compound, which had:

¹H NMR (250 MHz, Acetone-d₆) 1.35 (d, 3H,J=6.4 Hz,CH₃), 1.77(dd, 1H, J=4.5,12.9 Hz,2'-CH₂), 2.17 (dt,1H, J=3.7,12.9 Hz,2'-CH₂), 2.30 (s,3H, COCH₃), 2.56 (dd,1H, J=10.7,19.6 Hz,HCHa), 2.98 (dd,1H,J=4.2,19.8 Hz, HCHe),3.70 (broad s,1H,4'-CH), 4.2–4.4 (m, 1H,3'-CH), 4.60 (broad quartet,1H,5'-CH), 4.66 (dd,1H,J=4.2,11.5 Hz,O—CH—COCH₃), 5.52 (broad d,1H,1'-CH), 6.15 (s,1H,O—CH—O), 7.86–7.92 (m,2H,ArH), 8.07–8.11 (m,2H,ArH), 8.15 (broad d,1H,NH).

Step 6

(1'S,1S,3R)-Methyl (5,10-dioxo-1-(2',3',6'-trideoxy-3'-trifluoroacetamido-4'-hydroxy-L-lyxohexopyranose)-3,4,5,10-tetrahydronaphto [2,3-C] pyran-3-yl) ketone BCH-1146

The titled compound was prepared in 62% yield by cyclocondensing the 1'S, 1R, 3S-quinone glycoside from step 1 of this example with 1-methoxy-3-trimethylsilyloxybutadiene. The same procedure as described in step 2, in this example, was used.

¹H NMR (250 MHz, Acetone-d₆): 1.21 (d,3H,J=6.6 Hz,CH₃), 1.93 (m,1H, 2'-CH₂), 2.34 (s,3H,COCH₃), 2.49 (dd,1H,J=11.6,19.5 Hz,HCHa), 3.00 (dd,1H,J=4.1,19.5 Hz,HCHe), 4.57–4.69 (overlapped multiplets, 2H,3'-CH and 5'-CH),4.76 (dd,1H,J=4.0,11.5 Hz,O—CH—COCH₃), 5.49 (broad s, 1H,4'-CH), 5.73 (broad d,1H,1'-CH), 6.04 (s,1H, O—CH—O), 7.25 (dd, 1H,J=2.5,8.5 Hz,ArH), 7.46 (d,1H, J=2.5 Hz,ArH), 7.98 (d,1H,J=8.6 Hz, ArH), 8.38 (m,4H, ArH), 8.58 (broad d,1H,NH) 10.23 (broad s,1H, ArOH).

Step 7

(1'S,1R,3S)-Methyl (5,10-dioxo-1-(2',3',6'-trideoxy-3'-trifluoroacetamido-L-lyxohexopyranose)-7-hydroxy-3,4,5,10-tetrahydro [2,3-C] pyran-3-yl) ketone BCH-1181

Application of the hydrolysis procedure described in step 3 of this example to the 1'S, 1R, 3S tricyclic glycoside of step 8 resulted in the removal of the p-nitrobenzoyl protecting group. The titled compound had:

¹H NMR (250 MHz, Acetone-d₆): 1.63 (d,3H,J=6.4 Hz,CH₃), 2.14 (m, 1H, 2'-CH₂), 2.53 (m, 1H,2'-CH₂), 2.70 (s,3H,COCH₃), 2.87 (dd,1H,J=11.7, 19.4 Hz,HCHa), 3.35 (dd,1H,J=4.1,19.4 Hz,HCHe), 4.07 (broad s,1H,4'-CH), 4.65 (overlapped m,2H,3'-CH and 5'-CH), 5.07 (dd,1H, J=4.1, 11.7 Hz, O—CH—COCH₃), 5.91 (broad d,1H,1'-CH), 6.35 (s,1H,O—CH—O), 7.64 (dd,1H,J=2.5,8.5 Hz,ArH), 7.84 (d,1H,J=2.5 Hz,ArH), 8.35 (d,1H,J=8.5 Hz,ArH), 8.48 (broad d,1H,NH), 10.23 (broad s,1H,ArOH).

Step 8

(1'S,1S,3R)-Methyl (5,10-dioxo-1-(2',3',6'-trideoxy-3'-trifluoroacetamido-4'-O-p-nitrobenzoyl-L-lyxohexo-pyranose)-7-hydroxy-3,4,5,10-tetrahydronaphtho [2,3-C] pyran-3-yl) ketone The titled compound was prepared by applying the same procedure as described in step 8 on the 1'S, 1S, 3R, quinone glycoside of step 1 of this example.

¹H NMR (250 MHz, Acetone-d₆): 1.32 (d,3H,J=6.4 Hz,CH₃),2.08 (m,1H, 2'-CH₂), 2.51 (m,1H,2'-CH₂) 2.55 (dd,1H,J=11.5,19.5 Hz,HCHa), 2.96 (dd,1H, J=4.2,19.6 Hz, HCHe), 4.51–4.62 (m,1H,3'-CH), 4.68 (dd,1H, J=4.2,11.5 Hz,O—CH—COCH₃), 5.52 (broad s,1H,4'-CH), 5.73 (broad s,1H, 1'-CH), 6.18 (s,1H,O—CH—O), 7.28 (dd,1H, J=2.6,8.5 Hz,ArH), 7.47 (dd, 1H,J=2.6,8.5 Hz,ArH), 8.03 (d,1H,J=8.5 Hz,ArH), 8.38 (m,4H,ArH), 8.68 (broad d,1H, NH), 9.85 (broad s,1H,ArOH).

Step 9

(1'S,1S,3R) -Methyl (5,10-dioxo-1-(2',3',6'-trideoxy-3'-trifluoroacetamido-L-lyxohexopyranose)-7-hydroxy-3,4,5,10-tetrahydro [2,3-C] pyran-3-yl) ketone BCH-1180

Application of the hydrolysis procedure described in step 3 of this example to the 1'S, 1S, 3R tricyclic glycoside of step 11 resulted in the removal of the p-nitrobenzoyl protecting group. The titled compound had:

¹H NMR (250 MHz, Acetone-d₆) 1.73 (d,3H,J=6.6 Hz,CH₃), 2.17 (m,1H, 2'-CH₂), 2.58 (m,1H,2'-CH₂), 2.68 (s,3H, COCH₃), 2.90 (dd,1H,J=11.6, 19.7 Hz, HCHa), 3.33 (dd,1H,J=4.3,19.8 Hz,HCHe), 4.09 (broad s,1H,4'-CH), 4.63 (m,1H,3'-CH), 4.95–5.06 (overlapped m,2H,5'-CH, and OCH—COCH₃), 5.91 (broad d,1H,1'-CH), 6.51 (s,1H,O—CH—O), 7.65 (dd,1H, J=2.6,8.5 Hz,ArH), 7.85 (d,1H,J=2.6 Hz,ArH), 8.38 (d,H,J=8.5 Hz, ArH), 8.52 (broad d,1H,NH), 10.18 (broad s,1H,ArOH).

EXAMPLE 6

2-[4,-Hydroxy-1',2'-dioxo-3'-cyclobutenoxy] methyl-(5,10-dioxo-3,4,5,10-tetrahydronaphtho [2,3-C] pyran-3-yl) ketone

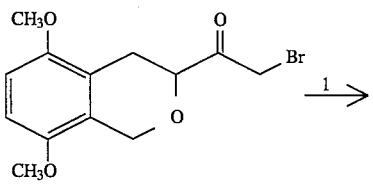

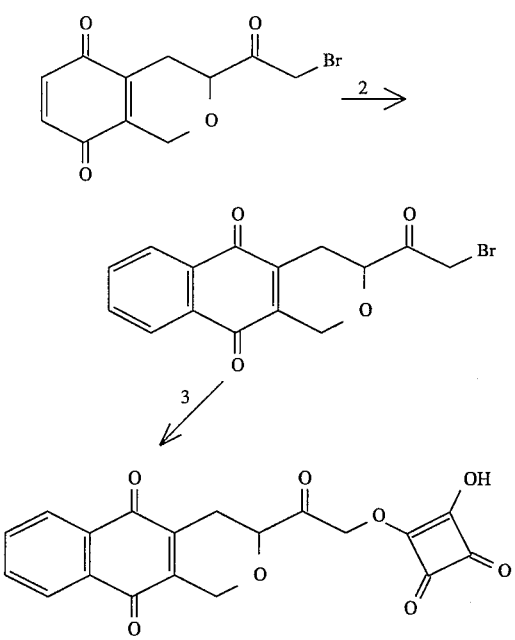

Step 1

Bromomethyl (5,8-dioxo-5,8-dihydrobenzo [2,3-C] pyran-3-yl) ketone

To a solution containing one equivalent of 5,8-dimethoxy-3-bromoacetoisochroman (380 mg, 1.1 mmol) in acetonitrile (18 ml), at 0° C. under argon, was added dropwise an aqueous solution of ceric ammonium nitrate (6.5 g in 28 ml H₂O). After stirring for 10 minutes, the mixture was extracted with 3×20 ml of CH₂Cl₂. The combined organic layer was dried over MgSO₄ and then evaporated to yield 263 mg of pure titled compound.

¹H NMR (250 MHz,CDCl₃): 2.43–2.69 (m,1H,CH₂), 2.82–3.07 (m,1H,CH₂), 4.24 (dd,2H,CH₂Br), 4.4–4.6 (m,2H,CH₂O and CHCOCH₂Br), 4.52 (d,1H, CH₂O), 6.74 (dd,2H,HC=CH).

Step 2

Bromomethyl (5,10-dioxo-5,10-dihydronaphtho [2,3-C] pyran-3-yl) Ketone

To a solution containing one equivalent of isochromandione (263 mg, 0.92 mmol) from step 1 (example 6) in 25 ml of dry toluene was added three equivalents (2.7 mmol) of acetoxybutadiene. The reaction mixture was stirred overnight under argon at room temperature and then two hours at 60° C. After removal of solvent, the crude product was flash chromatographed (toluene/EtOAc, 9:1). The titled orange compound was isolated (192 mg) in 62% yield.

¹H NMR (250 MHz,CDCl₃): 2.4–2.6 (m,1H,CH₂), 2.7–3.2 (m, 1H,CH₂), 4.3–4.4 (m,2H,CH₂Br), 4.45 (m, 1H,CH—O), 4.6–4.7 (m,1H,CH₂O), 4.9–5.05 (m,1H, CH₂O), 7.6 (m,2H,ArH), 8.1 (m,2H,ArH).

Step 3

2-[4'-Hydroxy-1',2'-dioxo-3'-cyclobutenoxy] methyl (5,10-dioxo-3,4,5,10-tetrahydro [2,3-C] pyran-3-yl) ketone Under argon at room temperature, two equivalents (0.9 mmol) of squaric acid and two equivalents of CsCO₃ (0.9 mmol) were disolved in 10 ml of dry dimethyl formamide (DMF) (non homogeneous solution). To this solution was added one equivalent (0.45 mmol) of the pyranonaphthoquinone from step 3 (example 6). The solution was treated at 60° C. for two hours. After cooling, 10 ml of $H_2O$ was added, and extraction was carried out with 3×10 ml ETOAc. After drying and evaporation, the residue was purified twice by preparative TLC. The titled compound was obtained in 30% yield.

$^1$H NMR (250 MHz, Acetone-$d_6$): 2.5–2.6 (m,1H,$CH_2$), 2.8–3.0 (m,1H, $CH_2$), 4.4 (m,1H,CH—O), 4.6 (overlapped m,2H,$COCH_2O$), 4.8–5.0 (m,2H, $CH_2O$), 7.7 (m,2H,ArH), 8.1 (m,2H,ArH).

EXAMPLE 7

Tricyclic pyranylnaphthoquinone glycosides with a squaric acid side chain

Example 7

Tricyclic pyranylnaphtoquinone glycosides with a squaric acic moiety

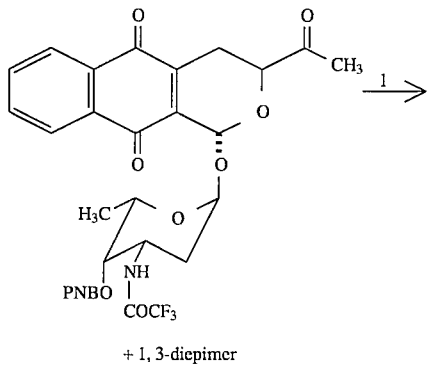
+ 1, 3-diepimer

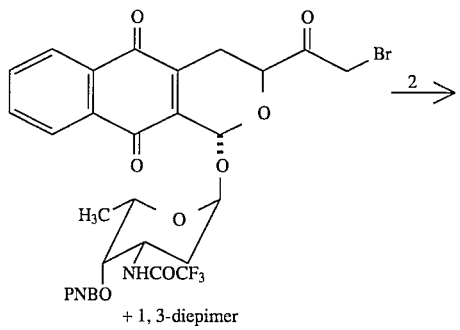
+ 1, 3-diepimer

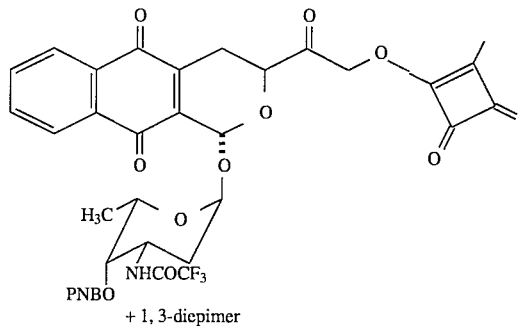
+ 1, 3-diepimer

Step 1

(1'S,1R,3S) and (1'S,1S,3R)-Bromomethyl (5,10-dioxo-1-(2',3',6'-trideoxy-4'-O-P-nitrobenzoyl-3'-trifluoro acetamido-L-lyxohexopyranose)-(3,4,5,10-tetrahydronaphtho [2,3-C] pyran-3-yl) ketone At room temperature, under $N_2$, to one equivalent (0.482 mmol) of a 1:1 mixture starting quinone glycosides from steps 3 and 6 (example 1) dissolved in 6 ml dry tetra hydro furan (THF) was added 1.1 equivalent of pyridinium hydrobromide perbromide. After two hours, to the solution was added 7 ml 5% $NaHCO_3$ solution and extracted with 3×10 ml EtOAc. After drying over $Na_2SO_4$ and evaporation, the residue was chromatographed using 95% toluene −5% EtOAc solvent. Two major fractions were isolated corresponding to the 2 isomers (yield 40% of pure compounds, ratio #1/1 isomer). PMRs of the separated isomers are described in step 1 (example 8) and step 1 (example 9).

Step 2

(1'S,1R,3S) and (1'S,1S,3R)-2-[4'-hydroxy-1',2'-dioxo-3'-cyclobutenoxy] methyl (5,10-dioxo-1-[2",3",6"-trideoxy-4"-O-p-nitrobenzoyl-3"-trifluoroacetaunido-L-lyxohexopyranose]-3,4,5,10-tetrahydronaphtho [2,3,c] pyran-3-yl) ketone The title compounds were obtained by applying the procedure described in step 4 (example 6) to the tricyclic glycosides from step 1 (example 7).

$^1$H NMR (250 MHz, $CD_3OD$): 1.2 (d,3H,5"-$CH_3$), 1.9 (dd,1H,2"-$CH_2$), 2.42 (m,1H,2"-$CH_2$), 4.6 (m,2H,CO—$CH_2$—O), 4.8 (m,1H,OCH—CO), 5.5 (m,1H,4"-CH), 5.8 (m,1H,1"-CH), 6.1 (m,1H,O—$C_1$H—O), 7.7–7.9 (m,2H, arom H), 8.05–8.1 (m,2H, arom H), 8.3–8.45 (m,4H, arom H), 8.7 (broad d,1H,NH), 3.1 (m,1H, $C_4$—H), 2.6 (m,1H, $C_4$—H), 4.6–4.2 (overlapped m, 2H, 3"-CH and 5"-CH).

EXAMPLE 8

Example 8

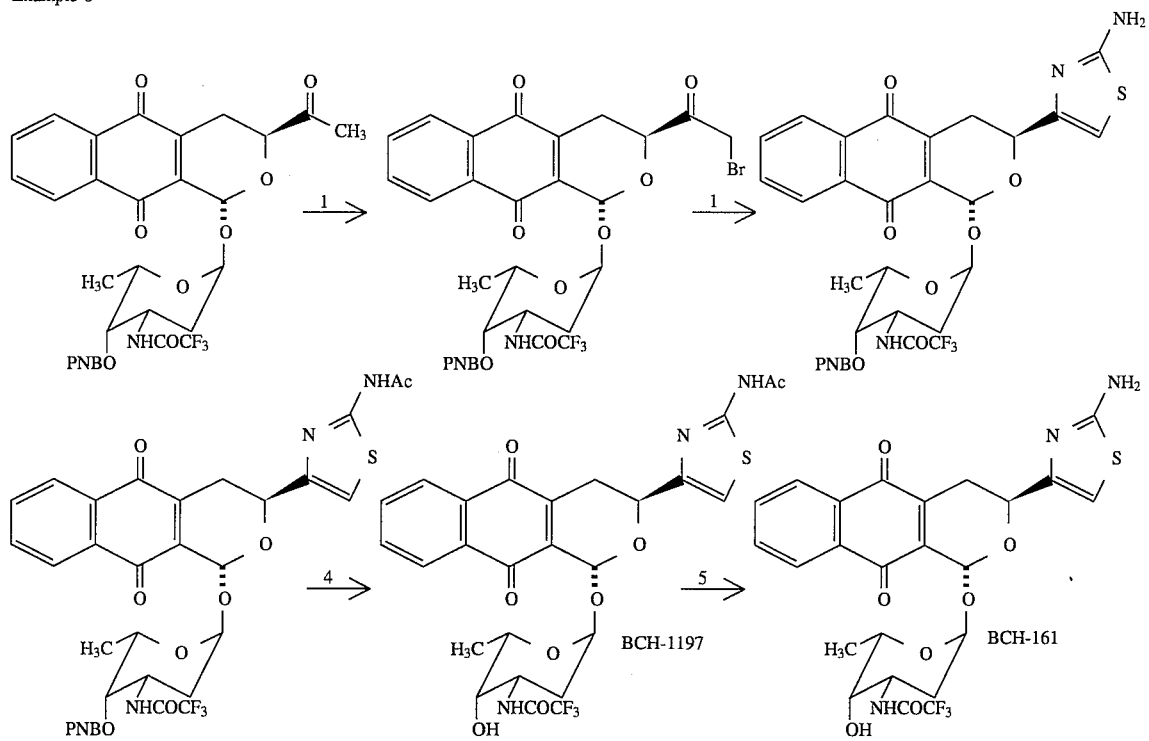

This example exemplifies interconversion of functional groups wherein a methyl ketone; at $R_6$ is eventually converted to a substituted thiazole ring.

Step 1

(1'-S, 1-R, 3-S)-1-(2'-3'-6'-trideoxy-4'-p-nitrobenzoyl-3'-trifluoroacetamido-L-lyxohexopyranose)-3-(2-bromo-acetyl)-5,10-dioxo-3,4,5,10-tetrahydro-1H-naphtho-(2,3-c)-pyran To a solution of (1'-S,1-R3-S)-1-(2',3',6'-trideoxy-4'-p-nitro-benzoyl-3'-trifluoroacetamido-L-lyxohexopyranose)-3-acetyl-5,10-dioxo-3,4,5,10-tetrahydro-1H-naphtho-(2,3-c)-pyran (87 mg, 0.135 mmole) in tetrahydrofuran (THF) (4.5 ml), stirred at room temperature, was added slowly a solution of pyridinium hydrobromide perbromide (43.1 mg, 0.136 mmole) in 3 ml of THF. The resulting yellow liquid was stirred for 2 hours at room temperature, then poured into water. Methylene chloride was used to extract the crude product from the aqueous layer. The combined methylene chloride extracts were washed with brine (10 ml) then dried over anhydrous sodium sulfate. The organic solvent was evaporated and the crude product was obtained as a orange oil (98 mg). Chromatographic purification (by volume, ethyl acetate:toluene ~1:5) of the crude product gave a yellow sticky solid (40 mg) as a pure compound. A mixture (48 mg) containing the product (>34% mol) and unreacted starting material (<66% mol) was also obtained.

M.P. (Electrothermal IA-9100): 125°–130° C.; decomposed at 175° C.

$^1$H NMR (250 MHz, acetone-$d_6$):1.25 (d,3H,J=6.5 Hz,6'-CH$_3$), 1.97 (dd, 1H,J=4.8 Hz,13.7 Hz,2'-HCHa), 2.48 (dt, 1H,J=4.2 Hz,13.7 Hz,2'-HCHe), 2.64 (dd,1H,J=11.6 Hz,25.6 Hz,4-HCHa), 3.14 (dd,1H,J=5.7 Hz,25.6Hz,4-HCHe), 4.66 (S,2H, COCH$_2$Br), 4.71 (qua,1H,J=6.5 Hz,5'-CH), 4.83 (overlapped m,1H,3'-CH), 5.08 (dd, 1H, J=5.7 Hz,11.6 Hz,3-CH), 5.52 (bs,1H,4'-CH), 5.79 (bd,1H,J=3.0 Hz,1'-CH), 6.10 (S,1H,1-CH), 7.90 (m,2H,7,8-ArH), 8.08 (m,2H, 6,9-ArH), 8.36 (d,2H,J=7.4 Hz,PNB—COC (CH)$_2$), 8.41 (d,2H,J=7.4 Hz,PNB—NO$_2$C(CH)$_2$), 8.75 (d,1H,J=7.7 Hz,3'-NHCOCF$_3$).

IR(Nicolet 205 FT, film on Nacl tablet), cm$^{-1}$, 3625.9 (br,w), 3346.4 (str) 3079.5, 2955.5, 172.2.6 (str), 1665.4 (str), 1596.0, 1530.9, 1274.5 (str), 1173.7, 1100.1, 974.04, 959.33 (m), 875.28, 721.29 (m).

Step 2

(1'S,1-R,3-S)-1-(2',3',6'-trideoxy-4'-p-nitrobenzoyl-3'-trifluoroacetamido-L-lyxohexopyranose)-3-(2-aza-3-aminothiazolyl)-5,10-dioxo-3,4,5,10-tetrahydro-1H-naphtho-(2,3-c)pyran To a suspension of thiourea (2.2 mg, 0.027 mmole) in ether (2 ml) was added a solution of bromomethyl ketone (20 mg, 0.026 mmole), from the previous step in methylene chloride (1 ml). The reaction mixture was stirred at room temperature for 20 minutes when a newly formed white suspension was observed. The reaction mixture was further stirred for 3 hours.

Solvents were removed under reduced pressure to give a white solid which was treated with saturated sodium bicarbonate aqueous solution and extracted with methylene chloride (4×3 ml). The organic layer was dried (over sodium sulfate) and evaporated to give a crude product which was chromatographed (by volume, chloroform:methanol 100:3, with one drop of pyridine) to yield the titled substance (3.5 mg) as a light colored solid.

M.P. (Electrothermal IA-9100): 142° C. (decomposed).

$^1$H NMR (250 MHz, acetone-$d_6$), δ: 1.13 (d,3H,J=6.7 Hz,6'-CH$_3$), 1.92 (dd,1H,J=5.4 Hz, 12.8 Hz,2'-HCHa), 2.42 (dt, 1H,J=3.4 Hz,12.8 Hz,2'-HCHe), 2.71 (dd,1H, J=12.2

Hz,20.3 Hz,4-HCHa), 3.12 (dd,1H,J=3.4 Hz,20.3 Hz,4-HCHe), 4.65 (m,1H,3'-CH), 4.67 (qua,1H,J=6.7 Hz,5'-CH), 5.18 (dd,1H,J=3.4 Hz, 12.2 Hz, 3-CH), 5.50 (bs,1H,4'-CH), 5.68 (d,1H,J=2.7 Hz,1'-CH), 5.99 (s,1H,1-CH), 6.67 (S,1H, thiazole—CH), 7.90 (m,2H,7,8-ArH), 8.11 (m,2H,6,9-ArH), 8.35 (d,2H,J=9.4 Hz,PNB—COC(CH$_2$), 8.42 (d,2H,J=9.4 Hz, PNB—NO$_2$C(CH$_2$)).

IR (Nicolet 205 FT, film on NaCl plate): cm$^{-1}$, 3455.4 (w), 3346.8 (str), 3119.6 (w), 2923.8, 2850.3, 1731.5 (str), 1665.0 (str), 1532.2 (str), 1273.4 (str), 1217.5, 1182.5 (m), 1161.5 (m), 1101.8, 1005.5, 957.36 (m), 874.2, 721.18 (m).

Step 3

(1'S,1-R,3-S)-1-(2',3',6'-trideoxy-3'-trifluoroacetamido-4'-p-nitrobenzoyl-L-lyxohexopyranose)-3-(2-aza-3-acetamidothiazolyl)-5,10-dioxo -3,4,5,10-tetrahydro-1H-naphtho-[2,3-c]-pyran A solution of bromomethyl ketone (10 mg, 8 mmol), from step 1 (example 8), in methylene chloride (0.5 ml) was added to an ether solution (2 ml) of 1-methylthiourea (1.1 mg, 1.0 mmol). The reaction mixture was stirred for 3 hours at room temperature then 3 hours at 40° C. Solvent was evaporated and the crude product was analyzed by $^1$H NMR to see if the reaction was incomplete. The reaction mixture was redissolved in methylene chloride (0.5 ml) and ether (4 ml) and then stirred with newly added 1-acetylthiourea (1 mg, 1.0 mmol) and sodium iodide (0.06 mg, 0.05 mol. eqv.) at 40° C. for 1 hour. Solvent was evaporated to give a crude product which was chromatographed (Eluent in volumn ratio, chloroform:methanol 20:1, with 1 drop of pyridine) to yield the title substance as a light colored solid (6 mg).

M.P. (Electrothermal IA-9100): 145°–150° C., decomposed at 195° C.

$^1$H NMR (250 MHz, acetone-d$_6$), δ: 1.09 (d,3H,J=7.4 Hz,6'-CH$_3$), 1.92 (dd,1H,J=4.7 Hz,12.1 Hz,2'-HCHa), 2.42 (dt,1H, J=2.3 Hz,12.1 Hz,2'-HCHe), 2.75 (dd,1H,J=11.7 Hz,19.5 Hz,4-HCHa), 3.14 (dd, 1H,J=2.3 Hz, 19.5 Hz,4-HCHe), 4.62 (qua,1H,J=7.4 Hz,5'-CH), 4.64 (m,1H,3'-CH), 5.31 (dd,1H,J=2.3 Hz, 11.7 Hz,3-CH), 5.47 (bs,1H,4'-CH), 5.68 (bs,1H, 1'-CH), 6.00 (s,1H,1-CH), 7.20 (s,1H,thiazole—CH), 7.90(m,2H,7.8-ArH), 8.11 (m,2H,6.9-ArH), 8.34 (d,2H,J=7.8 Hz,PNB:CO—C—(CH$_2$), 8.40 (d, 2H,J=7.8 Hz,PNB:NO$_2$-C—(CH$_2$)), 8.72 (d,1H,J=7.4 Hz, 3'-NH-COCF$_3$), 11.08 (S,1H, thiazole—NHAc).

IR (Nicolet 205 FT, film on NaCl plate): 3539.7 (br,w), 3296.1 (str), 3083.7, 2919.4 (str), 1732.7 (str), 1667.5 (str), 1593.9 (w), 1545.7 (str), 1528.7 (str), 1127.1 (str), 1217.2, 1183.2, 1166.2, 1104.0, 1008.9, 975.46, 956.53, 718.14 (m).

Step 4

(1'-S,1-R,3-S)-1-(2',3',6'-trideoxy-3'-trifluoro acetamido-L-lyxohexopyranose)-3-(2-aza-3-acetamido thiazolyl)-5,10-dioxo-3,4,5,10-tetrahydro-1H-naphtho-[2,3-c]-pyran To an ice-cold solution of PNB-derivative (3 mg, 4.1 mmol), from the previous step, in a tri-solvent system containing water (98 μl), MeOH (422 μl) and methylene chloride (158 μl) was added an aqueous solution (20 μl) of sodium bicarbonate (0.51 mg, 6.11 mmol). The reaction mixture was then stirred at room temperature for 1 hour. When the reaction was completed, (as judged by thin-layer-chromatography), the reaction mixture was poured into a bi-layer system of methylene chloride and saturated aqueous ammonium chloride solution (5 ml/5 ml). The well-shaken mixture was then allowed to settled and the organic layer was separated, dried over sodium sulfate, and evaporated to give the titled substance as a light colored solid (1.4 mg).

M.P. (Electrothermal IA-9100): 160°–165° C., decomposed at 195° C.

$^1$H NMR (250 MHz, acetone-d$_6$), δ: 1.12 (d,3H,J=7.9 Hz,6'-CH$_3$), 1.24 (dd,1H,J=6.7 Hz,15.0 Hz,2'-HCHa), 2.14 (dt,1H,J=4.2 Hz,15.0 Hz,2'-HCHe), 2.25 (s,3H,COCH$_3$), 2.64 (dd,1H,J=12.5 Hz,20.9 Hz,4-HCHa), 3.13 (dd,1H,J= 4.2 Hz,20.9 Hz,4-HCHe), 3.63 (bs,1H,4'-CH), 4.21 (qua,1H, J=7.9 Hz, 5'-CH), 4.30 (m,1H,3'-CH), 5.26 (dd,1H,J=4.2 Hz,12.5 Hz,3'-CH), 5.50 (d,1H,J=2.4 HZ,1'-CH), 5.97 (s,1H,1-CH), 7.12 (s, 1H, thiazole—CH), 7.90 (m,2H,7.8, ArH), 8.10 (m,2H,6.9,ArH), 11.07 (s,1H, thiazole—NHAc).

IR (Nicolet 205 FT, film on NaCl plate): 3668.0–3119.7 (peaked at 3268.3,br,str), 3073.7 (w), 2925.1, 1711.8 (str), 1669.4 (str), 1591.6 (w), 1549.1, 1375.8, 1290.9 (str), 1170.6, 1006.5 (w), 984.49(str), 716.33 (w).

Step 5

(1'-S,1-R,3-S)-1-(2',3',6'-trideoxy-3'-trifluoro acetamido-L-lyxohexopyranose)-3-(2-aza-3-aminothiazolyl)-5, O-dioxo-3,4,5,10-tetrahydro-1H-naphtho-[2,3-C] pyran To a sample of PNB-derivative (2.5 mg, 3.5 μmol) from step 2, dissolved in a tri-solvent system containing water (85.7 μl), methanol (370 μl) and methylene chloride (138 μl), at 0° C., was added a solution of sodium bicarbonate (0.66 mg, 70 μmol, in 30 μl of water). The reaction mixture was stirred at room temperature for 1.5 h untill a total consumption of the starting material. It was poured into a saturated sodium bicarbonate solution (4 ml) and evaporated with methylene chloride (5×2 ml). The organic layer was dried over sodium sulfate and then evaporated to give a crude product which was further purified by recrystalization from methylene chloride/hexane to give an off-white solid (1.5 mg).

M.P. (Electrothermal IA-9100): 142°–146° C.

$^1$H NMR (250 MHz, acetone-d$_6$), δ: 1.14 (d,1H,J=5.9 Hz,6'-CH$_3$), 1.74 (dd,1H,J=12.5 Hz,4.8 Hz,2'-HCHa), 2.11 (m,1H,2'-HCHe), 2.62 (dd,1H, J=11.8 Hz,18.4 Hz,4'-HCHa), 3.12 (dd,1H,J=4.2 Hz,18.4 Hz,4-HCHe), 3.65 (bs, 1H,4'-CH), 4.24 (qua,1H,J=5.9 Hz,5'-CH), 4.33 (m,1H,3'-CH), 5.11 (dd,1H,J=4.2 Hz,11.8 Hz,3-CH), 5.48 (bd,1H,J= 3.0 Hz,1'-CH), 5.92 (s,1H,1-CH), 6.57 (s,1H,thiazole—CH), 7.87 (m,2H,7.8,ArH), 8.08 (m,2H, 6.9,ArH).

IR (Nicolet 205FT, film on NaCl plate): 3423.9 (str), 3341.1 (str), 2927.0, 2853.4 (w), 1718.5 (str), 1664.4 (str), 1597.5, 1524.7, 1335.0, 1300.1 (str), 1174.0, 100.4, 984.61 (str), 724.51, 707.71.

EXAMPLE 9

Example 9

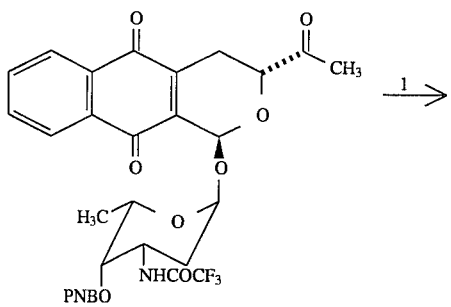

Example 9
-continued

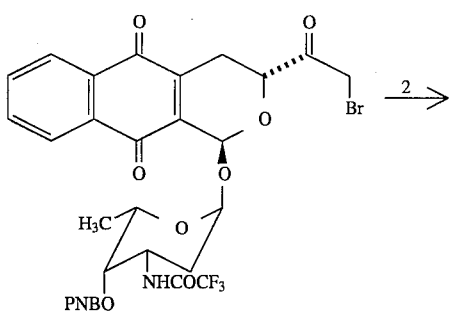

↓ 2

[Structure with NHAc thiazole group, PNBO, NHCOCF₃]

↓ 3

[Structure labeled BCH-1198 with OH, NHCOCF₃]

Step 1

(1'-S,1-S,3-R)-1-(2',3'-6'-trideoxy-4'-p-nitrobenzoyl-3'-trifluoroacetamido-L-lyxohexopyranose)-3-(2-bromoacetyl)-5,10-dioxo-3,4,5,10-tetrahydro-1H-naphtho-[2,3-c]-pyran To a solution of (1'-S,1-S,3-R)-1-(2',3',6'-trideoxy-4'-p-nitrobenzoyl-3'-trifluoroacetamido-L-lyxohexopyranose)-3-acetyl-5,10-dioxo-3,4,5,10-tetrahydro-1H-naphtho-[2,3-c]-pyran (50 mg, 0.077 mmol) in tetrahydrofuran (3 ml), stirred at room temperature, was added a solution of pyridinium hydrobromide perbromide (24.5 mg, 0.077 mmol) in THF. The reaction mixture was stirred for 2 hours at room temperature, then poured into water (10 ml) and extracted with methylene chloride (3×5 ml). The combined organic extracts were washed with brine (5 ml), and dried over sodium sulfate. The solvent was evaporated to give a crude product (68 mg) from which, via flash chromatography (eluent in volume ratio, toluene:ethyl acetate~10:3), a pure sample of the titled substance (27 mg) was obtained as a light yellow solid. Unreacted starting material (10 mg) was also obtained.

$^1$H NMR (250 MHz,acetone-d$_6$), δ: 1.33 (d,3H,J=6.8 Hz,6'-CH$_3$), 2.02 (dd, 1H,J=4.9 Hz,13.5 Hz,2'-HCHa), 2.48 (dt,1H,J=5.8 Hz,13.5 Hz,2'-HCHe), 2.78 (dd,1H,J=12.1 Hz,20.3 Hz,4-HCHa), 3.12 (dd,1H, J=4.0 Hz, J=20.3 Hz,4-HCHe), 4.29 (m,1H,3'-CH), 4.52 (d,1H,J=13.8 Hz,BrHCHre), 4.67 (d,1H,J=13.8 Hz,BrHCHsi), 4.88 (qua,1H,J=6.8 Hz,5'-CH), 5.04 (dd,1H, J=4.0 Hz,12.1 Hz,3-CH), 5.53 (bs,1H,4'-CH), 5.85 (bd,1H,J=3.4 Hz,1'-CH), 6.24 (s,1H,1-CH),7.90 (m,2H,7,8-ArH), 8.10 (m,2H,6,9-ArH), 8.48 (qua-like m,4H, PNB—ArH), 8.70 (bd,1H,J=7.4 Hz,3'-NH-COCF$_3$).

Step 2

(1'-S,1-S,3-R)-1-(2',3'-6'-trideoxy-4'-O-p-nitrobenzoyl-3'-trifluoroacetamido-L-lyxohexopyranose)-3-(2-aza-3-acetamido)-5,10-dioxo-3,4,5,10-tetrahydro-1H-naphtho-[2,3-c]-pyran A sample of 1-acetylthiourea (1.06 mg, 9.0 mmol) in ether (2 ml) was stirred at room temperature while a solution of bromomethyl ketone (9 mg, 8 mmol), from the previous step, in methylene chloride (0.5 ml) was added. The resulting mixture was stirred for 3 hours at room temperature and then for 4 hours at 40° C. Solvent was evaporated to give a crude product which was purified via flash chromatography (eluent in volume ratio chloroform:methanol~100:7, with 1 drop of pyridine added), to yield a product, which was further purified by recrystallization from CH$_2$Cl$_2$/hexane. The titled substance was obtained as an off-white solid (4 mg).

$^1$H NMR (250 MHz, acetone-d$_6$), δ: 1.33 (d,3H,J=7.5 Hz,6'-CH$_3$), 1.96 (dd,1H,J=5.8 Hz,15.2 Hz,2'-HCHa), 2.28 (s,3H,COCH$_3$), 2.49 (dt,1H, J=3.8 Hz,15.2 Hz,2'-HCHe), 2.76 (dd,1H,J=12.5 Hz,20.0 Hz,4-HCHa), 3.15 (dd,1H,J= 4.2 Hz,20.0 Hz,4-HCHe), 4.60 (m,1H,3'-CH), 4.92 (qua,1H, J=7.5 Hz,5'-CH), 5.24 (dd,1H,J=4.2 Hz,12.5 Hz,3-CH), 5.55 (bs,1H,4'-CH), 5.68 (bd,1H,J=3.0 Hz,1'-CH), 6.16 (s,1H,1-CH), 7.18 (s,1H, thiazole—CH), 7.92 (m,2H,7,8-ArH), 8.14 (m,2H,6,9-ArH), 8.36 (d,2H,J=8.3 Hz, PNB—OCOC(CH)$_2$), 8.42 (d,2H,J=8.3 Hz,PNB—NO$_2$C(CH)$_2$), 8.74 (bd,1H,J=7.9 Hz, 3'-NHCOCF$_3$), 11.07 (s,1H,thiazole—NHAC).

Step 3

(1'-S,1-S,3-R)-1-(2',3',6'-trideoxy-3'-trifluoro acetamido-L-lyxohexopyranose)-3-(2-aza-3-acetamido-thiazolyl)-5,10-dioxo-3,4,5,10-tetrahydro-1H-naphtho-[2,3-c]-pyran A sample of the PNB-derivative (4.0 mg, 5.5 mmol), from the previous step, was taken into a solvent system containing methylene chloride (212 μl) methanol (566 μl) and water (131 μl), and cooled to 0° C. An aqueous solution of sodium bicarbonate (0.69 mg, 8.2 mmol in 20 μl of water) was then added to the reaction mixture. The reaction proceeded at 0° C. for 1 hour and at room temperature for 20 minutes. The reaction mixture was poured into a mixture of methylene chloride and saturated ammonium chloride aqueous solution (5 ml/5 ml). The organic layer was separated, dried over sodium sulfate and then evaporated to dryness. The crude product was recrystalized from dichloromethane/hexane to yield the titled substance as a light-colored solid.

M.P. (Electrothermal IA-9100): Decomposed at 195° C.

$^1$H NMR (250 MHz, acetone-d$_6$), δ: 1.35 (d,3H,J=7.5 Hz,6'-CH$_3$), 1.76 (dd,1H,J=5.8 Hz,14.2 Hz,2'-HCHa), 2.16 (dt,1H,J=4.2 Hz,14.2 Hz,2'-HCHe), 2.75 (dd,1H,J=12.1 Hz,20.2 Hz,4-HCHa), 3.12 (dd,1H,J=4.0 Hz, 20.2 Hz,4-HCHe), 3.72 (bs,1H,4'-CH), 4.28 (m,1H,3'-CH), 4.58 (qua,1H, J=7.5 Hz,5'-CH), 5.18 (dd,1H,J=4.0 Hz,12.1 Hz,3-CH), 5.48

(bd,1H, J=2.9 Hz,1'-CH), 6.10 (s,1H,1-CH), 7.16 (s,1H, thiazole—CH), 7.90 (m,2H,7,8-ArH), 8.11 (m,2H,6,9-ArH), 8.17 (d,1H, overlapped,3'-NHCOCF$_3$), 11.07 (s,1H,thiazole—NHAc).

IR (Nicolet 205 FT, film on NaCl plate): 3746–3048 (peaked at 3388.3, br,str), 2923.2, 1712.9 (str), 1664.9 (str), 1591.9, 1550.1, 1535.5 (str), 1289.3 (str), 1243.4 (m), 1145.4 (w), 1124.5, 1080.7, 1001.5, 971.57 (str), 936.11, 709,75 (w).

EXAMPLE 10

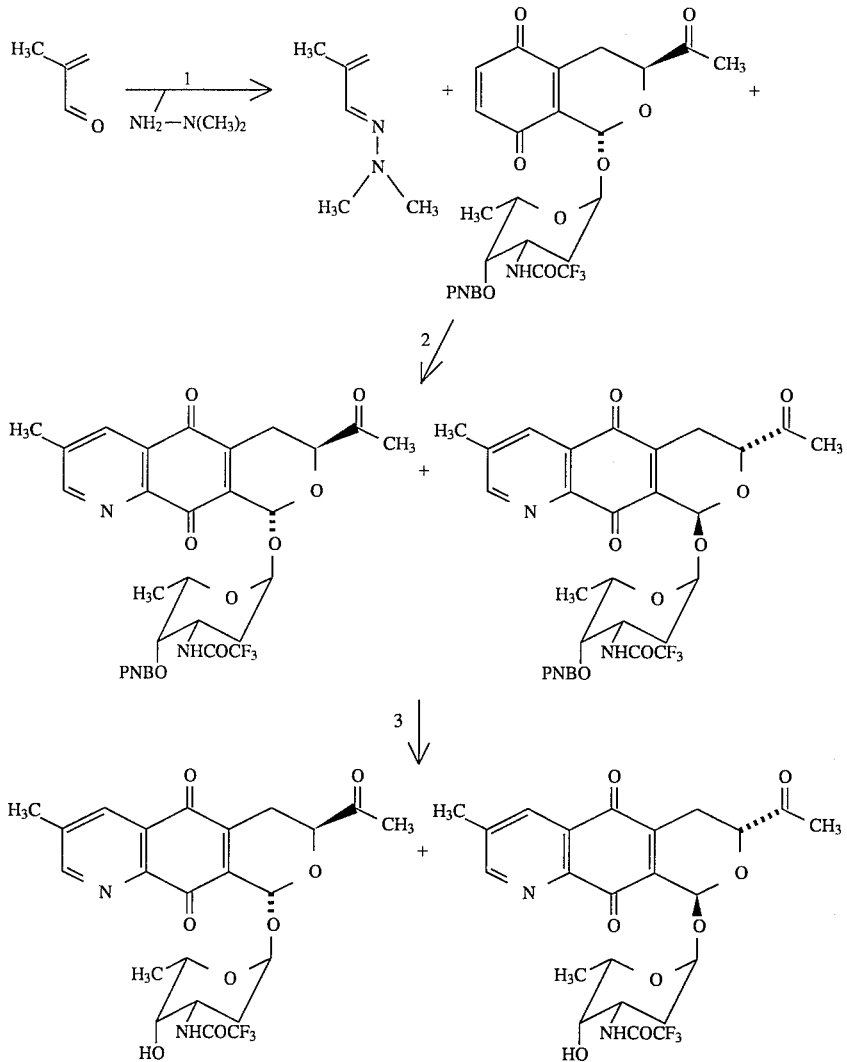

Step 1

Methacrolein-N,N-dimethylhydrazone

Under N$_2$, at room temperature, was mixed 3 g (50 mM) of dimethylhydrazine in sodium phosphate solution 7.1 g (50 mM) in 50 ml H$_2$O and 3.5 g (50 mM) methacrolein. The mixture was vigorously stirred for 10 minutes at 60° C. and then 30 minutes at room temperature. The solution was extracted with Et$_2$O (3×40 ml), dried over MgSO$_4$, and evaporated. The residue was flash chromatographed using CH$_2$Cl$_2$ as eluent; 5.1 g of colorless oil was isolated.

$^1$H NMR (250 MHz, CDC$_3$)δ: 2.13 (s,3H,CH$_3$) 3.04 (s,6H,N(CH$_3$)$_2$), 5.23 (broad s,1H,C=CH$_2$), 5.32 (broad s,1H, C=CH$_2$), 7.25 (s,1H,C=CH).

Step 2

(1'S,1S,3R) and (1'S,1R,3S) methyl (1-[2',3',6'-trideoxy-3'-trifluoroacetamido-4'-O-p-nitrobenzoyl-L-lyxohexo-pyranose]-5,10-dioxo-3,4,5,10-tetrahydro-7-methyl-9-aza naphtho [2,3-c] pyran-3-yl ketone Under N$_2$ at room temperature, to 235 mg (0.394 mM) of quinone from step 1 (example 5) dissolved in 20 ml of dry THF , was added 1.1 eq. (47 mg, 0.399 mol) of hydrazone from step 1 (example 10), and 1.1 eq of p-toluene sulfonic acid (0.4 mM, 76 mg). After stirring 1 day at room temperature, the mixture was poured into 20 ml of H$_2$O, and extracted with EtOAc (3×15 ml). After drying and evporation, the residue was flash chromatographed [EtOAc 1: toluene 3] to give 95.1 mg of titled compound (40% yield).

$^1$H NMR (250 MHz, CDCl$_3$)δ: 1.22 (d,3H,5'-CH$_3$), 1.75 (dd,1H,2'-CH$_2$), 2.18 (m,1H,2'-CH$_2$), 2.32 (s,3H,COCH$_3$), 2.59 (s,3H,C$_7$-CH$_3$), 2.62 (overlapped m,1H,H—C$_4$-H), 3.1–3.3 (m,1H,HC$_4$H), 4.32 (m,1H,5'-CH), 4.53 (m,1H,C HCOCH$_3$), 5.4 (m,1H,3'-CH); 5.5 (m,1H,4'-CH) 5.7 (m,1H, 1'-CH), 6.2 (s,1H,C$_1$-H); 6.4 (m, broad,1H,NH), 8.2 (overlapped m, 1H,C$_6$-H-arom), 8.2–8.4 (m,4H,p-nitobenzoyl), 8.2 (m,1H,C$_8$-H arom).

Step 3

(1'S,1S,3R) and (1'S,1R,3S) methyl-1-(2',3',6'-trideoxy-3'-trifluoroacetmido-4'-hydroxy-L-lyxohexopyranose)-5,10-dioxo-3,4,5,10-tetrahydro-7-methyl-O-azanaphtho [2,3-c] pyran-3-yl ketone To 80 mg (0.121 mM) of azaquinone from step 2 (example 10), dissolved in 13 ml MeOH and 3.2 ml H$_2$O, was added 10.4 mg (0.121 mM) of NaHCO$_3$. After stirring for 2 hours, the reaction was over, and 15 ml of H$_2$O was added. The mixture was extracted with 3×15 ml EtOAc. After drying and evaporation, the residue was purified by preparative TLC and yielded 30.4 mg of pure titled compounds (50% yield).

$^1$H NMR (250 MHz, CDCl$_3$)δ: 1.24 (d,3H,J=6.5 Hz,CH$_3$), 1.76 (dd,1H,2'-CH$_2$), 2.16 (m,1H,2'-CH$_2$), 2.30 (s,3H, COCH$_3$), 2.58 (s,3H,C$_7$-CH$_3$), 4.3 (m,1H;5'-CH), 4.52 (m,1H,C$\underline{H}$—COCH$_3$), 5.3 (dd,1H,3'-CH), 5.5 (dd,1H, 4'-CH), 5.6 (m,1H,1'-CH), 6.1 (s,1H,C$_1$-H), 6.4 (m, broad, 1H,NH), 8.2 (m,1H, C$_6$-H arom), 8.9 (m,1H, C$_8$-H arom).

EXAMPLE 11

Preparation of naphto[2,3-C]pyran glycosides of 2-deoxy fucose

Step 1

Di-p-nitrobenzoyl-L-fucal

To a stirred solution of diacetyl-L-fucal (114 mg, 0.53 mmol) in methanol (2.5 ml) was added a solution of sodium methoxide in methanol (25 μl, 4.37M, 0.1 mmol) after 45 minutes, methanol was evaporated under vacuum. The crude product was dissolved in CH$_2$Cl$_2$ (2.5 ml) and pyridine (1.5 ml) and at 0° C., p-nitrobenzoyl chloride (2.1 mmol, 390 mg) was added. After a few minutes at 0° C., the reaction mixture was poured in CH$_2$Cl$_2$ (20 ml) and washed with water, NaHCO$_3$ 10%, and then brine. The titled product was purified by flash chromatography (hexanes/acyl acetate (AcOet 5:1)) (MP: 130°–132° C.) (210 mg, 90%).

$^1$H NMR (250 MHz, CD$_2$Cl$_2$)δ: 1.40 (d,3H,—CH$_3$), 4.40 (q,1H,H-5), 4.85 (m,1H-2), 5.65 (m,1H,H-4), 5.90 (m,1H, H-3), 6.6 (m,1H,H-1).

Step 2

(1'S,1S,3R) and 1'S,1R,3S) -methyl-1-(2',6'-dideoxy-3',4'-di-O-p-nitrobenzoyl-L-lyxohexopyranose)-5,10-dioxo-3,4, 5,10-tetrahydronaphto [2,3-C] pyran-3-yl) ketone To a mixture of methyl (1-hydroxy-5,8-dioxo-5,8-dihydroisochroman-3-yl) ketone (698 mg, 3.1 mmol). 1,5-anhydro-3,4-di-O-para-nitrobenzoyl-2,6-dideoxy-L-lyxohex-1-enitol (1.58 g, 3.7 mmol), and molecular sieves 4° A (3.8 g) in CH$_2$Cl$_2$ (150 ml). at −60° C., was added triethylamine

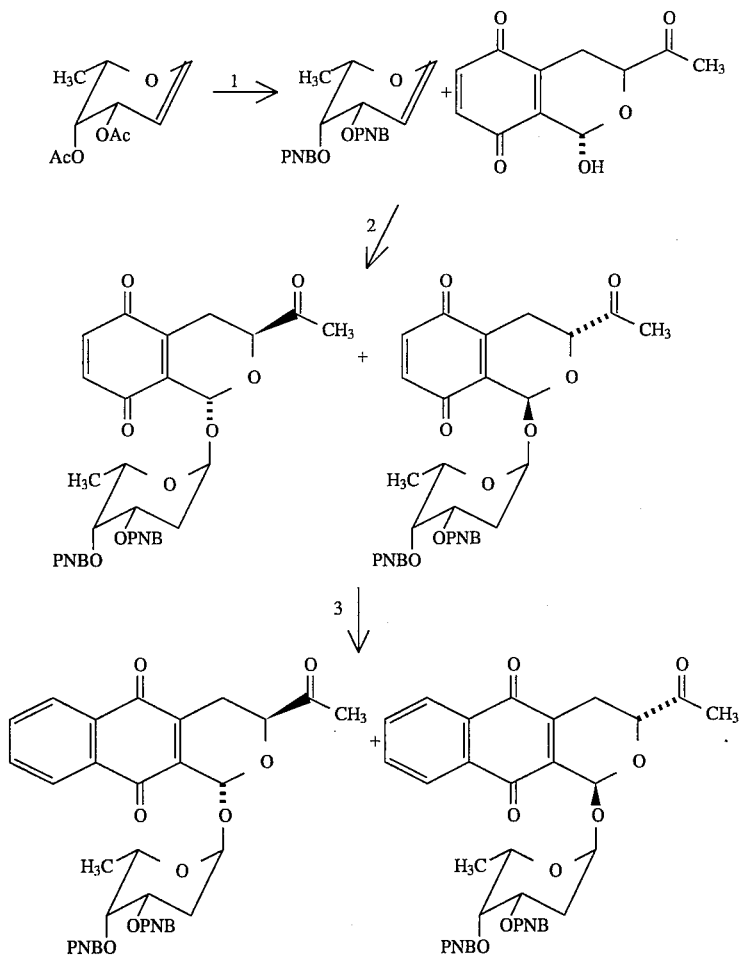

(0.24 ml, 1.7 mmol), and trimethylsilyl trifluoromethanesulfonate (0.64 ml, 3.3 mmol), subsequently. After stirring for 40 minutes, the reaction was quenched by adding aqueous NaHCO₃ (50 ml) at −60° C. and gradually warmed up to room temperature. Insolubles were filtered off and the filtrate was extracted into CH₂Cl₂. The organic phase was washed with aqueous HCl (0.1N), 100 ml, water and brine, dried over MgSO₄ and the solvent evaporated to give 2.36 g of crude isochromandione glycoside. This was used without any further purification. To a solution of the quinone (mixture of diastereomers: 0.16 g, 0.25 mmol) in 2.5 ml of dry toluene, under argon at room temperature, was added 1-acetoxybutadiene (0.15 ml, 5 eq) and the reaction mixture was stirred for 18 hours. Silica gel (1.0 g) was then added and air was bubbled through the suspension. After 15 minutes, the mixture was chromatographed (silica gel, 3:1 hexanes/ethyl acetate) to give 0.13 g (74%) of compound 178-24-01 (1:1 mixture of diastereomers) as a yellow solid:mp. 129–132. ¹H NMR (CDCl₃)δ: 8.34–7.73 (m,12H), 6.23+6.06 (2s,1H), 5.82+5.72 (2d,1H,J=2.8), 5.62–5.52 (m,2H), 4.88+4.43 (2q,1H,J=6.5), 4.62+4.58 (2dd,1H,J=4.1, 11.5), 3.10+3.02 (2dd,1H,J=4.1,6.1), 2.62–2.10 (m,3H), 2.35+2.33 (2s,3H), 1.42+1.28 (2d,3H,J=6.5).

EXAMPLE 12

Preparation of naptho-[2,3-C] pyran derivatives with an ethyl side chain

Step 1

2,5-Dimethoxy-6-(2-hydroxybutyl)-benzaldehydedioxane acetal

To a cooled (−15° C.) solution of 2,5-dimethoxybenzaldehydedioxane acetal (13.2 g; 44.6 mmol) in 300 ml of anhydrous diethylether was added dropwise, under argon, n-Butyllithium (32.2 ml of a 2.5M solution in hexanes,80.3 mmol). The mixture was warmed to −7° C. and was stirred at this temperature for 5 hours. The resulting mixture was cooled to −78° C., treated with boron trifluoride etherate (21.8 ml; 177 mmol), and 1,2 epoxybutane (10.2 ml; 119 mmol). After stirring at −78° C. for 60 minutes the reaction mixture was quenched with a saturated solution of bicarbonate and then extracted with ether. The organic layers were combined, washed with water, and brine, and were dried over MgSO₄. Removal of the solvent gave a crude oil which was purified by column chromatography on silica gel using 25% ethyl acetate in hexane to afford 2.39 g of pure starting material (18%) and 5.21 g (52% based on S.M. recovered) of 2,5 dimethoxy-6-(2 hydroxybutyl) benzaldehydedioxane acetal as an oil.

¹H NMR (250 MHz, CDCl₃)δ: 0.95 (t,J=7.3 Hz,3H,—CH₂CH₃), 1.35 (1H, dm,J=13.6 Hz,—CH₂—CH H_eq—CH₂), 1.55 (2H,m,—CH₂—CH₃), 2.18 (1H,m,—CH₂—CHH_ax—CH₂—) 2.98 (1H,dd,J=2.7 and 13.7 Hz,=C—CH₂—CH—O—), 3.36 (1H,dd, J=10.3 and 13.6 Hz=C—CH₂—CH—O) 3.65 (3H,s,—OCH₃), 3.66 (3H,s, —OCH₃), 3.60–4.10 (4H,m,—CHH_eq—O—,—CH—OH), 4.16 (2H,m,—CHH_ax—O—), 6.16 (1H, s,—O—C

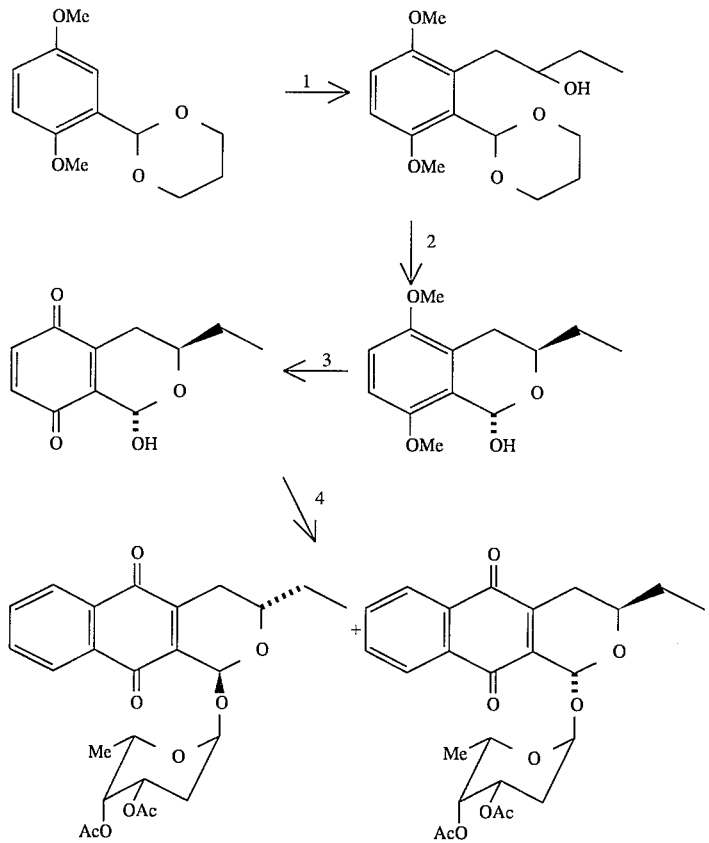

BCH-1607

H—O—), 6.61 (1H,d,J=9.0 Hz,Ar—H), 6.70 (1H,d,J=9.0 Hz,Ar—H).

Step 2

5,8-Dimethoxy-3-ethyl-1-hydroxy-isochroman

To a stirred solution of 2,5 dimethoxy-6-(2-hydroxybutyl) benzaldehydedioxane acetal (5.2 g; 17.6 mmol) in 700 ml of THF at room temperature was added dropwise 25 ml of a 1N solution of HCl. The resulting mixture was stirred for an hour at room temperature and then quenched with a saturated solution of sodium bicarbonate. It was then diluted with 1000 ml of dichloromethane and the aqueous layer, after separation, was extracted twice with dichloromethane. The combined organic layers were washed with brine and dried over $MgSO_4$. Evaporation of the solvent gave pure 5,8-dimethoxy-3-ethyl-1-hydroxy-isochroman (4.1 g; 98%) which could be recrystalized in dichloromethane/hexane to give white crystals (M.P.: 108.9°–110.1° C.).

$^1$H NMR (250 MHz, $C_6D_6$)δ: 1.02 (3H,t,J=7.4 Hz,$CH_2$—$CH_3$), 1.60 (1H,m, —CHH—$CH_3$), 1.76 (1H,m, —CHH—$CH_3$), 2.48 (1H,dd,J=11.6 and 17.3 Hz, Ar—CH—$H_{ax}$—), 2.88 (1H,dd,J=3.3 and 17.3 Hz, Ar—CH—$H_{eq}$), 2.98 (1H,d,J=3.9 Hz, —OH), 3.34 and 3.38 (6H,2S,—O—$CH_3$), 4.28 (1H,m,—CH—$CH_2$—$CH_3$), 6.40 (2H,m,ArH and —O—CH—O—), 6.46 (1H,d,J=8.8 Hz,ArH).

Step 3

3-Ethyl-1-hydroxy-isochroman-5,8-dione.

To a stirred solution of 5,8-dimethoxy-3-ethyl-1-hydroxy-isochroman (760 mg; 3.19 mmol) in 160 ml of acetonitrile at 0° C. was added dropwise a solution of ceric ammonium nitrate (CAN) (5.25 g; 9.57 mmol) and sodium bicarbonate (1.45 g; 17.2 mmol) in 40 ml of water. The resulting mixture was stirred for an hour at 0° C. and was quenched by adding a saturated bicarbonate solution. The aqueous layer was extracted 3 times with dichloromethane and the combined organic layer was washed with water, brine, and dried over $MgSO_4$. Evaporation of solvent gave a crude quinone which was suitably pure to undergo further reactions (600 mg; 90%).

$^1$H NMR ($CDCl_3$)δ: 1.02 (3H,t,J=7.4 Hz,—$CH_2$—$CH_3$), 1.70 (2H,m,—$CH_2$—$CH_3$), 2.15 (1H,ddd,J=1.1,12.4 and 19.5 Hz,Ar—CH—$H_{ax}$—), 2.60 (1H,dd,J=3.2 and 19.5 Hz,Ar—CH—$H_{eq}$—), 3.20 (1H,br s,—OH), 4.08 (1H,m, —CH—$CH_2$—$CH_3$), 5.91 (1H, s,—O—CH—O—), 6.76 (2H, 2 parts of an AB system, Ar—H).

Step 4

(1'S, 1S, 3S) and (1'S, 1R, 3R)-5,10-dioxo-3-ethyl-1-(2',3', 4',6'-tetradeoxy-3',4'-diacetoxy-L-lyxohexo-pyranose)-3,4,5,10-tetrahydro-1H-naphtho [2,3-C] pyran (BCH-1607)

To a cooled solution (–60° C.) of 3-ethyl-1-hydroxy-isochroman-5,8-dione (150 mg; 0.72 mmol) in dichloromethane (40 ml) were added sequentially molecular sieves (4A, 864 mg), 3,4-di-O-acetyl-L-fucal (246 mg; 1.15 mmol), triethylamine (56 µl) and trimethylsilyl trifluoromethanesulfonate (138 µl; 0.72 mmol). The resulting mixture was stirred at –60° C. for 3 hours and was quenched with an aqueous saturated bicarbonate solution. Extraction with dichloromethane was followed by washing of the combined organic layers with 1N HCl, brine, and then drying over $MgSO_4$. Following evaporation, 407 mg of the resulting crude thick oil was dissolved in 20 ml of toluene. To this solution was added 1-acetoxy-1,3-butadiene (521 mg; 4.82 mmol) and the resulting mixture was stirred at room temperature for 18 hours. Solvent was then partially evaporated to about 4 ml volume and the residue was applied to a column of silica gel (eluent, toluene, ethyl acetate 90:10) affording 2 fractions. The first one (48 mg, 14% overall) contained a 2:1 mixture favoring the (1'S, 1S,3S)-5,10-dioxo-3-ethyl-1- (2',3',4',6'-tetradeoxy-3',4'-diacetoxy-L-lyoxohexopyranose)-3,4,5,10-tetrahydro-1H-naphtho [2,3-C] pyran over its (1'S, 1R, 3R) isomer and a second fraction (157 mg; 46% overall) consisting in a 1.5:1 mixture of the same major diastereomer that was about 80% pure from $^1$H NMR analysis.

$^1$H NMR (1'S,1S,3S isomer, $CD_2Cl_2$)δ: 1.00 (3H,t,J=7.3 Hz,—$CH_2$—$CH_3$), 1.23 (3H,d,J=6.4 Hz,6'-$CH_3$), 1.55–2.20 (4H,m,—$CH_2$—$CH_3$ and H-2'), 1.89 and 2.12 (6H,2s, O=C—$CH_3$), 2.27 (1H,dd,J=11.3 and 19.3 Hz,$H_{ax}$-4), 2.74 (1H,dd,J=3.3 and 19.5 Hz,$H_{eq}$—4), 3.95 (1H,m,H-3), 4.58 (1H, q,J=6.5 Hz,H-5'), 5.10 (2H,m,H-3' and H-4'), 5.46 (1H,d,J=3.5 Hz,H-1'), 5.95 (1H,s,H-1), 7.75 and 8.05 (4H, 2m,Ar—H).

$^1$H NMR (1'S,1R,3R isomer, $CD_2Cl_2$)δ: 1.01 (3H, t,J=7.3 Hz,—$CH_2$—$CH_3$), 1.11 (3H, d,J=6.5 Hz,6'-$CH_3$), 1.55–2.35 (5H,m,—$CH_2$—$CH_3$,H-2' and $H_{ax}$-4), 1.89 and 2.12 (6H, 2s,O=C—$CH_3$), 2.74 (1H,dd,J=3.3 and 19.5 Hz, $H_{eq}$-4), 4.00 (1H,m,H-3), 4.22 (1H,q,J=6.5 Hz,H-5'), 5.10 (2H,m, H-3' and H-4'), 5.54 (1H,d,J=3.0 Hz,H-1'), 5.79 (1H,s,H-1), 7.75 and 8.05 (4H,2m,Ar—H). The (1'S,1S,3S) diastereoisomer was obtained pure by recrystalization.

EXAMPLE 13

Preparation of naptho[2,3-C] thiopyran aglycones

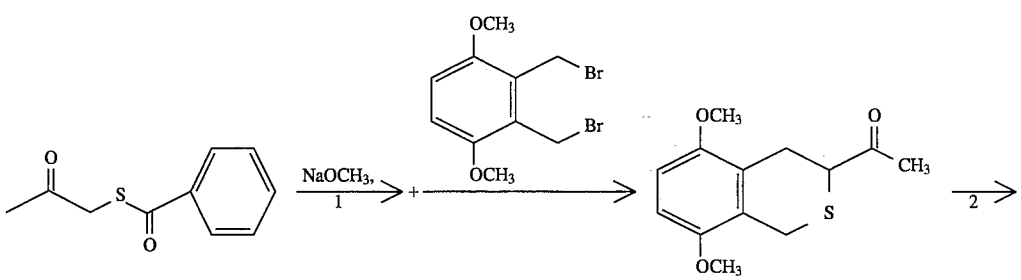

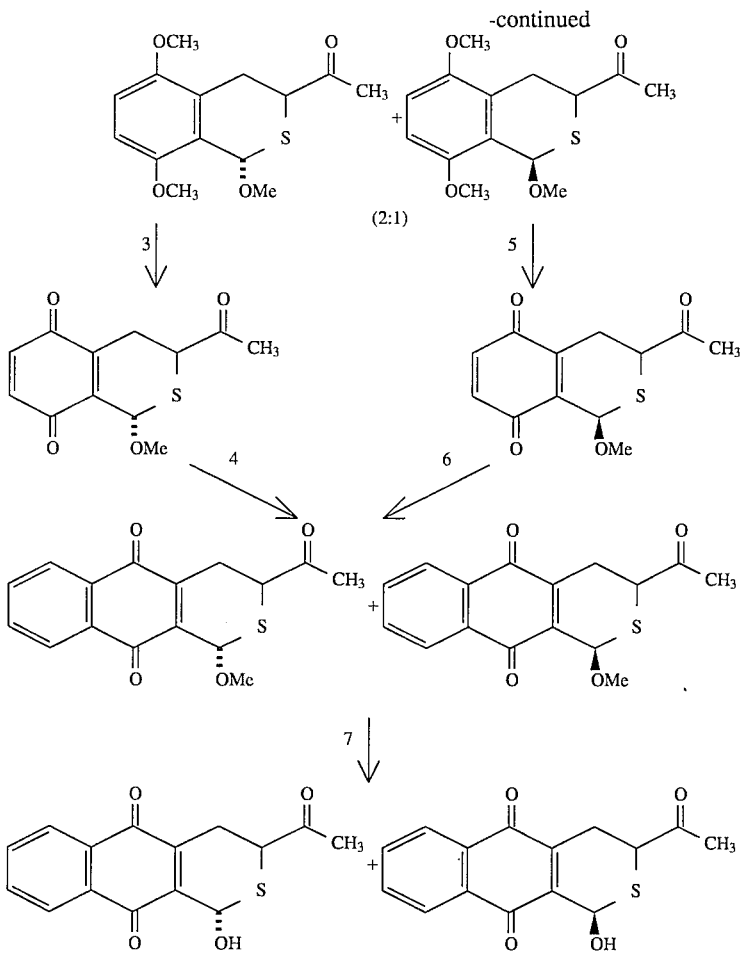

Step 1

3-Aceto-5,8-dimethoxythioisochroman

1-Thiobenzoate-propan-2-one (10.083 g, 51.97 mmole) was dissolved in MeOH (100 ml), cooled to 0° C., followed by the slow addition of NaOMe (4.37M, 14.3 ml, 62.36 mmol). The resulting mixture was stirred at 0° C. for ¾ hr. It was then cooled to −78° C. followed by the slow addition of 2,3-dibromomethyl-1,4-dimethoxybenzene (6.74 g, 20.79 mmol) in $CH_2Cl_2$: MeOH (60:20 ml). The resulting mixture was slowly warmed to R.T. and stirred for 2½ hrs. $NH_4Cl$ (saturated solution) was added and it was extracted with ethyl acetate. The combined organic phases were dried over $MgSO_4$, filtered and concentrated in vacuum. The crude obtained was flash chromatographed to give the titled compound (2.08 g, 8.25 mmol) in 41% yield.

$^1H$ NMR (250 MHz, $CD_3COCD_3$)δ: 2.31 (s, 3H, $CH_3$), 2.83 (dd, 1H, J=1.06, 8.55 Hz, $HCH_aCH—S$), 2.99 (dd, 1H, J= 2.44, 6.17 Hz, $HCH_eCH—S$), 3.44 (m, 1H, CH—S), 3.78 (2s, 6H, $OCH_3$), 3.85 (2H, $CH_2$—S), 6.78 (dd, 2H, J=8.95, 12.58 Hz, ArH). IR ($cm^{-1}$): 2900: CH, 1707: C=O.

Step 2

Trans-3-aceto-1,5,8-trimethoxythioisochroman and cis-3-aceto-1,5,8-trimethoxythioisochroman The thioisochroman from step 1 (Example 13) (100.0 mg, 0.40 mmmol) was dissolved in $CH_2Cl_2$ (12 ml) and MeOH (4 ml) followed by the addition of DDQ (109.0 mg, 0.48 mmol, 1.2 eq [2]) at R.T. The resulting mixture was stirred at room temperature overnight. $H_2O$ was added and it was extracted with $CH_2Cl_2$. The combined organic phases were washed with water, dried over $MgSO_4$, filtered and concentrated in vacuum. The crude obtained was flash chromatographed using toluene:ethylacetate (95:5) to give the trans titled compound (65.0 mg, 0.23 mmol) in 58% yield (MP: 84° C.).

$^1H$ NMR (250 MHz, $CDCl_3$)δ: 2.34 (s, 3H, $CH_3CO$), 2.91 (dd, 1H, J=11.73, 17.78 Hz, $HCH_aCHC—S$), 3.27 (dd, 1H, J= 4.10, 17.77 Hz, $HCH_eCHC—S$), 3.54 (s, 3H, $OCH_3$), 3.78 (s, 3H, $OCH_3$), 3.82 (s, 3H, $OCH_3$), 4.16 (dd, 1H, 4.13, 11.79 Hz, CH—S), 5.69 (s, 1H, O—CH—S), 6.75 (dd, 2H, J=8.96, 14.36 Hz, ArH). IR ($cm^{-1}$): 2925: CH, 1705.7: C=O. Cis-3-aceto-1,5,8-trimethoxythioisochroman (32.4 mg, 0.11 mmol) was obtained in 30% yield (MP: 129° C.).

$^1H$ NMR (250 MHz, $CDCl_3$)δ: 2.34 (s, 3H, $CH_3$), 3.25 (d, 2H, J=6.58 Hz, $H_aCH_eCHC—S$), 3.46 (s, 3H, $OCH_3$), 3.59 (dd, 1H, J=6.75, 13.55 Hz, CH—S), 3.79 (2s, 6H, $OCH_3$), 5.73 (s, 1H, O—CH—S), 6.76 (dd, 2H, J=9.50, 21.30 Hz, ArH).

Step 3

Trans-3-aceto-1-methoxy-5,8-dioxoisothiochroman

The thioisochroman derivative from step 2 (example 13) (178.2 mg, 0.63 mmole) was dissolved in acetonitrile (10 ml) and $H_2O$ (10 ml), followed by the addition of $NaHCO_3$ (190.8 mg, 1.22 mmole). The mixture was cooled to 0° C., followed by the slow addition of CAN (1.04 g, 1.89 mmole). After 20 minutes of stirring, $H_2O$ was added and the mixture was extracted with $CH_2Cl_2$. The combined organic phases were washed with H₂O, dried over MgSO₄, filtered and concentrated in vacuum. The crude obtained was found to be pure titled compound by ¹NMR and was used in the following step (>95% yield).

¹H NMR (250 MHz, CDCl₃)δ: 1.73 (s,3H,COCH₃), 2.62 (dd,1H,J=11.32, 19.81 Hz,HCHaCH—S), 2.87 (dd,1H,J= 4.28, 20.20 Hz,HCHeCH—S), 3.21 (s, 3H,OCH₃), 3.61 (dd,1H,J=4.31, 11.42 Hz,CHS), 5.97 (m,2H,HC═CH).

Step 4

Trans-3-aceto-1-methoxy-1,2,3,4-tetrahydro-(2-sulfur)anthracene-5,10-dione and cis-3-aceto-1-methoxy-1,2,3,4-tetrahydro-(2-sulfur)anthracene-5,10-dione Trans-3-aceto-1-methoxy-5,8-dioxoisothiochroman (0.66 mmole) was dissolved in dry toluene (14 ml), followed by the addition of the diene (120.0 mg, 1.07 mmole). The resulting mixture was stirred at room temperature overnight. Solvent was removed and the crude obtained was flash chromatographed using pure toluene to give the titled compounds in a ratio of about 1:1, in 48% yield.

¹H NMR (250 MHz, CDCl₃)δ: 2.37, 2.39 (2s,6H,CH₃, cis and/or trans), 2.75 (dd,1H,J=6.42,19.81 Hz,HCHaCH—S, cis or trans), 2.90 (dd, 1H, J=11.79, 20.08 Hz,HC Ha—CH—S, cis or trans), 3.27 (dd,1H,J=3.98, 20.0 Hz,HCHeCH—S, cis or trans), 3.58 (s,3H,OCH₃, cis or trans), 3.60 (s,3H,OCH₃, cis or trans), 3.64 (m,2H,CH—S, cis or trans), 4.11 (dd, 1H,J=3.92,11.80 Hz,CH—S, cis or trans), 5.30 (s,1H,OCH—S, cis or trans), 5.49 (s,1H,OCH—S, cis or trans), 7.74 (m, 4H,ArH, cis and trans), 8.10 (m,4H,ArH, cis and trans). IR (cm⁻¹): 2900:CH; 1709.4:C═O; 1668.1, 1631.9:C═O quinone.

Step 5 cis-3-aceto-1-methoxy-5,8-dioxoisothiochroman

Oxidative demethylation, by using the procedure from step 3 (example 13), of cis-3-aceto-1,5,8-trimethoxythioisochroman gave the titled compound in 98% yield.

H₁ NMR (250 MHz, CDCl₃)δ: 2.04 (s,3H,CH₃), 2.23 (dd,1H,J=4.88, 19.49 Hz, HCHaCH—S), 2.54 (d,1H,J=5.68 Hz,HCHeCH—S), 3.56 (dd,1H, J=2.10, 19.23 Hz,HCHa, e—S), 5.09 (s,1H,CH—S), 5.96 (dd,2H,J=10.30, 12.20 Hz,ArH).

Step 6 cis-3-aceto-1-methoxy-1,2,3,4-tetrahydro-(2-sulfur) anthracene-5,10-dione and trans-3-aceto-1-methoxy-1,2,3, 4-tetrahydro-(2-sulfur) anthracene-5,10-dione Application of the procedure described for step 4 (example 13) to trans-3-aceto-1-methoxy-5,8-dioxoisothiochroman gave pure titled compounds.

¹H NMR (250 MHz, CDCl₃)δ: 2.37 (s,3H,CH₃), 2.75 (dd,1H,J=6.42, 19.81 Hz,HCHaCH—S), 3.58 (s,3H,OCH₃), 3.64 (m,2H,CH—S,HCHeCH—S), 5.49 (s,1H,O—CH—S), 7.74 (m,2H,ArH), 8.10 (m,2H,ArH). IR (cm₋₁): 2900:CH; 1707.8:C═O; 1660.0, 1630.2, 1594.4:C═O quinone.

Step 7 trans-3-aceto-1-hydroxy-1,2,3,4-tetrahydro-(2-sulfur) anthracene-5,10-dione and cis-3-aceto-1-hydroxy-1,2,3,4-tetrahydro-(2-sulfur) anthracene-5,10-dione The mixture of compounds obtained from step 6 (example 13) (30.8 mg, 0.102 mmole) was dissolved in CH₃COOH:H₂O (2:0,4 ml) at 0° C. The resulting mixture was stirred at 0° C. for about 2 hours. NaHCO₃ (5%) was added and it was extracted with CH₂Cl₂. The combined organic phases were washed with H₂O, dried over MgSO₄, filtered and concentrated in vacuum. The crude product obtained was flash chromatographed using hexanes:ethyl acetate (7:3) to give the titled compounds in 7% yield. According to NMR one isomer is major:

¹H NMR (250 MHz, CDCl₃)δ: 2.74 (s,3H,CH₃), 3.00 (dd,1H, J=11.99, 20.74 Hz,HCHaCH—S), 3.26 (dd,1H,J= 3.96, 20.61 Hz,HCHeCH—S), 4.37 (dd, 1H,J=3.99,12.0 Hz,CH—S), 6.67 (s,1H,O—CH—S), 7.73 (m,2H,ArH), 8.08 (m,2H, ArH).

EXAMPLE 14

Thiopyranylnaphtoquinone glycosides

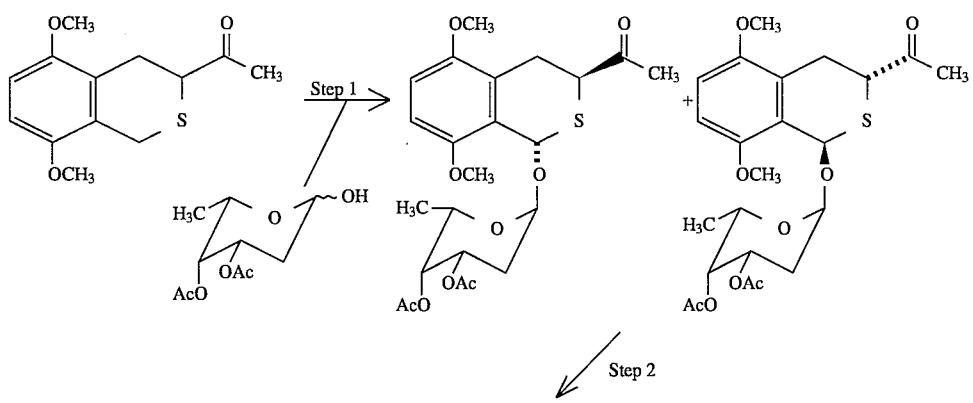

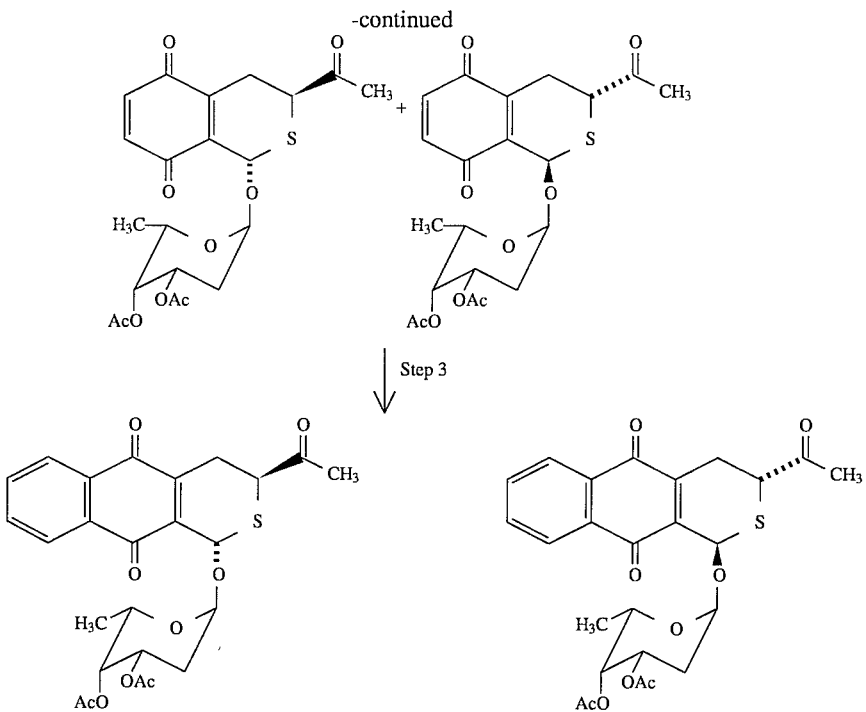

Step 1

(1'S,1R,3S) and (1'S,1S,3R) methyl (5,8-dimethoxy-1-(2',3', 4',6'-tetradeoxy-3',4'-diacetoxy-L-lyxohexo-pyranose)-3,4,-dihydrobenzo [2,3-c] thiopyran-3-yl) ketone A mixture of thioisochroman from step 1 (example 13) (96.0 mg, 0.38 mmol), dicyano dichloro benzoquinone (DDQ) (104.0 mg, 0.46 mmol) and 3,4-di-O-acetyl-2,6-dideoxy-L-lyxohexopyranose (_-anomer/β-anomer/=1:3; 106.4 mg, 0.46 mmol) in 5 ml of $CH_2Cl_2$ was stirred at room temperature under argon for 2.5 hours. After additions of 5 ml of $NaHCO_3$ solution (5%) and 10 ml of $H_2O$, the products were extracted with $CH_2Cl_2$ (25 ml×4). The combined organic phase was washed with $H_2O$ (15 ml), dried over $MgSO_4$, filtered and then concentrated. The residue was purified by flash chromatography (hexanes/$CH_2Cl_2$/ethyl acetate, 2=1=1) to provide a mixture of titled compounds (2=1, 116.9 mg, 0.24 mmol) in 64% yield along with recovered sugar (48 mg, 0.21 mmol).

$^1$H NMR ($CDCl_3$), the major isomersδ: 1.20 (d,3H,J=6.2 Hz), 1.70–2.30 (m,2H), 1.94 (s,3H), 2.20 (s,3H), 2.29 (s,3H), 2.98 (dd,1H, J=16.5 Hz,10.5 Hz), 3.28 (dd,1H,J= 16.5 Hz,5.1 Hz), 3.80 (s,6H), 4.14 (dd,1H,J=10.5 Hz,5.1 Hz), 4.42 (q,1H,J=6.3 Hz), J6.3 Hz), 5.10–5.25 (m, 2H), 5.65 (d,1H,J=3.2 Hz), 6.27 (s,1H), 6.72 (d,1H,J=9.8 Hz), 6.81 (d,1H,J=9.5 Hz); the minor isomer: 1.19 (s,3H), 1.70–2.30 (m,2H), 1.95 (s,3H), 2.19 (s,3H), 2.34 (s,3H), 2.96 (dd,1H,J=16.5 Hz, 10.5 Hz), 3.30 (dd,1H,J=16.5 Hz,5.1 Hz), 3.81 (s,6H), 4.22 (dd,1H, J=10.5 Hz,5.1 Hz), 4.42 (q,1H,J=6.3 Hz), 5.10–5.25 (m,2H), 5.50 (d,1H, J=3.2 Hz), 6.03 (s,1H), 6.70 (d,1H,J=9.8 Hz, 6.79 (d,1H,J=9.8 Hz).

Step 2

(1'S,1R,3S) and (1'S,1S,3R) methyl (5,8-dioxo-1-(2',3', 4',6'-tetradeoxy-3',4'-diacetoxy-L-lyxohexo-pyranose)-3,4,5,8-tetrahydrobenzo [2,3-c] thiopyran-3-yl) ketone To a stirred solution of the thioisochroman glycosides from step 1 (example 14) (106.0 mg, 0.22 mmol) in 5 ml of $CH_3CN$ was added a solution of $NaHCO_3$ (35.0 mg, 0.42 mmol) in 2 ml of water. After cooling to 0° C., a solution of CAN (362.0 mg, 0.66 mmol) in 2 ml of water was added dropwise. After being stirred at 0° C. for 20 minutes, the mixture was extracted with $CH_2Cl_2$ (25 ml×2). The organic layer was washed with $H_2O$, dried over $MgSO_4$, filtered and then concentrated. The residue (94.3 mg, 0.21 mmol) was found to be the title compounds (2:1) by $^1$H NMR. The yield was 95%.

$^1$H NMR ($CDCl_3$), the major isomer: δ: 1.28 (d,3H,J=7.6 Hz), 1.53–2.40 (m,2H), 1.99 (s,3H), 2.17 (s,3H), 2.33 (s,3H), 2.74 (dd,1H,J=18.8 Hz,11.0 Hz), 3.14 (dd,1H,J=18.8 Hz,4.8 Hz), 4.00 (dd,1H,J=11.0 Hz,4.8 Hz), 4.24 (q,1H,J= 7.6 Hz), 4.95–5.20 (m,2H), 5.56 Hz (d,1H,J=3.2 Hz), 6.00 (s,1H), 6.19 (d,1H,J=11.0 Hz), 6.85 (d,1H,J=11.0 Hz); the minor isomer: 1.18 (d,3H,J=7.5 Hz), 1.53–2.40 (m,2H), 1.99 (s,3H), 2.17 (s,3H), 2.37 (s,3H), 2.70 (dd,1H,J=19.0 Hz,10.5 Hz) 3.15 (dd,1H,J=19.0 Hz,4.8 Hz), 4.07 (dd,1H,J=10.5 Hz,4.8 Hz), 4.33 (q,1H,J=7.5 Hz), 4.95–5.20 (m,2H), 5.52 (d,1H,J=3.2 Hz), 5.77 (s,1H), 6.70 (d,1H,J=11.0 Hz), 6.78 (d,1H, J=11.0 Hz).

Step 3

(1'S,1R,3S) and (1'S,1S,3R) methyl (5,8-dioxo-1-(2',3', 4',6'-tetradeoxy-3',4'-diacetoxy-L-lyxohexopyranose)-3,4,5,10-tetrahydronaphtho [2,3-c] thiopyran-3-yl) ketone The procedure for the preparation of the titled compound is as described previously in step 1 (example 1). Thus, the reaction of the isochromandiones (94.3 mg, 0.21 mmol), obtained from the previous step with 1-acetoxy butadiene (0.10 ml, 94.5 mg, 0.84 mmol) gave the titled compounds 2:1 (74.2 mg, 0.15 mmol) in 70% yield after flash chromatography.

$^1$H NMR ($CDCl_3$), the major isomer had δ: 1.32 (d,3H, J=6.5 Hz), 1.70–2.40 (m,2H), 1.94 (s,3H), 2.17 (s,3H), 2.36 (s,3H), 2.91 (dd,1H, J=20.0 Hz,11.9 Hz), 3.30 (dd,1H,J= 19.9 Hz,4.2 Hz), 4.06 (dd,1H, J=12.0 Hz,4.1 Hz), 4.38 (m,1H), 5.05–5.22 (m,2H), 5.61 (d,1H, J=3.8 Hz), 6.23 (s,1H), 7.70–7.80 (m,2H), 8.05–8.15 (m,2H); the minor isomer had δ: 1.19 (d,3H,J=6.5 Hz), 1.70–2.40 (m,2H), 1.95 (s,3H), 2.17 (s,3H), 2.39 (s,3H), 2.87 (dd,1H,J=20.0 Hz,12.0 Hz), 3.32 (dd,1H,J=20.0 Hz,4.1 Hz), 4.15 (dd,1H,J=12.0 Hz,4.1 Hz), 4.38 (m,1H), 5.05–5.22 (m,2H), 5.63 (d,1H,J= 3.8 Hz), 6.00 (s,1H), 7.70–7.80 (m,2H), 8.05–8.15 (m,2H), IR (neat): 3866, 2987–2939, 1745(s), 1715, 1667, 1645, 1597, 1368, 1285, 1252, 1229, 1021, 988, 737 cm$_{-1}$.

EXAMPLE 15

In Vitro Cytotoxicity—Microculture Tetrazolium Assay

The microculture tetrazolium assay was used to test in vitro cytotoxicity. This assay is described in Plumb, J. A. et al., 1989 Cancer Research 49, 4435–4440, which is herein incorporated by reference. The cytotoxicity of compounds towards tumor cells is measured in vitro using the assay. This assay method is based upon the ability of live, but not dead cells to reduce the yellow water soluble dye 3-(4,5-dimethylthiazol-2-yl)-2,5-diphenyltetrazolium bromide (MTT) to its water insoluble purple formazan product.

The following reagents were used for:
tissue Culture, (Irvine Scientific Catalog)
  MEM containing nucleosides (Catalog #9144)
  Fetal Bovine Serum (Catalog #3000)
  Non-essential amino acids (Catalog #9304)
  Dulbecco's phosphate buffered saline (Catalog #9240)
  Sodium pyruvate (Catalog #9334).
  All other tissue culture and general reagents were from Sigma Chemical Company.
Human Tumor Cell lines, used were:
  SKOV3 (Ovarian adenocarcinoma)—provided by Dr. V. Ling, Ontario Cancer Institute.
  SKVLB (Ovarian; multidrug resistant)—Dr. V. Ling, Ontario Cancer Institute.
  T47D (Ductal carcinoma of breast)—ATCC catalog #HTB-133.
  Lox (Melanoma)—Southern Research Institute.
  HT 29 (Colon adenocarcinoma) ATCC catalog #HTB-38.

The cells were maintained in exponential growth in culture in minimal essential media (MEM) supplemented with non-essential amino acids, and containing 15% (v/v) fetal. bovine serum, 5 mM L-glutamine, 1 mM sodium pyruvate, and 0.1 U/ml insulin. All cell lines were grown at 37° C. in an atmosphere of 5% $CO_2$ in air.
Stock solutions, used were the following;
  MTT: 2 mg/ml in phosphate buffered saline (stable at 4° C. in dark for 1 week).
  Sorensen's buffer: 0.1M glycine/NaOH, pH 10.5, containing 0.1M NaCl.
  Test compounds: 20 mM in DMSO and diluted to a final concentration of 200 μM in culture medium before use.

The following is the generic description of the assay method. It should be noted that although the conditions described work well with the cells listed above, the initial plating density and the MTT concentration used should be verified for each new cell line used to test compounds.

For each assay, doxorubicin is included as an inter-assay standard. This allows us to monitor the behaviour of the assay in general, and in particular, to check that the SKVLB line has maintained its resistant phenotype.

The plate layout is done in the following manner:

The assays are carried out in 96-well (8 well×12 well) microtiter plates. Serial dilutions of the compound are tested along the length of the plate. A 1:3 serial dilution of compound in culture medium covers a concentration range from 100 μM to 1.7 nM. Each concentration of compound is tested in quadruplet, allowing two compounds to be tested per plate. Wells containing no cells (blank) and cells with no test compound (control) are included on each plate.

Cells are plated out in 100 μl of culture medium in the microtiter plates at a density of around 1,500–4,000 cells per well. The plates are incubated overnight to allow the cells to become adherent after which the test compound is added (100 μl of appropriate dilution per well). The cells are incubated with test compound at 37° C. for 48 h after which the compound is replaced with fresh medium. After a further 48 h incubation at 37° C., 50 μl of MTT solution (2 mg/ml) is added to each well. The plates are incubated in the dark for 4 h at 37° C. after which the medium is removed. The MTT formazan product is extracted from the cells by the addition of 200 μl DMSO followed by 50 μl of Sorensen's buffer. The plates are shaken briefly and the absorbance at 570 nm is read using a Molecular Devices UV max plate reader. Curves are fit to the MTT assay data using a four parameter logistic equation, and the data are normalized to fit a 0% to 100% survival scale.

RESULTS

Tables 1 and 2 show the antitumor activity of some of synthetic tricyclic pyranylnaphthoquinones of this invention. A range of potency is observed. In this set of compounds. Several tricyclic naphthoquinones are intensely potent and are effective in the multidrug resistant cell line SKVLB. In breast cancer, MCF-7, BCH-1146 is less potent than adriamycin but nearly as effective in the sensitive and adriamycin resistant cell line. These results suggest that tricyclic derivatives such as BCH-1184 and 1146 should be useful in the treatment of certain resistant cancers. Most notably BCH-2051, a "sugarless" tricyclic naphthoquinone, possesses intense in vitro antitumor potency while significantly avoiding multidrug resistance as observed from the SKVLB cell line.

| COMPOUND | SKOV3 | SKVLB | T47D | LOX | HT29 | VLB/OV3 |
| --- | --- | --- | --- | --- | --- | --- |
| Adriamycin | 0.012 | 1.49 | 0.07 | 0.034 | 0.090 | 121.5 |
| BCH1125 | >100 | 92.90 | 36.40 | 52.80 | >100 | |
| BCH1129 | 73.30 | >100 | 59.40 | 88.20 | 63.20 | |
| BCH1146 | 0.8910 | 6.97 | 5.87 | 3.82 | 0.9100 | 7.82 |
| BCH1148 | >100 | >100 | >100 | >100 | >100 | |
| BCH1169 | 7.14 | 60.10 | 26.50 | 9.63 | 6.29 | 8.42 |
| BCH1177 | 9.67 | 16.50 | 13.30 | 29.70 | 25.10 | 1.71 |
| BCH1180 | 0.8510 | 8.68 | 7.61 | 3.33 | 0.4680 | 10.20 |
| BCH1181 | 2.26 | 8.48 | 9.23 | 3.07 | 0.5360 | 3.75 |
| BCH1184 | 0.0050–0.0631 | 0.0536–0.3000 | 0.2840–0.5300 | 0.0186–0.2280 | 0.0023–0.0161 | 4.75–22.34 |
| BCH1188 | 0.8590 | 2.41 | 0.6640 | 0.9470 | 2.49 | 2.81 |

-continued

| COMPOUND | SKOV3 | SKVLB | T47D | LOX | HT29 | VLB/OV3 |
|---|---|---|---|---|---|---|
| BCH1189 | 6.50 | 26.60 | 12.50 | 14.30 | 16.60 | 4.09 |
| BCH1192 | 28.60 | | 31.60 | 29.90 | 37.60 | |
| BCH1607 | 7.26 | 19.80 | 14.70 | 8.97 | 21.60 | 2.73 |
| BCH1608 | 3.31 | 15.10 | 9.55 | 5.22 | 14.30 | 4.56 |
| BCH1620 | 0.0042 | 0.2160 | 0.1830 | 0.0227 | 0.0328 | 51.31 |
| BCH1643 | 1.74 | 5.17 | 3.49 | 1.65 | 6.71 | 2.97 |
| BCH1644 | 0.5050 | 1.52 | 1.27 | 0.6410 | 2.65 | 3.01 |
| BCH1648 | 0.0519 | 0.3150 | 0.3600 | 0.1380 | 0.3090 | 6.07 |
| BCH1649 | 0.1100 | 0.4590 | 0.3800 | 0.2170 | 0.3310 | 4.17 |
| BCH1654 | 0.7100 | 3.73 | 1.59 | 1.19 | 3.58 | 5.25 |
| BCH1658 | 0.2330 | 1.47 | 0.4940 | 0.3160 | 0.6610 | 6.31 |
| BCH1665 | 25.40 | 28.90 | | 11.50 | 60.40 | 1.14 |
| BCH1666 | 0.2720 | 0.2050 | | 0.1250 | 0.0783 | 0.75 |
| BCH1667 | 0.0122 | 0.0893 | | 0.0133 | 0.0016 | 7.32 |
| BCH1688 | 0.6340 | 2.77 | | 0.4020 | 1.35 | 4.37 |
| BCH1689 | 2.78 | 16.50 | | 1.72 | 3.66 | 5.94 |
| BCH1690 | 1.78 | 13.70 | | 1.62 | 3.01 | 7.70 |
| BCH1691 | 8.83 | 18.50 | | 4.49 | 7.16 | 2.10 |
| BCH1697 | 3.70 | 13.20 | 18.00 | 5.32 | 11.00 | 3.57 |
| BCH1998 | 0.1250 | 1.66 | 0.1140 | 0.0631 | 0.0363 | 13.28 |
| BCH2000 | 0.0950 | 6.64 | 0.3380 | 0.0905 | 0.0378 | 69.89 |
| BCH2014 | 21.50 | 39.80 | 61.80 | 35.90 | 61.30 | 1.85 |
| BCH2015 | 0.3670 | 1.17 | 0.9090 | 1.09 | 0.5570 | 3.19 |
| BCH2017 | 0.2500 | 8.94 | 0.4970 | 0.2500 | 0.4300 | 35.76 |
| BCH2018 | 3.11 | 17.70 | 8.56 | 2.38 | 14.20 | 5.69 |
| BCH2019 | 0.0633 | 0.3280 | 0.0486 | 0.0627 | 0.0230 | 4.95 |
| BCH2020 | 11.20 | 25.90 | 9.42 | 5.45 | 19.10 | 2.31 |
| BCH2021 | 12.40 | 46.40 | 19.00 | 10.60 | 37.80 | 3.74 |
| BCH2022 | 0.4420 | 1.87 | 0.9340 | 0.4840 | 0.5320 | 4.23 |
| BCH2023 | 0.73 | 3.2 | 5.5 | 0.67 | 0.98 | 4.39 |
| BCH2024 | 0.924 | 5.23 | 3.7 | 0.85 | 0.404 | 5.66 |
| BCH2026 | 15 | >100 | 31.40 | 2.12 | 22 | >7 |
| BCH2027 | 7.01 | 29 | 23.30 | 3.04 | 15.40 | 4.02 |
| BCH2031 | 6.0 | 18 | 16 | 2.8 | 8.5 | 3 |
| BCH2032 | 6.01–12 | 17.60–28 | 15.80–23 | 2.83–5.1 | 8.49–9.3 | 2–2.93 |
| BCH2035 | 0.28 | 6.23 | 1.5 | 0.75 | 2.31 | 22.33 |
| BCH2037 | 0.59–5.09 | 3.8–4.73 | 2.2–2.29 | 0.54–0.816 | 1.1–4.25 | 0.93–6.41 |
| BCH2038 | 0.832 | 3.5 | 2.0 | 0.173 | 2.0 | 4.16 |
| BCH2041 | 2.14 | 10 | 5.62 | 1.9 | 1.9 | 5 |
| BCH2042 | 3.8 | 13.20 | 8.0 | 2.22 | 1.2 | 3.51 |
| BCH2043 | 3.1 | 9.23 | 11 | 2.92 | 4.7 | 3 |
| BCH2044 | 1.44 | 5.11 | 4.25 | 0.38 | 0.194 | 3.55 |
| BCH2045 | 5.3 | 15 | 13 | 4.6 | 1.11 | 3 |
| BCH2046 | 0.0075 | 0.22 | 0.0675 | 0.015 | 0.0071 | 31 |
| BCH2047 | 0.017 | 0.523 | 0.151 | 0.021 | 0.0041 | 31 |
| BCH2051 | 0.0073–0.029 | 0.0675–0.403 | 0.0419–0.0685 | 0.0167–0.03 | 0.091–0.134 | 9.3–14.14 |
| BCH2052 | 5.4–7.01 | 20.50–28.20 | 9.54–23.30 | 3.04–3.22 | 10.60–15.40 | 3.78–4.02 |
| BCH2053 | 4.73 | 21.20 | 12.30 | 3.25 | 14 | 4.48 |
| BCH2054 | 6.33 | 11.30 | 4.95 | 3.23 | 4.30 | 1.79 |
| BCH2060 | 1.14 | 2.5 | 0.562 | 1.95 | 0.26 | 2.19 |
| BCH2061 | 0.0083 | 0.141 | 0.27 | 0.045 | 0.054 | 18 |
| BCH2062 | 0.8100 | 0.8420 | 0.7760 | 0.3540 | 1.14 | 1.04 |
| BCH2065 | 1.54 | 6.1 | 2.2 | 1.4 | 3.42 | 4 |
| BCH2067 | 1.2 | 2.24 | 0.54 | 1.1 | 0.323 | 2 |
| BCH2068 | 1.2 | 1.2 | 0.422 | 1.3 | 0.13 | 1 |
| BCH2069 | 0.0494 | 0.083–0.483 | 1.11 | 0.0903 | 0.35 | 2–9.78 |
| BCH2070 | 0.0084 | 0.12 | 0.018 | 0.015 | 0.006–0.534 | 14.34–15 |
| BCH2071 | 0.133 | 0.43 | 0.201 | 0.21 | 0.05 | 3.22 |
| BCH2072 | 0.0641–0.1130 | 0.315–0.991 | 0.0236–0.35 | 0.102 | 0.0539–0.101 | 2.79–15.46 |
| BCH2075 | 16 | 31 | 13 | 8.8 | 31 | 2 |
| BCH2076 | 1.43 | 12.40 | 6.53 | 1.8 | 2.6 | 9 |
| BCH2077 | 1.94 | 21 | 7.7 | 1.91 | 3.4 | 11 |
| BCH2078 | 0.4140 | 2.24 | 0.5070 | | 0.2690 | 5.41 |
| BCH2079 | 0.0163 | 0.124 | 0.032 | 0.066 | 0.005 | 8 |
| BCH2081 | 1.3 | 19 | 7.4 | 2.7 | 3.8 | 15 |
| BCH2082 | 1.8 | 5.6 | 4.0 | 1.6 | 2.6 | 3 |
| BCH2087 | 0.069 | 0.472 | 0.18 | 0.064 | 0.028 | 7 |
| BCH2090 | 11 | 36 | | | 10.40 | 3.29 |
| BCH2091 | 13.40 | 32 | 16 | 3.3 | 11.30 | 3 |
| BCH2092 | 1.1 | 3.0 | 0.98 | 0.30 | 2.42 | 3 |
| BCH2095 | 0.19 | 1.6 | 0.37 | 0.14 | 0.0996 | 8.16 |
| BCH2096 | 0.702 | 3.11 | 1.7 | 0.84 | 1.7 | 4.43 |
| BCH2098 | 8.0 | 30 | 10 | 4.2 | 17 | 4 |
| BCH2099 | 0.599–2.0 | 0.462–8.4 | 0.728–3.4 | 0.128–1.1 | 0.303–1.7 | 0.77–2 |
| BCH2100 | 2.7 | 8.22 | 4.0 | 3.0 | 5.12 | 3.04 |
| BCH2102 | 0.13 | 0.723 | 0.30 | 0.186 | 0.15 | 5.65 |
| BCH2104 | 0.21 | 1.1 | 0.613 | 0.24 | 0.171 | 5.05 |
| BCH2105 | 0.003 | 0.37 | 0.019 | 0.025 | 0.0069 | 123 |

-continued
| COMPOUND | SKOV3 | SKVLB | T47D | LOX | HT29 | VLB/OV3 |
|---|---|---|---|---|---|---|
| BCH2109 | 0.79 | 3.2 | 1.04 | 1.1 | 0.12 | 4.02 |
| BCH2112 | 0.104 | 1.7 | 0.27 | 0.21 | 0.065 | 15.96–17 |
| BCH2113 | 0.171 | 0.72 | 0.27 | 0.19 | 0.059 | 4.20 |
| BCH2114 | 0.4720 | 2.04 | 0.6550 | 0.3730 | 0.2570 | 4.32 |
| BCH2115 | 2.3 | >100 | 5.3 | 4.0 | 5.6 | >50 |
| BCH2117 | 0.0095 | 0.332 | 0.0374 | 0.073 | 0.03 | 35.13 |
| BCH2118 | 0.12 | 0.79 | 0.244 | | 0.203 | 6.68 |
| BCH2119 | >100 | >100 | >100 | | >100 | |
| BCH2121 | 0.21 | 1.3 | | 0.34 | .34 | |
| BCH2122 | 0.37 | 2.0 | | 0.73 | 0.64 | |
| BCH2126 | 0.6770 | 1.68 | 0.7060 | 0.3730 | 3.95 | 2.48 |
| BCH2127 | 0.35 | 4.1 | | 2.0 | 2.7 | |
| BCH2128 | 1.7 | 5.8 | | 1.4 | 1.6 | |
| BCH2129 | 0.3590 | 1.06 | 0.4520 | 0.2280 | 2.07 | 2.95 |
| BCH2131 | 35.80 | 34.60 | 12.80 | 12.50 | 43.40 | 0.97 |
| BCH2132 | 99.80 | 70.60 | 34.70 | 8.40 | >100 | 0.71 |
| BCH2135 | 0.66 | 1.3 | 1.1 | 0.31 | | 0.88 |
| BCH2138 | >100 | >100 | 90 | >100 | | >100 |
| BCH2140 | 2.2 | 13 | 1.5 | 0.45 | | 3.2 |
| BCH2141 | 8.12 | 9.96 | 3.79 | 1.82 | 6.44 | 1.23 |
| BCH2142 | 92 | 46 | 45 | 18 | | >100 |
| BCH2143 | | | | | | |
| BCH2144 | 21.40 | 16.10 | 7.22 | 3.28 | 5.93 | 0.75 |
| BCH2145 | 8.19 | 13.40 | 1.78 | 0.8300 | 2.48 | 1.64 |
| BCH2147 | 12.50 | 10.10 | 3.92 | 1.88 | 10.00 | .081 |
| BCH2148 | 12.60 | 9.93 | 2.36 | 1.55 | 7.50 | 0.79 |
| BCH2149 | 32.70 | 29.80 | 11.40 | 10.00 | 28.20 | 0.91 |
| BCH2157 | 0.1870 | 3.39 | 0.2330 | 0.0155 | 1.23 | 18.13 |
| BCH2160 | 4.93 | 9.12 | 9.59 | 7.43 | 15.70 | 1.85 |
| BCH2161 | 0.6250 | 3.08 | 1.35 | 0.6510 | 4.14 | 4.93 |
| BCH2166 | 0.14–0.1810 | 0.4950–1.2 | 0.2370 | | 0.4430–1.2 | 2.73 |
| BCH2167 | 0.0384 | | 0.1130 | | 0.0520 | |
| BCH2168 | 0.18–0.2760 | 0.98 | 0.5730 | | 0.3930–1.2 | |
| BCH2170 | 0.2590 | 0.3940 | | | 0.2440 | 1.52 |
| BCH2171 | 0.088–0.1950 | 0.4220–0.44 | 0.3980 | | 0.2190 | 2.16 |
| BCH2824 | 1.06 | 2.76 | | | 2.76 | 2.60 |
| BCH2825 | 12.50 | 27.10 | | | 25.50 | 2.17 |
| BCH2829 | 55.10 | >100 | | | 69.90 | |
| BCH2830 | 7.12 | 10.80 | | | 12.50 | 1.52 |
| BCH2839 | 0.0365–0.0461 | 0.2240–0.4600 | 0.0581–0.2910 | 0.2620–0.9750 | 0.1740–0.4900 | 6.14–9.98 |
TABLE 2
| | IC$_{50}$ μM | | | |
|---|---|---|---|---|
| COMPOUND | MCF-7 | MCF-7/ADR | MAT-B | MAT-B/ADR |
| Adriamycin | 0.005 | 6.5 | 0.0046 | 2.50 |
| 1146 | 0.044 | 0.19 | 0.46 | 0.56 |
| 1177 | >10.0 | 0.66 | >10.0 | >10.0 |
EXAMPLE 16
Preparation of naphthopyran derivatives
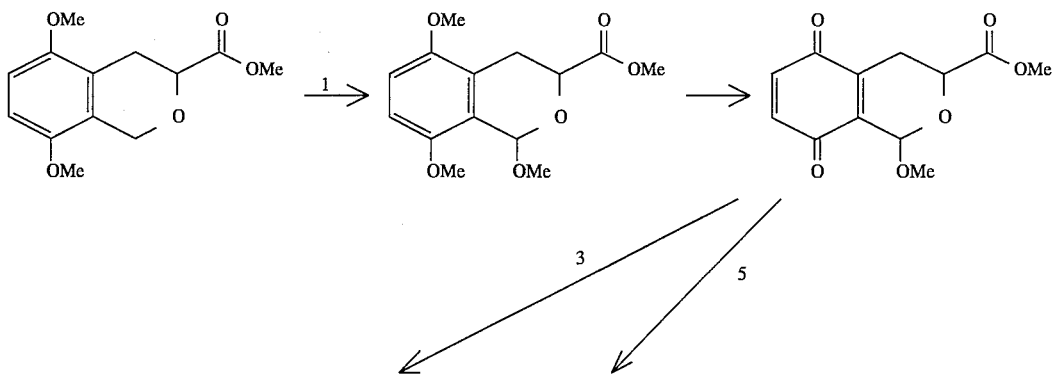

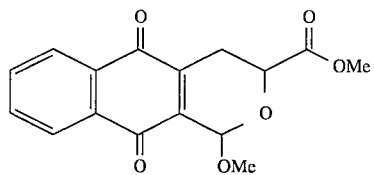 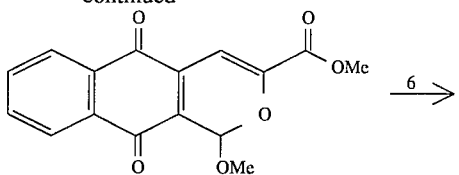

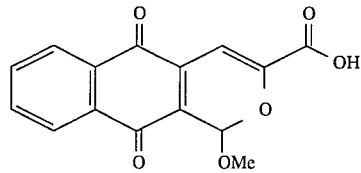 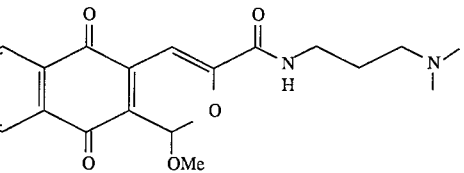

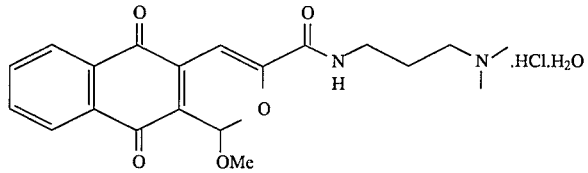

BCH-2051

Step 1

Methyl (1,5,8-trimethoxyisochroman-3-yl) formate

Methyl (5,8-dimethoxy-isochroman-3-yl) formate (15.00 g, 59.46 mmol) and DDQ (16.20 g, 71.35 mmol) were dissolved in dry dichloromethane (500 ml), and dry methanol (7.2 ml, 178.37 mmol) was added. The solution was stirred at ambient temperature overnight, then refluxed for 8 hours. Methanol (1.0 ml, 24.69 mmol) and DDQ (2.00 g, 8.81 mmol) was added and further refluxed for 8 hours. The reaction mixture was cooled down, filtered, and the filtrate was poured onto a saturated solution of sodium bicarbonate (200 ml). The organic phase was separated, washed with saturated sodium bicarbonate solution (100 ml), dried (MgSO$_4$) and evaporated under reduced pressure. The residue was recrystallized from methanol to give the title product (white crystals, 14.34 g, 85.1%).

$^1$H-NMR (250 MHz, Brucker, CDCl$_3$), d: 2.70 (1H, dd, J=11.8 and 17.1 Hz, 4-H$_{ax}$), 3.08 (1H, dd, J=4.2 and 17.1 Hz, 4-H$_{eq}$), 3.57 (3H, s, 1-MeO), 3.77 (3H, s, Ar—OMe), 3.80 (3H, s, Ar—OMe), 3.83 (3H, s, COOMe), 4.79 (1H, dd, J=4.2 and 11.8 Hz, 3-H$_{ax}$), 5.70 (1H, s, 1-H), 6.68 (1H, d, J=8 Hz, Ar—H), 6.74 (2H, d, J=8 Hz, Ar—H).

Step 2

Methyl (1-Methoxy-5,8-dioxo-5,8-dihydro-isochroman-3-yl) formate

The solution of CAN (83.24 g, 151.84 mmol) and sodium bicarbonate (8.50 g, 101.22 mmol) in water (500 ml) was added to the solution of methyl (1,5,8-trimethoxy-isochroman-3-yl) formate (14.34 g, 50.61 mmol) in acetonitrile (700 ml) at 0–5C.° over 20 minutes. The reaction mixture was stirred at 0 C.° for 20 minutes, then extracted with dichloromethane (4×200 ml). The combined organic phases were washed with brine (200 ml), dried (MgSO$_4$) and evaporated under reduced pressure to give a light yellow solid (12.76 g, quantitative yield) which was used for the next step without further purification.

$^1$H-NMR (250 MHz, Brucker, CDCl$_3$), d: 2.52 (1H, dd, J=11.4 and 19.4 Hz, 4-H$_{ax}$), 2.83 (1H, dd, J=4.2 and 19.4, 4-H$_{eq}$), 3.56 (1H, s, 1-MeO), 3.82 (1H, s, COOMe), 4.66 (1H, dd, J=4.2 and 11.4 Hz, 3-H$_{ax}$), 5.48 (1H, s, 1-H), 6.62 (1H, d, CHCO), 6.78 (1H, d, CHCO).

Step 3

Methyl (1-methoxy-5,10-dioxo-3,4,5,10-tetrahydro-1H-naphtho[2,3-c]pyran-3-yl) formate Methyl (1-methoxy-5,8-dioxo-5,8-dihydro-isochroman-3-yl) formate (12.70 g, 50.35 mmol), 1-acetoxybutadiene (30.00 g, 267.55 mmol) and dry toluene (100 ml) was stirred overnight at 50 C.°. The solvent was removed under reduced pressure, the residue was recrystallized from methanol to give yellow crystals (11.05 g). The product was dissolved in toluene (200 ml), silica gel (20 g) was added and stirred over 24 hours in an open flask at ambient temperature. The silica was filtered, the filtrate was concentrated to dryness. The residue was recrystallized in methanol. The mother liquor was concentrated to dryness and the silica gel treatment was repeated as above. After recrystallization the mother liquor was concentrated to dryness and the residue was purified by flash chromatography on silica. Eluent: toluene/ethyl acetate (4/1). All the crystals and the clean fraction from flash chromatography were combined to give 9.07 g, (59.6%) title product.

$^1$H-NMR (250 MHz, Brucker, CDCl$_3$), d: 2.68 (1H, dd, J=11.1 and 19.9 Hz, 4-H$_{ax}$), 3.07 (1H, dd, J=4.4 and 19.9 Hz, 4-H$_{eq}$), 3.62 (1H, s, 1-MeO), 3.83 (1H, s, COOMe), 4.72 (1H, dd, J=4.4 and 11.1 Hz, 3-H$_{ax}$), 5.70 (1H, s, 1-H), 7.75 (2H, m, Ar—H), 8.08 (2H, m Ar—H).

Step 4

Methyl (1-methoxy-5,10-dioxo-5,10-dihydro-1H-naphtho[2,3-c]pyran-3-yl) formate

Methyl (1-methoxy-5,10-dioxo-3,4,5,10-tetrahydro-1H-naphtho[2,3-c]pyran-3-yl) formate (6.12 g, 20.25 mmol) was dissolved in dichloromethane (120 ml), triethylamine (5.64 ml, 40.49 mmol) was added and stirred at ambient temperature over 1 hour. The reaction mixture was poured onto water (100 ml) and ethyl acetate(400 ml), then neutralized with acetic acid. The organic layer was separated, the water layer was extracted with ethyl acetate (3×30 ml). The combined organic layers were dried (MgSO$_4$) and concentrated to dryness. To the residue dichlorometane (60 ml) and saturated sodium bicarbonate solution (20 ml) was added, then stirred for 5 minutes. After separation the organic layer was dried (MgSO$_4$) and concentrated to 10 ml.

This solution was filtered through a short silica gel column. Eluent: dichloromethane and 5% ethyl acetate in dichloromethane. The clean fractions were combined and concentrated to dryness to give the title product (5.49 g, 90.3%).

$^1$H-NMR (250 MHz, Brucker, CDCl$_3$), d: 3.63 (3H, s, 1-MeO), 3.92 (3H, s, COOMe), 6.38 (1H, s, 1-H), 7.33 (1-H, s, 4-H), 7.75 (2H, m, Ar—H), 8.13 (2H, m, Ar—H).

Step 5

Methyl (1-methoxy-5,10-dioxo-5,10-dihydro-1H-naphtho [2,3-c]pyran-3-yl)formate.

Methyl (1-methoxy-5,8-dioxo-5,8-dihydro-isochroman-3-yl) formate (12.70 g, 50.35 mmol), 1-acetoxybutadiene (30.00 g, 267.55 mmol) and dry toluene (100 ml) was stirred overnight at 50 C.°. The solvent was removed under reduced pressure, the residue was recrystallized from methanol to give yellow crystals (11.05 g). The product was dissolved in dichloromethane (200 ml), triethylamine (10.2 ml, 73.11 mmol) was added and stirred at ambient temperature over 1 hour. The reaction mixture was poured onto water (200 ml) and ethyl acetate(800 ml), then neutralized with acetic acid. The organic layer was separated, the water layer was extracted with ethyl acetate (3×30 ml). The combined organic layers were dried (MgSO$_4$) and concentrated to dryness. To the residue dichlorometane(120 ml) and saturated sodium bicarbonate solution (40 ml) was added, stirred for 5 minutes. After separation the organic layer was dried (MgSO$_4$) and concentrated to dryness to give the title product (8.98 g, 59.4%).

$^1$H-NMR (250 MHz, Brucker, CDCl$_3$), d: 3.63 (3H, s, 1-MeO), 3.92 (3H, S, COOMe), 6.38 (1H, s, 1-H), 7.33 (1-H, s, 4-H), 7.75 (2H, m, Ar—H), 8.13 (2H, m, Ar—H).

Step 6

1-Methoxy-5,10-dioxo-5,10-dihydro- 1H -naphtho[2,3-c]pyran-3-carboxylic acid

Methyl (1-methoxy-5,10-dioxo-5,10-dihydro-1H-naphtho[2,3-c]pyran-3-yl) formate (6.31 g, 21.01 mmol) was suspended in tetrahydrofuran (126 ml) and sodium hydroxide (0.92 g, 23.12 mmol) dissolved in water (63 ml) was added dropwise at 0 C.° over 30 minutes. The reaction mixture was stirred at 0 C.° over 1 hour, then it was acidified to pH=3 with 5% hydrochloric acid. Sodium chloride (2 g) was added. The water layer was separated and extracted with ethyl acetate (3×40 ml). The water layer was acidified to pH=2. The crystals formed were filtered and washed with water. The filtrate was extracted with ethyl acetate (4×40 ml). All the organic fractions—including the previous extractions as well—were combined, dried (MgSO$_4$) and concentrated to dryness. The residue was combined with the crystals filtered out of the water phase before, and stirred with methanol (50 ml). for 15 minutes. The yellow crystals were filtered, washed with methanol to give the title product (5.21 g, 86.6%).

$^1$H-NMR (250 MHz, Brucker, DMSO-d$_6$), d: 3.50 (3H, s, 1-MeO), 6.37 (1H, s, 1-H), 7.02 (1H, s, 4-H), 7.90 (2H, m, Ar—H), 8.05 (2H, m, Ar—H).

Step 7

1-Methoxy-5,10-dioxo-5,10-dihydro-1H-naphtho[2,3-c]pyran-3-[N-(3-dimethyamino-propyl)carboxamide]

1-Methoxy-5,10-dioxo-5,10-dihydro-1H-naphtho[2,3-c]pyran-3-carboxylic acid (4.6 g, 16.13 mmol) was suspended in tetrahydrofuran (46 ml) and DMF (0.1 ml) was added. The suspension was cooled to 0 C.° and oxalyl chloride (3.24 ml, 37.09 mmol) was added dropwise over 10 minutes. The reaction mixture was stirred at 0 C.° over 30 minutes, then evaporated to dryness at reduced pressure. The residue was dissolved in tetrahydrofuran (50 ml), cooled to 0 C.° and N,N-dimethylaminopropylamine (2.23 ml, 17.74 mmol) was added dropwise over 10 minutes. The solution was stirred at 0 C.° over 15 minutes, then it was poured onto a saturated solution of potassium carbonate (20 ml). The organic layer was separated, the water layer was extracted with dichloromethane (3×10 ml). The combined organic phases were dried (MgSO$_4$) and concentrated to dryness. The residue was dissolved in methanol (50 ml) and stirred with charcoal at ambient temperature over 30 minutes. After filtration the filtrate was concentrated to dryness. The residue was dissolved in a minimal amount of methanol and ether (15 ml) was added. The crystals were filtered, washed with ether to give the title product (4.15 g, 69.6%).

$^1$H-NMR (250 MHz, Brucker, CDCl$_3$), d: 1.74 (2H, quint., CH$_2$), 2.29 (6H, s, NMe$_2$), 2.47 (2H, m, CH$_2$), 3.35–3.65 (2H, m, CH$_2$), 3.63 (3H, s, 1-MeO), 6.37 (1H, s, 1-H), 7.33 (1H, s, 4-H), 7.75 (2H, m, Ar—H), 8.15 (2H, m, Ar—H), 8.70 (1H, broad, NH).

Step 8

1-Methoxy-5,10-dioxo-5,10-dihydro-1H-naphtho[2,3-c]pyran-3-[N-(3-dimethylamino-propyl)carboxamide] hydrochloride monohydrate BCH-2051

1-Methoxy-5,10-dioxo-5,10-dihydro-1H-naphtho[2,3-c]pyran-3-[N-(3-dimethylamino-propyl)carboxamide] (4.15 g, 11.23 mmol) was dissolved in anhydrous dichloromethane (10 ml) and 1M hydrochloric acid solution in ether (11.3 ml, 11.23 mmol) was added dropwise at 0 C.°. At the end more ether (20 ml) was added and the suspension was stirred at 0 C.° over 30 minutes. The crystals were filtered under argon atmosphere, washed with dry ether and hexane to give the title product (4.32 g, 90.5%).

$^1$H-NMR (250 MHz, Brucker, DMSO-d$_6$), d: 1.90 (2H, m, 2'-CH$_2$), 2.72 (6H, s, NMe$_2$), 3.00 (2H, m, 3'-CH$_2$), 3.30 (2H, m, 1'-CH$_2$), 3.60 (3H, s,MeO), 6.35 (1H, s, 1-H), 7.00 (1H, s, 4-H), 7.90 (2H, m, Ar—H), 8.05 (2H, m, Ar—H), 8.92 (1H, t, CONH), 10.53 (1H, broad, NH$^+$).

$^{13}$C-NMR (250 MHz, Brucker, DMSO-d$_6$), d: 23.8, 36.1, 41.8, 54.0, 56.2, 94.9, 98.1, 124.5, 125.6, 126.1, 130.9, 131.5, 134.1, 134.5, 149.9, 159.6, 181.2, 181.4.

EXAMPLE 17

Dipeptide substituted naphthoquinone derivative

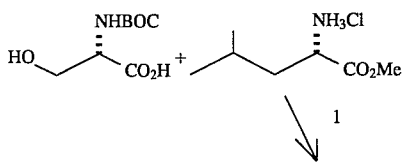

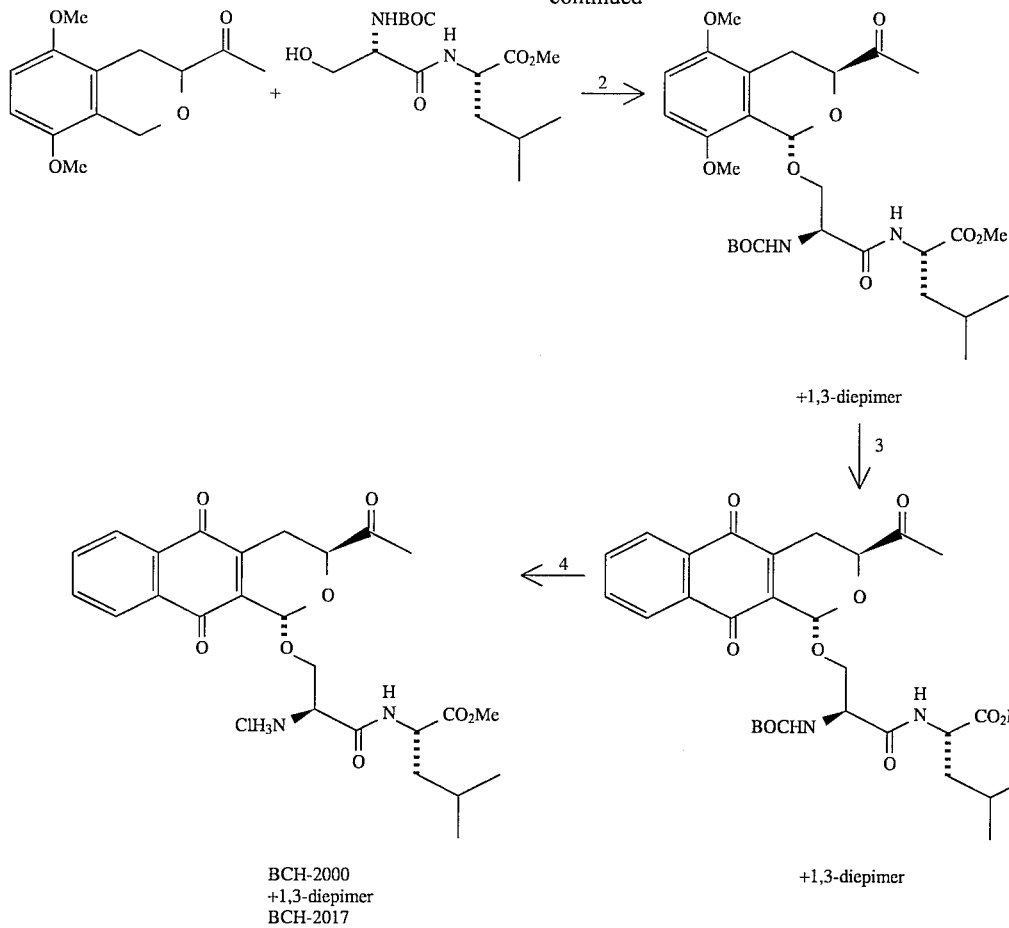

Step 1

N-BOC-Serine-Leucine-OMe

To a solution of Leucine-Me ester.HCl (0.91 eq, 0.40 g) and triethylamine (1.2 eq, 0.3 ml) in dry chloroform (24 ml), under argon, at room temperature, was added N-Boc-Serine (0.50 g, 2.43 mmols) and then EEDQ (1.3 eq, 0.71 g). The solution was stirred for 18 hours after which the solvent was evaporated. The residue was taken up in EtOAc and washed with 5% HCl (2×), sat. aq. NaHCO$_3$ and brine. The organic phase was dried over Na$_2$SO$_4$, the solids filtered and the solvent evaporated to give 0.71 g (87%) of N-Boc-Ser-Leu-OMe as a clear oil that was used without further purification.

$^1$H NMR (CDCl$_3$): δ 7.30 (bs, 1H, NH), 5.72 (bs, 1H, NH), 4.51 (m, 1H), 4.19 (m, 1H), 3.90 (m, 1H), 3.68 (s, 3H), 3.62 (m, 2H), 1.55 (m, 3H), 1.34 (s, 9H), 0.79 (m, 6H).

Step 2

(1S,2'S,3R,5'S) and (1R,2'S,3S,5'S)-1-[O-N-BOC-Serine-Leucine-Me ester]-3-aceto-5,8-dimethoxy-isochroman To a solution of 5,8-dimethoxy-3-aceto-isochroman (0.46 g, 1.93 mmole), the peptide from step 1 (example 17) (0.71 g, 1.1 eq) and activated 4A molecular sieves (500 mg) in dry CH$_2$Cl$_2$ (19 ml) was added DDQ (0.57 g, 1.3 eq). The solution was stirred for 18 hours after which it was filtered through celite. It was then poured in sat. aq. NaHCO$_3$ and the phases were separated. The aqueous phase was extracted with CH$_2$Cl$_2$ (2×) and the combined organic extracts were dried over MgSO$_4$. The solids were filtered and the solvent was evaporated to give the titled mixture of diastereomers that were separated by chromatography (silica gel, 1:1 hexanes/EtOAc).

The first running fraction: 0.395 g (36%). $^1$H NMR (CDCl$_3$): δ 7.00 (bs, 1H, NH), 6.74 (d, 1H, J=9.0, ArH), 6.68 (d, 1H, J=9.0, ArH), 5.81 (s, 1H, H-1), 5.64 (bs, 1H, NH), 4.52 (m, 2H), 4.29 (m, 1H), 4.05 (m, 1H), 3.88 (dd, 1H, J=7.4, 10.6), 3.81 (s, 3H, ArOMe), 3.73 (s, 3H, ArOMe), 3.57 (s, 3H, CO$_2$Me), 3.00 (dd, 1H, J=4.1, 17.6, H-4), 2.47 (dd, 1H, J=12.3, 17.6, H-4), 2.29 (s, 3H, COMe), 1.57–1.46 (m, 3H, CH$_2$—CH(Me)$_2$), 1.41 (s, 9H, t—Bu), 0,84 (d, 3H, J=3.3, isopropyl), 0.82 (d, 3H, J=3.3, isopropyl).

The second running fraction: 0.420 g (38%), $^1$H NMR (CDCl$_3$): δ 6.79 (m, 3H, 2ArH+NH), 6.10 (bs, 1H, NH), 5.74 (s, 1H, H-1), (4.62–4.33 (m, 3H), 3.91 (m, 2H), 3.77 (s, 6H, 2 ArOMe), 3.68 (s, 3H, CO$_2$Me), 3.01 (dd, 1H, J=4.0, 17.6, H-4), 2.50 (dd, 1H, J=12.3, 17.6, H-4), 2.33 (s, 3H, COMe), 1.50 (s, 9H, t—Bu), 1.48–1.25 (m, 3H, CH$_2$—CH(Me)$_2$), 0.70 (d, 3H, J=5.7, isopropyl), 0.61 (d, 3H, J=5.7, isopropyl).

Step 3

(1S,2'S,3S,5'S)-Methyl-(1-O-[N-BOC-Serine-Leucine-Me ester]-5,10-dioxo-3,4,5,10-tetrahydro-1-H-naphtho [2,3-c] pyran-3-yl) ketone To a solution of the peptido-isochroman from step 2 (example 17) (0.40 g, 0.68 mmols) in CH$_3$CN (9.7 ml), at 0° C., was added slowly a solution of CAN (1.5 g, 4 eq) and NaHCO$_3$ (0.4 g, 7 eq) in water (7.8 ml). The solution was stirred at 0° C. for 30 minutes after which it was poured in sat. aq. NaHCO$_3$. The aqueous layer was then extracted with CH$_2$Cl$_2$ (3×) and the combined organic extracts were dried over MgSO$_4$. The solids were filtered and the solvent evaporated. The crude quinone was then dissolved in dry toluene (7 ml) and acetoxybutadiene was added (0.4 ml, 5 eq). The solution was stirred for 18 hours. Silica gel was then added (1 g) and air was bubbled through the solution for 30 minutes. The silica gel was filtered through Celite and the solvent was evaporated. The brown oil obtained was purified by flash chromatography (silica gel, 1:1 hexanes/EtOAc) to give 115 mg (29%) of the titled tricyclic compound.

$^1$H NMR (CDCl$_3$): δ 8.12–8.02 (m, 2H, ArH), 7.76–7.73 (m, 2H, ArH), 4.91 (bs, 1H, NH), 5.92 (s, 1H, H-1), 5.52 (bs, 1H, NH), 4.62–4.47 (m, 3H, H-2'+H-5'+H-3), 4.17 (dd, 1H, J=4.4, 10.9, H-1'), 3.83 (dd, 1H, J=8.6, 10.9, H-1'), 3.56 (s, 3H, CO$_2$Me), 3.02 (dd, 1H, J=4.0, 19.9, H-4), 2.51 (dd, 1H, J=11.6, 19.9, H-4), 2.33 (s, 3H, COMe), 1.74–1.52 (m, 3H, CH$_2$—CH(Me)$_2$), 1.44 (s, 9H, t—Bu), 0.90 (d, 6H, J=6.3, isopropyl).

$^1$H NMR (DMSO-d$_6$): δ 8.98 (bs, 1H, NH amide), 8.42 (bs, 3H, NH$_3$Cl), 8.06–7.98 (m, 2H, ArH), 7.93–7.87 (m, 2H, ArH), 5.82 (s, 1H, H-1), 4.61 (dd, 1H, J=3.9, 11.4), 4.34–4.23 (m, 2H), 4.13 (m, 1H), 4.02 (dd, 1H, J=5.7, 9.8), 3.61 (s, 3H, CO$_2$Me), 2.88 (dd, 1H, J=3.9, 19.6, H-4), 2.47 (m, 1H, H-4 hidden under the DMSO peak), 2.30 (s, 3H, COMe), 1.62–1.49 (m, 3H, CH$_2$—CH(Me)$_2$), 0.88–0.82 (m, 6H, isopropyl).

EXAMPLE 18

Amino acid substituted naphthoquinone derivatives

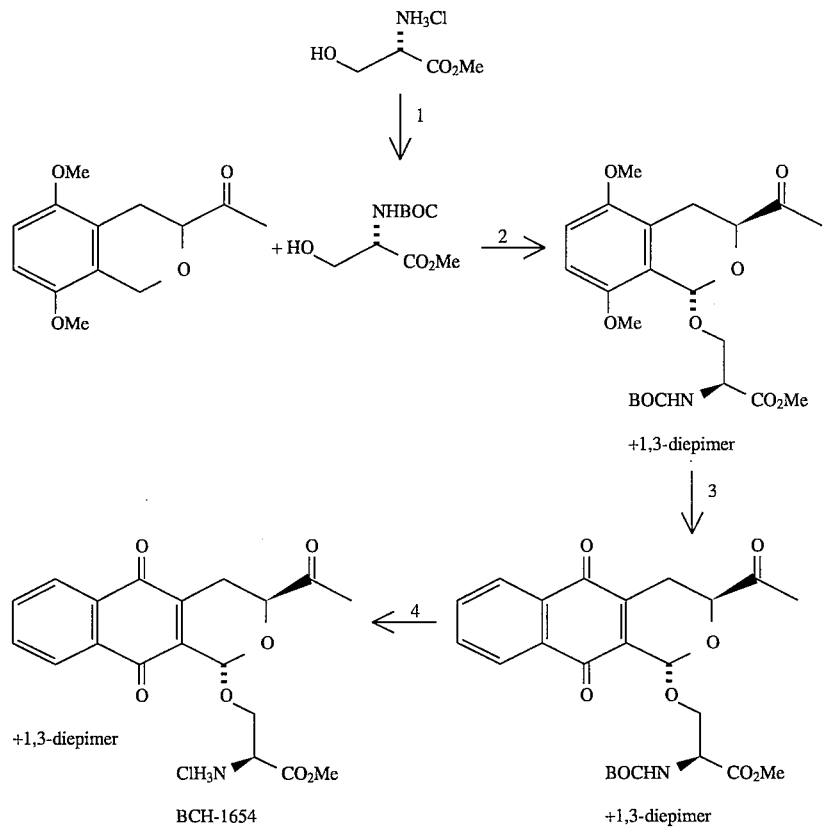

Step 4

(1S,2'S,3S,5'S)-Methyl-(1-O-[Serine-Leucine-Me ester]-5,10-dioxo-3,4,5,10-tetrahydro-1-H-naphtho [2,3-c] pyran-3-yl) ketone hydrochloride BCH-2000

A solution of the Boc protected tricyclic from step 3 (example 17) (54 mg, 0.092 mmol) in 96% formic acid (1 ml) was stirred at room temperature for 2 hours. The formic acid was evaporated and the residue dissolved in 0.1M HCl. The aqueous phase was washed with CH$_2$Cl$_2$ (2×) and the water was evaporated. The titled compound was obtained as a yellow oil was dried under high vacuum for 18 hours after which it had crystallized: 40 mg (83%).

Step 1

N-BOC-serine methyl ester

To a solution of serine methyl ester hydrochloride (0.12 g, 0.78 mmol) in 1.6 ml of dry MeOH, at room temperature, under argon, were added successively triethylamine (10% solution, 0.16 ml) and (BOC)$_2$O (0.19 g, 1.1 eq.) and the solution was stirred for 60 minutes. It was then poured in cold 2% HCl and the aqueous layer was extracted with CH$_2$Cl$_2$ (3×). The combined organic extracts were dried over MgSO$_4$, the solids were filtered and the solvents evaporated to give 0.17 g (100%) of the titled compound as a clear oil.

¹H NMR (CDCl₃): δ 5.56 (bs, 1H, NH), 4.34 (m, 1H, CH—CO₂Me), 3.88 (m, 2H, CH₂—OH), 3.75 (s, 3H, CO₂Me), 2.96 (bs, 1H, OH), 1.44 (s, 9H, BOC).

Step 2

(1S, 2'S, 3R) and (1R, 2'S, 3S)-1-[O-serine methyl ester]-3-aceto-5,8-dimethoxy isochroman.

The titled compounds were obtained as per procedure described in step 2, example 17. They were purified via flash chromatography (silica gel, 2:1 hexanes/EtOAc). The mixture of isomers is not separable by chromatography.

¹H NMR (CDCl₃): δ 6.73 (m, 2H, ArH), 6.07+5.78 (2d, 1H, NH), 5.72+5.70 (2s, 1H, H-1), 4.56–4.35 (m, 3H, H-1' and H-2'), 3.98 (m, 1H, H-3), 3.90+3.81+3.78+3.77+3.76+3.67 (6s, 18H [6×3H], Ar—OMe and CO₂Me), 3.04 (2dd, 1H, H-4), 2.50 (2dd, 1H, H-4), 2.32 (d, 3H, COCH₃), 1.47+1.43 (2s, 9H, BOC).

Step 3

(1S, 2'S, 3R) and (1R, 2'S, 3S)-methyl-(1-[O-N-BOC-serine methyl ester]-5,10-dioxo-3,4,5,10-tetrahydro-1-H-naphtho [2,3-C] pyran-3-yl) ketone.

The same procedure as described in step 3, example 17, was used for the titled compound, which was purified via flash chromatography (silica gel, 2:1 hexanes/EtOAc).

The mixture of isomers is not separable by chromatography.

¹H NMR (CDCl₃): δ 8.05 (m, 2H, ArH), 7.73 (m, 2H, ArH), 5.90+5.52 (2d, 1H, NH), 5.73+5.72 (2s, 1H, H-1), 4.60–4.05 (m, 4H, H-3, H-1' and H-2'), 3.81+3.70 (2s, 3H, CO₂CH₃), 3.01 (2m, 1H, H-4), 2.48 (m, 1H, H-4), 2.35 (2s, 3H, COCH₃), 1.47+1.43 (2s, 9H, BOC).

Step 4

(1S, 2'S, 3R) and (1R, 2'S, 3S)-methyl-(1-[O-serine methyl ester]-5,10-dioxo-3,4,5,10-tetrahydronaphtaleno [2,3-C] pyran-3-yl) ketone hydrochloride.

The titled compounds were obtained as per procedure described in step 4, example 17.

¹H NMR (DMSO): δ 8.05–7.82 (m, 4H, ArH), 5.83+5.78 (2s, 1H, H-1), 4.69–4.40 (m, 2H, H-1'), 4.27 (m, 1H, H-3), 4.16 (m, 1H, H-2'), 3.79+3.73 (2s, 3H, CO₂Me), 2.91+2.87 (2m, 1H, H-4), 2.50 (m, 1H, H-4), 2.31+2.29 (2s, 3H, COCH₃).

EXAMPLE 19

Amino alcohol substituted naphthoquinone derivative

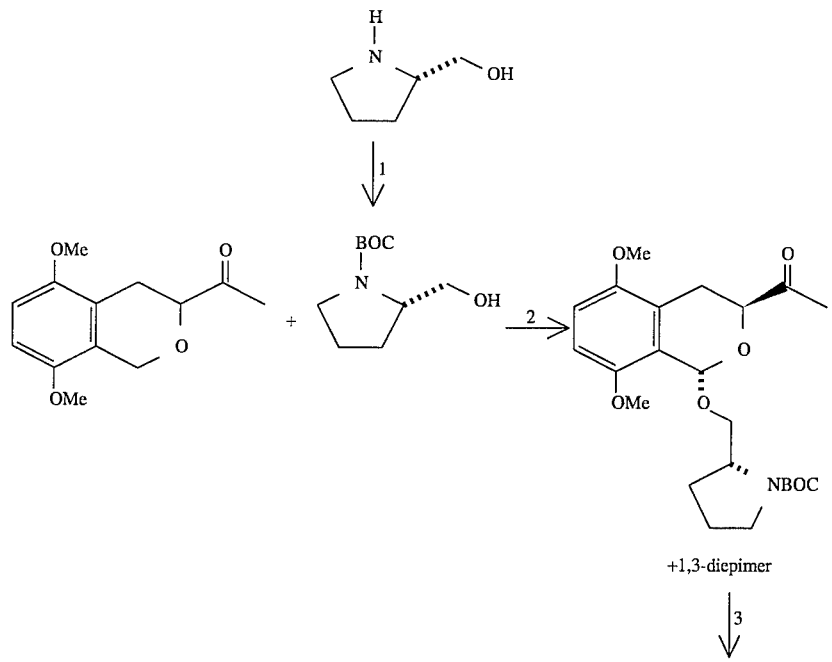

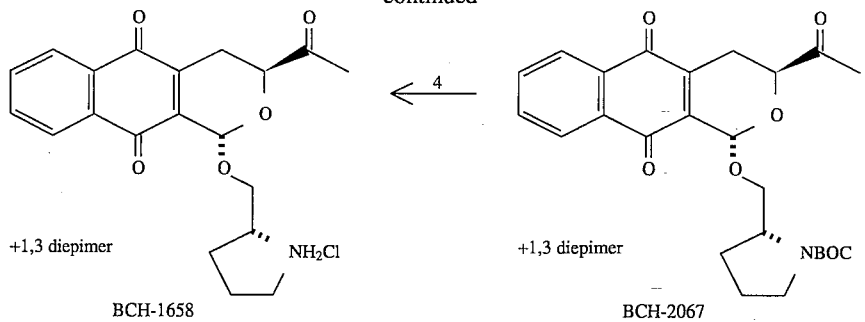

BCH-1658 (+1,3 diepimer, NH₂Cl)

BCH-2067 (+1,3 diepimer, NBOC)

Step 1

N-BOC-Prolinol

The titled compound was obtained as per procedure described in step 1, example 18.

¹H NMR (CDCl₃): δ 4.19 (bs, 1H, OH), 3.95 (m, 1H, H-2), 3.59 (m, 2H, CH₂—OH), 3.42 (m, 1H, H-5), 3.30 (m, 1H, H-5), 2.01 (m, 1H, H-3), 1.83 (m, 2H, H-4), 1.60 (m, 1H, H-3), 1.45 (s, 9H, BOC).

Step 2

(1S, 2'S, 3R) and (1R, 2'S, 3S)-1-[O-N-BOC-prolinol]-3-acetyl-5,8-dimethoxy isochroman The titled compounds were obtained as per procedure described in step 2, example 17. They were purified via flash chromatography (silica gel, 7:3 hexanes/EtOAc). The mixture of isomers is not separable by chromatography.

¹H NMR (CDCl₃): δ 6.72 (m, 2H, ArH), 5.82+5.77 (2s, 1H, H-1), 4.54 (m, 1H, H-3), 4.18–3.20 (m, 5H, H-1', H-2' and H-5'), 3.82+3.79 (2s, 6H, ArOMe), 3.05 (2m, 1H, H-4), 2.53 (m, 1H, H-4), 2.31 (s, 3H, COCH₃), 2.07–1.75 (m, 4H, H-3' and H-4'), 1.46 (s, 9H, BOC).

Step 3

(1S, 2'S, 3R) and (1R, 2'S, 3S)-methyl-(1-[O-N-BOC-prolinol]-5,10-dioxo-3,4,5,10-tetrahydro-1-H-naphtho [2,3-C] pyran-3-yl) ketone BCH-2067

The titled compounds were obtained as per procedure described in step 3, example 17. They were purified via preparative thin layer chromatography (silica gel, 7:3 hexanes/ethyl acetate).

¹H NMR (CDCl₃): δ 8.02 (m, 2H, ArH), 7.70 (m, 2H, ArH), 5.75+5.73 (2s, 1H, H-1), 4.47 (m, 1H, H-3), 4.15–3.18 (m, 5H, H-1', H-2' and H-5'), 2.97 (2m, 1H, H-4), 2.5 (m, 1H, H-4), 2.33+2.32 (2s, 3H, COCH₃), 2.05–1.72 (m, 4H, H-3' and H-4'), 1.48 (s, 9H, BOC).

Step 4

(1S, 2'S, 3R) and (1R, 2'S, 3S)-methyl-(1-[O-prolinol]-3,4,5,12-tetrahydronaphtho-[2,3-C] pyran-3-yl) ketone hydrochloride salt.

The titled compounds were obtained as per procedure described in step 4, example 17.

¹H NMR (DMSO): δ 8.02 (m, 2H, ArH), 7.88 (m, 2H, ArH), 5.73+5.71 (2s, 1H, H-1), 4.68 (m, 1H, H-3), 4.19–3.48 (m, 3H, H-2' and H-1'), 3.10 (m, 2H, H-5'), 2.39 (dd, 1H, H-4), 2.35 (m, 1H, H-4), 2.32+2.31 (2s, 3H, COCH₃), 2.10–1.55 (m, 4H, H-3' and H-4').

EXAMPLE 20

Preparation of naphtho-[2,3-c] pyran derivative with a cyano side chain

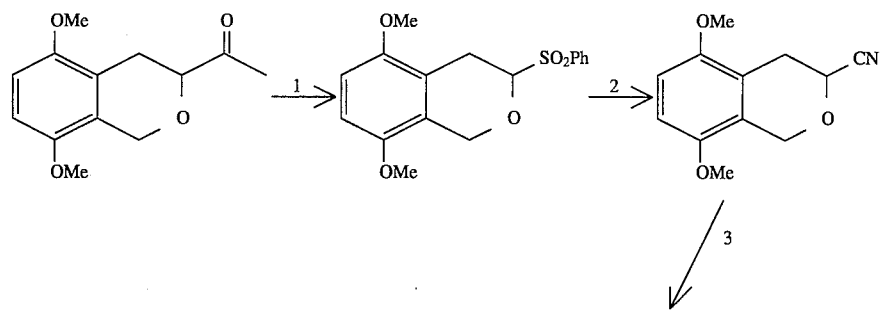

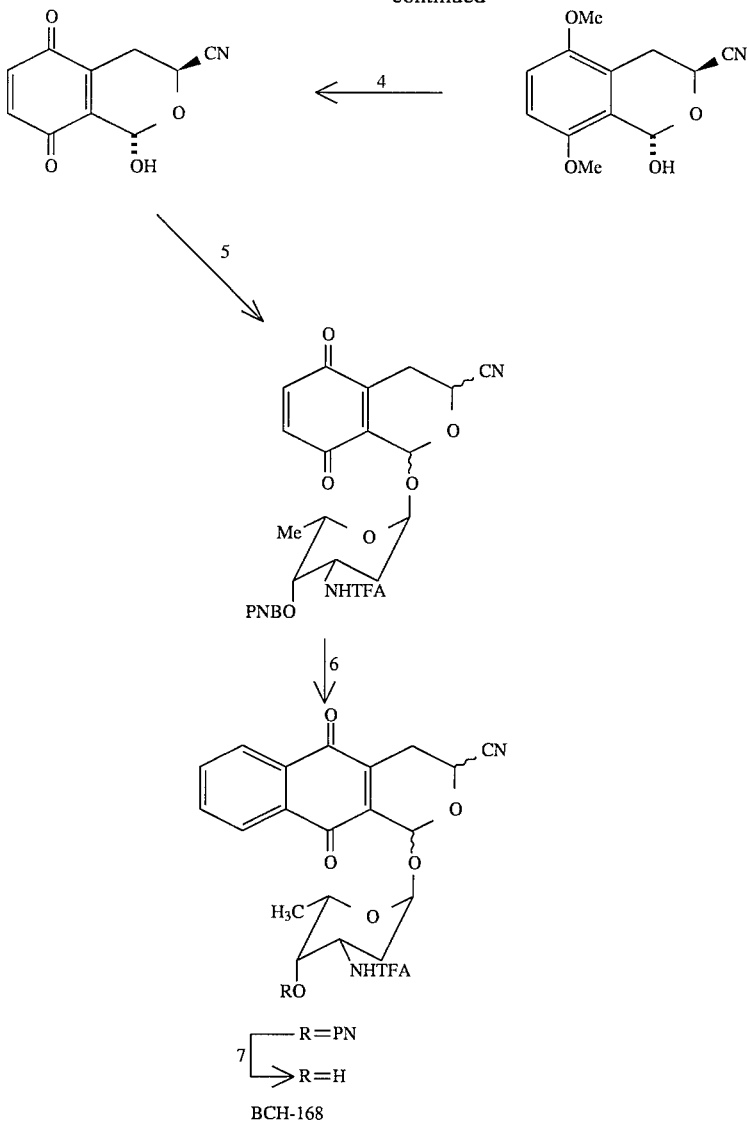

BCH-168

Step 1

5,8-dimethoxy-3-phenylsulphone isochroman

To a stirred solution of 5,8-dimethoxy-3-aceto isochroman (12.8 g, 54 mmol) in methylene chloride (350 ml) at room temperature was added 3-chloroperbenzoic acid 80% (18 g, 83 mmol) in portions over 15 minutes. After 2 hours, magnesium sulfate (6.8 g, 56 mmol) and sulfinic acid (10 g, 70 mmol) were added. After 2 hours, a saturated solution of potassium carbonate was added then the reaction mixture was washed with water and brine. The organic layer was dried over $MgSO_4$ and evaporated. The titled compound was purified by trituration in ether (11 g, 60%), m.p.: 118°–119° C.

$^1$H NMR (250 MHz, $C_6D_6$), δ: 7.99 (dd, J=1.5 and 8.0 Hz, 2H, Ar—H), 6.90 (m, 3H, Ar—H), 6.29 (2d, J=8.9 Hz, 2H, Ar—H), 5.08 (d, J=15.5 Hz, 1H, H-1), 4.53 (d, J=15.5 Hz, 1H, H-1), 4.40 (dd, J=4.7 and 9.2 Hz, 1H, H-3), 3.40 (dd, J=4.7 and 17.0 Hz, 1H, H-4), 3.28 (s, 3H, —OCH$_3$), 3.27 (dd, 9.2 and 17.0 Hz, 1H, H-4), 3.19 (s, 3H, —OCH$_3$).

Step 2

5,8-dimethoxy-3-cyano isochroman

To a stirred solution of $AlCl_3$ (1.39 g, 10.4 mmol) and TMS-CN (1.4 ml, 10.4 mmol) in $CH_2Cl_2$ (40 ml) at −78° C. under argon was added the pyranylsulfone from step 1 (example 2) (1.16 g, 3.5 mmol) then the temperature was slowly raised to −20° C. After 4 hours, the reaction mixture was worked up in methylene chloride and water. The organic layer was washed with brine and dried over $MgSO_4$. The solvent was evaporated and the residue was purified by flash chromatography (hexanes/AcOEt 3/1) to give the titled compound (596 mg, 78%).

$^1$H NMR (250 MHz, $CDCl_3$), δ: 6.30 (2d, J=8.2 Hz, 2H, Ar—H), 5.08 (d, J=16.3 Hz, 1H, H-1), 4.78 (d, J=16.3 Hz, 1H, H-1), 4.03 (t, J=5.1 Hz, 1H, H-3), 3.27 (s, 3H, —OCH$_3$), 3.18 (s, 3H, —OCH$_3$), 2.80 (dd, J=5.1 and 17.2 Hz, 1H, H-4), 2.66 (dd, J=5.1 and 17.2 Hz, 1H, H-4).

Step 3

1-hydroxy-3-cyano-5,8-dimethoxy isochroman

To a stirred solution of 2,5-dimethoxy-3-cyano isochroman (670 mg, 3.06 mmol) in $CCl_4$ (60 ml) were added N-bromosuccinimide (653 mg, 3.67 mmol) and a catalytic amount of AIBN. The mixture was heated to reflux and after 45 minutes, the solvent was evaporated and tetrahydrofurane (40 ml) and water (40 ml) were added. After 1 hour, the reaction mixture was worked up in ether. The organic layer was washed with brine and dried over $MgSO_4$. The solvent was evaporated and the residue purified by trituration in a small amount of ether to give the titled compound (453 mg, 63%).

$^1$H NMR (250 MHz, acetone $D_6$): 6.90 (2d, J=9.0 Hz, 2H, Ar—H), 6.06 (2d, J=5.2 Hz, 2H, H-1, —OH), 5.27 (dd, J=4.1 and 12.1 Hz, 1H, H-3), 3.81 (s, 3H, —OCH$_3$), 3.78 (s, 3H, —OCH$_3$), 3.09 (dd, J=4.1 and 17.1 Hz, 1H, H-4), 2.82 (dd, J=12.1 and 17.1 Hz, 1H, H-4).

Step 4

1-hydroxy-3-cyano-5,8-dioxo-5,8-dihydroisochroman

The titled compound was obtained in 77% yield by applying the procedure described in step 3, example 12, to the precursor of step 3 of this example.

$^1$H NMR (250 MHz, acetone $D_6$) δ: 6.86 (2d, J=10.1 Hz, 2H, —CH=CH—), 6.61 (d, J=5.7 Hz, 1H, H-1), 5.88 (d, J=5.7 Hz, 1H, —OH), 5.20 (dd, J=3.8 and 11.6 Hz, 1H, H-3), 2.98 (dd, J=3.8 and 18.9 Hz, 1H, H-4), 2.73 (dd, J=11.6 and 18.9 Hz, 1H, H-4).

Step 5 and 6

(1'S, 1S, 3R) and (1'S, 1R, 3S)-5,10-dioxo-3-cyano-1-(2',3',6',-trideoxy-3'-trifluoroacetamido-4'-O-p-nitrobenzoyl-L-lyxohexopyranose)-3,4,5,10-tetrahydro-1-H-naphtho-[2,3-c] pyran The titled compounds were obtained in 27% yield by following the procedure described in step 4, example 12, on the precursor of step 4 of this example.

$^1$H NMR (250 MHz, $CD_2Cl_2$) δ: 8.30 (m, 4H, Ar—H), 8.10 (m, 2H, Ar—H), 7.80 (m, 2H, Ar—H), 6.55 (m, 1H, —NH), 6.15 and 5.95 (2s, 1H, H-1), 5.70 (m, 1H, H-4'), 5.60 and 5.55 (m, 1H, H-1'), 5.10 (m, 1H, H-3), 4.70–4.20 (m, 2H, H-3', H-5'), 3.25–2.80 (m, 2H, H-4), 2.40–2.00 (m, 2H, H-2'), 1.30 and 1.20 (2d, J=6.7 Hz, 3H, H-6').

Step 7

(1'-S, 1-R, 3-S) and (1'-S, 1-S, 3-R)-3-cyano-1-[2',3',6'-trideoxy-3'-trifluoroacetamido-4'-hydroxy-L-lyxohexopyranose)-5,10-dioxo-3,4,5,10-tetrahydronaphtho-[2,3-C] pyran-3-yl BCH-1688

The titled compounds were obtained in 63% yield by following the procedure described in step 3, example 5, on the precursor from step 6 of this example.

$^1$H NMR (250 MHz, $CD_2Cl_2$) δ: 8.07 (m, 2H, Ar—H), 7.79 (m, 2H, Ar—H), 6.80 (m, 1H, N—H), 6.09 and 5.92 (2s, 1H, H-1), 5.52 and 5.42 (2d, 1H, H-1'), 5.04 (1m, 1H, H-3), 4.40–4.05 (m, 2H, H-3', H-5'), 3.70 (m, 1H, H-4'), 3.20–3.05 (1m, 1H, H-4), 3.00–2.80 (1m, 1H, H-4), 2.30–2.00 (m, 3H, —OH, H-2'), 1.38 and 1.29 (2d, J=6.7 Hz, 3H, H-6').

EXAMPLE 21

Preparation of some sugar derivatives

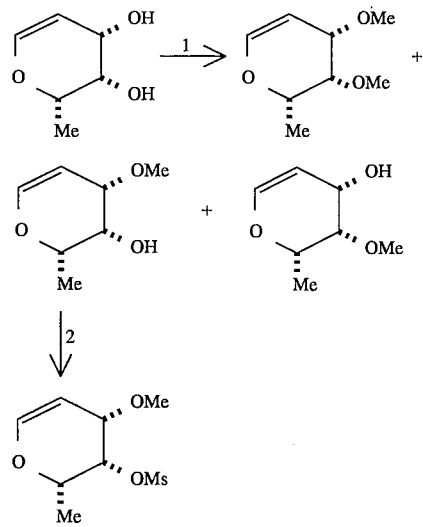

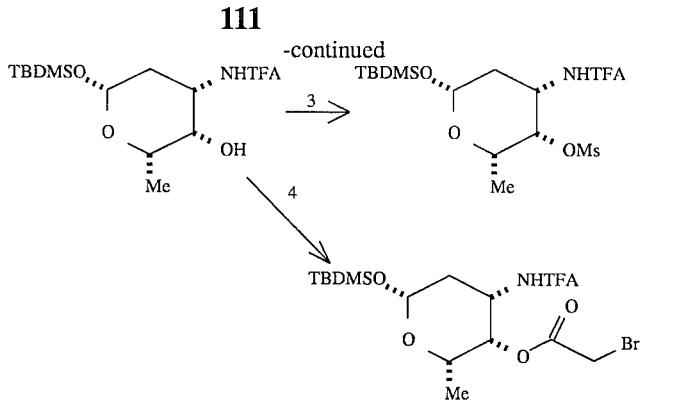

Step 1

3,4-dimethoxy-L-fucal, and 3-methoxy-L-fucal

To a stirred solution of L-fucal (400 mg, 3.1 mmol) in dimethylformamide (7.5 ml) were added methyl iodide (0.85 ml, 3.6 mmol) and silver oxide (1.16 g, 5.0 mmol). After 1.5 hour, the reaction mixture was worked up in $CH_2Cl_2$ and water. The organic layer was washed with brine and dried over $MgSO_4$. The solvent was evaporated. The products were separated by flash chromatography (hexanes/AcOEt 2/1) to give dimethoxy fucal (79 mg, $^1$H NMR (250 MHz, $CDCl_3$) δ: 6.29 (dd, J=1.3 and 6.2 Hz, 1H, H-1), 4.72 (m, 1H, H-2), 4.05 (m, 2H, H-5, H-4), 3.57 (s, 3H, —$OCH_3$), 3.44 (m, 1H, H-3), 3.39 (s, 3H, —$OCH_3$), 1.31 (d, J=6.6 Hz, 3H, H-6).

The 3-methoxy-L-fucal (20% yield) had:

$^1$H NMR (250 MHz, $CDCl_3$) δ: 6.36 (dd, J=1.2 and 6.2 Hz, 1H, H-1), 4.60 (m, 1H, H-2), 4.05–3.80 (m, 3H, H-3, H-4, H-5), 3.40 (s, 3H, —$OCH_3$), 2.37 (d, J=3.9 Hz, 1H, —OH), 1.36 (d, J=6.6 Hz, 3H, H-6).

Step 2

3-methoxy-4-mesyl-L-fucal

Mesylation of 3-methoxy-L-fucal yielded (84%) of the titled compound.

$^1$H NMR (250 MHz, $CDCl_3$) δ: 6.34 (dd, J=2.1 and 6.5 Hz, 1H, H-1), 4.95 (m, 1H, H-2), 4.73 (m, 1H, H-4), 4.13 (m, 2H, H-3, H-5), 3.45 (s, 3H, —$OCH_3$), 3.15 (s, 3H, —$SO_2CH_3$), 1.40 (d, J=6.6 Hz, 3H, H-6).

Step 3

1-t-Butyl dimethylsilyloxy-3-trifluoroacetamido-4-methanesulfonyl-2,3,6-trideoxy-L-lyxohexopyranose To a stirred solution of 1-t-butyl dimethylsilyloxy, 3-trifluoroacetamido-2,3,6-trideoxy-L-lyxohexopyranose (504 mg, 1.41 mmol) in $CH_2Cl_2$ (7 ml) at 0° C. were added methanesulfonyl chloride (218 μl, 2.82 mmol) and triethylamine (590 μl, 4.2 mmol). After 2 hours the reaction mixture was worked up with $CH_2Cl_2$ and HCl 0.1N. The organic layer was washed with a solution of $NaHCO_3$ and brine then dried over $MgSO_4$. The solvent was evaporated to give 1-t-butyl dimethyl silyloxy, 3-trifluoroacetamido-2,3,6 trideoxy-4 methanesulfonyl-L-lyxohexopyranose (604 mg, 98%).

$^1$H NMR (250 MHz, $CDCl_3$) δ: 7.28 (d, J=7.7 Hz, 1H, N—H), 4.83 (dd, J=2.1 and 9.1 Hz, 1H, H-1), 4.71 (d, J=2.2 Hz, 1H, H-4), 4.25 (m, 1H, H-3), 3.75 (q, J=6.4 Hz, 1H, H-5), 3.18 (s, 3H, —$SO_2$—$CH_3$), 2.0 (m, 1H, H-2), 1.75 (m, 1H, H-2), 1.31 (d, J=6.4 Hz, 3H, H-6), 0.89 (s, 9H, —$C(CH_3)_3$), 0.12 and 0.11 (2s, 6H, —$Si(CH_3)_2$).

Step 4

1-t-Butyl dimethylsilyloxy-3-trifluoroacetamido-4-O-bromoacetyl-2,3,6-trideoxy-L-lyxohexopyranose To a stirred solution of 1-t-butyl dimethylsilyloxy-3-trifluoroacetamido-2,3,6-trideoxy-L-lyxohexopyranose (81 mg, 0.18 mmol) in $CH_2Cl_2$ (2 ml) at 0° C. were added collidine (47 μl, 0.36 mmol), and bromoacetylbromide (24 μl, 0.27 mmol). After 1 hour, the reaction mixture was worked up with $CH_2Cl_2$ and water. The organic layer was washed with brine and dried over $MgSO_4$. The solvent was evaporated to give the titled compound (76 mg, 74%).

$^1$H NMR (250 MHz, $CDCl_3$) δ: 6.47 (d, J=8 Hz, 1H, N—H), 5.03 (d, J=3.0 Hz, 1H, H-4), 4.84 (dd, J=2.3 and 9.0 Hz, 1H, H-1), 4.35 (m, 1H, H-3), 4.00 and 3.80 (2d, J=10.5 Hz, 2H, —$CH_2$—Br), 3.75 (dq, J=1 Hz, 6.5 Hz, 1H, H-5), 2.05–1.70 (m, 2H, H-2), 1.20 (d, J=6.5, 3H, —H6), 0.9 (s, 9H, —$C(CH_3)_3$), 0.13 (2s, 6H, —$Si(CH_3)_2$).

EXAMPLE 22

Preparation of naphtho-[2,3-c] pyran derivatives

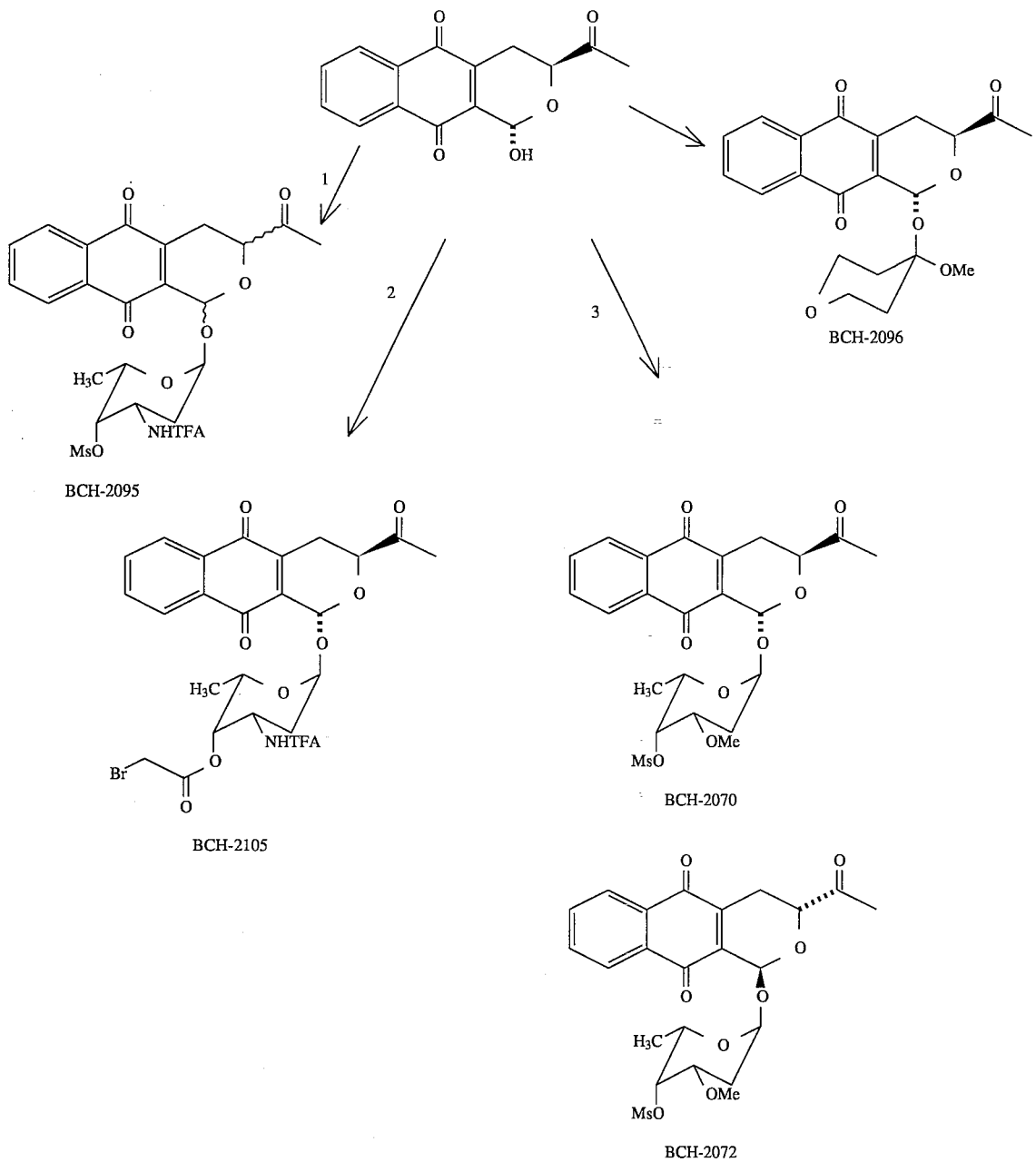

Step 1

(1'-S, 1-S, 3-R) and (1'-S, 1-R, 3-S)-methyl-(1-[2',3',4',6' tetradeoxy-3'-trifluoroacetamido-4'-O-methanesulfonyl-L-lyxohexopyranose)-5,10-dioxo-3,4,5,10 tetrahydronaphtho-[2,3-c] pyran-3-yl) ketone BCH-2095

The titled compound was obtained in 45% yield by using the procedure described in step 2 of this example but with the sugar obtained from step 3, example 21. It was purified by flash chromatography (toluene/acetone 95/5).

$^1$H NMR (250 MHz, CDCl$_3$) δ: 8.10 (m, 2H, Ar—H), 7.80 (m, 2H, Ar—H), 7.15 (2d, J=8.0 Hz, 1H, N—H), 6.16 and 6.00 (2s, 1H, H-1), 5.62 and 5.50 (2d, J=1.5 Hz, 1H, H-1'), 4.89 and 4.84 (2 broad s, 1H, H-4'), 4.75 and 4.25 (2q, J=6.6 Hz, H-5'), 4.50 (m, 2H, H-3, H-3'), 3.23 and 3.21 (2s, 3H, —SO$_2$CH$_3$), 3.10 (m, 1H, H-4), 2.55 (m, 1H, H-4), 2.33 and 2.32 (2s, 3H, —CO—CH$_3$), 2.00 (m, 2H, H-2'), 1.45 and 1.30 (2d, J=6.6 Hz, H-6').

Step 2

(1'-S, 1-S, 3-R)-methyl-(1-[2',3',4',6' tetradeoxy-3'-trifluoro-acetamido-4'-O-(2-bromo-acetyl)-n-lyxopyranose]-5,10-dioxo-3,4,5,10 tetrahydronaphtho-[2,3-c] pyran-3-yl) ketone BCH-2105

To a stirred solution of the aglycone from example 3 (30 mg, 0.11 mmol), 4-bromoacetyl-1-t-butyl dimethylsilyloxy-3-trifluoro-acetamido daunosamine derivative (76 mg, 0.13 mmol) molecular sieves Å (62 mg) in CH$_2$Cl$_2$ (1.2 ml) at −50° C. under argon was added trimethylsilyl trifluoromethanesulfonate (23 μl, 0.12 mmol). After 2 hours at −30° C., the reaction mixture was worked up with a solution of NaHCO₃ 10% and CH₂Cl₂. The organic layer was washed with brine and dried over MgSO₄, the residue was purified by flash chromatography (hexanes/AcOEt 2:1) to give the titled compound (8 mg, 12%).

¹H NMR (250 MHz, CDCl₃) δ: 8.12 (m, 2H, Ar—H), 7.77 (m, 2H, Ar—H), 6.33 (d, J=8.1 Hz, 1H, N—H), 6.00 (s, 1H, H-1), 5.67 (s, 1H, H-1'), 5.16 (s, 1H, H-4'), 4.53 (dd, J=3.9 and 11.6 Hz, 1H, H-3), 4.53 (m, 1H, H-3'), 4.23 (q, J=6.7 Hz, 1H, H-5'), 3.90 (2d, J=10.9 Hz, 2H, —CH₂—Br), 3.08 (dd, J=3.9 and 19.8 Hz, 1H, H-4), 2.53 (dd, J=11.6 and 19.8 Hz, 1H, H-4), 2.34 (s, 3H, —CO—CH₃), 2.02 (m, 2H, H-2'), 1.19 (d, J=6.7 Hz, 3H, H-6').

Step 3

(1'-S, 1-R, 3-S)-methyl-(1-[2',3',4',6' tetradeoxy-3'-methoxy-4'-O-methanesulfonyl-L-lyxohexopyranose)-5,10-dioxo-3,4,5,10 tetrahydronaphtho-[2,3-c] pyran-3-yl) ketone BCH-2070

The titled compound was obtained in 22% yield by applying the procedure described in step 4, example 12, to the aglycone from example 3 and the glycal from step 2, example 21. Purification was carried out by flash chromatography (toluene/acetone: 95/5) M.P. 85°–89° C.

¹H NMR (250 MHz, CDCl₃) δ: 8.11 (m, 2H, Ar—H), 7.77 (m, 2H, Ar—H), 5.98 (s, 1H, H-1), 5.62 (d, J=2.8 Hz, 1H, H-1'), 4.85 (s, 1H, H-4'), 4.46 (dd, J=4.0 and 11.6 Hz, 1H, H-3), 4.04 (q, J=6.5 Hz, 1H, H-5'), 3.62 (m, 1H, H-3'), 3.39 (s, 3H, —OCH₃), 3.14 (s, 3H, —SO₂—CH₃), 3.05 (dd, J=4.0 and 19.5 Hz, 1H, H-4), 2.50 (dd, J=11.6 and 19.5 Hz, 1H, H-4), 2.33 (s, 3H, —CO—CH₃), 2.00 (m, 2H, H-2'), 1.33 (d, J=6.5 Hz, 3H, H-6').

Step 3

(Cont'd): (1'-S, 1'S, 3-R)-methyl-(1-[2',3',4',6' tetradeoxy-3'-methoxy-4'-O-methanesulfonyl-L-lyxohexopyranose)-5,10-dioxo-3,4,5,10 tetrahydronaphtho-[2,3-c] pyran-3-yl) ketone BCH-2072

The titled compound was obtained in 11% yield by using the procedure described in step 3 of this example but using the 1,3-diepimeric aglycone. M.P. 139°–141° C.

¹H NMR (250 MHz, CDCl₃) δ: 8.12 (m, 2H, Ar—H), 7.77 (m, 2H, Ar—H), 6.15 (s, 1H, H-1), 5.52 (d, J=1.5 Hz, 1H, H-1'), 4.95 (d, J=1.5 Hz, 1H, H-4'), 4.59 (q, J=6.5 Hz, 1H, H-5'), 4.49 (dd, J=4.1 and 11.6 Hz, 1H, H-3), 3.60 (m, 1H, H-3'), 3.38 (s, 3H, —SO₂CH₃), 3.15 (s, 3H, —OCH₃), 3.07 (dd, J=4.1 and 19.9 Hz, 1H, H-4), 2.55 (dd, J=11.6 and 19.9 Hz, 1H, H-4), 2.33 (s, 3H, —CO—CH₃), 1.95 (m, 2H, H-2'), 1.50 (d, J=6.5 Hz, 3H, H-6').

Step 4

(1-S, 3-R) and (1-R, 3-S)-methyl-(1-(1-methoxy-4-oxocyclohexyloxy)-5,10-dioxo-3,4,5,10 tetrahydronaphtho-[2,3-c] pyran-3-yl) ketone BCH-2096

To a stirred solution of the aglycone from example 3 (7 mg, 0.026 mmol) in tetrahydrofurane (1.6 ml) were added 5,6-dihydro-4-methoxy-2H-pyran (29 μl, 0.26 mmol) and a catalytic amount of PTSA. After 4 hours, the reaction was worked up with CH₂Cl₂ and NaHCO₃ 5%. The organic layer was washed with brine and dried over MgSO₄. The solvent was evaporated to give the titled compound (10 mg, 96%).

¹H NMR (250 MHz, CDCl₃) δ: 8.10 (m, 2H, Ar—H), 7.70 (m, 2H, Ar—H), 6.34 (s, 1H, H-1), 4.66 (dd, J=4.3 and 11.6 Hz, 1H, H-3), 3.80–3.50 (m, 4H, —CH₂—O—CH₂—), 3.40 (s, 3H, —OCH₃), 3.06 (dd, J=4.3 and 19.7 Hz, 1H, H-4), 2.52 (dd, J=11.6 and 19.0 Hz, 1H, H-4), 2.30 (s, 3H, —CO—CH₃), 2.20–1.85 (m, 4H, —CH₂—C—CH₂—).

EXAMPLE 23

Preparation of naphtho-[2,3-c] pyran derivative with a homo methyl ketone side chain

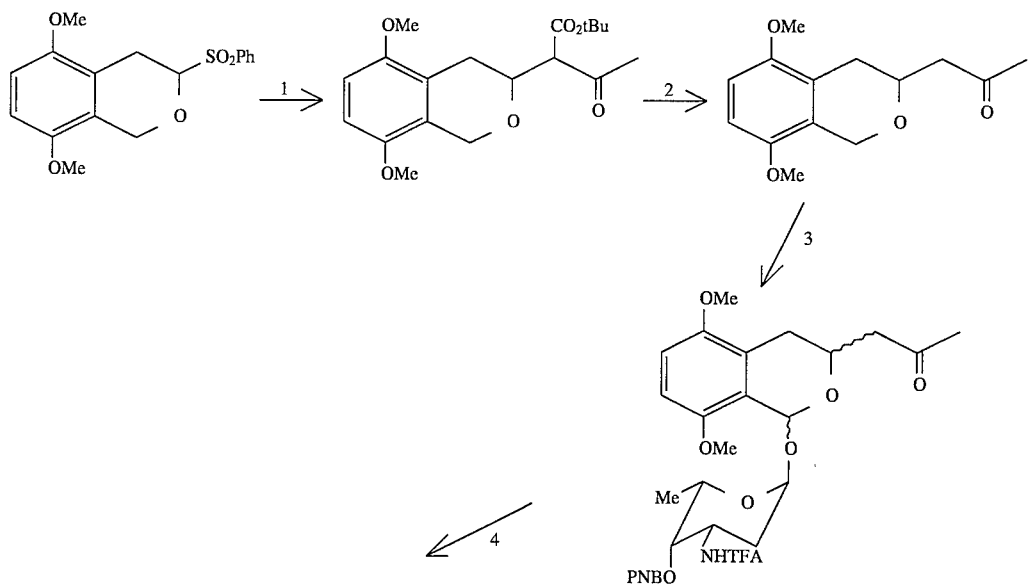

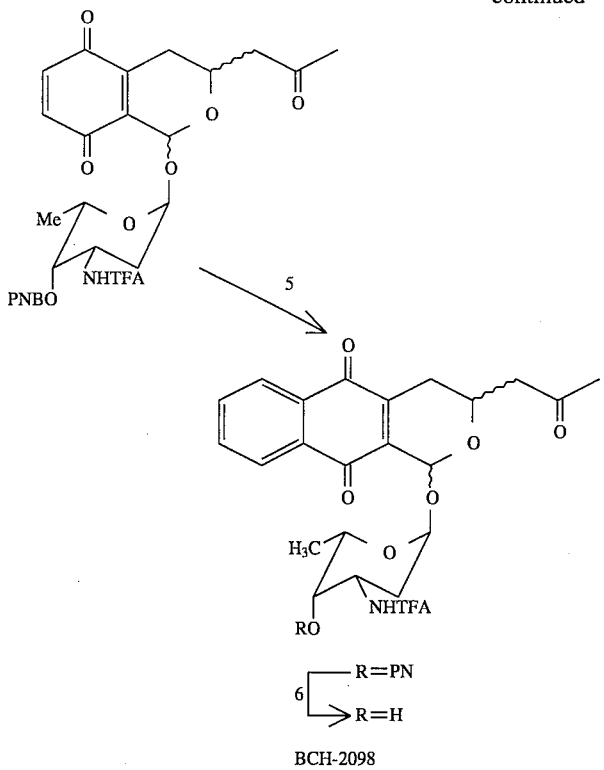

BCH-2098

Step 1

5,8-Dimethoxy-3-(t-butyl acetoacetato) isochroman

To a stirred solution of pyranosulfone from step 1, example 20, (1.12 g, 3.35 mmol) in CH$_2$Cl$_2$ (40 ml) at −78° C. were added a solution of silyl enol ether of t-butyl acetoacetate (10 mmol) in CH$_2$Cl$_2$ (10 ml) and AlCl$_3$ (1.33 g, 10 mmol). Temperature was then raised to −30° C. for 2 hours. The reaction mixture was worked up with CH$_2$Cl$_2$ and HCl 0.1N. The organic was washed with brine and dried over MgSO$_4$. The solvent was evaporated to give the title β-ketoester (519 mg, 43%).

$^1$H NMR (250 MHz, CDCl$_3$), δ: 6.63 (m, 2H, Ar—H), 4.91 and 4.85 (2d, J=9.8 Hz, 1H, H-1), 4.60 and 4.53 (2d, J=7.9 Hz, 1H, H-1), 4.20 (m, 1H, H-3), 3.76–3.74 (3s, 6H, —OCH$_3$), 3.62 (t, J=9.5 Hz, 1H), 2.90 (m, 1H, H-4), 2.45 (m, 1H, H-4), 2.32 and 2.28 (2s, 3H, —CO—CH$_3$), 1.49 and 1.47 (2s, 9H, —C(CH$_3$)$_3$).

Step 2

5,8-Dimethoxy-3-(propane-2-one) isochroman

The product from step 1 of this example was decarboxylated, in 91% yield, with concentrated aqueous HBr in acetone.

$^1$H NMR (250 MHz, CDCl$_3$) δ: 6.63 (2d, J=9.0 Hz, 2H, Ar—H), 4.88 (d, J=15.9 Hz, 1H, H-4), 4.58 (d, J=15.9 Hz, 1H, H-4), 4.06 (m, 1H, H-3), 3.77 and 3.75 (2s, 6H, —OCH$_3$), 2.85 (m, 2H, —CH$_2$—CO—), 2.63 (dd, J=4.8 and 16.5 Hz, 1H, H-4), 2.40 (dd, J=10.9 and 16.5 Hz, 1H, H-4), 2.24 (s, 3H, —CO—CH$_3$).

Step 3

5,8-Dimethoxy-3-(propane-2-one)-1-(2',3',6'-trideoxy-3'-trifluoroacetamido-4'-O-p-nitrobenzoyl-L-lyxohexopyranose)-isochroman The isochroman from 2 herein was glycosidated as per procedure described in step 3, example 34. The title compound was obtained in 97% yield.

$^1$H NMR (250 MHz, CDCl$_3$) δ: 8.26 (d, J=2.0 Hz, 4H, Ar—H), 6.74 (m, 2H, Ar—H), 6.50 and 6.35 (2d, J=7.0 Hz, 1H, —NH), 6.02 and 5.88 (2s, 1H, H-1), 5.59 (s, 1H, H-1'), 5.49 and 5.46 (2s, 1H, H-4'), 4.70 (m, 2H, H-3', H-3), 3.80 and 3.78 (2s, 6H, —OCH$_3$), 3.00–2.50 (m, 2H, H-4, —CH$_2$—CO—), 2.50–2.00 (m, 2H, H-4, —CH$_2$—CO—), 2.24 and 2.22 (2s, 3H, —CO—CH$_3$), 1.25 and 1.15 (2d, J=6.5 Hz, 3H, H-6').

Step 4

5,8-Dioxo-3-(propane-2-one)-1-(2',3',6'-trideoxy-3'-trifluoroacetamido-4'-O-p-nitrobenzoyl-L-lyxohexopyranose)-isochroman The titled compound was obtained in 94% yield via oxidative demethylation of the isochroman obtained from step 3 herein as per procedure described in step 4, example 34.

$^1$H NMR (250 MHz, CDCl$_3$), δ: 8.30 (d, J=5.7 Hz, 4H, ArH), 6.80 (m, 2H, Ar—H), 6.42 and 6.35 (2d, J=7.0 Hz, 1H, N—H), 5.81 and 5.70 (2s, 1H, H-1), 5.59 and 5.54 (2s, 1H, H-1'), 5.45 (2d, J=1.5 Hz, 1H, H-4'), 4.80–4.40 (m, 3H, H-3', H-5', H-3), 2.90 (m, 1H, H-4), 2.70 (m, 2H, —CH$_2$—CO), 2.40–1.90 (m, 3H, H-4, H-2'), 2.23 and 2.21 (2s, 3H, —CO—CH$_3$), 1.28 and 1.15 (2d, J=6.5 Hz, 3H, H-6').

Step 5

5,10-Dioxo-3-(propane-2-one)-1-(2',3',6'-trideoxy-3'-trifluoroacetamido-4'-O-p-nitrobenzoyl-L-lyxohexopyranose)-3,4,5,10-tetrahydro-1H-naphtho-[2,3-c] pyran

119

The titled compound was obtained via cycloaddition between 1-acetoxybutadiene and the quinone from step 4 herein by following the procedure described in step 5, example 34.

$^1$H NMR (250 MHz, CDCl$_3$), δ: 8.31 (2d, J=9.1 Hz, 4H, Ar—H), 8.11 (m, 2H, Ar—H), 7.78 (m, 2H, Ar—H), 6.45 and 6.33 (2d, J=7.3, 1H, N—H), 5.99 and 5.88 (2s, 1H, H-1), 5.71 and 5.60 (2s, 1H, H-1'), 5.48 (1s, 1H, H-4'), 4.80–4.40 (m, 3H, H-3, H-3', H-4'), 3.00–2.60 (m, 3H, H-4, —CH$_2$—CO—), 2.50–2.00 (m, 3H, H-4, H-2'), 2.25 and 2.23 (2s, 3H, —CO—CH$_3$), 1.33 and 1.17 (2d, J=6.5 Hz, 3H, H-6').

Step 6

(1'-S, 1-S, 3-R) and (1'-S, 1-R, 3-S)-1-(6-hydroxy-1-(2',3',6'-trideoxy-3'-trifluoroacetamido,4-hydroxy-L-lyxopyranose)-5,10-dioxo-3,4,5,10 tetrahydronaphtho-[2,3-c] pyran-3-yl) propane-2-one BCH-2098

120

The titled compound was obtained following deprotection of the glycoside from step 5 herein as per procedure described in step 6, example 34.

$^1$H NMR (250 MHz, CDCl$_3$) δ: 8.10 (m, 2H, Ar—H), 7.75 (m, 2H, Ar—H), 6.73 (d, J=7.5 Hz, 1H, N—H), 5.93 and 5.81 (2s, 1H, H-1), 5.52 and 5.41 (2d, J=2.7 Hz, 1H, H-1'), 4.80–4.20 (m, 3H, H-3, H-3', H-5'), 3.70 (m, 1H, H-4'), 3.00–2.60 (m, 3H, H-4, —CH$_2$—CO—), 2.40–1.70 (m, 4H, H-4, H-2', —OH), 2.23 and 2.20 (2s, 3H, —CO—CH$_3$), 1.41 and 1.20 (2d, J=6.6 Hz, 3H, H-6').

EXAMPLE 24

Preparation of naphtho-[2,3-c] pyran derivative with a C-2' glycoside linkage

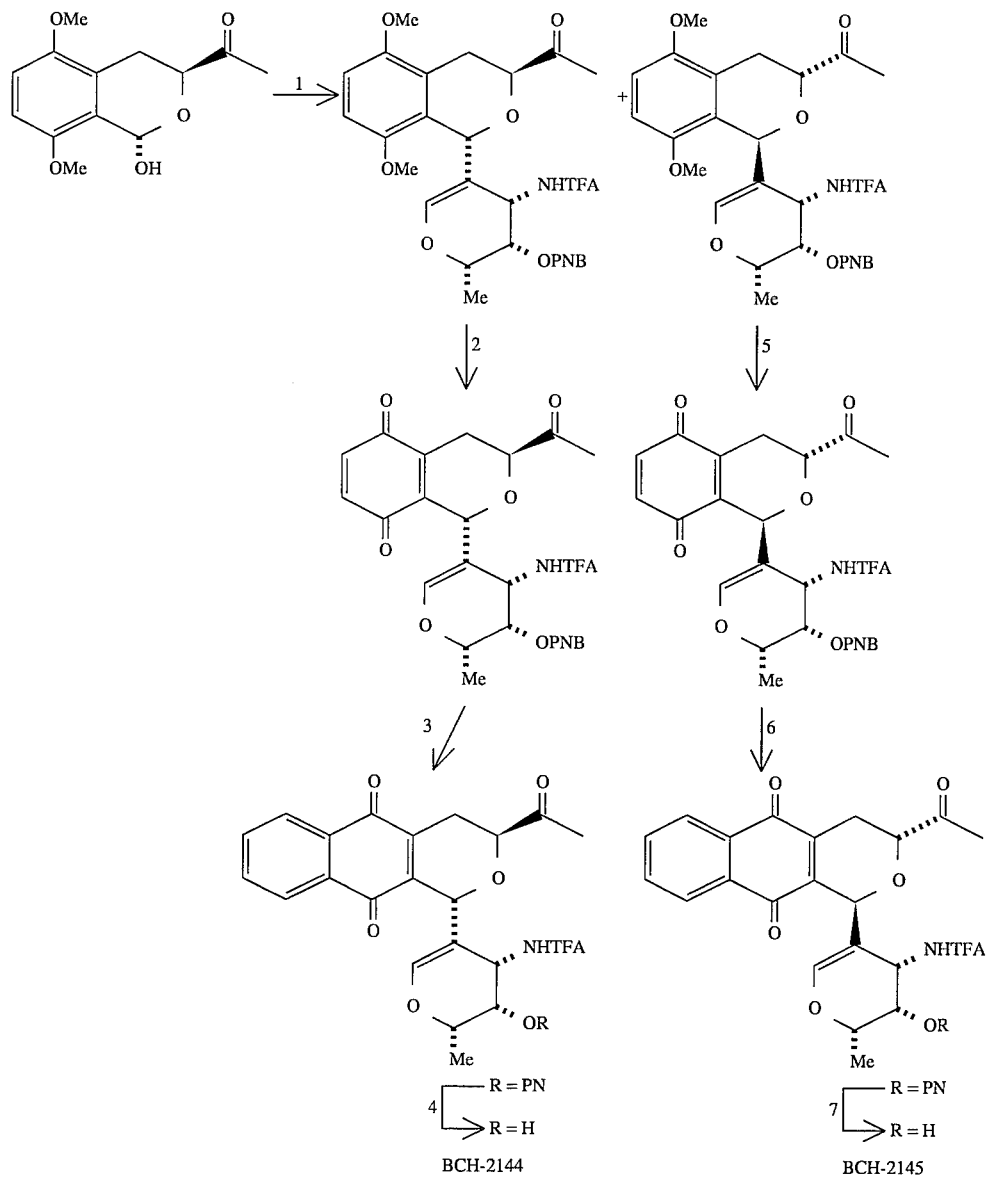

BCH-2144        BCH-2145

Step 1

(1R, 3S) and (1-S, 3R)-1-(2',3',6'-trideoxy-3'-trifluoroacetamido-4'-O-p-nitrobenzyloxy-1,5-dihydro-L-lyxohexo-pyranose-2-yl)-5,8-dimethoxy-3-acetoisochroman 2,5-Dimethoxy-1-hydroxy-3-acetoisochroman was reacted with 1,4-di-O-p-nitrobenzoyl-N-trifluoroacyl daunosamine as per procedure from step 1, example 5. The titled products were separated by flash chromatography (CH$_2$Cl$_2$/acetone 99/1).

$^1$H NMR (250 MHz, CDCl$_3$) δ: 8.30 (m, 3H, Ar—H, N—H), 8.09 (d, J=8.7 Hz, 2H, Ar—H), 6.71 (2d, J=8.8 Hz, 2H, Ar—H), 6.02 (s, 1H, H-1'), 5.84 (d, J=3.6 Hz, 1H, H-4'), 5.62 (s, 1H, H-1), 5.30 (m, 1H, H-3'), 4.45 (m, 2H, H-3, H-5'), 3.81 (1s, 3H, —OCH$_3$), 3.76 (1s, 3H, —OCH$_3$), 3.11 (dd, J=3.9 Hz and 17.3 Hz, 1H, H-4), 2.61 (dd, J=12.1 and 17.3 Hz, 1H, H-4), 1.95 (s, 3H, —COCH$_3$), 1.28 (d, J=6.6 Hz, 3H, H-6').

The second diastereomer had:

$^1$H NMR (250 MHz, CDCl$_3$) δ: 8.28 (2d, J=9.0 Hz, 4H, Ar—H), 6.90 (d, J=7.8 Hz, 1H, N—H), 6.70 (2d, J=9.0 Hz, 2H, Ar—H), 6.18 (d, J=1.5 Hz, 1H, H-1'), 5.75 (d, J=4.8 Hz, 1H, H-4'), 5.55 (s, 1H, H-1), 5.30 (m, 1H, H-3'), 4.30 (m, 2H, H-5', H-4), 3.80 (s, 3H, —OCH$_3$), 3.60 (s, 3H, —OCH$_3$), 3.02 (dd, J=4.3 and 17.6 Hz, 1H, H-4), 2.57 (dd, J=11.6 and 7.6 Hz, 1H, H-4), 2.29 (s, 3H, —CO—CH$_3$), 1.29 (d, J=6.6 Hz, 3H, H-6').

Step 2

(1R, 3S)-1-(2',3',6'-trideoxy-3'-trifluoroacetamido-4'-O-p-nitrobenzyloxy-1,5-dihydro-L-lyxohexopyranose-2-yl)-5,8-dioxoisochroman The (1R, 3S) product from step 1 herein was oxidatively demethylated as per procedure in step 3, example 12.

$^1$H NMR (250 MHz, CDCl$_3$) δ: 8.23 (d, J=8.7 Hz, 2H, Ar—H), 8.03 (d, J=8.7 Hz, 2H, Ar—H), 7.65 (d, J=6.6 Hz, 1H, N—H), 6.75 (2d, J=10.3 Hz, 2H, Ar—H), 6.28 (d, J=1.4 Hz, 1H, H-1), 5.78 (d, J=3.8 Hz, 1H, H-4'), 5.37 (s, 1H, H-1'), 5.21 (m, 1H, H-3'), 4.43 (q, J=6.5 Hz, 1H, H-5'), 4.24 (dd, J=3.8 and 11.2 Hz, 1H, H-3), 2.90 (dd, J=3.8 and 19.5 Hz, 1H, H-4), 2.40 (ddd, J=1.6, 11.2 and 19.5 Hz, 1H, H-4), 1.88 (s, 3H, —COCH$_3$), 1.26 (d, J=6.5 Hz, 3H, H-6').

Step 3

(1R, 3S)-1-(2',3',6'-trideoxy-3'-trifluoroacetamido-4'-O-p-nitrobenzyloxy-1,5-dihydro-L-lyxohexopyranose-2-yl)-5,10-dioxo-3,4,5,10-tetrahydro-1H-naphtho [2,3-c] pyran The quinone from step 2 herein was cycloadded with 1-acetoxybutadiene as per procedure from step 4, example 12. The product had:

$^1$H NMR (250 MHz, CDCl$_3$) δ: 8.30 (d, J=8.7 Hz, 2H, Ar—H), 8.10 (m, 4H, Ar—H), 7.80 (m, 2H, Ar—H), 6.36 (d, J=1.9 Hz, 1H, H-1), 5.86 (d, J=3.9 Hz, 1H, H-4'), 5.60 (s, 1H, H-1'), 5.31 (m, 1H, H-3'), 4.49 (q, J=6.6 Hz, 1H, H-5'), 4.35 (dd, J=3.9 Hz, and 11.4 Hz, 1H, H-3), 3.12 (dd, J=3.9 Hz and 19.4 Hz, 1H, H-4), 2.62 (ddd, J=1.9, 11.4 Hz, 19.4 Hz, 1H, H-4), 1.98 (s, 3H, —CO—CH$_3$), 1.31 (d, J=6.6 Hz, 3H, H-6').

Step 4

(1R, 3S)-1-(2',3',6'-trideoxy-3'-trifluoroacetamido-4'-hydroxy-1,5-dihydro-L-lyxohexopyranose-2-yl)-5,10-dioxo-3,4,5,10-tetrahydro-1H-naphtho-[2,3-c] pyran BCH-2144

The tricyclic product from step 3 herein was deprotected as per procedure from step 3, example 5. The title product had:

$^1$H NMR (250 MHz, CDCl$_3$) δ: 8.20 (m, 2H, Ar—H), 7.75 (m, 3H, N—H, Ar—H), 6.25 (d, J=1.7 Hz, 1H, H-1), 5.55 (s, 1H, H-1'), 5.11 (m, 1H, H-3'), 4.32 (dd, J=4.0 Hz and 11.1 Hz, 1H, H-3), 4.23 (q, J=6.5 Hz, 1H, H-5'), 4.05 (d, J=3.7 Hz, 1H, H-4'), 3.00 (dd, J=4.0 and 19.8 Hz, 1H, H-4), 2.59 (ddd, J=1.7, 11.1 and 19.8 Hz, 1H, H-4), 2.28 (s, 3H, —CO—CH$_3$), 1.70 (broad s, 1H, —OH), 1.34 (d, J=6.5 Hz, 3H, H-6').

Step 5

(1S, 3R)-1-(2',3',6'-trideoxy-3'-trifluoroacetamido-4'-O-p-nitrobenzyloxy-1,5-dihydro-L-lyxohexopyranose-2-yl)-5,8-dioxoisochroman The (1S, 3R) product from step 1 herein was oxidatively demethylated as per procedure in step 3, example 12.

$^1$H NMR (250 MHz, CDCl$_3$) δ: 8.32 (d, J=9.0 Hz, 2H, Ar—H), 8.20 (d, J=9.0 Hz, 2H, Ar—H), 7.58 (d, J=8.3 Hz, 1H, N—H), 6.80 (2d, J=10.1 Hz, 2H, Ar—H), 6.46 (d, J=1.3 Hz, 1H, H-1), 5.73 (d, J=4.8 Hz, 1H, H-4'), 5.33 (d, J=1.9 Hz, 1H, H-1'), 5.25 (m, 1H, H-3'), 4.35 (q, J=6.6 Hz, 1H, H-5'), 4.20 (dd, J=4.1 Hz and 10.5 Hz, 1H, H-3), 2.88 (dd, J=4.1 and 19.9 Hz, 1H, H-4), 2.40 (ddd, J=1.9, 10.5 and 19.9 Hz, 1H, H-4), 2.27 (s, 3H, —COCH$_3$), 1.32 (d, J=6.6 Hz, 3H, H-6').

Step 6

(1S, 3R)-1-(2',3',6'-trideoxy-3'-trifluoroacetamido-4'-O-p-nitrobenzyloxy-1,5-dihydro-L-lyxohexopyranose-2-yl)-5,10-dioxo-3,4,5,10-tetrahydro-1H-naphtho-[2,3-c] pyran The quinone from step 5 herein was cycloadded with 1-acetoxybutadiene as per procedure from step 4, example 12. The titled product had:

$^1$H NMR (250 MHz, CDCl$_3$) δ: 8.30 (d, J=8.9 Hz, 2H, Ar—H), 8.22 (d, J=8.9 Hz, 2H, Ar—H), 8.20 (m, 1H, Ar—H), 8.00 (m, 2H, N—H, Ar—H), 7.86 (m, 2H, Ar—H), 6.53 (s, 1H, H-1), 5.77 (d, J=4.7 Hz, 1H, H-4'), 5.50 (s, 1H, H-1'), 5.30 (m, 1H, H-3'), 4.37 (q, J=6.6 Hz, 1H, H-5'), 4.27 (dd, J=4.0 and 10.7 Hz, 1H, H-3), 3.08 (dd, J=4.0 and 19.8 Hz, 1H, H-4), 2.55 (ddd, J=1.0, 10.7 and 19.8 Hz, 1H, H-4), 2.31 (s, 3H, —CO—CH$_3$), 1.31 (d, J=6.6 Hz, 3H, H-6').

Step 7

(1S, 3R)-1-(2',3',6'-trideoxy-3'-trifluoroacetamido-4'-hydroxy-1,5-dihydro-L-lyxohexopyranose-2-yl)-5,10-dioxo-3,4,5,10-tetrahydro-1H-naphtho-[2,3-c] pyran BCH-2145

The tricyclic product from step 6 herein was deprotected as per procedure from step 3, example 5. The titled product had:

$^1$H NMR (250 MHz, CDCl$_3$) δ: 8.19 (d, J=8.9 Hz, 1H, N—H), 8.10 (d, J=7.3 Hz, 1H, Ar—H), 7.90 (d, J=7.3 Hz, 1H, Ar—H), 7.70 (m, 2H, Ar—H), 6.26 (s, 1H, H-1), 5.47 (s, 1H, H-1'), 5.10 (m, 1H, H-3'), 4.20 (m, 2H, H-3, H-5'), 3.97 (d, J=4.0 Hz, 1H, H-4'), 3.00 (dd, J=4.0 and 20.0 Hz, 1H, H-4), 2.55 (dd, J=10.8 Hz, and 20.0 Hz, 1H, H-4), 2.32 (s, 3H, —CO—CH$_3$), 1.70 (broad s, 1H, —OH), 1.36 (d, J=6.4 Hz, 3H, H-6').

EXAMPLE 25

Preparation of 3,3-bis-(methoxycarbonyl)-5,10-dioxo-3,4,5,10-tetrahydro-1H-naphtho-[2,3-c]-pyran (BCH-1665)

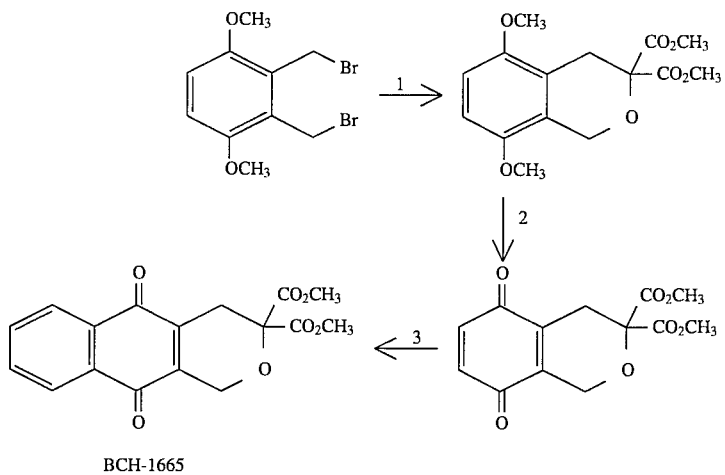

BCH-1665

Step 1

5,8-dimethoxy-3,3 bis (methoxycarbonyl)-isochroman

To a solution of 2,3 bis (bromomethyl)-1,4-dimethoxybenzene (1.30 g; 4.00 mmol) in 40 ml of a 1:1 mixture of tetrahydrofuran and dimethylformamide were added benzoyloxy-dimethylmalonate (1.06 g; 4.19 mmol), potassium carbonate (1.16 g; 8.38 mmol) and cesium carbonate (1.37 g; 4.19 mmol). The resulting mixture was stirred at 80° C. (oil bath temperature) for 2.5 hours. It was then cooled to room temperature and filtered on a pad of silica gel and the solvents were evaporated using a vacuum pump to yield 2.3 g of crude alkylated product which was dissolved in methanol (60 ml). To this solution was added a solution of sodium methoxyde in methanol (4.57 ml; 4.37M; 5 eq). The resulting mixture was stirred at room temperature for 2 hours and was then concentrated to a volume of ~10 ml. It was quenched with 1N HCl and extracted with dichloromethane. The combined organic layers were washed with brine and dried over MgSO$_4$. The crude product was purified by column chromatography on silica gel using 10–25% ethyl acetate in hexane to afford the title compound (452 mg; 36% overall):

$^1$H NMR (250 MHz; CDCl$_3$) δ: 3.25 (2H, s, H-4), 3.72, 3.78, 3.79 (12H, 3s, 4×OCH$_3$), 4.88 (2H, s, H-1), 6.59 and 6.65 (2H, AB doublets, Ar—H).

Step 2

5,8-dioxo-3,3 bis (methoxycarbonyl)-5,8-dihydro-isochroman

To a solution of 5,8-dimethoxy-3,3 bis (methoxycarbonyl)-isochroman (70 mg; 0.23 mmol) in acetonitrile (5 ml) at room temperature was added dropwise a solution of ceric ammonium nitrate (378 mg; 0.69 mmol) in water (1 ml). The resulting mixture was then stirred at room temperature for 5 minutes and was quenched by adding saturated sodium bicarbonate solution. The product was extracted with dichloromethane and the combined organic layers were washed with brine and dried over MgSO$_4$. Evaporation afforded the crude quinone (60 mg; 95%) which was used without further purification:

$^1$H NMR (CDCl$_3$, 250 MHz) δ: 3.03 (2H, t, J=3 Hz, H-4), 3.81 (6H, s, OCH$_3$), 4.67 (2H, t, J=3 Hz, H-1), 6.70 and 6.77 (2H, AB doublets, Ar—H).

Step 3

3,3 bis (methoxycarbonyl)-5,10-dioxo-3,4,5,10-tetrahydro-1H-naphtho-[2,3-c] pyran To a solution of 5,8-dioxo-3,3 bis (methoxycarbonyl)-5,8-dihydroisochroman (50 mg; 0.17 mmol) in toluene (4 ml) at room temperature was added 1-acetoxy-1,3 butadiene (113 μl; 1 mmol). The resulting mixture was stirred at room temperature for 24 hours. Air was then bubbled through for 30 minutes and the mixture was concentrated to a volume of ~1 ml and applied to silica gel column. Elution with 30% ethyl acetate in hexane afforded pure title compound (20 mg; 34%) as a yellow solid; m.p.: 210°–222° C. (dec):

$^1$H NMR (250 MHz, CDCl$_3$) δ: 3.22 (2H, t, J=2.5 Hz, H-4), 3.84 (6H, s, CO$_2$CH$_3$), 4.86 (2H, t, J=2.5 Hz, H-1), 7.75 (2H, m, Ar—H), 8.10 (2H, m, Ar—H).

IR (film): 2963, 1743, 1662, 1641, 1591, 1438, 1288, 1175, 1055, 791 and 692 cm$^{-1}$.

EXAMPLE 26

Preparation of (1'S, 1R, 3S) and (1'S, 1S, 3R)-5,10-dioxo-3-methoxymethyl-1-(2',3',6'-trideoxy-3'-trifluoroacetamido-L-lyxohexopyranose)-3,4,5,10-tetrahydro-1H-naphtho-[2,3-c]-pyran (BCH-1691) and BCH-1693)

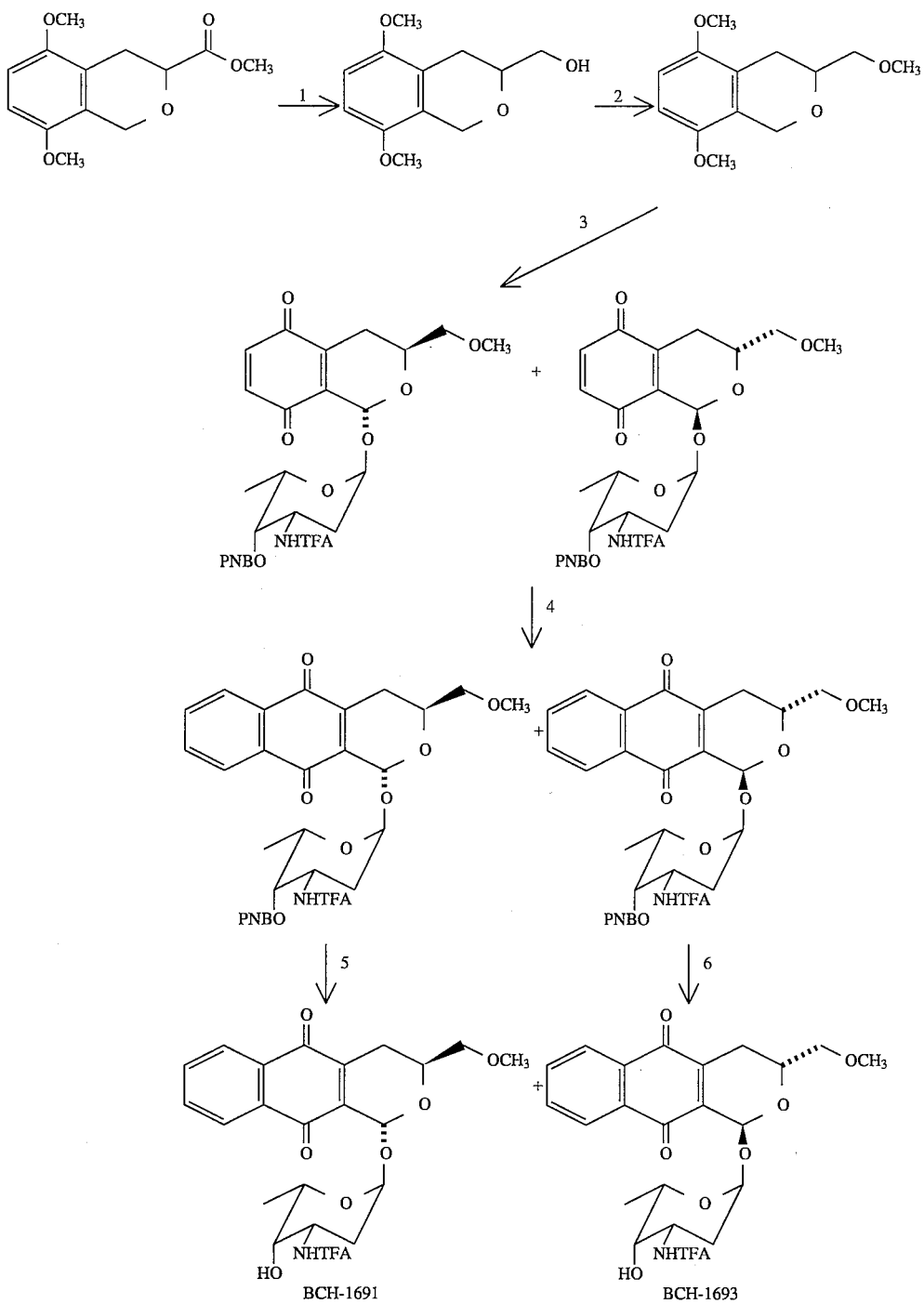

Step 1

5,8-dimethoxy-3-hydroxymethyl-isochroman

To a solution of 5,8-dimethoxy-3-methoxycarbonyl-isochroman (310 mg; 1.23 mmol) in 5 ml of tetrahydrofuran at 0° C. was added lithium aluminum hydride (47 mg; 1.23 mmol). The mixture was stirred at 0° C. for 15 minutes and was quenched with 1N HCl. The product was extracted with ether and the combined organic layers were washed with brine and dried over MgSO$_4$ affording crude title alcohol (246 mg; 90%) used as such for subsequent steps:

$^1$H NMR (250 MHz, CDCl$_3$) δ: 2.42 (1H, m, H-4 ax), 2.55–2.75 (2H, m, H-4 eq and —OH), 3.60–3.90 (2H, m, CH$_2$—OH), 3.76 (3H, s, —OCH$_3$), 3.77 (3H, s, —OCH$_3$), 4.62 (1H, br d, J=16.0 Hz, H-1), 4.97 (1H, d, J=16.0 Hz, H-1), 6.61 and 6.65 (2H, AB doublets, ArH).

Step 2

5,8-dimethoxy-3-methoxymethylisochroman

To a suspension of sodium hydride (70 mg of 60% in oil; 1.78 mmol) in tetrahydrofuran (3 ml) was added a solution of 5,8-dimethoxy-3-hydroxymethyl-isochroman (330 mg; 1.48 mmol) in 7 ml of tetrahydrofuran. The resulting mixture was stirred at room temperature until H$_2$ evolution ceased (~15 minutes) and iodomethane (500 μl; 5 eq) was added. The mixture was then stirred at room temperature for 30 minutes. Since the reaction was not complete another equivalent of sodium hydride was added along with 20 mg of cesium carbonate. The mixture was stirred for 15 minutes and was quenched with saturated ammonium chloride solution and extracted with dichloromethane. The combined organic layers were washed with brine and dried over $MgSO_4$. The crude was purified by column chromatography on silica gel using 25% ethyl acetate in hexane to afford the title compound (301 mg; 86%):

$^1$H NMR (250 MHz, $CDCl_3$) δ: 2.45 (1H, br dd, J=11.0 and 17 Hz, H-4 ax), 2.69 (1H, dm, J=17.0 Hz, H-4 eq), 3.44 (3H, s, $CH_2$—O—$CH_3$), 3.55 (2H, d, J=5.5 Hz, —C$H_2$—O), 3.75 (3H, s, $OCH_3$), 3.77 (3H, s, $OCH_3$), 4.63 (1H, br d, J=16.0 Hz, H-1), 4.97 (1H, d, J=16.0 Hz, H-1), 6.61 and 6.64 (2H, AB doublets, Ar—H).

Step 3

(1'S, 1R, 3S)-5,8-dioxo-3-methoxymethyl-1-(2',3',6'-trideoxy-3'-trifluoroacetamido-4'-O-p-nitrobenzoyl-L-lyxo-hexopyranose)-5,8-dihydroisochroman and its (1'S, 1S, 3R) diastereomer To a solution of 5,8-dimethoxy-3-methoxymethyl-isochroman (280 mg; 1.18 mmol) in 16 ml of dichloromethane were added 2,3,6-trideoxy-3-trifluoroacetamido-4-O-p-nitrobenzoyl-α-L-lyxohexopyranose (555 mg; 1.42 mmol), 4 Å molecular sieves (500 mg) and 2,3 dichloro-5,6-dicyanobenzoquinone (360 mg; 1.6 mmol). The dark green reaction mixture was stirred at room temperature for 14 hours. It was quenched with saturated $NaHCO_3$ solution and extracted with dichloromethane. The combined organic layers were washed with saturated $NaHCO_3$, brine and were dried over $Na_2SO_4$ affording, after evaporation, 671 mg of a crude adduct which was dissolved in acetonitrile (20 ml) at 0° C. A solution of ceric ammonium nitrate (3.3 g; 6 mmol) in 10 ml of water was treated by portions with solid sodium bicarbonate (886 mg). The resulting yellow solution was added dropwise to the isochroman solution. After the addition, the mixture was stirred at 0° C. for 20 minutes, quenched with saturated $NaHCO_3$ solution and extracted with dichloromethane. The combined organic layers were washed with brine and dried over $Na_2SO_4$ to afford after evaporation a crude quinone which was recrystallized from dichloromethane:pentane yielding 225 mg of a diastereomeric quinone mixture favoring the title compound (2:1):

$^1$H NMR (250 MHz, $CDCl_3$): 1.20 (3H, t, J=6.5 Hz, H-6'), 1.90–2.70 (4H, m, H-2' and H-4), 3.41 (3H, s, —$OCH_3$), 3.35–3.65 (3H, m, C$H_2$—$OCH_3$ and H-3'), 4.15–4.70 (2H, m, H-3 and H-5'), 5.44 (1H, br s, H-1'), 5.60 (1H, br s, H-4'), 5.78 (1H, s, H-1), 6.30 (1H, m, NH), 6.65–6.90 (2H, m, Ar—H), 8.30 (4H, m, PNB): signals for minor (1'S, 1S, 3R) isomer are δ: 1.30 (3H, d, J=6.5 Hz, H-6'), 1.90–2.70 (4H, m, H-2' and H-4), 3.43 (3H, s, —$OCH_3$), 3.35–3.65 (3H, m, C$H_2$—O—$CH_3$ and H-3'), 4.15–4.70 (2H, m, H-3 and H-5'), 5.40 (1H, br s, H-1'), 5.59 (1H, br s, H-4'), 5.91 (1H, s, H-1), 6.40 (1H, m, NH), 6.65–6.90 (2H, m, Ar—H), 8.30 (2H, m, Ar—H).

Step 4: (1'S, 1R, 3S)-5,10-dioxo-3-methoxymethyl-1-(2',3',6'-trideoxy-3'-trifluoroacetamido-4'-O-p-nitrobenzoyl-L-lyxohexo-pyranose)-3,4,5,10-tetrahydro-1H-naphtho-[2,3-c]-pyran To a solution of the quinone mixture from step 3 of this example, (100 mg; 0.17 mmol) in 6 ml of toluene at room temperature was added 1-acetoxy-1,3-butadiene (113 μl; 1 mmol). The rest of the procedure is identical to step 2, example 5, affording the title compound (42 mg; 40%):

$^1$H NMR ($CD_2Cl_2$, 250 MHz) δ: 1.17 (3H, d, J=6.5 Hz, H-6'), 1.90–2.20 (2H, m, H-2'), 2.37 (1H, dd, J=11.5 and 19.5 Hz, H-4 ax), 2.70 (1H, dd, J=3.5 and 19.5 Hz, H-4 eq), 3.38 (3H, s, O—$CH_3$), 3.55 (2H, m, —$CH_2$—$OCH_3$), 4.25–4.70 (3H, m, H-3, H-3' and H-5'), 5.41 (1H, br s, H-1'), 5.65 (1H, br s, H-4'), 5.90 (11H, s, H-1), 6.44 (1H, br d, J=7 Hz, N—H), 7.75 (2H, m, Ar—H), 8.05 (2H, m, Ar—H), 8.27 (4H, m, PNB).

The second diastereomer:

(1'S, 1S, 3R)-5,10-dioxo-3-methoxymethyl-1-(2',3',6'-trideoxy-3'-trifluoroacetamido-4'-O-p-nitrobenzoyl-L-lyxohexo-pyranose)-3,4,5,10-tetrahydro-1H-naphtho-[2,3-c] pyran was obtained in 19% yield and had:

$^1$H NMR (250 MHz, $CD_2Cl_2$) δ: 1.30 (3H, d, J=6.5 Hz, H-6'), 1.90–2.30 (2H, m, H-2'), 2.47 (1H, dd, J=11 and 19.5 Hz, H-4 ax), 2.71 (1H, dd, J=4 and 19.5 Hz, H-4 eq), 3.89 (3H, s, —$OCH_3$), 3.57 (2H, d, J=5 Hz, $CH_2$—$OCH_3$), 4.27 (1H, m, H-3), 4.52 (1H, m, H-3'), 4.75 (1H, q, J=6.5 Hz, H-5'), 5.41 (1H br s, H-1'), 5.56 (1H, br s, H-4'), 6.03 (1H, s, H-1), 6.46 (1H, br d, J=7.5 Hz, NH), 7.75 (2H, m, Ar—H), 8.07 (2H, m, Ar—H), 8.28 (4H, m, PNB).

Step 5: (1'S, 1R, 3S)-5,10-dioxo-3-methoxymethyl-(2',3',6'-trideoxy-3'-trifluoroacetamido-L-lyxohexopyranose)-3,4,5,10-tetrahydro-1H-naphtho-[2,3-c]-pyran (BCH-1691)

To a solution of (1'S, 1R, 3S)-5,10-dioxo-3-methoxymethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-C] pyran (19 mg; 0.029 mmol) in methanol (0.4 ml) and tetrahydrofuran (1.5 ml) at 0° C. was added 0.86 μl (0.1 eq) of a 4.37M solution of sodium methoxyde in methanol. The resulting mixture was stirred at 0° C. for 20 minutes and was quenched with saturated $NH_4Cl$. Extraction with dichloromethane followed by washing of the combined organic layers with brine and drying with $Na_2SO_4$ furnished a crude product which was purified by column chromatography on silica gel using 5–10% acetone in benzene as eluent yielding the title compound (14 mg; 96%) which was recrystallized from dichloromethane:ether:pentane to give yellow crystals: M.P.: 140°–159° C.; IR (neat): 3500, 3422, 3320, 2938, 1715, 1667, 1597, 1295, 1178 and 980 $cm^{-1}$;

$^1$H NMR (250 MHz, $CD_2Cl_2$) δ: 1.21 (3H, d, J=7.6 Hz, H-6'), 1.52 (1H, br s , O—H), 1.70–2.20 (2H, m, H-2'), 2.35 (1H, dd, J=11.7 and 19.3 Hz, H-4 ax), 2.68 (1H, dd, J=3.4 and 19.3 Hz, H-4 eq), 3.56 (3H, s, $OCH_3$), 3.52 (2H, d, J=4.8 Hz, $CH_2$—$OCH_3$), 3.58 (1H, br s, H-4'), 4.15–4.40 (3H, m, H-3, H-3', H-5'), 5.46 (1H, br s, H-1'), 5.83 (1H, s, H-1), 6.73 (1H, br d, J=7 Hz, N—H), 7.75 (2H, m, Ar—H), 8.05 (2H, m, Ar—H).

Step 6: (1'S, 1S, 3R)-5,10-dioxo-3-methoxymethyl-1-(2',3',6'-trideoxy-3'-trifluoroacetamido-L-lyxohexopyranose)-3,4,5,10-tetrahydro-1H-naphtho [2,3-c] pyran (BCH-1693)

The starting protected alcohol from step 4 of this example (18 mg; 0.028 mmol) in 0.4 ml methanol and 1.5 ml of tetrahydrofuran was treated with 83 μl of a 4.37M solution of sodium methoxide in methanol following the procedure from step 5 herein to afford the title compound (12.5 mg; 90%): m.p.: 92°–102° C.; IR (neat): 3485, 3424, 3323, 2937, 1715, 1666, 1595, 1296, 1175, 1117, 980 $cm^{-1}$.

$^1$H NMR ($CD_2Cl_2$, 250 MHz) δ: 1.35 (3H, d, J=6.5 Hz, H-6'), 1.85 (2H, m, H-2'), 2.01 (1H, br d, J=7 Hz, O—H), 2.46 (1H, dd, J=11.5 and 20 Hz, H-4 ax), 2.69 (1H, dd, J=3.7 and 20 Hz, H-4 eq), 3.36 (3H, s, $OCH_3$), 3.54 (2H, d, J=4.7 Hz, $CH_2$—$OCH_3$), 3.60 (1H, m, H-4'), 4.15–4.40 (2H, m, H-3' and H-3), 4.55 (1H, 5, J=6.5 Hz, H-5'), 5.39 (1H, br s, H-1'), 5.98 (1H, s, H-1), 6.78 (1H, br d, J=7 Hz, —NH), 7.75 (2H, m, Ar—H), 8.05 (2H, m, Ar—H).

EXAMPLE 27
Preparation of (1'S,1R,3S) and 1'S,1S,3S)-5,10-dioxo-3-ethyl-1-(2',3',6'-trideoxy-3'trifluoroacetamido-L-lyxohexopyranose)-3,4,5,10-tetrahydro-1H-naphtho-[2,3-c]-pyran: (BCH-2026) and BCH-2020) and (1'S,1S,3S)-5,10-dioxo-3-ethyl-1-(2',3',6'-trideoxy-3'-amino-L-lyxohexopyranose)-3,4,5,10-tetrahydro-1H-naphtho-[2,3-c]-pyran hydrochloride: (BCH-2021)
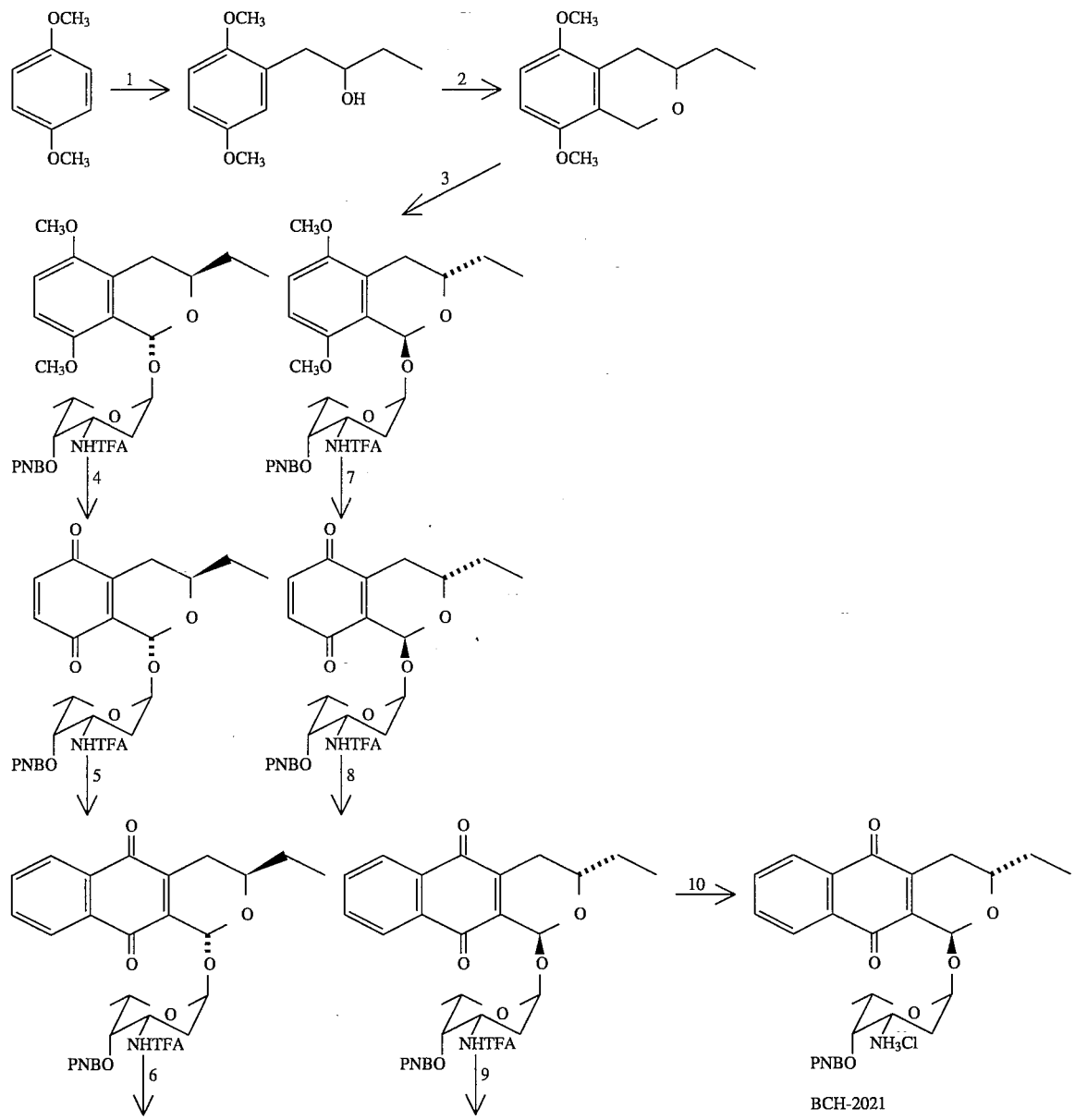

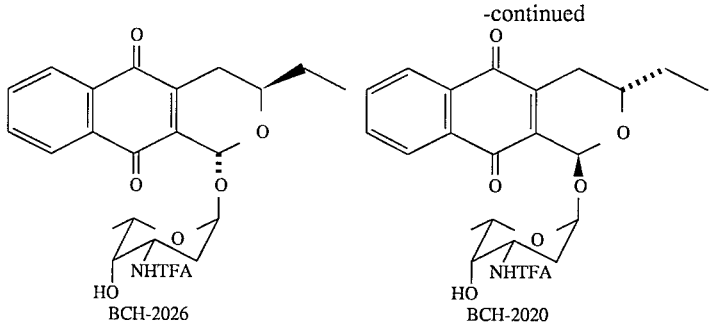

Step 1-(2,5-dimethoxyphenyl)-2-butanol

Under argon atmosphere, 1,4-dimethoxybenzene 10.0 g (72.37 mmol) was dissolved in dry THF and this solution was cooled to 0° C. n-BuLi (2.5M/hexanes) 28.8 ml (72.37 mmol) was then added and the reaction mixture was warmed up to room temperature and stirring was left for 4 hours. After 4 hours, the reaction was cooled to −78° C. and 1,2-epoxybutane 5.2 g (72.37 mmol) was added followed by 10.2 g (72.37 mmol) of boron trifluoro etherate. Stirring was then continued for a period of 1 hour. The reaction mixture was then quenched by pouring it into 125 ml of aqueous $NH_4Cl$. Extractions of the aqueous layer were done using $CH_2Cl_2$. The combined organic layers were dried over $Na_2SO_4$, filtered and the solvent was removed. The crude material was purified by flash chromatography with hexanes-ethyl acetate (9:1) then (8:2) as the eluent. The isolated titled compound was a white solid (11.4 g, 75%).

NMR $^1H$ (250 MHz) ($CDCl_3$; ppm): 6.75 (3H, m, aromatics), 3.79 (3H, s, $OCH_3$), 3.77 (1H, m, $H_{2'}$), 3.76 (3H, s, $OCH_3$), 2.85 (1H, dd, $J_1=3.8$ Hz, $J_2=13.5$ Hz, $H_{1'a}$), 2.65 (1H, dd, $J_1=8.1$ Hz, $J_2=13.5$ Hz, $H_{1'b}$), 2.16 (1H, d, J=3.7 Hz, OH), 1.52 (2H, m, $H_{3'}$) 0.99 (3H, dd, $J_1=J_2=7.4$ Hz, —$CH_3$).

Step 2: 5,8-dimethoxy-3-ethyl-isochroman

Under argon atmosphere, the starting material from step 1 of this example, 5.00 g (23.78 mmol) was dissolved in 100 ml of dry ether. Dimethoxy methane 3.0 ml (33.90 mmol) and boron trifluoro etherate 9.0 ml (71.35 mmol) were then added and stirring was left overnight. The reaction was then quenched using aqueous $NaHCO_3$. Extractions were done using ether and the combined organic extracts were dried over $Na_2SO_4$, filtered and the solvent was removed. The isolated residue was then purified by flash chromatography; hexanes-ethyl acetate (8:2) was used as the eluent. The desired titled compound was isolated as a white solid (4.9 g; 92%).

NMR $^1H$ (250 MHz) ($CDCl_3$; ppm): 6.63 (2H, d, J=3.4 Hz, aromatics), 4.93 (1H, d, J=15.9 Hz, $H_{1a}$), 4.57 (1H, d, J=15.9 Hz, $H_{1b}$), 3.78 (3H, s, $OCH_3$), 3.76 (3H, s, $OCH_3$), 3.47 (1H, m, $H_3$), 2.74 (1H, ddd, $H_{4a}$), 2.38 (1H, dd, $H_{4b}$), 1.68 (2H, m, —$CH_2$—side chain) 1.03 (3H, dd, $J_1=J_2=7.4$ Hz, —$CH_3$).

Step 3: (1'S, 1R, 3R)-5,8-dimethoxy-3-ethyl-1-(2',3',6'-trideoxy-3'-trifluoroacetamido-4'-O-p-nitrobenzoyl-n-lyxohexopyranose)-isochroman Application of the first part of the procedure described in step 3, example 26, on the isochroman precursor from step 2 herein resulted with the titled compound as a yellow solid; 62%.

NMR $^1H$ (250 MHz) ($C_6D_6$; ppm): 7.72 (4H, m, aromatics), 6.48 (2H, d, J=4.7 Hz, aromatics), 6.17 (1H, s, $H_1$), 5.95 (1H, m, NH), 5.67 (1H, d, $H_{4'}$), 5.29 (1H, d, $H_{1'}$), 4.67 (1H, m, $H_3$,), 4.26 (1H, q, $H_{5'}$), 4.20 (1H, m, $H_3$), 3.49 (3H, s, $OCH_3$), 3.40 (3H, s, $OCH_3$), 3.01 (1H, dd, $H_{4a}$), 2.52 (1H, dd, $H_{4b}$), 1.90 (1H, m, —$CH_2$ side chain), 1.75 (1H, m, —$CH_2$—side chain), 1.61 (2H, m, —$CH_2$—sugar), 1.06 (3H, d, —$CH_3$ sugar), 1.03 (3H, m, $CH_3$ side chain).

IR (film) ($cm^{-1}$): 3316 (NH), 2933 (CH aliphatic), 1733 (C=O), 1707 (C=O), 1603 (C=C), 1532 (C—N), 1259 and 1175 (C—O).

Step 4: (1'S, 1R, 3R)-5,8-dioxo-3-ethyl-1-(2',3',6'-trideoxy-3'-trifluoroacetamido-4'-O-p-nitrobenzoyl-n-lyxohexopyranose)-isochroman Application of the second part of the procedure (CAN) described in step 3, example 26, on the glycosylated isochroman precursor from the previous step resulted in an 87% yield of the titled compound.

NMR $^1H$ (250 MHz) ($C_6D_6$; ppm): 7.80 (4H, m, aromatics), 6.92 (1H, $s_{broad}$, NH), 6.08 (2H, m, quinone ring), 5.72 (1H, s, $H_1$), 5.54 (1H, s, $H_{4'}$), 5.53 (1H, s, $H_{1'}$), 4.74 (1H, m, $H_3$,), 4.36 (1H, m, $H_{5'}$), 3.68 (1H, m, $H_3$), 2.28 (1H, dd, $J_1=3.2$ Hz, $J_2=19.3$ Hz, $H_{4a}$), 1.88 (2H, m, —$CH_2$—sugar), 1.80 (1H, dd, $H_{4b}$), 1.49 (2H, m, —$CH_2$—side chain), 1.15 (3H, d, J=6.5 Hz, $CH_3$ sugar), 0.89 (3H, dd, $J_1=J_2=7.4$ Hz, —$CH_3$ side chain).

Step 5: (1'S, 1R, 3R)-5,10-dioxo-3-ethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c] pyran The titled compound was obtained via Diels-Alder cycloaddition between 1-acetoxylbutadiene and the quinone from step 4 from this example using the procedure described in step 4 from example 26.

NMR $^1H$ (250 MHz) ($CD_2Cl_2$; ppm): 8.28 (4H, d, J=4.3 Hz, aromatics), 8.05 (2H, m, aromatics), 7.73 (2H, m, aromatics), 6.31 (1H, d, NH), 5.87 (1H, s, $H_1$), 5.67 (1H, s, $H_{4'}$), 5.42 (1H, s, $H_{1'}$), 4.58 (1H, m, $H_{3'}$), 4.42 (1H, q, J=6.3 Hz, $H_{5'}$), 4.05 (1H, m, $H_3$), 2.78 (1H, dd, $J_1=3.4$ Hz, $J_2=19.5$ Hz, $H_{4a}$), 2.24 (1H, dd, $J_1=11.3$ Hz, $J_2=19.0$ Hz, $H_{4b}$), 2.05 (2H, m, —$CH_2$—sugar), 1.70 (2H, m, —$CH_2$—side chain), 1.18 (3H, d, J =6.5 Hz, —$CH_3$ sugar), 1.35 (3H, dd, $J_1=J_2=7.4$ Hz, —$CH_3$ side chain).

IR (film) ($cm^{-1}$): 3332 (NH), 2955 and 2929 (CH aliphatic), 1740 (C=O), 1669 (C=C), 1529 (C—N), 1279 and 1180 (C—O).

Step 6: (1'S, 1R, 3R)-5,10-dioxo-3-ethyl-1-(2',3',6'-trideoxy-3'-trifluoroacetamido-L-lyxohexopyranose)-3,4,5,10-tetrahydro-1H-naphtho-[2,3-c] pyran (BCH-2026)

The titled compound was in 64% yield from the glycoside of step 5 of this example as per procedure described in step 5 of example 26.

NMR $^1H$ (250 MHz) ($CD_2Cl_2$; ppm): 8.03 (2H, m, aromatics), 7.71 (2H, m, aromatics), 6.77 (1H, d, NH), 5.81 (1H, s, $H_1$), 5.50 (1H, d, J=2.8 Hz, $H_{1'}$), 4.26 (1H, m, $H_{3'}$), 4.22 (1H, m, $H_{5'}$), 4.05 (1H, m, $H_3$), 3.58 (1H, d, J=2.2 Hz, $H_{4'}$), 2.76 (1H, dd, $J_1=3.5$ Hz, $J_2=19.5$ Hz, $H_{4a}$), 2.21 (1H, ddd, $J_1=0.9$ Hz, $J_2=11.0$ Hz, $J_3=19.5$ Hz, $H_{4b}$), 2.07 (1H, $s_{(broad)}$, OH), 1.83 (2H, m, —$CH_2$—sugar), 1.67 (2H, m, —CH$_2$—side chain), 1.23 (3H, d, J=6.6 Hz, —CH$_3$ sugar ), 1.02 (3H, dd, J$_1$=J$_2$=7.5 Hz, —CH$_3$ side chain).

Step 7: (1'S, 1S, 3S)-5 8-dioxo-3-ethyl-1-(2',3',6'-trideoxy-3'-trifluoroacetamido-4'-O-p-nitrobenzoyl-L-lyxohexopyranose)-5,8-dihydro-isochroman To a solution of (1'S, 1S, 3S)-5,8-dimethoxy-3-ethyl-1-(2',3',6'-trideoxy-3'-trifluoroacetamido-4'-O-p-nitro-benzoyl-L-lyxohexopyranose)-isochroman (372 mg; 0.60 mmol) in acetonitrile (12 ml) was added a solution of CAN prepared by dissolving ceric ammonium nitrate (2.0 g; 3.6 mmol) in 6 ml of water and then slowly adding solid sodium bicarbonate (531 mg). The resulting mixture was stirred at 0° C. for 20 minutes and was then quenched with saturated bicarbonate solution. The product was extracted with dichloromethane and the combined organic layers were washed with brine and dried over Na$_2$SO$_4$ to give after evaporation the crude title compound:

(360 mg; 100%): $^1$H NMR (250 MHz; CDCl$_3$) δ: 1.02 (3H, t, J=7.5 Hz, CH$_2$—CH$_3$), 1.29 (3H, d, J=6.5 Hz, H-6'), 1.65 (2H, m, CH$_2$—CH$_3$), 1.80–2.30 (3H, m, H-2' and H-4 ax), 2.60 (1H, dd, J=3.5 and 19.5 Hz, H-4 eq), 3.89 (1H, m, H-3), 4.50–4.80 (2H, m, H-3' and H-5'), 5.41 (1H, br s, H-1') 5.55 (1H, br s, H-4'), 5.87 (1H, s, H-1), 6.58 (1H, br d, J=7.5 Hz, NH), 6.75 and 6.81 (2H, AB doublets, ArH), 8.28 (4H, br s, PNB).

Step 8: (1'S, 1S, 3S)-5,10-dioxo-3-ethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c]-pyran Using the procedure described in step 4, example 26, the starting quinone from step 7 herein (330 mg; 0.57 mmol) was treated with 1-acetoxy-1,3-butadiene (379 µl; 3.4 mmol) in 20 ml of toluene to afford after chromatography the title compound (165 mg; 46%).

$^1$H NMR (250 MHz, CD$_2$Cl$_2$) δ: 1.03 (3H, d, J=7.5 Hz, CH$_2$—CH$_3$), 1.30 (3H, d, J=6.5 Hz, H-6'), 1.69 (2H, qn, J=7.5 Hz, CH$_2$—CH$_3$), 1.95 (1H, m, H-2 eq), 2.12 (1H, td, J=13 and 3.5 Hz, H-2' ax), 2.29 (1H, dd, J=11.5 and 19.5 Hz, H-4 ax), 2.75 (1H, dd, J=3.5 and 19.5 Hz, H-4 eq), 3.97 (1H, m, H-3), 4.55 (1H, m, H-3'), 4.78 (1H, q, J=6.5 Hz, H-5'), 5.41 (1H, br s, H-1'), 5.57 (1H, d, J=6.5 Hz, H-4'), 6.01 (1H, s, H-1), 6.51 (1H, br d, J=7.5 Hz, —NH), 7.75 (2H, m, ArH), 8.07 (2H, m, Ar—H), 8.27 (4H, s, PNB).

Step 9: (1'S, 1S, 3S)-5,10-dioxo-3-ethyl-1-(2',3',6'-trideoxy-3'-trifluoroacetamido-L-lyxohexopyranose)-3,4,5,10-tetrahydro-1H-naphtho-[2,3-c]-pyran (BCH-2020)

The starting protected alcohol from step 8 herein (20 mg; 0.032 mmol) was treated with sodium methoxide in methanol (4.37M, 1 µl) in 1 ml of tetrahydrofuran and 0.3 ml of methanol according to the procedure described in step 5, example 26, affording after chromatography (15% acetone in benzene) the title compound (11.5 mg, 75%), M.P. 208°–211° C.

IR (neat): 3540, 3292, 2978, 1705, 1666, 1556, 1295, 1187, 1165 and 990 cm$^{-1}$.

$^1$H NMR (250 MHz, CD$_2$Cl$_2$): 1.00 (3H, t, J=7.5 Hz, CH$_2$—CH$_3$), 1.35 (3H, d, J=6.5 Hz, H-6'), 1.65 (2H, qn, J=7.5 Hz, CH$_2$—CH$_3$), 1.80–2.20 (3H, m, H-2' and O—H), 2.27 (1H, dd, J=11.0 and 19.5 Hz, H-4 ax), 2.75 (1H, dd, J=3.5 and 19.5 Hz, H-4 eq), 3.61 (1H, br s, H-4'), 3.96 (1H, m, H-3), 4.25 (1H, m, H-3'), 4.58 (1H, q, J=6.5 Hz, H-5'), 5.40 (1H, t, J=2.0 Hz, H-1'), 5.97 (1H, s, H-1), 6.77 (1H, m, N—H), 7.75 (2H, m, Ar—H), 8.05 (2H, m, Ar—H).

Step 10: (1'S, 1S, 3S)-5,10-dioxo-3-ethyl-1-(2',3',6'-trideoxy-3'-amino-L-lyxohexopyranose)-3,4,5,10-tetrahydro-1H-naphtho-[2,3-c]-pyran (BCH-2021)

To a solution of the starting protected amino-alcohol from step 9 herein (43 mg; 0.07 mmol) in acetonitrile (6 ml) was added dropwise 0.1N sodium hydroxide (3 ml). The mixture was stirred at 0° C. for 30 minutes and an extra 1 ml of sodium hydroxide solution was added and the resulting mixture was stirred for 1 hour at 0° C. It was then quenched with 0.1N HCl and extracted with dichloromethane. The water layer was neutralized to pH ~7 by addition of dilute sodium hydroxide. It was then extracted with dichloromethane. To the organic extract were added 1.5 ml of 0.1N HCl, 5 ml of methanol and 25 ml of ether and the mixture was evaporated partially in order to induce crystallization. Since no crystallization occured, the solvents were evaporated completely and the residue was dissolved in methanol (1 ml) and 200 µl of 0.1N HCl were added followed by 25 ml of ether. A precipitate formed which was filtered and washed with ether yielding the crude title compound (3.8 mg; 13%).

$^1$H NMR (250 MHz, DMSO-D6), δ: 0.97 (3H, t, J=7.0 Hz, CH$_2$—CH$_3$), 1.23 (3H, d, J=6.5 Hz, H-6'), 1.50–1.80 (3H, m, CH$_2$—CH$_3$ and H-2' eq), 1.97 (1H, m, H-2' ax), 2.23 (1H, dd, J=11.0 and 19.5 Hz, H-4 ax), 2.72 (1H, dd, J=3.0 and 19.5 Hz, H-4 eq), 3.63 (1H, m, H-4'), 3.87 (1H, m, H-3), 4.33 (1H, m, H-5'), 5.29 (1H, br s, H-1'), 5.53 (1H, m, H-3'), 5.82 (1H, s, H-1), 7.85 (2H, m, Ar—H), 8.05 (5H, m, Ar—H and N—H).

EXAMPLE 28

Preparation of trans-5,10 dioxo-1-acetamido-3-ethyl-3,4,5,10-tetrahydro-1H-naphtho-[2,3-c]-pyran: (BCH-2027) and 3-ethyl-5,10-dioxo-3,4,5,10-tetrahydro-1H-naphtho-[2,3 -c]-pyran: (BCH-2154)

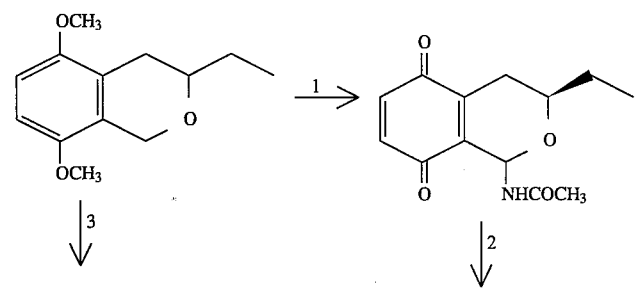

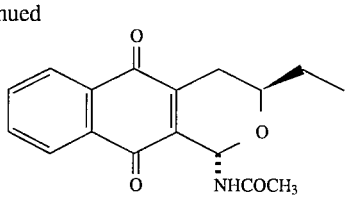

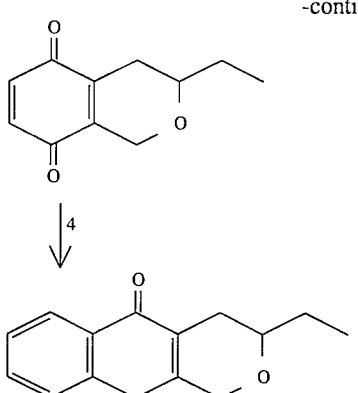

BCH-2154

BCH-2027

Step 1: (trans)-1-acetamido-5,8-dioxo-3-ethyl-5,8-dihydro-isochroman

To a solution of 5,8-dimethoxy-3-ethyl-isochroman (1.0 g; 4.5 mmol) in dichloromethane (30 ml) at room temperature were added methanol (211 μl; 5.4 mmol), 4 Å molecular sieves (2 g) and 2,3-dichloro-5,6-dicyano-benzoquinone (1.21 g; 5.4 mmol). The resulting dark mixture was stirred for 5 hours and was then quenched with saturated $NaHCO_3$ solution. It was extracted with dichloromethane and the combined organic layers were washed with bicarbonate, brine and then dried over $Na_2SO_4$ affording after evaporation 1.0 g of crude adduct of which 300 mg (1.19 mmol assumed) were placed in a pear-shaped flask along with acetamide (70 mg; 1.19 mmol). The solid mixture was then heated to 130° C. for 30 minutes. It was then cooled to room temperature and dichloromethane was added followed by pentane yielding a precipitate (160 mg) of which 120 mg (0.43 mmol assumed) was dissolved in acetonitrile (15 ml) and treated with a solution of CAN prepared by slowly dissolving sodium bicarbonate (384 mg) in water (5 ml) containing cerium ammonium nitrate (1.46 g; 2.5 mmol). The resulting mixture was stirred at room temperature for 15 minutes and was quenched with saturated $NaHCO_3$ solution followed by extraction with dichloromethane. The combined organic extracts were washed with brine and dried over $Na_2SO_4$ to afford the titled compound as a yellow solid (125 mg; 42% overall).

$^1H$ NMR (250 MHz, $CDCl_3$) δ: 0.99 (3H, t, J=7.5 Hz, $CH_3-CH_2$), 1.65 (2H, m, $-CH_2-CH_3$), 2.02 (3H, s, $-CH_3$), 2.20 (1H, m, H-4 ax ), 2.60 (1H, dd, J =3.5 and 19.5 Hz, H-4 eq), 3.70 (1H, m, H-3), 6.12 (2H, br s, H-1 and N—H), 6.73 and 6.78 (2H, AB system, Ar—H).

Step 2: Trans-5,10-dioxo-1-acetamido-3-ethyl-3,4,5,10-tetrahydro-1H-naphtho-[2,3-c]-pyran To a solution of the starting quinone from step 1 herein (56 mg; 0.22 mmol) in toluene (50 ml) was added 1-acetoxy-1,3-butadiene (30 μl; 11 eq). The mixture was stirred overnight at room temperature and was then concentrated and applied to a column of silica gel using 1–15% acetone in benzene to elute the product which was then recrystallized from dichloromethane:pentane affording the title compound as a yellow solid (10 mg; 15%).

$^1H$ NMR (250 MHz, DMSO-D6), δ: 0.90 (3H, t, J=7.5 Hz, $CH_3-CH_2$), 1.58 (2H, m, $CH_2-CH_3$), 1.82 (3H, s, $CH_3-C=O$), 2.20 (1H, m, H-4 ax), 2.64 (1H, br d, J=16.0 Hz, H-4 eq), 3.71 (1H, m, H-3), 6.17 (1H, d, J=8.0 Hz, H-1), 7.88 (2H, m, Ar—H), 8.01 (2H, m, Ar—H), 8.78 (1H, d, J=8.0 Hz, N—H).

Step 3: 5,8-dioxo-3-ethyl-5,8-dihydro-isochroman

To a solution of 3-ethyl-5,8-dimethoxy-isochroman (300 mg; 1.35 mmol) in acetonitrile (10 ml) at room temperature was added dropwise a solution of CAN (prepared by dissolving ceric ammonium nitrate (2.22 g; 4.0 mmol) in water (5 ml)). The resulting mixture was quenched with saturated bicarbonate solution and extracted with dichloromethane. The combined organic layers were washed with brine and dried over $Na_2SO_4$ affording the crude title compound (251 mg; 97%) which was used as such for subsequent steps.

$^1H$ NMR (250 MHz, $CDCl_3$) δ: 0.97 (3H, t, J=7.5 Hz, $CH_2-CH_3$), 1.60 (2H, m, $-CH_2-CH_3$), 2.10 (1H, m, H-4), 2.52 (1H, m, H-4), 3.35 (1H, m, H-3), 4.30 (1H, m, H-1), 4.62 (LH, br d, J=16 Hz, H-1), 6.68 (2H, m, Ar—H).

Step 4: 3-ethyl-5,10-dioxo-3,4,5,10-tetrahydro-1H-naphtho-[2,3-c]pyran

Following the procedure described in step 4, example 26, the starting quinone from step 3 herein (250 mg; 1.30 mmol) and 1-acetoxy-1,3-butadiene (876 μl; 7.8 mmol) were reacted in toluene (10 ml) to yield after chromatography using 2% ethyl acetate in toluene the title compound (62 mg; 20%) along with mixed fractions containing a lot of desired titled product (230 mg), M.P.: 98°–101° C.

IR (neat): 2963, 2938, 2876, 1658, 1636, 1593, 1337, 1299, 1176 and 698 $cm^{-1}$.

$^1H$ NMR (250 MHz, $CDCl_3$) δ: 1.04 (3H, t, J=7.5 Hz, $CH_3$—), 1.70 (2H, m, $CH_2-CH_3$), 2.30 (1H, m, H-4 ax), 2.75 (1H, br d, J=19.0 Hz, H-4 eq), 3.45 (1H, m, H-3), 4.50 (1H, dt, J=4.0 and 18.5 Hz, H-1), 4.86 (1H, dd, J=2.5 and 18.5 Hz, H-1), 7.72 (2H, m, Ar—H), 8.18 (2H, m, Ar—H).

EXAMPLE 29

Preparation of (1'S,1R,3S) and (1'S,1S,3R)-5,10-dioxo-3-isopropyl-1-(2',3',6'-trideoxy-3'-trifluoroacetamido-L-lyxohexopyranose)-3,4,5,10-tetrahydro-1H-naphtho-[2,3-c]-pyran: (BCH-2053) and (BCH-2052)

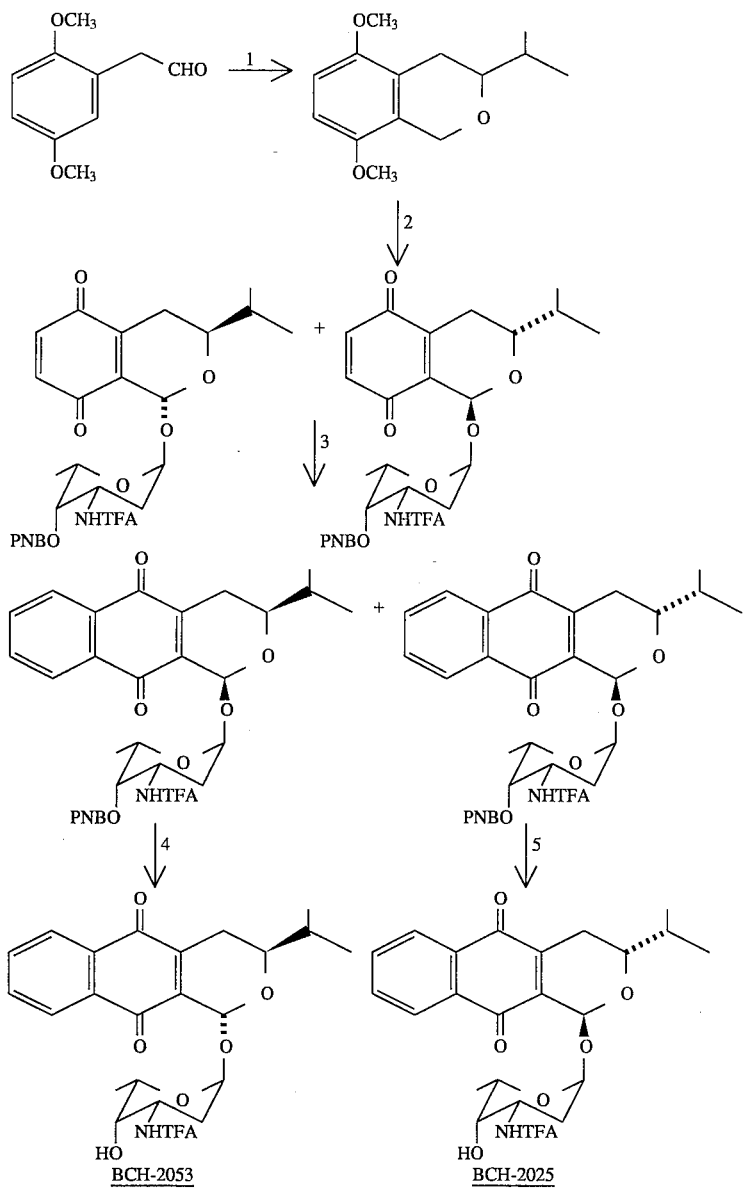

Step 1: 3-isopropyl-5,8-dimethoxy-isochroman

To a solution of the starting aldehyde (1.16 g; 6.44 mmol) in tetrahydrofuran (25 ml) at 0° C. was added a solution of isopropyl magnesium chloride (2M in THF; 6.4 ml; 12.88 mmol). The resulting mixture was stirred at 0° C. for 1 hour and at room temperature for 30 minutes. It was then quenched with saturated ammonium chloride solution and extracted with ether. The combined organic layers were washed with brine and dried over MgSO$_4$ to yield a crude alcohol (1.29 g) which was dissolved in ether (40 ml). To this solution were added dimethoxymethane (777 μl; 8.55 mmol) and boron trifluoride-etherate (2.02 ml; 17.1 mmol). The resulting mixture was stirred at room temperature for 20 hours and was then quenched with saturated sodium bicarbonate solution. It was then extracted with ether and the combined organic layers were washed with brine and dried over MgSO$_4$. The crude product was then purified by column chromatography on silica gel using 20–30% ethyl acetate in hexane as eluent to give the title compound (607 mg; 40% overall).

$^1$H NMR (CDCl$_3$) δ: 1.00 and 1.05 (6H, 2d, J=7 Hz, —CH—(CH$_3$)$_2$), 1.84 (1H, sept., J=7 Hz, CH—(CH$_3$)$_2$), 2.42 (1H, dd, J=11 and 17 Hz, H-4 ax), 2.74 (1H, dm, J=17 Hz, H-4 eq), 3.22 (1H, m, H-3), 3.76 (3H, s, OCH$_3$), 3.79 (3H, s, OCH$_3$), 4.56 (1H, dm, J=16 Hz, H-1), 4.95 (1H, d, J=16 Hz, H-1), 6.63 (2H, AB sytem, Ar—H).

Step 2: (1'S, 1R, 3S) and (1'S, 1S, 3R)-5,8-dioxo-3-isopropyl-1-(2',3',6'-trideoxy-3'-trifluoroacetamido-4'-O-p-nitrobenzoyl-L-lyxohexopyranose)-5,8-dihydro-isochroman (40:60)

Using the procedure described in step 3, example 26, the starting isochroman from step 1 herein (300 mg; 1.27 mmol) afforded a crude diastereomeric mixture of glycosidated isochromans (515 mg) which was reacted with CAN as described in step 3, example 26, to afford a diastereomeric title quinones mixture (450 mg; 59%) in a ratio of (40:60) favoring the 1'S, 1S, 3R isomer which were used as such for the next reactions.

For minor isomer: $^1$H NMR (250 MHz, CDCl$_3$) δ: 0.90–1.40 (9H, m, H-6' and —CH(—CH$_3$)$_2$), 1.70–2.35 (4H, m, H-2', H-4 ax and CH—CH$_3$), 2.62 (1H, m, H-4 eq), 3.80 (1H, m, H-3), 4.42 (1H, q, J=6.5 Hz, H-5'), 4.50–4.70 (1H, m, H-3'), 5.44 (1H, br s, H-1'), 5.63 (1H, br s, H-4'), 5.74 (1H, s, H-1), 6.32 (1H, m, N—H), 6.70–6.90 (2H, m, Ar—H), 8.30 (4H, m, PNB).

For major isomer: 0.90–1.40 (9H, m, H-6' and CH(—CH$_3$)$_2$), 1.70–2.35 (4H, m, H-2', H-4 ax and CH—CH$_3$), 2.62 (1H, m, H-4 eq), 3.69 (1H, m, H-3), 4.50–4.75 (2H, m, H-3' and H-5'), 5.42 (1H, br s, H-1'), 5.56 (1H, d, J=3 Hz, H-4'), 5.88 (1H, s, H-1), 6.43 (1H, br d, J=7.5 Hz, N—H), 6.70–6.90 (2H, m, Ar—H), 8.30 (4H, m, PNB).

Step 3: (1'S, 1S, 3R)-5,10-dioxo-3-isopropyl-1-(2',3',6'-trideoxy-3'-trifluoroacetamido-4'-O-p-nitrobenzoyl-L-lyxo-hexo-pyranose)-3,4,5,10-tetrahydro-1H-naphtho-[2,3-c]-pyran Using the procedure described in step 4, example 26, the starting quinone mixture from step 2 herein (100 mg; 0.167 mmol) was treated with 1-acetoxy-1,3-butadiene (112 µl; 1 mmol) in 5 ml of toluene to afford the title compound (34 mg pure+9 mg of 1:1 mixture of diastereomers).

$^1$H NMR (250 MHz, CD$_2$Cl$_2$)δ: 1.01 and 1.04 (6H, 2d, J=6.5 Hz, —CH—(CH$_3$)$_2$), 1.31 (3H, d, J=6.5 Hz, H-6'), 1.70–2.02 (2H, m, H-2' and CH—(CH$_3$)$_2$), 2.13 (1H, t d, J=3.5 and 13 Hz, H-2'), 2.34 (1H, dd, J=11.5 and 19.5 Hz, H-4 ax), 2.78 (1H, dd, J=3.5 and 19.5 Hz, H-4 eq), 3.76 (1H, m, H-3), 4.55 ([H, m, H-3'), 4.80 (1H, q, J=6.5 Hz, H-5'), 5.42 (1H, d, J=2.5 Hz, H-1'), 5.58 (1H, d, J=3 Hz, H-4'), 6.03 (1H, s, H-1), 6.52 (1H, br d, J=7.5 Hz, —NH), 7.75 (2H, m, Ar—H), 8.05 (2H, m, Ar—H), 8.28 (4H, s, PNB).

The second diastereomer:

(1'S, 1R, 3S)-5,10-dioxo-3-isopropyl-1-(2',3',6'-trideoxy-3'-trifluoroacetamido-4'-O-p-nitrobenzoyl-L-lyxohexo-pyranose)-3,4,5,10-tetrahydro-1H-naphtho-[2,3-c]-pyran, obtained in 16% yield, had $^1$H NMR (250 MHz, CD$_2$Cl$_2$) δ: 0.90–1.10 (6H, m, CH—(CH$_3$)$_2$), 1.17 (3H, d, J=6.5 Hz, H-6'), 1.70–2.40 (4H, m, H-2', CH—(CH$_3$)$_2$ and H-4), 2.60–2.90 (1H, m, H-4), 3.87 (1H, m, H-3), 4.44 (1H, q, J=6.5 Hz, H-5'), 4.58 (1H, m, H-3'), 5.42 (1H, br s, H-1'), 5.69 (1H, br s, H-4'), 5.89 (1H, s, H-1), 6.40 (1H, br d, J=7.5 Hz, —NH), 7.75 (2H, m, Ar—H), 8.06 (2H, m, Ar—H), 8.28 (4H, m, PNB).

Step (1'S, 1R, 3S)-5,10-dioxo-3-isopropyl-1-(2',3',6'-trideoxy-3'-trifluoroacetamido-L-lyxohexopyranose)-3,4,5,10-tetrahydro-1H-naphtho-[2,3-c]-pyran (BCH-2053)

Using the procedure described in step 5, example 26, the starting protected alcohol from step 3 herein (11 mg; 0.017 mmol) was treated with NaOMe/MeOH (4.37M; 1 µl; 0.26 eq) to yield after column chromatography (7% acetone in benzene) the title compound (5 mg; 59%), M.P.: 180°–185° C.

IR (neat): 3491, 3423, 3325, 2962; 2938, 1721, 1670, 1596, 1293, 1179, 982 cm$^{-1}$.

$^1$H NMR (250 MHz, CD$_2$Cl$_2$): 1.00 and 1.01 (6H, 2d, J=6.5 Hz, —CH—(CH$_3$)$_2$), 1.22 (3H, d, J=6.5 Hz, H-6'), 1.60–2.00 (4H, m, —CH—(CH$_3$)$_2$, H-2' and OH), 2.27 (1H, br dd, J=11.0 and 19.5 Hz, H-4 ax), 2.74 (1H, dd, J=3.5 and 19.5 Hz, H-4 eq), 3.58 (1H, d, J=2.5 Hz, H-4'), 3.85 (1H, m, H-3), 4.25 (2H, m, H-3' and H-5'), 5.52 (1H, d, J=3.0 Hz, H-1'), 5.82 (1H, s, H-1), 6.75 (1H, m, NH), 7.74 (2H, m, Ar—H), 8.03 (2H, m, Ar—H).

Step 5: (1'S, 1S, 3R)-5,10-dioxo-3-isopropyl-1-(2',3',6'-trideoxy-3'-trifluoroacetamido-L-lyxohexopyranose)-3,4,5, 10-tetrahydro-1H-naphtho-[2,3-c]-pyran (BCH-2052)

Using the procedure described in step 5, example 26, the starting protected alcohol from step 3 herein (32 mg; 0.0495 mmol) afforded after flash chromatography using 7% acetone in benzene as eluent, a gummy product which was dissolved in dichloromethane and precipitated with pentane yielding the title product (16 mg; 65%), M.P.: 212°–213° C.

IR (neat): 3509, 3421, 3333, 2961, 2944, 1718, 1667, 1592, 1292, 1166 and 979 cm$^{-1}$.

$^1$H NMR (250 MHz, CD$_2$Cl$_2$): 0.98 and 1.00 (6H, 2d, J=6.7 Hz, —CH(CH$_3$)$_2$) 1.36 (3H, d, J=6.5 Hz, H-6'), 1.70–2.00 (4H, m, —CH(CH$_3$)$_2$, H-2' and —OH), 2.32 (1H, dd, J=11.5 and 19.5 Hz, H-4 ax), 2.76 (1H, dd, J=3.5 and 19.5 Hz, H-4 eq), 3.61 (1H, br s, H-4'), 3.74 (1H, ddd, J=3.5, 6.5 and 11.5 Hz, H-3), 4.24 (1H, m, H-3'), 4.59 (1H, q, J=6.5 Hz H-5'), 5.39 (1H, t, J=2.0 Hz, H-1'), 5.97 (1H, s, H-1), 6.77 (1H, m, NH), 7.72 (2H, m, Ar—H), 8.05 (2H, m, Ar—H).

EXAMPLE 30

Preparation of (1'S,1R,3S) and (1'S,1S,3R)-5,10-dioxo-3-isopropenyl-1-(2',3',6'-trideoxy-3'-trifluoroacetamido-L-lyxohexopyranose)-3,4,5,10-tetrahyaro-1H-naphtho-[2,3-c]-pyran: (BCH-2153) and (BCH-2152) and trans-5,10-dioxo-3-isopropenyl-1-methoxy-3,4,5,10-tetrahydro-1H-naphtho-[2,3-c]-pyran: (BCH-2148)

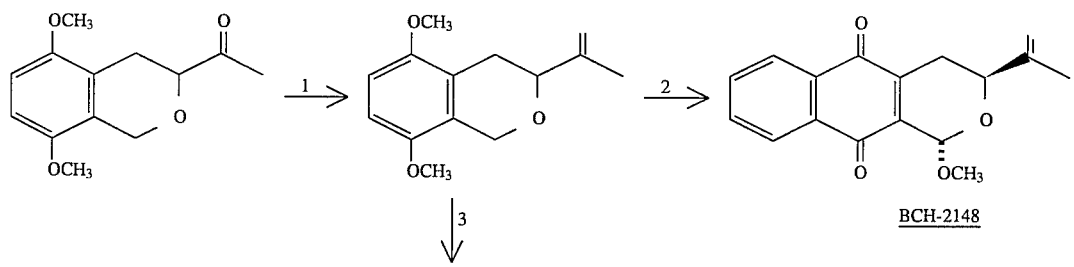

BCH-2148

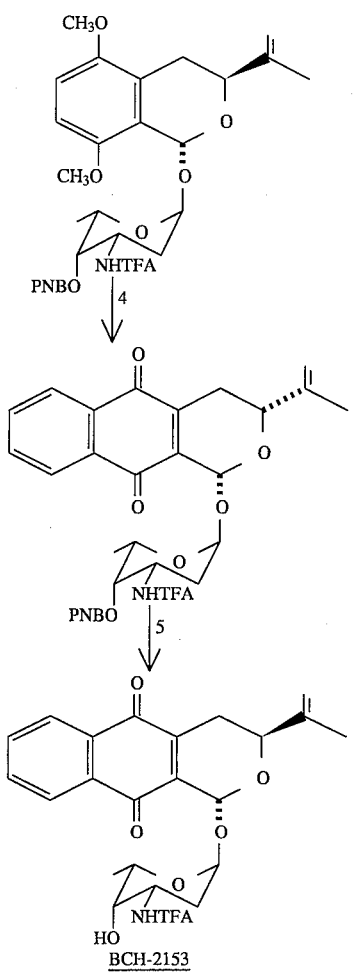

BCH-2153

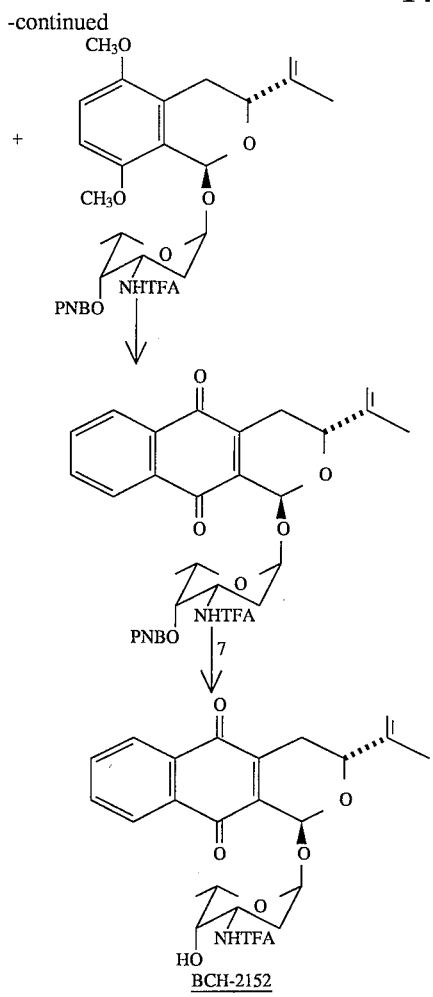

BCH-2152

Step 1: 5,8-dimethoxy-3-isopropenyl-isochroman

To a solution of methyltriphenylphosphonium bromide (2.26 g; 6.4 mmol) in ether (75 ml) at room temperature (not totally soluble) was added n-BuLi (2.5M in hexanes; 2.03 ml; 5.1 mmol). The resulting mixture was stirred at room temperature for 1 hour. A solution of 5,8-dimethoxy-3-(1-acethyl)-isochroman (1.0 g; 4.2 mmol) was then added to the yellow-orange mixture and the resulting solution was stirred at room temperature for 3 hours. The mixture was then quenched with $NH_4Cl$ (sat.) and extracted with ether. The combined organic layers were washed with brine and dried over $Na_2SO_4$. The crude mixture was then purified by column chromatography in silica gel using 25% ethyl acetate in hexane as eluent to afford the title compound (541 mg; 55%).

$^1$H NMR (250 MHz, $CDCl_3$) δ: 1.86 (3H, s, =C—$CH_3$), 2.58 (1H, br dd, J=11 and 17 Hz, H-4 ax), 2.85 (1H, ddd, J=1.5, 3.5 and 17 Hz, H-4 eq), 3.77 and 3.79 (6H, 2s, —O—$CH_3$), 4.00 (1H, dd, J=3.5 and 11 Hz, H-3), 4.66 (1H, br d, J=16 Hz, H-1), 4.93 (1H, br s, =$CH_2$), 4.99 (1H, d, J=16Hz, H-1), 5.09 (1H, br s, =$CH_2$), 6.62 and 6.67 (2H, 2d (AB), J=9 Hz, Ar—H).

Step 2: (trans)-5,10-dioxo-3-isopropenyl-1-methoxy-3,4,5,10-tetrahydro-1H-naphtho-[2,3-c]-pyran (BCH-2148)

Using the procedure described in step 3, example 26, the starting isochroman (150 mg; 0.64 mmol) and methanol (25 mg; 0.76 mmol) were treated with DDQ to afford a crude adduct (160 mg) which was then treated with CAN. This reaction yielded an impure crude quinone (91 mg) which was treated with 1-acetoxy-1,3-butadiene as described in step 4, example 26, affording after chromatographic purification (0–2% ethyl acetate in toluene) the title compound as 18 mg of slightly impure form and 5 mg of pure product (13% overall).

$^1$H NMR ($CDCl_3$, 250 MHz) δ: 1.87 (3H, s, =C—$CH_3$), 2.49 (1H, dd, J=11.5 and 19.5Hz, H-4 ax), 2.84 (1H, dd, J=3.5 and 19.5 Hz, H-4 eq), 3.61 (3H, s, —$OCH_3$), 4.50 (1H, dd, J=3.5 and 11.5 Hz, H-3), 5.00 (1H, s, =CH), 5.15 (1H, s, =CH), 5.63 (1H, s, H-1), 7.75 (2H, m, Ar—H), 8.10 (2H, m, Ar—H).

Step 3: (1'S, 1S, 3R)-5,8-dimethoxy-3-isopropenyl-1-(2',3',6'-trideoxy-3'-trifluoroacetamido-4'-O-p-nitrobenzoyl-L-lyxohexo-pyranose) isochroman Following the procedure described in the first part of step 3, example 26, the starting isochroman from step 1 herein (250 mg; 1.07 mmol) was treated with α-2,3,6-trideoxy-3-trifluoroacetamido-4-O-p-nitrobenzoyl-L-lyxohexopyranose (461 mg; 1.17 mmol) and DDQ (337 mg; 1.49 mmol) in dichloromethane (20 ml) containing 4 Å molecular sieves (500 mg) to yield after chromatography on silica gel using 25% ethyl acetate in hexane with 0.1% triethylamine, the title compound as a mixture with its (1'S, 1R, 3S) diastereomer (1:1; 310 mg). Another fraction gave pure titled compound (131 mg; 19%).

$^1$H NMR (250 MHz, $CD_2Cl_2$) δ: 1.22 (3H, d, J=6.5 Hz, H-6'), 1.83 (3H, s, =C—$CH_3$), 1.75–2.20 (2H, m, H-2'), 2.48 (1H, dd, J=12 and 17.5 Hz, H-4 ax), 2.89 (1H, dd, J=3.5 and 17.5 Hz, H-4 eq), 3.77 (3H, s, $OCH_3$), 3.78 (3H, s, OCH$_3$), 4.40–4.65 (2H, m, H-3 and H-3'), 4.73 (1H, q, J=6.5 Hz, H-5'), 4.92 (1H, s, =CH), 5.09 (1H, s, =CH), 5.42 (1H, br s, H-1'), 5.57 (1H, d, J=3 Hz, H-4'), 6.12 (1H, s, H-1), 6.31 (1H, br d, J=6 Hz, N—H), 6.73 and 6.79 (2H, AB doublets, Ar—H), 8.27 (4H, m, PNB). The (1'S, 1R, 3S)-5,8-dimethoxy-3-isopropenyl-1-(2',3',6'-trideoxy-3'-trifluoroacetamido-4'-O-p-nitrobenzoyl-L-lyxohexo-pyranose) isochroman had $^1$H NMR (CD$_2$Cl$_2$, 250 MHz) δ: 1.10 (3H, d, J=6.5 Hz, H-6'), 1.83 (3H, s, =C—CH$_3$), 1.90–2.20 (2H, m, H-2'), 2.39 (1H, dd, J=12 and 17.5 Hz, H-4 ax), 2.89 (1H, dd, J=3.5 and 17.5 Hz, H-4 eq), 3.76 (3H, s, OCH$_3$), 3.77 (3H, s, OCH$_3$), 4.35 (1H, q, J=6.5 Hz, H-5'), 4.50–4.70 (2H, m, H-3 and H-3'), 4.90 (1H, br s, =CH), 5.10 (1H, br s, =CH), 5.38 (1H, br s, H-1'), 5.54 (1H, br s, H-4'), 5.94 (1H, s, H-1), 6.31 (1H, m, N—H), 6.71 and 6.77 (2H, AB system, Ar—H), 8.27 (4H, m, PNB).

Step 4: (1'S, 1R, 3S)-5,10-dioxo-3-isopropenyl-1-(2',3',6'-trideoxy-3'-trifluoroacetamido-4'-O-p-nitrobenzoyl-L-lyxohexo-pyranose) 3,4,5,10-tetrahydro-1H-naphtho-[2,3-c]-pyran Using the same procedure as described in step 6 of this example, the starting isochroman from step 3 herein (80 mg; 0.13 mmol) afforded after CAN oxidation and Dieis-Alder the title product (35 mg; 42% overall) contaminated by what looks like aglycone systems.

$^1$H NMR (250 MHz, CDCl$_3$) δ: 1.17 (3H, d, J=6.5 Hz, H-6'), 1.87 (3H, s, =C—CH$_3$), 2.09 (2H, m, H-2'), 2.45 (1H, m, H-4 ax), 2.90 (1H, m, H-4 eq), 4.34 (1H, q, J=6.5 Hz, H-5'), 4.50–4.75 (2H, m, H-3 and H-3'), 5.00 (1H, s, =C—H), 5.17 (1H, s, =C—H), 5.44 (1H, br s, H-1'), 5.72 (1H, s, H-4'), 5.99 (1H, s, H-1), 6.40 (1H, br d, J=7.5 Hz, NH), 7.75 (2H, m, Ar—H), 8.10 (2H, m, Ar—H), 8.28 (4H, m, PNB).

Step 5: (1'S, 1R, 3S)-5,10-dioxo-3-isopropenyl-1-(2',3',6'-trideoxy-3'-trifluoroacetamido-L-lyxohexopyranose)-3,4,5,10-tetrahydro-1H-naphtho-[2,3-c]-pyran (BCH-2153)

Using the procedure described in step 3, example 32, the starting protected alcohol from step 6 herein (slightly impure, 30 mg; 0.047 mmol) afforded the title compound (11 mg; 48%), M.P.: 170° C. (dec).

IR (neat): 3417, 2936, 1716, 1664, 1596, 1293, 1167 and 983 cm$^{-1}$.

$^1$H NMR (250 MHz, CDCl$_3$) δ: 1.22 (3H, d, J=6.5 Hz, H-6'), 1.70–2.10 (3H, m, H-2' and O—H), 1.85 (3H, s, =C—CH$_3$), 2.41 (1H, dd, J=11.5 and 19.5 Hz, H-4 ax), 2.89 (1H, dd, J=3.5 and 19.5 Hz, H-4 eq), 3.59 (1H, m, H-4'), 4.16 (1H, q, J=6.5 Hz, H-5'), 4.35 (1H, m, H-3'), 4.52 (1H, dd, J=3.5 and 11.5 Hz, H-3), 4.96 (1H, s, =CH), 5.13 (1H, s, =CH), 5.54 (1H, d, J=3.5 Hz, H-1'), 5.93 (1H, s, H-1), 6.71 (1H, br d, J=8.5 Hz, —NH), 7.75 (2H, m, Ar—H), 8.10 (2H, m, ArH).

Step 6: (1'S, 1S, 3R)-5,10-dioxo-3-isopropenyl-1-(2',3',6'-trideoxy-3'-trifluoroacetamido-4'-O-p-nitrobenzoyl-L-lyxohexo-pyranose) 3,4,5,10-tetrahydro-1H-naphtho-[2,3-c]-pyran To a solution of the starting isochroman from step 3 herein (120 mg; 0.19 mmol) in acetonitrile (4 ml) at 0° C. was added a solution of CAN (prepared by dissolving ceric ammonium nitrate (630 mg; 1.15 mmol) in water (2 ml) and then adding slowly sodium bicarbonate (169 mg)). After the addition, the mixture was stirred for 10 minutes and was then quenched with saturated sodium bicarbonate solution. The product was extracted with dichloromethane and the combined organic extracts were washed with brine and dried over Na$_2$SO$_4$ to yield a crude quinone (112 mg) which was dissolved in toluene (5 ml) and reacted with 1-acetoxy-1,3-butadiene (113 µl; 1 mmol) at room temperature for 15 hours. After this time, silica gel was added and air was bubbled through for 30 minutes. The residue was applied to a silica gel column and eluted with 0–5% ethyl acetate in toluene affording slightly impure title compound (54 mg) along with pure product (17 mg; total yield 57%).

$^1$H NMR (250 MHz, CDCl$_3$) δ: 1.36 (3H, d, J=6.5 Hz, H-6'), 1.86 (3H, s, =C—CH$_3$), 1.99 (1H, br dd, J=5 and 12.5 Hz, H-2' eq), 2.13 (1H, td, J=3.5 and 12.5 Hz, H-2' ax), 2.52 (1H, dd, J=11.5 and 19 Hz, H-4 ax), 2.91 1H, dd, J=3.5 and 19 Hz, H-4 eq), 4.48 (1H, br d, J=11.5 Hz, H-3), 4.62 (1H, m, H-3'), 4.84 (1H, q, J=6.5 Hz, H-5'), 5.00 (1H, br s, =CH), 5.14 (1H, br s, =C—H), 5.47 (1H, br s, H-1'), 5.62 (1H, d, J=2.5 Hz, H-4'), 6.13 (1H, s, H-1), 6.47 (1H, br d, J=7.5 Hz, —NH), 7.78 (2H, m, Ar—H), 8.12 (2H, m, Ar—H), 8.29 (4H, m, PNB).

Step 7: (1'S, 1S, 3R)-5,10-dioxo-3-isopropenyl-1-(2',3',6'-trideoxy-3'-trifluoroacetamido-L-lyxohexopyranose)-3,4,5, 10-tetrahydro-1H-naphtho-[2,3-c]-pyran (BCH-21-52)

Using the procedure described in step 3, example 32, the starting protected alcohol from step 6 herein (16 mg; 0.0248 mmol) afforded the title compound (11 mg; 90%), M.P.: 102°–105° C.

IR (neat): 3418, 2934, 1718, 1669, 1295, 1167, 982 and 965 cm$^{-1}$.

$^1$H NMR (250 MHz, CDCl$_3$) δ: 1.42 (3H, d, J=6.5 Hz, H-6'), 1.84 (3H, s, =C—CH$_3$), 1.86 (2H, m, H-2'), 1.99 (1H, d, J=8.0 Hz, —OH), 2.51 (1H, dd, J=11.5 and 19.5 Hz, H-4 ax), 2.89 (1H, dd, J=3.5 and 19.5 Hz, H-4 eq), 3.65 (1H, m, H-4'), 4.35 (1H, m, H-3'), 4.46 (1H, dd, J=3.5 and 11.5 Hz, H-3), 4.63 (1H, q, J=6.5 Hz, H-5'), 4.98 (1H, s, =CH), 5.12 (1H, s =CH), 5.43 (1H, br s, H-1'), 6.07 (1H, s, H-1), 6.72 (1H, m, —NH), 7.75 (2H, m, Ar—H), 8.12 (2H, m, Ar—H).

EXAMPLE 31

Preparation of (1'S,1R,3S)-5,10-dioxo-3-methoxycarbonyl-1-(2',3',6'-trideoxy-3'-trifluoroacetamido-L-lyxohexopyranose)-3,4,5,10-tetrahydro-1H-naphtho-[2,3-c]-pyran: (BCH-2128)

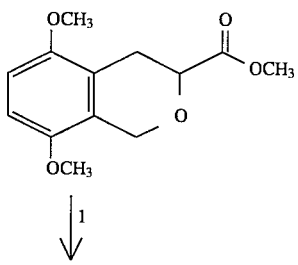

-continued

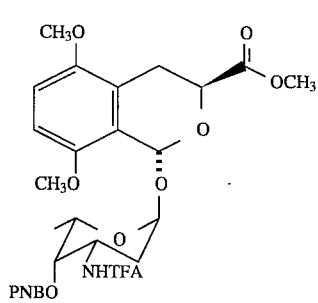
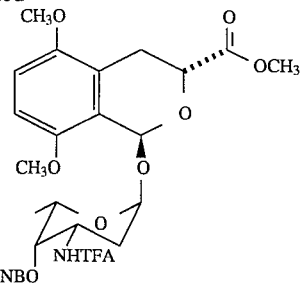

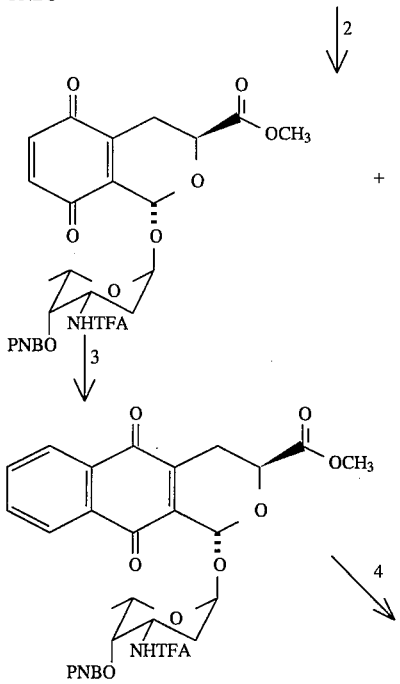
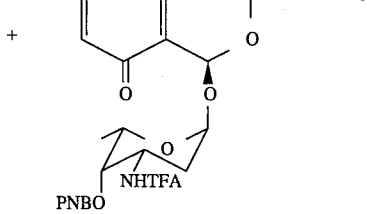
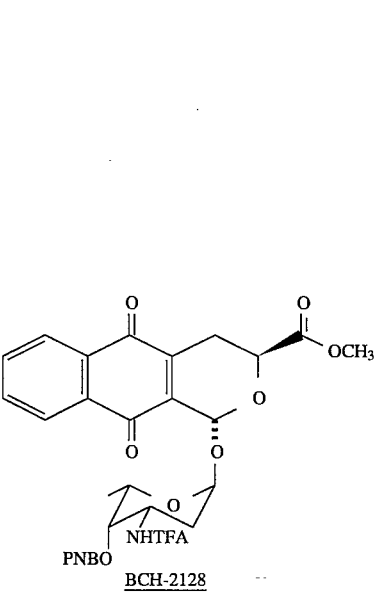

BCH-2128

Step 1: (1'S, 1R, 3S) and (1'S, 1S, 3R)-5,8 dimethoxy-3-methoxycarbonyl-1-(2',3',6'-trideoxy-3'-trifluoroacetamido-4'-O-p-nitrobenzoyl-L-lyxohexopyranose)-isochroman Using the procedure described in step 2, example 32, the starting isochroman (500 mg; 1.98 mmol) afforded after flash chromatography (5–20% acetone in benzene containing a trace of triethylamine) the mixture of title compounds (490 mg; 40% (~1:1)).

$^1$H NMR (250 MHz, CD$_2$Cl$_2$) δ: (for 1'S, 1R, 3S): 1.15 (3H, d, J=6.5 Hz, H-6'), 1.70–2.25 (2H, m, H-2'), 2.65 (1H, m, H-4 ax), 3.10 (1H, m, H-4 eq), 3.76–3.78 (9H, superimposed singlets, OCH$_3$), 4.38 (1H, q, J=6.5 Hz, H-5'), 4.45–4.85 (2H, m, H-3 and H-3'), 5.41 (1H, m, H-1'), 5.57 (1H, m, H-4'), 5.97 (1H, s, H-1), 6.45 (1H, br d, J=7.5 Hz, —NH), 6.65–6.85 (2H, m, Ar—H), 8.26 (4H, m, PNB); δ (for 1'S, 1S, 3R): 1.22 (3H, d, J=6.5 Hz, H-6'), 1.70–2.20 (2H, m, H-2'), 2.66 (1H, m, H-4 ax), 3.10 (1H, m, H-4 eq), 3.76–3.78 (9H, superimposed singlets, OCH$_3$), 4.45–4.85 (3H, m, H-3, H-3' and H-5'), 5.42 (1H, m, H-1'), 5.57 (1H, m, H-4'), 6.16 (1H, s, H-1), 6.45 (1H, br d, J=7.5 Hz, —N—H), 6.65–6.85 (2H, m, Ar—H), 8.26 (4H, m, PNB).

Step 2: (1'S, 1R, 3S) and (1'S, 1S, 3R)-5,8dioxo-3-methoxycarbonyl-1-(2',3',6'-trideoxy-3'-trifluoroacetamido-4'-O-p-nitrobenzoyl-L-lyxohexopyranose)-5,8-dihydro-isochroman To a solution of the starting isochroman from step 1 herein (475 mg; 0.74 mmol) in acetonitrile (15 ml) at 0° C. was added a solution of CAN (prepared by dissolving ceric ammonium nitrate (2.42 g) in water (7 ml) and then buffering with sodium bicarbonate (652 mg) added slowly). After the addition, the mixture was stirred at 0° C. for 15 minutes and was then quenched with saturated sodium bicarbonate solution and extracted with dichloromethane. The combined organic layers were washed with brine and dried over Na$_2$SO$_4$ giving a crude mixture of the title quinones (422 mg; 93%) used as such for the next reaction.

¹H NMR (250 MHz, CD₂Cl₂) δ: 1.15 (3H, d, J=6.5 Hz, H-6', A*), 1.27 (3H, d, J=6.5 Hz, H-6', B), 1.70–2.25 (2H, m, H-2', A and 2H, m, H-2', B), 2.55 (1H, m, H-4 ax, A and 1H, m, H-4 ax, B), 2.85 (1H, m, H-4 eq, A and 1H, m, H-4 eq, B), 3.76 (3H, s, OCH₃, B), 3.77 (3H, s, OCH₃, A), 4.34 (1H, q, J=6.5 Hz, H-5', A), 4.40–4.70 (2H, m, H-3' and H-3, A and 3H, m, H-3', H-3 and H-5', B), 5.39 (1H, m, H-1', A and 1H, m, H-1', B), 5.54 (1H, d, J=3H, H-4', B), 5.57 (1H, d, J=3Hz, H-4', A), 5.80 (1H, s, H-1, A), 5.95 (1H, s, H-1, B), 6.60 (1H, m, NH, A and 1H, m, NH, B), 6.80 (2H, m, Ar—H, A and 2H, m, Ar—H, B), 8.26 (4H, m, PNB, A and 4H, m, PNB, B).

* A is (1'S, 1R, 3S) diastereomer and B is (1'S, 1S, 3R) diastereomer.

Step 3: (1'S, 1R, 3S)-5,10-dioxo-3-methoxycarbonyl-1-(2', 3',6'-trideoxy-3'-trifluoroacetamido-4'-O-p-nitrobenzoyl-L-lyxohexopyranose)-3,4,5,10-tetrahydro-1H-naphtho-[2,3-c]-pyran Using the procedure described in step 4, example 26, the starting quinone from step 2 herein (400 mg; 0.658 mmol of a 1:1 mix of 1'S, 1R, 3S and 1'S, 1S, 3R) afforded pure title product (13 mg) along with a ~1:1 mixture of (1'S, 1R, 3S) and (1'S, 1S, 3R) isomers (275 mg).

¹H NMR (250 MHz, CD₂Cl₂) δ: 1.18 (3H, d, J=6.5 Hz, H-6'), 1.90–2.20 (2H, m, H-2'), 2.68 (1H, dd, J=11.5 and 19 Hz, H-4 ax), 3.08 (1H, dd, J=4 and 19 Hz, H-4 eq), 3.80 (3H, s, OCH₃), 4.38 (1H, q, J=6.5 Hz, H-5'), 4.57 (1H, m, H-3'), 4.75 (1H, dd, J=4 and 11.5 Hz, H-3), 5.42 (1H, br s, H-1'), 5.69 (1H, br s, H-4'), 5.99 (1H, s, H-1), 6.42 (1H, br d, J =7 Hz, —NH), 7.75 (2H, m, Ar—H), 8.08 (2H, m, Ar—H), 8.28 (4H, m, PNB).

Step 4: (1'S, 1R, 3S)- 5,10-dioxo-3-methoxycarbonyl-1-(2', 3',6',trideoxy-3'-trifluoroacetamido-L-lyxohexopyranose)-3, 4,5,10-tetrahydro-1H-naphtho- [2,3 -c]-pyrano (BCH-2128)

Using the procedure described in step 5, example 26, the starting protected alcohol from step 3 herein (12 mg; 0.018 mmol) afforded after column chromatography (10% acetone in dichloromethane), the title compound (5 mg; 54%) as a yellow solid. M.P. 92°–105° C.

¹H NMR (250 MHz, CD₂Cl₂) δ: 1.22 (3H, d, J=6.5 Hz, H-6'), 1.55 (1H, br s, OH), 1.70–2.00 (2H, m, H-2'), 2.66 (1H, dd, J=12.0 and 19.0 Hz, H-4 ax), 3.06 (1H, dd, J=4.0 and 19.0 Hz, H-4 eq), 3.59 (1H, br s, H-4'), 3.79 (3H, s, —CO₂CH₃), 4.17 (1H, q, J=6.5 Hz, H-5'), 4.28 (1H, m, H-3'), 4.73 (1H, dd, J=4.0 and 11.5 Hz, H-3), 5.52 (1H, br s, H-1'), 5.92 (1H, s, H-1), 6.75 (1H, m, —NH), 7.75 (2H, m, Ar—H), 8.05 (2H, m, Ar—H).

EXAMPLE 32

Preparation of (1'S, 1R, 3S)-isopropyl- [5,10-dioxo-1-(2',3',6'-trideoxy-3'-trifluoroacetamido-L-lyxohexopyranose)-3,4,5,10-tetrahydro-1H-naphtho-[2,3-c]-pyranyl]-ketone: (BCH-2112)

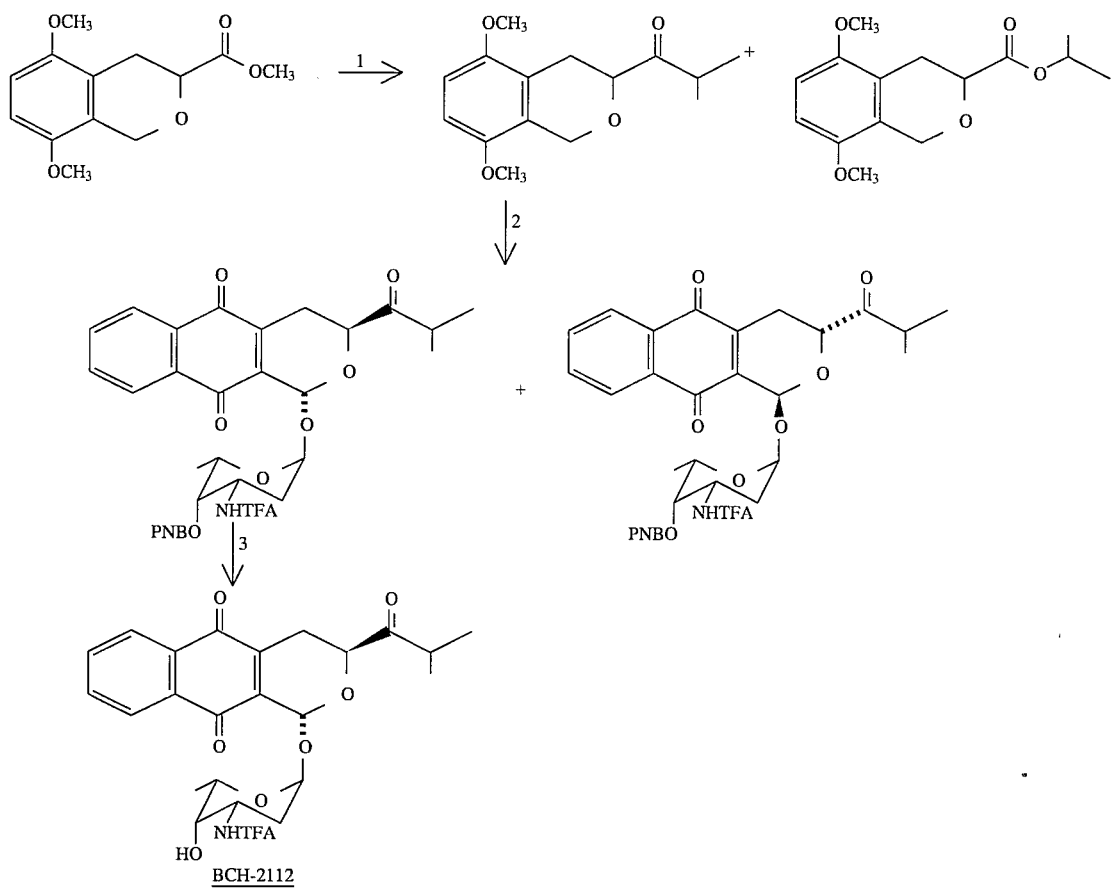

Step 1: isopropyl-(5,8-dimethoxy-isochroman-3-yl)-ketone

To a solution of the starting ester (1.0 g; 3.97 mmol) in tetrahydrofuran (30 ml) at 0° C. was added isopropyl magnesium chloride (2M, 4.17 mmol). The mixture was stirred at 0° C. for 20 minutes and at room temperature for 1 hour. It was then quenched with saturated ammonium chloride solution and extracted with dichloromethane. The combined organic layers were washed with brine and dried over $MgSO_4$ to afford after evaporation, the title compound (240 mg; 23% (40% based on S.M. recovered)).

$^1$H NMR (250 MHz, $CDCl_3$) δ: 1.13 (3H, d, J=6.5 Hz, $CH_3$—CH), 1.16 (3H, d, J=6.5 Hz, $CH_3$—CH), 2.59 (1H, br dd, J=11.5 and 17 Hz, H-4 ax), 3.04 (1H, dm, J=17 Hz, H-4 eq), 3.17 (1H, m, CH—$CH_3$), 3.76 (3H, s, $OCH_3$), 3.78 (6H, s, $OCH_3$), 4.17 (1H, dd, J=3.5 and 11.5 Hz, H-3), 4.64 (1H, br d, J=16 Hz, H-1), 5.03 (1H, d, J=16 Hz, H-1), 6.65 (2H, AB system, Ar—H).

5,8-dimethoxy-3-isopropoxycarbonyl-isochroman was obtained as a by-product resulting from oxidation of the Grignard reagent.

$^1$H NMR (250 MHz, $CDCl_3$) 67 : 1.29 (3H, d, J=6Hz, $CH_3$—CH), 1.30 (3H, d, J =6 Hz, $CH_3$—CH), 2.74 (1H, br dd, J=11 and 17 Hz, H-4 ax), 3.05 (1H, dm, J=17 Hz, H-4 eq), 3.75 (3H, s, $OCH_3$), 3.78 (3H, s, $OCH_3$), 4.19 (1H, dd, J=4 and 11 Hz, H-3), 4.65 (1H, br d, J=16 Hz, H-1), 5.04 (1H, d, J=16 Hz, H-1), 5.15 (1H, sept., J=6 Hz, CH—$CH_3$), 6.64 (2H, AB system, Ar—H).

Step 2: (1'S, 1R, 3S)-isopropyl-[1-(2',3',6'-trideoxy-3'-trifluoroacetamido-4'-O-p-nitrobenzoyl-L-lyxohexopyranose)-5,10-dioxo-3,4,5,10-tetrahydro-1H-naphtho-[2,3-c]-pyranyl]-ketone To a solution of α-2',3',6'-trideoxy-3'-trifluoroacetamido-4'-O-p-nitrobenzoyl-L-lyxohexopyranose (408 mg; 1.04 mmol) and starting ketone from step 1 herein (230 mg; 0.87 mmol) in dichloromethane (15 ml), were added 4 Å molecular sieves (400 mg) and 2,3-dichloro-5,6-dicyano-benzoquinone (270 mg; 1.2 mmol). The mixture was stirred at room temperature for 14 hours and was then quenched with saturated bicarbonate solution and extracted with dichloromethane. The combined organic layers were washed with brine and dried over $Na_2SO_4$ to afford a crude adduct (590 mg) which was dissolved in acetonitrile (20 ml) at 0° C. and treated dropwise with a solution of ceric ammonium nitrate (3.15 g; 5.7 mmol) in water (10 ml) containing sodium bicarbonate (847 mg). After the addition, the mixture was stirred at 0° C. for 15 minutes and was quenched with saturated $NaHCO_3$ and extracted with dichloromethane. The combined organic layers were washed with brine and dried over $Na_2SO_4$ to afford a crude quinone mixture (557 mg) of which 100 mg (0.16 mmol) were dissolved in toluene (6 ml) and treated with 1-acetoxy-1,3-butadiene (113 µl; 1 mmol) at room temperature for 14 hours. Silica gel was added to the mixture and air was bubbled through for 1 hour while toluene partly evaporated. The residue was applied to a column of silica gel and eluted with 0–10% ethyl acetate in toluene affording the title compound (20 mg) slightly contaminated by its (1S, 3R) diastereomer (~3:1).

$^1$H NMR (250 MHz, $CDCl_3$) δ: 1.00–1.30 (9H, m, H-6' and CH—$(CH_3)_2$), 1.60–2.40 (2H, m, H-2'), 2.52 (1H, m, H-4 ax), 3.00–3.35 (2H, m, H-4 eq and CH—$(CH_3)_2$), 4.32 (1H, q, J=6.5 Hz, H-5'), 4.50–4.90 (2H, m, H-3 and H-3'), 5.44 (1H, br s, H-1'), 5.75 (1H, br s, H-4'), 6.06 (1H, s, H-1), 6.49 (1H, br d, J=7.5 Hz, —NH), 7.78 (2H, m, Ar—H), 8.07 (2H, m, Ar—H), 8.27 (4H, m, PNB), apparent signals for (1S, 3R) diastereomer are: 6.22 (1H, s, H-1) and 6.58 (1H, br d, J=7.5 Hz, NH).

Step 3: (1'S, 1R, 3S)-isopropyl-[1-(2',3',6'-trideoxy-3'-trifluoroacetamido-L-lyxohexopyranose)-5,10-dioxo-3,4,5,10-tetrahydro-1H-naphtho-[2,3-c]-pyranyl]-ketone (BCH-2112)

To a solution of starting protected alcohol from step 2 herein (20 mg; 0.0296 mmol) in methanol (0.3 ml): tetrahydrofuran (1 ml) at 0° C. was added sodium methoxide in methanol (4.37M; 0.7 µl; 0.1 eq). The mixture was stirred at 0° C. for 20 minutes and was then quenched with saturated $NH_4Cl$ solution and was extracted with dichloromethane. The combined organic layers were washed with brine and dried over $Na_2SO_4$ to afford a crude residue which was purified by column chromatography on silica gel using 10% acetone in benzene yielding the titled compound (6.4 mg; 63%).

$^1$H NMR ($CD_2Cl_2$, 250 MHz), δ: 1.11 (6H, d, J=6.5 Hz, —CH—$(CH_3)_2$), 1.20 (3H, d, J=6.5 Hz, H-6'), 1.65 (1H, s, OH), 1.75–2.05 (2H, m, H-2'), 2.48 (1H, dd, J=11.5 and 19.5 Hz, H-4 ax), 3.01 (1H, dd, J=4.0 and 19.5 Hz, H-4 eq), 3.15 (1H, sept., J=6.5 Hz, CH—$(CH_3)_2$), 3.58 (1H, d, J =2.5 Hz, H-4'), 4.10 (1H, q, J=7.0 Hz, H-5'), 4.28 (1H, m, H-3'), 4.68 (1H, dd, J=4.0 and 11.5 Hz, H-3), 5.55 (1H, d, J=3.5 Hz, H-1'), 5.97 (1H, s, H-1), 6.72 (1H, m, N—H), 7.75 (2H, m, Ar—H), 8.05 (2H, m, Ar—H).

EXAMPLE 33

Preparation of (1'S,1S,3R) and (1'S,1R,3S)-5,10-dioxo-3-isopropoxycarbonyl-1-(2',3',6'-trideoxy-3'-trifluoroacetamido-L-lyxohexopyranose)-3,4,5,10-tetrahydro-1H-naphtho-[2,3-c]-pyran: (BCH-2122) and (BCH-2121)

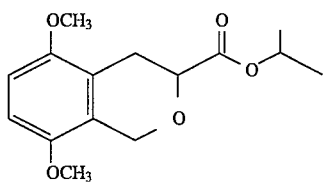

↓ 1

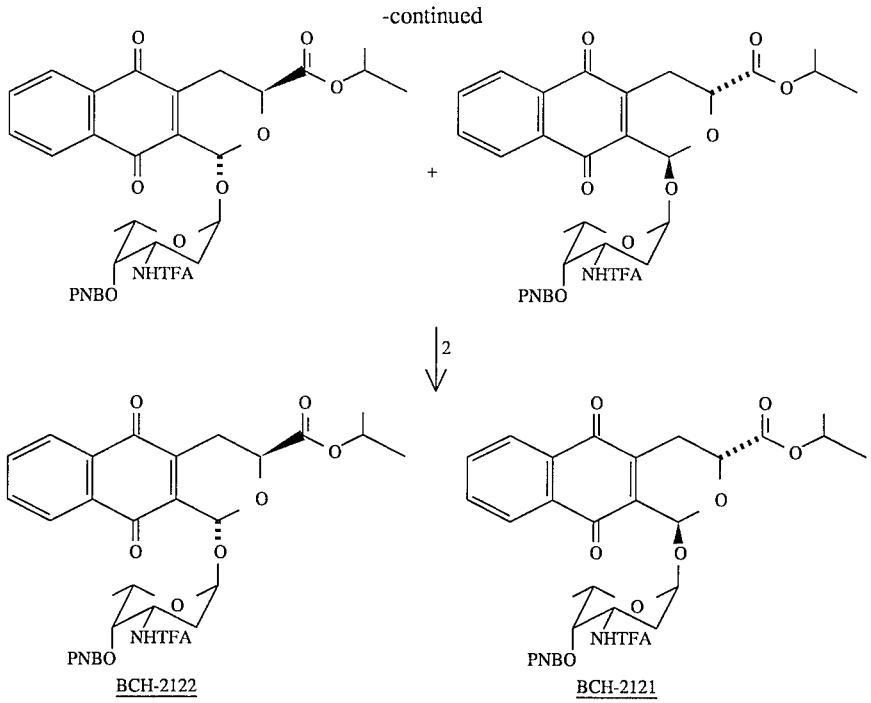

BCH-2122       BCH-2121

Step 1: (1'S, 1R, 3S), and (1'S, 1S, 3R)-5,10-dioxo-3-isopropoxycarbonyl-1-(2',3',6'-trideoxy-3',trifluoroacetamido-4'-O-p-nitrobenzoyl-L-lyxohexopyranose)-3,4,5,10-tetrahydro-1H-naphtho-[2,3-c]-pyran Using the procedure described in step 2, example 32, the starting isochroman from step 1, example 32, (300 mg; 1.07 mmol) afforded a crude glycosylated adduct (417 mg) which was treated with CAN to give a crude quinone mixture (355 mg) of which 250 mg were reacted with acetoxybutadiene. This reaction yielded a slightly impure mixture of the title compounds (113 mg; 15% overall) (~55:45) favoring the (1'S, 1R, 3S) isomer.

$^1$H NMR (250 MHz, CDCl$_3$) δ: (for 1'S, 1R, 3S): 1.15–1.42 (9H, m, H-6'and CH—(CH$_3$)$_2$), 1.90–2.20 (2H, m, H-2'), 2.68 (1H, dd, J=12 and 19 Hz, H-4 ax), 3.12 (1H, m, H-4 eq), 4.40 (1H, q, J=6.5 Hz, H-5'), 4.50–4.80 (2H, m, H-3 and H-3'), 5.18 (1H, m, CH—(CH$_3$)$_2$), 5.44 (1H, br s, H-1'), 5.74 (1H, br s, H-4'), 6.03 (1H, s, H-1), 6.55 (1H, br d, J=7.5 Hz, N—H), 7.77 (2H, m, Ar—H), 8.11 (2H, m, ArH), 8.27 (4H, m, PNB); (for 1'S, 1S, 3R): 1.15–1.42 (9H, m, H-6' and CH(CH$_3$)$_2$), 1.90–2.20 (2H, m, H-2'), 2.69 (1H, dd, J=12 and 19 Hz, H-4 ax), 3.12 (1H, m, H-4 eq), 4.50–4.80 (3H, m, H-3, H-3' and H-5'), 5.18 (1H, m, CH(CH$_3$)$_2$), 5.45 (1H, br s, H-1'), 5.65 (1H, d, J=3 Hz, H-3'), 6.18 (1H, s, H-1), 6.61 (1H, br d, J=7.5 Hz; —NH), 7.77 (2H, m, Ar—H), 8.11 (2H, m, Ar—H), 8.27 (4H, m, PNB).

Step 2: (1'S, 1R, 3S)-5,10-dioxo-3-isopropoxycarbonyl-1-(2',3',6'-trideoxy-3'-trifluoroacetamido-L-lyxohexopyranose)-3,4,5,10-tetrahydro-1H-naphtho-[2,3-c]-pyran (BCH-2122)

Using the procedure described in step 3, example 32, the starting protected alcohol from step 1 herein (113 mg; 0.16 mmol) afforded (after multiple chromatographic separations using 10% acetone in benzene or in dichloromethane) the pure title compound (7 mg; 8%). M.P.: 93°–101° C.

$^1$H NMR (CDCl$_3$) δ: 1.29 and 1.33 (6H, 2d, J=6.5 Hz, —CH—(CH$_3$)$_2$), 1.33 (3H, d, J=6.5 Hz, H-6'), 1.70–2.10 (3H, m, H-2' and O—H), 2.68 (1H, dd, J=11.5 and 19.5 Hz, H-4 ax), 3.11 (1H, dd, J=4.0 and 19.5 Hz, H-4 eq), 3.65 (1H, m, H-4'), 4.21 (1H, q, J=6.5 Hz, H-5'), 4.38 (1H, m, H-3'), 4.66 (1H, dd, J=4.0 and 11.5 Hz, H-3), 5.18 (1H, sept., J=6.5 Hz, CH—(CH$_3$)$_2$), 5.56 (1H, br s, H-1'), 5.98 (1H, s, H-1), 6.72 (1H, m, NH), 7.75 (2H, m, Ar—H), 3.10 (2H, m, Ar—H). (1'S, 1S, 3R)-5,10-dioxo-3-isopropoxycarbonyl-1-(2',3',6'-trideoxy-3'-trifluoroacetamido-L-lyxohexopyranose)-3,4,5,10-tetrahydro-1H-naphtho-2,3-c]-pyran (BCH-2121) was isolated after multiple chromatographic separations (5 mg; 6%). M.P.: 155° C. (dec).

$^1$H NMR (CDCl$_3$) δ: 1.32 (6H, d, J=6.5 Hz, CH—(CH$_3$)$_2$), 1.41 (3H, d, J=6.5 Hz, H-6'), 1.87 (2H, m, H-2'), 2.05 (1H, m, OH), 2.70 (1H, dd, J=12.0 and 19.5 Hz, H-4 ax), 3.10 (1H, dd, J=4.0 and 19.5 Hz, H-4 eq), 3.63 (1H, m, H-4'), 4.32 (1H, m, H-3'), 4.55 (1H, q, J=6.5 Hz, H-5'), 4.62 (1H, dd, J=4.0 and 12.0 Hz, H-3), 5.16 (1H, sept., J=6.5 Hz, CH—(CH$_3$)$_2$), 5.47 (1H, br s, H-1'), 6.14 (1H, s, H-1), 6.75 (1H, m, N—H), 7.75 (2H, m, Ar—H), 8.12 (2H, m, Ar—H).

EXAMPLE 34

Preparation of (1'S,1S)-5,10-dioxo-3,3-dimethoxymethyl-1-(2',3',6'-trideoxy-3'-trifluoroacetamido-4'-O-p-nitrobenzoyl-L-lyxohexopyranose)-isochroman (BCH-1697)

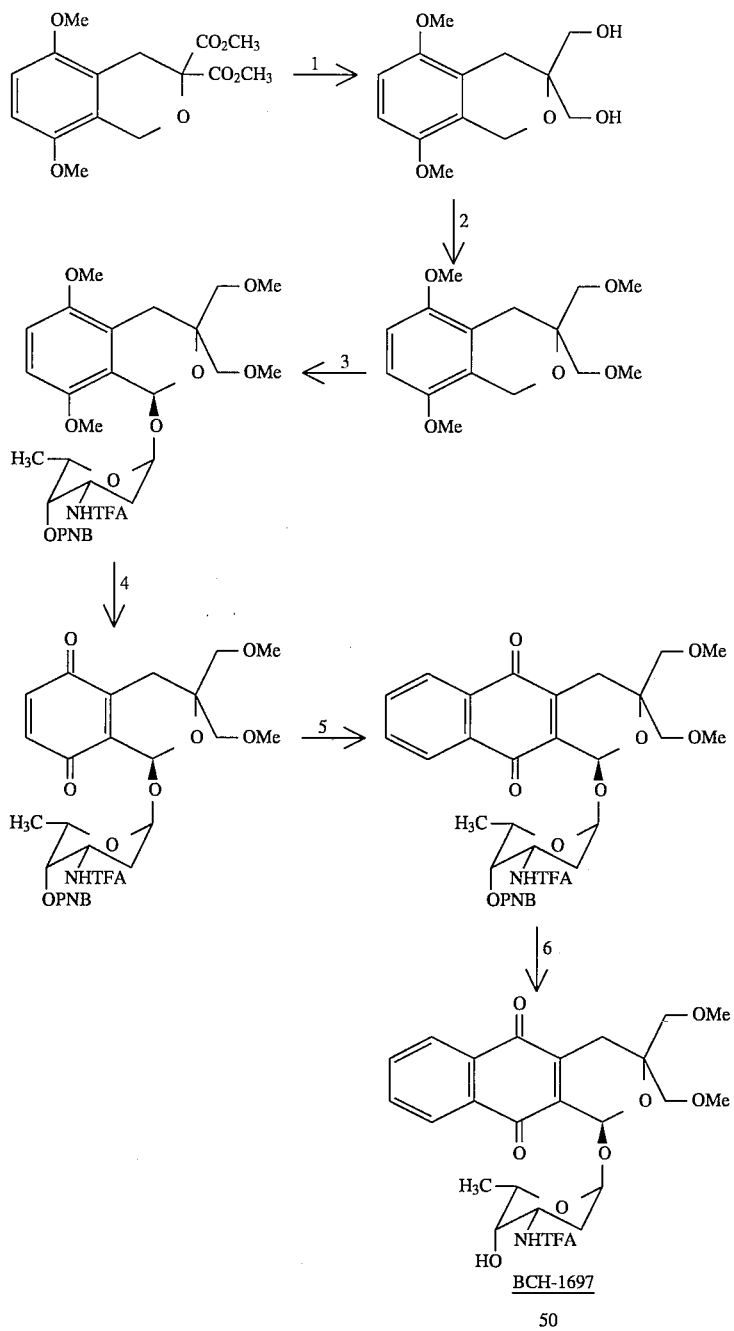

50

Step 1: 5,8-dimethoxy-3,3 bis (dihydroxymethyl)-isochroman

Under argon atmosphere, 110 mg (2.90 mmol) of LAH were added to 15 ml of dry THF, previously cooled to 0° C. To this solution was added 0.450 g (1.45 mmol) of 5,8-dimethoxy-3,3-bis (dicarbomethoxy)-isochroman dissolved in 15 ml of THF. The temperature was allowed to warm up to room temperature, and stirring was continued for 3 hours. After that time, another 160 mg (4.22 mmol) of LAH was then added and the reaction mixture was stirred for another hour. After that time, the reaction mixture was poured into 50 ml of a 0.1N aqueous solution of HCl. Extractions of the aqueous layer are done using $CH_2Cl_2$. The combined organic layers are dried over $Na_2SO_4$, filtered, and the solvent is removed. The isolated titled compound is used without further purification (0.333 g; 90%).

NMR $^1$H (250 MHz) ($CDCl_3$;ppm): 6.64 (2H, 2d, aromatics); 4.80 (2H, s, $H_{1a}$-$H_{1b}$); 3.76 (6H, s, 2×$OCH_3$); 3.71 (4H, m, 2—$CH_2$—); 2.53 (2H, s, 2×OH); 1.85 (2H, m, $H_{4a}$-$H_{4b}$).

Step 2: 5,8-dimethoxy-3,3 bis (dimethoxymethyl)-isochroman

Under argon atmosphere, 0.333 g (1.31 mmol) of the starting material from step 1 herein were placed in 70 ml of dry THF. To this solution were then added 0.105 g (2.62 mmol) of NaH. After a few minutes of stirring, 0.41 ml (6.55 mmol) of MeI were added to the reaction mixture and stirring was left for 1.5 hour. After that time, another 0.145 g of NaH and 0.7 ml of MeI were added to the reaction which was completed after another hour of stirring. Aqueous HCl (0.1N) was then added and extractions were done using $CH_2Cl_2$. The combined organic extracts were washed with an aqueous solution of sodium bicarbonate, dried over $Na_2SO_4$, filtered, and the solvent was removed. The obtained titled compound was used for next step without further purification. Isolated product (0.470 g; >99%).

NMR $^1H$ (250 MHz) ($CDCl_3$;ppm): 7.26 (2H, 2d, aromatics); 4.74 (2H, s, $H_{1a}$-$H_{1b}$); 3.76 (6H, 2s, $2\times OCH_3$); 3.54 (2H, d, J=9.7 Hz, —$CH_2$—side chain); 3.41 (2H, d, J=9.7 Hz, —$CH_2$—side chain); 3.38 (6H, s, $2\times OCH_3$); 2.64 (2H, s, $H_{4a}$-$H_{4b}$).

IR (film) ($cm^{-1}$) 2925 (CH aliphatic), 1580 (C=C), 1475 ($CH_2$), 1450 and 1360 ($CH_3$), 1100 and 1248 (C—O).

Step 3: (1'S, 1S)-5,8-dimethoxy-3,3-dimethoxymethyl-1-(2', 3',6'-trideoxy-3'-trifluoroacetamido-4'-O-p-nitrobenzoyl-L-lyxohexopyranose)-isochroman Under argon atmosphere, the following reagents: product from step 2 herein, 0.477 g (1.70 mmol), 2,3,6-trideoxy-3-trifluoroacetamido-4-O-p-nitrobenzoyl-α-L-lyxohexopyranose 0.378 g (2.00 mmol) and DDQ 0.452 g (2.00 mmol) were dissolved in 50 ml of dichloromethane. The reaction mixture was stirred at room temperature for a period of 16 hours. After that time, an excess of DDQ was then added to the reaction mixture and stirring was left for another hour. The reaction mixture was then quenched with aqueous $NH_4Cl$ and extractions of the aqueous layer was done using $CH_2Cl_2$. The combined organic layers were dried over $Na_2SO_4$, filtered and the solvent was removed. The crude material was purified by flash chromatography; eluent:hexanes-ethyl acetate (70:30) then (60:40). The obtained titled compound was a pale yellow solid (0.434 g; 39%).

NMR $^1H$ (250 MHz) ($C_6D_6$; ppm): 7.89 (2H, m, aromatics), 7.68 (2H, m, aromatics), 6.53 (2H, m, aromatics), 6.52 (1H, NH), 6.08 (1H, s, $H_1$), 5.62 (1H, s, $H_{1'}$), 4.70 (1H, m, $H_5$,), 4.60 (1H, m, $H_3$,), 3.82 (2H, m, $CH_2$—OMe), 3.74 (1H, m, $H_{4'}$), 3.55 (2H, m, $CH_2$—OMe), 3.48 and 3.42 (6H, 2s, $2\times OCH_3$), 3.40 (2H, m, $H_{2'a}$ and $H_{2'b}$), 3.18 and 3.11 (6H, 2s, $2\times OCH_3$), 2.13 (1H, m, $H_{4a}$), 1.86 (1H, m, $H_{4b}$), 1.21 (3H, d, J=6.2 Hz, $CH_3$sugar).

Step 4: (1'S, 1S)-5,8-dioxo-3,3-dimethoxymethyl-1-(2',3',6'-trideoxy-3'-trifluoroacetamido-4'-O-p-nitrobenzoyl-L-lyxohexopyranose)-isochroman The starting material from step 3 herein, 0.430 g (0.65 mmol), was dissolved in acetonitrile at 0° C. A solution of $NaHCO_3$ 0.107 g (1.30 mmol) in 7 ml of water was then added and the solution was stirred for 10 minutes. After that time, 1.053 g (1.95 mmol) of CAN diluted in 12 ml of water were then added to the reaction mixture in a dropwise manner. The reaction was complete after 10 minutes. A very diluted solution of $NaHCO_3$ in water was then added to the reaction mixture. Extractions of the reaction mixture were done using $CH_2Cl_2$. The combined organic layers are dried over $Na_2SO_4$, filtered and the solvent was removed. The titled compound was used for next step without further purification, (0.387 g; 95%).

NMR $^1H$ (250 MHz) ($C_6D_6$; ppm): 7.94 (2H, d, J=7.5 Hz, aromatics), 7.75 (2H, d, J=7.5 Hz, aromatics), 7.42 (1H, m, NH), 6.20 (2H, m, quinone ring), 5.98 (1H, s, $H_1$), 5.92 (1H, s, $H_{1'}$), 5.41 (1H, s, $H_{4'}$), 4.90 (1H, q, $H_5$,), 4.67 (1H, m, $H_3$,), 3.47 (2H, $CH_2$—OMe), 3.29 (2H, $CH_2$—OMe), 3.16 (3H, s, $OCH_3$), 3.11 (3H, s, $OCH_3$), 2.50 (2H, 2d, $H_{2'a}$, $H_{2'b}$), 2.22 (1H, m, $H_{4a}$), 1.97 (1H, m, $H_{4b}$), 1.27 (3H, d, J=6.3 Hz, —$CH_3$ sugar).

Step 5: (1'S, 1S)-5,10-dioxo-3,3-dimethoxymethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c] pyran Under argon atmosphere, 0.173 g (0.27 mmol) of the product from step 4 herein was dissolved in 10 ml of dry toluene. To this solution was added 0.2 ml (1.65 mmol) of 1-acetoxy-1,3-butadiene. The reaction mixture was left stirring overnight at room temperature. Silica gel was then added to the reaction mixture and air was bubbled in it for a period of 2 hours. Without removing the solvent, the reaction mixture was put on top of a silica gel column and toluene was used as the first eluent. Toluene-ethyl acetate (1:1) was then used to elute the desired compound. The titled compound was isolated (0.06 g, 32%) as a yellow solid.

NMR $^1H$ (250 MHz) ($CD_2Cl_2$; ppm): 8.29 (4H, m, aromatics), 8.07 (2H, m, aromatics), 7.76 (2H, m, aromatics), 6.45 (1H, d, NH), 6.05 (1H, s, $H_1$), 5.70 (1H, s, $H_{1'}$), 5.43 (1H, s, $H_{3'}$), 4.82 (1H, m, $H_{5'}$), 4.52 (1H, m, $H_{4'}$), 3.27–3.52 (4H, m, $2\times$—$CH_2$—side chains), 3.35 (3H, s, $OCH_3$), 3.27 (3H, s, $OCH_3$), 2.72 (2H, 2d overlapped, $H_{4a}$ and $H_{4b}$), 1.87–2.18 (2H, m, —$CH_2$—sugar), 1.28 (3H, d, J=6.5 Hz, —$CH_3$ sugar).

Step 6: (1'S, 1S)-5,10-dioxo-3,3-dimethoxymethyl-1-(2',3',6'-trideoxy-3'-trifluoroacetamido-4'-O-p-nitrobenzoyl-L-lyxohexo-pyranose)-isochroman (BCH-1697)

Under argon atmosphere, the product from step 5 herein, 0.06 g (0.09 mmol) was dissolved in a mixture of 5 ml of dry methanol and 2 ml of dry THF. This solution was cooled to 0° C. 2 µl of a 4.37M solution of sodium methoxide in methanol were added to the reaction mixture. The reaction was completed in 10 minutes, it was then quenched by adding aqueous $NH_4Cl$. Extractions of the aqueous layer was done using dichloromethane. The combined organic layers were dried over $Na_2SO_4$, filtered and the solvent was removed. The crude material was then purified by flash chromatography, eluent: ethyl acetate-dichloromethane (35:75). The isolated titled compound was a yellow solid (0.03 g, 67%).

NMR $^1H$ (250 MHz) ($CDCl_3$; ppm): 8.05 (2H, m, aromatics), 7.74 (2H, m, aromatics), 6.81 (1H, d, NH), 6.00 (1H, s, $H_1$), 5.49 (1H, d, J=2.8 Hz, $H_{1'}$), 4.58 (1H, q, $H_{5'}$), 4.23 (1H, m, $H_{4'}$), 3.60 (1H, d, J=2.3 Hz, $H_{3'}$), 3.45 (2H, m, —$CH_2$—(OMe)), 3.37 (2H, m, —$CH_2$—(OMe)), 3.34 (3H, s, $OCH_3$), 3.25 (3H, s, $OCH_3$), 2.71 (2H, d, J=3.5 Hz, $H_{4a}$ and $H_{4b}$), 2.09 (1H, $_{(broad)}$s, OH), 1.79 (2H, m, —$CH_2$—sugar), 1.32 (3H, d, J=6.6 Hz, —$CH_3$ sugar).

IR (film) ($cm^{-1}$): 3450 (OH bonded), 2950 (CH aliphatic), 1675 (C=C), 1000 and 1290 (C—O).

EXAMPLE 35

Preparation of (1'S,1R,4R)-5,10-dioxo-4-ethyl-1-(2',3',6'-trideoxy-3'-trifluoroacetamido-L-lyxohexopyranose)-3,4,5,10-tetrahydro-1H-naphtho-[2,3-c] pyran (BCH-2091)

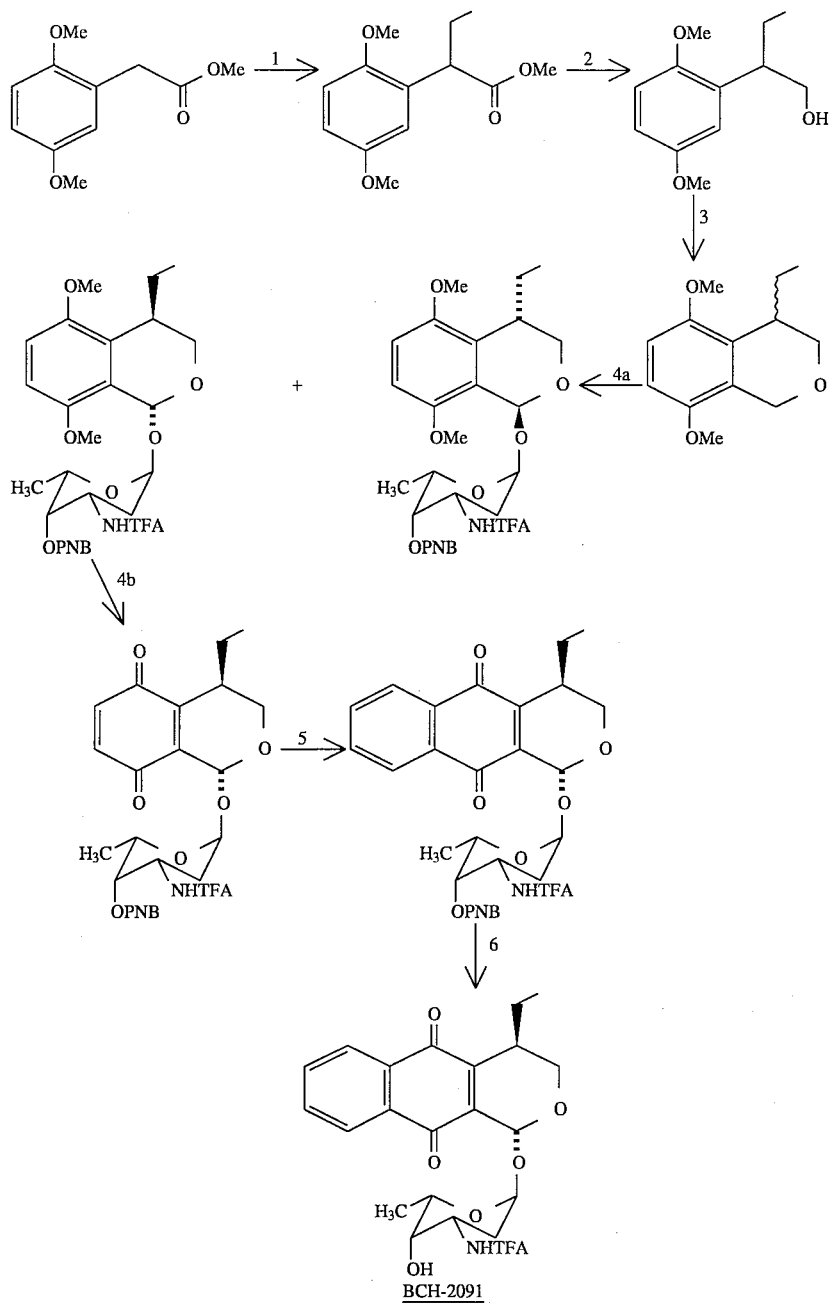

Step 1: methyl-2-(2',5'-dimethoxyphenyl) butanoate

Under argon atmosphere, 3.08 ml (26.16 mmol) of diso-propylamine was added to 85 ml of THF precooled to 0° C. n-BuLi 10.5 ml (26.16 mmol) was then added to this solution and this mixture was then stirred for 30 minutes. After that time, the reaction mixture was cooled to −78° C. and the ester 5.00 g (23.78 mmol), 208-186-01 in 65 ml of THF was then added dropwise. After the addition, the mixture was stirred for 5 minutes before HMPA 4.55 ml (26.16 mmol) was added. After another 10 minutes of stirring following the last addition, ethyliodide 5.0 ml (47.56 mmol) was then added to the reaction mixture. The reaction mixture was then stirred for 30 minutes before removal of the dry ice-acetone bath to allow the temperature to reach room temperature and the reaction was monitored by TLC. The reaction mixture was left stirring at room temperature for 15 hours. The reaction mixture was then quenched by adding aqueous $NH_4Cl$ and extracting with ether. The combined organic layers were washed with brine, dried over $Na_2SO_4$, filtered and the solvent was removed. The crude was purified by flash chromatography using hexanes-ethyl acetate as eluent; 3.36 g of pure titled compound as a white solid were obtained.

NMR $^1H$ (250 MHz) ($CDCl_3$; ppm): 6.84 (1H, m, aromatic), 6.76 (2H, m, aromatics), 3.90 (1H, t, J=7.6 Hz, $H_3$), 3.77 (3H, s, $OCH_3$), 3.75 (3H, s, $OCH_3$), 3.64 (3H, s, ($CO_2$)—$CH_3$), 2.03 (1H, m, $H_{3a}$), 1.72 (1H, m, $H_{3b}$), 0.88 (3H, t, J=7.3 Hz, —$CH_3$ terminal).

Step 2: 2-(2',5'-dimethoxyphenyl)-1-butanol

Under argon atmosphere, the product from step 1 herein, 3.36 g (14.08 mmol) was dissolved in 100 ml of dichloromethane. This solution was cooled to 0° C. and DIBAL-H, 31.0 ml (30.98 mmol) was added in a dropwise manner. The reaction was complete after 20 minutes so HCl 1N was then added to the reaction mixture and extractions were done using dichloromethane. The combined organic layers were dried over $Na_2SO_4$, filtered, and the solvent was removed. The isolated titled compound was used for next step without further purification.

NMR $^1$H (250 MHz) (CDCl$_3$; ppm): 6.76 (3H, m, aromatics), 3.77 (3H, s, OCH$_3$), 3.76 (3H, s, OCH$_3$), 3.75 (2H, m, H$_{1a}$ and H$_{1b}$), 3.19 (1H, m, H$_2$), 1.74 (2H, m, H$_{3a}$ and H$_{3b}$), 1.51 (1H, t, J=6.2 Hz, OH), 0.85 (3H, t, J=7.4 Hz, —CH$_3$ terminal).

Step 3: 5,8-dimethoxy-4-ethyl-isochroman

Under argon atmosphere, the product from step 2 herein, 2.74 g (13.03 mmol) was dissolved in 55 ml of dry ether. Dimethoxy methane 1.65 ml (19.55 mmol) and boron trifluoro etherate 4.9 ml (39.09 mmol) were then added to this solution. The obtained reaction mixture was left stirring overnight. The reaction mixture was quenched using aqueous NaHCO$_3$ and extractions were done using ether. The combined organic extracts were dried over Na$_2$SO$_4$, filtered, and the solvent was removed. The residue was purified by flash chromatography using hexanes-ethyl acetate (80:20) and (70:30) as eluent. The isolated titled product was a white solid (1.56 g; 54%).

NMR $^1$H (250 MHz) (CDCl$_3$; ppm): 6.64 (2H, m, aromatics), 4.85 (1H, d, J=16.1 Hz, H$_{1a}$), 4.55 (1H, d, J=16.0 Hz, H$_{1b}$), 4.09 (1H, d, J=11.3 Hz, H$_{3a}$), 3.79 (3H, s, OCH$_3$), 3.75 (3H, s, OCH$_3$), 3.58 (1H, dd, J$_1$=2.7 Hz, J$_2$=11.4 Hz, H$_{3b}$), 2.62 (1H, m, H$_4$), 1.67 (2H, m, —CH$_2$—ethyl), 1.01 (3H, t, J=7.5 Hz, —CH$_3$).

Step 4a: (1'S, 1R, 4R)-5,8-dimethoxy-4-ethyl-1-(2',3',6'-trideoxy-3'-trifluoroacetamido-4'-O-p-nitrobenzoyl-L-lyxo-hexo-pyranose)-isochroman The titled compound was obtained by applying the procedure from step 3, example 34, to the isochroman from step 3 herein.

NMR $^1$H (250 MHz) (C$_6$D$_6$; ppm): 7.81 (2H, d, J=8.8 Hz, aromatics), 7.65 (2H, d, J=8.9 Hz, aromatics), 6.48 (2H, dd, J$_1$=9.0 Hz, J$_2$=18.1 Hz, aromatics), 6.35 (1H, s, H$_1$), 6.26 (1H, d, J=6.9 Hz, NH), 5.81 (1H, s, H$_{1'}$), 5.52 (1H, s, H$_{3'}$), 4.75 (1H, q, H$_{5'}$), 4.58 (1H, m, H$_{4'}$), 4.24 (1H, dd, J$_1$=2.9 Hz, J$_2$=11.4 Hz, H$_{3a}$), 3.88 (1H, d, J=11, 0.4 Hz, H$_{3b}$), 3.38 (3H, s, OCH$_3$), 3.37 (3H, s, OCH$_3$), 2.84 (1H, m, H$_4$), 1.89 (2H, m, —CH$_2$—sugar), 1.85–1.55 (2H, m, —CH$_2$—side chain), 1.18 (3H, d, J=6.6 Hz, —CH$_3$ sugar), 1.05 (3H, t, J=7.3 Hz, —CH$_3$ side chain).

(1'S, 1S, 4S)-5,8-dimethoxy-4-ethyl-1-(2',3',6'-trideoxy-3'-trifluoroacetamido-4'-O-p-nitrobenzoyl-L-lyxohexopyranose)-isochroman was also obtained.

NMR $^1$H (250 MHz) (C$_6$D$_6$; ppm): 7.81 (2H, d, J=8.7 Hz, aromatics), 7.61 (2H, d, J=8.7 Hz, aromatics), 6.54 (2H, m, aromatics), 6.55 (1H, NH), 6.09 (1H, s, H$_1$), 5.69 (1H, s, H$_{1'}$), 5.45 (1H, s, H$_{3'}$), 4.72 (1H, m, H$_{4'}$), 4.32 (1H, m, H$_{5'}$), 4.26 (1H, dd, J$_1$=2.9 Hz, J$_2$=11.4 Hz, H$_{3a}$), 3.89 (1H, d, J=11.2 Hz, H$_{3b}$), 3.45 (3H, s, OCH$_3$), 3.39 (3H, s, OCH$_3$), 2.80 (1H, m, H$_4$), 1.88 (2H, m, —CH$_2$—sugar), 1.82 (2H, m, —CH$_2$—side chain), 1.12 (3H, d, J=6.4 Hz, CH$_3$ sugar), 1.04 (3H, t, J=7.4 Hz, —CH$_3$ side chain).

Step 4b: (1'S, 1R, 4R)-5,8-dioxo-4-ethyl-1-(2',3',6'-trideoxy-3'-trifluoroacetamido-4'-O-p-nitrobenzoyl-L-lyxohexopyranose)-isochroman The (1'S, 1R, 4R) glycoside from step 4 herein was oxidatively demethylated as per procedure described in step 4, example 34. The titled compound had:

NMR $^1$H (250 MHz) (C$_6$D$_6$; ppm): 7.80 (2H, d, J=8.9 Hz, aromatics), 7.62 (2H, d, J=8.8 Hz, aromatics), 6.89 (1H, d, J=6.9 Hz, NH), 6.04 (2H, dd, J$_1$=10.1 Hz, J$_2$=18.3 Hz, quinone ring), 5.87 (1H, s, H$_1$), 5.63 (1H, s, H$_{1'}$), 5.16 (1H, s, H$_{3'}$), 4.80 (1H, q, J=6.5 Hz, H$_{5'}$), 4.56 (1H, m H$_{4'}$), 3.75 (1H, dd, J$_1$=3.0 Hz, J$_2$=11.6 Hz, H$_{3a}$), 3.54 (1H, d, J=11.5 Hz, H$_{3b}$), 2.25 (1H, m, H$_4$), 1.89 (2H, m, —CH$_2$—sugar), 1.47 (2H, m, —CH$_2$—side chain), 1.27 (3H, d, J=6.5 Hz, —CH$_3$ sugar), 0.86 (3H, t, J=7.3 Hz, —CH$_3$ side chain).

Step 5: (1'S, 1R, 4R)-5,10-dioxo-4-ethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c]-pyran The titled compound was obtained in 19% yield following cycloaddition between the quinone from step 5 herein and 1-acetoxybutadiene, as per procedure as described in step 5, example 34.

NMR $^1$H (250 MHz) (C$_6$D$_6$; ppm): 8.02 (2H, m, aromatics), 7.77 (2H, d, J=8.9 Hz, aromatics), 7.63 (2H, d, J=8.9 Hz, aromatics), 6.02 (2H, m, aromatics), 6.53 (1H, d, NH), 6.11 (1H, s, H$_1$), 5.67 (1H, d, H$_{1'}$), 4.97 (1H, s, H$_{3'}$), 4.95 (1H, m, H$_{4'}$), 4.49 (1H, m, H$_{5'}$), 3.83 (1H, dd, H$_{3a}$), 3.60 (1H, d, J=11.4 Hz, H$_{3b}$), 2.50 (1H, m, H$_4$), 1.95 and 1.72 (2H, 2dd, —CH$_2$—side chain), 1.58 (2H, m, —CH$_2$—sugar), 1.31 (3H, d, J=6.4 Hz, —CH$_3$ sugar), 0.92 (3H, t, J=7.3 Hz, —CH$_3$ side chain).

Step 6: (1'S, 1R, 4R)-5,10-dioxo-4-ethyl-1-(2',3',6'-trideoxy-3'-trifluoroacetamido-L-lyxohexopyranose)-3,4,5,10-tetrahydro-1H-naphtho-[2,3-c] pyran (BCH-2091)

The titled compound was obtained via deprotection of the tricyclic glycoside from step 6 herein as per procedure from step 6, example 34.

NMR $^1$H (250 MHz) (CDCl$_3$; ppm): 8.10 (2H, m, aromatics), 7.75 (2H, m, aromatics), 6.72 (1H, d, NH), 5.91 (1H, s, H$_1$), 5.41 (1H, s, H1,), 4.59 (1H, q, J=6.6 Hz, H$_{5'}$), 4.46 (1H, m, H$_{4'}$), 4.32 (1H, m, H$_{3'}$), 4.03 (1H, dd, J$_1$=3.0 Hz, J$_2$=11.6 Hz, H$_{3a}$), 3.85 (1H, d, J=11.6 Hz, H$_{3b}$), 3.64 (1H, m, OH), 2.66 (1H, m, H$_4$), 1.99 (1H, d, J=8.3 Hz, —CH$_2$—side chain), 1.86 (2H, m, H$_{2'a}$ and —CH$_2$—side chain), 1.65 (1H, m, H$_{2'b}$), 1.41 (3H, d, J=6.5 Hz, —CH$_3$ sugar), 1.06 (3H, t, J=7.3 Hz, —CH$_3$ side chain).

IR (film) (cm$^{-1}$): 3422 (OH), 2932 (CH aliphatic), 1710 (C=O), 1668 (C=C), 1299 and 1165 (C—O).

EXAMPLE 36

Preparation of (1'S,1R,3S)-5,10-dioxo-3-phenyloxymethyl-1-(2',3',6'-trideoxy-3'-trifluoroacetamido-L-lyxohexopyranose)-3,4,5,10-tetrahydro-1H-naphtho-[2,3-c] pyran

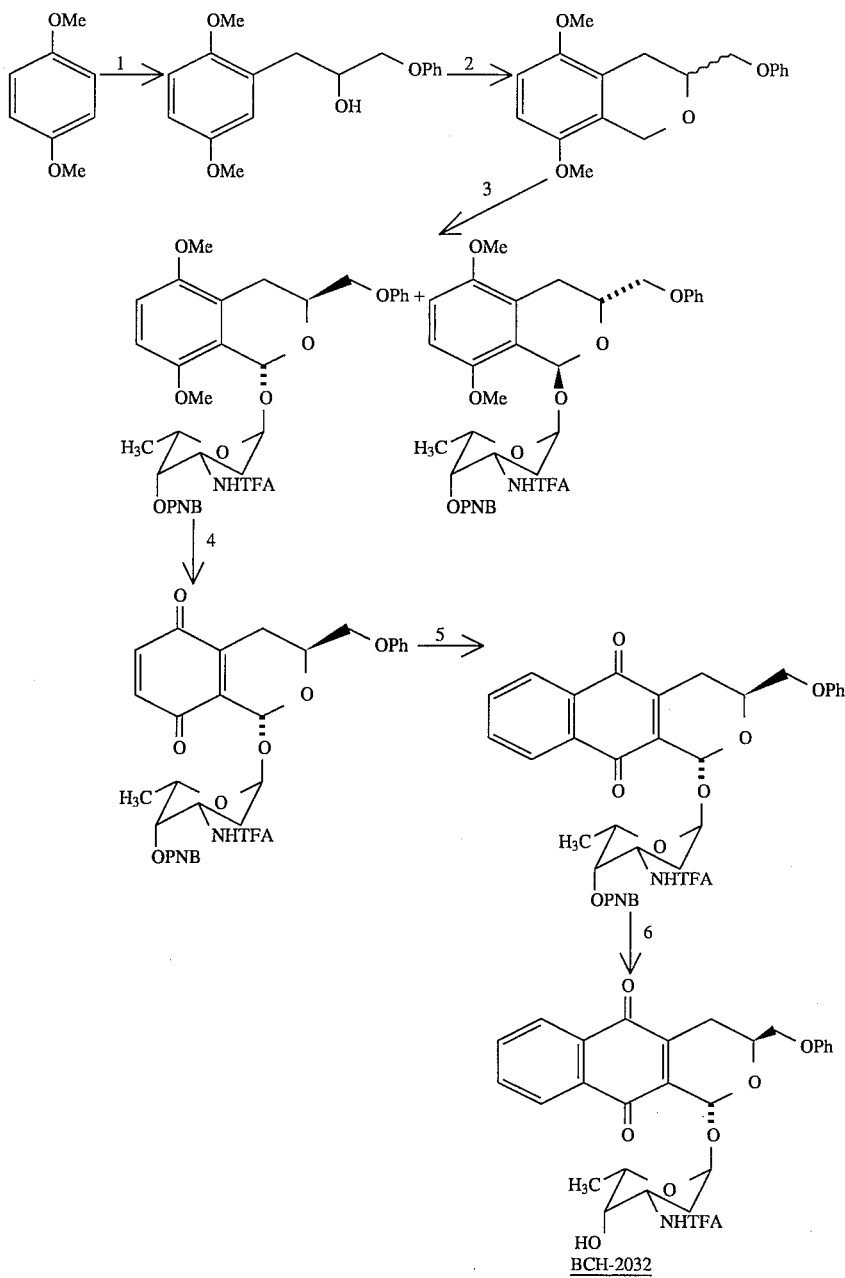

Step 1: α-phenoxymethyl-2,5-dimethoxy-phenetyl alcohol

To a solution of 1,4-dimethoxybenzene (2.0 g; 14.5 mmol) in tetrahydrofuran at 0° C. was added n-butyl-lithium (2.5M in hexane; 5.8 ml; 14.5 mmol). The mixture was warmed to room temperature and stirred for 4 hours. It was then cooled to −78° C. and 1,2 epoxy-3-phenoxy-propane (1.95 g; 13 mmol) was added followed by boron trifluoride etherate (1.85 g; 13 mmol). The resulting mixture was stirred at −78° C. for 2 hours. It was quenched with saturated NaHCO$_3$ solution and extracted with dichloromethane. The combined organic layers were washed with bicarbonate, brine and were dried over MgSO$_4$. The crude residue was purified by column chromatography on silica gel using 25% ethyl acetate in hexane to yield the title product (2.4 g; 64%).

$^1$H NMR (250 MHz, CDCl$_3$) δ: 2.75 (1H, d, J=4 Hz, —OH), 2.85–3.10 (2H, m, Ar—CH$_2$—), 3.71 (3H, s, OCH$_3$), 3.79 (3H, s, OCH$_3$), 3.95 (2H, m, CH$_2$—O), 4.29 (1H, m, —CH—O), 6.70–7.00 (6H, m, Ar—H), 7.28 (2H, m, Ar—H).

Step 2: 5,8-dimethoxy-3-phenoxymethyl-isochroman

To a solution of α-phenoxymethyl-2,5-dimethoxyphenetyl alcohol (2.1 g; 7.24 mmol) in ether (40 ml) at room temperature was added dimethoxymethane (966 μl; 10.8 mmol) and then boron trifluoride etherate (2.68 ml; 21.6 mmol). The rest of the procedure is identical to the second part, step 1, example 29, to yield the title product (715 33%).

$^1$H NMR (250 MHz, CDCl$_3$) δ: 2.65 (1H, dd, J=11 and 17 Hz, H-4 ax), 2.89 (1H, dd, J=2 and 17 Hz, H-4 eq), 3.79 (3H, s, —OCH$_3$), 3.82 (3H, s, —OCH$_3$), 4.00–4.30 (3H, m, —CH$_2$-OPh and H-3), 4.73 (1H, d, J=16 Hz, H-1), 5.07 (1H, d, J=16 Hz, H-1), 6.68 (2H, AB doublets, Ar—H), 7.01 (3H, m, Ar—H), 7.33 (2H, m, Ar—H).

Step 3: (1'S, 1R, 3S)-5,8-dimethoxy-3-phenyloxymethyl-1-(2',3',6'-trideoxy-3'-trifluoroacetamido-4'-O-p-nitrobenzoyl-L-lyxohexopyranose)-isochroman The isochroman from step 3 herein was glycosidated in 57% yield as per procedure described in step 3, example 34.

NMR $^1$H (250 MHz) (CDCl$_3$; ppm): 8.31 (4H, m, aromatics), 7.31 (2H, m, aromatics), 6.97 (3H, m, aromatics), 6.76 (2H, m, aromatics), 6.22 (1H, d, NH), 6.02 (1H, s, H$_1$), 5.63 (1H, s, H$_{1'}$), 5.42 (1H, s, H$_3$), 4.67 (1H, m, H$_{4'}$), 4.66 (1H, m, H$_{5'}$), 4.57 (1H, m, H$_3$), 4.18 (2H, m, —CH$_2$—side chain), 3.82 (3H, s, OCH$_3$), 3.81 (3H, s, OCH$_3$), 2.90 (1H, dd, H$_{4a}$), 2.56 (1H, dd, H$_{4b}$), 2.00–2.18 (2H, m, —CH$_2$—sugar), 1.16 (3H, d, J=6.5 Hz, —CH$_3$ sugar).

Step 4: (1'S, 1R, 3S)-5,8-dioxo-3-phenyloxymethyl-1-(2',3', 6'-trideoxy-3'-trifluoroacetamido-4'-O-p-nitrobenzoyl-L-lyxohexopyranose)-isochroman The (1'S, 1R, 3S) glycoside from step 3 herein was oxidatively demethylated as per procedure described in step 4, example 34.

NMR $^1$H (250 MHz) (C$_6$D$_6$;ppm): 7.73 (4H, dd, aromatics), 7.17 (2H, m, aromatics), 6.90 (3H, d, aromatics), 6.71 (1H, d, NH), 6.08 (2H, d, quinone ring), 5.80 (1H, :9, H$_1$), 5.76 (1H, s, H$_{1'}$), 5.50 (1H, s, H$_3$), 4.70 (1H, m, H$_{4'}$), 4.62 (1H, m, H$_{5'}$), 4.22 (1H, m, H$_3$), 3.85 (1H, m, CH$_2$side chain), 3.66 (1H, dd, CH$_2$ side chain), 2.27 (1H, dd, H$_{4a}$), 1.94 (1H, dd, H$_{4b}$), 1.85 (2H, m, —CH$_2$ side chain), 1.34 (2H, m, —CH$_2$—sugar), 1.18 (3H, d, —CH$_3$ sugar).

Step 5: (1'S, 1R, 3S)-5,10-dioxo-3-phenyloxymethyl-1-(2', 3',6'-trideoxy-3'-trifluoroacetamido-4'-O-p-nitrobenzoyl-L-lyxohexopyranose)-3,4,5,10-tetrahydro-1H-naphtho-[2,3-c]pyran Cycloaddition between 1-acetoxybutadiene and the quinone from step 4 herein as per procedure described in step 5, example 34, afforded the titled compound, yield 148%.

NMR $^1$H (250 MHz) (CDCl$_3$; ppm): 8.30 (3H, m, aromatics), 8.11 (2H, m, aromatics), 7.77 (2H, m, aromatics), 7.30 (4H, m, aromatics), 6.96 (2H, m, aromatics), 6.40 (1H, d, J=7.5 Hz, NH), 6.01 (1H, s, H$_1$), 5.75 (1H, s, H$_{1'}$), 5.43 (1H, s, H$_3$), 4.63 (1H, m, H$_{4'}$), 4.61 (1H, m, H$_3$), 4.60 (1H, m, H$_{5'}$), 4.20 (2H, m, —CH$_2$—side chain), 2.89 (1H, dd, J$_1$=3.4 Hz, J$_2$=19.3 Hz, H$_{4a}$), 2.57 (1H, dd, J$_1$=11.5 Hz, J$_2$=19.4 Hz, H$_{4b}$), 2.07 (2H, dd, —CH$_2$—sugar), 1.19 (3H, d, J=6.5 Hz, —CH$_3$ sugar).

Step 6: (1'S, 1R, 3S)-5,10-dioxo-3-phenyloxymethyl -1-(2', 3',6'-trideoxy-3'-trifluoroacetamido-L-lyxohexopyranose)-3,4,5,10-tetrahydro-1H-naphtho-[2,3-c] pyran (BCH-2032)

The glycoside from step 5 herein was deprotected as per procedure described in step 6, example 34, to afford the titled compound in 81% yield.

NMR $^1$H (250 MHz) CDCl$_3$; ppm): 8.11 (2H, m, aromatics), 7.78 (2H, m, aromatics), 7.33 (2H, m, aromatics), 6.98 (1H, m, aromatic), 6.91 (2H, d, J=8.3 Hz, aromatics), 6.69 (1H, d, NH), 5.95 (1H, s, H1), 5.55 (1H, d, H$_{1'}$), 4.61 (1H, m, H$_{4'}$), 4.41 (1H, m, H$_{5'}$), 4.38 (1H, m, H$_3$), 4.16 (2H, m, —CH$_2$—side chain), 3.64 (1H, m, OH), 2.89 (1H, dd, H$_{4a}$), 2.57 (1H, dd, H$_{4b}$), 1.93 (2H, m, —CH$_2$—sugar), 1.24 (3H, d, J=6.5 Hz, —CH$_3$ sugar).

IR (film) (cm$^{-1}$): 3425 (OH, NH), 2929 (Ch aliphatic), 1716 (C=O), 1668 (C=C), 1596 (C—N), 1297 and 1160 (C—O).

EXAMPLE 37

Preparation of naphtho-[2,3-c] pyran derivatives with an allyl side chain

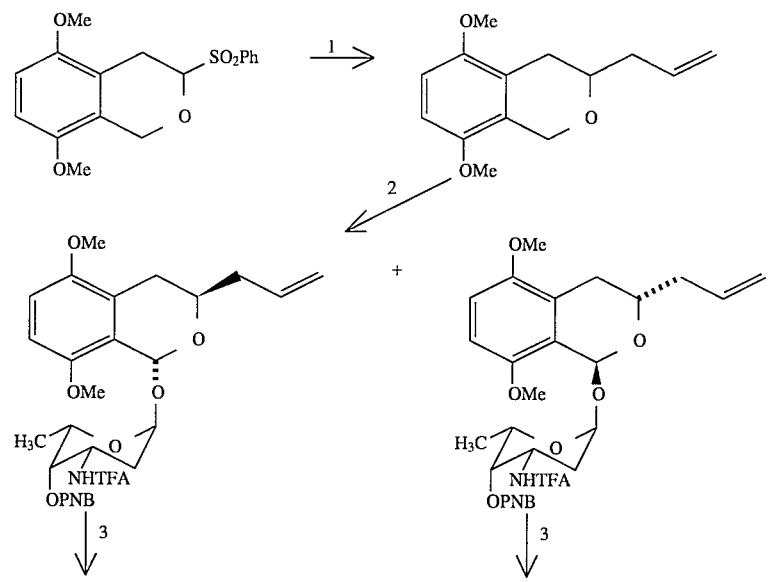

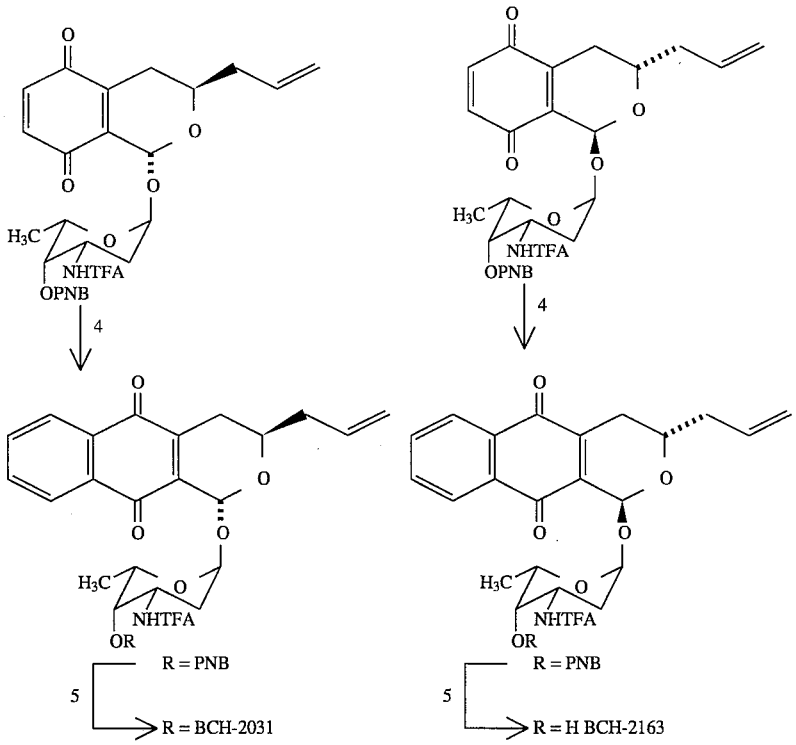

Step 1: 5,8-dimethoxy-3-(2-propenyl)-isochroman

To a stirred solution of pyranosulfone (670 mg, 2.0 mmol) in CH$_2$Cl$_2$ (20 ml) at −78° C. were added allyltrimethylsilane (636 μl, 4.0 mmol) and AlCl$_3$ (533 mg, 4.0 mmol). Temperature was then raised to −35° C. few minutes, then HCl (0.1N, 10 ml) was added. The reaction mixture was worked up with CH$_2$Cl$_2$ and water. The organic layer was washed with brine and dried over MgSO$_4$. The solvent was evaporated to give the allyl isochroman (450 mg, 96%).

$^1$H NMR (250 MHz, CDCl$_3$) δ: 6.63 (2d, J=8.9 Hz, 2H, Ar—H), 5.96 (m, 1H, —CH═C), 5.17 (d, J=17 Hz, 1H, —CH═CH$_2$), 5.10 (d, J=9.9 Hz, 1H, —CH═CH$_2$), 4.93 (d, J=16.3 Hz, 1H, H-1), 4.58 (d, J=16.0 Hz, 1H, H-1), 3.78 and 3.75 (2s, 6H, 2×OCH$_3$), 3.65 (m, 1H, H-3), 2.75 (broad d, J=17.0 Hz, 1H, H-$_4$), 2.45 (m, 3H, H-4, —CH$_2$—CH═C).

Step 2: (1'S,1S,3S) and (1'S,1-R,3-R)-1-(2',3',6',-trideoxy-3'-trifluoroacetamido-4'-O-paranitrobenzoyl-L-lyxohexopyranose)-5,8-dimethoxy-3-(2-propenyl)-isochroman To a mixture of 5,8-dimethoxy-3-(2-propenyl)-isochroman (400 mg, 1.72 mmol), 2',3',6'-trideoxy-3-trifluoroacetamido-4-O-paranitrobenzoyl-1-α,β-hydroxy-lyxohexopyranose 2 (1.2 eq., 810 mg, 2.06 mmol) and MS4 Å (500 mg) in CH$_2$Cl$_2$ (17 ml) at room temperature was added DDQ (1.5 aq., 586 mg, 2.58 mmol). The reaction mixture was stirred for 3 hours and 30 minutes, then filtered and the filtrate was washed by extraction with NaHCO$_3$ sat. solution. Evaporation of the solvent and purifying by FC (CH$_2$Cl$_2$:Hex:EtOAc 8:12:1) gave 427 mg of the titled product (50%) and 531 mg of its diastereoisomer (50%). The (1'S,1S,3S) diastereomer was prepared using the same procedure.

$^1$H NMR (250 MHz, acetone-d$_6$) δ (ppm): 8.65 (bd, 1H,NH), 8.4 (d,8.9Hz,2H, PNB-H), 8.34 (d,8.9Hz,2H, PNB-H), 6.86 (d,8.8Hz,1H,Ar—H), 6.8 (d,8.8Hz,1H,Ar—H), 6.0 (m, 1H, C═CH—C), 5.88 (s,1H,H-1), 5.56 (bs, 1H,H-1'), 5.47 (bs,1H,H-4'), 5.14 (bm,2H,C═CH$_2$), 4.6 (m,2H,H-3', H-5'), 4.3 (m, 1H,H-3), 3.8 (s,3H,ACOCH$_3$), 3.78 (s,3H, Ar—OCH$_3$), 2.75 (m,1H,H-4), 2.47 (m,2H,C═C—CH$_2$), 2.4 (m, 1H,H-4), 2.3 (m, 1H-2'), 1.9 (m, 1H,H-2'), 1.16 (d,6.4Hz,3H,H-6').

Step 3: (±)-Methyl ketone hydroxy-1-isochroman quinone

To a stirred solution of the methyl ketone hydroxy-1 isochromane (3.000 g, 11.891 mmol) in 180 ml of acetonitrile at 0° C. was added dropwise an aqueous solution of CAN (26.076 g, 47.56 mmol) and NaHCO$_3$ (7.19 g, 85.6 mmol) in water. The reaction mixture was then dropped in a mixture of 200 ml of CH$_2$Cl$_2$ and 200 ml of water and extracted with CH$_2$Cl$_2$ and back extracted with Ethyl Acetate. Combined organic layers were washed with water (3×300 ml) and then dried (Na$_2$SO$_4$). Recristallisation of the residue gave 2.237 g (85% yield) of the pure methyl ketone hydroxy-1 isochromane quinone.

PMR (CDCl$_3$, 300MHz)δ: 2.30 (s, 3H, COCH$_3$), 2.39 (ddd, 1H, J=20.0 Hz, 12.0 Hz and 1.2 Hz, CH$_a$CHCO), 2.88 (dd, 1H, J=19.5 Hz and 3.9 Hz, CH$_e$CHCO), 3.42 (broad m, 1H, OH-1), 4.64 (dd, 1H, J=11.7 Hz and 4 Hz, H-3), 6.03 (broad s, 1H, H-1), 6.78 (2×d, 2H, quinone-H).

Step 4: (1'S,1S,3S) and (1'-S,1-R,3-R)-3-([2',3',6'-trideoxy-3'-trifluoroacetamido-4'-paramitrobenzoyl-L-lyxohexopyranose)-5,10-dioxo-3,4,5,10-tetrahydronaphtho-[2,3-c]-pyran-3-yl)-propene To a solution of (1,-S,1-R,3-R)-1-(2',3',6'-trideoxy-3'-trifluoroacetamido-4'-paranitrobenzoyl-L-lyxohexopyranose)-5,8-dioxo-3-propenyl-1,4,5,8-tetrahydrobenzo-[2,3-c]-pyran (205 mg, 0.34 mmol) in toluene (10 ml) at room temperature was added 1-acetoxy-1,3-butadiene (0.250 ml, 1.72 mmol). The mixture was stirred overnight followed by adding silica gel (4.2 g) and bubbling air. After 2 hours, the solution was filtered and solvent removed form the filtrate. Purifying of the crude by FC (Tol.: EtOAc 15:1) and recrystalization gave 133 mg of the titled product. The (1'S,1S,3S) diastereomer was prepared the same way.

$^1$H NMR (250 MHz, CD$_2$Cl$_2$) δ (ppm): 8.3 (m,4H,PNB-H), 8.1 (m,2H,Ar—H), 7.75 (m,2H,Ar—H), 6.35 (2Dd, 1H,NH), 5.95 (1H,C═CH—C), 5.9 (s,1H,H-1), 5.7 (s,1H, H-1'), 5.43 (bs,1H, H-4'), 5.25 (m,2H,C=CH$_2$), 4.6 (m, 1H,H-3'), 4.43 (q,6.4Hz,1H,H-5'), 4.21 (m, 1H-3), 2.8 (dd, 19.4Hz,3.2Hz,1H,H-4), 2.47 (m,2H,C=C—CH$_2$), 2.33 (dd, 19.4Hz, 11Hz,1H,H-4), 2.07 (m,2H,H-2'), 1.2 (d, 6.4Hz, 3H,H-6').

Step 5: (1'S, 1S, 3S) and (1'S, 1-R, 3 -R)-3-([2',3',6'-trideoxy-3'-trifluoroacetamido-4'-hydroxy-L-lyhohexopyranose]-5,10-dioxo-3,4,5,10-tetrahydronaphtho-[2,3-c]-pyran-3-yl)-propene (BCH-2031)

To a solution of (1'-S, 1-R, 3-R)-3-([2',3',6'-trideoxy-3'-trifluoroacetamido-4'-paranitrobenzoyl-L-lyxohexopyranose)-5,10-dioxo-3,4,5,10-tetrahydronaphtho-[2,3-c]-pyran-3-yl] propene (133 mg, 0.2 mmol) in MeOH (2 ml) at 0° C. was added NaOMe (4.37M in MeOH, 60μl, 0.26 mmol) and stirred for 15 minutes. The reaction was quenched by adding NH$_4$Cl sat. and extracted with CH$_2$Cl$_2$. The organic phase was then dried over MgSO$_4$, evaporated to give 64 mg crude. Purifying by preparative TLC (Tol.: EtOAc 6:1) gave 25 mg (253) of the desired product. The (1'S,1S,3S) diastereomer BCH-2163 was prepared the same way.

$^1$H-NMR (250MHz,CD$_2$Cl$_2$) δ (ppm): 8.05 (m,2H,Ar—H), 7.75 (m,2H,Ar—H), 6.25 (bd, 1H,NH), 5.95 (m, 1H,C=CH), 5.84 (s,1H,H-1), 5.51 (bd, 1H,H-1'), 5.2 (m,2H, C=CH$_2$), 4.25 (m,4H,H-3,3',4',5'), 3.6 (bs, 1H,OH), 2.78 (dd,19.4Hz,3.3Hz,1H,H-4), 2.44 (m,2H,C=C—CH$_2$), 2.3 (dd,19.4Hz,11Hz,1H,H-4), 1.85 (m,2H,H-2'), 1.75 (d,6.6Hz,3H,H-6').

EXAMPLE 38

Preparation of naphtho-[2,3-c] pyran derivatives with a methyl ketone side chain from a bicyclic quinone aglycal

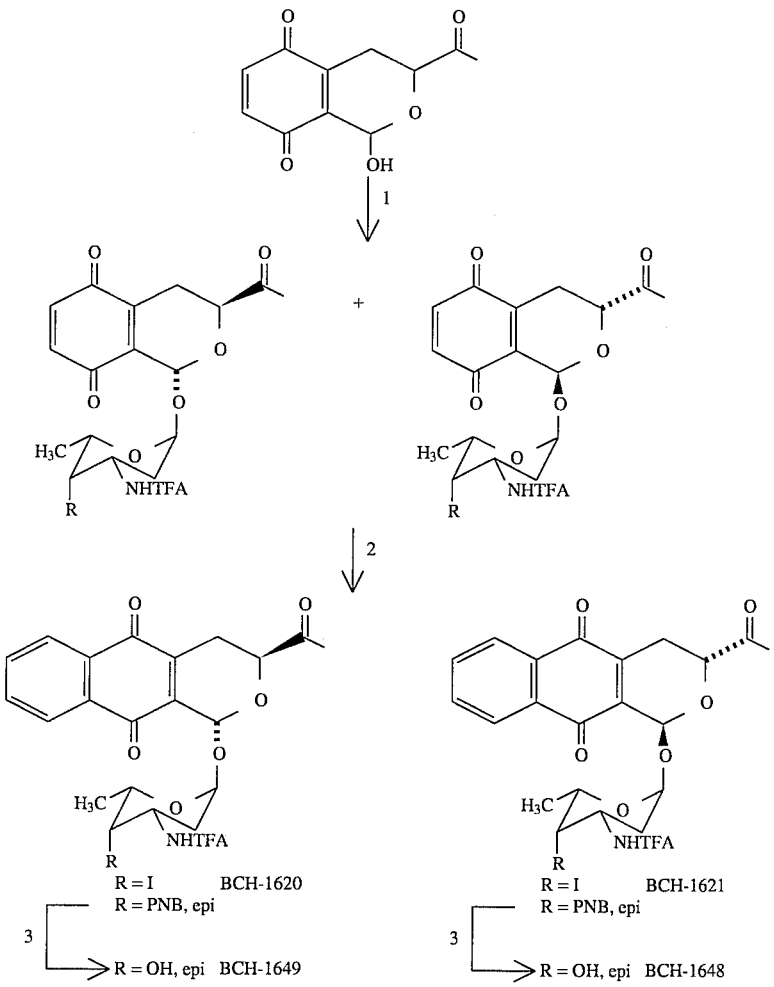

Step 1 and 2: (1'-S, 1-R,3-S)-methyl-(1-[2',3',6'-trideoxy-3'-trifluoroacetamido-4'-iodo-L-lyxohexopyranose]-5,10-dioxo-3,4,5,10-tetrahydronaphtho-[2,3-c]-pyran-3-yl)-ketone (BCH-1620)

To a stirred suspension of molecular sieves 4 Å (1.3 g), 2-(dimethyl-t-butyl-silyloxy)-3-acetamido-4-iodo-2,3,6-trideoxy-α, β-L-lyxohexopyranose (478 mg, 1.02 mmol) and 3-acetyl-5,8-dioxo- 1-hydroxy-1,4,5,8-tetrahydrobenzo-[2,3-c]-pyran (178 mg, 0.8 mmol) in a solution of CH$_2$Cl$_2$/ acetone (15.4 ml, 10:1) at –50° C. was added trimethylsilyl trifluoromethansulfonate (TMS-OTf, 0.222 ml, 1.15 mmol). The reaction mixture was then stirred at –30° C. for 50 minutes, followed by addition of aq. NaHCO$_3$ 5% and warmed up to room temperature. After filtering off solids, the filtrate was extracted with CH$_2$Cl$_2$. The organic phase was then washed with brine and dried over MgSO$_4$. Evaporation of the solvent gave 563 mg of the crude.

From the crude product obtained as described above, 116 mg was utilized in the next step by stirring with 1-acetoxy-1,3-butadiene (98 μl, 0.82 mmol) in toluene (10 ml) for overnight at room temperature and under argon. Silica gel was next added and air was bubbled into the reaction mixture and stirring for 2 hours. The crude product was recovered by filtering and washing of the silica gel with ethyl acetate. Evaporation of the solvent gave 139 mg of the crude product. Purifying by preparative TLC (hex: OAc 4:1) gave 7.4 mg of the title product and 2.2 mg of its diastereoisomer for a total of 9% yield. The (1'S,1S,3R) diastereomer BCH-1621 was prepared using the same method.

$^1$H NMR (250 MHz, acetone) δ (ppm): 8.43 (bd, 1H,N—H), 8.0 (m,2H,ArH), 7.9 (m,2H,Ar—H), 6.0 (s, 1H, H-1), 5.6 (bd, 5.4Hz,1H,H-1'), 4.89 (bs,1H,H-3'), 4.75 (dd, 11.6Hz,4.0Hz,1H,H-3), 3.75 (m, 1H,H-4'), 3.7 (q,6.1Hz,1H, H-5'), 3.0 (dd,19.6Hz,4Hz,1H,H-4), 2.55 (dd,19.6Hz, 11.6Hz,1H,H-4), 2.3 (s,3H,COCH$_3$), 2.26 (m, 1H,H-2'), 1.8 (m, 1H,H-2'), 1.25 (d,6.1Hz,3H,H-6').

Step 3: (1'-S,1-R,3-S)-3-([2',3',6'-trideoxy-3'-trifluoroacetamido-4'-hydroxy-L-lyhohexopyranose]-5,10-dioxo-3,4,5, 10-tetrahydronaphtho-[2,3-c]-pyran-3-yl)-propene (BCH-1649)

To a solution of (1'-S,1-R,3-S)-3-([2',3',6'-trideoxy-3'-trifluoroacetamido-4'-paranitrobenzoyl-L-lyxohexopyranose]-5,10-dioxo-3,4,5,10-tetrahydronaphtho-[2,3-c]-pyran-3-yl) propene (133 mg, 0.2 mmol) in MeOH (2 ml) at 0° C. was added NaOMe (4.37M in MeOH, 60 μl, 0.26 mmol) and stirred for 15 minutes. The reaction was quenched by adding NH$_4$Cl sat. and extracted with CH$_2$Cl$_2$. The organic phase was then dried over MgSO$_4$, evaporated to give 64 mg crude. Purifying by preparative TLC (tol: EtOAc 6:1) gave 25 mg (25%) of the desired product. The (1'S,1S,3R), BCH-1648, diastereomer was obtained using the same method.

$^1$H NMR (250MHz,CD$_2$Cl$_2$) δ (ppm): 8.05 (m,2H,Ar—H), 7.75 (m,2H,Ar—H), 6.25 (bd, 1H,NH), 5.95 (m, 1H,C=CH), 5.84 (s,1H,H-1), 5.51 (bd, 1H,H-1'), 5.2 (m,2H,C=CH$_2$), 4.25 (m,4H, H-3,3',4',5'), 3.6 (bs, 1H,OH), 2.78 (dd,19.4Hz,3.3Hz,1H,H-4), 2.44 (m,2H,C=C—CH$_2$), 2.3 (dd,19.4Hz,11Hz,1H, H-4), 1.85 (m,2H,H-2'), 1.25 (d,6.6Hz,3H,H-6').

EXAMPLE 39

Preparation of 4a, 10a-epoxy-naphtho-[2,3-c] pyran derivatives ketone (15 mg, 30 μmol) in THF (1 ml) at 0° C. was added H$_2$O$_2$ (30% aq. solution, 5.2 μl, 46 μmol). After 10 minutes, NaOH (0.1N, 0.364 ml) was added and the reaction mixture was stirred at 0° C. for 30 minutes. Workup was carried out by adding brine to the mixture, extracting with CH$_2$Cl$_2$ and drying the organic phase over MgSO$_4$. The crude obtained after evaporation of the solvent was purifying by recrystalization to give 8 mg (50%) of the pure titled product. The (1'S, 1S, 3R, 4aR, 10aR), BCH-2149, diastereomer was obtained using the same method $^1$H NMR (250MHz, CDCl$_3$) δ (ppm): 8.05 and 7.8 (m,4H,ArH), 6.15 (s,1H,H-1), 5.55 (bd, 1H,H-1'), 4.86 (bs, 1H,H-4'), 4.3 (dd,9Hz,3Hz,1H,H-3), 4.05 (q,6.6Hz,1H,H-5'), 3.65 (m, 1H,H-3'), 3.45 (s,3H, SO$_2$CH$_3$), 3.15 (s,3H, OMe), 2.75 (dd,12.3Hz,3Hz,1H,H-4), 2.35 (m, 1H-4), 2.3 (s,3H,COCH$_3$), 1.9–2.2 (m,2H,H-2'), 1.25 (d,6.6Hz,3H,H-6').

EXAMPLE 40

Monoaminosugar substituted naphthoquinone derivative

Step 1: (1'-S,1-R,3-S,4a-S,10a-S)-methyl-(1-[2',3',4',6'-tetradeoxy-3'-methoxy-4'-O-methanesulfonyl-L-lyxohexopyranose)-4a,10a-epoxy-5,10-dioxo-3,4,5,10-tetrahydronaphtho-[2,3-c] pyran-3-yl) ketone (BCH-2141)

To a solution of (1'-S,1-R,3-S)-methyl-(1-[2',3',4',6'-tetradeoxy-3'-methoxy-4'-O-methansulfonyl-L-lyxohexopyranose)-5,10-dioxo-3,4-dihydronaphtho-[2,3-c] pyran-3-yl)

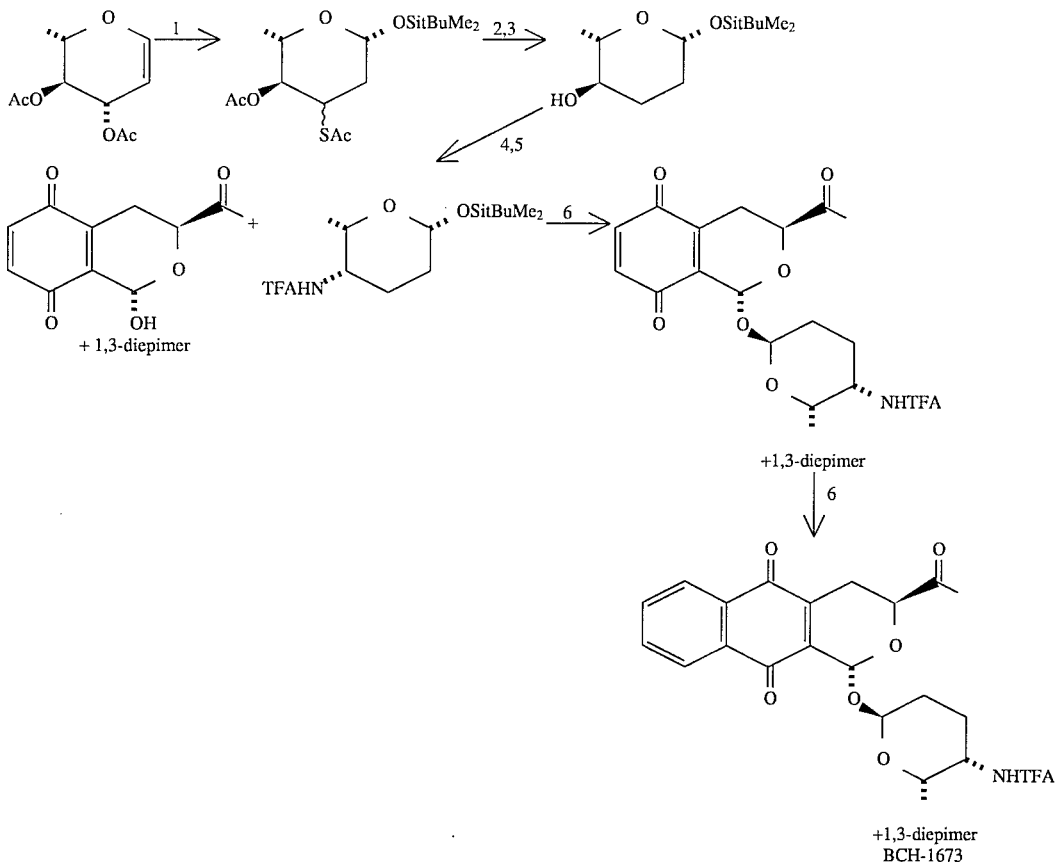

Step 1: (2R,4R,5S,6S) and (2R,4S,SS,6S)-2-tert-butyldimethylsilyloxy-4-thioacetoxy-5-acetoxy-6-methyl-tetrahydropyran A solution of rhamnal diacetate (0.514 g, 2.4 mmols) in H$_2$O (24 ml) is heated at 80° C. for 30 minutes. The solution is then cooled down to 0° C. and CH$_3$COSH (0.51 ml, 3 eq.) is then added. The cloudy solution is stirred at room temperature for 2 hours after which NaHCO$_3$ (1.2 g, 6 eq.) is added to neutralize the excess CH$_3$COSH. The water is evaporated and the residue is dissolved in CH$_2$Cl$_2$ and dried over MgSO$_4$. The solids are filtered and the solvent evaporated. A solution of the oil obtained after evaporation in CH$_2$Cl$_2$ (24 ml) is treated with imidazole (0.33 g, 2 eq.) and t-BuMe$_2$SiCl (0.43 g, 1.2 eq.). The solution is stirred at room temperature, under argon, for 18 hours. It is poured in sat. aq. NaHCO$_3$ and the phases are separated. The aqueous layer is extracted with CH$_2$Cl$_2$ (2×) and the combined organic extracts are dried over MgSO$_4$. The solids are filtered and the solvents evaporated. The oil obtained is purified by flash chromatography (silica gel, 9:1 hexanes/EtOAc) to give a 1:1 mixture of titled isomers: 0.50 g (60%) as a clear oil.

$^1$H NMR (CDCl$_3$): δ4.90+4.85 (2dd, 1H, H-1), 4.73+4.62 (2dd, 1H, H-4), 4.30+3.75 (q+m, 1H, H-5), 3.71+3.55 (2ddd, 1H, H-3), 2.36+2.30 (2s, 3H, SAc), 2.19 (m, 1H, H-2), 2.03+1.99 (2s, 3H, OAc), 1.77 (m, 1H, H-2), 1.22+1.18 (2d, 3H, H-6), 0.88 (s, 9H, t-Bu), 0.09+0.10 (2s, 6H, SiMe$_2$).

Step 2: (2R, 5R, 6S)-2-tert-butyldimethylsilyloxy-5-acetoxy-6-methyl-tetrahydropyran A solution of the thio-sugar from step 1 herein (51 mg, 0.14 mmol) in ethanol (2 ml) was treated with an excess of Raney-Ni. The suspension was vigorously stirred for 30 minutes and was then filtered through Celite. The ethanol was evaporated to give 36 mg (89%) of the titled compound as a clear oil.

$^1$H NMR (CDCl$_3$): δ4.74 (dd, 1H, J=2.0, 8.6, H-1), 4.42 (ddd, 1H, J=4.7, 10.5, 10.5, H-4), 3.98 (dq, 1H, J=6.16, 9.23, H-5) 2.10 (m, 1H, H-2 or H-3), 2.02 (s, 3H, OAc), 1.86–1.35 (m, 3H, H-2 and H-3), 1.17 (d, 3H, J=6.16, H-6), 0.88 (s, 9H, t-Bu), 0.10 (s, 3H, SiMe), 0.08 (s, 3H, SiMe).

Step 3: (2R, 5R, 6S)-2-tert-butyldimethylsilyloxy-5-hydroxy-6-methyl-tetrahydropyran To a solution of the acetate from step 2 herein (36 mg, 0.13 mmol) in dry MeOH (1.3 ml), at room temperature, was added 1N NaOH (0.14 ml, 1.1 eq.) and the solution was stirred for 45 minutes. It was then poured in H$_2$O and the aqueous phase was extracted 3× with CH$_2$Cl$_2$. The combined organic extracts were dried over MgSO$_4$, the solids were filtered and the solvent evaporated to give 30 mg (96%) of the pure titled alcohol.

$^1$H NMR (CDCl$_3$): δ4.72 (dd, 1H, J=1.9, 8.7, H-1), 3.28–3.24 (m, 2H, H-4 and H-5), 2.04–1.41 (m, 4H, H-2 and H-3), 1.27 (d, 3H, J=5.5, H-6), 0.88 (s, 9H, t-Bu), 0.10 (s, 3H, SiMe), 0.09 (s, 3H, SiMe).

Step 4: (2R, 5 S, 6S)-2-tert-butyldimethylsilyloxy-5-azido-6-methyl-tetrahydropyran To a solution of the alcohol from step 3 herein (62 mg, 0.25 mmol) in dry THF (2.5 ml), at room temperature, under argon, were added successively Ph$_3$P (66 mg, 1 eq.), DEAD (40 μl, 1 eq.) and (PhO)$_2$PON$_3$ (54 μl, 1 eq.) and the solution was stirred for 18 hours. The THF was evaporated and the crude oil was purified by flash chromatography (silica gel, 95:5 hexanes/EtOAc) to give 38 mg (56%) of the titled azide as a clear oil.

$^1$H NMR (CDCl$_3$): δ4.71 (dd, 1H, J=3.0, 7.9, H-1), 3.64 (dq, 1H, J=1.7, 6.3, H-5), 3.33 (m, 1H, H-4), 2.15–1.60 (m,

4H, H-2 and H-3), 1.26 (d, 3H, J=6.3, H-6), 0.89 (s, 9H, tBu), 0.11 (s, 3H, SiMe), 0.09 (s, 3H, SiMe).

Step 5: (2R, 5S, 6S)-2-tert-butyldimethylsilyloxy-5-trifluoroacetamido-6-methyl-tetrahydropyran To a solution of the azide from step 4 herein (0.20 g, 0.72 mmol) in dry EtOAc (7.2 ml) at room temperature, was added Pd/C 10% (0.10 g, 50% wt.) and the black suspension was placed under a H₂ atmosphere for 3 hours. The catalyst was then filtered through Celite and the solvent was evaporated to dryness. The crude amine (0.18 g, 0.72 mmol) was dissolved in dry CH₂Cl₂ (7.2 ml) and Et₃N (0.20 ml, 2 eq.) was added. The solution was cooled to 0° C. and TFA₂O (0.11 ml, 1.1 eq.) was added slowly. The solution was stirred at 0° C. for 5 hours and was then poured in sat. aq. NaHCO₃. The phases were separated and the aqueous layer was extracted with CH₂Cl₂ (2×). The combined organic extracts were dried over MgSO₄, the solids filtered and the solvent evaporated to give 0.17 g (71%) of the crude titled trifluoroacetamide that was used as such.

¹H NMR (CDCl₃): δ6.70 (bs, 1H, NH), 4.75 (dd, 1H, H-1), 3.92 (m, 1H, H-4), 3.73 (dq, 1H, H-5), 2.06–1.45 (m, 4H, H-2 and H-3), 1.19 (d, 3H, H-6), 0.88 (s, 9H, t-Bu), 0.11 (s, 3H, SiMe), 0.09 (s, 3H, SiMe).

Step 6: (1S,3R,1'S,5'S,6'S) and (1R,3S,1'S,5'S,6'S)-methyl-(1-[4'trifluoroacetamido-5'-methyltetrahydropyranyl]-5,10-dioxo-3,4,5,10-tetrahydronaphthaleno-[2,3-c] pyran-3-yl) ketone (BCH-1673)

The titled compounds were obtained in 30% yield by following the procedure described in step 4, example 12, on the precursor of step 5 herein. The titled compounds were purified via flash chromatography (silica gel, 3:1 hexanes/EtOAc). The mixture of isomers was not separable by chromatography.

¹H NMR (CDCl₃): δ8.14–8.07 (m, 2H, ArH), 7.79–7.73 (m, 2H, ArH), 6.17+5.99 (2s, 1H, H-1), 5.50+5.39 (2bs, 1H, H-1'), 4.68+4.24 (2q, 1H, J=6.5, H-5'), 4.56+4.49 (2dd, 1H, J=4.2, 11.8, H-3), 4.05 (m, 1H, H-4'), 3.08+3.07 (2dd, 1H, J=4.2, 19.9, H-4), 2.57 (dd, 1H, J=11.8, 19.9, H-4), 2.34+2.33 (2s, 3H, COCH₃), 2.00–1.53 (m, 4H, H-2' and H-3'), 1.31+1.13 (2d, 3H, J=6.5, H-6').

EXAMPLE 41

(1'S, 1S, 3R)-3-(oximoethyl)-5,10-dioxo-1(2,3,6-trideoxy-3-trifluoroacetamido-L-lyxohexopyranose)-3,4,5,10-tetrahydro-1H-naphtho[2,3-c] pyran (BCH-2101) and 1,3-diepimer (BCH-2115)

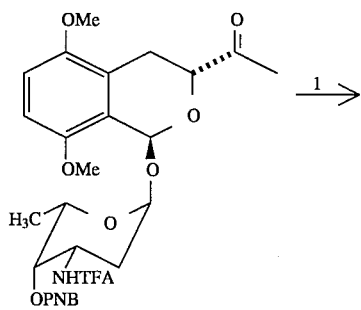

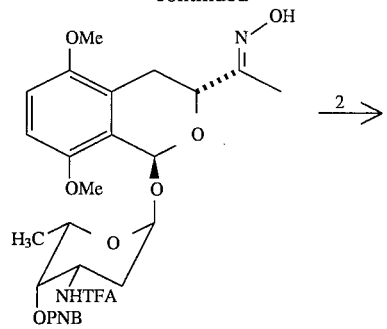

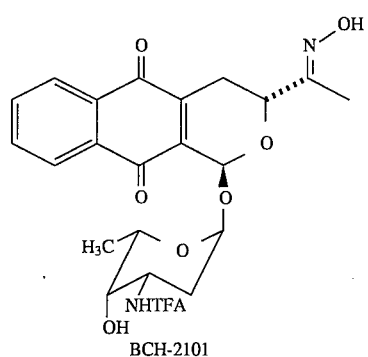

BCH-2101

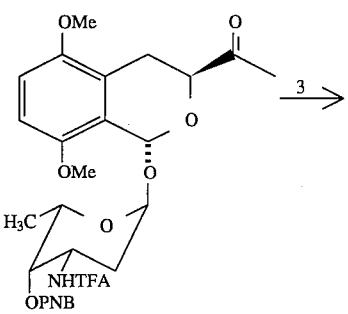

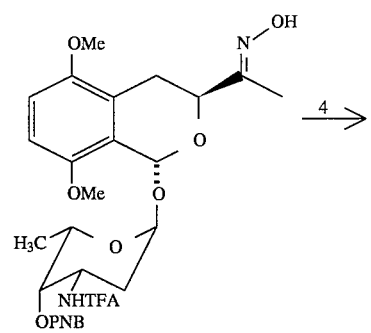

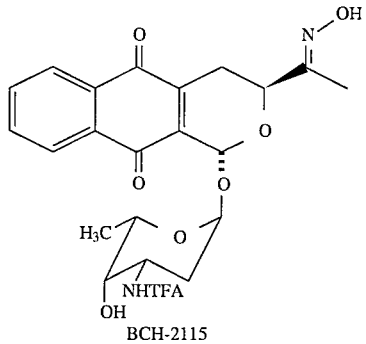

BCH-2115

Step 1: (1S,3R)-3 (oximoethyl)-1 (2,3,6-trideoxy-3-trifluoroacetamido-4-p-nitrobenzoyl-L-lyxohexopyranose)-5,8-dimethoxy-isochroman To a solution of hydroxylamine-hydrochloride (60 mg; 0.86 mmol) in a mixture of ethanol (4 ml) and water (0.4 ml) was added sodium hydroxide (33 mg) in ethanol (2 ml). The mixture was stirred at room temperature for 0.5 hour. The solution was filtered. The filtrate was added to 3-acetyl-isochroman glycoside from step 1, example 5, (92 mg; 0.147 mmole). The reaction was complete in 10 minutes. The mixture was evaporated down to dryness, dissolved in small volume of water (5 ml), extracted with $CH_2Cl_2$ (3×50 ml), washed with sat. NaCl, dried and evaporated. The crude product was passed through a small column of silica gel prewashed with 0.2% triethylamine in hexane (eluent: 15%, 20% and 25% EtOAc in hexane) yielding pure oxime (63 mg; 67%).

NMR (acetone-$d_6$; δ): 1.26 (3H, d, J=6.8 Hz; —$CH_3$), 1.26 (3H, d, J=8.3 Hz; —$CH_3$), 1.89 (1H, dd, J=4.4, 13.2 Hz; H-2 of the sugar), 1.96 (3H, s, $CH_3$ of the side chain), 2.47 (1H, dt, J=3.6, 13.1 Hz; H-2), 3.81, 3.88 (3H, s each; Ar—$OCH_3$), 4.60–4.66 (1H, m; sugar-H), 4.72 (1H, t, J=7.8 Hz; H-3), 4.83 (1H, q; J=6.5 Hz; H-5 of the sugar), 5.51 (1H, br singlet; H-1 of the sugar), 5.61 (1H, d, J=2.9 Hz; H-4 of the sugar), 6.15 (1H, s; H-1), 6.87, 6.90 (1H, d each; J=8.9 Hz; Ar—H), 8.36, 8.41 (2H, d each; J=8.8 Hz; Ar—H of PNB-group), 8.70 (1H, d, J=8.0 Hz; —NHTFA), 10.02 (1H, s; =NOH).

Step 2: (1'S,1S,3R)-3 (oximoethyl)-5,10-dioxo-1 (2,3,6-trideoxy-3-trifluoroacetamido-L-lyxohexopyranose)-3,4,5,10-tetrahydro-1H-naphtho-[2,3-c] pyran (BCH-2101)

Acetylation was done on the oxime from step 1 herein (33 mg; 0.051 mmole) in $CH_2Cl_2$ (4 ml) using pyridine (0.2 ml), acetic anhydride (0.1 ml) and catalytic amount of DMAP. After stirring at room temperature for 3 hours, the mixture was poured into ice, extracted with $CH_2Cl_2$ (3×50 ml), washed with water (15 ml), dried and evaporated. The crude product was pumped for 16 hours before using in the next step. CAN oxidation was done on the crude acetate (40 mg) using sodium bicarbonate following the general procedure as described in other examples. It resulted in 32 mg of crude quinone. The quinone was reacted with acetoxy butadiene (100 μl) in toluene following the general procedure. On purification through a column of silica gel (30% EtOAc in toluene, 50% EtOAc in toluene and $CH_2Cl_2$:MeOH=9:i as eluents) pure tricyclic glycoside (29 mg) was obtained. Finally, deprotection of acetate and PNB groups was done by using sodium methoxide (catalytic) in methanol (3 ml) at 0° C. After stirring at 0° C. for 14 minutes, the mixture was neutralized with dil. HCl to pH~7, diluted with water (5 ml), extracted with $CH_2Cl_2$ (3×30 ml), washed with water (10 ml), dried and evaporated. The crude product was purified by column chromatography over a small column of silica gel (1% methanol in $CH_2Cl_2$ as eluent) and preparative TLC ($CH_2Cl_2$:MeOH=9:1) yielding pure titled oxime (3.7 mg; 14% in 4 steps), m.p.=125°–27° C.

NMR (acetone-$d_6$) δ: 1.35 (3H,d,J=6.6Hz; $CH_3$ of the sugar), 1.75 (1H,dd,J=4.6,13.0Hz;H-2 of the sugar), 1.95 (3H, s,$CH_3$ of the side-chain), 3.71 (1H, br.signal; H-4 of the sugar), 4.27 (2H,m;sugar-H), 4.57 (1H,q,J=6.6Hz;H-5 of the sugar), 4.70 (1H, t,J=7.5Hz;H-3), 5.44 (1H,d,J=3.3Hz;H-1 of the sugar), 6.07 (1H, S;H-1), 7.87–7.90 (2H,m;Ar—H), 8.08–8.12 (2H,m;Ar—H), 10.15 (1H,bit br. singlet;=NOH).

Step 3: (1R,3S)-3-(oximoethyl)-1 (2,3,6-trideoxy-3-trifluoroacetamido-4-p-nitrobenzoyl-L-lyxohexopyranose)-5,8-dimethoxy-isochroman Oxime was prepared from 3-acetyl isochroman glycoside (60 mg; 0.096 mmol) using hydroxylamine hydrochloride (39 mg; 0.56 mmole) in EtOH (2.6 ml) and water (0.26 ml), and sodium hydroxide (21.5 mg) in EtOH (1.3 ml) following the procedure described in step 1 herein. After chromatography over silica gel prewashed with triethylamine titled oxime (in diastereomeric mixture of 5:1 ratio) was obtained in 81% yield (50 mg).

NMR (acetone-$d_6$δ): 1.10 (3H, d, J=6.6 Hz; $CH_3$ of sugar), 1.98 (3H, s; methyl of the side-chain), 2.39 (1H, dt, J=3.6, 12.9 Hz; H-4), 3.81 (6H, s; Ar—$OCH_3$), 4.63–4.73 (1H, m; H-3 of sugar), 5.45 (1H, br signal; H-1 of sugar; same of the other diastereomer overlapped), 5.56 (1H, br signal; H-4 of the sugar; same of the other diastereomer overlapped), 5.95 (1H, s, H-1), 6.81–6.95 (m; Ar—H), 8.30–8.43 (m; A-H of PNB group), 8.66 (1H, br d, J=5.9 Hz; NHTFA), 10.05 (1H, s; =N—OH), (There were few other signals which were due to the other diastereomer and to a small impurity which were not detailed.).

Step 4: (1'S, 1R, 3S)-3 (oximoethyl)-5,10-dioxo-1 (2,3,6-trideoxy-3-trifluoroacetamido-L-lyxohexopyranose)-3,4,5,10-tetrahydro-1H-naphtho-(2,3-c)-pyran (BCH-2115)

Acetylation of the oxime (50 mg; 0.078 mmole) was done following the procedure described in step 2, first part. CAN oxidation was done on the acetate (54 mg) using sodium bicarbonate following the general procedure. It resulted in 50 mg of crude quinone. Quinone (50 mg) was reacted with acetoxybutadiene (0.1 ml) in toluene (2 ml) following the general procedure. On purification by column chromatography over silica gel (20% EtOAc in toluene, 50% EtOAc in toluene and 5% methanol in $CH_2Cl_2$ as eluents) gave 33 mg of slightly impure tricyclic compound. Finally, deprotection of acetate and PNB groups was done by using sodium methoxide (catalytic) in methanol (2 ml) at 0° C. following the procedure described in step 2, last part. The titled crude product was passed through two columns of silica gel (1% and 2% methanol in $CH_2Cl_2$ as eluents) yielding the oxime in 12.5% yield (5 mg) (contaminated with the other diastereomer in 5.6:1 ratio).

NMR (acetone-$d_6$; δ): 1.18 (3H, d, J=6.4Hz; $CH_3$ of the sugar), 1.76 (1H,dd,J=4.8,12.9Hz;H-2 of the sugar), 1.98 (3H, s,$CH_3$ of the side chain), 2.18 (1H, dd,J=3.7,12.9Hz, H-4), 3.67 (1H,br.d,J=3.9Hz;sugar-H), 4.21–4.29 (2H,m, sugar-H), 4.77 (1H,dd,J=5.4, 9.6Hz;H-3), 5.48 (1H,d,J=3.2; H-1 of the sugar), 5.91 (1H,s,H-1), 7.86–7.92 (2H,m;Ar—H), 8.06–8.10 (2H,m;Ar—H), 10.14 (1H, s,=N—OH), (there were small signals due to the other diastereomer present in the spectrum which were not detailed).

EXAMPLE 42

Preparation of (1'S,1S,3R)-3 (trifluoroacetamidoethyl)-5,10-dioxo-1 (2,3,6-trideoxy-3,4-dihydroxy-L-lyxohexopyranose)-3,4,5,10-tetrahydro-1H-naphtho [2,3-c] pyran (BCH-2018)

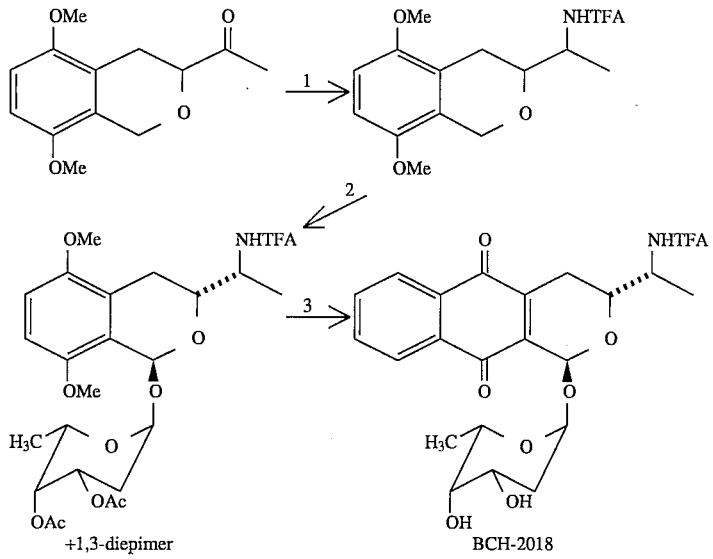

Step 1: 3-(Trifluoroacetamido-ethyl)-5,8-dimethoxy isochroman

To a solution of hydroxylamine-hydrochloride (1.4 g; 20.1 mmole) in a mixture of ethanol (30 ml) and water (3 ml) was added sodium hydroxide (720 mg) in ethanol (15 ml). The mixture was stirred for 0.5 hour. The solution was filtered. The filtrate was added to 5,8-dimethoxy-3-acetyl-isochroman (1 g; 4.23 mmole). The mixture was stirred at room temperature for 1.5 hour and evaporated to dryness. The residue was dissolved in small volume of water (10 ml), extracted with $CH_2Cl_2$ (3×100 ml), washed with brine (20 ml), dried and evaporated. The crude product (900 mg) obtained was dissolved in toluene (30 ml) and cooled to −40° C. Red-Al (9 ml) was added during 25 minutes. The mixture was stirred at −40° C. for 40 minutes. The temperature of the cooling mixture was raised slowly to 25° C. and the reaction was stirred at 25° C. for 16 hours. Excess reagent was destroyed by careful addition of cold water (6 ml) followed by 10% sodium hydroxide (1 ml). The mixture was extracted with ether (3×100 ml), washed with brine (25 ml), dried and evaporated. The crude product (800 mg) was dissolved in $CH_2Cl_2$ (50 ml). Pyridine (8 ml) and DMAP (15 mg) were added and the mixture was cooled to 0° C. Trifluoroacetic anhydride (3 ml) was added slowly and the mixture was stirred at room temperature for 16 hours. It was poured into ice, neutralized with saturated sodium bicarbonate, extracted with $CH_2Cl_2$ (3×100 ml), washed with water (25 ml), dried and evaporated. The solid residue was recrystallized twice from a mixture of hexane and ether (4:1) yielding pure titled product (purity by NMR:>92%; yield =330 mg; 23.4% in three steps).

NMR ($CDCl_3$; δ): 1.29 (3H, d, J=6.8 Hz; —$CH_3$), 2.52 (1H, dd, J=11.3, 16.9 Hz; H-4), 2.69 (1H, dd, J=2.2, 16.4 Hz; H'-4), 3.65 (1H, ddd, J=3.2, 6.3, 11.2 Hz; H-3), 3.75, 3.78 (3H, s each, Ar-$OCH_3$), 4.24 (1H, m; —CH(NHCOCF$_3$)CH$_3$), 4.58 (1H, d, J=15.8 Hz; H-1), 4.97 (1H, d, J=15.8 Hz; H'-1), 6.62, 6.67 (1H, d each, J=8.9 Hz; Ar—H).

Step 2: (1S',1S,3R)-3-(trifluoroacetamidoethyl)-5,8-dimethoxy-1-(2',3',6'-trideoxy-3',4'-dihydroxy-L-lyxohexopyranose)-isochroman Coupling with sugar was done using DDQ in $CH_2Cl_2$ following general procedure (step 1, example 14). The product was isolated as diastereomeric mixture from crude reaction mixture by column chromatography over silica gel prewashed with 0.5% triethylamine (eluent:hexane:ethyl acetate=80:20) in 75% yield. To a solution of the diastereomeric mixture (100 mg) in $CH_3CN$ (6 ml) at 0° C. was added 0.1N NaOH (4 equiv.). The mixture was stirred at 0° C. for 0.5 hour. Ice bath was removed and it was stirred at room temperature for 1.5 hr. The mixture was diluted with water (10 ml), extracted with $CH_2Cl_2$ (3×100 ml), washed with water (20 ml), dried and evaporated. The crude product was chromatographed over silica gel (prewashed with 0.2% triethylamine) eluent: 50%, 60%, 70%, 80% EtOAc in hexane and finally by pure EtOAc) yielding pure title compound (yield =25 mg; 29.4%), and 1,3-diepimer (37 mg; 80% pure; 34.5%).

NMR (Acetone-d$_6$; δ) of the title compound: 1.28, 1.35 (3H, d each, J=6.5 Hz; $CH_3$ of the side chain and $CH_3$ of the sugar), 1.58 (1H, dd, J=5.1,12.6 Hz; H-2 of the sugar), 1.91 (1H, dt, J=3.8, 12.3 Hz; H-2 of the sugar), 2.41 (1H, dd, J=11.6, 17.4 Hz, H-4), 2.79 (1H, dd, J=3.4, 17.6 Hz; H'-4), 3.42 (1H, d, J=4.4, sugar-H), 3.55 (1H, br signal; H-4 of the sugar), 3.64 (]H, d, J=6.7 Hz; sugar-H), 3.77, 3.78 (3H, s, each, Ar—$OCH_3$), 4.16–4.29 (2H, m, —CH(NHTFA) $CH_3$ and sugar-H), 4.36 (1H, q, J=6.5 Hz; H-5 of sugar), 5.36 (1H, d, J=3.3 Hz; H-1 of the sugar), 6.04 (1H, s, H-1), 6.79, ,5.88 (1H, d each, J=8.9Hz; Ar—H), 8.50 (1H, br d, J=7.0; NHTFA).

NMR of 1,3-diepimer (acetone-d$_6$; δ): 1.21 (3H, d, J=6.5 Hz; $CH_3$), 1.36 (3H, d, J=6.3 Hz; $CH_3$), 2.37 (1H, dd, J=6.1, 11.3 Hz; H-4), 2.80 (1H, dd, J=3.3, 17.3 Hz; H'-4), 3.45 (1H, d, J=4.8 Hz; sugar-H), 3.53 (1H, br signal; sugar-H), 3.66 (1H, d, J=6.9 Hz; sugar-H), 3.78, 3.81 (3H, s each; Ar-$OCH_3$), 4.08 (1H, q, J=6.7 Hz; H-5 of the sugar), 4.16–4.29 (2H, m; CH(NHTFA) $CH_3$ and sugar-H), 5.36 (1H, br singlet, H-1 of sugar), 5.85 (1H, s; H-1), 6.78–6.89 (2H, m; A-H), (There were few signals due to the other diastereomer which are not detailed.).

Step 3: (1'S, 1S, 3R)-3 -(trifluoroacetamidoethyl)-5,10-dioxo-1-(2',3',6'-trideoxy-3',4'-dihydroxy-L-lyxohexopyranose)-3,4,5,10-tetrahydro-1H-naphtho-[2,3-c]-pyran (BCH-2018)

CAN oxidation was done on dimethoxy-compound following the general procedure (step 3, example 12).

The crude quinone was reacted with acetoxy-butadiene in toluene following the general procedure. Pure titled product was obtained by column chromatography over silica gel (eluent: toluene: EtOAc=70:30 and 60:40) followed by preparative TLC (eluent: CH$_2$Cl$_2$:MeOH=9:1) (5 mg; 19% yield) as a light yellow solid, mp: 180°-3° C. (dec.).

NMR (acetone-d$_6$; δ): 1.34 (3H,d,J=6.4Hz;—CH$_3$), 1.38 (3H,d,J=6.7Hz;—CH$_3$), 1.60 (1H,dd,J=4.7,12.6Hz;H-2 of the sugar), 1.92 (1H,dd,J=3.7,12.2Hz;H-2 of the sugar), 2.47 (1H,dd,J=10.2,19.0Hz;H-4), 2.82 (1H,dd,J=2.9,19.0Hz;H'-4), 3.49 (1H,d,J=4.3Hz;—OH of the sugar), 3.59 (1H, br.signal which became sharp on D$_2$O-exchange;H-4 of sugar), 3.68 (1H,d,J=6.7Hz;—OH of the sugar), 3.82 (1H, m;H-3), 4.19–4.30 (2H,m, overlapping—CHCH$_3$(NHTFA) and sugar-proton), 4.42 (1H,q,J=6.5Hz,H-5 of the sugar), 5.36 (1H, d,J=3.5Hz,H-1 of the sugar), 6.0 (1H, s,H-1), 7.86–7.90 (2H,m;Ar—H), 8.05–8.10 (2H,m;Ar—H), 8.56 (1H,br. signal;—NHTFA). (Stereochemistry of NHTFA is not yet determined).

EXAMPLE 43

Preparation of (1'R, 1R, 3S)-3-aceto-5,10-dioxo-1-(2-deoxy-2-chloroethylnitrosoureido-D-glucopyranose)-3,4,5,10-tetrahydro-1H-naphtho [2,3-c] pyran (BCH-2038)

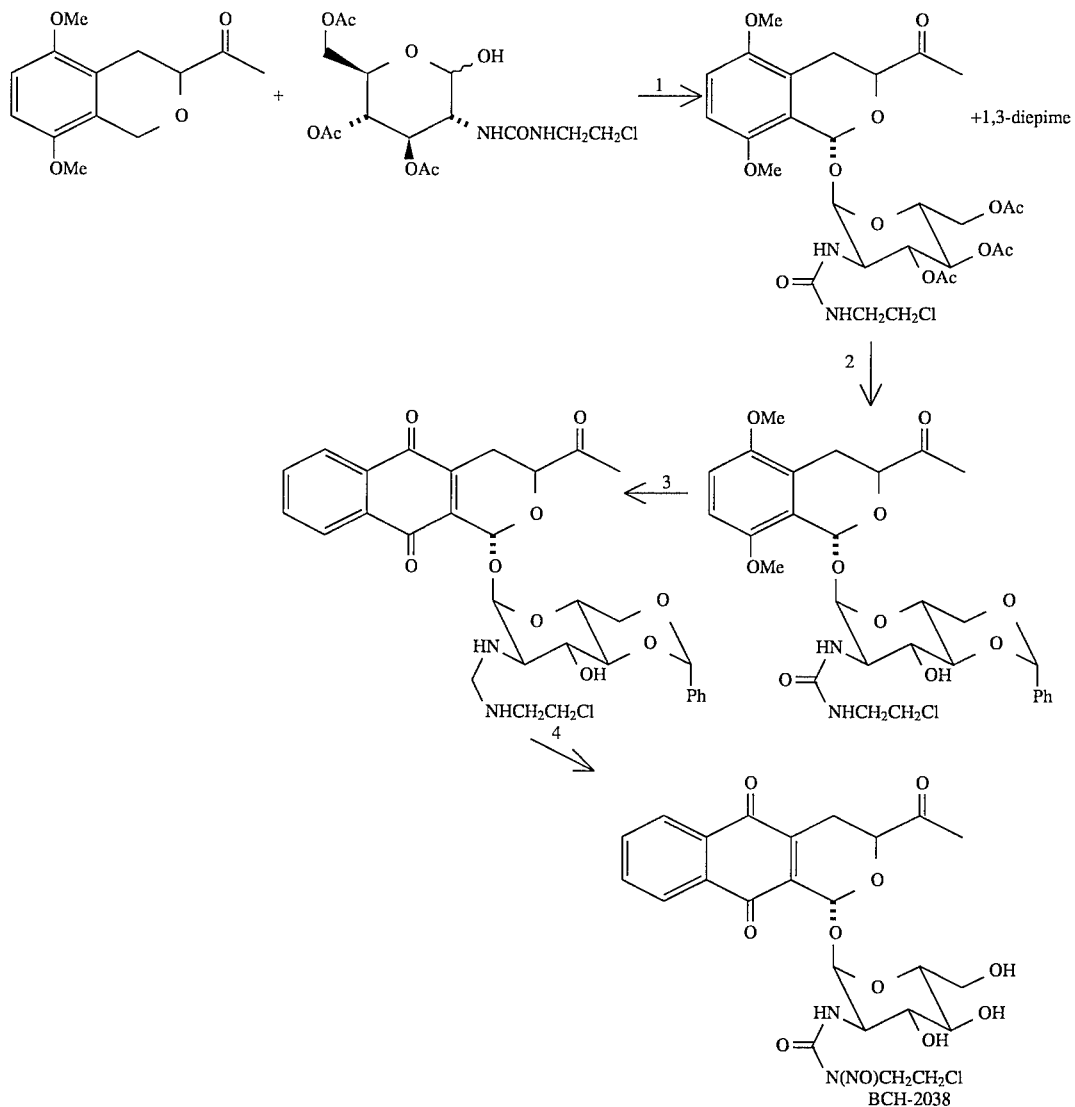

Step 1: (1'R, 1R, 3S)-3-aceto-5,8-dimethoxy-1(2-deoxy-2-chloroethylureido-3,4,6-triacetyl-D-glucopyranose)-isochroman 2-Deoxy-2-chloroethylureido-3,4,6-triacetyl-D-glucopyranose was prepared following known procedure (Ref: T. P. Johnston, G. S. McCaleb and J. A. Montgomery, *J, Med. Chem.*, 18, 104 (1975)). This compound was coupled with 3-aceto-5,8-dimethoxy-isochroman using DDQ following the general procedure outlined before (step 1, example 14). Purification was done by column chromatography over silica gel (eluent:hexane:EtOAc=7:3) yielding the title compound (29.4%) and 1,3-diepimer (31%).

NMR (acetone-d$_6$; δ) of the title compound: 1.91, 1.95, 2.00 (3H, s each; acetyl groups) 2.32 (3H, 5, keto-methyl), 2.50 (1H, dd, J=12.3, 17.6 Hz; H-4), 3.01 (1H, dd, J=4.0, 17.6 Hz; H'-4), 3.49 (2H, m; —NH—CH₂—group), 3.63 (2H, t, J=6.2 Hz; —CH₂—Cl group); 3.83, 3.88 (3H, s each; Ar—OCH₃), 4.14 (4H, m; H-5, H-2, H-6 and H-6 of the sugar overlapping), 4.60 (1H, dd, J=4.1, 12.2 Hz; H-3), 5.08 (pair of double-doublets overlapping; H-3 and H-4 of the sugar), 5.46 (1H, d, J=3.5 Hz; H-1 of the sugar), 5.49 (1H, broad s; —NH—CO—), 6.02 (1H, s; H-1), 6.15 (1H, br signal; CONH—CH₂), 6.87, 6.96 (1H, d each, J=9.0 Hz; Ar—H).

NMR (acetone-d₆; δ) of the 1,3-diepimer: 1.92, 2.00, 2.06 (3H, s each; acetate-groups), 2.28 (3H, s; keto-methyl), 2.48 (1H, dd, J=12.0, 17.8 Hz; H-4), 2.91 (1H, dd, J=4.2, 11.7 Hz; H'-4), 3.26–3.51 (2 multipiers, 1H each; —HN—CH₂—), 3.56 (2H, t, J=6.2 Hz; —CH₂Cl), 3.84 (6H, s; Ar—OCH₃), 4.14–4.23 (2H, m; sugar-H), 4.34 (1H, dd, J=4.7; 12.1 Hz; sugar-H), 4.62 (2H, dd, another proton overlapped; J=4.3, 12 Hz; H-3), 5.05–5.18 (2H, m; H-3 and H-4 of sugar), 5.51 (1H, d, J=3.7 Hz; H-1 of the sugar), 5.81 (1H, d, J=9.6 Hz; —NH—CO), 5.98 (1H, br, triplet; —NH—CH₂), 6.16 (1H, s; H-1), 6.91, 6.99 (1H, d each, J=9.0 Hz; Ar—H).

Step 2: (1'R, 1R, 3S)-3-aceto-5,8-dimethoxy-1(2-deoxy-2-chloroethylureido-4,6-benzylidene-D-glucopyranose)-isochroman To a cold solution of triacetyl derivative (120 mg; 0.19 mmol) in CH₃CN was added 0.1N NaOH (8.6 ml; 4.6 eq.). The mixture was stirred at 0° C. until TLC revealed complete reaction. It was carefully neutralized with 0.1N HCl to pH~8 and extracted with ethyl acetate (3×100 ml), washed with 2.5% NaHCO₃-NaCl-solution (1:1) (10 ml), dried and evaporated. To a solution of the crude product in DMF (5 ml), benzaldehyde dimethyl acetal (30 μl; 1.2 eq.) and p-TSA (10 mg; catalytic) was added. The reaction flask was connected to welter aspirator and held at 50° C. for 15 minutes. Sodium bicarbonate solution (2.5%; 10 ml) was added and the mixture was extracted with CH₂Cl₂ (3×50 ml), washed with saturated NaCl solution, dried and evaporated. The crude product was washed with a mixture of hexane and ether, yieldin pure titled benzylidene derivative (77 mg; 68%).

NMR (acetone-d₆; δ): 2.33 (3H, s, keto-methyl), 2.50 (1H, dd, J=12.2, 17.6 Hz; H-4), 2.99 (1H, dd, J=4.1, 17.6 Hz; H'-4), 3.49 (2H, t, J=5.8 Hz; —CH₂—Cl), 3.63 (2H, m, —NH—CH₂—), 3.82, 3.91 (3H, s, Ar—OCH₃), 4.19 (1H, dd, J=4.5, 9.,5 Hz; sugar-H), 4.62 (1H, dd, J=4.1, 12.2 Hz; H-3), 5.46 (1H, d, J=3.8 Hz; H-1 of the sugar), 5.62 (1H, s, —CH Ph), 5.68 (1H, d, J=8.5 Hz; —NH—), 6.00 (1H, s, H-1), 6.18 (1H, br s, —NH CH₂—), 6.87, 6.95 (1H, d each, J=8.9 Hz; Ar—H), 7.34 (3H, m; Ar—H), 7.46 (2H, m; Ar—H).

Step 3 (1'R, 1R, 3S)-3-aceto-5,10-dioxo-1-(2-deoxy-2-chloroethylureido-4,6-benzylidene-D-glucopyranose)-3,4,5,10-tetrahydro-1H-naphtho-[2,3-C] pyran To a solution of benzylidene derivative (77 mg; 0.127 mmol) in acetonitrile (6 ml) was added a solution of ceric ammonium nitrate (146 mg; 0.266 mmol) in water (2.5 ml) at room temperature. The mixture was stirred for 5 minutes, diluted with water (10 ml), extracted with CH₂Cl₂ (3×75 ml), washed with water (15 ml), dried, evaporated. The crude product (60 mg) was pumped for 2 hours before going to the next step. The crude product was taken up in dry toluene (3 ml) and acetoxy-butadiene (1.2 ml) was added. The mixture was stirred at room temperature for 16 hours. The solution was not quite homogeneous and TLC showed some starting material. Acetoxy-butadiene (0.5 ml) was further added and stirred for 20 hours. The mixture was diluted with toluene (10 ml). Silica gel (500 mg) was added and air was bubbled through the mixture for 1 hour. The crude reaction mixture was passed through a column of silica gel (eleunt:toluene:EtOAc=7:3 and CH₂Cl₂:MeOH= 9:1). Fraction containing the product was further purified by preparative TLC (eluent:EtOAc) yielding 12 mg of pure titled product (15%) (poor yield because of separation problem).

NMR (acetone-d₆; δ): 2.3.5 (3H, s; keto-methyl), 2.58 (1H, dd, J=11.4, 19.7 Hz; H-4), 3.01 (1H, dd, J=3.9, 19.6 Hz; H'-4) 3.55, 3.67 (m each, HN CH₂—CH₂Cl), 4.22 (1H, dd, J=4.6, 9.7 Hz; sugar-H), 4.65 (1H, d, J=3.9 Hz; —OH), 4.73 (1H, dd, J=4.0, 11.4 Hz; H-3), 5.52 (1H, d, J=3.8 Hz; H-1 of the sugar), 5.,53 (2H, br s; CH-Ph and —NH—CO), 5.94 (1H, t, J =5.7 Hz; —NH—CH₂), 6.04 (1H, s; H-1), 7.33 (3H, m, Ar—H), 7.46 (3H, m; Ar—H), 7.91 (2H, m, Ar—H), 8.14 (2H, m; Ar—H).

Step 4: (1'R, 1R, 3S)-3-aceto-5,10-dioxo-1-(2-deoxy-2-chloroethyl-nitrosoureido-D-glucopyranose)-3,4,5,10-tetrahydro-1H-naphtho-[2,3-C] pyran To a solution of benzylidene derivative (6 mg; 0.01 mmol) in 96% formic acid (1 ml) at 5° C. was added NaNO₂ (10 mg) in two portions. The reaction was complete in 2 minutes. It was diluted with water (5 ml), extracted with CH₂Cl₂ (3×25 ml), washed with water (10 ml; 15 ml), dried over Na₂SO₄ and evaporated. The crude product (4.5 mg) was passed through a small column of silica gel (eluent-:EtOAc and 10% methanol in CH₂Cl₂) yielding pure titled product (yield=0.9 mg; 17%) (HPLC: 92%)

NMR (acetone-d₆; δ): 2.35 (3H, s, keto-methyl), 2.51 (1H, dd, J=12.9, 19.2 Hz; H-4), 2.98 (1H, dd, J=4.1, 19.6 Hz; H'-4), 3.52–3.89 (two multiplets; some of the sugar protons, and overlapping A₂B₂ system due to —HN(CH₂)₂Cl), 4.08 (H, dd, J=3.5, 6.0 Hz; sugar-H), 4.26 (1H, dd, J=6.6, 11.3 Hz; sugar-H), 4.43 (1H, dd, J=4.7, 7.5 Hz; sugar-H), 4.66 (1H, dd, J=4.0, 11.5 Hz; H-3), 5.66 (1H, d, J=3.6; H-1 of the sugar), 5.99 (1H, s, H-1), 7.59 (1H, d, J=8.6 Hz; NH—CO), 7.88, 8.08 (two multiplets, Ar—H).

EXAMPLE 44

Preparation of 3-aceto-5,10-dioxo-1-methoxy-5,10-dihydro-1H-naphtho [2,3-c] pyran (BCH-2129)

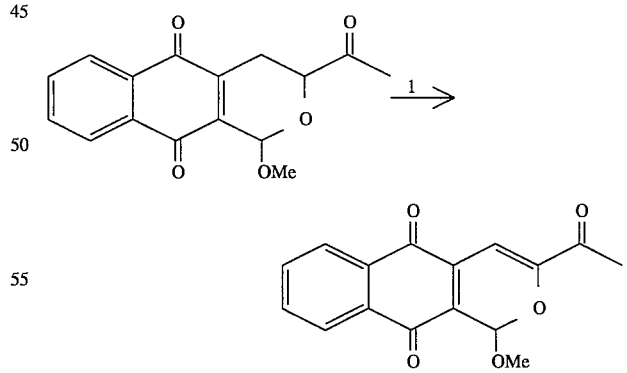

BCH-2129

Step 1: 3-Aceto-5,10-dioxo-1-methoxy-5,10-dihydro-1H-naphtho-(2,3-c)-pyran (BCH-2129)

To a solution of 3-acetyl-5,10-dioxo-1-methoxy-3,4-5,10-tetrahydro-1H-naphtho (2,3-c) pyran (50 mg, 0.175 mmole) in CH₃CN (8 ml) and THF (4 ml) at 0° C. was added 0.5N sodium hydroxide (1 equiv.). The mixture was stirred at 0°

C. for 15 minutes and it was allowed to come to room temperature. After 1.5 hour at room temperature the mixture was acidified with dil. HCl to pH~6. Saturated NH₄Cl (5 ml) was added and the mixture was extracted with CH₂Cl₂ (3×50 ml), washed with water (10 ml), dried and evaporated. The crude titled product was subjected to preparative TLC (eluent: toluene:EtOAc=96:4) and pure product was isolated as a light yellow solid, mp. 154°–56° C. (3 mg; 6%).

NMR (acetone-d₆, δ): 2.50 (3H, s,ketomethyl), 3.63 (3H, s, —OCH₃), 6.42 (1H, s,H-1), 7.11 (1H, s;H-4), 7.92 (2H, m;Ar—H), 8.14 (2H,m;Ar—H).

EXAMPLE 45

Preparation of (1R, 3S) and (1S, 3R)-3-aceto-5,10-dioxo-1 (4-chloroethylnitrosoureidocyclohexyl-oxy)-3,4,5,10-tetrahydro-1H-naphtho[2,3-c] pyran (BCH-2114)

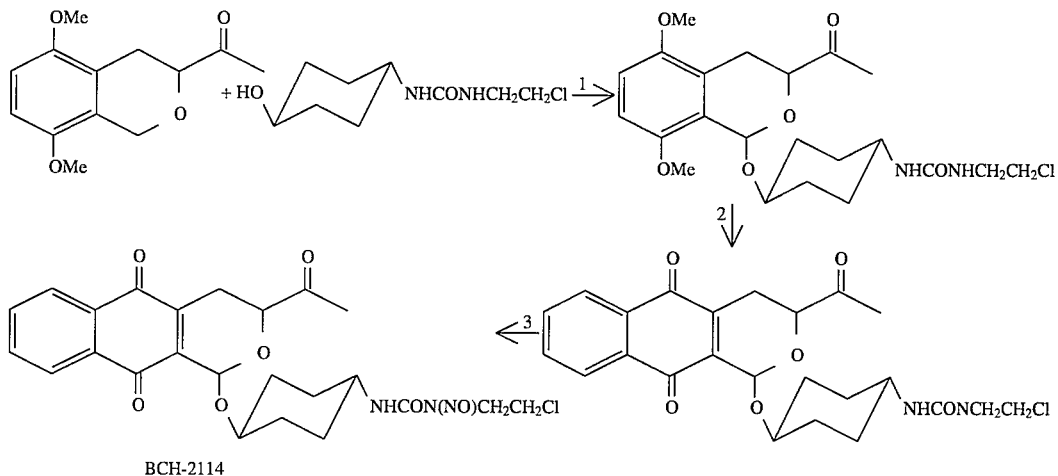

BCH-2114

Step 1: (1R,3S) and (1S,3R)-3-Aceto-1 (4-chloroethylureido-cyclohexyloxy)-5,8-dimethoxy-isochroman 3-Acetyl isochroman was coupled to 4-chloroethyl ureido-cyclohexanol (prepared by known procedure, ref.: T. P. Johnston, G. S. McCaleb, P. S. Opliger, W. R. Laster and J. A. Montgomery, *J. Med. Chem,*, 14, 600 (1971)) using DDQ following the general procedure (step 1, example 14). Enantiomeric mixture of the titled products was isolated from the crude reaction mixture by column chromatography over silica gel (eluent: 50% and 80% EtOAc in hexane) yield= 100mg (52%).

NMR (acetone-d₆; δ): 1.26–48 (two multiplets; CH₂-groups of cyclohexyl ring), 1.78–1.80 (multiplet,—CH₂ of cyclohexyl ring), 2.27 (3H, s, keto-methyl), 2.45 (1H, dd, J :=12.1, 17.8 Hz; H-4), 2.90 (1H, dd, J=4.2, 17.7 Hz; H'-4), 3.42 (2H, m; —HNCH₂Cl), 3.59 (2H, t, J=6.0 Hz; —CH₂—Cl), 3.78, 3.79 (3H, s each, Ar—OCH₃), 3.86 (1H, m; H-1 of the cyclohexyl ring), 4.61 (1H, dd, J=,4.2, 12.0 Hz; H-3), 5.51 (1H, d, J=7.4 Hz; —NH—CO—), 5.67 (1H, br signal; —CONHCH₂—), 5.90 (1H, s, H-1), 6.79, 6.87 (1H, d each, J=8.9 Hz; Ar—H).

Step 2: (1R,3S) and (1S,3R)-3-Aceto-5,10-dioxo-1 (4-chloroethylureidocyclohexyl-oxy)-3,4,5,10-tetrahydro-1H-naphtho-(2,3-c)-pyran CAN oxidation was performed on the dimethoxy-isochroman from step 1 herein (35 mg; 0.077 mmole) following the general procedure (step 2, example 14).

The crude product (32 mg) was dissolved in dry toluene (3 ml) and acetoxybutadiene (0.5 ml) was added. The mixture was stirred at room temperature for 18 hours. Silica gel (500 mg) was added and air was bubbled for 0.5 hour. The crude product was passed through a column of silica gel (30% EtOAc in toluene, 50% EtOAc in Toluene, and CH₂Cl₂: MeOH=19:1 as eluents) yielding pure tricyclic titled compounds (15 yield 41%).

NMR (acetone-d₆δ): 1.24–2..54 (6H, m, CH₂ group of the cyclohexyl ring), 2.30 (3H, s, ketomethyl), 2.51 (1H, dd, J=11.6, 19.5 Hz; H-4), 3.42 (2H, m; —NHCH₂—CH₂Cl), 3.,50 (2H, t, J=6.2 Hz; —CH₂Cl), 3.95 (1H, m, H-1 of the cyclohexyl ring), 4.64 (1H, dd, J=4.2, 11.5 Hz; H-3), 5.54 (1H, br d, J=6.9 Hz; NHCO—), 5.69 (1H, br signal; —CONH—CH₂—), 5.92 (1H, s; H-1), 7.86–7.91 (2H, m; Ar—H), 8.06–8.10 (2H, m; ArH).

Step 3: (1R,3S) and (1S,3R)-3-aceto-5,10-dioxo-1 (4-chloroethylnilrosoureidocyclohexyl-oxy)-3,4,5,10-tetrahydro-1H-naphtho-(2,3-c)-pyran (BCH-2114)

To a solution of chloroethyl ureido-derivative from step 2 herein (14 0.03 mmole) in formic acid (1.2 ml) at 5° C. was added sodium nitrite (20 mg) in two portions. Reaction was complete in 3 minutes. It was diluted with water (10 ml), extracted with CH₂Cl₂ (3×50 ml), washed with water (2×10 ml), dried and evaporated. The crude product was purified by passing through a small column of silica gel (eluent: 1% methanol in CH₂Cl₂) and finally by washing with hexane-ether mixture yielding pure titled nitroso-derivative, mp=58°–63° C. (yield=5 mg;34%).

NMR (acetone-d₆;δ): 1.48–1.80 (6H,m;CH₂ of the cyclohexyl group), 2.32 (3H, s,ketomethyl), 2.52 (1H,dd,J=11.6, 19.6Hz;H-4), 2.93 (1H,dd,J=4.3,19.7Hz;H'-4), 3.60 (2H, t,J=6.5Hz;—CH₂—Cl), 3.76–4.05 (m, H-1 and H-4 of the cyclohexyl group), 4.16 (2H,t,J=6.6Hz;—N(NO)CH₂—), 4.66 (1H,dd,J=4.3,11.4Hz;H-3), 5.97 (1H, s,H-1), 7.77 (1H, br.d, J=7.8Hz; —NHCO—), 7.87–7.90 (2H,m;Ar—H), 8.07–8.11 (2H,m;Ar—H).

EXAMPLE 46

1-methoxy-5,10-dioxo-3,4,5,10-tetrahydro-1H-naphtho-[2,3-c]-pyran-3-carboxamides

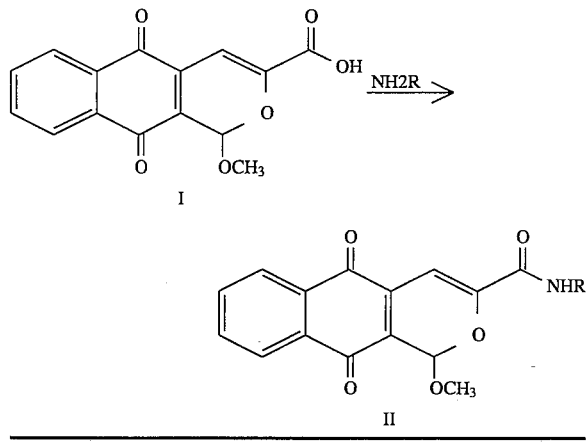

STEP:

1, R = –phenyl

BCH-2044

2, R = –CH₂CH₂CH₂–(2-oxopyrrolidin-1-yl)

BCH-2166

3, R = –CH₂CH₂CH₂–(imidazol-1-yl)

4, R = –CH₂CH₂CH₂–(imidazolium)·NH⁺Cl⁻

BCH-2157

5, R = –(CH₂)₃–morpholino

BCH-2170

6, R = –(CH₂)₃–morpholino·HCl

BCH-2171

7, R = –CH₂CH₂–(2-pyridyl)

8, R = –CH₂CH₂–(2-pyridyl)·HCl

BCH-2835

9, R = –CH₂–(2-pyridyl)

BCH-2840

10, R = –CH₂–(2-pyridyl)·HCl

BCH-2841

11, R = –CH₂CH₂–(pyrrolidin-1-yl)

12, R = –CH₂CH₂–(pyrrolidin-1-yl)·HCl

BCH-2839

13, R = –(CH₂)₃–CH(OEt)₂

BCH-2848

14, R = –(CH₂)₄–OH

BCH-2849

Step 1: 1-methoxy-3-N-anilinylcarbonyl-5,10-dioxo-5,10-dihydro-1H-naphtho-[2,3-c]-pyran (BCH-2044)

Using a similar procedure as described in step 7, example 16, the carboxylic acid from step 6, example 16, was converted to the titled compound.

dec. 140° C.; m.p. 200° C.

¹H NMR (CDCl₃, 250 MHz, Bruker): δ, 3.68 (3H, s, OCH₃), 6.48 (1H, s, 1—CH), 7.18 (1H, tr, J=7.,5 Hz, p-Ani-H), 7.49 (2H, tr, J=8.0 Hz, m-Ani-H), 7.50 (1H, s, 4—CH), 7.66 (2H, d, J=7.8 Hz, O-Ani-H), 7.79 (2H, m, 7, 8—ArH), 8.15 (2H, m, 6, 9—ArH), 8.40 (1H, s, NHCO).

IR (Nicolet, 205 FT, film on NaCl plate): cm⁻¹, 3322.9, 2929.3 2848.3, 1682.9, 1659.8, 1594.2, 1327.7, 1443.7, 1374.2, 1297.0, 1258.4, 1063.2, 947.6, 863.1, 719.7, 693.,3.

Step 2: 1-methoxy-3-(3-N-pyrrolidinomylpropylaminocarbonyl)-5,10-dioxo-5,10-dihydro-1H-naphtho-[2,3-c]-pyran (BCH-2166)

60 mg of the acid from step 6, example 16,(compound I) was dissolved in 6.8 ml of dry THF, cooled to 0° C. and 63 µl of oxalyl chloride was added. The mixture was allowed to stir at 0° C. for 20 minutes, and then at room temperature for 20 minutes. The solvent was then evaporated, the residue was redissolved in dichloromethane and evaporated, and then the residue was again dissolved into dry THF. The solution was cooled to −10° C. 29.3 µl of triethylamine and 19.90 µl of 1-(3-aminopropyl)-2-pyrrolidinone was added and allowed to stir for 45 minutes at −10° C. and then 2 hours at room temperature. The solvent was then evaporated to half of its original volume, the remaining solution was poured onto sat. brine and extracted into dichloromethane. The organic layer was then washed with sat. sodium bicarbonate solution, dried over sodium sulfate, and evaporated to dryness to give 24 mg of pure titled product(compound II).

NMR (CDCl$_3$ 250 MHz, Bruker): δ, 1.86 (2H, Quin, J=6.6 Hz, C—CH$_2$—C), 2.08 (2H, Quin, J=7.5 Hz, 4'-pyrr—CH$_2$), 2.45 (2H, t, J=7.5 Hz, 3'-pyrr—CH$_2$), 3.15–3.34 (2H, m, CONHCH$_2$), 3.36–3.55 (4H, m, CH$_2$-pyrr, 5'-pyrr—CH$_2$), 3.74 (3H, s, —OCH$_3$), 6.43 (s, 1H, 4—CH), 7.32 (s, 1H, 1—CH), 7.70–7.78 (2H, m, 6, 9—ArH), 8.08–8.16 (3H, m, 7, 8—ArH, NH).

IR (Nicolet, 205 FT, film on NaCl plate): cm$^{-1}$, 3320.9, 2936.7, 2871.3, 1679.9, 1658.1, 1597.0, 1527.2, 1335.2, 1291.5, 1278.4, 1082.1, 947.98, 857.41, 801.34, 723.70.

Step 3: (3-N-imidazolylpropyl)-1-methoxy-5,10-dioxo-5,10-dihydro-1H-naphtho-[2,3-c]-pyran-3-carboxamide To a stirred solution of Compound I (0.185 mmol, 53 mg) and catalytic amounts of DMF in 6 ml of THF at 0° C. was added oxalyl chloride (0.426 mmol). After stirring at 0° C. for one hour, and at room temperature for a further 20 minutes, the solvent was evaporated to dryness. 6 ml of THF was then added, and the mixture divided into two. 3 ml of solution was then cooled to −10° C., and 1-(3-amminopropyl)-imidazole (8.39 µl, 0.20 mmol) dissolved in 1 ml of THF was added dropwise. The mixture was allowed to stir for one hour at which time it was poured onto sat. sodium bicarbonate solution, extracted into methylene chloride, washed with brine, dried over sodium sulfate and the solvent evaporated. Purification on TLC using 8% methanol/chloroform system produced 6 mg of pure titled product, compound II.

$^1$H NMR (acetone-d$_6$, 250 MHz, Bruker), δ: 2.10 (m, 2H, CH$_2$-imidazol), 3.42 (m, 2H, C—CH$_2$—C), 3.60 (s, 3H, OCH$_3$), 4.14 (t, 2H, CH$_2$NCO, 6.34 (s, 1H, 4—CH), 6.96 (s, 1H, 4—CH (imidazol)), 7.16 (s, 1H, 1—CH), 7.18 (s, 1H, 5—CH (imidazol)), 7.7,](s, 1H, 2—CH (imidazol)), 7.90 (m, 2H, 6, 9—ArH), 8.12 (m, 2H, 7, 8—ArH), 8.29 (m, 1H, NH).

IR (Nicolet 205 FT, film on NaCl plate), cm$^{-1}$: 3313.5, 2932.1, 2853.4, 1676.1, 1665.4, 1593.2, 1552.8, 1334.1, 1274.0, 1087.5, 950.72, 859.52, 718.64.

Step 4: (3-N-hydrochloroimidazolylpropyl)-1-methoxy-5,10-dioxo-5,10-dihydro-1H-naphtho-[2,3-c]-pyran-3-carboxamide (BCH-2157)

6 mg of product from step 3 herein was dissolved in 2 ml of ether. To this was added 6 µl of 1M HCl/ether solution (from Aldrich). The mixture was stirred, and then the solvent evaporated to give 6.7 mg of the HCl salt, compound II.

$^1$H NMR (acetone-d$_6$, 250 MHz, Bruker) for salt, δ: 2.29 (m, 2H, CH$_2$—imidazol), 3.53 (m, 2H, C—CH$_2$—C), 3.62 (s, 3H, OCH$_3$), 4.50 (m, 2H, CH$_2$NHCO, 6.33 (s, 1H, 4—CH), 7.14 (s, 1H, 1—CH), 7.55 (s, 1H, 5—CH(imi)), 7.76 (s, 1H, 4—CH(imi)), 7.88 (m, 2H, 7, 8—ArH), 8.05 (m, 2H, 6, 9—ArH), 8.64 (m, 1H, NH), 9.285 (s, 1H, 2—CH(imi)).

IR (Nicolet 205 FT, film on NaCl plate) cm$^{-1}$: 3345.8, 1676.5, 1652.2, 1527.0, 1280.4, 1090.9, 9.55.01.

Step 5: 1-methoxy-3-[2-(N-morpholino) ethyl amino carbonyl]-5,10-dioxo-5,10-dihydro-1H-naphtho-[2,3-c]-pyran (BCH-2170)

The title compound was prepared using a similar method as detailed in example 16, step 7. During the process, compound I, was present in an amount of 20 mg, oxalyl chloride in the amount of 9.2 µl, 0.105 mmol, 4-(2-aminoethyl) morpholine in the amount of 9.3 µl, 0.07 mmol, to produce 33 mg of the title compound II $^1$H NMR (CDCl$_3$, 250 MHz, Bruker), δ: 2.50 (4H, tr, J=6.1 Hz, morph-H), 2.58 (2H, tr, J=5.8 Hz, CON—C—CH$_2$), 3.50 (2H, m, CON—CH$_2$), 3.63 (3H, s, OCH$_3$), 3.71 (4H, tr, J=6.1 Hz, morph-H), 6.37 (1H, s, 1-H), 7.30 (1H, br s, NH), 7.33 (1H, s, 4-H), 7.75 (2H, m, 7, 8—ArH), 8.12 (2H, m, 6, 9—ArH).

Step 6: 1-methoxy-3-[2-(N-morpholine) ethyl amino carbonyl]-5,10-dioxo-5,10-dihydro-1H-naphtho-[2,3-c]-pyran (BCH-2171)

The title compound was prepared using similar steps as detailed in example 16, step 8. During the process, compound from step 5 herein, was present in the amount of 33 mg, 0.081 mmol, HCl (0.25 µl in ether) in the amount of 0.4 ml, 0.103 mmol, and 30 mg, 0.068 mmol of the title compound was produced.

dec. 130° C., m.p. 187° C.

$^1$H NMR (Acetone-d$_6$, 250 MHz, Bruker), δ: 3.22 (2H, br tr, J=10 Hz, morph—CH$_2$), 3.40 (2H, m, 3ONHCH$_2$CH$_2$), 3.62 (2H, br d, J=11.0 Hz, morph—CH$_2$), 3.74 (3H, s, OCH$_3$), 3.88 (2H, m, CONHCH$_2$—CH$_2$), 4.00 (2H, br d, J=11 Hz, morph—CH$_2$), 4.22 (2H, br tr, J=10 Hz, morph—CH$_2$), 6.35 (1H, s, 1-H), 7.15 (1H, s, 4-H), 7.93 (2H, m, 7, 8—ArH), 8.13 (2H, m, 6, 9—ArH), 9.46 (1H, br s, NH).

IR (Nicolet, 205 FT, film on NaCl plate): cm$^{-1}$, 3765.4 (strong), 2936.3, 2581.9, 1679.2, 1650.4, 1527.3, 1274.5, 1102.4, 948.4, 857.87, 720.70.

Step 7: 1-methoxy-3-[2-(2-pyridinyl) ethyl amino carbonyl]-5,10-dioxo-5,10-dihydro-1H-naphtho-[2,3 - c]-pyran The title compound was prepared using a similar method as detailed in example 16, step 7. During the process, compound I was present in the amount of 20 mg, 0.070 mmol, oxalyl chloride was present in the amount of 9.2 µl, 0.105 mmol, THF in the amount of 4 ml, DMF in the amount of 1 µl, and 1-(2-aminoethyl)-pyrrolidine in the amount of 8.28 µl, 0.070 mmol.

$^1$H NMR (CDCl$_3$, 250 MHz, Bruker), δ: 3.07 (2H, tr, J=6 Hz, CH$_2$-py), 3.56 (3H, s, OCH$_3$), 3.83 (2H, m, NCH$_2$), 6.35 (1H, s, 1—CH), 7.18 (2H, m, py-H), 7.31 (1H, s, 4—CH), 7.63 (1H, tr d, J=8.3 H, 2 Hz, py-H), 7.73 (2H, m, 7, 8—ArH), 8.00 (1H, tr, J=6 Hz, NH), 8.11 (2H, m, 6, 9—ArH), 8.53 (1H, d, J=4.8 Hz, py-H).

Step 8: 1 -methoxy-3-[2-(2-pyridinyl) ethyl amino carbonyl]-5,10-dioxo-5,10-dihydro-1H-naphtho-[2,3-c]-pyran hydrochloride (BCH-2835)

Preparative details: See example 16, step 8. compound I: 23 mg, 0.059 mmol HCl (0.25M in ether): 0.26 ml, 0.065 mmol compound II: 20 mg, 0.047 mmol m.p. 135° C. (dec. 113° C.).

$^1$H NMR (Acetone-d$_6$, 250 MHz, Bruker), δ: 3.60 (3H, s, OCH$_3$), 3.60 (2H, m, CH$_2$py), 3.94 (2H, m, NHCH$_2$), 6.81 (1H, s, 1-H), 7.08 (1H, s, 4-H), 7.91 (2H, m, 7, 8—ArH), I]. 0 (2H, m, py-H), 8.12 (2H, m, 6, 9—ArH), 8.53 (1H, tr, J=6Hz, py-H), 8.71 (1H, d, J=6Hz, py-H), 8.71 (1H, br s, NH).

IR (Nicolet 205 FT, film on NaCl plate): cm$^{-1}$, 3324 (strong) 2926.1, 1677.6, 1651.0, 1522.6, 1274.3, 1083.6, 723.39.

Step 9: 1-methoxy-3-[(2-pyridinyl) methyl amino carbonyl] -3-methoxy-5,10-dioxo-5,10-dihydro-1H-naphtho-[2,3-c]-pyran (BCH-2840)

Preparative details: See example 16, step 7. compound I: 20 mg, 0.07 mmol Oxalyl chloride: 9.2 μl, 0.10 mmol compound II: 23 mg $^1$H NMR (CDCl$_3$, 250 MHz, Bruker), δ: 3.65 (3H, s, OCH$_3$), 4.72 (2H, d, J=5.4 Hz, NHCH$_2$), 6.43 (1H, s, 1-H), 7.23 (1.H, m, py-H), 7.30 (1H, d, J=7.9 Hz, py-H), 7.38 (1H, s, 4-H), 7.69 (1H, tr d, J=8.9 Hz, 1.2 Hz, py-H), 7.75 (2H, m, 7, 8—ArH), 8.12 (2H, m, 6, 9—ArH), 8.12 (1H, over-lapped, NHCO), 8.56 (1H, d, J=4.2 Hz, py-H).

IR (Nicolet, 205 FT, film on NaCl plate): cm$^{-1}$, 3360.1, 2934.7, 1675.5, 1655.5, 1595.5, 1518.4, 1292.9, 1270.0, 1084.4, 950.23, 861.04, 719.77.

Step 10: 1-methoxy-3-[(2-pyridinyl) methyl amino carbonyl]-3-methoxy-5,10-dioxo-5,10-dihydro-1H-naphtho-[2,3-c]-pyran hydrochloride salt(BCH-2841)

Preparative details: See example 16, step 8. compound I: 12 mg HCl in ether: 1 eq compound II: 11 mg $^1$H NMR (DMSO-d$_6$, 250 MHz, Bruker), δ: 3.61 (3H, s, OCH$_3$), 4.64 (2H, tr, J=4.8 Hz, CONHCH$_2$), 6.40 (1H, s, 1-H), 7.03 (1H, s, 4-H), 7.50 (2H, m, py-H), 7.92 (2H, m, 7, 8—ArH), 8.06 (2H, m, 6, 9—ArH), 8.05 (2H, m, py-H), 8.63 (1H, br d, J=4.23 Hz, py-H), 9.36 (1H, tr, J=4.9 Hz, NHCO).

Step 11: 1-methoxy-3-[2-(N-pyrrolidinyl) ethyl amino carbonyl]-5,10-dioxo-5,10 -dihydro-1H-naphtho-[2,3 - c]-pyran Preparative details: See example 16, step 7. compound I: 20 mg, 0.07 mmol Oxalyl chloride: 9.2 μl, 0.105 mmol 1-(2-aminoethyl)-pyrrolidine: 9.1 μl, 0.07 mmol compound II: 24.9 mg $^1$H NMR (CDCl$_3$, 250 MHz, Bruker), δ: 1.81 (4H, br s, pyrr-H), 2.60 (4H, br s pyrr-H), 2.72 (2H, m, CH$_2$-pyrr), 3.52 (2H, qua, J=5.4 Hz, NHCH$_2$), 3.62 (3H, s, OCH$_3$), 6.38 (1H, s, 1-H), 7.33 (1H, s, 4-H), 7.47 (1H, br s, NHCO), 7.75 (2H, m, 7, 8—ArH), 8.12 (2H, m, 6, 9—ArH).

IR (Nicolet, 205 FT, film on NaCl plate): cm$^1$, 3356.7, 2960.5, 2935.8, 2797.8, 1676.5, 1651.7, 1520.8, 1276.7, 1097.4, 1083.4, 953.25, 863.58, 794.8, 722.19.

Step 12 1-methoxy-3-[2-(N-pyrrolidinyl) ethyl amino carbonyl]-5,10-dioxo-5,10-dihydro-1H-naphtho-[2,3-c]-pyran hydrochloride salt (BCH-2839)

Preparative details: See example 16, step 8. compound I: 24.9 mg, 0.068 mmol HCl in ether: 1 eq compound II: 23 mg $^1$H NMR (DMSO-d$_6$, 250 MHz, Bruker), δ: 1.85 (2H, m, pyrr-H), 2.01 (2H, m, pyrr-H, other pyrrolidine signals were covered by solvents), 3.05 (2H, m, CH$_2$pyrr), 3.59 (3H, s, OCH$_3$), 3.59 (2H, m, CONHCH$_2$), 6.37 (1H, s, 1-H), 7.02 (1H, s, 4-H), 7.93 (2H, m, 7, 8—ArH), 8.07 (2H, m, 6, 9—ArH), 8.96 (1H, tr J=5.7 Hz, NHCO), 9.32 (1H, br s, NH$^+$).

Step 13: 1-methoxy-3-[(4-diethoxy) butyl amino carbonyl] -5,10-dioxo-5,10-dihydro-1H-naphtho-[2,3-c]-pyran (BCH-2848)

Preparative details: see example 12. compound I: 20 mg, 0.07 mmol Oxalyl chloride: 9.2 μl, 0.105 mmol 4-aminobu-tynaldehyde diethylacetyl: 13.6 μl, 0.077 mmol compound II: 29 mg $^1$H NMR (CDCl$_3$, 250 MHz, Bruker), δ: 1.20 (6H, tr, J=7.9 Hz, 2×CH$_3$), 1.69 (4H, m, —CH$_2$CH$_2$—), 3.54–3.41 (4H, m, 2×OCH$_2$), 3.61 (3H, s, OCH$_3$), 3.64 (2H, m, CONHCH$_2$), 4.50 (1H, br s, CH(OEt)$_2$), 6.36 (1H, s, 1-H), 6.93 (1H, tr, J=5.4 Hz, NHCO), 7.34 (1H, s, 4-H), 7.74 (2H, m, 7, 8—ArH), 8.10 (2H, m, 6, 9—ArH).

IR (Nicolet, 205FT, film on NaCl plate): cm$^{-1}$, 3337.8, 2967.7, 2932.3, 2877.2, 1676.3, 1652.7, 1522.8, 1294.4, 1270.8, 1129.8, 1085.0, 952.02, 863.71, 798.63, 721.95.

Step 14: 1-methoxy-3-(3-hydroxy) propyl amino carbonyl-5,10-dioxo-5,10-dihydro-1H-naphtho-[2,3-c]-pyran (BCH-2849)

Preparative details: see example 16, step 7. compound I: 20 mg, 0.07 mmol Oxalyl chloride: 9.2 μl, 0.105 mmol diisopropyl ethyl amine: 14.75 μl, 0.077 mmol 3-amino-1-propanol: 5.35 μl, 0.07 mmol compound II: 26.3 mg $^1$H NMR (CDCl$_3$, 250 MHz, Bruker), δ: 1.81 (2H, quin, J=6.1 Hz, C—CH$_2$—C), 2.26 (1H, br, OH), 3.57 (2H, m, CONHCH$_2$), 3.61 (3H, s, OCH$_3$), 3.72 (2H, tr, J=5.4 Hz, CH$_2$OH), 6.36 (1H, s, 1-H), 7.24 (1H, br s, NHCO), 7.34 (1H, s, 4-H), 7.75 (2H, m, 7, 8—ArH), 8.11 (2H, m, 6, 9—ArH).

IR (Nicolet, 205FT, film on NaCl plate): cm$^{-1}$, 3365.4, 2928.4, 1676.3, 1652.7, 1526.7, 1275.5, 1D85.5, 950.95, 862.66, 795.81, 721.91.

EXAMPLE 47

Preparation of 3-ethylthiocarbonyl-1,3,4,5,10-pentahydro-5,10-dioxo-naphtho-[2,3-c] pyran (BCH-2003) and 3-(5'-tosyloxazolyl)-1,3,4,5,10-pentahydro-5,10-dioxo-naphtho-[2,3-c]-pyran (BCH-2155)

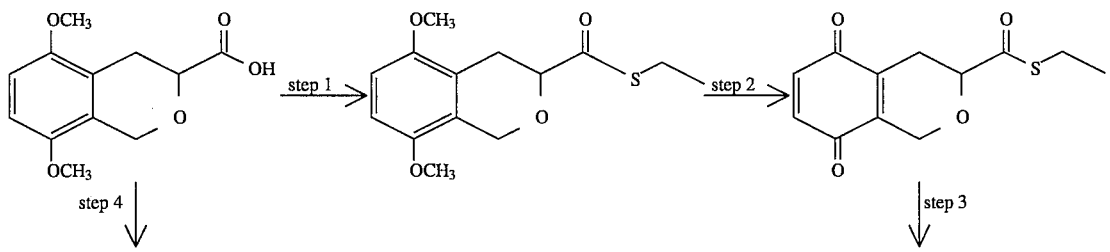

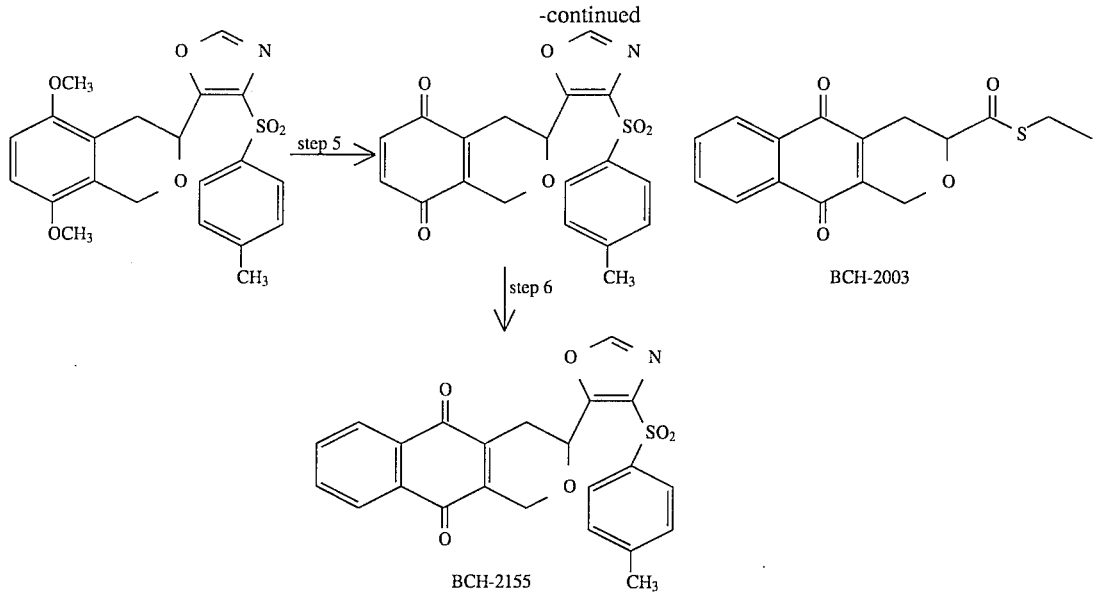

Step 1: 3-ethylthiocarbonyl-5,8-dimethoxy-isochroman 5,8-dimethoxy-3-carboxyisochroman (300 mg, 1.26 mmol) in THF (6 ml) was stirred with 1,1'-carbonyldiimidazole (225 mg, 1.386 mmol) at room temperature for 30 minutes. More THF (6 ml) was added to dilute the forming suspension. After one hour, ethanethiol (103 µl, 1.40 mmol) was added and the mixture was stirred for 18 hours at room temperature. Solvent was evaporated and the crude titled product was chromatographed (hex:EtOAc=4:1) to give desired product as a solid (200 mg, m.p. 99.2° C.).

$^1$H NMR (CDCl$_3$, 250 MHz, Bruker): δ, 1.28 (3H, tr, J=7.6 Hz, CH$_3$), 2.68 (1H, dd, J=17.6 Hz, 11.2 Hz, 4-HCH$_a$), 2.92 (1H, qua, J=7.6 Hz, —CH$_2$—), 3.12 (1H, dd, J=11.2 Hz, 3.5 Hz, 4-HCH$_e$), 3.76 (3H, s, OCH$_3$), 3.78 (3H, s, OCH$_3$), 4.24 (1H, dd, J=11.2 Hz, 3.0 Hz, 3—CH), 4.70 (1H, d, J=15.3 Hz, 1-HCH$_a$), 5.06 (1H, d, J=15.3 Hz, 1-HCH$_e$), 6.64 (1H, d, J=8.0 Hz, ArH), 6.67 (1H, d, J=8.0 Hz, ArH).

IR (Nicolet, 205 FT, film on NaCl plate): cm$^{-1}$, 2936.2 2836.2, 1679.2 1604.8, 1486.8, 1461.8, 1258.5 ,1094.3, 1078.9, 1022.5, 796.81, 714.69.

Step 2: 3-ethylthiocarbonyl-5,8-dioxo-1,3,4,5,8-penta-1H-benzo-[2,3-c]-pyran

The compound from step 1 herein (100 mg, 0.35 mmol) was dissolved in acetonitrile (6 ml), then cooled to 0° C. Sodium bicarbonate (58.8 mg, 0.7 mmol) was added. This was followed by addition of a solution of ammonium cerium nitrate (583 mg, 0.0063 mmol) in 2 ml of water. The reaction mixture was allowed stirred for 5 minutes at 0° C. TLC showed completion of the reaction. It was poured to water and extracted with methylene chloride. The organic layer was dried over Na$_2$SO$_4$ and evaporated to give a crude titled product (83 mg).

$^1$H NMR (CDCl$_3$, 250 MHz, Bruker): δ, 1.24 (3H, tr, J=7.6 Hz, CH$_3$), 2.51 (1H, dd tr, J=17.6 Hz, 9.2 Hz, 3 Hz, 4-HCH$_a$), 2.85 (1H, d, J=17.6 Hz, 4-HCH$_e$), 2.88 (1H, qua, J=7.6 Hz, —CH$_2$—), 4.18 (1H, dd, J=9.2 Hz, 3 Hz, 3—CH), 4.47 (1H, d tr, J=17.5 Hz, 3 Hz, 1-HCH$_a$), 4.81 (1H, br d, J=17.6 Hz, 1-HCH$_e$), 6.71 (1H, d, J=9.7 Hz, Quin-H), 6.76 (1H, d, J=9.7 H, Quin-H).

IR (Nicolet, 205 FT, film on NaCl plate): cm$^{-1}$, 2972.6, 2929.5, 2882.4, 1678.5, 1655.5, 1599.3, 1418.9, 1313.1, 1147.5, 1125.6, 993.09, 827.00, 766.77, 729.32, 667.58, 629.13.

Step 3: 3-ethylthiocarbonyl-5,8-dioxo-1,3,4,5,10-pentahydro-naphtho-[2,3-c]-pyran (BCH-2003)

The compound from step 2 herein (42 mg, 0.167 mmol) in toluene (6 ml) was stirred with 1-acetoxy-1,3-butadiene (119 µl, 1.0 mmol) at 60° C. for 22 hours. Solvent was evaporated and the crude product was chromatographed (toluene/EtOAc=100/15) to give desired titled product (41 mg) as a solid (m.p. 95.4°–96.5° C.).

$^1$H NMR (CDCl$_3$, 250 MHz, Bruker): δ, 1.26 (3H, tr, J=7.6 Hz, CH$_3$), 2.65 (1H, dd tr, J=19.4 Hz, 9.4 Hz, 3 Hz, 4-HCH$_a$), 2.91 (2H, qua, J=7.6 Hz, CH$_2$), 3.04 (1H, d tr, J=19.4 Hz, 3 Hz, 4-HCH$_e$), 4.25 (1H, dd, J=9.4 Hz, 3 Hz, 3—CH), 4.61 (1H, d tr, J=18.2 Hz, 3 Hz, 1-HCH$_a$), 4.97 (1H, dd, J=18.2 Hz, 1.8 Hz, 1-HCH$_e$), 7.71 (2H, m, 7, 8—ArH), 8.04 (2H, m, 6, 9—ArH).

IR (Nicolet, 205 FT, film on NaCl plate): cm$^{-1}$, 2969.3, 2931.3, 2874.3, 1680.8, 1661.8, 1641.4, 1594.2, 1334.2, 1296.4, 1175.1, 1108.9, 1027.0, 874.2, 787.5, 694.6.

Step 4: 3-(5'-tosyloxazolyl)-5,8-dimethoxy isochroman

To 5,8-dimethoxy-3-carboxyisochroman (211 mg, 0.887 mmol) dissolved in THF (2.0 ml) cooled to 0° C. was added oxalyl chloride (86.09 µl, 0.975 mmol). The mixture was stirred for 20 minutes then at room temperature for 20 minutes. The reaction mixture was evaporated to dryness to give desired acid chloride. It was redissolved in THF (4 ml) and cooled to −78° C. A solution of tosylmethyl isocyamide anion (made from the treatment of tosylmethyl isocyamide, 180 mg, 0.92 mmol, by n-butyllithium, 1.6M in hexane, 0.61 ml, 0.975 mmol at −78° C. for 10 minutes) was added to the above cold acid chloride solution. The reaction mixture was stirred for 24 hours as it warmed to room temperature. Then, it was poured to NH$_4$Cl (sat.) and extracted with methylene chloride. The organic layer was dried (over Na$_2$SO$_4$) and evaporated to give a crude product which was chromatographed to give the desired titled product as a white solid 115 mg, m.p. 138°–140° C.

$^1$H NMR (CDCl$_3$, 250 MHz, Bruker): δ, 2.41 (3H, s, tosy—CH$_3$), 2.99 (2H, d, J=7.4 Hz, 4—CH$_2$), 3.76 (6H, s, 2×CH$_3$), 4.85 (1H, d, J=17.5 Hz, 1-HCH$_a$), 4.03 (1H, d, J=17.5 Hz, 1-H$_e$CH), 5.54 (1H, tr, J=7.4 Hz, 3—CH), 6.67 (2H, br s, 6, 7—ArH), 7.33 (2H, d, J=8.2 Hz, 3',5', tosyl-H), 7.82 (1H, s, oxa-H), 7.92 (2H, J=8.2 Hz, 2, 6-tosyl-H).

IR (Nicolet 205 FT, film on NaCl plate): cm$^{-1}$, 3134.2, 2951.5, 2837.5, 1595.5, 1511.7, 1485.6, 1463.6, 1437.5, 1331.7, 1261.6, 1194.3, 1149.0, 1089.9, 1072.0, 809.60, 798.61.

Step 5: 3-(5'-tosyloxazolyl)-5,8-dioxo-1,3,4,5,8-pentahydrobenzo-[2,3-c]-pyran

The compound from step 4 herein (10 mg, 0.024 mmol) was dissolved in acetonitrile (2 ml) and cooled to 0° C. A solution of ammonium cerium nitrate (39.5 mg, 0.072 mmol) in 0.5 ml of water was added dropwise. The reaction mixture was stirred at 0° C. for 5 minutes, then poured to water and extracted with dichloromethane. The organic layer was washed with brine, dried and evaporated to give the titled compound as a white solid (9 mg, dec. 150° C.; m.p. 177° C.).

$^1$H NMR (CDCl$_3$, 250 MHz, Bruker): δ, 2.42 (3H, s, tosyl—CH$_3$), 2.82 (2H, m, 4—CH$_2$), 4.65 (1H, d tr, J=17.6 Hz, 4.1 Hz, 1-HCH$_a$), 4.82 (1H, d tr, J=17.6 Hz, 1.8 Hz, 1-HCH$_e$), 5.52 (1H, tr, J=7.0 Hz, 3—CH), 6.75 (1H, d, J=9.1 Hz, quin-H), 6.81 (1H, d, J=9.1 Hz, quin-H), 7.35 (2H, d, J=8.2 Hz, 3',5'-tosyl-H), 7.83 (1H, s, oxa-H), 7.90 (2H, d, J=8.2 Hz, 2',6'-tosyl-H).

Step 6: 3-(5'-tosyloxazolyl)-5,10-dioxo-1,3,4,5,10-pentahydro-naphtho-[2,3-c]-pyran (BCH-2155)

A solution of tosyloxazolyl pyranoquinone from step 5 herein in 4 ml of toluene and 0.5 ml of tetrahydrofuran (9 mg, 0.023 mmol) was heated with 1-acetoxy 1,3-butadiene (55 μl, 0.47 mmol) at 50° C. for 20 hours. Solvent was evaporated to dryness and the crude product was purified by means of chromatography (Tol:EtOAc=100:15) to give desired titled product as a light colored solid (6.6 mg obtained).

M.P. >240° C.

$^1$H NMR (CDCl$_3$, 250 MHz, Bruker): δ, 2.43 (3H, s, ARCH$_3$), 2.99 (2H, m, 4—CH$_2$), 4.78 (1H, d tr, J=18.8 Hz, 3.3 Hz, 1-HCH$_a$), 4.96 (1H, d, J=18.8 Hz, 1-HCH$_e$), 5.57 (1H, dd, J=8.9 Hz, 5.0 Hz, 3—CH), 7.36 (2H, d, J=8.2 Hz, 3',5'-tosyl-H), 7.75 (2H, m, 7, 8—ArH), 7.85 (1H, s, oxa-H), 7.92 (2H, d, J=8.2 Hz, 2',6'-tozyl-H), 8.11 (2H, m, 6, 9—ArH).

IR (Nicolet 205 FT, film on NaCl plate): cm$^{-1}$, 2955.7, 2921.3, 2854.0, 1662.8 (str), 1592.2, 1508.6, 1398.6, 1334.6, 1319.9, 1298.5, 1147.6, 1106.6, 1086.9, 1013.0, 811.2, 794.8.

EXAMPLE 48

Preparation of (1'S,1S,3R)-1-(3'-trifluoroacetamido-2',3',6'-trideoxy-lyxo-L-hexopyranose)-3-methoxycarbonyl-3-methyl-3,4,5,10-tetrahydro-5,10-dioxo-naphtho-[2,3-c] pyran (BCH-2076)

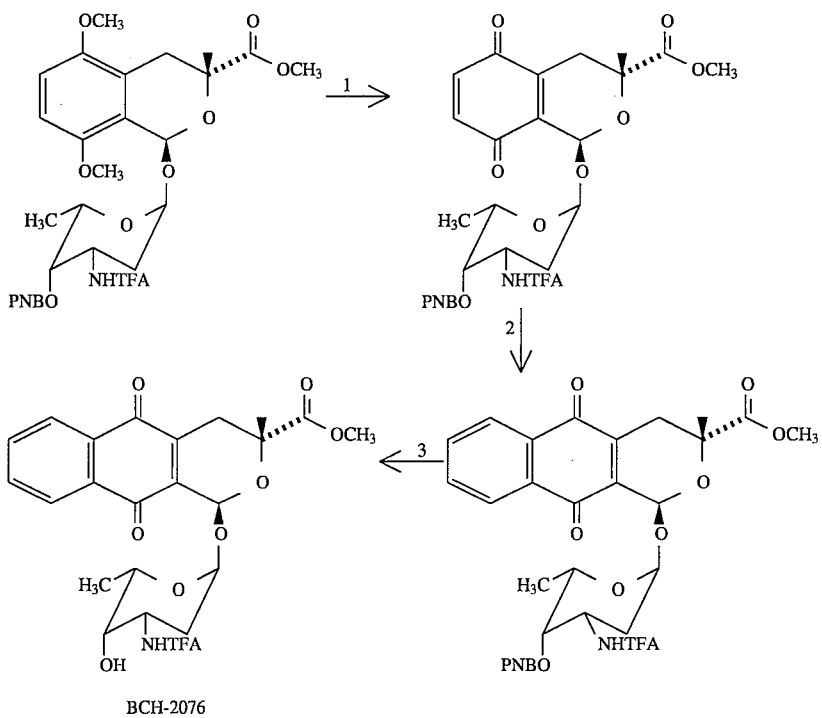

BCH-2076

Step 1: (1'S, 1S, 3R)-1-(4'-p-nitrobenzoyl-3'-trifluoroacetamido-2',3',6'-trideoxy-lyxohexopyranose)-3-methoxy-carbonyl-3-methyl-5,8-dioxo-4,5,8-trihydro-1H-benzo-[2,3-c]-pyran (1S,1S,3R) 1-(2',3',6'-trideoxy-3-trifluoroacetamido-4'-O-p-nitrobenzoyl-L-lyxohexopyranose-5,8-dimethoxy-3-aceto-3-methylisochroman (62 mg, 0.0945 mmol) in acetonitrile (3 ml) was stirred at 0° C. while a solution of ammonium cerium nitrate (165.5 mg, 0.284 mmol) in water (1.5 ml), pre-treated with sodium bicarbonate (15.1 mg, 0.18 mmol), was added dropwise. The solution was stirred for 5 minutes at 0° C. then poured to water and extracted with dichloromethane. The organic layer was dried and evaporated to give desired titled product (40 mg, 0.064 mmol).

$^1$H NMR (CDCl$_3$ 250 MHz, Bruker): δ, 1.27 (3H, d, J=6.5 Hz, 6'-CH$_3$), 1.57 (3H, s, 3-CCH$_3$), 1.91 (1H, dd, J=11.8 Hz, 4.7 Hz, 2'-CH), 2.10 (1H, d tr, J=11.8 Hz, 3.6 Hz, 2'-CH), 2.72 (1H, d, J=17.9 Hz, 4-CH), 2.94 (1H, dd, J=17.9 Hz, 0.9 Hz, 4-CH), 3.75 (3H, s, OCH$_3$), 4.54 (1H, m, 3'-CH), 4.64 (1H, qua, J=6.5 Hz, 5'-CH), 5.40 (1H, s, 4'-CH), 5.65 (1H, d, J=2.4 Hz, 1'-CH), 6.06 (1H, s, 1-CH), 6.52 (1H, d, J=8.2 Hz, NHCOCF$_3$), 6.77 (1H, d, J=10 Hz, Quin-H), 6.83 (1H, d, J=10 Hz, Quin-H), 8.27 (4H, m, PNB).

IR (Nicolet, 205 FT, film on NaCl plate): cm¹, 3336.1, 3083.4 2956.1 2849.7, 1734.5, 1664.2, 1529.4, 1352.7, 1272.9, 1162.7, 989.8, 949.9, 839.70, 721.95.

Step 2: (1'S, 1S, 3R)-1-(4'-p-nitrobenzoyl-3'-trifluoroacetamido-2', 3', 6'-trideoxy-lyxohexopyranose)-3-methoxy-carbonyl-3-methyl-5,10-dioxo-4,5,10-trihydro-1H-naphtho-[2,3-c]-pyran The titled compound was obtained as per procedure described in step 2, example 5, but using the quinone from step 1 herein.

$^1$H NMR (CDCl$_3$ 250 MHz, Bruker): δ, 1.32 (3H, d, J=6.6 Hz, 6'-CH$_3$), 1.95 (1H, dd, J=12.4 Hz, 5.0 Hz, 2'-CH), 2.10 (1H, d tr, J=12.4 Hz, 3.5 Hz, 2'-CH), 2.88 (1H, d, J=18.2 Hz, 4-CH), 3.13 (1H, dd, J=18.2 Hz, 1.0 Hz, 4-CH), 3.75 (3H, s, OCH$_3$), 4.56 (1H, m, 3'-CH), 4.76 (1H, qua, J=6.6 Hz, 5'-CH), 5.45 (1H, s, 4'-CH), 5.72 (1H, d, J=2.0 Hz, 1'-CH), 6.26 (1H, s, 1-CH), 6.45 (1H, d, J=7.1 Hz, NHCOCF$_3$), 7.78 (2H, m, 7, 8-ArH), 8.12 (2H, m, 6, 9-ArH), 8.29 (4H, m, PNB). IR (Nicolet, 205 FT, film on NaCl plate): cm$^{-1}$, 3329.3, 2955.6, 2926.9, 2855.3, 1732.9, 1709.5, 1668.3, 1596.8, 1532.3, 1349.5, 1272.6, 1217.6, 1184.7, 1164.1, 996.5, 952.5, 729.90, 720.30.

Step 3: (1'S, 1S, 3R)-1-(3'-trifluoroacetamido-2', 3', 6'-trideoxy-L-lyxohexopyranose)-5,10-dioxo-4,5,10-trihydro-1H-naphtho-[2,3-c]-pyran (BCH-2076)

The titled compound was obtained from the glycoside from step 2 herein via base hydrolysis as per procedure described in step 3, example 5.

$^1$H NMR (CDCl$_3$, 250 MHz, Bruker): δ, 1.38 (3H, d, J=6.0 Hz, 6'-CH$_3$), 1.60 (3H, s, 3-CCH$_3$), 1.85 (1H, d, J=6.8 Hz, 4'-OH), 1.85 (1H, dd, J=9.4 Hz, 2.6 Hz, 2'-HCH$_a$), 1.96 (1H, d, J=9.4 Hz, 2'-HCH$_e$), 2.87 (1H, d, J=18.8 Hz, 4-HCH$_a$), 3.12 (1H, dd, J=18.8 Hz, 0.6 Hz, 4-HCH$_e$), 3.63 (1H, br d, J=6.8 Hz, 4'-CH), 3.75 (3H, s, OCH$_3$), 4.28 (1H, qua, J=8.8 Hz, 3'-CH), 4.55 (1H, qua, J=6.0 Hz, 5'-CH), 5.54 (1H, s, 1'-CH), 6.21 (1H, s, 1-CH), 6.71 (1H, br d, J=9.4 Hz, NHCOCF$_3$), 7.75 (2H, m, 7, 8-ArH), 8.11 (2H, m, 6, 9-ArH), IR (Nicolet, 205 FT, film on NaCl plate): cm$^{-1}$, 3420.1 (br str), 2955.6, 1718.7, 1668.3, 1595.5, 1377.3, 1329.7, 1287.7, 1161.8, 982.68, 921.12, 730.64.

EXAMPLE 49

(1,3-trans)-anline-(1-methoxy-5,10-dioxo-3,4,5,10-tetrahydro-1H-naphtho-[2,3-c]-pyran)-3-carboxamide (BCH-2041) and (1,3-cis)-anline-(1-methoxy-5,10-dioxo-3,4,5,10-tetrahydro-1H-naphtho-[2,3-c]-pyran)-3-carboxamide (BCH-2042)

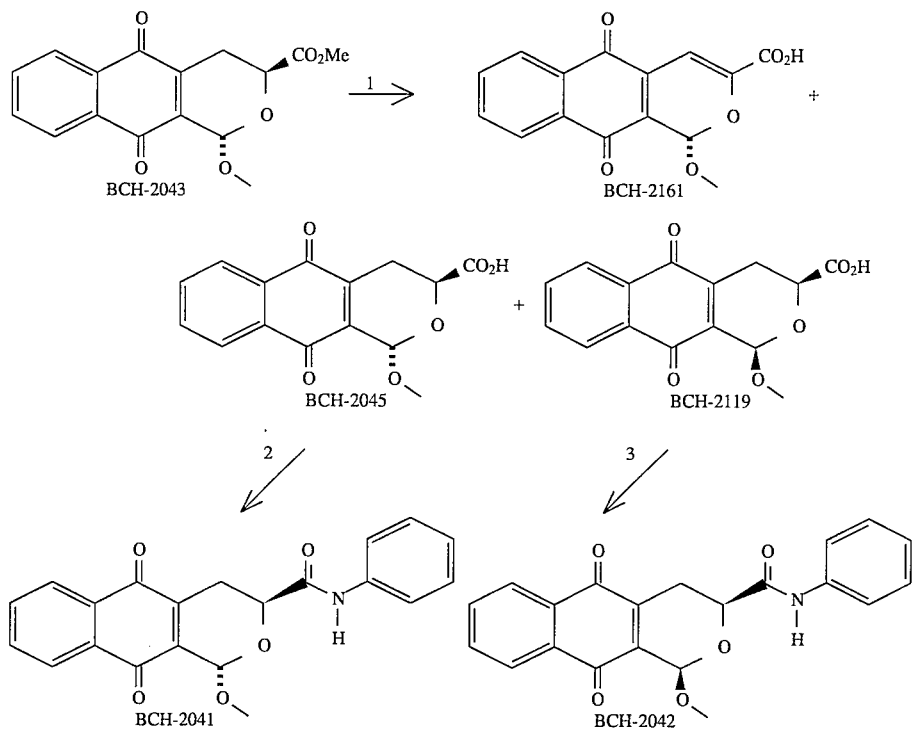

Step 1:

The compound from step 3, example 16, (21 mg, 0.0695 mmol) was dissolved in acetonitrile (10 ml) and then cooled to 0° C. NaOH (0.1N, 1.4 ml, 0.14 mmol) solution was then added slowly. After 10 minutes, the brown solution was poured to water, extracted with ethyl acetate. The aqueous layer was acidified with dilute HCl and extracted with ethyl acetate. The organic layer containing acid was dried and evaporated to give a mixture of 3 products (18 mg). Chromatography (CHCl$_3$/MeOH/HOAc=100:15:2) allowed separation of the 3 compounds. One of the products was the same as the one obtained in step 6, example 16, and had:

$^1$H NMR (CD$_3$COCD$_3$, 250 MHz, Bruker): δ, 3.58 (3H, s, OCH$_3$), 6.36 (1H, s, 1-CH), 7.22 (1H, s, 4-CH), 7.91 (2H, m, 7, 8-ArH), 8.12 (2H, m, 6, 9-ArH).

The second product (1,3-trans)-1-methoxy-3-carboxyl-5, 10-dioxo-3,4,5,10-tetrahydro-1H-naphtho-[2,3-c]-pyran, BCH-2045 had:

$^1$H NMR (CD$_3$SOCD$_3$ 250 MHz, Bruker): δ, 2.55 (1H, dd, J=18.5 Hz, 12.4 Hz, 4-HCH$_a$), 2.88 (1H, dd, J=18.5 Hz, 3.5 Hz, 4-HCH$_e$), 3.47 (3H, s, OCH$_3$), 4.49 (1H, dd, J=12.4

Hz, 3.5 Hz, 3-CH), 5.55 (1H, s, 1-CH), 7.88 (2H, m, 7, 8-ArH), 8.00 (2H, m, 5, 9-ArH).

IR (Nicolet, 205 FT, film on NaCl plate): cm$^{-1}$, 3549.2~3183.8, 2922.8 1722.1, 1289.0, 1107.4, 1012.3, 951.08, 808.9, 793.5.

The third product: (1,3-cis)-1-methoxy-3-carboxyl-5,10-dioxo-3,4,5,10-tetrahydro-1H-naphtho-[2,3-c]-pyran, (BCH-2119), had:

$^1$H NMR (CD$_3$SOCD$_3$ 250 MHz, Bruker): δ, 1.28 (1H, dd, J=15.3 Hz, 11.5 Hz, 4-HCH$_a$), 2.58 (1H, dd, J=11.5 Hz, 2.9 Hz, 4-HCH$_e$), 3.45 (3H, s, OCH$_3$), 4.17 (1H, dd, J=11.5 Hz, 2.9 Hz, 3-CH), 5.62 (1H, s, 1-CH), 7.89 (4H, m, 6, 7, 8, 9-ArH).

Step 2: (1,3- trans)-1-methoxy-3-N-anilinylcarbonyl-5,10-dioxo-3,4,5,10-tetrahydro-1H-naphtho-[2,3-c]-pyran, BCH-2041:

A solution of acid from step 1 herein (20 mg, 0.069 mmol) in THF (4 ml) was cooled to 0° C. To the solution was added DMF (1 μl, as a catalyst) and then oxalyl chloride (12 μl, 0.138 mmol). The mixture was stirred at 0° C. for 45 minutes and at room temperature for 20 minutes. Solvent was evaporated. The residue was redissolved in. methylene chloride and then evaporated. The residue was dissolved again in methylene chloride (4 ml) and half of the volume was taken for coupling with aniline (4 μl, 0.044 mmol) as follows: To the ice-cold solution of the acid chloride was added aniline (1 eq.) in 1 ml of methylene chloride. The reaction mixture was stirred for 10 minutes. It was poured to water and extracted with methylene chloride. The organic layer was dried and evaporated to give a crude product which was purified by recrystallization from methylene chloride and hexane. The desired titled product was obtained (11 mg) as a light yellow solid.

M.P. 183°–184° C.

1H NMR (CDCl$_3$, 250 MHz, Bruker): δ, 2.63 (1H, dd, J=19.4 Hz, 12.5 Hz, 1-HCH$_a$), 3.30 (1H, dd, J=19.3 Hz, 4.2 Hz, 1-HCH$_e$), 3.67 (3H, s, OCH$_3$), 4.74 (1H, dd, J=12.5 Hz, 4.5 Hz, 3-CH), 5.77 (1H, s, 1-CH), 7.16 (1H, tr, J=8.5 Hz, 4'-Ani-H), 7.47 (2H, tr, J=8.5 Hz, 3', 5'-Ani-H), 7.52 (2H, d, J=8.5 Hz, 2',6'-Ani-H), 7.75 (2H, m, 7, 8-ArH), 8.10 (2H, m, 6, 9-ArH), 8.31 (1H, s, NHCO).

IR (Nicolet 205 FT, film on NaCl plate): cm$^{-1}$, 3278.8, 2923.0, 1665.0 1593.4, 1533.0, 1445.7, 1798.0, 1060.7, 960.0, 755.6, 688.2, 679.0.

Step 3: (1,3-cis) -1-methoxy-3-N-anilinylcarbonyl-5,10-dioxo-3,4,5,10-tetrahydro-1H-naphtho-[2,3-c]-pyran, BCH-2042, A similar to the procedure described previously in step 2, the cis acid from step 1 herein was converted to the titled product.

M.P. 217°–219° C.

$^1$H NMR (CDCl$_3$, 250 MHz, Bruker): δ, 2.49 (1H, dd, J=15.6 Hz, 11.2 Hz, 4-HCH$_a$), 3.08 (1H, dd, J=15.6 Hz, 3.2 Hz, 4-HCH$_e$), 3.65 (3H, s, OCH$_3$), 4.50 (1H, dd, J=11.2 Hz, 3.2 H, 3-CH), 5.94 (1H, s, 1-CH), 7.14 (1H, tr, J=7.6 Hz, p-Ani-H), 7.35 (2H, tr, J=7.6 Hz, m-Ani-H), 7.56 (2H, d, J=7.6 Hz, O-Ani-H), 7.78 (2H, m, 7, 8 -ArH), 8.00 (2H, m, 6, 9-ArH), 8.21 (1H, s, NHCO).

IR (Nicolet, 205 FT, film on NaCl plate): cm$^{-1}$, 3353.5, 3052.9, 2928.1, 2853.9, 1694.6, 1597.5, 1531.8, 1443.3, 1300.6, 1172.1, 1117.8, 1060.7, 1043.6, 1026.5, 906.7, 753.6, 712.5, 692.6.

EXAMPLE 50

Preparation of (1S, 1R, 3S)-1-(3'-trifluoroacetamido-2',3',6'-trideoxy-lyxohexpyranose)-3-(5"-tosyloxazolyl)-3,4,5,10-tetrahydro-5,10-dioxo-naphtho-[2,3-c]pyran (BCH-2150)

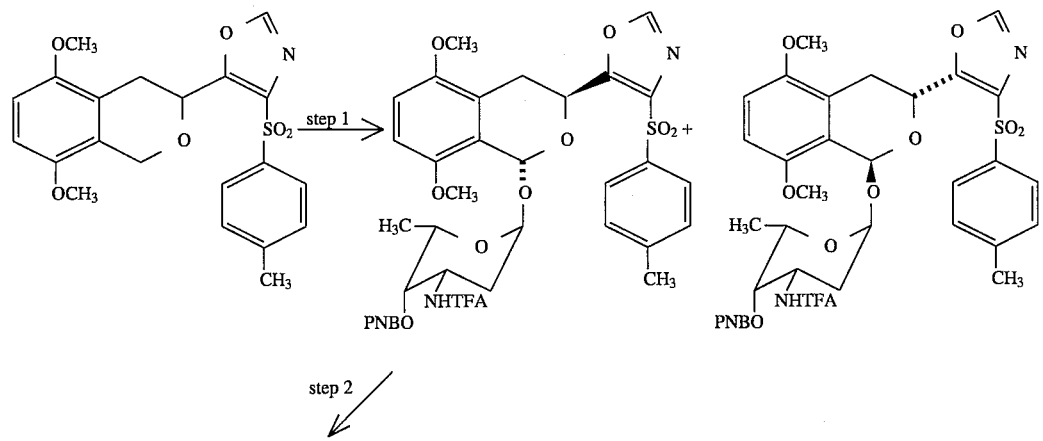

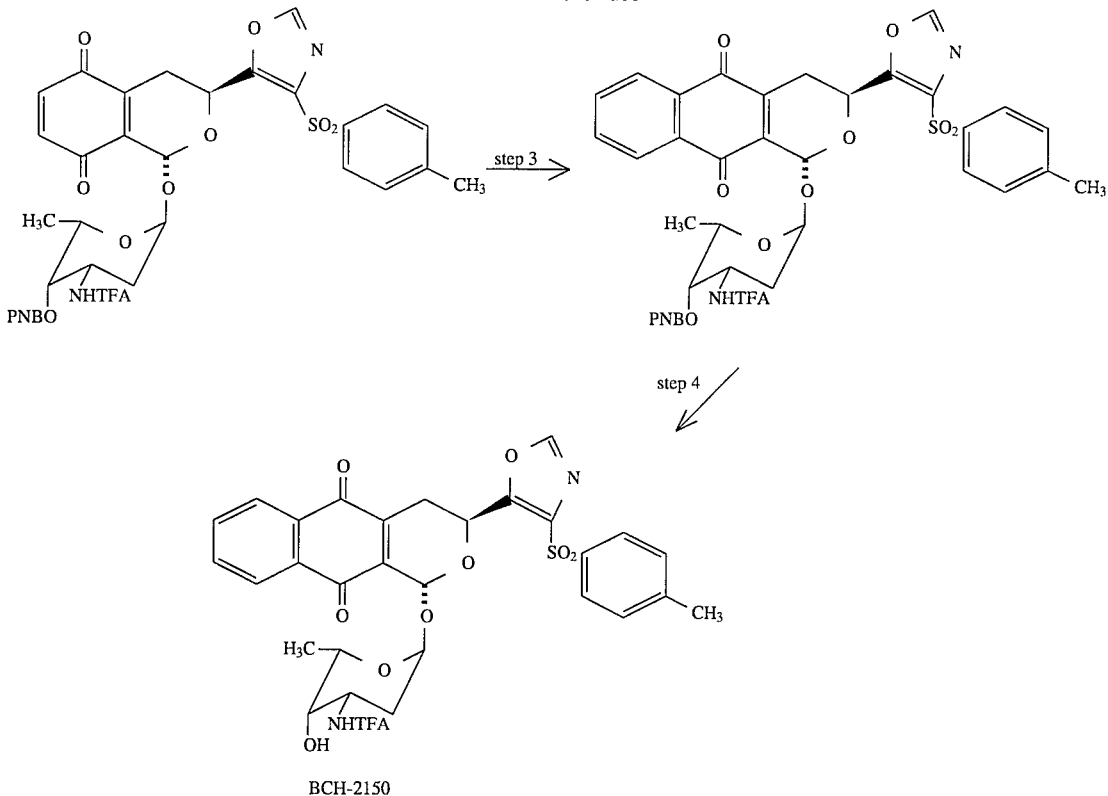

BCH-2150

Step 1: (1'S, 1S, 3R)-1-(4'-p-nitrobenzoyl-2',3',6'-trideoxy-3'-trifluoroacetamido-L-lyxohexopyranose)-3-(5"-tosyloxazolyl)-5,8-dimethoxy isochroman To the compound from step 4, example 47, (50 mg, 0.120 mmol) in dichloromethane (15 ml) stirred with 5'-p-nitrobenzoyl-3',4',7'-trideoxy- 3'-trifluoroacetamido-L-lyxohexopyranose (49 mg, 0.125 mmol) was added 1,2-dichloro-4,5-dicyano-benzoquinone (35.6 mg, 0.157 mmol). The resulting mixture was stirred for 18 hours at 40° C. Solvent was evaporated and the crude product was chromatographed (hexane/ethyl acetate=3/2) to give the titled compound (17 mg) and the (1'S, 1R, 3S) diastereomer (12 mg).

The titled compound had:
$^1$H NMR (acetone-$d_6$, 250 MHz, Bruker): δ, 1.27 (3H, d, J=5.9 Hz, 6'-$CH_3$), 2.14–2.30 (2H, m, 2'-$CH_2$), 2.44 (3H, s, tosyl-$CH_3$), 3.01 (2H, d, J=6.5 Hz, 4-$CH_2$), 3.82 (3H, s, $OCH_3$), 3.92 (3H, s, $OCH_3$), 4.65 (1H, m, 3'-CH), 4.86 (1H, qua, J=5.9 Hz, 5'-CH), 5.71 (1H, d, J=2.4 Hz, 4-CH), 6.17 (1H, tr, J=6.5 Hz, 3-CH), 6.24 (1H, s, 1-CH), 6.95 (2H, m, 6, 7-ArH), 7.48 (2H, d, J=7.4 Hz, 3",5"-tosyl-H), 7.95 (2H, d, J=7.4 Hz, 2",6"-tosyl-H), 8.38 (4H, m, PNB), 8.37 (1H, s, oxa-H), 8.66 (1H, d, J=7.4 Hz, $NHCOCF_3$).

The (1'S, 1R, 3S) -1- (4'-p-nitrobenzoyl-2',3',6'-trideoxy-3'-trifluoroacetamido-L-lyxohexopyranose)-3-(5"-tosyloxazolyl)-5,8-dimethoxy isochroman had:
$^1$H NMR (acetone-$d_6$, 250 MHz, Bruker): δ, 0.80 (3H, d, J=6.8 Hz, 6'-$CH_3$), 2.19 (1H, m, 2'-$HCH_a$), 2.48 (1H, d tr, J=11.8 Hz, 4.1 Hz, 2'-$HCH_e$), 2.46 (3H, s, tosyl-$CH_3$), 2.88 (1H, dd, J=17.6 Hz, 11.8 Hz, 4-$HCH_a$), 3.04 (1H, dd, J=17.6 Hz, 4.4 Hz, 4-$HCH_e$), 3.83 (3H, s, $OCH_3$), 3.86 (3H, s, $OCH_3$), 4.42 (1H, qua, J=6.8 Hz, 5'-CH), 4.84 (1H, m, 3'-CH), 5.48 (1H, s, 4'-CH), 5.58 (1H, d, J=3.5 Hz, 1'-CH), 6.01 (1H, s, 1-CH), 6.92 (1H, d, J=6.5 Hz, ArH), 6.96 (1H, d, J=6.5 Hz, ArH), 7.54 (2H, d, J=9.1 Hz, 3", 5"-tosyl-H), 8.06 (2H, d, J=9.1 Hz, 2", 6"-tosyl-H), 8.35 (1H, s, oxa-H), 8.49 (4H, m, PNB), 8.62 (1H, d, J=6.8 Hz, $NHCOCF_3$).

Step 2: (1'S, 1S, 3R)-1-(4'-p-nitrobenzoyl-2',3',6'-trideoxy-3'-trifluoroacetamido-L-lyxohexopyranose)-3-(5"-tosyloxazolyl)-5,8-dioxo-3,4,5,8-tetrahydrobenzo-[2,3-c]-pyran.

The compound from step 1 herein (17 mg, 0.021 mmol) in acetonitrile (2 ml) was cooled to 0° C. and ammonium cerium nitrate (35.5 mg, 0.0648 mmol, pretreated with sodium bicarbonate, 3.6 mg, 0.042 mmol) was added dropwise. The reaction mixture was stirred for 15 minutes at 0° C. then poured to water. It was extracted with dichloromethane. The organic phase was washed with brine, dried (over sodium sulfate) and evaporated to give a crude product which was purified on silica gel (hexane/EtOAc=2:1) to give the desired titled product (7 mg).

$^1$H NMR (acetone-$d_6$, 250 MHz, Bruker): δ, 1.04 (3H, d, J=6.5 Hz, 6'-$CH_3$), 2.12–2.35 (2H, m, 2'-CH2), 2.45 (3H, s, tosyl-$CH_3$), 2.80–2.93 (2H, m, 4-$CH_2$), 4.55 (1H, qua, J=6.5 Hz, 5'-CH), 4.86 (1H, m, 3'-CH), 5.49 (1H, s, 4'-CH), 5.61 (1H, d, J=2.1 Hz, 1'-CH), 5.85 (1H, s, 1-CH), 6.12 (1H, dd, J=10.6 Hz, 4.7 Hz, 3-CH), 6.80 (1H, d, J=10.6 Hz, Quin-H), 6.85 (1H, d, J=10.6 Hz, Quin-H), 7.48 (2H, d, J=8.8 Hz, 3", 5"-tosyl-H), 7.88 (1H, s, oxa-H), 7.94 (2H, d, J=8.8 Hz, 2", 6"-tosyl-H), 8.28 (4H, m, PNB).

Step 3: (1'S, 1R, 3S)-1-(4'-p-nitrobenzoyl-3-trifluoroacetamido-2',3',6'-trideoxy-L-lyxohexopyranose)-3-(5"-tosyl-oxazolyl)-5,10-dioxo-3,4,5,10-tetrahydro-1H-naphtho-[2,3-c]-pyran The compound from step 2 herein (9 mg, 0.012 mmol) was stirred with 1-acetoxy-1,3-butadiene (28 μl, 0.236 mmol) in toluene (4 ml) and THF (0.5 ml) at 50° C. for 18 hours. Solvent was evaporated and the crude product was chromatographed (toluene/ethyl acetate=5/1) to give the desired titled product (4.8 mg).

$^1$H NMR ($CDCl_3$ 250 MHz, Bruker): δ, 1.06 (3H, d, J=6.2 Hz, 6'-$CH_3$), 2.00 (1H, d tr, J=11.5 Hz, 2.9 Hz, 2'-$HCH_a$), 2.25 (1H, dd, J=11.5 Hz, 4.4 Hz, 2'-$HCH_e$), 2.44 (3H, s, tosyl-CH₃), 2.98 (1H, d, J=5.6 Hz, 4-CH), 2.99 (1H, d, J=11.0 Hz, 4-CH), 4.60 (1H, qua, J=6.2 Hz, 5'-CH), 4.87 (1H, m, 3'-CH), 5.40 (1H, s, 4'-CH), 5.72 (1H, d, J=2.0 Hz, 1'-CH), 6.05 (1H, s, 1-CH), 6.19 (1H, dd, J=11.0 Hz, 5.6 Hz, 3-CH), 6.66 (H, d, J=6.5 Hz, NHCOCF₃), 7.49 (2H, d, J=8.8 Hz, 3", 5"-tosyl-H), 7.79 (2H, m, 7, 8-ArH), 7.90 (1H, s, oxa-H), 7.95 (2H, d, J=8.8 Hz, 2",6"-tosyl-H), 8.13 (2H, m, 6, 9-ArH), 8.31 (4H, m, PNB).

Step 4: (1'S, 1R, 3S)-2',3',6'-trideoxy-3'-trifluoroacetamido-L-lyxohexopyranose-3-[5'-tosyloxazolyl]-5,10-dioxo-3,4,5,10-tetrahydro-1H-naphtho-[2,3-c]-pyran (BCH-2150)

EXAMPLE 51

Preparation of (1'S, 1S, 3R)-1-(3'trifluoroacetamido-2',3',6'-trideoxy-lyxo-L-hexopyranose)-3-(5"-tosyloxazolyl)-3,4,5,10-tetrahydro-5,10-dioxo-naphtho-[2,3-c]pyran (BCH-2151)

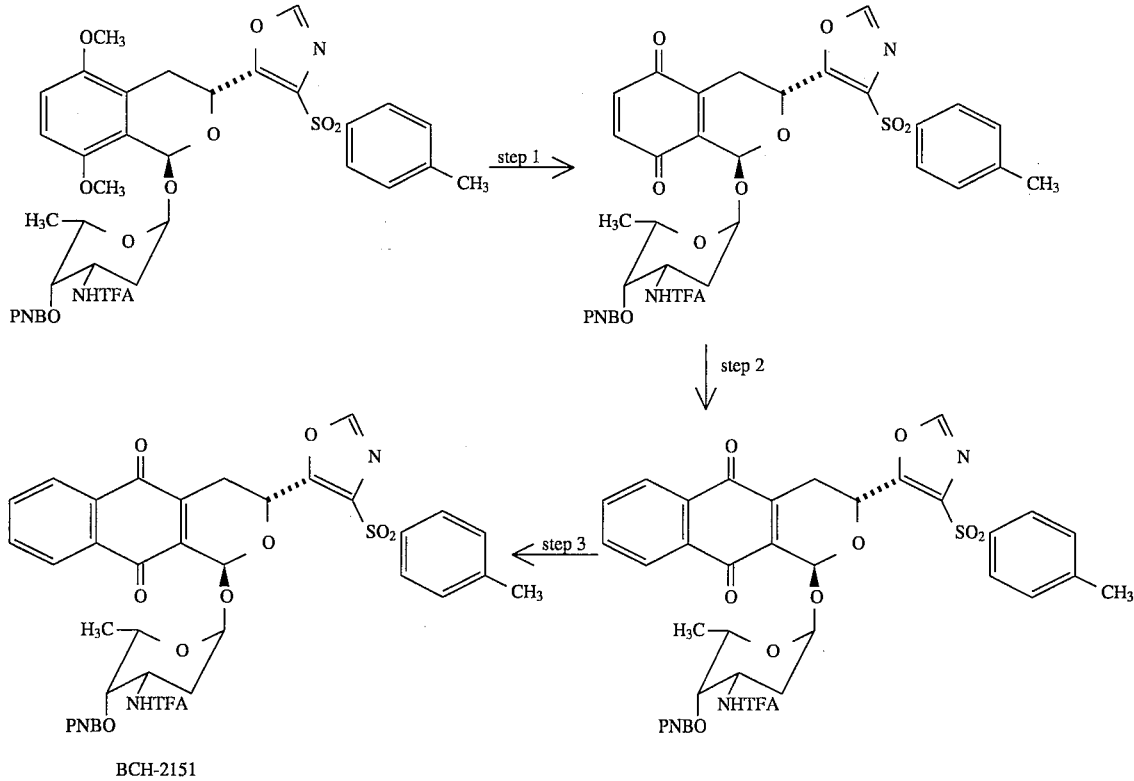

BCH-2151

To the compound from step 3 herein (4.8 mg, 5.92 mmol) in THF (0.5 ml) and methanol (1.5 ml) cooled to 0° C. was added sodium methoxide (4.37M, 1.4 μl, 5.92 mmol). After 5 minutes, the reaction was quenched with dilute hydrochloride acid and extracted with methylene chloride. The organic layer was dried (over Na₂SO₄) and evaporated to give a crude product which was purified on TLC (CHCl₃:MeOH= 100:7) to give desired titled product as an off-white solid (1.3 mg).

M.P. 130°–135° C.

¹H NMR (CDCl₃, 250 MHz, Bruker): δ, 1.13 (3H, d, J=6.5 Hz, 6'-CH₃), 1.78 (1H, tr d, J=11.2 Hz, 2'-HCH_a), 2.05 (1H, m, 2'-HCH_e, due to solvent overlap, this is an estimation), 2.43 (3H, s, tol-CH₃), 2.92 (1H, d, J=5.9 Hz, 4-HCH_a), 2.94 (1H, d, J=10.5 Hz, 4-HCH_e), 3.71 (1H, m, 4'-OH), 4.20 (1H, dd, J=5.9 Hz, 3–2 Hz, 4'-OH), 4.47 (1H, qua, J=6.5 Hz, 5'-CH₃), 4.58 (1H, m, 3'-CH), 5.55 (1H, d, J=3.0 Hz, 1-CH), 5.99 (1H, s, 1-CH), 6.16 (1H, dd, J=10.6 Hz, 5.9 Hz, 3-CH), 6.77 (1H, d, J=10.6 Hz, NHCOCF₃ ), 7.36 (2H, d, J=8.8 Hz, tosyl-H), 7.79 (2H, m, 7, 8-ArH), 7.90 (1H, s, oxa-H), 7.91 (2H, d, J=8.8 Hz, tosyl-H), 8.11 (2H, m, 6, 9-ArH).

IR (Nicolet 205 FT, film on NaCl plate): cm⁻¹, 3379.1, 2956.4, 2927.8, 2854.7, 1716.9, 1669.3, 1335.6, 1297.4, 1148.0, 985.2.

Step 1: (1'S, 1S, 3R)-1-(4'-p-nitrobenzoyl-2',3',6'-trideoxy-3'-trifluoroacetamido-L-lyxohexopyranose)-3-(5"-tosyloxazolyl)-5,8-dioxo-3,4,5,8-tetrahydrobenzo-[2,3-c]-pyran Starting with the (1'S, 1S, 3R) diastereomer from step 1, example 50, (12 mg, 0.015 mmol), using the same materials (ammonium cerium nitrate, 25 mg, 0.046 mmol; NaHCO₃, 2.55 mg, 0.0304 mmol; acetonitrile, 1.5 ml; H₂O, 0.4 ml) and following the same procedures as described in step 2, example 50, the desired titled product was obtained (9 mg).

¹H NMR (acetone-d₆, 250 MHz, Bruker): δ, 1.27 (3H, d, J=6.6 Hz, 6'-CH₃), 2.20 (2H, m, 2'-CH₂), 2.45 (3H, s, tosyl-CH₃), 2.95 (1H, d, J=6.8 Hz, 4-CH), 2.95 (1H, d, J=8.8 Hz, 4-CH), 4.56 (1H, m, 3'-CH), 4.74 (1H, qua, J=6.6 Hz, 5'-CH), 5.53 (1H, s, 4'-CH), 5.68 (1H, d, J=2.9 Hz, 1'-CH), 6.01 (1H, s, 1-CH), 6.09 (1H, dd, J=8.8 Hz, 6.8 Hz, 3-CH), 6.93 (1H, d, J=11.8 Hz, Quin-H), 6.96 (1H, d, J=11.8 Hz, Quin-H), 7.49 (2H, d, J=8.8 Hz, 3", 5"-tosyl-H), 7.93 (2H, d, J=8.8 HZ, 2", 6"-tosyl-H), 8.36 (1H, s, oxa-H), 8.39 (4H, m, PNB), 8.68 (1H, d, J=8.8 Hz, NHCOCF₃ ).

Step 2: (1'S, 1S, 3R) -1- (4'-p-nitrobenzoyl-3-trifluoroacetamido-2',3',6'- trideoxy-L-lyxohexopyranose)-3-(5"- tosyloxazolyl)-5,10-dioxo-3,4,5,10-tetrahydro-1H-naphtho-[2,3-c]-pyran The compound from step 2 herein (7 mg, 0.009 mmol) was reacted with 1-acetoxy-1,3-butadiene (21 μl, 0.184 mmol) in toluene (3 ml) at 50° C. for 18 hours. The solvent was evaporated to give a crude product. After chromatography (toluene/ethyl acetate=5:1) desired titled product was obtained (6.4 mg).

¹H NMR (CDCl₃ 250 MHz, Broker): δ, 1.34 (3H, d, J=7.1 Hz, 6'-CH₃), 2.15 (1H, d tr, J=12.9 Hz, 4.1 Hz, 2'-HCH$_a$), 2.32 (1H, dd, J=12.9 Hz, 4.1 Hz, 2'-HCH$_e$), 2.45 (3H, s, tosyl-CH₃), 2.96 (1H, dd, J=18.2 Hz, 4.1 Hz, 4-HCH$_a$), 3.13 (1H, dd, J=18.2 Hz, 11.2 Hz, 4-HCH$_e$), 4.64 (1H, m, 3'-CH), 4.77 (1H, qua, J=7.1 Hz, 5'-CH), 5.52 (1H, s, 4'-CH), 5.76 (1H, d, J=2.0 Hz, 1'-CH), 6.08 (1H, dd, J=11.2 Hz, 4.1 Hz, 3-CH), 6.20 (1H, s, 1-CH), 6.21 (1H, m, HNCOCF₃), 7.37 (2H, d, J=8.2 Hz, 3", 5"-tosyl-H), 7.71 (2H, m, 7, 8-ArH), 7.89 (2H, d, J=8.2 Hz, 2", 6"-tosyl-H), 7.90 (1H, s, oxa-H), 8.15 (1H, m, 6, 9-ArH), 8.31 (4H, m, PNB).

7.78 (2H, m, 7, 8-ArH), 7.87 (1H, s, oxa-H), 7.88 (2H, d, J=8.8 Hz, tosyl-H), 8.12 (2H, m, 6, 9-ArH).

IR (Nicolet 205 FT, film on NaCl plate): cm⁻¹, 3368.3 2961.8, 2930.2, 2848.9, 1715.0, 1669.9, 1463.0, 1332.8, 1289.0, 1153.4, 975.46.

EXAMPLE52

Preparation of (1,3-trans)-1-methoxy-3-(3'-aminothiazolyl)-5,10-dioxo-3,4,5,10-tetrahydro-1H-naphtho [2,3-c]-pyran (BCH-1616) and (1,3-trans)-1-methoxy-3-dimethoxyphosphonoacetyl-5,10-dioxo-3,4,5,10-tetrahydro-1H-naphtho [2,3-c]-pyran (BCH-1674)

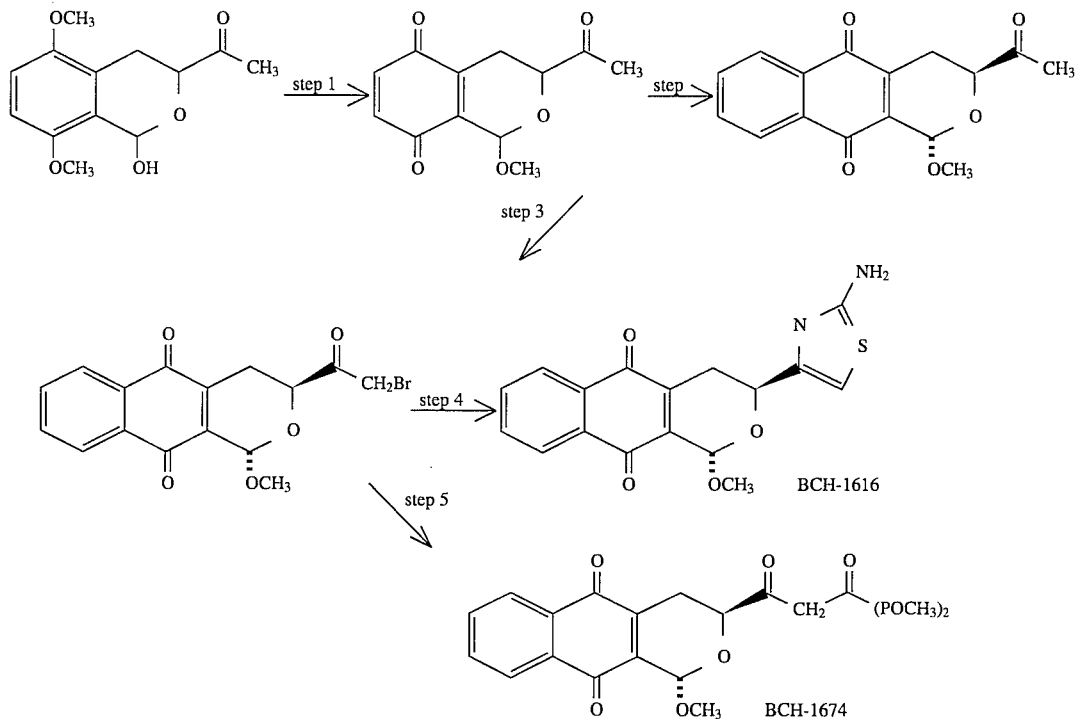

Step 1: 1-methoxy-3-acetyl-5,8-dioxo-3,4,5,8-tetrahydrobenzo-[2,3-c]-pyran

A sample of 5,8-dimethoxy-1-hydroxy-3-acetoisochroman (200 mg, 0.79 mmol) in MeOH (10 ml) was stirred at room temperature while a solution of CAN (2.16 g, 3.95 mmol) in wetter (9 ml) was added dropwise. After 5 minutes, the reaction mixture was poured to water and then extracted with methylene chloride. The organic layer was dried (over sodium sulfate), and evaporated to give a yellow sticky solid (157 mg). ¹H NMR showed that desired titled product was obtained with 89% purity.

¹H NMR (CDCl₃, 250 MHz Bruker), δ: 2.28 (s, 3H, COCH₃), 2.35 (dd, 1H, J=20.5 Hz, 12.1 Hz, 4-Ha), 2.78 (dd, 1H, J=20.5 Hz, 4.3 Hz, 4-He), 3.56 (s, 3H, OCH₃), 4.44 (dd, 1H, J=12.1 Hz, 4.3 Hz, 3-H), 5.46 (s, 1H, 1-H), 6.73 (m, 2H, 6.7-quinone).

Step 2: 1-methoxy-3-acetyl-5,10-dioxo-3,4,5,10-tetrahydro-1H-naphtho-[2,3-c]-pyran The bicyclic quinone from step 1 herein (157 mg, 0.66 mmol) was stirred with 1-acetoxy-1,3-butadiene (632 μl, 5.32 mmol) in toluene (20 ml) at 40° C. for 16 hours. Solvent was evaporated and the crude product was chromatographed Step 3: (1'S, 1S, 3R) -2',3',6'-trideoxy-3'-trifluoroacetamido-L-lyxohexopyranose-3-[5'-tosyloxazolyl)]-5,10-dioxo-3,4, 5,10-tetrahydro-1H-naphtho-[2,3-C]-pyran (BCH-2151)

To PNB derivative from step 2 herein (6.4 mg, 0.0079 mmol) stirred in tetrahydrofuran (0.5 ml) and methanol (1.5 ml) at 0° C. was added sodium methoxide (4.373M, 1.8 μl, 0.0079 mmol). After 5 minutes, the pink solution was quenched with dilute HCl. The product was extracted with methylene chloride. The organic layer was dried and evaporated to give a crude product which was purified by thin-layer-chromatography (CHCl₃:MeOH=100:7) to desired titled product as an off-white solid (0.8 mg).

M.P. 100°–105° C.

¹H NMR (CDCl₃, 250 MHz, Bruker): δ, 1.41 (3H, d, J=5.9 Hz, 6'-CH₃), 1.92 (1H, tr d, J=11 Hz, 3.5 Hz, 2'-HCH$_a$, estimation), 2.20 (1H, m, 2'-HCH$_e$, estimation), 2.44 (3H, s, tol-CH₃), 2.95 (1H, dd, J=18.5 Hz, 4.7 Hz, 4-HCH$_e$), 3.12 (1H, dd, J=18.5 Hz, 11.2 Hz, 4-HCH$_a$), 4.00 (1H, m, 4'-CH), 4.37 (m, 1H, 3'-CH), 4.60 (1H, qua, J=5.9 Hz, 5'-CH), 5.10 (1H, br s, 4'-OH, estimation), 5.58 (1H, d, J=3.5 Hz, 1'-CH), 6.05 (1H, dd, J=11.2 Hz, 4.7 Hz, 3-CH), 6.15 (1H, s, 1-CH), 6.66 (1H, m, NHCOCF₃), 7.36 (2H, d, J=8.8 Hz, tosyl-H), (toluene:EtOAc=100:25) to give desired titled tricyclic quinone as a yellow solid (190 mg).

M.P. 169.8°–170.8° C.

$^1$H NMR (CDCl$_3$, 250 MHz Broker), δ: 2.34 (s, 3H, COCH$_3$), 2.53 (dd, 1H, J=20.7 Hz, 10.7 Hz, 4-Ha), 3.00 (dd, 1H, J=10.7 Hz, 4.3 Hz, 4-He), 3.63 (s, 3H, OCH$_3$), 4.54 (dd, 1H, J=10.7 Hz, 4.3 Hz, 3-H), 5.66 (s, 1H, 1-H), 7.73 (m, 2H, 7.8-ArH), 8.06 (m, 2H, 6.8-ArH).

IR (Nicolet 205 FT, film on NaCl plate), cm$^{-1}$: 2923.4, 2827.6, 1717.7, 1668.2, 1637.3, 1597.1, 1368.3, 1331.3, 1300.3, 1281.8, 1179.8, 1105.6, 1083.9, 1046.8, 875.5, 799.8, 714.2, 686.1.

Step 3: 3-bromoacethyl-1-methoxy-5,10-dioxo-3,4,5,10-tetrahydro-1H-naphtho-[2,3-c]-pyran To a solution of product from step 2 herein (50 mg, 0.175 mmol) in THF (3 ml) at room temperature was added pyridinium hydrobromide perbromide (1.3 eq.) in THF (2 ml). The mixture was stirred for 45 minutes at room temperature. It was poured to water and extracted with methylene chloride. The organic layer was dried and evaporated to give a product. TLC and $^1$H NMR both showed that the desired titled product (76 mg) was obtained with purity >90%.

M.P. 169.8°–170.8° C.

$^1$H NMR (CDCl$_3$, 250 MHz Bruker), δ: 2.53 (dd, 1H, J=20.3 Hz, 11.0 Hz, 4-Ha), 3.02 (dd, 1H, J=20.3 Hz, 4.1 Hz, 4-He), 3.64 (s, 3H, OCH$_3$), 4.15 (d, 1H, J=12.7 Hz, BrCH$_A$H), 4.35 (d, 1H, J=12.7 Hz, Br CHH$_B$), 4.84 (dd, 1H, J=11.0 Hz, 4.2 Hz, 3-H), 5.65 (s, 1H, 1-H), 7.72 (m, 2H, 7.8-ArH), 8.02 (m, 2H, 6.9-ArH).

Step 4: (1,3-trans)-1-methoxy-3-(3'-aminothiazolyl)-5,10-dioxo-3,4,5,10-tetrahydro-1H-naphtho [2,3-c]pyran (BCH-1616)

Bromomethyl ketone from step 3 herein (20 mg, 0.054 mmol) was stirred with thiourea at room temperature for 3.5 hours in ether (2 ml) and dichloromethane (2 ml). It was poured to sat. sodium bicarbonate and extracted with dichloromethane. The organic layer was evaporated to give crude product which was chromatographed (MeOH:CHCl$_3$:HOAc=4:100:1) to give desired titled product (5.3 mg). A polar by-product was also obtained (8 mg).

$^1$H NMR (CDCl$_3$, 250 MHz Bruker), δ: 2.77 (1H, dd, J=18.8 Hz, 11.8 Hz, 4-HCH$_a$), 3.00 (1H, dd, J=18.8 Hz, 5.2 Hz, 4-HCH$_e$), 3.63 (3H, s, OCH$_3$), 5.03 (1H, dd, J=11.8 Hz, 5.2 Hz, 3-CH), 5.67 (1H, s, 1-CH), 6.53 (1H, s, thia-H), 7.73 (2H, m, 6, 9-ArH), 8.08 (2H, m, 7, 8-ArH).

IR (Nicolet 205 FT, film on NaCl plate), cm$^{-1}$: 3429.8, 3346.7, 3130.7, 2957.8, 2921.3, 2854.8, 1664.9, 1641.6, 1591.7, 1521.9, 1455.5, 1408.9, 1327.1, 1294.1, 1102.0, 1039.9, 731.92, 708.07.

Step 5: 1-methoxy-3-dimethyl phosphonoacetyl-5,10-dioxo-3,4,5,10-tetrahydro-1H-naphtho-[2,3-c]-pyran (BCH-1674)

A solution of bromomethylketone from step 3 herein (10 mg, 0.027 mmol) was refluxed with trimethylphosphite (3.54 μl, 0.03 mmol) and sodium iodide (0.2 mg, 0.05 mmol) in THF at 70° C. overnight. Solvent was evaporated and the brown residue was chromatographed (CHCl$_3$:MeOH 50:1) to give desired titled product as a light-colored solid (2 mg).

$^1$H NMR (CDCl$_3$, 250 MHz, Bruker): δ, 2.60 (1H, dd, J=19.8 Hz, 11.6 Hz 4-HCH$_a$), 2.94 (1H, dd, J=19.8 Hz, 3.5 Hz, 4-H$_e$CH), 3.62 (3H, s, 1-OCH$_3$), 3.85 (3H, s, POCH$_3$), 3.88 (3H, s, POCH$_3$), 4.59 (1H, dd, J=11.6 Hz, 3.5 Hz, 3-CH), 5.02 (1H, br s, CHP), 5.15 (1H, br s, CHP), 5.62 (1H, s, 1-CH), 7.73 (2H, m, 6, 9-ArH), 8.08 (2H, m, 7, 8-ArH).

EXAMPLE 53

Preparation of (1'S, 1R, 3S)-1-(3-trifluoroacetamido-2',3',6'-trideoxy-L-lyxohexopyranose)-3-methoxycarbonyl-3-methyl-3,4,5,10-tetrahydro-5,10-dioxo-1H-naphtho-[2,3-c]pyran (BCH-2077)

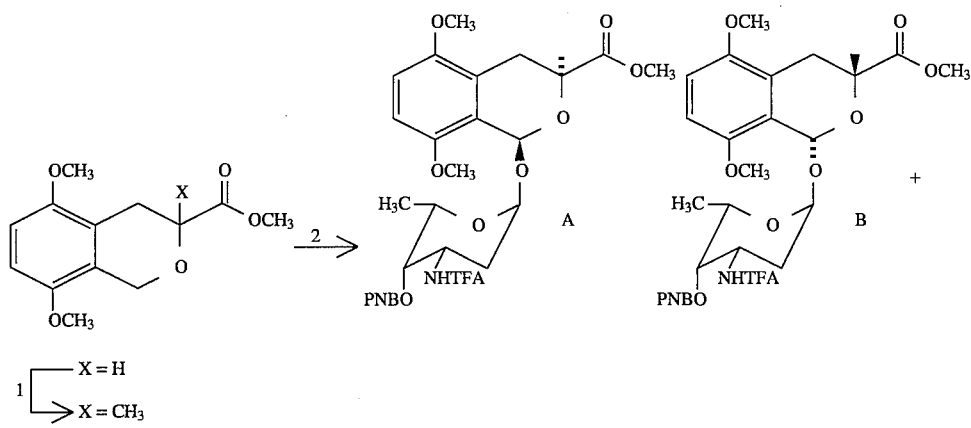

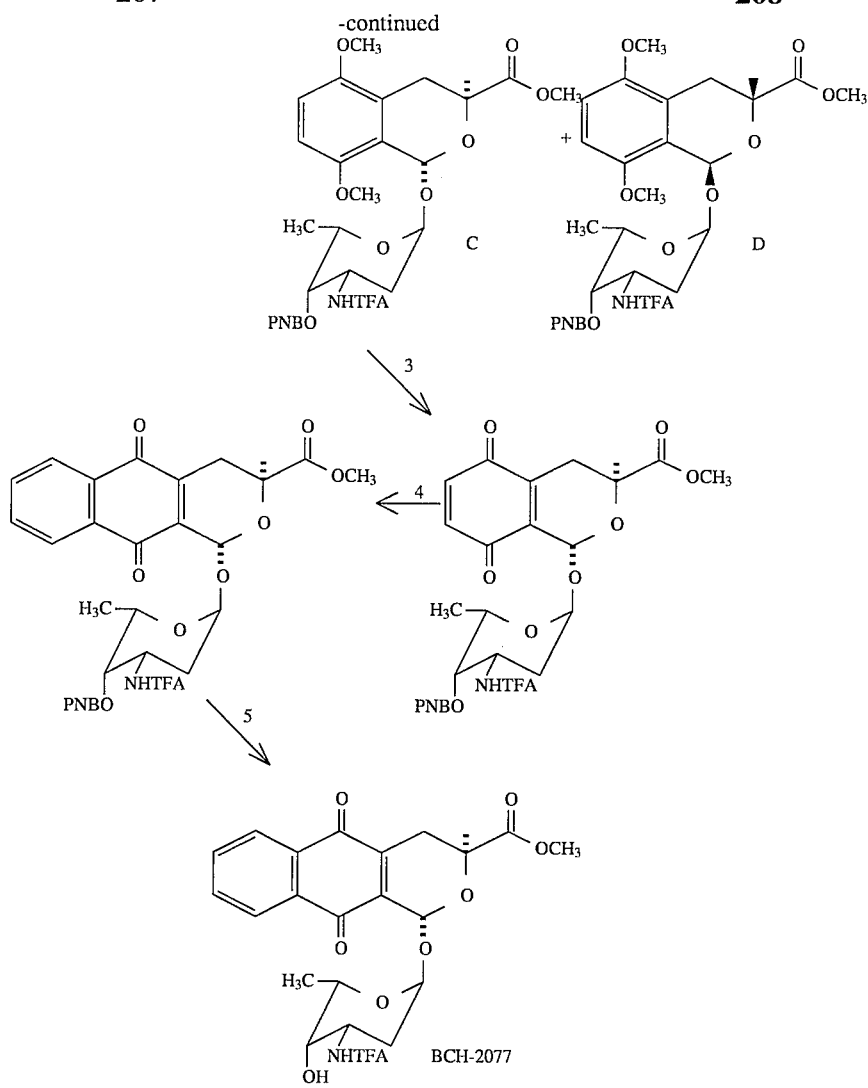

Step 1: 3-methoxycarbonyl-3-methyl-5,8-dimethoxy isochroman

A solution of di-isopropylamine (616.8 μl, 4.37 mmol) in THF (10 ml) was cooled to 0° C. and degassed briefly. n-Butyl lithium (1.6M in hexane, 2.60 ml, 4.17 mmol) was added. After stirred for 30 minutes at 0° C., the solution was further cooled to −78° C. A solution of 5,8-dimethoxy-3-methoxycarbonylisochroman (1.0 g, 3.97 mmol) in THF (10 ml), predegassed, was added slowly. The resulting yellow solution was stirred for 1 hour at −78° C. before; the addition of methyliodide (1.01 ml, 16 mmol). After stirred fursher for 45 minutes, sat. NH$_4$Cl solution was added. The mixture was diluted with water and extracted with ethyl acetate. The organic layer was dried and evaporated to give a crude product which was chromatographed (hexane:EtOAc=3:1) to give the desired product as a solid (650 mg, m p. 73.0°–74.5° C.) and another fraction (192 mg) which contained 66% of titled product and 34% of the starting material.

M.P. 73°–74.5° C.

$^1$H NMR (CDCl$_3$ 250 MHz, Bruker): δ, 1.50 (3H, s, 3-CCH$_3$), 2.58 (1H, d, J=17.1 Hz, 4-CH), 3.25 (1H, d, J=17.1 Hz, 4-CH), 3.64 (3H, s, OCH$_3$), 3.68 (3H, s, OCH$_3$), 3.72 (3H, s, OCH$_3$), 4.76 (1H, d, J=17.1 Hz, 1-CH), 4.84 (1H, d, J=17.1 H, 1-CH), 6.53 (1H, d, J=7.1 Hz, ArH), 6.59 (1H, d, J=7.1 Hz, ArH).

IR (Nicolet, 205 FT, film on NaCl plate): cm$^{-1}$, 2949.9, 2833.2, 1736.6, 1489.0, 1365.2, 1344.0, 1259.1, 1206.0, 1142.3, 1114.0, 1060.7, 295.7, 713.8.

Step 2: (1'S, 1R, 3S)-1-(4'-p-nitrobenzoyl-3'-trifluoroacetamido-2',3',6'-trideoxy-Llyxohexopyranose)-3-methoxy-carbonhyl-3-methyl-5,8-dimethoxy-isochroman.

The compound from step 1 herein (133 mg, 0.5 mmol) was reacted with DDQ (136 mg, 0.6 mmol) and 5'-p-nitrobenzoyl-3',4',7'-trideoxy-3'-trifluoroacetamido-L-lyxohexopyranose (196 mg, 0.5 mmol) at 45° C. for 16 hours, the same way as described in step 2, example 13. After chromatography (hexane:EtOAc=2.5:1), four isomers were obtained: C, 49 mg; B, 24 mg; D, 73 mg; A, 56 mg.

For C, $^1$H NMR (CDCl$_3$ 250 MHz, Bruker): δ, 1.22 (3H, d, J=6.1 Hz, 6'-CH$_3$), 1.45 (3H, s, 3-CCH$_3$), 1.89 (1H, dd, J=11.8 Hz, 4.7 Hz, 2'-CH), 2.05 (1H, d, tr, J=11.8 Hz, 3.0 Hz, 2'-CH), 2.77 (1H, d, J=17.1 Hz, -CH), 3.82 (1H, d, J=17.1 Hz, 4-CH), 3.64 (3H, s, OCH$_3$), 3.78 (3H, s, OCH$_3$), 3.81 (3H, s, OCH$_3$), 4.52 (1H, m, 3'-CH), 4.60 (1H, qua, J=6.1 Hz, 5'-CH), 5.42 (1H, s, 4'-CH), 5.74 (1H, d, J=1.7 Hz, 1'-CH), 6.22 (1H, s, 1-CH), 6.36 (1H, d, J=8.2 Hz, NHCOCF$_3$), 6.71 (1H, d, J=8.8 Hz, ArH), 6.80 (1H, d, J=8.8 Hz, ArH), 8.28 (4H, m, PNB).

IR (Nicolet, 205 FT, film on NaCl plate): cm$^{-1}$ 3328.4, 3077.3, 2946.4 843.8, 1740.1, 1527.9, 1492.5, 1259.1, 1114.0, 1054.2, 974.90, 947.90, 803.50, 716.80

The (1'S, 1S, 3S)-1-(4'-p-nitrobenzoyl-3'-trifluoroacetamido-2',3',6'-trideoxylyxohexopyranose)-3-methoxy-carbonyl-3-methyl-5,8-dimethoxy-isochroman had:

$^1$H NMR (CDCl$_3$ 250 MHz, Bruker): δ, 1.16 (3H, d, J=7.3 Hz, 6'-CH$_3$), 1.63 (3H, s, 3-CCH$_3$), 2.02 (2H, m, 2'-CH$_2$), 2.86 (1H, d, J=15.9 Hz, 4-CH), 3.21 (1H, d, J=15.9 Hz, 4-CH), 3.65 (3H, s, OCH$_3$), 3.76 (6H, s, 2×OCH$_3$), 4.10 (1H, qua, J=7.2 Hz, 5'-CH), 4.61 (1H, m, 3'-CH), 5.45 (1H, s, 4'-CH), 5.55 (1H, s, 1'-CH), 6.24 (1H, s, 1-CH), 6.68 (1H, d, J=9.4 Hz, ArH), 6.76 (1H, d, J=9.4 Hz, ArH), 6.23 (1H, s, NHCOCF$_3$), 8.26 (4H, m, PNB).

IR (Nicolet, 205 FT, film on NaCl plate): cm$^{-1}$, 3332.0, 2924.7, 2857.1, 1732.5, 1708.0, 1531.6, 1488.5, 1353.3, 1265.1, 1167.0, 957.18, 718.76.

The (1'S, 1S, 3R)-1-(4'-p-nitrobenzoyl-3'-trifluoroacetamido-2',3',6'-trideoxy-L-lyxohexopyranose)-3-methoxycarbonyl-3-methyl-5,8-dimethoxy-isochroman had:

$^1$H NMR (CDCl$_3$ 250 MHz, Bruker): δ, 1.19 (3H, d, J=6.1 Hz, 6'-CH$_3$), 1.60 (3H, s, 3-CCH$_3$), 1.87 (1H, dd, J=12.4 Hz, 4.7 Hz, 2'-CH), 2.11 (1H, d tr, J=12.4 Hz, 3.0 Hz, 2'-CH), 2.86 (1H, d, J=16.5 Hz, 4-CH), 3.33 (1H, d, J=16.5 Hz, 4-CH), 3.62 (3H, s, OCH$_3$), 3.78 (6H, s, 2×OCH$_3$), 4.54 (1H, qua, J=6.1 Hz, 5'-CH), 4.57 (1H, m, 3'-CH), 5.41 (1H, s, 4'-CH), 5.69 (1H, d, J=2.93 Hz, 1'-CH), 6.40 (1H, s, 1-CH), 6.45 (1H, d, J=7.6 Hz, NHCOCF$_3$), 6.71 (1H, d, J=8.9 Hz, ArH), 6.81 (1H, d, J=8.9 Hz, ArH), 8.24 (4H, s, PNB).

IR (Nicolet, 205 FT, film on NaCl plate): cm$^{-1}$, 3325.5, 3077.2 2951.9 2541.1, 1737.3, 1705.9, 1609.5, 1530.0, 1489.0, 1354.1, 1264.9, 970.9, 951.60, 804.80, 720.90.

The (1'S, 1R, 3R)-1-(4'-p-nitrobenzoyl-3'-trifluoroacetamido-2',3',6'-trideoxy-L-lyxohexopyranose)-3-methoxycarbonyl-3-methyl-5,8-dimethoxy-isochroman had:

$^1$H NMR (CDCl$_3$ 250 MHz, Bruker): δ, 1.20 (3H, d, J=6.0 Hz, 6'-CH$_3$), 1.53 (3H, s, 3-CCH$_3$), 1.93 (1H, dd, J=11.8 Hz, 2.9 Hz, 2'-CH), 2.05 (1H, m, 2'-CH), 2.60 (1H, d, J=16.5 Hz, 4-CH), 3.39 (1H, d, J=16.5 Hz, 4-CH), 3.73 (3H, s, OCH$_3$), 3.76 (3H, s, OCH$_3$), 3.80 (3H, s, OCH$_3$), 4.71 (1H, m, 3'-CH), 4.86 (1H, qua, J=6.0 Hz, 5'-CH), 5.45 (1H, s, 4'-CH), 5.55 (1H, d, J=1.74 Hz, 1'-CH), 6.01 (1H, s, 1-CH), 6.49 (1H, d, J=6.8 Hz, NHCOCF$_3$), 6.24 (1H, d, J=10.2 Hz, ArH), 6.82 (1H, d, J=0.2 Hz, ArH), 8.29 (4H, s, PNB).

Step 3: (1'S, 1R, 3S)-1-(4'-p-nitrobenzoyl-3'-trifluoroacetamido-2',3',6'-trideoxy-lyxohexopyranose)-3-methoxycarbonyl-3-methyl-5,8-dioxo-4,5,8-trihydro-1H-benzo-[2,3-c]-Pyran The titled compound was obtained via CAN oxidation (step 3, example 13) of the (1'S, 1R, 3S) precursor from step 2 herein.

$^1$H NMR (CDCl$_3$ 250 MHz, Bruker): δ, 1.30 (3H, d, J=6.5 Hz, 6'-CH$_3$), 1.57 (3H, s, 3-CCH$_3$), 1.93–2.05 (2H, m, 2'-CH$_2$), 2.36 (1H, d, J=20 Hz, 4-CH), 3.31 (1H, d, J=20 Hz, 4-CH), 3.67 (3H, s, OCH$_3$), 4.46 (1H, m, 3'-CH), 4.66 (1H, qua, J=6.5 Hz, 5'-CH), 5.36 (1H, s, 4'-CH), 5.62 (1H, s, 1'-CH), 5.93 (1H, s, 3.-CH), 6.56 (1H, d, J=7.1 Hz, NHCOCF$_3$), 6.77 (1H, d, J=9.7 Hz, Quin-H). 6.85 (1H, d, J=9.7 Hz, Quin-H), 8.30 (4H, m, PNB).

IR (Nicolet, 205 FT, film on NaCl plate): cm$^{-1}$, 3347.1, 2924.7, 2851.4 1736.3, 1663.1, 1527.9, 1351.4, 1272.6, 1167.4, 951.60, 837.00, 718.80.

Step 4: (1'S, 1R, 3S)-1-(4'-p-nitrobenzoyl-3'-trifluoroacetamido-2',3',6'-trideoxy-lyxohexopyranose)-3-methoxycarbonyl-3-methyl-5,10-dioxo-4,5,10-trihydro-1H-naphtho-[2,3'c]pyran The titled compound was obtained following cycloaddition between 1-acetoxybutadiene and the precursor from step 3 herein as per previously described procedure.

$^1$H NMR (CDCl$_3$ 250 MHz, Bruker): δ, 1.34 (3H, d, J=6.5 Hz, 6'-CH$_3$), 1.59 (3H, s, 3-CCH$_3$), 1.90–2.10 (2H, m, 2'-CH$_2$), 2.50 (1H, d, J=19.4 Hz, 4-CH), 3.49 (1H, d, J=19.4 Hz, 4-CH), 3.65 (3H, s, OCH$_3$), 4.46 (1H, m, 3'-CH), 4.79 (1H, qua, J=6.5 Hz, 5'-CH), 5.40 (1H, br s, 4'-CH), 5.65 (1H, d, J=2.5 Hz, 1'-CH), 6.10 (1H, s, 1-CH), 6.51 (1H, d, J=7.6 Hz, NHCOCF$_3$), 7.76 (2H, m, 7, 8-ArH), 8.13 (2H, m, 6, 9-ArH), 8.31 (4H, m, PNB).

IR (Nicolet, 205 FT, film on NaCl plate): cm$^{-1}$, 3333.8, 2919.5, 2851.0, 1739.0, 1667.4, 1533.4, 1790.5, 1271.8, 1212.6, 1187.7, 1103.6, 994.58, 949.75, 723.70.

Step 5: (1'S, 1R, 3S)-1-(3'-trifluoroacetamido-2',3',6'-trideoxy-L-lyxohexopyranose)-5,10-dioxo-4,5,10-trihydro-1H-naphtho-[2,3-c]-pyran (BCH-2077)

The titled compound was obtained following methanolysis of the precursor from step 4.

$^1$H NMR (CDCl$_3$, 250 MHz, Bruker): δ, 1.39 (3H, d, J=6.0 Hz, 6'-CH$_3$), 1.58 (3H, s, 3-CCH$_3$), 1.77 (1H, dd, J=12.0 Hz, 4.1 Hz, 2'-HCH$_a$), 1.84 (1H, dd, J=12.1 Hz, 5.9 Hz, 2'-HCH$_a$), 1.96 (1H, d, J=8.7 Hz, 4'-OH), 2.48 (1H, d, J=19.5 Hz, 4-HCH$_a$), 3.47 (1H, d, J=19.5 Hz, 4-HCH$_e$), 3.60 (1H, d, J=8.7 Hz, 4'-CH), 3.64 (3H, s, OCH$_3$), 4.17 (1H, m, 3'-CH), 3.56 (1H, qua, J=6.0 Hz, 5'-CH), 5.46 (1H, d, J=2.9 Hz, 1'-CH), 6.05 (1H, s, 1-CH), 6.71 (1H, d, J=8.8 Hz, NHCOCF$_3$), 7.75 (2H, m, 7, 8-ArH), 8.10 (2H, m, 6, 9-ArH).

IR (Nicolet, 205 FT, film on NaCl plate): cm$^{-1}$, 3420.6, 2934.5, 1735, 1721.8, 1665.8, 1291.8, 12.82.3, 1166.3, 1112.9, 776.7, 944.6, 912.6, 728.97.

EXAMPLE 54

Preparation of (1'S, 1S, 3R)-1-(3'-trifluoroacetamido-2',3',6'-trideoxy-lyxo-L-hexopyranose)-3-acetyl-3-methyl-3,4,5,10-tetrahydro-5,10-dioxo-naphtho-[2,3-c]pyran (BCH-2082)

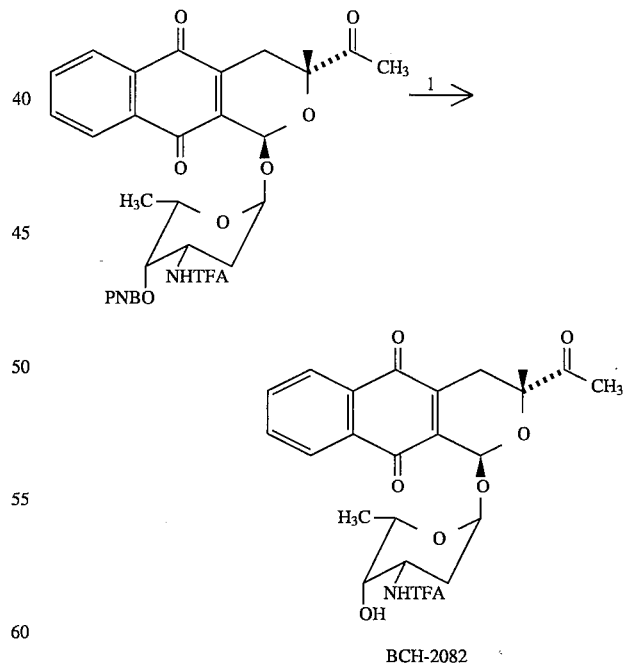

Step 1: (1'S, 1S, 3R)-1-(3'-trifluoroacetamido-2',3',6'-trideoxy-L-lyxohexopyranose)-3-acetyl-3-methyl-5,10-dioxo-4,5,10-trihydro-1H-naphtho-[2,3-c]-pyran (BCH-2082)

Methanolysis of the p-nitrobenzoylated precursor yielded the titled product.

¹H NMR (CDCl₃, 250 MHz, Bruker): δ, 1.31 (1H, d, J=6.6 Hz, 6'-CH₃), 1.45 (3H, s, 3-CCH₃), 1.80 (1H, d, J=8.8 Hz, 2'-CH), 1.81 (1H, d, J=10 Hz, 2'-CH), 2.24 (3H, s, COCH₃), 2.52 (1H, d, J=18.5 Hz, 4-HCH$_a$), 3.38 (1H, d, J=18.5 Hz, 4-HCH$_e$), 3.60 (1H, br s, 4'-CH), 4.19 (1H, br qua, J=10 Hz, 3'-CH), 4.41 (1H, qua, J=6.6 Hz, 5'-CH), 5.45 (1H, s, 1'-CH), 6.13 (1H, s, 1-CH), 6.63 (1H, d, J=10 Hz), 7.75 (2H, m, 7, 8-ArH), 8.09 (2H, m, 6, 9-ArH).

IR (Nicolet, 205 FT, film on NaCl plate): cm⁻¹, 3375.1 (br str), 3091.1, 2929.6, 1715.2, 1671.2, 1597.7, 1293.3, 1172.9, 981.5, 729.22.

EXAMPLE 55

Preparation of (1'S, 1S, 3R)-1-(3'-trifluoroacetamido-2',3',6'-trideoxy-lyxo-L-hexopyranose)-3-dimethoxyphosphonoacetyl-3,4,5,10-tetrahydro-5,10-dioxo-naphtho-[2,3-c]pyran (BCH-1690)

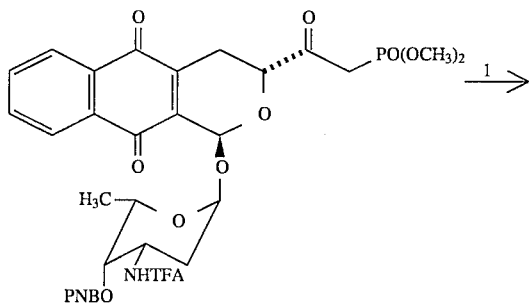

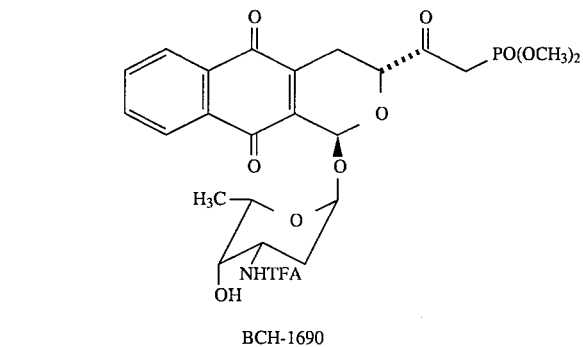

BCH-1690

Step 1: (1'S, 1S, 3R)-1-(2',3',6'-trideoxy-3'-trifluoroacetamido-L-lyxohexopyranose)-3-dimethylphosphonoacetyl-5,10-dioxo-3,4,5.10-tetrahydro-1H-naphtho-[2,3-c]-Pyran (BCH-1690)

The p-nitrobenzoyl precursor was hydrolyzed with catalytic sodium methoxide in methanol as per previously described procedure. The titled compound had:

M.P. 91°–93° C.,

¹H NMR (CDCl₃, 250 MHz, Bruker): δ, 1.40 (3H, d, J=7.6 Hz, 6'-CH₃), 1.89 (2H, m, 2'-CH₂), 2.62 (1H, dd, J=18.2 Hz, 11.8 Hz, 4-HCH$_a$), 3.00 (1H, dd, J=18.2 Hz, 4.2 Hz, 4-HCH$_e$), 3.65 (1H, br s, 4-CH), 3.83 (3H, s, POCH₃), 3.87 (3H, s, POCH₃), 4.32 (1H, qua, J=7.6 Hz, 5'-CH), 4.56 (1H, m, 3-CH), 4.99 (1H, br s CHP), 5.13 (1H, br s, CHP), 5.44 (1H, s, 1'-CH), 6.09 (1H, s, 1-CH), 6.83 (1H, br d, J=7.6 Hz, NHCOCF₃), 7.77 (2H, m, 7, 8-ArH), 8.09 (2H, m, 6, 9-ArH).

IR (Nicolet 205 FT, film on NaCl plate): cm⁻¹, 3421.9, 2958.3, 1716.0, 1665.6, 1592.5, 1287.6, 1181.8, 1045.7, 977.7, 858.4, 727.5.

EXAMPLE 56

Preparation of (1'S, 1S, 3S)-1-(3'-trifluoroacetamido-2',3',6'-trideoxy-lyxo-L-hexopyranose)-3-methoxycarbonyl-3-methyl-3,4,5,10-tetrahydro-5,10-dioxo-naphtho-[2,3-c]pyran (BCH-2081)

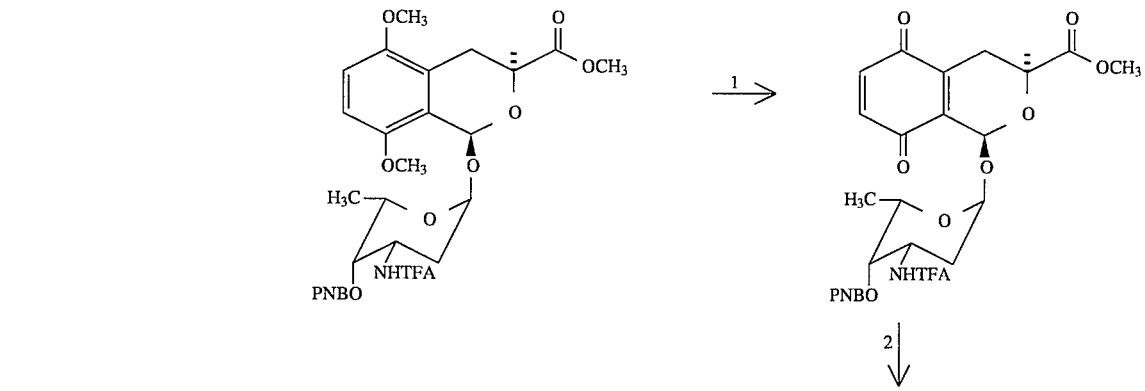

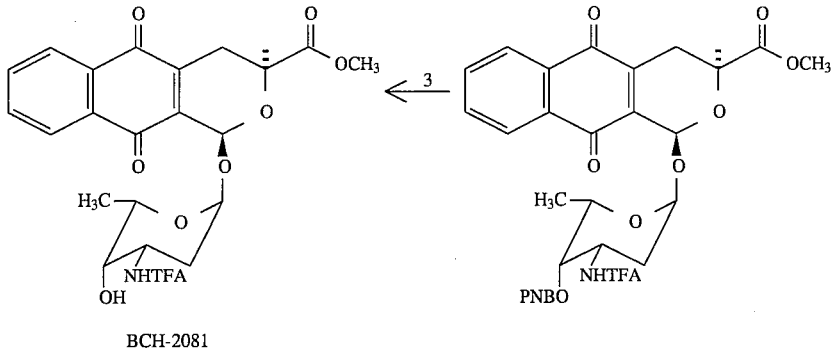

BCH-2081

Step 1: (1'S, 1S, 3S)-1-(4'-p-nitrobenzoyl-3'-trifluoroacetamido-2',3',6'-trideoxy-lyxohexopyranose)-3-methoxycarbonyl-3-methyl-5,8-dioxo-4,5,8-trihydro-1H-benzo-[2,3-c]-pyran.

CAN oxidation of the (1'S, 1R, 3S) precursor from step 2, example 53, yielded the titled compound.

¹H NMR (CDCl₃ 250 MHz, Bruker): δ, 1.14 (3H, d, J=6.0 Hz, 6'-CH₃), 1.61 (3H, s, 3-CCH₃), 1.96 (1H, d tr, J=11.7 Hz, 4.1 Hz, 2'-CH), 2.10 (1H, dd, J=11.7 Hz, 2.9 Hz, 2'-CH), 2.58 (1H, d, J=18.2 Hz, 4-CH), 3.00 (1H, d, J=18.2 Hz. 4-CH), 3.71 (3H, s, OCH₃) 4.50 (1H, qua, J=6.0 Hz, 5'-CH), 4.60 (1H, m, 3'-CH), 5.42 (1H, s, 4'-CH), 5.56 (1H, s, 1'-CH), 6.03 (1H, s, 1-CH), 6.58 (1H, d, J=7.4 Hz, NHCOCF₃), 6.72 (1H, d, J=8.8 Hz, Quin-H), 6.78 (1H, d, J=8.8 Hz, Quin-H), 8.24 (4H, br s, PNB).

IR (Nicolet, 205 FT, film on NaCl plate): cm⁻¹, 3340.0 3084.6, 2950.7, 2857.2, 1732.8, 1664.3, 1533.4, 1349.7, 1268.7, 1159.7, 1013.3, 955.70, 837.03, 735.00.

Step 2: (1'S, 1S, 3S)-1-(4'-p-nitrobenzoyl-3'-trifluoroacetamido-2',3',6'-trideoxy-lyxohexopyranose)-3-methoxy-carbonyl-3-methyl-5,10-dioxo-4,5,10-trihydro-1H-naphtho-[2,3-c]-pyran The titled compound was obtained following cycloaddition between 1-acetoxybutadiene and the quinone from step 1 herein.

¹H NMR (CDCl₃ 250 MHz, Bruker): δ, 1.16 (3H, d, J=6.0 Hz, 6'-CH₃), 1.67 (3H, s, 3-CCH₃), 2.05 (2H, m, 2'-CH₂), 2.77 (1H, dd, J=17.6 Hz, 0.6 Hz, 4-HCH_a), 3.22 (1H, dd, J=17.6 Hz, 1.8 Hz, 4-HCH_e), 3.73 (3H, s, OCH₃), 4.57 (1H, qua, J=6.0 Hz, 5'-CH), 4.64 (1H, m, 3'-CH), 5.45 (1H, d, J=2.1 Hz, 4'-CH), 5.57 (1H, s, 1'-CH), 6.22 (1H, s, 1-CH), 6.34 (1H, d, J=8.2 Hz, NHCOCF₃), 7.76 (2H, m, 7, 8-ArH), 8.08 (2H, m, 6, 9-ArH), 8.28 (4H, m, PNB).

IR (Nicolet, 205 FT, film on NaCl plate): cm⁻¹, 3331.7, 2957.1, 1734.1 1708.5, 1666.4, 1595.6, 12527.9, 1271.3, 1216.2, 1181.61, 1165.8, 1104.5, 1013.2, 954.94, 731.40, 721.98.

Step 3: (1'S, 1S, 3S)-1-(3'-trifluoroacetamido-2',3',6'-trideoxy-lyxohexopyranose)-3-methoxycarbonyl-3-methyl-5,10-dioxo-4,5,10-trihydro-1H-naphtho-[2,3-c]-pyran (BCH-2081)

The precursor from step 2 herein was hydrolyzed with sodium methoxide (catalytic) as per previously described procedure. The product had:

¹H NMR (CDCl₃ 250 MHz, Bruker): δ, 1.23 (3H, d, J=6.1 Hz, 6'-CH₃), 1.64 (3H, s, 3-CH₃), 1.79 (1H, d tr, J=12.9 Hz, 3.8 Hz, 2'-HCH_a), 1.88 (1H, dd, J=13.0 Hz, 4.7 Hz, -2'-HCH_e), 1.94 (1H, d, J=7.6 Hz, 2'-OH), 2.74 (1H, d, J=18.8 Hz, 4-HCH_a), 3.17 (1H, d, J=18.8 Hz, 4-HCH_e) 3.61 (1H, d, J=7.8 Hz, 4'-CH), 3.71 (3H, s, OCH₃), 4.32 (1H, m, 3'-CH), 4.40 (1H, qua, J=6.1 Hz, 5'-CH), 5.50 (1H, d, J=3.5 Hz, 1'-CH), 6.15 (1H, s, 1-CH), 6.67 (1H, d, J=8.8 Hz, NHCOCF₃), 7.74 (2H, m, 7, 8-ArH), 8.07 (2H, m, 6,9-ArH).

IR (Nicolet, 205 FT, film on NaCl plate): cm⁻¹, 3422.1 (br str) 2928.1 2853.9, 1720.3, 1668.9, 1594.7, 1292.0, 1183.5, 1166.4, 1009.3, 986.49, 728.24.

EXAMPLE 57

Preparation of (1'S, 1S, 3S)-1-(3'-trifluoroacetamido-2',3',6'-trideoxy-lyxo-L-hexopyranose)-3-dimethoxyphosphonoacetyl-3,4,5,10-tetrahydro-5,10-dioxo-naphtho-[2,3-c]thiopyran (BCH-2037.001)

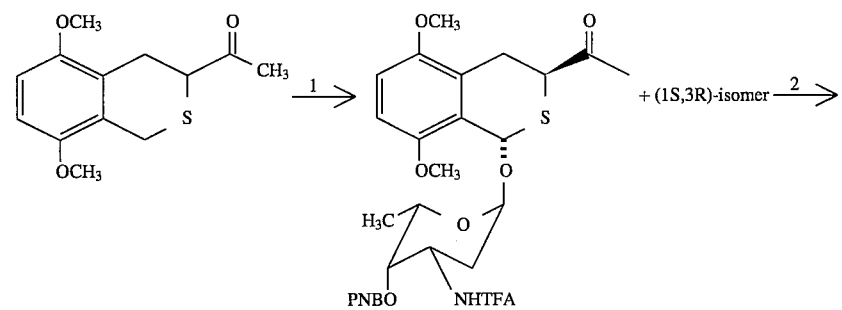

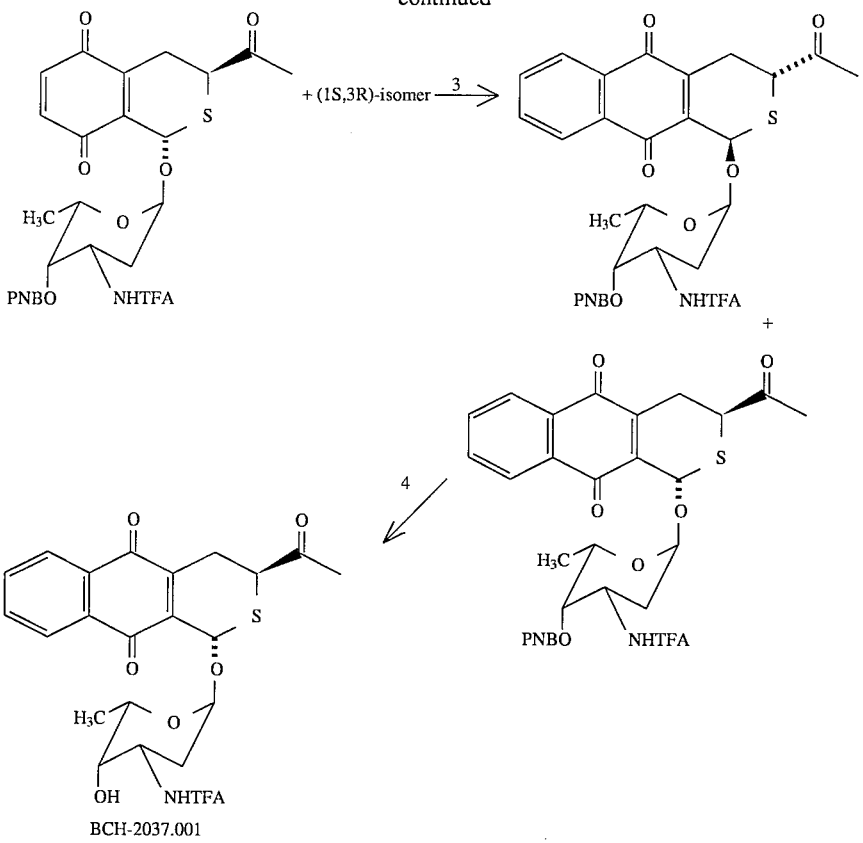

Step 1: Preparation of (1'S, 1S, 3S) and (1'S, 1R, 3R)-1-(3'-trifluoroacetamido-2',3',6'-trideoxy-L-lyxohexopyranose)-3-acetyl-5,8-dimethoxy-thioisochroman The compound from step 1, example 13, and daunosamine precursor (259 mg, 0.66 mmole) were dissolved in CH$_2$Cl$_2$ (25 ml) and left stirring in presence of molecular sieve for 30 minutes before DDQ (150 mg, 0.66 mmole) was added. The resulting mixture was stirred for 2½ hours. NaHCO$_3$ (5% solution) was added and the aqueous layer was extracted with CH$_2$Cl$_2$. The combined organic phases were washed with H$_2$O, dried over MgSO$_4$, filtered and concentrated in vacuo. The crude obtained was flash chromatographed using Tol:EE (9:1) to give a pure mixture of two titled isomers (in 60% yield) which was used to carry out the next step.

Step 2: Preparation of (1'S, 1S, 3S) and (1'S, 1R, 3R)-1-(4'-p-nitrobenzoyl-3'-trifluoroacetamido-2',3',6'-trideoxy-L-lyxohexopyranose)-3-acetyl-5,8-dioxo-4,5,8-trihydro-1H-benzo-[2,3-c]-pyran The compound from step 1 herein (112.7 mg, 0.18 mmole) was dissolved in acetonitrile (5 ml), cooled to 0° C., followed by the addition of NaHCO$_3$ (29 mg, 0.34 mmole) and some H$_2$O. The resulting mixture was stirred for 5 minutes before CAN (296 mg, 0.54 mmole) was added. After all CAN was added, the reaction mixture was stirred 10 minutes extra 0° C., then warmed to room temperature. H$_2$O was added and it was extracted with CH$_2$Cl$_2$. The combined organic phases were washed with H$_2$O, dried over MgSO$_4$, filtered and concentrated in vacuoo The crude containing a mixture of two titled diastereoisomers was used in the following step.

Step 3: (1'S, 1S, 3S)-1-(4'-p-nitrobenzoyl-3'-trifluoroacetamido-2',3',6'-trideoxy-L-lyxohexopyranose)-3-acetyl-5,10-dioxo-3,4,5,10-tetrahydro-1H-naphtho-[2,3-c]-thiopyran Following the example 1, step 1, a mixture of the two titled adducts was obtained which could be seperated via flash chromatography. The first eluent had:

$^1$H NMR (acetone-d$_6$, 250 MHz, Bruker): δ, 1.23 (3H, d, J=5.6 Hz, 6'-CH$_3$), 1.70–1.90 (2H, m, 2'-CH$_2$), 2.44 (3H, s, COCH$_3$), 2.84 (1H, dd, J=17.8 Hz, 11.8 Hz, 4-HCH$_a$), 3.36 (1H, dd, J=17.8 Hz, 4.1 Hz, 4'-HCH$_e$), 4.53 (1H, dd, J=11.8 Hz, 4.1 Hz, 3-CH), 4.60 (1H, m, 3'-CH), 4.75 (1H, qua, J=5.6 Hz, 5'-CH), 5.53 (1H, s, 4'-CH), 5.70 (1H, d, J=2.3 Hz, 1'-CH), 6.13 (1H, s, 1-CH), 7.90 (2H, m, 7, 8-ArH), 8.12 (2H, m, 6, 9-ArH), 8.39 (4H, m, PNB), 8.65 (1H, d, J=5.8 Hz, NHCOCF$_3$).

The second eluent had:

$^1$H NMR (acetone-d$_6$, 250 MHz, Bruker): δ, 1.32 (3H, d, J=6.8 Hz, 6'-CH$_3$), 2.39 (3H, s, COCH$_3$), 1.94 (1H, dd, J=12.3 Hz, 4.1 Hz, 2'-HCH$_a$), 2.50 (1H, tr d, J=12.3 Hz, 2.9 Hz, 2'-HCH$_e$), 2.89 (1H, dd, J=18.2 Hz, 11.2 Hz, 4-HCH$_a$), 3.35 (1H, dd, J=18.2 Hz, 3.5 Hz, 4-HCH$_e$), 4.41 (1H, dd, J=11.2 Hz, 3.5 Hz, 3-CH), 4.52 (1H, m, 3'-CH), 4.66 (1H, qua, J=6.8 Hz, 5'-CH), 5.47 (1H, s, 4'-CH), 5.74 (1H, d, J=2.9 Hz, 1'-CH), 6.31 (1H, s, 1-CH), 7.91 (2H, m, 7, 8-ArH), 8.14 (2H, m, 6, 9-ArH), 8.38 (4H, m, PNB), 8.68 (1H, d, J=7.1 Hz, NHCOCF$_3$).

Step 4: (1'S, 1S, 3S)-1-(3'-trifluoroacetamido-2',3',6'-trideoxy-L-lyxohexopyranose)-5,10-dioxo-3,4,5,10-tetrahydro-1H-naphtho-[2,3-c]-thiopyran (BCH-2037.001)

$^1$H NMR (CDCl$_3$ 250 MHz, Bruker): δ, 1.43 (3H, s, 6'-CH$_3$), 1.83–1.98 (2H, m, 2'-CH$_2$), 2.37 (3H, s, COCH$_3$), 2.90 (1H, dd, J=17.8 Hz, 12 Hz, 4-HCH$_a$), 3.32 (1H, dd, J=17.8 Hz, 4.1 Hz, 4-HCH$_e$), 3.61 (1H, br s, 4'-CH), 4.07 (1H, dd, J=12.0 Hz, J=4.1 Hz, 3-CH), 5.53 (1H, s, 1'-CH), 6.21 (1H, s, 1-CH), 6.74 (1H, d, J=7.6 Hz, NHCOCF$_3$), 7.76 (2H, m, 7, 8-ArH), 8.12 (2H, m, 6, 9-ArH).

EXAMPLE 58

Preparation of (1'S, 1R, 3R)-1-(3'trifluoroacetamido-2',3',5'-trideoxy-L-hexopyranose)-3-dimethoxyphosphonoacetyl-3,4,5,10-tetrahydro-5,10-dioxo-naphtho-[2,3-c]pyran (BCH-2127)

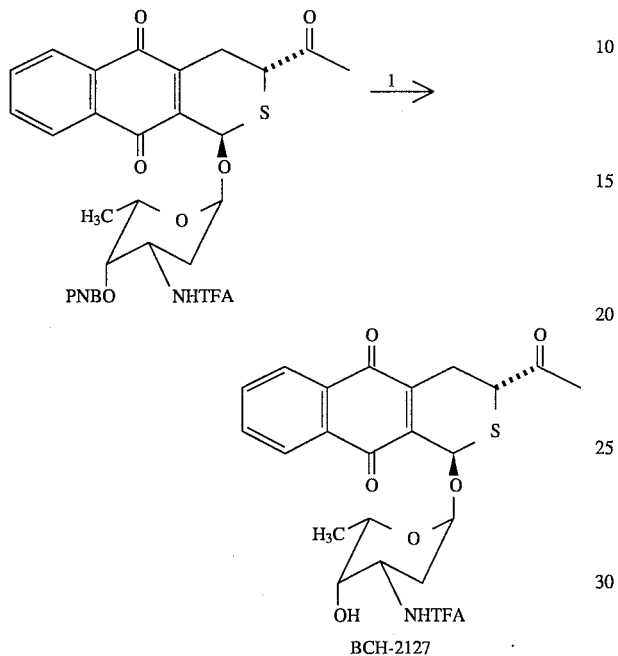

Step 1: (1'S, 1R, 3R)-1-(3'-trifluoroacetamido-2',3',6'-trideoxy-L-lyxohexopyranose)-3-acetyl-5,10-dioxo-3,4,5,10-tetrahydro-1H-naphtho-[2,3-c]-thiopyran (BCH-2127)

The second eluent from step 3, example 57, was hydrolyzed with catalytic sodium methoxide in methanol. The titled compound had:

$^1$H NMR (CDCl$_3$ 250 MHz, Bruker): δ, 1.43 (3H, d, J=6.5 Hz, 6'-CH$_3$), 1.80–2.00 (2H, m, 2'-CH$_2$), 2.37 (3H, s, COCH$_3$), 2.91 (1H, dd, J=18.3 Hz, 11.8 Hz, 4-HCH$_a$), 3.33 (1H, dd, J=18.3 Hz, 4.7 Hz, 4-HCH$_e$), 3.60 (1H, br s, 4-CH), 4.07 (1H, dd, J=11.8 Hz, 4.7 Hz, 3-CH), 4.25 (1H, m, 3'-CH), 4.35 (1H, qua, J=6.5 Hz, 5'-CH), 5.53 (1H, d, J=2.4 Hz, 1'-CH), 6.21 (1H, s, 1-CH), 6.74 (1H, d, J=7.6 Hz, NHCOCF$_3$), 7.76 (1H, m, 7, 8-ArH), 8.14 (2H, m, 6, 9-ArH).

EXAMPLE 59

Preparation of (1'S, 1S, 3S)-1-(3'-trifluoroacetamido-2',3',6'-trideoxy-lyxo-L-hexopyranose)-3-acetyl-3-methyl-3,4,5,10-tetrahydro-5,10-dioxo-1H-naphtho-[2,3-c]pyran (BCH-2090)

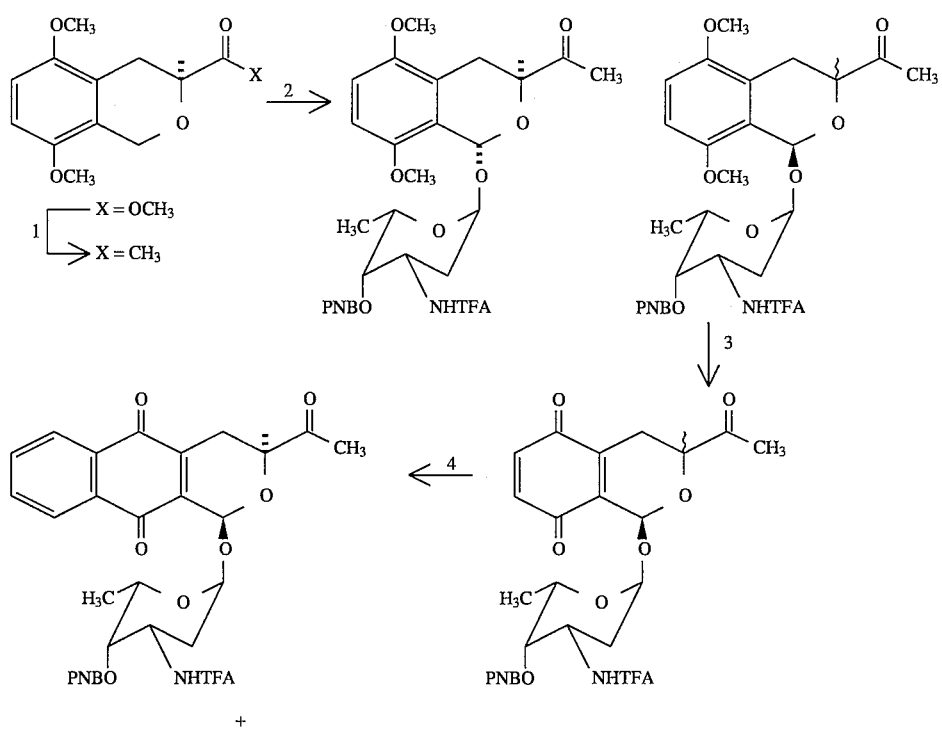

+

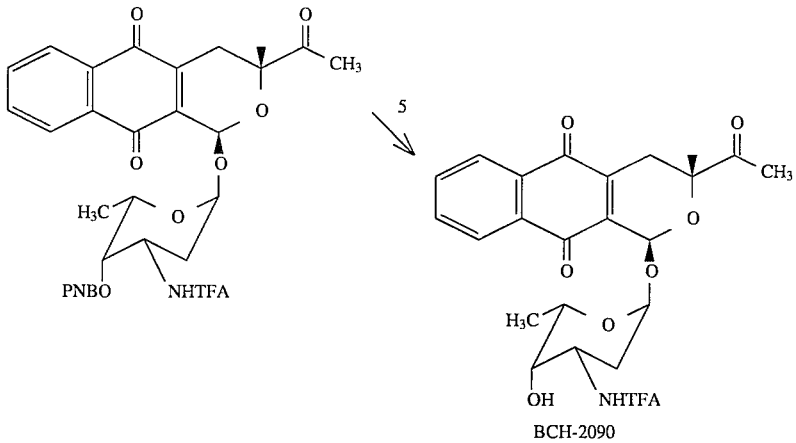

BCH-2090

Step 1: 3-acetyl-3-methyl-5,8-dimethoxy isochroman

The compound from step 1, example 53, (126.5 mg, 0.474 mmol) was dissolved in ether and then cooled to −78° C. Methyllithium (1.4M in ether (0.71 ml, 0.995 mmol) was added. After 10 minutes methanol was added. The reaction mixture was acidified with HCl (0.5N) and extracted with ethyl acetate. The organic layer was dried over sodium sulfate and then evaporated to give a crude product (121 mg). $^1$H NMR showed that it was a mixture of starting material and product in 1:1 ratio. Chromatography allowed isolation of the desired titled product as a gel.

$^1$H NMR (CDCl$_3$ 250 MHz, Bruker): δ, 1.37 (3H, s, 3-CCH$_3$), 2.24 (3H, s, COCH$_3$), 2.59 (1H, d, J=17.6 Hz, 4-CH), 2.99 (1H, d, J=17.6 Hz, 4-CH), 3.74 (3H, s, OCH$_3$), 3.76 (3H, s, OCH$_3$), 4.77 (2H, s, 1-CH$_2$), 6.57 (1H, d, J=9.4 Hz, ArH), 6.62 (1H, d, J=9.4 Hz, ArH).

IR (Nicolet, film on NaCl plate): cm$^{-1}$, 2941.9, 2834.4, 1721.6, 1482.4, 1340.2, 1257.0, 1061.4, 795.30, 716.80

Step 2: (1'S, 1S, 3S) and (1'S, 1S, 3R)-1-(4'-p-nitrobenzoyl-3'-trifluoroacetamido-2',3',6'-trideoxy-L-lyxohexopyranose)-3-acetyl-3-methyl-5,8-dimethoxy-isochroman The compound from step 1 herein (67 mg, 0.268 mmol) was stirred with DDQ (91.3 mg, 0.422 mmol) and 4',5'-protected daunosamine (157 mg, 0.402 mmol) in methylene chloride at 40° C. for 24 hours. The solvent was evaporated. The crude product was chromatographed (hex:EtOAc=10:4) to give the titled compounds (88 mg containing two isomers in 2:1 ratio inseparable).

$^1$H NMR (CDCl$_3$ 250 MHz, Bruker): δ, 1.23 (3H, d, J=6.0 Hz, A-6'-CH$_3$), 1.22 (3H, d, J=6.0 Hz, B-6'-CH$_3$), 1.44 (3H, s, A-3-CCH$_3$), 1.66 (3H, s, B-3-CCH$_3$), 1.84 (1H, m, A-2'CH), 1.84 (1H, m, A-2'-CH), 1.84 (1H, m, B-2'-CH), 2.14 (1H, m, A-2'CH), 2.15 (1H, m, B-2'-CH), 2.80 (1H, d, J=15.9 Hz, A-4-CH), 3.02 (2H, s, B-4-CH$_2$), 3.14 (1H, d, J=15.9 Hz, A-4-CH), 3.77 (6H, s, B-OCH$_3$), 3.80 (6H, s, A-OCH$_3$), 4.41 (1H, qua, J=6.0 Hz, B-5'-CH), 4.47 (1H, m, B-3'-CH), 4.56 (1H, qua, J=6.0 Hz, A-5'-CH), 4.61 (1H, m, A-3'-CH), 5.40 (1H, s, B-4'-CH), 5.44 (1H, s, A-4'-CH), 5.61 (1H, d, J=2.5 Hz, B-1'-CH), 5.70 (1H, d, J=2.2 Hz, A-1'-CH), 6.35 (1H, s, B-1-CH), 6.37 (1H, s, A-1-CH), 6.41 (1H, d, J=7.6 Hz, B-NHCOCF$_3$), 6.46 (1H, d, J=7.8 Hz, A-NHCOCF$_3$), 6.76 (2H, m, B-ArH), 6.81 (2H, m, A-ArH), 8.25 (8H, br s, A-PNB, B-PNB).

IR (Nicolet, 205 FT, film on NaCl plate): cm$^{-1}$, 3327.9, 2945.2, 2840.3, 1732.6, 1528.4, 1489.4, 1351.8, 1263.4, 1167.8, 11167.3, 1105.2, 969.06, 948.80, 801.62, 720.66.

Also obtained from this reaction (34 mg) was (1'S, 1R, 3S)-1-(4'-p-nitrobenzoyl-3'-trifluoroacetamido-2',3',6'-trideoxylyxohexopyranose)-3-acetyl-3-methyl-5,8-dimethoxy-isochroman which had:

$^1$H NMR (CDCl$_3$ 250 MHz, Bruker): δ, 1.18 (3H, d, J=7.6 Hz, 6'-CH$_3$), 1.51 (3H, s, 3-CCH$_3$), 2.00–2.10 (2H, m, 2'-CH$_2$), 2.84 (1H, d, J=17.1 Hz, 4-CH), 2.96 (1H, d, J=17.1 Hz, 4-CH), 3.77 (3H, s, OCH$_3$), 3.78 (3H, s, OCH$_3$), 4.54 (1H, qua, J=7.6 Hz, 5'-CH), 4.62 (1H, m, 3'-CH), 5.46 (1H, d, J=2.1 Hz, 4'-CH), 5.56 (1H, s, 1'-CH), 6.14 (1H, s, 1-CH), 6.41 (1H, d, J=7.6 Hz, NHCOCF$_3$), 6.70 (1H, d, J=8.8 Hz, ArH), 6.76 (1H, d, J=8.8 Hz, ArH), 8.26 (4H, m, PNB).

IR (Nicolet, 205 FT, film on NaCl plate): cm$^{-1}$, 3336.5 2940.0, 2834.3, 1730.3, 1527.2, 1481.4, 1266.3, 1163.6, 975.8, 718.02.

Step 3: (1'S, 1S, 3S) and (1'S, 1S, 3R)-1-(4,-p-nitrobenzoyl-3'-trifluoroacetamido-2',3',6'-trideoxy-lyxohexopyranose)-3-acetyl-3-methyl-5,8-dioxo-4,5,8-trihydro-1H-benzo-[2,3'c]pyran CAN oxidation of the products from step 2 herein gave the titled quinones (as per procedure step 2, example 14).

$^1$H NMR (CDCl$_3$ 250 MHz, Bruker): δ, 1.30 (3H, d, J=6.0 Hz, A-6'-CH$_3$), 1.27 (3H, d, J=6.1 Hz, B-6'-CH$_3$), 1.44 (3H, s, A-3-CCH$_3$), 1.44 (3H, s, B-3-CCH$_3$), 1.80–2.30 (4H, m, A-2'-CH$_2$, B-2'-CH$_2$), 2.62 (1H, d, J=18.1 Hz, A-4-HCH$_a$), 2.72 (1H, d, J=18.1 Hz, A-4-HCH$_e$), 2.70 (1H, d, J=18.0 Hz, B-4-CH), 3.25 (1H, d, J=18 Hz, B-4'-CH), 4.41 (1H, m, B-3'-CH), 4.56 (1H, m, A-3'-CH), 4.57 (1H, qua, J=6 Hz, B-5'-CH), 4.72 (1H, qua, J=6 Hz, A-5'-CH), 5.38 (1H, s, B-4'-CH), 5.42 (1H, s, A-4'-CH), 5.58 (1H, d, J=2.4 Hz, B-1'-CH), 5.66 (1H, d, J=2.9 Hz, A-1'-CH), 5.98 (1H, s, B-1-CH), 6.02 (1H, s, A-1-CH), 6.45 (1H, d, J=8.1 Hz, B-NHCOCF$_3$), 6.55 (1H, d, J=8 Hz, A-NHCOCF$_3$), 6.70–6.87 (4H, m, A-6, 7-Quin, B-6, 7-Quin), 8.28 (8H, m, A-PNB, B-PNB).

IR (Nicolet, 205 FT, film on NaCl plate): cm$^{-1}$, 3327.5, 3084.6, 2984.9, 2938.2, 1723.4, 1661.1, 1533.4, 1352.8, 1278.0, 1215.7, 1169.0, 1122.3, 948.30, 730.86.

Step 4: (1'S, 1S, 3S) and (1'S, 1S, 3R)-1-(4'-p-nitrobenzoyl-3'-trifluoroacetamido-2',3',6'-trideoxy-lyxohexopyranose)-3-acetyl-3-methyl-5,10-dioxo-4,5,10-trihydro-1H-naphtho-[2,3-c]-pyran The quinone from step 3 herein was cycloadded with 1-acetoxybutadiene as per procedure described in step 3, example 14. The (1'S, 1S, 3R) titled compound had:

$^1$H NMR (CDCl$_3$ 250 MHz, Bruker): δ, 1.35 (3H, d, J=5.9 Hz, 6'-CH$_3$), 1.49 (3H, s, 3-CCH$_3$), 1.95 (1H, dd, J=12.6 Hz, 4.7 Hz, 2'-CH), 2.12 (1H, d tr, J=12.6 Hz, 2.9 Hz, 2'-CH), 2.71 (1H, d, J=18.2 Hz, 4-CH), 2.89 (1H, d, J=18.2 Hz, 4-CH), 4.60 (1H, m, 3'-CH), 4.85 (1H, qua, J=5.9 Hz, 5'-CH), 5.47 (1H, br s, 4'-CH), 5.71 (1H, d, J=2 Hz, 1'-CH), 6.21 (1H, d, J=1.2 Hz, 1-CH), 6.42 (1H, d, J=7.6 Hz, NHCOCF$_3$), 7.78 (2H, m, 7, 8-ArH), 8.14 (2H, m, 6, 9-ArH), 8.31 (4H, m, PNB).

IR (Nicolet, 205 FT, film on NaCl plate): cm$^{-1}$, 3336.3, 2922.6 2852 6, 2852.6, 1728.0, 1666.8, 1532.8, 1346.3, 1273.5, 1212.3, 1165.6, 1119.0, 1098.6, 996.7, 952.96, 836.3, 722.58.

The (1'S, 1S, 3S) diastereomer had:

$^1$H NMR (CDCl$_3$ 250 MHz, Bruker): δ, 1.31 (3H, d, J=5.9 Hz, 6'-CH$_3$), 1.47 (3H, s, 3-CCH$_3$), 1.89 (1H, dd, J=11.8 Hz, 5.3 Hz, 2'-HCH$_a$), 2.06 (1H, d tr, J=11.8 Hz, 4.1 Hz, 2'-HCH$_e$), 2.55 (1H, d, J=17.8 Hz, 4-HCH$_a$), 3.40 (1H, d, J=17.8 Hz, 4-HCH$_e$), 4.45 (1H, m, 3'-CH), 4.66 (1H, qua, J=5.9 Hz, 5'-CH), 5.43 (1H, s, 4'-CH), 5.63 (1H, d, J=2.3 Hz, 1'-CH), 6.17 (1H, s, 1-CH; 6.30 (1H, d, J=11.8 Hz, NHCOCF$_3$), 7.77 (2H, m, 7, 8-ArH), 8.13 (2H, m, 6, 9-ArH), 3.30 (4H, m, PNB).

Step 5: (1'S, 1S, 3S)-1-(3'-trifluoroacetamido-2',3',6'-trideoxy-L-lyxohexopyranose)-3-acetyl-3-methyl-5,10-dioxo-4,5,10-trihydro-1H-naphtho-[2,3-c]-pyran (BCH-2090)

Hydrolysis of the (1'S, 1S, 3S) precursor from step 4 herein gave the titled compound.

M.P. 95° C.

1H NMR (CDCl$_3$, 250 MHz, Bruker): δ, 1.41 (3H, d, J=5.9 Hz, 6'-CH$_3$), 1.46 (3H, s, 3-CCH$_3$), 1.85 (2H, m, 2'-CH$_2$), 2.27 (3H, s, COCH$_3$), 2.84 (2H, d, J=5.9 Hz, 4-CH$_2$), 3.65 (1H, s, 4'-CH), 4.31 (1H, m, 3'-CH), 4.64 (1H, qua, J=6.0 Hz, 5'-CH), 5.53 (1H, br s, 1'-CH), 6.15 (1H, s, 1-CH), 6.71 (1H, br d, J=8.8 Hz, NHCOCF$_3$), 7.75 (2H, m, 7, 8-ArH), 8.11 (2H, m, 6, 9-ArH).

IR (Nicolet, 205 FT, film on NaCl plate): cm$^{-1}$, 3423.2, 3342.2, 3087.5, 2987.2, 2933.2, 1717.6, 1667.5, 1590.3, 1289.3, 1216.0, 1179.1, 1167.6, 1124.2, 980.89, 940.05, 918.55, 734.22.

EXAMPLE 60

Preparation of (1'S, 1R, 3S)-1-(3'-trifluoroacetamido-2',3',6'-trideoxy-lyxo-L-hexopyranose)-3-dimethoxyphosphonoacetyl-3,4,5,10-tetrahydro-5,10-dioxo-naphtho-[2,3-c]pyran (BCH-1689)

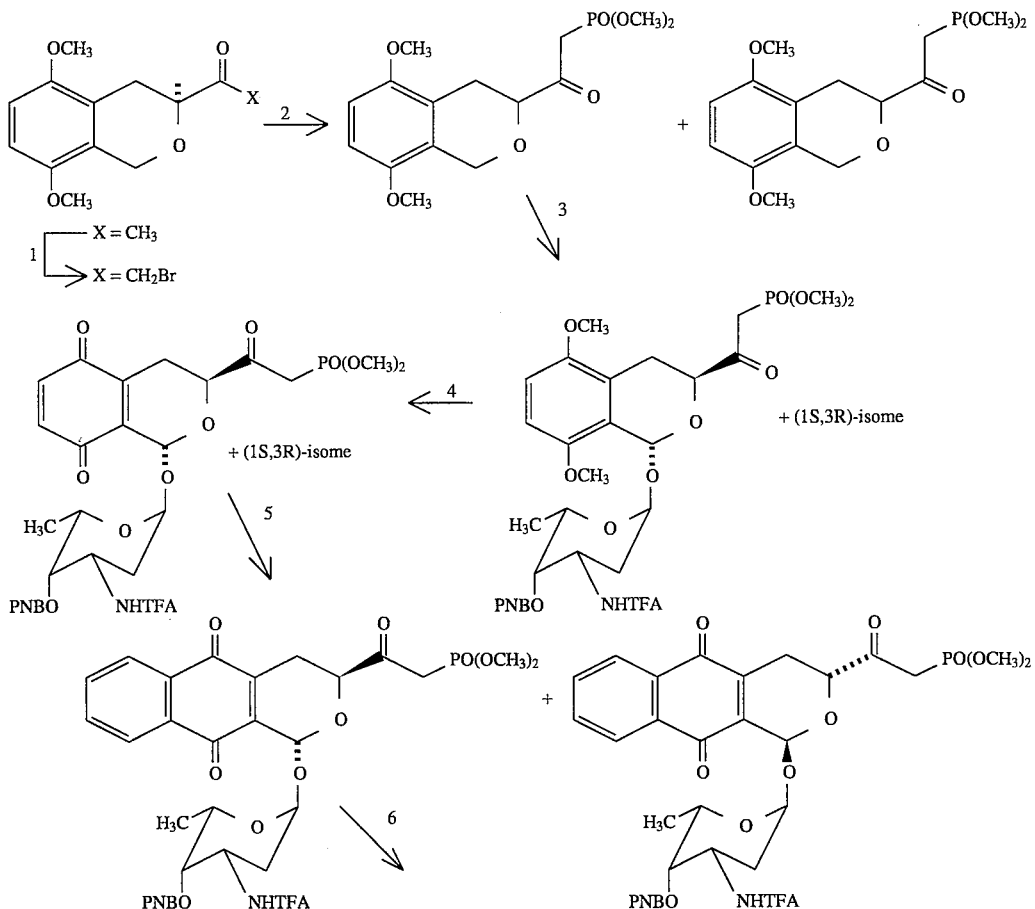

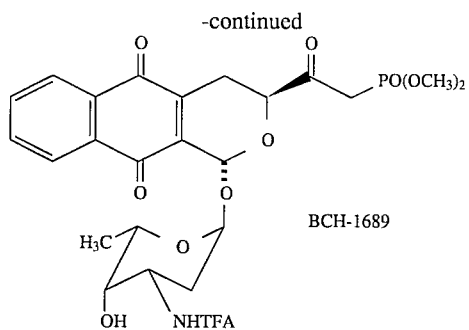

BCH-1689

Step 1: 3-bromoacetyl-5,8-dimethoxy-isochroman

The titled compound was prepared by using 5,8-dimethoxy-3-acetoisochroman and the procedure from step 1, example 8.

$^1$H NMR (CDCl$_3$, 250 MHz, Bruker): 2.59 (1H, dd, J=15.9 Hz, 11.8 Hz, 4-HCH$_a$), 3.03 (1H, dd, J=15.9 Hz, 2.9 Hz, 4-HCH$_e$), 3.74 (3H, s, OCH$_3$), 3.75 (3H, s, OCH$_3$), 4.23 (1H, dd, J=11.8 Hz, 2.9 Hz), 4.27 (1H, d, J=13.5 Hz, CHBr), 4.34 (1H, d, J=13.5 Hz, CHBr), 4.63 (1H, d, J=15.9 Hz, 1-HCH$_a$), 4.96 (1H, d, J=15.9 Hz, 1-HCH$_e$), 6.63 (2H, m, ArH).

Step 2: 3-dimethoxy phosphinoacetyl-5,8-dimethoxy-isochroman

The titled compound was obtained following treatment of the product from step 1 herein with P(OCH$_3$)$_3$.

$^1$HNMR (CDCl$_3$, 250 MHz, Bruker), δ: 2.57 (dd, 1H, J=16.9 Hz, 11 Hz, 4-HCH$_a$), 2.98 (dd, 1H, J=16.9 Hz, 2.9 Hz, 4-HCH$_e$), 3.26 (dd, 1H, J=21.5 Hz, 14.5 Hz, COCHP), 3.54 (dd, 1H, J=21.5 Hz, 14.5 Hz, COCHP), 3.71 (s, 3H, ArOCH$_3$), 3.72 (s, 3H, ArOCH$_3$), 3.74 (d, 3H, J=4.3 Hz, POCH$_3$), 3.78 (d, 3H, J=4.3 Hz, POCH$_3$), 4.11 (dd, 1H, J=11 Hz, 3.4 Hz, 3-CH), 4.63 (d, 1H, J=16.3 Hz, 1 HCH$_a$), 4.97 (d, 1H, J=16.3 Hz, 1-HCH$_e$), 6.60 (m, 2H, 6.7-ArH).

IR (Nicolet, 205 FT, film on NaCl plate), cm$^{-1}$: 2954.3, 2836.7, 1725.5 (str), 1603.9 (W), 1482.2, 1259.2 (str), 1034.7, 799.10, 715.8.

Step 3: (1'S, 1S, 3R) (1'S, 1R, 3S)-5,8-dimethoxyl(2',3',6'-trideoxy-3'-trifluoroacetamido-4'-p-nitrobenzoyl-L-lyxohexopyranose)-3-dimethylphosphonoacetyl isochroman To a stirred solution of the phosphonate from step 2 herein (199 mg, 0.58 mmole) with 4 - PNB - 3 - TFA - daunosamine (270 mg, 0.69 mmole) in clichloromethane (60 ml) was added 4 pelets of molecular sieves (4A$^-$). This was followed by addition of dichlorodisyanoquinone (DDQ, 170 mg, 0.75 mmole) in one portion. The resulting green liquid was stirred at 40° C. (controlled by an Ikamag-Ret-G-Heating-Stirring system) in a enclosed system for 25 hours then at room temperature (without heating) for 48 hours. The resulting muddy mixture was evaporated and then directly chromatographed (Hex:EA=1:1.5) to yield the desired titled glycosides (diastereomeric mixture A and B, as light-colored glassy material, 407 mg).

$^1$HNMR (CDCl$_3$, 250 MHz, Bruker), δ: 1.20 (d, 3 H, J=7.0 Hz, 6'-CH$_{3A}$), 1.23 (d, 3H, J=7.0 Hz 6'-CH$_{3B}$), 1.82 (dd, 1H, J=12.2 Hz, 4.5 Hz, 2'-HCH$_{Aa}$), 1.91 (dd, 1H, J=12.3 H$_8$, 4.6 Hz, 2'-HCH$_{Ba}$), 2.07 (dt, 1 H, J=12.3 Hz, 3.5 Hz, 2'-HCH$_{Ae}$), 2.20 (dr, 1H, J=12.4 Hz, 4 Hz, 2'-HCH$_{Be}$), 2.54 (dd, 1H, J=16.9 Hz, 13.4 Hz, 4 - HCH$_{Ba}$), 2.60 (dd, 1H, J=17 Hz, 11 Hz, 4 - HCH$_{Aa}$), 2.96 (dd, 1H, J=11 Hz, 3.5 Hz, 4-HCH$_{Ae}$), 3.03 (dd, 1H, J=11.1 Hz, 3.3 Hz, 4 -HCH$_{Be}$), 3.74–3.87 (8×s, 24 H, 2×ArOCH$_{3A}$, 2×ArOCH$_{3B}$, 2×POCH$_{3A}$, 2×POCH$_{3B}$), 4.41 (qua, 1H, J=6.0 Hz, 5'-CH$_B$), 4.50–4.68 (M, 4 H, 3'-CH$_A$, 3'-CH$_B$, 3-CH$_A$, 3-CH$_B$), 4.70 (qua, 1H, J=7.0 Hz, 5'-CH$_A$), 4.99 (d, 2H, J=16 Hz, COCH$_{2A}$P), 5.03 (d, 2H, J=16.7 Hz, COCH$_{2B}$P), 5.41 (s, 1H, 4'-CH$_B$), 5.47 (s, 1H, 4'-CH$_A$), 5.57 (s, 1H, 1'-CH$_B$), 5.61 (s, 1H, 1'-CHA), 5.98 (s, 1H, 1-CH$_B$), 6.15 (s, 1H, 1- CH$_A$), 6.71 (qua, 2H, J=8.7 Hz, 6.7-ArH$_B$), 6.75 (qua, 2H, J=8.5 Hz, 6.7-ArH$_A$), 6.89 (d, 1H, J=7.0 Hz, NH$_B$COCF$_3$), 7.05 (d, 1H, J=7.0 Hz, NH$_A$COCF$_3$), 8.21 (m, 8H, 4×COArH$_A$NO$_2$, 4×COArH$_B$NO$_2$).

Step 4: [(1'S, 1S, 3R), and (1'S, 1R, 3S)-1-(2',3,6'-trideoxy-3'-trifluoroacetamido-4'-p-nitrobenzoyl-L-lyxohexopyranose)-3-dimethylphosphonoacetyl-3,4,5,8-tetrahydronaphthaleno-[2,3-c]-pyran To a solution of glycoside from step 3 herein (98 mg, 0.13 mmole) in 8 ml of acetonitrile cooled to 0° C. was added sodium bicarbonate powder (22 mg, 0.27 mmole). This was followed by dropwise addition of aqueous cerium ammonium nitrate (CAN, 298 mg, 0.54 mmole in 3.0 ml of water). After 10 minutes at 0° C., the reaction mixture was poured to water (20 ml) and extracted with dichloromethane (4×10 ml). The organic layer was dried (over sodium sulfate) and evaporated to give the titled quinones as a glassy mixture (85 mg).

$^1$HNMR (CDCl$_3$, 250 MHz, Bruker), δ: 1.15 (d, 1H, J=6.4 Hz, 6'-CH$_{3B}$), 1.30 (d, 1H, J=6.4 Hz 6'-CH$_{3A}$), 2.44–1.80 (M, 4H, 2-HCH$_{Aa}$, 2-HCH$_{Ba}$, 2-HCH$_{Ae}$, 2-HCH$_{Be}$), 2.41 (dd, 1H, J=16.6 Hz, 11.6 Hz, 4-HCH$_{Ba}$), 2.48 (dd, 1H, J-16.6 Hz, 11.3 Hz, 4- HCH$_{Aa}$), 2.83 (dd, 1H, J=17.0 Hz, 5.23 Hz, 4-HCH$_{Ae}$), 2.85 (dd, 1H, J=16.8 Hz, 5.0 Hz, 4-HCH$_{Be}$), 3.79 (s, 3H, POCH$_{3A}$), 3.84 (s, 3H, POCH$_{3A}$), 3.82 (d, 3H, J=2.1 Hz, POCH$_{3B}$), 3.87 (d, 3H, J=2.1 Hz, POCH$_{3B}$), 4.34 (qua, 1H, J=7.0 Hz, 5'CH$_B$), 4.48–4.60 (m, 4H, 3- CH$_A$, 3 CH$_B$, 3'-CH$_A$, 3'-CH$_B$), 4.64 (qua, 1H, J=7.0 Hz, 5'- CH$_A$), 5.04 (d, 2H, J=25 Hz, COCH$_{2A}$P), 5.05 (d, 2H, J=31 Hz, COCH$_{2B}$P), 5.43 (s, 2H, 4', CH$_A$, 4'-CH$_B$), 5.55 (s, 1H, 1'-CH$_A$), 5.61 (s, 1H, 1'-CH$_B$), 5.81 (s, 1H, 1-CH$_B$), 5.97 (s, 1H, 1- CH$_A$), 6.79 (m, 2 H, 6.7- ArH$_B$), 6.82 (m, 2H, 6.7- ArH$_A$), 8.27 (s, 8H, 4×COArH$_A$NO$_2$, 4×COArH$_B$NO$_2$).

Step 5: (1'S, 1R, 3S)-1-(2',3',6'-trideoxy-4'-p-niprobenzoyl-3'-trifluoroacetamido-L-lyxohexopyranose)-3-dimethylphosphonoacetyl-5,10-dioxo-3,4,5,10-tetrahydro-1H-naphtho[2,3-c]-pyran The compounds from step 4 herein (85 mg, 0.121 mmol) were heated with 1-acetoxy-1,3-butadiene (86 μl, 0.723 mmol) in toluene at 45° C. for 28 hours. Solvent was evaporated and the crude product was chromatographed three times (toluene:EtOAc: HOMe: acetone:HOAc= 240:75:10:10:1) to give the (1'S, 1R, 3S) isomer (21 mg) and the (1'S, 1S, 3R) isomer (18 mg). The titled compound had:

$^1$H NMR (CDCl$_3$, 250 MHz, Bruker): δ, 1.19 (3H, d, J=7.0 Hz, 6'-CH$_3$), 2.03 (1H, m, 2-HCH$_a$), 2.07 (1H, m, 2-HCH$_e$), 2.56 (1H, dd, J=18.2 Hz, 11.8 Hz, 4-HCH$_a$), 3.05 (1H, dd, J=18.2 Hz, 4.7 Hz, 4-HCH$_e$), 3.85 (3H, d, J=2.0 Hz, POCH$_3$), 3.91 (3H, d, J=2.0 Hz, POCH$_3$), 4.40 (1H, qua, J=7.0 Hz, 5'-CH), 4.60 (1H, m, 3'-CH), 4.65 (1H, dd, J=11.8 Hz, 4.7 Hz), 5.04 (1H, br s, CHP), 5.17 (1H, tr, J=2.0 Hz, CHP), 5.42 (1H, s, 4'-CH), 5.71 (1H, s, 1'-CH), 6.00 (1H, s, 1-CH), 6.48 (1H, d, J=7.6 Hz, NHCOCF$_3$), 7.76 (2H, m, 7, 8-ArH), 8.10 (2H, m, 6, 9-ArH), 8.27 (2H, d, J=8.0 Hz, PNB), 8.32 (2H, d, J=8.0 Hz, PNB).

IR (Nicolet 205 FT, film on NaCl plate): cm$^{-1}$, 3323.0, 3242.5, 3077.6, 2965.0, 1730.3, 1661.9, 3593.5, 1529.2, 1271.8, 1193.2, 1050.8, 864.0, 835.7, 722.1.

The second compound, (1'S, 1S, 3R)-1-(2',3',6'-trideoxy-4'-p-niprobenzoyl-3'-trifluoroacetamido-L-lyxohexo pyranose)-3-dimethyl phosphonoacetyl-5,10-dioxo-3,4,5,10-tetrahydro-1H-naphtho[2,3-c]-pyran had:

M.P. 135°–137° C.

$^1$H NMR (CDCl$_3$, 250 MHZ, Bruker): δ, 1.33 (3H, d, J=6.4 Hz, 6'-CH$_3$), 2.01 (1H, br tr, J=11.8 Hz, 3'-HCH$_a$), 2.15 (1H, br tr, J=11.8 Hz, 3'-HCH$_e$), 2.62 (1H, dd, J=18.8 Hz, 12.1 Hz, 4-HCH$_a$), 3.01 (1H, dd, J=18.8 Hz, 4.4 Hz, 4-HCH$_e$), 3.81 (3H, s, POCH$_3$), 3.86 (3H, s, POCH$_3$), 4.58 (1H, m, 4'-CH), 4.60 (1H, dd, J=12.1 Hz, 4.4 Hz, 3-CH), 4.79 (1H, qua, J=6.4 Hz, 6-CH), 5.02 (1H, br s, PCH), 5.13 (1H, br s, PCH), 5.46 (1H, s, 5'-CH), 5.62 (1H, s, 1'-CH), 6.14 (1H, s, 1-CH), 6.63 (1H, d, J=8.2 Hz, NHCOCF$_3$), 7.79 (2H, m, 7, 8-ArH), 8.16 (2H, m, 6, 9-ArH), 8.30 (4H, m, PNB).

IR (Nicolet 205 FT, film on NaCl plate): cm$^{-1}$, 3322.0, 3242.5, 3083.5, 2959.0, 2853.0, 1729.5, 1668.6, 1597.0, 1525.5, 1276.4, 1183.7, 1045.9, 853.9, 724.2.

Step 6: (1'S, 1R, 3S)-1-(2',3',6'-trideoxy-3'-trifluoroacetamido-L-lyxohexopyranose)-3-dimethylphosphonoacetyl-5,10-dioxo-3,4,5,10-tetrahydro-1H-naphtho-[2,3-c]-pyran (BCH-1689)

The PNB-protected ketophosphonate from step 5 herein (21 mg, 0.028 mmol) was dissolved in THF-MeOH (3 ml of each) and cooled to 0° C. Sodium methoxide (4.3 m, 6.5 μl) was added. After stirred for 5 minutes at 0° C., the crude mixture (pink) was acidified with 0.1N aqueous hydrogen chloride. It was extracted with methylene chloride, dried (over sodium sulfate) and evaporated to give a crude product which was recrystallized from methylene chloride and hexane to give the desired product (10 mg) as an off-white solid.

M.P. 95°–97° C.

$^1$H NMR (CDCl$_3$, 250 MHz, Bruker): δ, 1.25 (3H, d, J=8.2 Hz, 6'-CH$_3$), 1.83–1.98 (2H, m, 2'-CH$_2$, 2.53 (1H, dd, J=17.6, 11.8 Hz, 4-HCH$_a$), 3.00 (1H, dd, J=17.6 Hz, 3.5 Hz, 4-HCH$_e$), 3.62 (1H, br s, 4'-CH), 3.82 (3H, s, POCH$_3$), 3.86 (3H, s, POCH$_3$), 4.16 (1H, qua, J=8.2 Hz, 5'-CH), 4.34 (1H, m, 3'-CH), 4.62 (1H, dd, J=11.8 Hz, 3.5 Hz, 3-CH), 5.01 (1H, s, CHP), 5.12 (1H, s, CHP), 5.54 (1H, s, 1'-CH), 5.94 (1H, s, 1-CH), 6.82 (1H, d, J=7.1 Hz, NHCOCF$_3$), 7.74 (2H, m, 7, 8-ArH), 8.06 (2H, m, 6, 9-ArH).

IR (Nicolet 205 FT, film on NaCl plate): cm$^{-1}$, 3421.4 (br), 3080.8, 2960.1, 1718.4, 1664.5, 1556.7, 1457.6, 1283.0, 1188.1, 1043.7, 983.4, 858.9, 728.4.

EXAMPLE 61

Various C-2'axialy iodinated pyranylnaphthoquinone glycosides

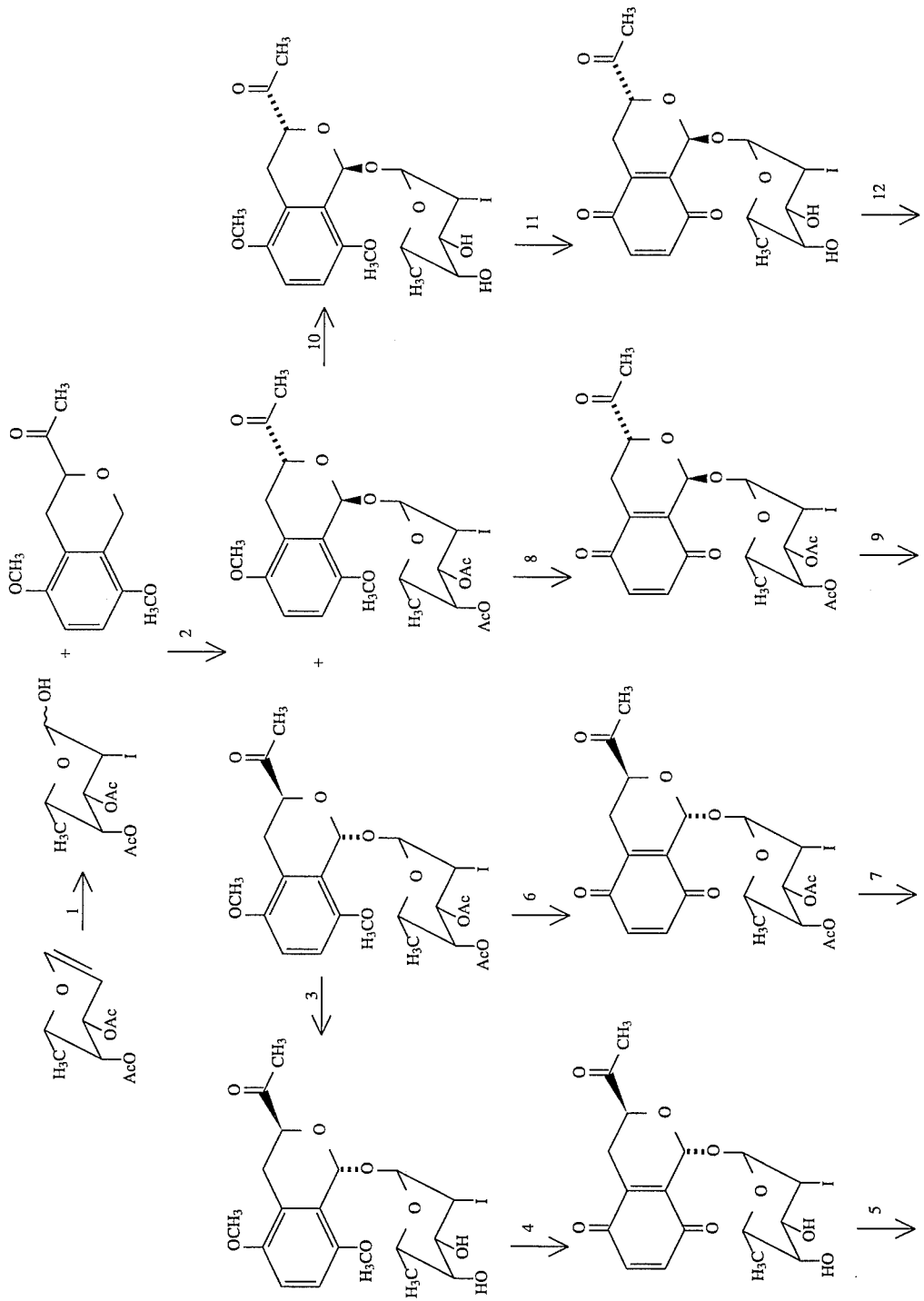

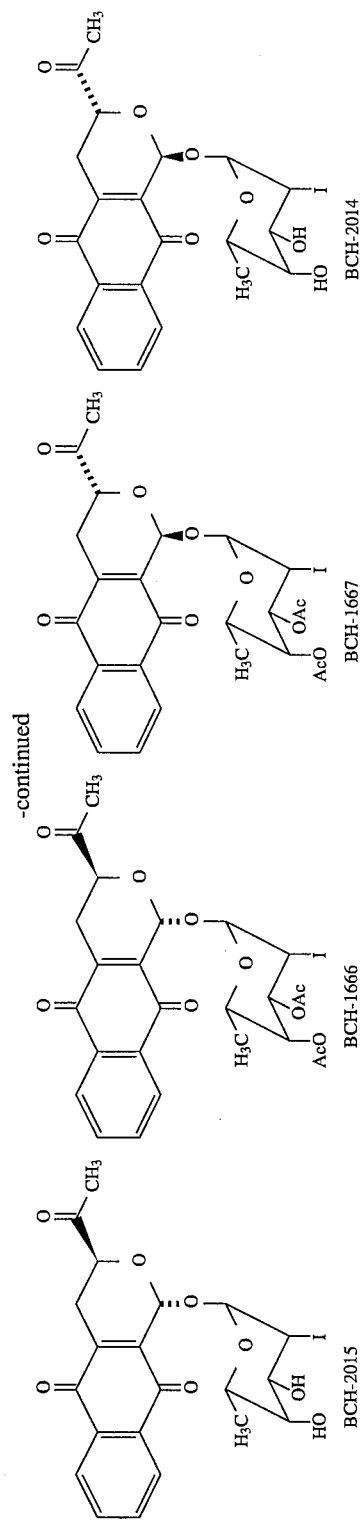

Step 1: 3,4-DI-dO-acetyl-2-iodo-2,6-dideoxyfucose

To a mixture of di-O-acetyl fucal (3.029 g, 14.140 mmol) in 180 ml of acetonitrile and 18 ml of water was added portionwise the NIS (3.590 g, 15.554 mmol). After stirring for 30 minutes the mixture was extracted with $CH_2Cl_2$ (2x) and the combined organic extracts were washed with 10% sodium thiosulfate solution, water and finally dried ($Na_2SO_4$) to give 4.403 g (87% yield) of the desired sugar.

PMR (acetone-$d_6$, 250 MHz) δ: 1.12 (d, 3H, J=6.4 Hz, $CH_3$-6'), 1.99 and 2.11 (2s, 2×3H, 2×OAc), 4.36 (d, 1, J=5.1 Hz, H-2), 4.48 (q, 1H, J=6.6 Hz, H-5), 4.98 (unresolved dd, 1H, H-3), 5.18 (broad s, 1H, H-4), 5.59 (broad s, 1H, H-1), 5.94 (d, 1H, OH).

Step 2: (1'S, 1R, 3S) and (1'S, 1S, 3R)-2,5-Dimethoxy-1-(2',6'-dideoxy-3',4'-diacetoxy-2'-iodo-L-lyxohexopyranose)-3-acetoisochroman To a mixture of sugar from step 1 herein (910 mg, 2.539 mmol) and methyl ketone isochroman (500 mg, 2.116 mmol) in dry $CH_2Cl_2$ under argon atmosphere and room temperature was added some molecular sieve (4A). After stirring for 20 minutes DDQ (577 mg, 2.539 mmol) was added. After stirring for 72 hours, while additions of 0.5 equivalent of sugar and 0.5 equivalent of DDQ were done after 24 and 48 hours, the reaction was worked up by addition of 1.00 ml of $NaHCO_3$ 5% and water mixture (1:3). Extractions with $CH_2Cl_2$ (3×100 ml) following by washing with the same aqueous mixture and drying ($Na_2SO_4$). Flash chromatography of the crude ($CH_2Cl_2$:Hex:EtOAc; 9:4:1) gave 361 mg of the non-natural (1'S, 1S, 3R) glycoside and 435 mg of the natural (1'S, 1R, 3S) one. The arbitrarily assigned (1'S, 1S, 3R) titled compound had:

PMR (acetone-$d_6$, 250 MHz) δ: 1.27 (d, 3H, J=6.5 Hz, $CH_3$-6'), 1.94 and 2.16 (2s, 2×3H, 2×OAc), 2.30 (s,3H, $COCH_3$), 2.50 (dd, 1H, J=17.8 Hz and 12.1 Hz, $CH_a$CHO), 2.95 (dd, 1H, J=17.8 and 4.3 Hz, $CH_e$CHO), 3.80 and 3.83 (2s, 2×3H, 2×$OCH_3$), 5.52 (d, 1H, J=5.0 Hz, H-2'), 4.75 (m, 3H, H-3, H-3' and H-5'), 5.24 (broad s, 1H, H-4'), 5.89 (s, 1H, H-1'), 6.15 (s, 1H, H-1), 6.90 (2d, 2H, Ar-H).

The second (1'S, 1S, 3R) titled compound had:

PMR (acetone-$d_6$, 250 MHz) δ: 1.16 (d, 3H, J=6.6 Hz, $CH_3$-6'), 1.97 and 2.15 (2s, 2×3H, 2×OAc), 2.30 (s, 3H, $COCH_3$), 2.45 (dd, 1H, J=17.6 Hz and 12.2 Hz, $CH_a$CHO), 2.96 (dd, 1H, J=17.6 and 4.1 Hz, $CH_e$CHO), 3.80 and 3.82 (2s, 2×3H, 2×$OCH_3$), 4.48 (d, 1H, J=5.0 Hz, H-2'), 4.54 (m, 2H, H-3, H-5'), 4.83 (unresolved dd, 1H, H-3'), 5.20 (broad s, 1H, H-4'), 5.86 (s, H, H-1'), 6.03 (s, 1H, H-1), 6.88 (2d, 2H, Ar-H).

Step 3: (1'S, 1R, 3S)-5,8-Dimethoxy-3-aceto-1-(2',6'-dideoxy-2'-iodo-L-lyxohexopyranose)-isochroman To mixture of the compound from step 2 herein (500 mg, 0.844 mmol) in 90 ml of dry THF maintained at 0° C. and under argon atmosphere were added 90 ml of NaOH 0.5N. After stirring for 1 hour the reaction mixture was neutralized with 160 ml of $NH_4Cl$ sat.:$NaHCO_3$ sat. (4:1) and extracted with $CH_2Cl_2$ (3×200 ml). the combined organic layers were dried over $MgSO_4$. Flash chromatography (toluene:ethyl acetate; 8:2) of the crude gave 248 mg (49% yield) of pure titled compound.

PMR (acetone-$d_6$, 250 MHz) δ: 1.26 (d, 3H, J=6.5 Hz, $CH_3$-6'), 2.29 (s, 3H, $COCH_3$), 2.44 (dd, 1H, J=17.5 and 12.2 Hz, $CH_a$CHO), 2.93 (dd, 1H, J=17.7 and 4.1 Hz, $CH_e$CHO), 3.16 (d, 1H, J=6.0 Hz, OH), 3.49 (m, 1H, H-3'), 3.77 (m, 1H, H-3'), 3.79 and 3.84 (2×s, 2×3H, $OCH_3$), 4.09 (d, 1H, J=7.4 Hz, OH), 4.25 (q, 1H, J=6.6 Hz, H-5'), 4.37 (d, 1H, J=5.0 Hz, H-2'), 4.54 (dd, 1H, J=12.2 Hz, 4.1 Hz, H-3), 5.84 (s, 1H, H-1'), 5.99 (s, 1H, H-1), 6.88 (2×d, 2×H, ArH)

Step 4: (1'S, 1R, 3S)-3-aceto-1- (2',6'-dideoxy-2'-iodo-L-lyxohexopyranose)-5,8-dioxo-5,8-dihydroisochroman The titled compound was obtained following CAN oxidation of the product from step 3 herein as per previous procedure.

PMR ($CDCl_3$, 250 MHz) δ: 1.32 (d, 3H, J=6.6 Hz, $CH_3$-6'), 1.86 (large d, 1H, OH), 2.33 (s, 3H, $COCH_3$), 2.39 (dd, 1H, J=19.9 and 11.9 Hz, $CH_a$-CHO), 2.81 (large s, 1H, OH), 2.90 (dd, 1H, J=19.7 Hz and 3.9 Hz, $CH_e$-CHO), 3.32 (large s, 1H, H-3'), 3.78 (large unresolved d, 1H, H-4'), 4.17 (broad q, 1H, J=5.0 Hz, H-5'), 4.39 (m, 2H, H-3 and H-2'), 6.81 (s, 1H, H-1'), 6.89 (s, 1H, H-1), 6.81 (2×d, 2H, quinone ring-H).

IR (film) $v_{max}$: 3486, 3400, 2937, 1711, 1657, 1307, 968 $cm^{-1}$.

Step 5: (1'S, 1R, 3S)-methyl-(1-[2',6'-dideoxy-3',4'-dihydroxy-2,-iodo-L-lyxohexopyranose]-5,10-dioxo-3,4,5,10-tetrahydronaphtho[2,3-c]-pyran-3-yl) ketone (BCH-2015)

Starting from 50 mg (0.105 mmol) of the compound from step 4 herein and 1 ml of 1-acetoxybutadiene, the procedure described in step 2, example 5, has been followed. After purification, 15.8 mg (29% yield) of pure titled compound was isolated.

PMR ($CDCl_3$, 250 MHz) δ: 1.32 (d, 3H, J=6.7 Hz, $CH_3$-6'), 1.91 (large d, 1H, J=11.0 Hz, OH), 2.36 (s, 3H, $COCH_3$), 2.53 (dd, 1H, J=19.5 Hz, 11.4 Hz, $CH_a$CHO), 2.81 (large d, 1H, J=10.4 Hz, OH), 3.08 (dd, 1H, J=19.9 Hz and 4.1 Hz, $CH_e$CHO), 3.34 (m, 1H, H-3'), 3.80 (m, 1H, H-4'), 4.17 (broad q, 1H, 6.9 Hz, H-5'), 4.45 (m, 2H, H-3 and H-4'), 5.98 (2×s, 2×1H, H-1 and H-1'), 7.78 and 8.11 (2×m, 2×2H, ArH).

IR (film) $v_{max}$: 3477 broad, 2928, 1722, 1670, 1298, 961, 732 $cm^{-1}$.

Step 6: (1'S, 1R, 3S)-5,8-Dioxo-3-aceto-1-(2',6'-dideoxy-3', 4'-diacetoxy-2'-iodo-L-lyxohexopyranose)-5,8-dihydroisochroman CAN oxidation of the (1'S, 1R, 3S) diastereomeric product from step 2, example 61, yielded the titled compound.

PMR ($CDCl_3$, 250 MHz) δ: 1.21 (d, 3H, J=6.6 Hz, $CH_3$-6'), 2.07 and 2.22 (2s, 2×3H, 2×OAc), 2.32 (s, 3H, $COCH_3$), 2.41 (dd, 1H, J=24.1 Hz, 11.8 Hz, $CH_a$CHO), 2.92 (dd, 1H, J=19.7 Hz and 3.9 Hz, $CH_e$CHO), 4.29 (q, 1H, J=6.5 Hz, H-5'), 4.36 (d, 1H, J=5.1 Hz, H-2'), 4.41 (dd, 1H, J=11.2 Hz and 4.0 Hz, H-3), 4.78 (dd, 1H, J=4.0 Hz, H-3'), 5.23 (broad s, 1H, H-4'), 5.82 (1s, 1H, H-1'), 5.87 (1s, 1H, H-1), 6.81 (2d, 2H, quinone ring-H).

Step 7: (1'S, 1R, 3S)-methyl-(1-[2',6'-dideoxy-3'-4'-diacetoxy-2'-iodo-L-lyxohexopyranose]-5,10-dioxo-3,4,5,10-tetrahydronaphtho[2,3-c]-pyran-3-yl) ketone (BCH-1666)

To a mixture of glycoside from step 6 herein (55 mg, 0.098 mmol) in 1.5 ml of dry toluene and under argon atmosphere, was added 1-acetoxybutadiene (66 mg, 0.587 mmol). After 18 hours of stirring the mixture was directly flash chromatographed (toluene:ethyl acetate; 9:1) to give 17 mg of pure titled compound (28% yield).

PMR ($CD_2Cl_2$, 250 MHz) δ: 1.20 (d, 3H, J=1.20 Hz, $CH_3$-6'), 2.13 and 2.44 (2s, 2×3H, 2×$OCH_3$), 2.31 (s, 3H, $COCH_3$), 2.62 (dd, 1H, J=19.5 Hz and 11.5 Hz, $HC\underline{H}_aCHC=O$), 3.16 (dd, 1H, J=19.5 Hz, 4.0 Hz, $HCH_eCHC=O$), 4.45 (broad q, 1H, J=6.6 Hz, H-5'), 4.51 (d, 1H, J=5.0 Hz, H-2'), 4.62 (unresolved dd, 1H, J=11.7 Hz and 4.0 Hz, H-3), 4.88 (dd, 1H, J=4.0 Hz, H-3'), 5.32 (broad s, 1H, H-4'), 6.06 (s, 1H, H-1'), 6.16 (s, 1H, H-1), 7.71 and 8.22 (2×m, 2×2H, ArH).

IR (film) $v_{max}$: 2991, 2935, 1746, 1668, 1238, 970, 730 $cm^{-1}$.

Step 8: (1'S, 1S, 3R)-5,8-Dioxo-3-aceto-1-(2',6'-dideoxy-3',4'-diacetoxy-2'-iodo-L-lyxohexopyranose)-5,8-dihydroisochroman CAN oxidation of the (1'S, 1S, 3R) glycoside from step 2, example 61, gave the titled compound.

PMR (CDCl₃, 250 MHz) δ: 1.35 (d, 3H, J=6.6 Hz, CH₃-6'), 2.07 and 2.23 (2s, 2×3H, 2×OAc), 2.32 (s, 3H, COCH₃), 2.46 (dd, 1H, J=20.3 Hz and 11.7 Hz, CH$_a$CHO), 2.90 (dd, 1H, J=19.7 Hz and 4.1 Hz, CH$_e$CHO), 4.25 (d, 1H, J=5.2 Hz, H-2'), 4.43 (dd, 1H, J=11.6 Hz and 4.1 Hz, H-3), 4.61 (q, 1H, J=6.2 Hz, H-5'), 4.75 (dd, 1H, J=3.6 Hz, H-3'), 5.26 (broad s, 1H, H-4'), 5.82 (s, 1H, H-1'), 5.97 (s, 1H, H-1), 6.81 (2d, 2H, quinone ring-H).

IR (film) ν$_{max}$: 2945, 1747 broad, 1663, 1237, 969 cm⁻¹.

Step 9: (1'S, 1S, 3R)-methyl-(1-[2',6'-dideoxy-3',4'-diacetoxy-2'-iodo-L-lyxohexopyranose]-5,10-dioxo-3,4,5,10-tetrahydronaphtho[2,3-c]-pyran-3-yl) ketone (BCH-1667)

Starting from 70 mg (0.118 mmol) of compound from step 8 herein and 79.6 mg of 1-acetoxybutadiene and following the procedure described in step 2, example 5, we obtained after purification 25 mg (35% yield) of titled compound.

PMR (CDCl₃, 250 MHz) δ: 1.40 (d, 3H, J=6.4 Hz, CH₃-6'), 2.05 and 2.24 (2s, 2×3H, 2×OCH₃), 2.35 (s, 3H, COCH₃), 2.57 (dd, 1H, J=20.0 and 12.4 Hz, HC H$_a$CHCO), 3.07 (dd, 1H, J=20.0 Hz and 4.2 Hz, HCH$_e$CHC=O), 4.27 (d, 1H, J=5.0 Hz, H-2'), 4.49 (dd, 1H, J=11.6, 4.2 Hz, H-3), 4.75 (m, 2H, H-3'and H-5'), 5.28 (large s, 1H, H-4'), 5.86 (s, 1H, H-1'), 6.14 (s, 1H, H-1), 7.77 and 8.11 (2m, 2×2H, ArH).

IR (film) ν$_{max}$: 2945, 1743 broad, 1668, 1236 broad, 958, 734 cm⁻¹.

Step 10: (1'S, 1S, 3R)-5,8-Dimethoxy-3-aceto-1-(2',6'-dideoxy-2'-iodo-L-lyxohexopyranose)-isochroman The titled compound was obtained via base hydrolysis of the (1'S, 1S, 1R) precursor from step 2 herein as per procedure from step 3 herein.

PMR (acetone-d₆, 250 MHz) δ: 1.35 (d, 3H, J=6.6 Hz, CH₃-6'), 2.30 (s, 3H, COCH₃), 2.50 (dd, 1H, J=17.6 and 11.5 Hz, CH$_a$CHO), 2.94 (dd, 1H, J=17.9 and 4.3 Hz, CH$_e$CHO), 3.20 (d, 1H, OH), 4.44 (m, 1H, H-3'), 3.80 (large s, 7H, 2×OCH₃ and H-4'), 4.12 (d, 1H, OH), 4.41 (d, 1H, J=5.0 Hz, H-2'), 4.55 (q, 1H, J=6.4 Hz, H-5'), 4.70 (dd, 1H, J=12.1 Hz and 4.5 Hz, H-3), 5.87 (1S, 1H, H-1'), 6.14 (1s, 1H, H-1), 6.88 (2d, 2H, ArH).

Step 11: (1'S, 1S, 3R)-3-aceto-1-(2',6'-dideoxy-2'-iodo-L-lyxohexopyranose)-5,8-dioxo-5,8-dihydroisochroman The titled compound was oDtained following CAN oxidation of the product from step 10 herein as per previous procedure.

PMR (CDCl₃, 250 MHz) δ: 1.45 (d, 3H, J=6.6 Hz, CH₃-6'), 1.90 (broad s, 1H, OH), 2.31 (s, 3H, COCH₃), 2.43 (dd, 1H, J=20.1 Hz and 11.8 Hz, CH$_a$CHO), 2.80 (m, 1s, OH), 2.88 (dd, 1H, J=19.8 Hz and 4.1 Hz, CH$_e$CHO), 3.32 (m, 1H, H-3'), 3.84 (m, 1H, H-4'), 4.24 (d, 1H, J=4.4 Hz, H-2'), 4.42 (dd, 1H, J=11.8 Hz and 4.2 Hz, H-3), 5.82 (s, 1H, H-1'), 5.95 (s, 1H, H-1), 6.79 (2×d, 2H, quinone ring-H).

Step 12: (1'S, 1S, 3R)-methyl-(1-[2',6'-dideoxy-3',4'-dihydroxy-2'-iodo-L-lyxohexopyranose]-5,10-dioxo-3,4,5,10-tetrahydronaphtho[2,3-c]-pyran-3-yl)-ketone (BCH-2014)

A mixture of compound from step 11 herein (1 ml) and 1-acetoxy-butadiene (96 mg, 0.201 mmol) in 2 ml of dry toluene was stirred for 18 hours under argon atmosphere and then flash chromatographed (Toluene:Ethyl acetate; 8:2) to give 42 mg (40% yield) of pure titled compound. PMR (CDCl₃, 250 MHz) δ: 1 52 (d, 3H, CH₃-6'), 2.36 (s, 3H, COCH₃), 2.58 (dd, 1H, J=19.7 Hz and 11.4 Hz, HCH$_a$CHCO), 2.78 (broad m, 1H, OH), 3.09 (dd, 1H, J=20.0 Hz and 4.21 Hz, HCH$_e$CHCO), 3.34 (m, 1H, H-3'), 3.89 (m, 1H, H-4'), 4.27 (d, 1H, J=4.5 Hz, H-2'), 4.49 (dd, 1H, J=11.7 Hz and 4.2 Hz, H-3), 4.66 (broad q, 1H, J=5.4 Hz, H-5'), 5.30 (s, 1H, H-1'), 5.89 (s, 1H, H-1), 7.53 and 8.13 (2m, 2×2H, Ar-H).

IR (film) ν$_{max}$: 3434 broad, 2934 broad, 1720, 1669, 1292, 995, 955 cm⁻¹.

EXAMPLE 62

C-2'axialy brominated pyranylnaphthoquinone glycosides

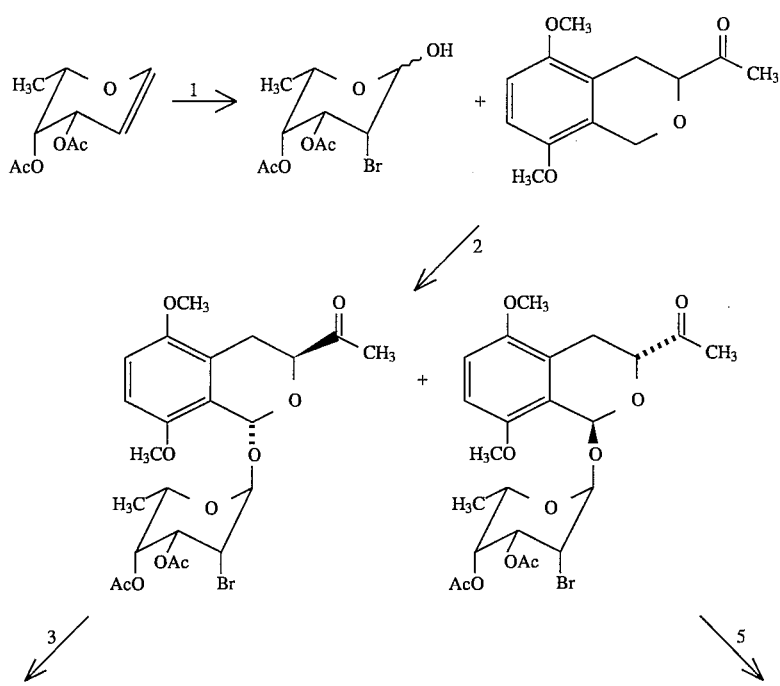

235

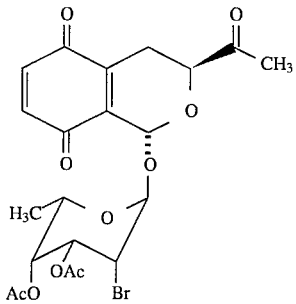

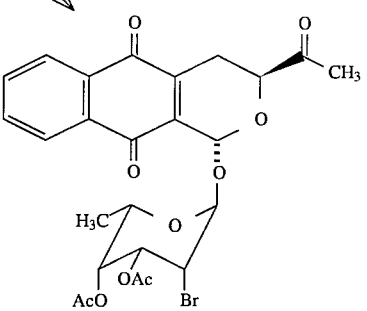

236 -continued

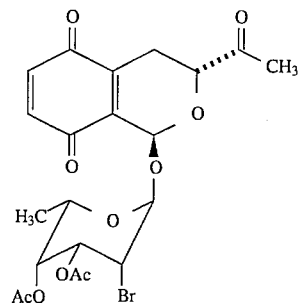

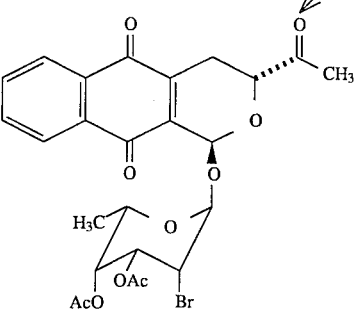

Step 1: 3,4-Di-O-acetyl-2-bromo-2,6-dideoxyfucose

Following the procedure described in step 1, example 61, we obtained after work-up 89% yield of a mixture of four compounds. Probably axial and equatorial bromo sugars and α and β isomers of each.

Step 2: (1'S, 1R, 3S) and (1'S, 1S, 3R)-2,5-Dimethoxy-1-(2',6'-dideoxy-3',4'-diacetoxy-2'-bromo-L-lyxohexopyranose)-3-acetoisochroman Following the procedure described in step 2, example 61, we obtained after purification (Dichloromethane:Hexane:Ethyl acetate; 12:7:1) 35% yield of a separable (1'S, 1R, 3S and 1'S, 1S, 3R) 1:1 mixture of titled diastereoisomers.

(1'S, 1S, 3R): PMR (acetone-$d_6$, 250 MHz) δ: 1.27 (d, 3H, J=6.5 Hz, $CH_3$-6'), 1.94 and 2.11 (2×s, 2×3H, 2×OAc), 2.29 (s, 3H, $COCH_3$), 2.50 (dd, 1H, J=17.7 Hz and 12.1 Hz, $CH_a$CHO), 2.96 (dd, 1H, J=17.8 and 4.2 Hz, $CH_e$CHO), 3.80 and 3.84 (2×s, 2×3H, 2×$OCH_3$), 4.42 (d, 1H, J=4.2 Hz, H-2'), 4.71 (dd, 1H, J=12.2 Hz and 4.2 Hz, H-3), 4.81 (q, 1H, J=6.4 Hz, H-5'), 5.22 (m, 2H, H-3' and H-4'), 5.74 (s, 1H, H-1'), 6.17 (s, 1H, H-1), 6.90 (2×d, 2H, Ar-H).

IR (film) $v_{max}$: 2937, 1748, 1486, 1260 and 1237, 970 $cm^{-1}$.

(1'S, 1R, 3S): PMR (acetone, 250 MHz) δ: 1.16 (d, 3H, J=6.6 Hz, $CH_3$-6'), 1.97 and 2.10 (2×s, 2×3H, 2×OAc), 2.30 (s, 3H, $COCH_3$), 2.45 (dd, 1H, J=17.6 Hz and 12.2 Hz, $CH_a$CHO), 2.97 (dd, 1H, J=17.6 Hz and 4.0 Hz, $CH_e$CHO), 3.80 and 3.82 (2×s, 2×3H, 2×$OCH_3$), 4.38 (d, 1H, J=4.6 Hz, H-2'), 4.53 (q, 1H, J=6.4 Hz, H-5'), 5.16 (broad s, 1H, H-4'), 5.27 (dd, 1H, J=4.2 Hz, H-3'), 5.71 (s, 1H, H-1'), 6.05 (s, 1H, H-1), 6.89 (2×d, 2H, Ar-H).

Step 3: (1'S, 1R, 3S)-5,8-dioxo-1-(2',6'-dideoxy-3',4'-diacetoxy-2'-bromo-L-lyxohexopyranose)-5,8-dihydroisochroman CAN oxidation of the compound from step 2 herein yielded the titled compound.

PMR (CDCl₃, 250 MHz) δ: 1.19 (d, 3H, J=6.6 Hz, $CH_3$-6'), 2.04 and 2.16 (2×s, 2×3H, 2×OAc), 2.29 (s, 3H, $COCH_3$), 2.38 (dd, 1H, J=19.9 Hz and 11.6 Hz, $CH_a$CHO), 2.88 (dd, 1H, J=19.8 Hz and 3.9 Hz, $CH_e$CHO), 4.25 (m, 2H, H-2'and H-5'), 4.39 (dd, 1H, J=11.6 Hz and 3.8 Hz, H-3), 5.16 (broad s, 1H, H-4'), 5.19 (dd, 1H, J=4.0 Hz, H-3'), 5.71 (s, 1H, H-1'), 5.81 (s, 1H, H-1), 6.79 (2×d, 2H, Ar-H).

Step 4: (1'S, 1R, 3S)-methyl-(1- [2',6'-dideoxy-3',4'-diacetoxy-2'-bromo-L-lyxohexopyranose]-5,10-dioxo-3,4,5,10-tetrahydronaphtho-[2,3-c]-pyran-3-yl) ketone (BCH-2100)

The titled compound was obtained following the procedure described in step 2, example 5, from the compound from step 3 herein. HPLC purification gave 9% of desired (1'S, 1R, 3S) natural titled glycoside.

PMR (CDCl₃, 250 MHz) δ: 1.23 (d, 3H, J=6.4 Hz, $CH_3$-6'), 2.06 and 2.19 (2s, 2×3H, 2×OAc), 2.35 (s, 3H, $COCH_3$), 2.54 (dd, 1H, J=19.7 Hz and 11.7 Hz, $CH_a$CHO), 3.09 (dd, 1H, J=19.8 Hz and 4.0 Hz, $CH_e$CHO), 4.29 (m, 2H, H-2'and H-5'), 4.47 (dd, 1H, J=11.7 Hz and 4.0 Hz, H-3), 5.18 (broad s, 1H, H-4'), 5.23 (unresolved dd, 1H, H3'), 5.83 (s, 1H, H-1'), 6.01 (s, 1H, H-1), 7.77 and 8.11 (2m, 2×2H, Ar-H).

IR (film) $v_{max}$: 2991 and 2943, 1748,1665, 1241, 975 $cm^{-1}$.

Step 5: (1'S, 1R, 3S)-5,8-dioxo-3-aceto-1-(2',6'-dideoxy-3',4'-diacetoxy-2'-bromo-L-lyxohexopyranose)-5,8-dihydroisochroman CAN oxidation of the (1'S, 1R, 3S) diastereomer from step 2 herein yielded the titled product.

IR (film) $v_{max}$: 2939, 1743, 1674, 1241, 968 $cm^{-1}$.

Step 6: (1'S, 1S, 3R)-methyl-(1- [2',6'-dideoxy-3',4'-diacetoxy-2'-bromo-L-lyxohexopyranose]-5,10-dioxo-3,4,5,10-tetrahydronaphtho-[2,3-c]-pyran-3-yl) ketone (BCH-2099)

The titled compound was obtained following the procedure described in step 2, example 5, from the quinone from step 5 herein. Flash chromatography (Toluene:Ethyl acetate; 9:1) gave 30% of desired titled compound.

PMR (CDCl₃, 250 MHz) δ: 1.41 (d, 3H, J=6.4 Hz, $CH_3$-6'), 2.05 and 2.21 (2s, 2×3H, 2×OAc), 2.34 (s, 3H, $COCH_3$), 2.58 (dd, 1H, J=20.1 Hz and 11.6 Hz, $CH_a$CHO), 3.08 (dd, 1H, J=20.0 Hz and 4.2 Hz, $CH_e$CHO), 4.16 (d, 1H, J=4.5 Hz, H-2'), 4.48 (dd, 1H, J=11.6 Hz and 4.1 Hz, H-3),
4.76 (q, 1H, J=5.9 Hz, H-5'), 5.20 (unresolved dd, 1H, H-3'),
5.25 (broad s, 1H, H-4'), 5.72 (1s, 1H, H-1'), 6.17 (1s, 1H,
H-1), 7.78 and 8.12 (2m, 2×2H, Ar-H).
IR (film) $\nu_{max}$: 2937, 1750, 1672, 1243, 964 cm$^{-1}$.
EXAMPLE 63
C-2'-axialy iodinated daunosaminyl pyranylnaphthoquinone glycosides
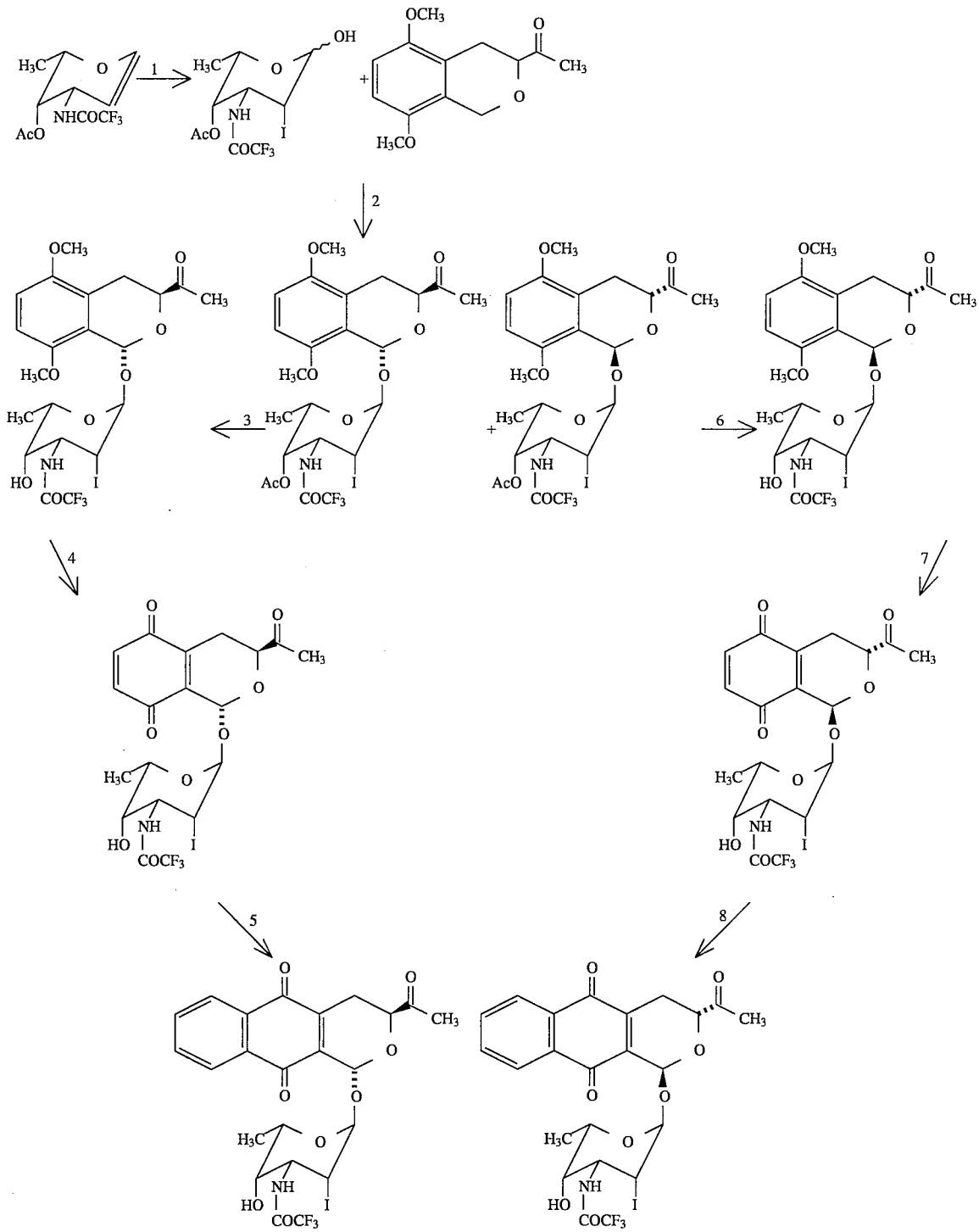

Step 1: 2',3',6'-trideoxy-2'-iodo-3'-trifluoroacetamido-4'-O-acetyl-L-lyxohexopyranose Following the procedure described in step 1, example 61, we obtained after work-up 94% yield of a non-separable α-β mixture (2:1) of titled halogenated sugar.

PMR (acetone-$d_6$, 250 MHz) δ: 1.08 (d, 3H, J=6.6 Hz, $CH_3$-6), 2.13 (s, 3H, OAc-4), 4.47 (m, 1H, H-3), 4.53 (d, 1H, J=4.3 Hz, H-2), 4.56 (broad q, 1H, J=5.2 Hz, H-5), 5.17 (broad s, 1H, H-4), 5.65 (d, 1H, J=3.8 Hz, H-1), 6.04 (d, 1H, J=3.8 Hz, OH).

Step 2: (1'S, 1R, 3S) and (1'S, 1S, 3R)-2,5-Dimethoxy-3-aceto-1-(2',3',6'-trideoxy-2'-iodo-3'-trifluoroacetamido-4'-O-acetyl-L-lyxohexopyranose)-isochroman Following the same procedure as described in step 2, example 61, we obtained after purification (Toluene:Ethyl acetate; 9:1) 38% yield of a separable (1'S, 1R, 3S and 1'S, 1S, 3R) mixture of titled diastereoisomers (1:1).

The natural (1'S, 1R, 3S) glycoside: PMR (acetone-$d_6$, 250 MHz) δ: 1.16 (d, 3H, J=6.6 Hz, $CH_3$-6'), 2.15 (s, 3H, AcO-4'), 2.30 (s, 3H, $COCH_3$), 2.41 (unresolved dd, 1H, $CH_aCHCO$), 2.97 (dd, 1H, J=17.7 Hz and 3.89 Hz, $CH_eCHO$), 3.80 and 3.84 (2xs, 2×3H, 2×$OCH_3$), 4.36 (m, 1H, H-3'), 4.63 (m, 3H, H-3, H-2' and H-5'), 5.19 (broad s, 1H, H-4'), 5.90 (s, 1H, H-1'), 6.06 (s, 1H, H-1), 6.87 (2×d, 2H, Ar-H), 7.95 (broad s, 1H, $NHCOCF_3$).

The non-natural glycoside (1'S, 1S, 3R): PMR (acetone-$d_6$, 250 MHz) δ: 1.23 (s, 3H, J=6.5 Hz, $CH_3$-6'), 2.16 (s, 3H, AcO-4'), 2.30 (s, 3H, $COCH_3$), 2.51 (dd, 1H, J=18.2 Hz and 12.0 Hz, $CH_aCHO$), 2.97 (dd, 1H, J=17.8 Hz and 4.3 Hz, $CH_eCHO$), 3.80 and 3.83 (2xs, 2×3H, 2×$OCH_3$), 4.30 (m, 1H, H-3'), 4.69 (d, 1H, J=4.72 Hz, H-2'), 4.74 (dd, 1H, J=12.1 Hz and 4.3 Hz, H-3), 4.88 (q, 1H, J=5.0 Hz, H-5'), 5.24 (broad s, 1H, H-4'), 5.92 (s, 1H, H-1'), 6.18 (s, 1H, H-1), 6.90 (2×d, 2×1H, Ar-H), 7.95 (broad s, 1H, $NHCOCF_3$).

Step 3: (1'S, 1R, 3S)-5,8-Dimethoxy-3-aceto-1-(2',3',6'-trideoxy-3'-trifluoroacetamido-2'-iodo-L-lyxohexopyranose)-isochroman Base hydrolysis of the compound from step 2 herein as per procedure from step 3, example 61, yielded the titled compound. PMR (acetone-$d_6$, 250 MHz) δ: 1.28 (d, 3H, J=6.6 Hz, $CH_3$-6'), 2.30 (s, 3H, $COCH_3$), 2.45 (dd, 1H, J=17.6 Hz and 12.2 Hz, $CH_aCHO$), 2.95 (dd, 1H, J=17.6 Hz and 4.0 Hz, $CH_eCHO$), 3.79 and 3.84 (2s, 2×3H, 2×$OCH_3$), 4.03 (m, 2H, H-4' and OH-4'), 4.44 (broad q, 1H, J=6.4 Hz, H-5'), 4.58 (m, 2H, H-3 and H-2'), 5.89 (s, 1H, H-1'), 6.04 (s, 1H, H-1), 6.89 (2d, 2×H, Ar-H), 7.65 (broad s, 1H, $NHCOCF_3$).

IR (film) $v_{max}$: 3539 and 3414, 2941 and 2844, 1728, 1488, 1260, 1175, 970 $cm^{-1}$.

Step 4: (1'S, 1R, 3S)-3-aceto-1-(2',3',6'-trideoxy -2'-iodo-3'-trifluoroacetamido-L-lyxohexopyranose)-5,8-dioxo-5,8-dihydroisochroman CAN oxidation of the product from step 3 herein yielded the titled product.

PMR (CDCl$_3$, 250 MHz) δ: 1.32 (d, 3H, J=6.6 Hz, $CH_3$-6'), 2.06 (broad d, 1H, OH-4'), 2.32 (s, 3H, $COCH_3$), 2.41 (dd, 1H, J=20.4 Hz and 11.7 Hz, $CH_aCHO$), 2.93 (dd, 1H, J=19.6 and 3.9 Hz, $CH_eCHO$), 3.75 (broad d, 1H, H-4'), 3.96 (m, 1H, H-3'), 4.28 (q, 1H, J=6.7 Hz, H-5'), 4.42 (m, 2H, H-3 and H-2'), 5.82 (s, 1H, H-1'), 5.90 (s, 1H, H-1), 6.82 (2×d, 2H, Ar-H), 7.06 (broad d, 1H, $NHCOCF_3$).

IR (film) $v_{max}$: 3541 and 3417, 2992 and 2944, 1729, 1664, 1174, 967 $cm^{-1}$.

Step 5: (1'S, 1R, 3S)-methyl-(1-[2',3',6'-trideoxy-2'-iodo-3'-trifluoroacetamido-4'-hydroxy-L-lyxohexopyranose]-5,10-dioxo-3,4,5,10-tetrahydronaphtho-[2,3-c]-pyran-3-yl) ketone (BCH-2023)

The titled compound was obtained as per procedure described in step 2, example 5, but using the product from step 4 herein. Purification was effected by flash chromatography (Toluene: Ethyl acetate; 8:2 ).

PMR (CDCl$_3$, 250 MHz) δ:1.34 (d, 3H, J=6.6 Hz, $CH_3$-6'), 2.35 (s, 3H, $COCH_3$), 2.53 (dd, 1H, J=19.6 Hz and 11.5 Hz, $CH_aCHO$), 3.11 (dd, 1H, J=19.6 Hz and 4.1 Hz, $CH_eCHO$), 3.76 (broad s, 1H, H-4'), 3.97 (m, 1H, H-3'), 4.30 (q, 1H, J=6.6 Hz, H-5'), 4.49 (dd+d, 2H, H-3 and H-2'), 6.00 (1s, 2H, H-1 and H-1'), 7.01 (broad d, 1H, $NHCOCF_3$), 7.78 and 8.13 (2×m, 2×2H, Ar-H).

IR (film) $v_{max}$: 3529 and 3414, 2991 and 2930, 1727, 1666, 1298, 1177, 963 $cm^{-1}$.

Step 6: (1'S, 1S, 3R)-5,8-dimethoxy-3-aceto-1-(2',3',6'-trideoxy-3'-trifluoroacetamido-2'-iodo-L-lyxohexopyranose) isochroman To a mixture of (1'S, 1S, 3R) glycoside from step 2 herein (103 mg, 0.16 mmol) in 15 ml of anhydros methanol was added, at 0° C. and under argon atmosphere, 2 drops of NaOCH$_3$, 4.37M (cat.). After stirring for 45 minutes, the reaction was worked up by adding 10 ml of a mixture NH$_4$Cl sat. :NaHCO$_3$ sat. (8:3) and extracted with CH$_2$Cl$_2$ (2×30 ml). The combined organic layers were washed with the same aqueous mixture (30 ml) and dried (MgSO$_4$). Flash chromatography (Toluene:Ethyl acetate; 9:1) gave 70 mg of pure titled glycoside (73% yield).

PMR (acetone-$d_6$, 250 MHz) δ: 1.38 (d, 3H, J=6.5 Hz, $CH_3$-6'), 2.30 (s, 3H, $COCH_3$), 2.50 (dd, 1H, J=17.7 Hz and 12.0 Hz, $CH_aCHO$), 2.97 (dd, J=17.8 Hz and 4.3 Hz, $CH_eCHO$), 3.80 and 3.81 (2×s, 2×3H, 2×$OCH_3$), 4.00 (m, 3H, H-3', H-4' and OH-4'), 4.62 (d, 1H, J=4.8 Hz, H-2'), 4.74 (m, 2H, H-3 and H-5'), 5.92 (1s, 1H, H-1'), 6.18 (1s, 1H, H-1), 6.88 (2×d, 2H, Ar-H), 7.65 (broad s, 1H, $NHCOCF_3$).

IR (film) $v_{max}$: 3530, 3410, 2942 and 2837, 1723 broad, 1491, 1263, 1175, 958 $cm^{-1}$.

Step 7: (1'S, 1S, 3R)-3-aceto-1-(2',3',6'-trideoxy-2'-iodo-3'-trifluoroacetamido-L-lyxohexopyranose)-5,8-dioxo-5,8-dihydroisochroman CAN oxidation of the product from step 6 herein yielded the titled product.

PMR (CDCl$_3$, 250 MHz) δ: 1.47 (d, 3H, J=6.61 Hz, $CH_3$-6'), 2.22 (broad d, 1H, OH-4'), 2.32 (1s, 3H, $COCH_3$), 2.46 (dd, 1H, J=19.6 Hz and 11.7 Hz, $CH_aCHO$), 2.92 (dd, 1H, J=19.9 Hz and 4.2 Hz), 3.78 (broad d, 1H, H-4'), 3.91 (m, 1H, H-3'), 4.37 (d, 1H, J=4.8 Hz, H-2'), 4.43 (dd, 1H, J=11.7 Hz and 4.1 Hz, H-3), 4.64 (q, 1H, J=6.3 Hz, H-5'), 5.84 (s, 1H, H-1'), 5.97 (s, 1H, H-1), 6.82 (2×d, 2-H, Ar-H), 7.06 (broad d, 1H, $NHCOCF_3$).

IR (film) $v_{max}$: 3531 and 3406, 2929, 1726, 1663, 1181 broad, 960 $cm^{-1}$.

Step 8: (1'S, 1S, 3R)-methyl-(1-[2',3',6'-trideoxy-2'-iodo-3'-trifluoroacetamido-4'-hydroxy-L-lyxohexopyranose)-5,10-dioxo-3,4,5,10-tetrahydronaphtho-[2,3-c]-pyran-3-yl) ketone (BCH-2022)

The titled compound was obtained as per procedure described in step 2, example 5, but using the product from step 7 herein. Purification by flash chromatography (Toluene:Ethyl acetate; 9:1).

PMR (CDCl$_3$, 250 MHz) δ: 1.51 (d, 3H, J=6.5 Hz, $CH_3$-6'), 2.11 (broad d, 1H, OH-4'), 2.34 (s, 3H, $COCH_3$), 2.58 (dd, 1H, J=19.4 Hz and 11.6 Hz, $CH_aCHO$), 3.10 (dd, 1H, J=19.8 Hz and 4.1 Hz, $CH_eCHO$), 3.82 (broad d, 1H, H-4'), 3.92 (dd, 1H, J=11.6 Hz and 4.1 Hz, H-3), 4.79 (q, 1H, J=6.5 Hz, H-5'), 5.88 (s, 1H, H-1'), 6.14 (s, 1H, H-1), 7.07 (broad d, 1H, $NHCOCF_3$), 7.78 and 8.11 (2×m, 2×2H, Ar-H).

IR (film) $v_{max}$: 3539 and 3414, 2946, 1731, 1666, 1293, 1174, 961 $cm^{-1}$.

EXAMPLE 64

(1'S, 1R, 1S) and (1'S, 1S, 3R)-methyl-(1-[2',6'-dideoxy-3',4'-diacetoxy-2'-iodo-L-arabino-hexopyranose]-5,10-dioxo-3,4,5,10-tetrahydronaphtho-[2,3-c]-pyran-3-yl) ketone (BCH-2065)

compound which was used in the next step without purification:

PMR (Benzene-$d_6$, 250 MHz) δ: 1.17 (d, 3H, J=6.2 Hz, $CH_3$-6), 4.04 (m, 1H, H-5), 4.48 (d, 1H, J=4.2 Hz, H-2), 4.84 (dd, 1H, J=9.5 Hz and 4.2 Hz, H-3), 5.01 (large s, 1H, H-1), 5.51 (dd, 1H, J=9.7 Hz, H-4).

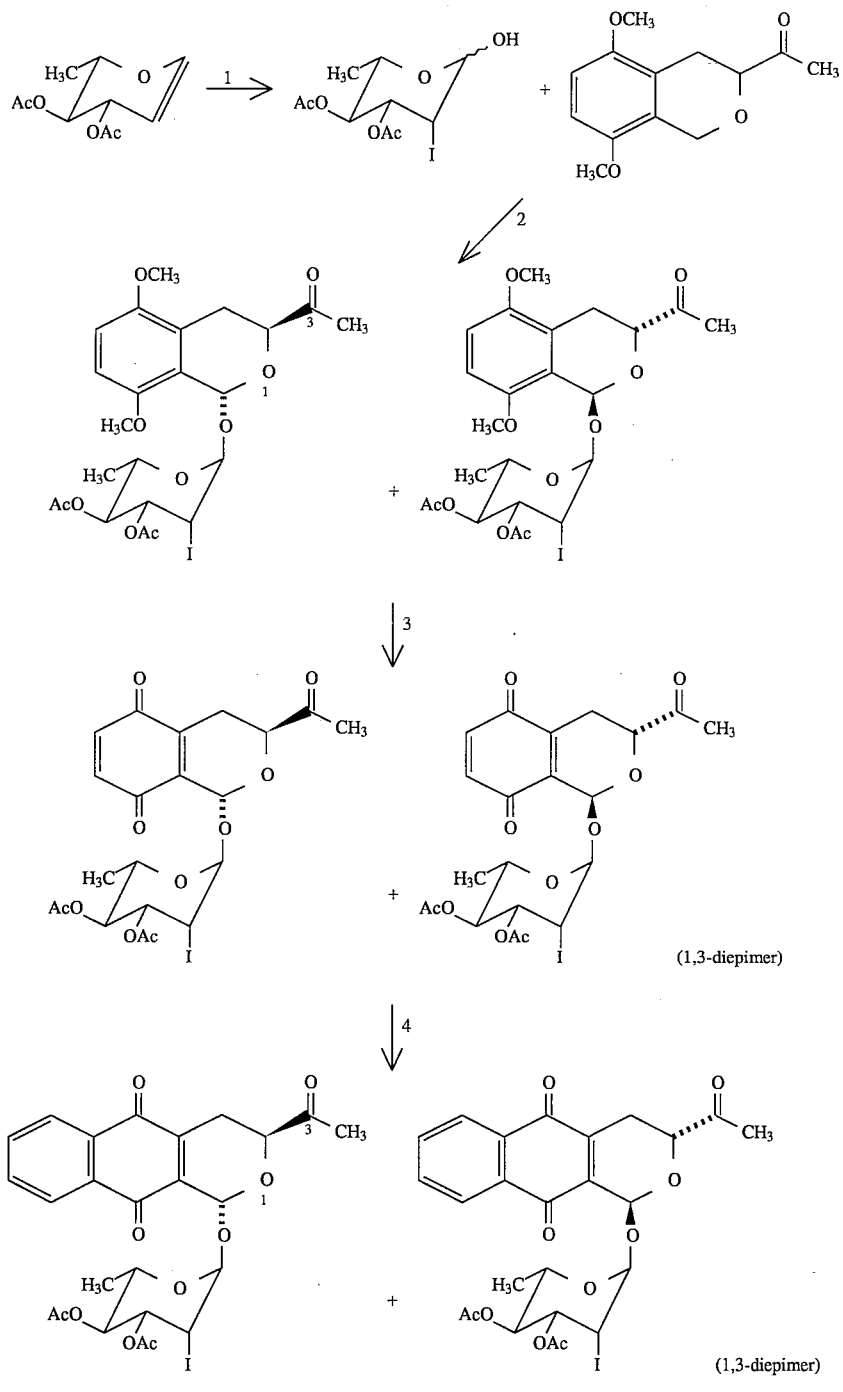

BCH-2065

Step 1: 2',6'-dideoxy-3',4'-diacetoxy-2'-iodo-L-arabinohexopyranose

Following the procedure described in step 1, example 61, we obtained after work-up a quantitative yield of the desired Step 2: (1'S, 1S, 3R) and (1'S, 1R, 3S)-5,8-Dimethoxy-3-aceto-1-(2',6'-dideoxy-3',4'-diacetoxy-2'-iodo-L-arabinohexopyranose)isochroman Following the same procedure as described in step 2, example 61, we obtained after flash chromatography (Toluene:Ethyl acetate; 9:1) a mixture of the titled stereoisomers (non-separable).

PMR (Benzene-$d_6$, 250 MHz) δ: 1.20 and 1.38 (2d, 2×3H, 2×CH$_3$-6'), 1.61, 1.66, 1.67 and 1.69 (4s, 4×3H, 4×OAc), 1.95 and 2.12 (2s, 2×3H, 2×OCH$_3$), 2.76 (m, 2×H, 2×CH$_a$-CHO), 3.20 (m, 2H, 2×CH$_e$CHO), 2.30, 2.31 and 2.32 (3s, 4×3H, 4×OCH$_3$), 4.18 (m, 1H, H-5'), 4.35 and 4.47 (2×dd, 2H, J=12.0 Hz and 4.2 Hz, 2×H-3), 4.82 (m, 5H, 2×H-3', 2×H-2'; and H-5'), 5.62 and 5.70 (2×dd, 2H, J=9.5 Hz, 2×H-4'), 5.84 and 5.93 (2 large s, 2H, 2×H-1'), 5.95 (s, 1H, H-1), 6.33 (m, 5H, 2×2 Ar-H and H-1).

Step 3: (1'S, 1R, 3S) and (1'S, 1S, 3R)-3-aceto-1-(2',6'-dideoxy-3-iodo-L-arabinohexopyranose)-5,8-dioxo-5,8-dihydroisochroman The titled compounds were obtained following CAN oxidation of the products from step 2 herein as per previous procedures.

PMR (CDCl$_3$, 250 MHz) δ: 1.23 and 1.36 (2d, 2×3H, J=6.2 Hz, 2×CH$_3$-6'), 2.03, 2.04, 2.06 and 2.07 (4s, 4×3H, 4×OAc), 2.29 and 2.30 (2S, 2×3H, 2×COCH$_3$), 2.46 (m, 2H, 2×CH$_a$CHO), 2.90 (dd, 2H, J=19.7 Hz and 3.8 Hz, 2×CH$_e$CHO), 4.02 (m, 1H, H-5'), 4.49 (m, 7H, 2×H-2', 2×-3', 2×H-3 and H-5'), 5.15 (m, 2H, 2×H-4'), 5.62 and 5.68 (2S, 2H, 2×H-1'), 5.79 and 5.95 (2s, 2H, 2×H-1), 6.75 (2×2d, 4H, 4×Ar-H).

Step 4: (1'S, 1R, 1S) and (1'S, 1S, 3R)-methyl-(1- [2',6'-dideoxy-3-diacetoxy-2'-iodo-L-arabino-hexopyranose]-5, 10-dioxo-3,4,5,10-tetrahydronaphtho-[2,3-c]-pyran-3 -yl) ketone (BCH-2065)

Following the reported procedure in step 2, example 5, and starting from the two stereoisomers from step 3 herein, titled compounds (9%) were isolated after flash chromatography (Toluene:Ethyl acetate; 19:1).

PMR (CDCl$_3$, 250 MHz) δ: 1.41 (d, 3H, J=6.2 Hz, CH$_3$-6'), 2.06 and 2.08 (2s, 2×3H, 2×OAc), 2.33 (s, 3H, COCH$_3$), 2.57 (dd, 1H, J=19.5 Hz and 11.7 Hz, CH$_a$CHO), 3.09 (dd, 1H, J=19.8 Hz and 4.2 Hz, CH$_e$CHO), 4.46 (m, 4H, H-3, H-2', H-3'and H-5'), 5.21 (dd, 1H, J=9.5 Hz, H-4'), 5.67 (s, 1H, H-1'), 6.14 (s, 1H, H-1), 7.78 and 8.13 (2m, 2×2H, Ar-H).

IR (film) $v_{max}$: 2941, 1750 and 1739, 1665, 1298, 1236 large, 971 cm$^{-1}$.

EXAMPLE 65

C-2'deoxyfucose pyranylnaphthoquinone glycosides

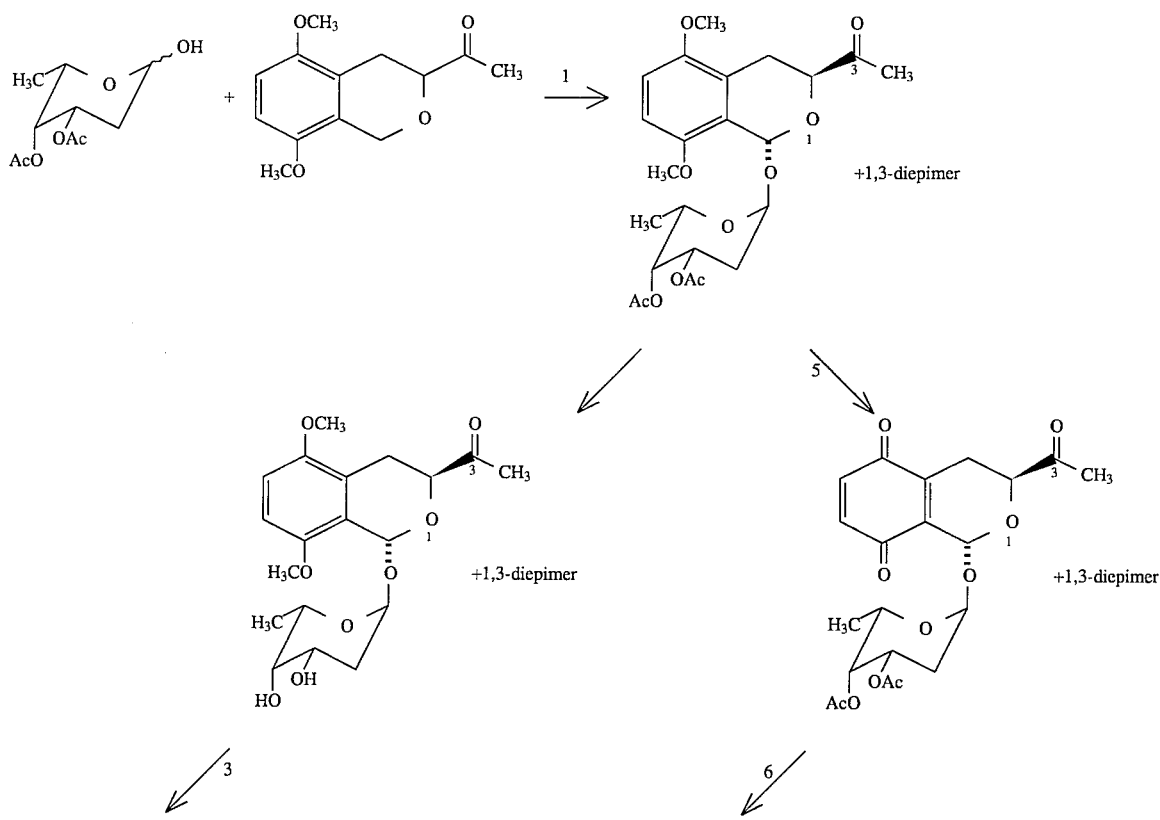

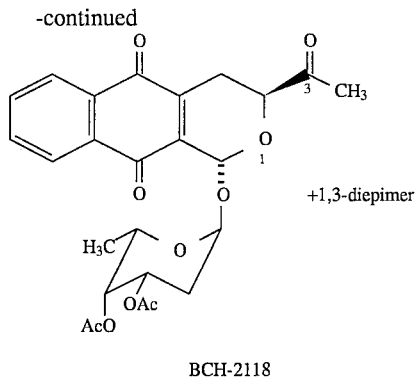

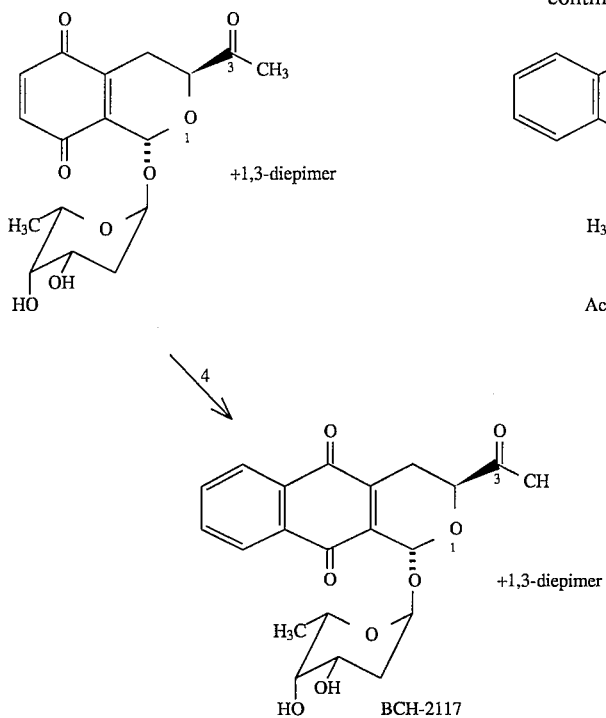

BCH-2117

Step 1: (1'S, 1S, 3R) and (1'S, 1R, 3S)-5,8-dimethoxy-3-aceto-1-(2',6'-dideoxy-3',4'-diacetoxy-L-lyxohexopyranose) isochroman The procedure described in step 2, example 61, was applied to 5,8-dimethoxy-3-acetoisochroman and 3,4-diacetoxy-2,6-dideoxy fucose. Flash chromatography (dichloromethane:Hexane:Ethyl acetate; 6:3:1) gave a 50% yield of the two non-separable titled stereoisomers mixture (1:1).

PMR (acetone-$d_6$, 250 MHz) δ: 1.11 and 1.20 (2d, 2×3H, J=6.6 Hz, $CH_3$-6'), 1.87, 1.88, 2.10 and 2.10 (4s, 4×3H, 4×OAc), 2.28 and 2.29 (2s, 2×3H, 2×COCH$_3$), 2.45 (m, 2×3H, 2×CH$_a$CHO), 2.94 (m, 2H, 2×CH$_e$CHO), 3.79, 3.81 and 3.83 (3s, 4×3H, 4×OCH$_3$), 4.34 (q, 1H, J=6.53 Hz, H-5'), 4.62 (m, 3H, 2×H-3 and H-5'), 5.14 (m, 4H, 2×H-3' and 2×H-4'), 5.54 and 5.61 (2 broad s, 2H, 2×H-1'), 5.97 and 6.16 (2s, 2H, H-1), 6.88 (m, 2×2H, 2×Ar-H).

Step 2: (1'S, 1S, 3R) and (1'S, 1R, 3S)-5,8-dimethoxy-3-aceto-1-(2', -dideoxy-L-lyxohexopyranose) isochroman The same procedure described in step 3, example 61, was applied to the products from step 1 herein. Flash chromatography of the crude (Toluene:Ethyl acetate; 6:4) gave 39% yield of non-separable titled diastereoisomers (1:1).

PMR (acetone-$d_6$, 250 MHz) δ: 1.16 and 1.25 (2d, 2×3H, J=6.6 Hz, 2×CH$_3$-6'), 1.80 (m, 4H, 4×H-2'), 2.24 (s, 2×3H, 2×COCH$_3$), 2.45 (unresolved dd, 2H, CH$_a$CHO), 2.87 (dd, 2H, CH$_e$CHO), 3.37 (s, 1H, H-3'), 3.56 (m, 3H, H-3'and 2×H-4'), 3.75 (s, 3×3H, 3×OCCH$_3$), 3.77 (s, 3H, OCH$_3$), 4.00 and 4.34 (2d, 2H, J=6.6 Hz, 2×H-5'), 4.54 (2 unresolved dd, 2H, H-3), 5.35 and 5.41 (2 broad s, 2H, 2×H-1'), 5.8.9 and 6.10 (2s, 2H, 2×H-1), 6.83 (2×2d, 4H, Ar-H).

Step 3: (1'S, 1S, 3R) and (1'S, 1R, 3S)-5,8-dioxo-3-aceto-1-(2',6'-dideoxy-L-lyxohexopyranose)-5,8-dihydroisochroman The titled products were obtained following CAN oxidation of the products from step 2 herein.

PMR (CDCl$_3$, 250 MHz) δ: 1.29 and 1.42 (2d, 2×2H, J=6.6 Hz, 2×CH$_3$-6'), 1.70 (m, 4H, 4×OH), 1.89 (m, 4H, 4×H-2'), 2.30 and 2.31 (2s, 2×3H, 2×COCH$_3$), 2.43 (2 overlapping dd, 2H, 2×CH$_a$CHO), 2.89 (2 overlapping dd, 2H, 2×CH$_e$CHO), 3.65 and 3.70 (2 broad s, 2H, 2×H-4'), 3.90 (m, 2H, 2×H-3'), 3.99 (unresolved q, 1H, H-5'), 4.36 (q, 1H, J=6.8 Hz, H-5'), 4.43 (2 overlapping, 2H, 2×H-3), 5.41 and 5.49 (2 broad s, 2H, 2×H-1), 5.81 and 5.98 (2S, 2H, 2×H-1), 6.79 (2×2d, 4H, Ar-H).

Step 4: (1'S, 1S, 3R) and (1'S, 1R, 3S)-methyl-(1-[dideoxy-2',6'-dihydroxy-3',4'-L-lyxohexopyranose]-5,10-dioxo-3,4,5,10-tetrahydronaphtho-[2,3-c]-pyran-3-yl) ketone (BCH-2117)

The titled compounds were obtained in 43% yield by following the procedure described in step 2, example 5, and using the products from step 3 herein. Flash chromatography (Toluene:Ethyl acetate; 4:6) and final purification by preparative TLC (same solvent conditions) was required.

PMR (DMSO-$d_6$, 250 MHz) δ: 1.10 and 1.23 (2d, 2×3H, J=6.3 Hz, 2×CH$_3$-6'), 1.54 and 1.87 (2m, 2×2H, 2×2H-2'), 2.25 (s, 6H, 2×COCH$_3$), 2.46 (m, 2H, 2×CH$_a$CHO), 2.86 (2 overlapping dd, 2H, CH$_e$CHO), 3.73 (m, 2H, 2×H-3'), 3.89 (q, 1H, J=6.5 Hz, H-5'), 4.28 (q, 1H, J=6.3 Hz, H-5'), 4.38 (broad s, 1H, H-4'), 4.52 (2×unresolved dd, 2H, 2×H-3), 4.54 (broad s, 1H, H-4'), 5.11 (m, 2H, 2×OH), 5.31 and 5.38 (2 broad s, 2H, 2×H-1'), 5.49 (m, 2H, 2×OH), 5.86 and 5.94 (2s, 2H, 2×H-1), 8.32 and 9.58 (2m, 8H, Ar-H).

Step 5: (1'S, 1S, 3R) and (1'S, 1R, 3S) -5,8-dioxo-3-aceto-1-(2',6'-dideoxy-3',4'-diacetoxy-L-lyxohexopyranose) isochroman The titled compounds were obtained following CAN oxidation of the products obtained from step 1 herein.

PMR (CDCL$_3$, 250 MHz) δ: 1.10 and 1.22 (2d, 2×3H, J=6.5 Hz, 2×CH$_3$-6'), 1.93 (large m, 2×2H, 2×2H-2'), 1.92, 1.96, 2.11 and 2.12 (4s, 4×3H, 4×OAc), 2.23 and 2.25 (2s, 2×3H, 2×COCH$_3$), 2.39 (2 overlapping dd, 2H, 2×CH$_a$-CHO), 2.80 (2 overlapping dd, 2H, 2×CH$_e$CHO), 4.10 (q, 1H, J=6.5 Hz, H-5'), 4.40 (m, 3H, 2×H-3 and H-5'), 5.10 (m, 4H, 2×H-3', and 2×H-4'), 5.44 and 5.50 (2 broad s, 2H, 2×H-1'), 5.76 and 5.94 (2s, 2H, 2×H-1), 6.57 (2×2d, 4H, Ar-H).

Step 6: (1'S, 1S, 3R) and (1'S, 1R, 3S)-methyl-(1-[dideoxy-2',6'-diacetoxy-3',4'-L-lyxohexopyranose]-5,10-dioxo-3,4,5,10-tetrahydronaphtho-[2,3-c]-pyran-3-yl) ketone (BCH-2118)

The titled compounds were obtained in 51% yield by following the procedure described in step 2, example 5, and using the products from step 5 herein. Aromatization by flash chromatography (Toluene:Ethyl acetate; 8:2). Final purification by preparative TLC (same solvent conditions).

PMR (CDCl$_3$, 250 MHz) δ: 1.17 and 1.33 (2d, 2×3H, J=6.6 Hz, 2×CH$_3$-6'), 1.88 (m, 2H, 2×H-2'), 1.96 (s, 2×3H, 2×OAc), 2.16 (large m, 2H, 2×H-2'), 2.18 and 2.19 (2s, 2×3H, 2×OAc), 2.32 and 2.34 (2s, 2×3H, 2×COCH$_3$), 2.54 (2×overlapping dd, 2H, 2×CH$_a$CHO), 3.07 (2×overlapping dd, 2H, ×CH$_e$CHO), 4.17 (q, 1H, J=6.7 Hz, H-5'), 4.51 (2×aoverlapping dd, 2H, 2×H-3), 4.63 (q, 1H, J=6.4 Hz, H-5'), 5.19 (m, 4H, 2×H-3'; and 2×H-4'), 5.55 and 5.67 (2 broad s, 2H, 2×H-1'), 6.00 and 6.18 (2s, 2H, 2×H-1), 7.76 and 8.10 (2m, 8H, Ar-H).

EXAMPLE 66

Phenolic pyranylnaphthoquinone glycosides

Step 1: Methyl-(6-hydroxy-5,10-dioxo-3,4,5,10-tetrahydronaphtho-[2,3-c]-pyran-3-yl) ketone and methyl-(9-hydroxy-5,10-dioxo-3,4,5,10-tetrahydronaphtho-[2,3-c]-pyran-3-yl) ketone (BCH-2062)

The titled compounds were obtained by following the procedure described in step 2 herein and using 1-acetoxybutadiene and 3-acetoisochroman-5,8-dione.

PMR (CDCl$_3$, 250 MHz) δ: 2.33 (2s, 2×3H, COCF$_3$), 2.56 (m, 2H, CH$_a$CHO), 3.00 (m, 2H, CH$_e$CHO), 4.07 (dd, 2H, J=10.1 Hz and 3.9 Hz, H-3), 4.60 (m, 2H, H-1), 4.95 (m, 2H, H-1), 7.26 (m, 2H, Ar-H), 7.62 (m, 2×2H, Ar-H), 11.84. and 11.96 (2s, 2H, OH-5 and OH-8).

Step 2: (1'S, 1S, 3R)-methyl-(6 and 9-hydroxy-1-(2',3',6'-trideoxy-3'-trifluoroacetamido-4'-O-p-nitrobenzoyl-L-lyxohexopyranose)-5,10-dioxo-3,4,5,10-tetrahydro-1H-naphtho-[2,3-c]-pyran-3-yl) ketone To a mixture of (1'S, 1S, 3R) glycoside from step 1, example 5, (200 mg, 0.335 mmol) in dry toluene (2.5 ml) under argon atmosphere, was added dropwise the 1-trimethylsilyloxy-1,3-butadiene. After stirring for 18 hours at room temperature the solvent was removed in vacuo. The residue was dried over vacuum for 10 minutes, dissolved in 5 ml of THF and cooled to 0° C. Addition of HCl 1N (5 ml) gave

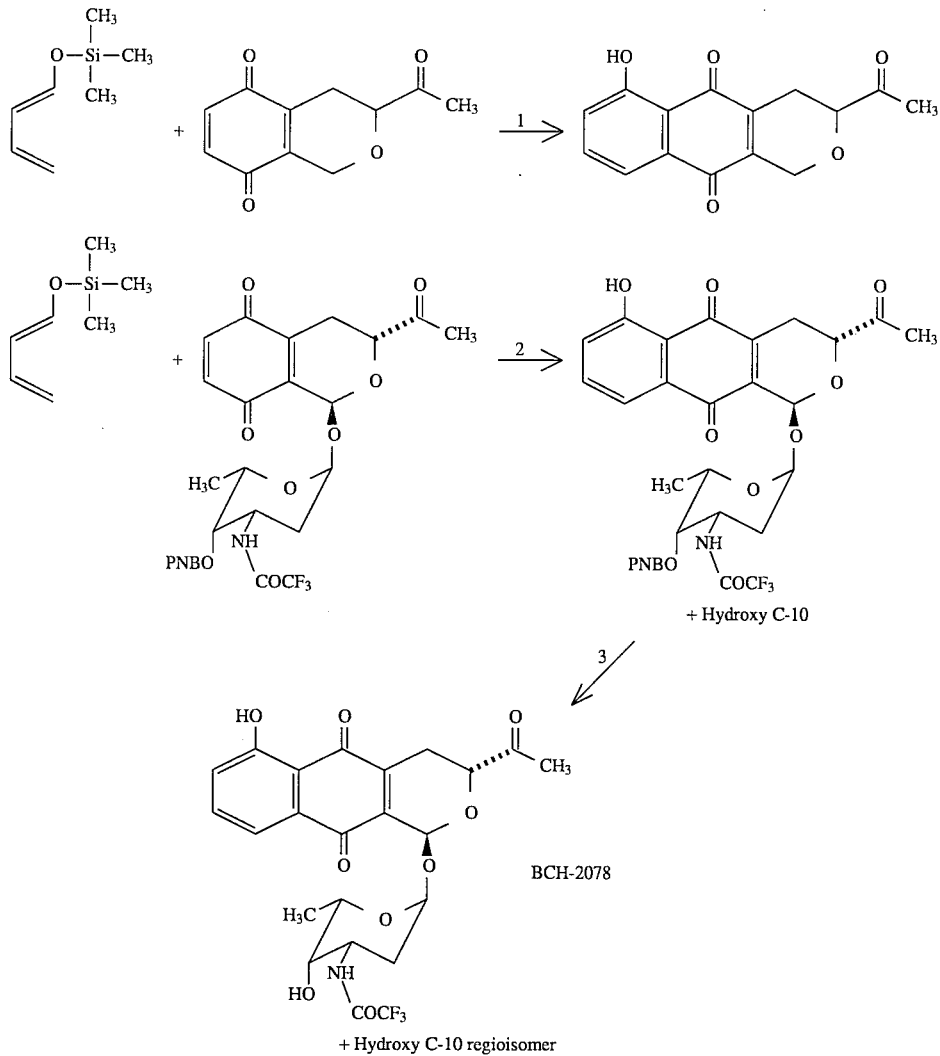

after 30 minutes stirring a complete cleavage of the silyl group. Extractions were done with $CH_2Cl_2$ (3×30 ml) and the combined organic layers were dried with $Na_2SO_4$ and then evaporated. The residue was dissolved with 10 ml of dry $CH_2Cl_2$, at room temperature and under argon, and treated with 200 mg of PCC. After 30 minutes stirring, the reaction mixture was dropped on $SiO_2$ and flash chromatographed (Toluene:Ethyl acetate; 8:2) to give 162 mg (72% yield) of a non-separable titled regioisomers (1:1).

PMR ($CDCl_3$, 250 MHz) δ: 1 36 and 1.37 (2d, 2×3H, J=6.4 Hz, $CH_3$-6'), 2.14 (2×m, 2×2H, H-2'), 2.34 and 2.35 (2s, 2×3H, $COCH_3$), 2.57 (dd, 2×1H, J=20.1 Hz and 11.8 Hz, $CH_aCHO$), 3.09 (dd, 2×1H, J=19.9 Hz and 4.1 Hz, $CH_eCHO$), 4.53 (2×unresolved dd, 2×1H, H-3), 4.61 (2×m, 2×1H, H-3'), 4.77 (2×unresolved q, 2×1H, H-5'), 5.45 (broad s, 2×1H, H-4'), 5.63 (broad s, 2×H, H-1'), 6.19 and 6.21 (2s, 2H, H-1), 6.46 (broad s, 2H, $NHCOCF_3$), 7.32 (m, 2H, Ar-H), 7.67 (m, 2×2H, Ar-H), 8.32 (m, 2×2H, Ar-H), 11.89 and 11.90 (2s, 2H, OH-5 and OH-8).

Step 3: (1'S, 1S, 3R)-methyl-(6 and 9-hydroxy-1-[2',3',6'-trideoxy-3'-trifluoroacetamido-4'-hydroxy-L-lyxohexopyranose]-5,10-dioxo-3,4,5,10-tetrahydronaphtho-[2,3-c]-pyran-3-yl-ketone (BCH-2078)

Hydrolysis of the glycosides from step 2 herein with catalytic sodium methoxide in methanol yielded the titled compounds. Flash chromatography (Toluene:Ethyl acetate:acetone; 6:4:2) of the crude gave 83% yield of pure titled regioisomers mixture (1:1).

PMR $CDCl_3$, 250 MHz) δ: 1.40 and 1.42 (2×d, 2×3H, J=6.4 Hz, $CH_3$-6'), 1.91 (m, 2×2H, H-2'), 2.31 and 2.32 (2×s, 2×3H, $COCH_3$), 2.56 (dd, 2×1H, J=19.7 Hz and 11.4 Hz, $CH_aCHO$), 3.08 (dd, 2H, J=19.9 Hz and 4.2 Hz, $CH_eCHO$), 3.67 (broad d, 2H, H-4'), 4.33 (m, 2H, H-3'), 4.53 (m, 4H, H-3 and H-5'), 5.44 and 5.45 (2s, 2H, H-1'), 6.13 and 6.15 (2S, 2H, H-1), 6.74 (broad d, 2H, $NHCOCF_3$), 7.30 (m, 2H, Ar-H), 7.65 (m, 2×2H, Ar-H), 11.89 and 11.91 (2s, 2H, OH-5 and OH-8).

EXAMPLE 67

3-(3'-aminothiazolyl)-5,10-dioxo-1,3,4,5,10-pentahydronaphtho-[2,3-c]-pyran (BCH-1189)

Step 1: 3-aceto-5,8-dioxo-3,4,5,8-tetrahydro-1H-benzo-[2,3-c]-pyran

CAN oxidation of 5,8-Dimethoxy-3-acetoisochroman yielded the titled compound.

$^1$H NMR ($CDCl_3$, 250 MHz, Bruker) δ: 2.23 (3H, s, $COCH_3$), 2.36 (1H, dd tr, J=17.8 Hz, 11.0 Hz, 2.9 Hz, 4-$HCH_a$), 2.75 (1H, d tr, J=17.8 Hz, 2.9 Hz, 4-$HCH_e$), 3.96 (1H, dd, J=11 Hz, 5.3 Hz, 3-CH), 4.41 (1H, d tr, J=17.8 Hz, 3.5 Hz, 1-$HCH_a$), 4.72 (1H, d tr, J=17.5 Hz, 1 Hz, 1-$HCH_e$), 6.71 (2H, m, ArH).

Step 2: 3 -aceto-5,10-dioxo-3,4,5,10-tetrahydro-1H-naphtho-[2,3-c]-pyran

The titled compound was obtained by following the procedure described in step 2, example 5, and using the product from step 1 herein.

$^1$H NMR: ($CDCl_3$, 250 MHz, Bruker) δ: 2.30 (3H, s, $COCH_3$), 2.56 (1H, dd tr, J=18 Hz, 11.2 Hz, 2.9 Hz, 4-$HCH_a$), 3.01 (1H, d, J=18.0 Hz, 4-$HCH_e$), 4.05 (1H, dd, J=11.2 Hz, 3.8 Hz, 3-CH), 4.60 (1H, d tr, J=17.8 Hz, 4.1 Hz, 1-$HCH_a$), 4.95 (1H, d m, J=17.8 Hz, 1-$HCH_e$), 7.73 (2H, m, 7, 8-ArH), 8.08 (2H, m, ArH).

Step 3: 3-bromoacetyl-5,10-dioxo-3,4,5,10-tetrahydro-1H-naphtho-[2,3-c]-pyran

The titled compound was obtained by following the procedure described in step 1, example 7, and using the product from step 2 herein.

$^1$H NMR ($CDCl_3$, 250 MHz, Bruker) δ: 2.57 (1H, dd tr, J=18.8 Hz, 11.2 Hz, 3 Hz, 4-$HCH_a$), 3.02 (1H, d m, J=18.8 Hz, 4-$HCH_e$), 4.21 (1H, d, J=12.9 Hz, CHBr), 4.30 (1H, d, J=12.9 Hz, CHBr), 4.34 (1H, dd, J=11.2 Hz, 4.7 Hz, 3-CH), 4.58 (1H, d tr, J=18.0 Hz, 3.0 Hz, 1-$HCH_a$), 4.90 (1H, d m, J=18.0 Hz, 1-$HCH_e$), 7.70 (2H, m, 7, 8-ArH), 8.04 (2H, m, 6, 9-ArH).

Step 4: 3-(3'-aminothiazolyl)-5,10-dioxo-1,3,4,5,10-pentahydronaphtho-[2,3-c]-pyran Bromomethyl ketone from step 3 herein (270 mg, 0.81 mmol) was stirred with thiourea (60 mg, 0.88 mmol) in ether (80 ml) and methylene chloride (10 ml) at room temperature for 4 hours. Three pellets of molecular sieves were used to take up water. Solvent was evaporated to give a white solid. The crude product was washed with chloroform/ether (8:1) first, then basified with potassium carbonate. It was

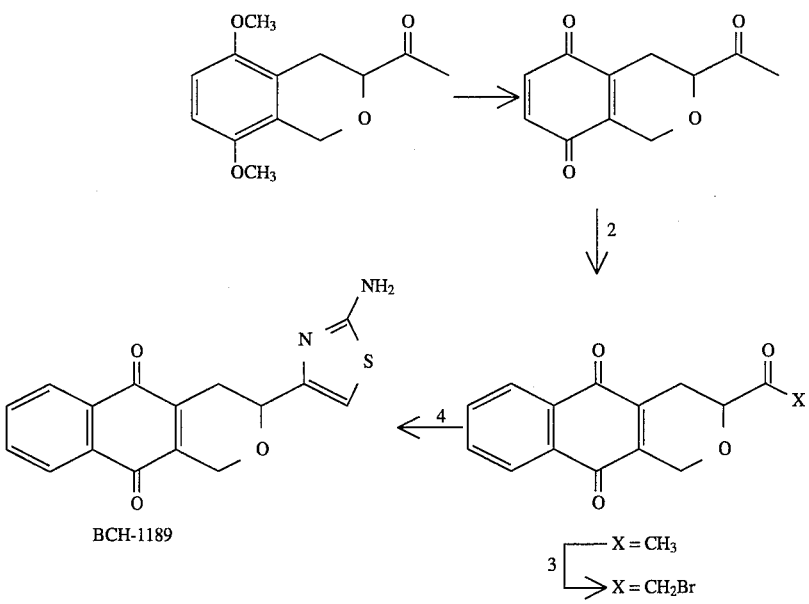

extracted with chloroform. The organic phase was evaporated to give a crude product which was chromatographed to give desired titled product.

dec. 130° C.

¹H NMR (CDCl₃, 250 MHz, Bruker), 2.80 (1H, m, 4-HCH$_a$), 3.09 (1H, br d, J=18.2 Hz, 4-HCH$_e$), 4.58 (1H, dd, J=10.0 Hz, 3.5 Hz, 3-CH), 4.68 (1H, d tr, J=18.8, 2.9 Hz, 1-HCH$_a$), 4.95 (1H, dd, J=18.8 Hz, 2.3 Hz, 1-HCH$_e$), 5.54 (1H, br s, NH), 6.54 (1H, s, thia-H), 7.73 (1H, m, ArH), 8.08 (1H, m, ArH).

EXAMPLE 68

Cyclic amine substituted naphthoquinone derivative

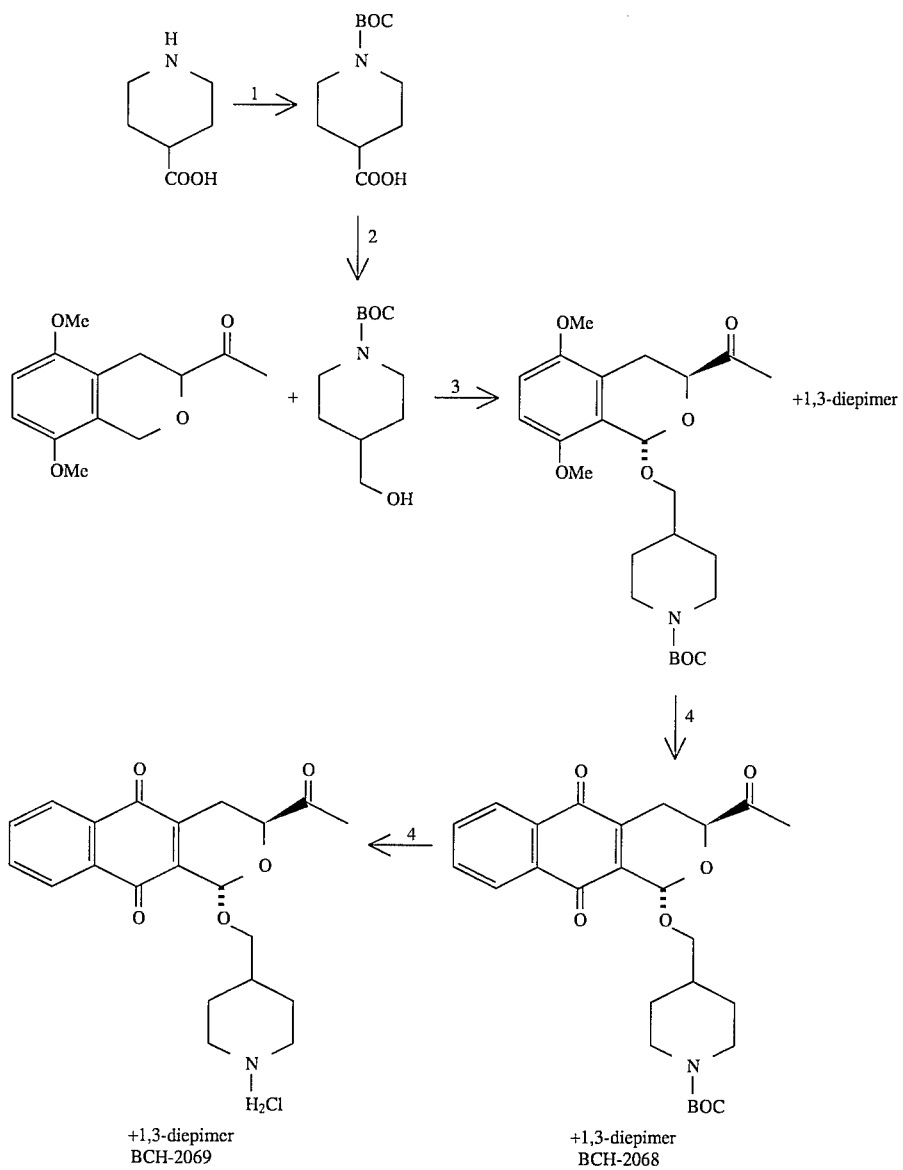

Step 1: N-BOC-isonipecotic acid

The titled compound was obtained following standard conditions.

¹H NMR (CDCl₃): δ 4.02 (m, 2H, CH₂N), 2.73 (m, 2H, CH₂N), 2.50 (m, 1H, CHCOOH), 1.91 (m, 2H, CH₂CHCOOH), 1.64 (m, 2H, CH₂CHCOOH).

Step 2: N-BOC-4-piperidinemethanol

To a solution of the acid from step 1 (0.11 g, 0.48 mmol) in dry THF (4.8 ml), under argon, at 0° C., was added dropwise BH₃-THF 1.0M/THF (0.72 ml, 1.5 eq). The solution was stirred at 0° C. for 30 minutes and at room temperature for 15 hours. Methanol (10 ml) was then carefully added to destroy the excess BH₃ and the solvents were evaporated. The residue was poured in CH₂Cl₂ sat. aq. NaHCO₃ and the phases were separated. The aqueous layer was extracted with CH₂Cl₂ (2×) and the combined organic extracts were dried over MgSO₄. The solids were filtered and the solvent evaporated to give the titled alcohol as a clear oil (0.092 g, 89%). ¹H NMR (CDCl₃): δ 4.09 (m, 2H, CH₂N), 3.44 (d, 2H, CH₂OH), 2.67 (m, 2H, CH₂N), 2.08 (bs, 1H, OH), 1.73–1.52 (m, 2H, CH₂—CH₂N), 1.48 (s, 9H, BOC), 1.22–1.01 (m, 2H, CH₂—CH₂N).

Step 3: 1-O-[N-BOC-4-piperidinemethanol]-3-acetyl-5,8-dimethoxy isochroman racemic The titled compound was obtained via DDQ induced coupling of the alcohol from step 2 herein with 3-aceto-5, 8-dimethoxy isochroman. Purification: flash chromatography (silica gel, 2:1 Hex/EtOAc).

$^1$H NMR (CDCl$_3$): δ 6.76 (d, 1H, J=8.8, ArH), 6.70 (d, 1H, J=8.8, ArH), 5.77 (s, 1H, H-1), 4.59 (dd, 1H, J=4.2, 12.2, H-3), 4.08 (m, 2H, CH$_2$N), 3.78 (s, 3H, ArOMe), 3.77 (s, 3H, ArOMe), 3.72 (dd, 1H, J=6.4, 9.7, H-1'), 3.57 (dd, 1H, J=6.4, 9.7, H-1'), 3.04 (dd, 1H, J=4.2, 17.6, H-4), 2.70 (m, 2H, CH$_2$N), 2.53 (dd, 1H, J=12.2, 17.6, H-4), 2.33 (s, 3H, COCH$_3$), 1.76 (m, 3H, C$\underline{H}_2$CH—CH$_2$O), 1.21 (m, 2H, C$\underline{H}_2$CHCH$_2$O).

Step 4: Methyl-(1-O-[2'-piperidinemethanol]-5,10-dioxo-3,4,5,10-tetrahydronaphthaleno-[2,3-c]pyran-3-yl) ketone, racemic, hydrochloride (BCH-2069)

The titled compound was obtained from the precursor from step 3 herein as per previously described procedure.

$^1$H NMR (DMSO): δ 8.05–7.80 (m, 4H, ArH), 5.69 (s, 1H, H-1), 4.48 (m, 1H, H-3), 3.88 (m, 4H, CH$_2$N and NH$_2$Cl), 3.74 (m, 1H, H-1'), 3.60 (m, 1H, H-1'), 3.25 (m, 1H, H-4+H$_2$O), 2.82 (m, 3H, CH$_2$N and H-4), 2.31 (s, 3H, COCH$_3$), 2.01–1.70 (m, 3H, C$\underline{H}_2$CH—CH$_2$O), 1.57–1.38 (m, 2H, C$\underline{H}_2$CHCH$_2$O).

EXAMPLE 69

Diamino-sugar substituted naphthoquinone derivative

Step 1: (2R, 4S, 5S, 6S )-2-tert-butyldimethylsilyloxy-4-trifluoroacetamido-5-hydrox-6-methyl-tetrahydropyran To a solution of the hemiacetal (0.51 g, 2.08 mmol) in dry CH$_2$Cl$_2$ (20 ml), under argon, at room temperature, were added successively imidazole (0.28 g, 2 eq) and t-BuMe$_2$SiCl (0.34 g, 1.1 eq). The solution was stirred at room temperature for 15 hours after which it was poured in sat. aq. NaHCO$_3$. The phases were separated and the aqueous layer was extracted with CH$_2$Cl$_2$ (2×). The combined organic extracts were dried over MgSO$_4$, the solids were filtered and the solvent evaporated to give 0.72 g (97%) of the titled silyloxy-sugar as a white solid.

$^1$H NMR (CDCl$_3$): δ 6.82 (bd, 1H, NH), 4.78 (dd, 1H, J=2.2, 9.2, H-1), 4.09 (m, 1H, H-3), 3.62 (q, 1H, J=6.6, H-5), 3.48 (d, 1H, J=2.6, H-4), 2.44 (bs, 1H, OH), 2.08 (dd, 1H, J=5.0, 13.0, H-2), 1.55 (ddd, 1H, J=9.2, 13.0, 13.0, H-2), 1.29 (d, 3H, J=6.6, H-6), 0.89 (s, 9H, t-Bu), 0.12 (s, 3H, SiMe), 0.11 (s, 3H, SiMe).

Step 2: (2R, 4S, 5R, 6S)-2-tert-butyldimethylsilyloxy-4-trifluoroacetamido-5-azido-6-methyl-tetrahydropyran To a solution of the alcohol (0.40 g, 1.11 mmol) in dry CH$_2$Cl$_2$ (11.1 ml), under argon, at −30° C. were added successively pyridine (0.45 ml, 5 eq) and Tf$_2$O (0.37 ml, 2 eq) and the solution was stirred at −10° C. for 1 hour. It was then poured in sat. aq. NaHCO$_3$ and the phases were separated. The aqueous layer was extracted with CH$_2$Cl$_2$ (2×) and the combined organic extracts were dried over MgSO$_4$. The solids were filtered and the solvents were

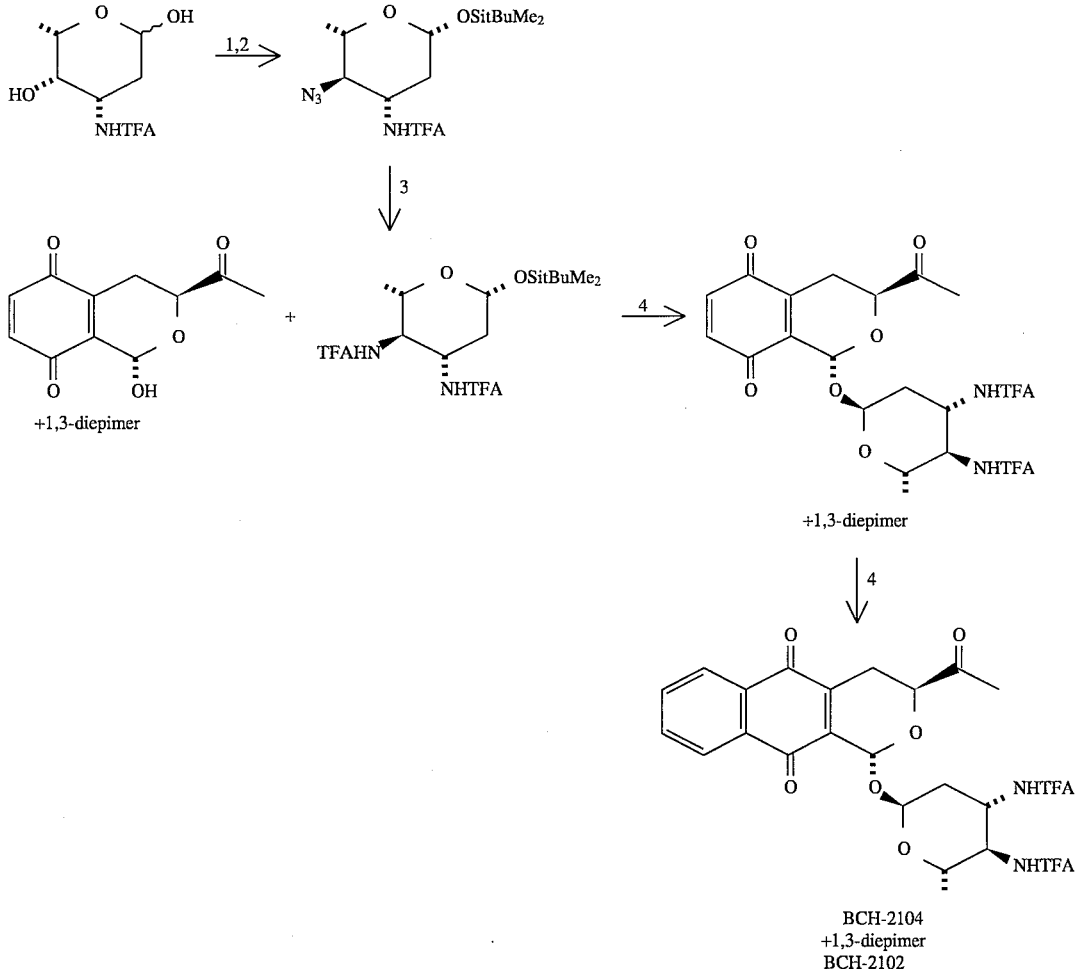

evaporated to dryness. The red oil obtained was dissolved in dry DMF (11.1 ml), under argon, at room temperature, and NaN₃ (0.236 g, 5 eq) was added. The suspension was stirred for 5 hours after which it was poured in EtOAc. This organic phase was washed with water (3×) and brine. It was then dried over MgSO₄, the solids were filtered and the solvent evaporated to give the titled azido-trifluoroacetamide as a clear oil (0.27 g, 68%).

$^1$H NMR (CDCl₃): δ 6.44 (bd, 1H, J=8.6, NH), 4.82 (dd, 1H, J=2.1, 8.8, H-1), 4.09 (ddd, 1H, J=4.7, 9.7, 12.8, H-3), 3.41 (dq, 1H, J=6.1, 9.2, H-5), 2.97 (dd, 1H, J=9.7, 9.7, H-4), 2.21 (ddd, 1H, J=2.1, 4.7, 12.8, H-2), 1.67 (ddd, 1H, J=8.8, 12.8, 12.8, H-2), 1.39 (d, 3H, J=6.1, H-6), 0.89 (s, 9H, tBu), 0.12 (s, 3H, SiMe), 0.10 (s, 3H, SiMe).

Step 3: (2R, 4S, 5R, 6S)-2-tert-butyldimethylsilyloxy-4,5-bis-trifluoroacetamido-6-methyl-tetrahydro-pyran The azido saccharide from step 2 was reduced as per standard contiditons. Purification: flash chromatography (silica gel, 85:15 Hexanes/EtOAc).

$^1$H NMR (CDCl₃): δ 7.85 (bd, 1H, J=9.4, NH), 7.48 (bd, 1H, J=9.7, NH), 4.84 (d, 1H, J=7.8, H-1), 4.38 (m, 1H, H-3), 3.96 (m, 1H, H-4), 3.56 (dq, 1H, J=6.1, 9.6, H-5), 2.19 (m, 1H, H-2), 1.78 (m, 1H, H-2), 1.29 (d, 3H, J=6.1, H-6), 0.89 (s, 9H, t-Bu), 0.12 (s, 3H, SiMe), 0.11 (s, 3H, SiMe).

Step 4: (1R, 3S, 1'S) and (1S, 3R, 1'S)-Methyl-(1-[2',3',4',6'-tetradeoxy-3',4'-bis-trifluoroacetamido-L-arabinohexopyranose]-5,10-dioxo-3,4,5,10-tetrahydronaphthaleno-[2,3-c]pyran-3-yl) ketone (BCH-2104 and BCH-2102)

To a solution of the hydroxyquinone (72 mg, 0.33 mmole) and di-trifluoroacetamido sugar from step 3 herein (162 mg, 1.1 eq) in 6.5 mL of a 9:1 mixture of anhydrous CH₂Cl₂/ Acetone, under argon, at −30 °C., were added activated 4A M.S. (200 mg) and TMSOTf (94 mL). The solution was stirred at −30 °C. for 4 hr and 5% NaHCO₃ (5mL) was added. The biphasic solution was stirred for 15 min while the temperature was allowed to go back to r.t. It was then filtered through Celite and poured in water. The phases were separated and the aqueous layer was extracted with CH₂Cl₂ (2×) 0 The combined organic extracts were dried over MgSO₄, The solids were filtered and the solrants evaporated. The pale brown solid obtained was dissolved in dry toluene (6.5 mL) and 1-acetoxybutadiene (0.19 mL, 5 eq) was added. The solution was stirred at r.t., under argon for 15 hr. Silica gel was added and air was bubbled through the solution. This suspension was then placed on top of a silica gel column and the column was eluted with hexanes (1 reservoir). When the hexanes was all gone, it was replaced with 2:1 hexanes/ethyl acetate and themixture of isomers was collected. This mixture was further purified by chromatography (10% acetone/ toluene) to give 58 mg (30%) of the titled separated isomers.

The faster running fraction had: 33 mg, m.p.: 180°–195° C. dec.

$^1$H NMR (Acetone-d₆) : d 8.47 (d, 1H, J=9.1, NH), 8.36 (d, 1H, J=9.4, NH), 8.11–8.04 (m, 2H, ArH), 7.92–7.85 (m, 2H, ArH), 6.03 (s, 1H, H-1), 5.65 (s, 1H, H-1'), 4.68 (dd, 1H, J=4.1, 11.6, H-3), 4.58–4.36 (m, 2H, H-3' and H-4'), 3.85 (q, 1H, J=10.1, H-5'), 3.02 (dd, 1H, J=4.1, 19.6, H-4), 2.51 (dd, 1H, J=11.6, 19.6, H-4), 2.32 (s, 3H, COMe), 2.28–2.09 (m, 2H, H-2'), 1.28 (d, 3H, J=6.3, H-6').

The slower running fraction had: 25 mg, m.p.: 143–153 dec.

$^1$H NMR (CDCl₃): d 8.55 (d, 1H, J=9.2, NH), 8.46 (d, 1H, J=9.1, NH), 8.13–8.07 (m, 2H, ArH), 7.95–7.88 (m, 2H, ArH), 6.17 (s, 1H, H-1), 5.63 (t, 1H, J=2.5, H-1'), 4.71 (dd, 1H, J=4.3, 11.6, H-3), 4.61–4.34 (m, 2H, H-3' and H-4'), 3.86 (q, 1H, J=10.2, H-5'), 2.99 (dd, 1H, J=4.3, 19.7, H-4), 2.58 (dd, 1H, J=11.6, 19.7, H-4), 2.32 (s, 3H, COMe), 2.28–2.13 (m, 2H, H-2'), 1.37 (d, 3H, J=6.2, H-6').

EXAMPLE 70

4'-iododaunosamine substituted naphtoquinone derivative

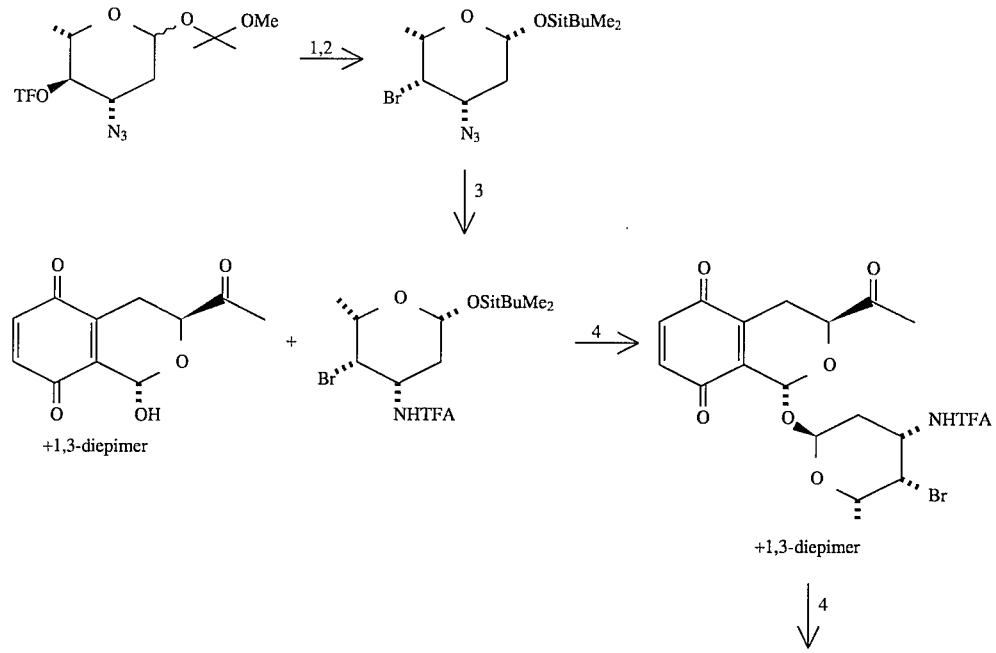

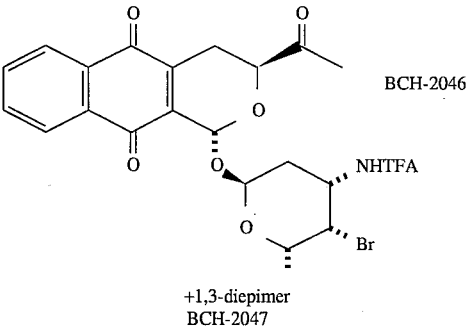

BCH-2046

NHTFA

Br

+1,3-diepimer
BCH-2047

Step 1: (2S, 4S, 5S, 6S)-2-(2'-methoxy-2'-propanoxy)-4-azido-5-bromo-6-methyl-tetrahydropyran To a solution of the triflate (1.06 g, 2.80 mmol) in a 1:1 mixture of $CH_2Cl_2$/toluene (15 ml), under argon, at room temperature, was added $nBu_4NBr$ (1.34 g, 1.5 eq) and the solution was stirred for 3 hours. It was then poured in sat. aq. $NaHCO_3$ and the phases were separated. The aqueous layer was extracted with $CH_2Cl_2$ (2×) and the combined organic extracts were dried over $MgSO_4$. The solids were filtered and the solvents evaporated to give a crude oil that was purified by flash chromatogrphy (silica gel, 85:15 Hexanes/EtOAc). The titled bromo-azide was obtained in 66% yield (0.57 g).

$^1$H NMR ($CDCl_3$): δ 5.34 (d, 1H, J=3.4, H-1), 4.27 (s, 1H, H-4), 4.02 (q, 1H, J=6.2, H-5), 3.96 (m, 1H, H-3), 3.20 (s, 3H, OMe), 2.23 (ddd, 1H, J=3.4, 12.5, 12.5, H-2), 1.74 (dd, 1H, J=4.26, 12.5, H-2), 1.40 (s, 3H, gemdimethyl), 1.3.5 (s, 3H, gemdimethyl), 1.25 (d, 3H, J=6.2, H-6).

Step 2: (2R, 4S, 5S, 6S)-2-tert-butyldimethylsilyloxy-4-azido-5-bromo-6-methyl-tetrahydropyran To a solution of the bromo-azide from step 1 (0.57 g, 1.84 mmol) in dry $CH_2Cl_2$ (9.0 ml), under argon, at 0° C., was added slowly $CF_3COOH$ (7 µl, 0.05 eq) and the solution was stirred for 60 minutes. The solvent and reagent were then evaporated to dryness and the crude hemiacetal was dissolved in a dry mixture (15:1) of $CH_2Cl_2$/DMF (9.2 ml). Imidazole (0.25 g, 2 eq) was then added followed by t-BuMe$_2$SiCl (0.31 g, 1.1 eq). The solution was stirred at room temperature for 15 hours after which it was poured in sat. aq. $NaHCO_3$. The phases were separated, the aqueous layer was extracted with $CH_2Cl_2$ (2×) and the combined organic extracts were dried over $MgSO_4$. The solids were filtered and the solvent evaporated to give the titled TBDMS protected bromo-azide (0.30 g, 46%) as a clear oil.

$^1$H NMR ($CDCl_3$): δ 4.80 (dd, 1H, J=2.5, 8.7, H-1), 4.15 (dd, 1H, J=1.2, 3.3, H-4), 3.57 (ddd, 1H, J=3.3, 4.4, 11.8, H-3), 3.44 (dq, 1H, J=1.2, 6.1, H-5), 2.11–1.138 (m, 2H, H-2), 1.33 (d, 3H, J=6.1, H-6), 0.90 (s, 9H, t-Bu), 0.14 (s, 3H, SiMe), 0.11 (s, 3H, SiMe).

Step 3: (2R, 4S, 5S, 6S)-2-tert-butyldimethylsilyloxy-4-trifluoroacetamido-5-bromo-6-methyl-tetrahydropyran To a solution of the azide from step 2 herein (0.30 g, 0.84 mmol) in a 19:1 mixture of THF/$H_2O$ (8.4 ml) was added $Ph_3P$ (0.33 g, 1.5 eq) and the solution was heated at 50° C. for 3 hours. It was then poured in sat. aq. $NaHCO_3$ and the aqueous phase was extracted with $CH_2Cl_2$ (3×). The combined organic extracts were dried over $MgSO_4$. The solids were filtered and the solvent evaporated to dryness to give a crude amine that was dissolved in dry $CH_2Cl_2$ (8.4 ml). To this solution, under argon, at −30° C., were added successively dry pyridine (0.14 ml, 2 eq) and $TFA_2O$ (0.13 ml, 1.1 eq). The solution was stirred for 90 minutes at −30° C. and was then poured in sat. aq. $NaHCO_3$. The phases were separated, the aqueous layer was extracted with $CH_2Cl_2$ (2×) and the combined organic extracts were dried over $MgSO_4$. The solids were filtered and the solvent was evaporated to give the titled crude bromo-trifluoroacetamide in 72% yield (0.26 g).

$^1$H NMR ($CDCl_3$): δ 6.67 (bd, 1H, J=7.3, NH), 4.84 (dd, 1H, J=5.4, 6.5, H-1), 4.28–4.17 (m, 2H, H-3 and H-4), 3.58 (q, 1H, J=6.1, H-5), 1.89–1.83 (m, 2H, H-2), 1.32 (d, 3H, J=6.1, H-6), 0.88 (s, 9H, t-Bu), 0.12 (s, 3H, SiMe), 0.10 (s, 3H, SiMe).

Step 4: (1R, 3S, 1'S)-Methyl-(1-[2',3',4',6'-tetradeoxy-3'-trifluoroacetamido-4'-bromo-L-lyxohexopyranose]-5,10-dioxo-3,4,5,10-tetrahydronaphthaleno-[2,3-c]pyran-3-yl) ketone The titled compound was obtained as per previous procedures from the sugar of step 3 and the isochromandione. Purification: flash chromatography (silica gel, toluene/acetone 95:5). The two isomers are separable by chromatography.

$^1$H NMR ($CDCl_3$): δ 8.15–8.07 (m, 2H, ArH), 7.81–7.76 (m, 2H, ArH), 6.46 (bd, 1H, J=8.4, NH), 6.01 (s, 1H, H-1), 5.62 (d, 1H, J=3.2, H-1'), 4.54 (dd, 1H, J=4.0, 11,7, H-3), 4.42 (m, 1H, H-3'), 4.37 (s, 1H, H-4'), 4.11 (q, 1H, J=6.5, H-5'), 3.11 (dd, 1H, J=4.0, 19.7, H-4), 2.53 (dd, 1H, J=11.7, 19.7, H-4), 2.35 (s, 3H, COMe), 2.14 (td, 1H, J=3.2, 12.9, H-2'), 1.91 (dd, 1H, J=4.5, 12.9, H-2'), 1.32 (d, 3H, J=6.5, H-6').

The (1S, 3R, 1'S)-Methyl-(1-[2',3',4',6'-tetradeoxy-3'-trifluoroacetamido-4'-bromo-L-lyxohexopyranose]-5,10-dioxo-3,4,5,10-tetrahydronaphthaleno-[2,3-c]pyran-3-yl) ketone (BCH-2047) had:

$^1$H NMR ($CDCl_3$): δ8.15–8,08 (m, 2H, ArH), 7.82–7.74 (m, 2H, ArH), 6.50 (bd, 1H, J=8.5, NH), 6.18 (s, 1H, H-1), 5.49 (d, 1H, J=3.4, H-1'), 4.58 (q, 1H, J=6.4, H-5'), 4.48 (dd, 1H, J=4.2, 11.6, H-3), 4.40 (s, 1H, H-4'), 4.40 (m, 1H, H-3'), 3.08 (dd, 1H, J=4.2, 19.7, H-4), 2.57 (dd, 1H, J=11.6, 19.7, H-4), 2.32 (s, 3H, COMe), 2.18 (td, 1H, J=3.4, 13.0, H-2'), 1.79 (dd, 1H, J=4.4, 13.0, H-2'), 1.49 (d, 3H, J=6.4, H-6').

EXAMPLE 71

Cyclic amine substituted naphthoquinone derivative

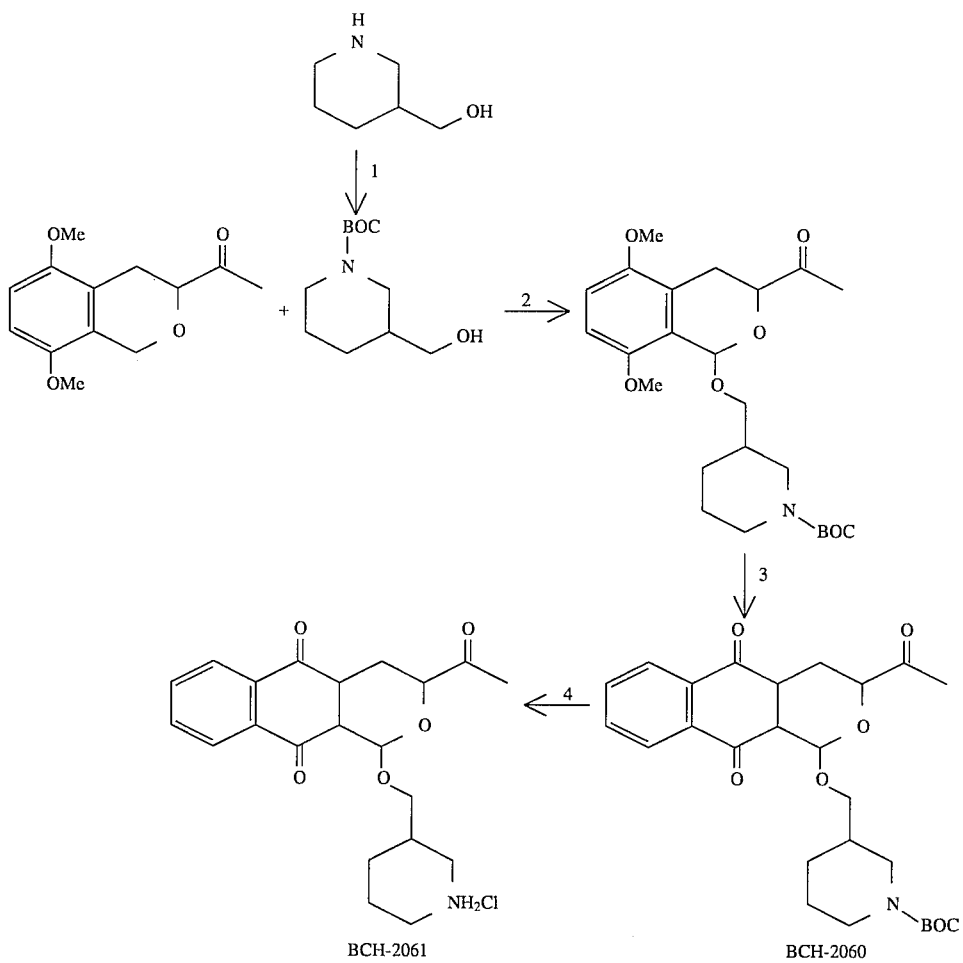

Step 1: N-BOC-3-piperidinemethanol

The titled compound obtained following protection with BOC had:

$^1$HNMR (CDCl$_3$): δ 3.90–3.65 (m, 2H), 3.48 (d, 2H, CH$_2$OH), 3.25–2.75 (m, 2H), 2.28 (bs, 1H, OH), 1.86–1.54 (m, 4H), 1.25 (m, 1H).

Step 2: 1-O-N-BOC-3-piperidinemethanol]-3-acetyl-5,8-dimethoxy isochroman, mixture of isomers The titled compound was obtained from the precursor of step 1 herein and 5,8-dimethoxy-3-acetoisochroman as per procedure described earlier. Purification: flash chromatography (silica gel, 2:1 Hexanes/EtOAc). The isomers were not separable by flash chromatography.

$^1$H NMR (CDCl$_3$): δ 6.75–6.65 (m, 2H, ArH), 5.74+5.73 (2s, 1H, H-1), 4.60 (m, 1H, H-3), 4.05–3.56 (m, 4H, H-1'and CH$_2$N), 3.04 (dd, 1H, H-4), 2.86–2.62 (m, 2H, CH$_2$N), 2.53 (dd, 1H, H-4), 2.33 (s, 3H, COCH$_3$), 1.94–1.79 (m, 2H), 1.68 (m, 1H), 1.48 (s, 9H, BOC), 1.37–1.24 (m, 2 H).

Step 3: Methyl-(1-O-[N-BOC-3-piperidinemethanol]-5,6-dioxo-3,4,5,10-tetrahydronaphthaleno-[2,3-c]pyran-3-yl) ketone, mixture of isomers (BCH-2060)

The titled compound was obtained from the product from step 2 herein, following previously described procedures. Purification: flash chromatography (silica gel, 2:1 Hexanes/ EtOAc). The isomers were not separable by flash chromatography.

$^1$HNMR (CDCl$_3$): δ 8.12–8.03 (m, 2H, ArH), 7.78–7.67 (m, 2H, ArH), 6.72 (s, 1H, H-1), 4.54 (m, 1H, H-3), 4.10–3.55 (m, 4H, H-1'and CH$_2$N), 3.04 (dd, 1H, H-4), 2.90–2.60 (m, 2H, CH$_2$N), 2.51 (dd, 1H, H-4), 2.30 (s, 3H, COCH$_3$), 1.97–1.72 (m, 2H). 1.61 (m, 1H), 1.48 (s, 9H, BOC), 1.34–1.15 (m, 2H).

Step 4: Methyl-(1-O-[3-piperidinemethanol]-5,10-dioxo-3,4,5,10-tetrahydronaphthaleno-[2,3-c]pyran-3-yl) ketone hydrochloride salt, mixture of isomers (BCH-2061)

The titled compound was obtained from the tricyclic product from step 3 herein following acidic hydrolysis.

$^1$H NMR (DMSO-d$_6$): δ 8.23–7.84 (m, 4H, ArH), 5.68+ 5.67 (2s, 1H, H-1), 4.48 (m, 1H, H-3), 3.83–3.57 (m, 2H, H-1'), 3.29–3.15 (m, 2H, CH$_2$N), 2.84 (dd, 1H, H-4), 2.66 (m, 2H, CH$_2$N), 2.43 (m, 1H, H-4), 2.29 (s, 3H, COCH$_3$), 1.74–1.72 (m, 4H), 1.25 (m, 1H).

EXAMPLE 72

Preparation of BCH$_{2818}$ and 2819 (1'S, 2'R, 3'S, 5'R, 1S, 3R) and (1'S, 2'R, 3'S, 5'R, 1R, 3S) -1-(3-trifluoroacetamido-2-hydroxy-1-methyltetrahydropyran-5-yl)-methyl-3-ethyl-5,10-dioxo-3,4,5,10-tetrahydro-1H-naphtho[2,3-C]pyran

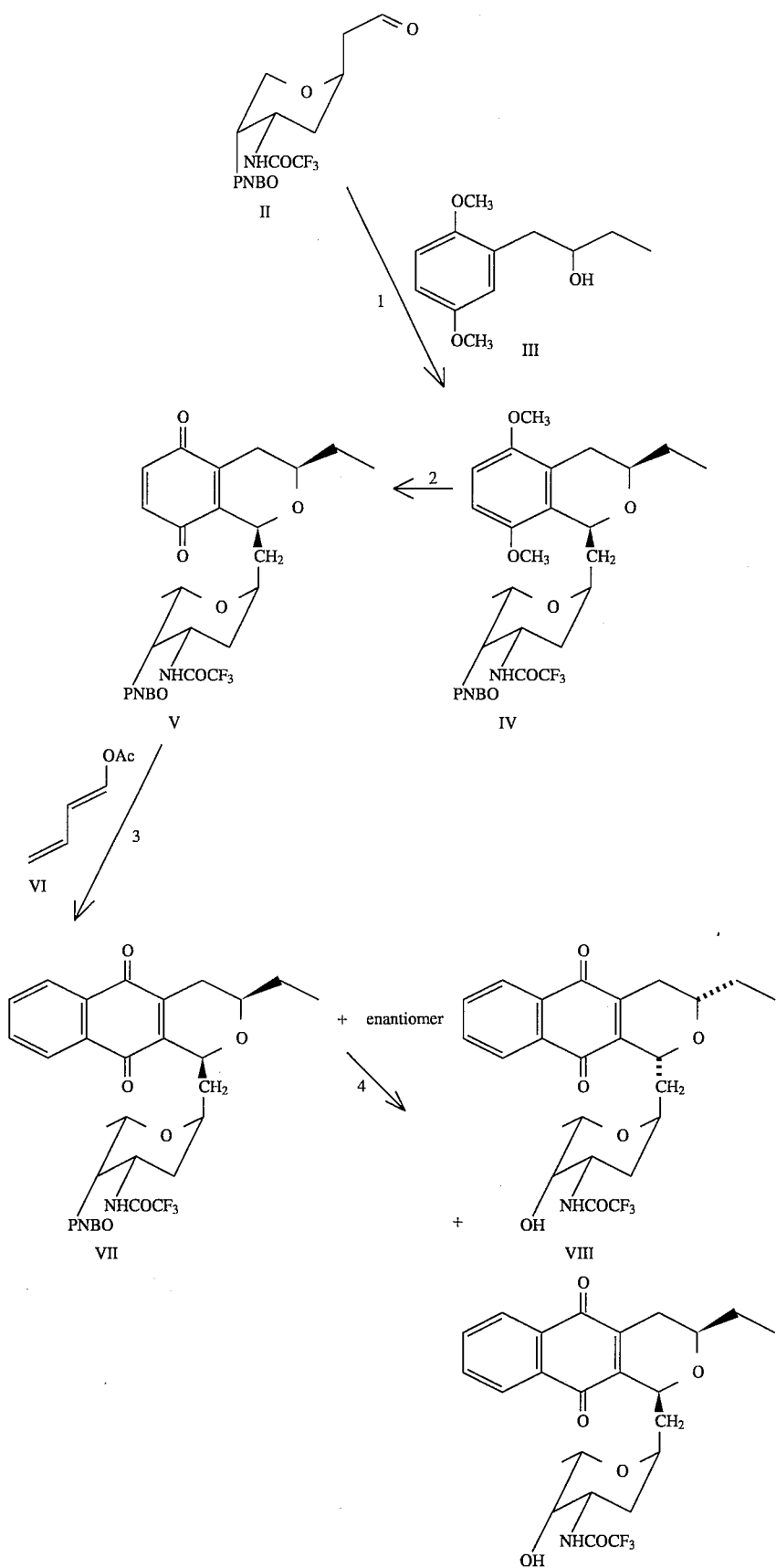

Step 1: To a mixture of compounds II (406 mg, 0.97 mmol) and III (200 mg, 0.951 mmol) in dry diethylether, $BF_3Et_2O$ (0.34 ml, 2.775 mmol) was added dropwise and under argon atmosphere. The reaction was quenched after 40 minutes of stirring by adding $NHCO_3$ sat (20 ml) and extracted with $Et_2O$ (2×20 ml). The combined organic layers were washed with NaCl sat (40 ml) and dried over $MgSO_4$. Flash chromatography of the crude gave 386 mg (66% yield) of a pure stereoisDmer mixture (1:1) (compound IV) non separable.

Step 2: To a stirred mixture of compound IV (363 mg, 0.594 mmol) in acetonitrile (6 ml) maintained at 0° C., 1.304 g (2.378 mmol) of CAN in 4 ml of water was added dropwise. After 15 minutes of stirring, the mixture was diluted with water (20 ml) and extracted with $CH_2Cl_2$ (3×20 ml). The combined organic layers were then washed with water and dried ($MgSO_4$). Evaporation of the solvent gave 340 mg (99% yield) of crude product V.

Step 3: The procedure shown in Example 61, step 7 was used in this step. Aromatization by flash chromatography (Toluene:acetone; 93.1) gave 95 mg of desired product VII as a pure stereoisomer mixture (3:2).

Step 4: (1'S, 2'R, 3'S, 5'R, 1S, 3R)-1-(3-trifluoroacetamido-2-hydroxy-1-methyl tetrahydropyran-5-yl)-methyl-3-ethyl-5, 10-dioxo-3,4,5,10-tetrahydro-1H-naphtho[2,3-C]pyran The procedure shown in example 5, step 3 was used. Flash chromatography (toluene:acetone; 8:2) gave 42 mg (65% yield) of a pure stereoisomers mixture (1:1). HPLC separation gave the pure stereoisomer and the other stereoisomer described below.

PMR(CDCl$_3$, 250 MHz) δ: 0.79 (3H, d, J=6.5 Hz, H-6'), 1.00(3H, t, J=7.4 Hz,CH$_2$C$\underline{H}_3$), 1.68 (4H, m, H$_e$-2', —C$\underline{H}_2$CH$_3$, OH), 1.90(H, ddd, J=19.2 Hz, 12.9 Hz and 6.2 Hz, H$_a$-2'), 2.07 (1H,m, CH$_2$), 2.24 (1H, ddd, J=18.6 Hz, 14.6 Hz and 4.2 Hz, H$_a$-4), 2.79 (2H, m, H$_e$-4 and —CH$_2$), 3.36 (1H, m, H-3), 3.48 (1H, S, H-4'), 3.68 (1H, q, J=6.4 Hz, H-5'), 4.20 (1H, m, H-3'), 4.34 (1H, m, H-1), 4.87 (1H, m, H-1), 6.71 (1H, broadd, NHCOCF$_3$), 7.73 and 8.07 (2×2H, 2m, Ar-H).

(1'S, 2'R, 3'S, 5'R, 1R, 3S)-1-(3-trifluoroacetamido-2-hydroxy-1-methyl tetrahydropyran-5-yl)-methyl-3-ethyl-5, 10-dioxo-3,4,5,10-tetrahydro-1H-naphtho[2,3-C]pyran See procedure above. HPLC separation gave the pure stereoisomer.

PMR(CDCl$_3$, 250 MHz) δ: 1.01 (3H, t, J=7.5 Hz, —CH$_2$C$\underline{H}_3$), 1.33 (3H, d, J=6.5 Hz, H-6), 1.42 (1H, m, -CH$_2$), 1.70(4H, m, C$\underline{H}_2$CH$_3$), H$_e$-2', OH), 1.95 (1H, m, H$_a$-2'), 2.24 (1H, m, H$_a$-4), 2.86(2H, m, H$_e$-4 and —CH$_2$), 3.35 (1H, m, H-3), 3.63 (1H, S, H-4'), 4.29 (2H, m, H-3'and H-5'), 4.47 (1H, m, H-1'), 4.86 (1H, m, H-1), 6.76 (1H, broad d, N$\underline{H}$COCF$_3$), 7.74 and 8.06 (2×2H, 2m, Ar-H).

EXAMPLE 73

Preparation of BCH$_{2820}$ and 2821 (1'S, 2'R, 3'S, 5'R, 1R, 3R) and (1'S, 2'R, 3'S, 5'R, 1S, 3S)-1-(3-trifluoroacetamido-2-hydroxy-1-methyl tetrahydropyran -5-yl)methyl-3-methylketone-5,10-dioxo-3,4,5,10-tetrahydro-1H-naphtho[2,3-C]pyran.

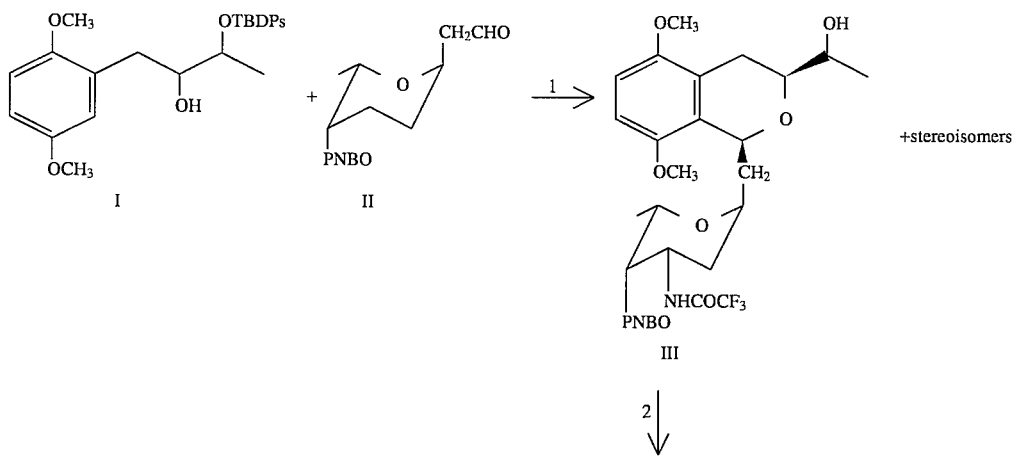

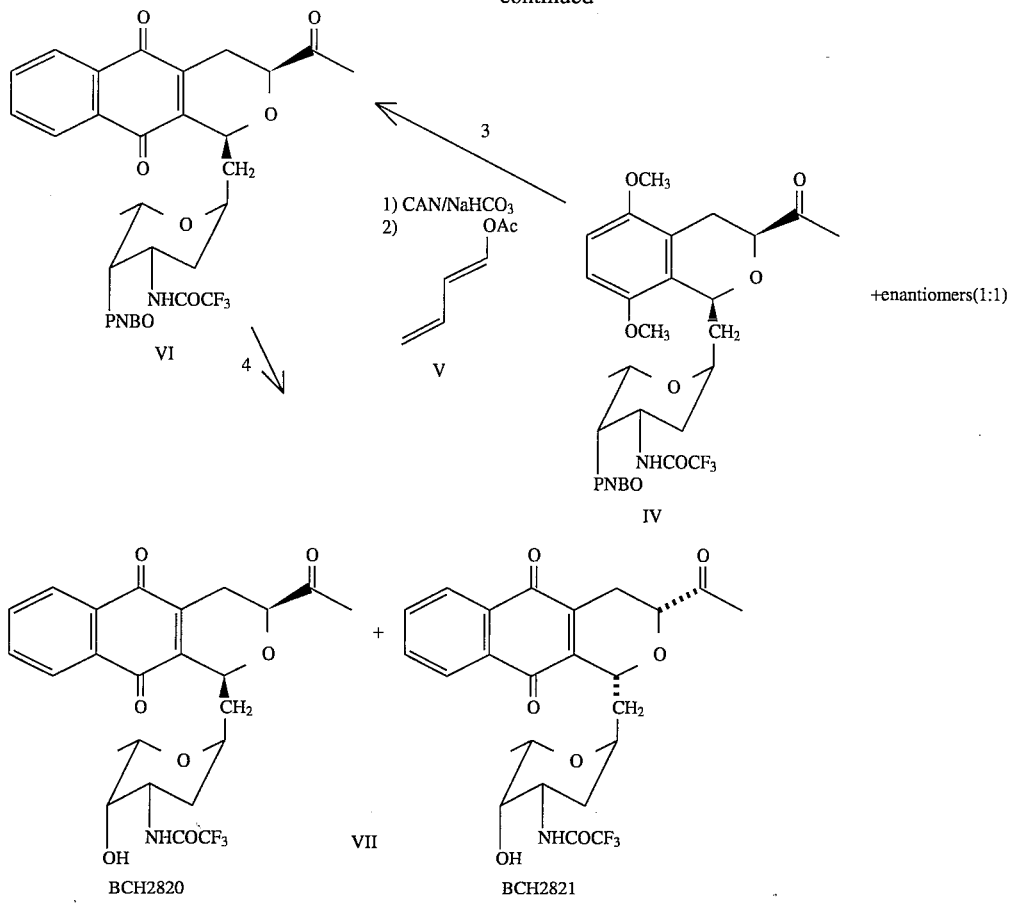

Step 1: To a mixture of compounds I (50 mg, 0.108 mmol) and II (45 mg, 0.108 mmol) in dry acetonitrile, 0.34 μl of trimethylsilyl trifluoro methanesulfonate (0.162 mmol) was added dropwise and under argon atmosphere. After 20 minutes of stirring, the reaction was quenched with NaHCO₃ sat (10 ml) and extractions were done with Et₂O (2×10 ml). The combined organic layers were washed with NaCl sat(15 ml) and dried (MgSO₄). Flash chromatography of the residue (hexane:acetone; 7:3) gave 46 mg of a stereoisomer mixture of product III (68% yield).

Step 2: Under argon atmosphere, a glycoside mixture of compound III (46 mg, 0.074 mmol) was dissolved in dry dichloromethane (4 ml). To this mixture was added 46 mg of molecular sieves (4A) and 19 mg (0.088 mmol) of pyridinium chlorochromate (PCC). This mixture was stirred for 6 hours while an addition of 19 mg of PCC was done after the two first hours, and flash chromatographied (Hexane:acetone; 8:2) to give 40 mg (87% yield) of the methyl ketone derivative mixture (compound IV).

Step 3: Following the same procedure as described in example 100, step 3, the quinone glycoside mixture was obtained. Following the same procedure as described in example 61, step 7, we obtained after flash chromatography (Toluene:ethyl acetate:acetone; 18:1:1) 139 mg (43% yield) of a stereoisomer mixture (compound VI; 3:2).

Step 4: (1'S, 2'R, 3'S, 5'R, 1R, 3R)-1-(3-trifluoroacetamido-2-hydro -methyl tetrahydropyran-5-yl) methyl-3-methylketone-5,10-dioxo-3,4,5,10-tetrahydro-1H-naphtho[2,3-C]pyran. BCH₂₈₂₁

The procedure shown in example 6, step 3, was used to produce the titled compound. Flash chromatography (toluene:ethyl acetate; 6:4) of the crude gave 48 mg of the more polar stereoismer impure. HPLC purification gave 18 mg (18% yield) of the pure stereoisomer.

PMR(CDCl₃, 250 MHz) δ: 1.33 (3H, d, J=6.4 Hz, H-6'), 1.48 (m, 1H, CH₂) 1.67 (dd, 1H, J=13.4 Hz and 5.0 Hz, H$_e$-2'), 2.01 (ddd, 1H, J=19.4 Hz, 13.1 Hz and 6.5 Hz, H$_a$-2'), 2.32 (S,3H, COCH₃), 2.45 (ddd, 1H, J=18.8 Hz,10.8 Hz and 4.0 Hz, H$_a$-4), 2.96 (m, 1H, CH₂), 3.13 (ddd, 1H, J=18.8 Hz and 2.9 Hz, H$_e$-4), 3.65 (s, 1H, H-4'), 3.97 (dd, J=10.8 Hz and 2.8 Hz, H-3), 4.28 (m, 2H, H-3' and H-5'), 4.50 (m, 1H, H-1'), 4.96 (broad d, 1H, J=10.2 Hz, H-1), 6.79 (broad d, 1H, NHCOCF₃), 7.76 (m, 2H, Ar-H), 8.05 and 8.11 (2m, 2H, Ar-H).

IR(film) D$_{max}$: 3419, 2985 and 2933, 1720 and 1665, 1300, 1220 and 1175, 745 cm⁻¹.

(1'S, 2'R, 3'S, 5'R, 1S, 3S) -1-(3-trifluoroacetamido-2-hydroxy-1-methyl tetrahydropyran-5-yl)methyl-3-methylketone-5,10-dioxo-3,4,5,10-tetrahydro-1H-naphtho[2,3-C]pyran. BCH2820

See procedure above. Flash chromatography (toluene:ethyl acetate; 6:4) of the crude gave 18 mg (18% yield) of the less polar stereoismer and 18 mg (18% yield) of the more polar stereoisomer described above.

PMR(CDCl₃, 250 MHz) δ: 0.76(3H, d, J=6.3 Hz, H-6'), 1.75 (1H, dd, J=13.0 Hz and 4.7 Hz, H$_e$-2') 1.94 (1H, ddd, J=19.2 Hz, 13.0 Hz and 6.3 Hz, H$_a$-2'), 2.15 (1H, m, CH₂), 2.31 (3H, S, COCH₃), 2.47 (1H, ddd, 1H, J=18.6 Hz, 11.0 Hz and 3.9 Hz, H$_a$-4), 2.90 (1H, m, CH₂), 3.12 (1H, unresolved ddd, J=18.6 Hz, H$_e$-4), 3.49 (1H, broad D, H-4'), 3.66 (1H, q, J=6.3 Hz, H-5'), 3.97 (1H, dd, J=11 Hz and 2.9 Hz, H-3), 4.22 (1H, m, H-3'), 4.34 (1H, m, H-1'), 5.02(1H, m, H-1), 671 (1H, broad d, NHCOCF₃), 7.75 and 8.09 (2×2H, 2m, Ar-H).

EXAMPLE 74

1-methoxy-3-methoxy carbonyl-5,10-dioxo-5,10-dihydro-1H-naphtho-[2,3-c]-pyran (BCH-2160)

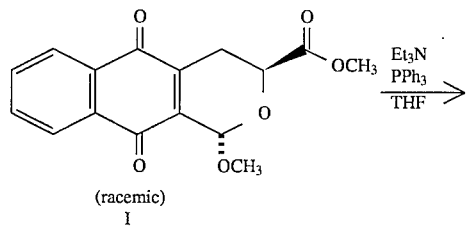

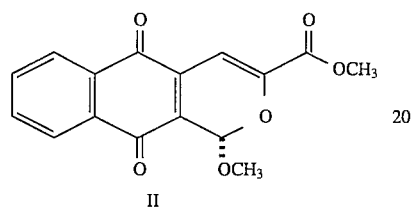

Triethylamine (0.479, 4.6 mmol) was added to a solution of compound I (0.709, 2.32 mmol) and triphenylphosphine (1.82 g, 6.95 mmol) in THF (15 ml). The mixture was stirred at room temperature for 3 hours. Silica gel (10 g) was added. The residue from solvent evaporation was chromatographed on silica gel, eluting with ethyl acetate:hexane=3:7. Evaporation of the fractions provided the titled compound (II) as a yellow solid (0.53 g, 76%).

$^1$H NMR (CDCl$_3$, 300 MHz, Bruker), δ: 3.69 (3H, s, COOCH$_3$), 3.95 (3H, s, OCH$_3$), 6.41 (1H, s, 1-H), 7.37 (1H, s, 4-H), 7.80 (2H, m, Ar-H), 8.17 (2H, m, Ar-H).

IR (Nicolet 205 FT, film on NaCl plate): cm$^{-1}$, 2947 2938, 2855 1734, 1678, 1659, 1595, 1562, 1344, 1384, 1327, 1294, 1275, 1234, 1133, 1069, 1001, 957, 863, 799, 770, 718.

EXAMPLE 75

Preparation of 1-propyl-3-(3-dimethyl amino propyl amino carbonyl)-5,10-dihydro-5,10-dioxo-1H-naphtho-[2,3-c]-pyran (BCH-2168)

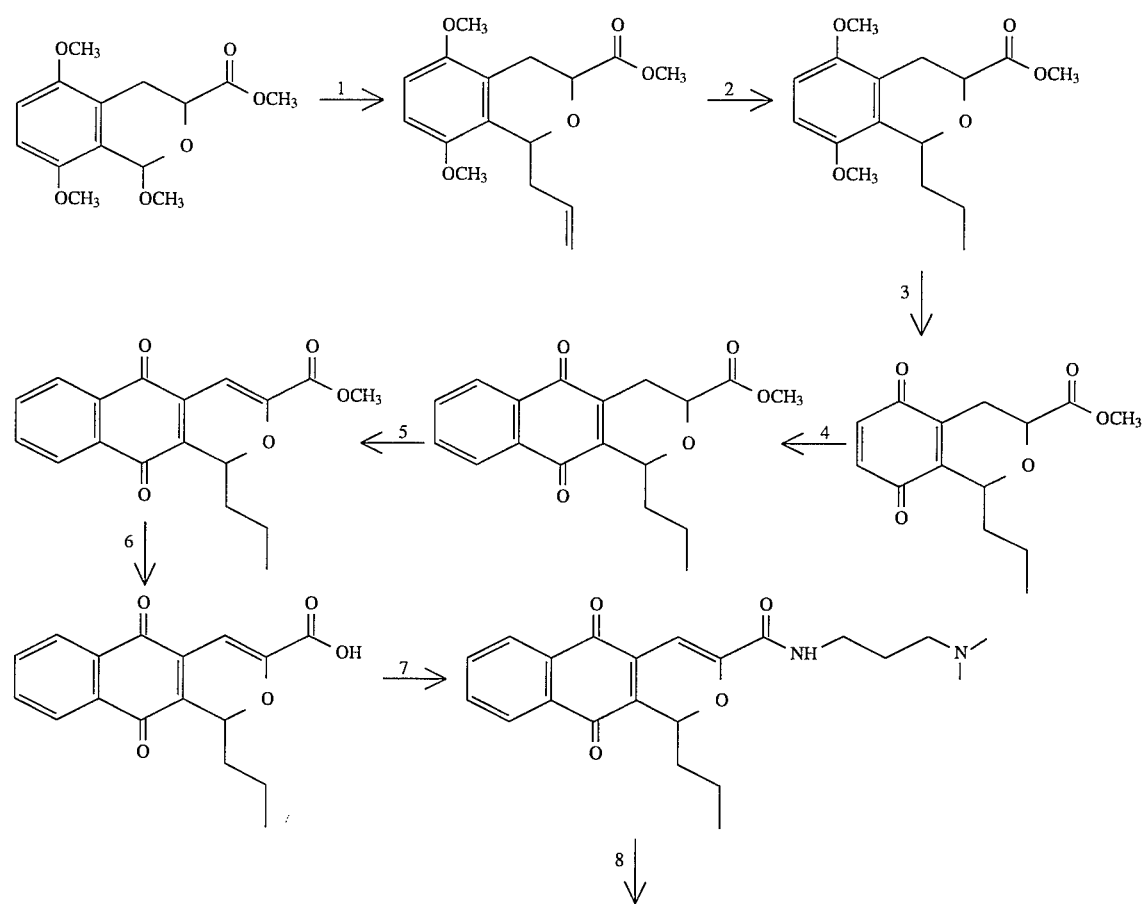

-continued

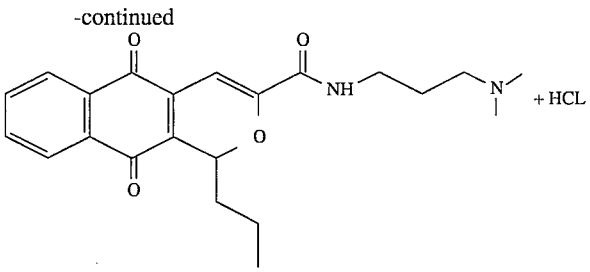

Step 1: (1,3-trans)-1-allyl-3-methoxy carbonyl-5,8-dimethoxy-isochroman

At −10° C., to a solution of isochroman as described in example 74, step 1 (500 mg, 1,773 mmol) and allyl trimethyl silane (571 µl, 3.55 mmol) in 20 ml of dichloromethane was added boron trifluoride etherate (436.12 µl, 3.55 mmol). The resulting liquid was stirred for 2 hours as it warmed to 20° C. The crude product was diluted with dichloroform, washed with sodium bicarbonate (10%), 0.01N hydrogen chloride and brine. The organic layer was dried and evaporated to give desired product (525.0 mg, 90%).

m.p. 67.7°–68.5° C.

$^1$H NMR (CDCl$_3$, 250 MHz, Bruker), δ: 2.52 (1H, m, CH$_2$—CH=CH$_2$), 2.69 (1H, m, CH$_2$—CH=CH$_2$), 2.77 (1H, dd, J=18.2 Hz, 10.9 Hz, 4-H$_a$), 3.02 (1H, dd, J=18.2 Hz, 5.4 Hz, 4-H$_e$), 3.75 (3H, s, OCH$_3$), 3.77 (6H, s, 2×OCH$_3$), 4.58 (1H, dd, J=10.9 Hz, 5.4 Hz, 3-H), 5.13–5.03 (2H, m, CH=CH$_2$), 5.15 (1H, dd, J=9.6 Hz, 3.6 Hz, 1-H), 5.96 (1H, m, CH=CH$_2$), 6.65 (2H, m, ArH).

Step 2: 1-propyl-3-methoxy carbonyl-5,8-dimethoxy-isochroman

The (1,3-trans)-1-allyl-3-methoxy carbonyl-5,8-dimethoxy-isochroman described in step 1 (734 mg, 2.51 mmol) was dissolved in 40 ml of THF and subjected to hydrogenation conditions (1 at m, Pd/c-10%, 27 mg, 0.0251 mmol). After 2 hours at room temperature, the reaction mixture was filtered. The filtrate was evaporated to give desired product (772 mg, 95%).

$^1$H NMR (CDCl$_3$, 250 MHz, Bruker), δ: 0.95 (3H, tr, J=6.6 Hz, CH$_3$), 1.45–1.90 (4H, m, CH$_2$CH$_2$), 2.74 (1H, dd, J=18.1 Hz, 11.0 Hz, 4-Ha), 3.01 (1H, dd, J=18.1 Hz, 4.2 Hz, 4-H$_e$), 3.74 (3H, s, OCH$_3$), 3.76 (3H, s, OCH$_3$), 3.79 (3H, s, OCH$_3$), 4.52 (1H, dd, J=11.0 Hz, 4.2 Hz, 3-H), 5.06 (1H, dd, J=10.9 Hz, 1-H), 6.63 (2H, br s, ArH).

Step 3: 1-propyl-3-methoxycarbonyl-3,4,5,8-tetrahydro-5,8-dioxo-1H-benzo-[2,3-c]-pyran.

The 1-propyl-3-methoxy carbonyl-5,8-dimethoxy-isochroman isochroman described in step 2 (93 mg, 0.316 mmol) was dissolved in acetonitrile (8 ml) and then cooled to 0° C. A solution of ammonium cerium (IV) nitrate (519.7 mg, 0.948 mmol) in 2.0 ml of water buffered with sodium bicarbonate (53 mg, 0.632 mmol) was added dropwise. After 10 minutes the reaction mixture was poured to dichloromethane. The organic layer was washed with brine, dried and evaporated to give the titled compound (77 mg, 92%).

$^1$H NMR (CDCl$_3$, 250 MHz, Bruker), δ: 0.94 (3H, tr, J=6.6 Hz, CH$_3$), 1.45–1.75 (4H, m, CH$_2$CH$_2$), 2.62 (1H, ddd, J=18.9 Hz, 9.7 Hz, 1.8 Hz, 4-H$_a$), 2.80 (1H, ddd, J=18.9 Hz, 5.4 Hz, 0.8 Hz, 4-H$_e$), 3.76 (3H, s, OCH$_3$), 4.44 (1H, dd, J=9.7 Hz, 5.4 Hz, 3-H), 4.84 (1H, br d, J=9.6 Hz, 1-H), 6.67 (1H, d, J=10.3 Hz, ArH), 6.73 (1H, d, J=10.3 Hz, ArH).

IR (Nicolet, 205 FT, film on NaCl plate): cm$^{-1}$, 2958.4, 2932.9, 2873.2, 1745.3, 1657.2, 1489.6, 1461.2, 1444.1, 1304.9, 1262.3, 1219.7, 1097.5, 1040.7, 840.8.

Step 4: 1-propyl-3-methoxycarbonyl-3,4,5,10-tetrahydro-5,10-dioxo-1H-naphtho-[2,3-c]-pyran.

The 1-propyl-3-methoxycarbonyl-3,4,5,8-tetrahydro-5,8-dioxo-1H-benzo-[2,3-c]-pyran described in step 3 (76 mg, 0.288 mmol) was stirred with 1-acetoxyl-1,3-butadiene (136 µl, 1.152 mmol) at 45° C. for 20 hours. Solvent was evaporated and the crude product was chromatographed (toluene/ethyl acetate ~100/15, v/v) to give the titled compound (65 mg, 71.9%).

m.p. 111.5°–113.6° C.

$^1$H NMR (CDCl$_3$, 250 MHz, Bruker), δ: 0.97 (3H, tr, J=6.7 Hz, CH$_3$), 1.45–1.85 (4H, m, CH$_2$CH$_2$) 2.7[; (1H, ddd, J=19.9 Hz, 10.4 Hz, 1.2 Hz, 4-H$_a$), 2.97 (1H, dd, J=19.9 Hz, 5.4 Hz, 7-H$_e$), 3.80 (3H, s, OCH$_3$), 4.51 (1H, dd, J=10.4 Hz, 5.4 Hz, 3-H), 5.04 (1H, br d, J=8.5 Hz, 1-H), 7.72 (2H, m, 7, 8 -ArH), 8.07 (2H, m 6, 9-ArH).

IR (Nicolet, 205 FT film on NaCl plate): cm$^{-1}$, 2959.3, 2931.1, 2877.2, 1751.1, 1663.8, 1594.6, 1461.2, 1440.7, 1330.4, 1291.9, 1284.2, 1225.2, 1179.0, 1179.0, 1104.5, 872.11, 790.4, 717.4.

Step 5: 1-propyl-3-methoxycarbonyl-5,10-dioxo-5,10-dihydro-1H-naphtho-[2,3-c]-pyran.

The 1-propyl-3-methoxycarbonyl-3,4,5,10-tetrahydro-5,10-dioxo-1H-naphtho-[2,3-c]-pyran described in step 4 (50 mg, 0.159 mmol) was stirred with triphenylphosphine (166.6 mg, 0.636 mmol) and 1,4-diaza bicyclo-[2,2.2]-octane (19.6 mg, 0.175 mmol) in presence of air for a few hours at room temperature until the starting material was entirely consumed. The reaction mixture was evaporated to dryness. The crude product obtained was chromatographed (toluene/ethyl acetate=10/1, v/v) to give the titled compound (35 mg, 70%).

$^1$H NMR (CDCl$_3$, 250 MHz, Bruker), δ: 0.93 (3H, tr, J=6.9 Hz, CH$_3$), 1.35–1.60 (4H, m, CH$_2$CH$_2$), 3.87 (3H, s, OCH$_3$), 5.69 (1H, dd, J=4.3 Hz, 10.9 Hz, 1-H), 7.07 (1H, s, 4-H), 7.74 (2H, m, 7, 8-ArH), 8.07 (2H, m, 6, 9-ArH).

IR (Nicolet, 205 FT, film on NaCl plate): cm$^{-1}$, 2959.8, 2876.4, 1737.3, 1669.0, 1652.3, 1596.2, 1564.3, 1438.4, 1397.5, 1268.0, 1233.7, 1133.6, 1133.6, 1074.4, 716.45.

Step 6: 1-propyl-3-carboxyl-5,10-dihydro-5,10-dioxo-1H-naphtho-[2,3-c]-pyran.

1-propyl-3-methoxycarbonyl-5,10-dioxo-5,10-dihydro-1H-naphtho-[2,3-c]-pyran (63 mg, 0.201 mmol) was dissolved in tetrahydrofuran (4 ml) and cooled to 0° C. A solution of sodium hydroxide (2.41 ml, 0.1N, 0.241 mmol) was added dropwise. The resulting lyeaction mixture was stirred for 1 hour at room temperature. It was then acidified with 0.1N HCl and extracted with ethyl acetate. After evaporation of the solvent, the titled compound was obtained (58 mg, 96%).

$^1$H NMR (Acetone-d$_6$, 250 MHz, Bruker), δ: 0.96 (3H, tr, J=6.4 Hz, CH$_3$), 1.40–1.68 (4H, m, CH$_2$CH$_2$), 5.64 (1H, dd, J=9.7 Hz, 3.1 Hz, 1-H), 7.03 (1H, s, 4-H), 7.87 (2H, m, 7, 8-ArH), 8.07 (2H, m, 6, 9-ArH).

IR (Nicolet, 205 FT, film on NaCl plate): cm$^{-1}$, 3667–2500 (strong) 2864.6, 2927.4, 2869.6, 2634.0, 1732.9, 1712.3, 1670.9, 1654.4, 1592.4, 1567.6, 1394.0, 1332.0, 1298.9, 1265.9, 1227.6, 1071.1, 719.09.

Step 7: 1-propyl-3-(3-dimethyl amino propyl amino carbonyl)-5,10-dihydro-5,1,]-dioxo-1H-naphtho-[2,3-c]-pyran.

Using similar steps as explained in example 74, step 7, this compound was prepared. During the preparation, 29 mg of 1-propyl-3-carboxyl-5,10-dihydro-5,10-dioxo-1H-naphtho-[2,3-c]-pyran, 21.2 µl, 0.243 mm of oloxalyl chloride, and 12.5 µl, 0.99 mmol of 3-dimethyl amino propyl amine was used to produce 33.6 mg, 90% of the title compound.

Step 8: 1-propyl-3-(3-dimethyl amino propyl amino carbonyl)-5,10-dihydro-5,10-dioxo-1H-naphtho-[2,3-c]-pyran (BCH-2168)

This compound was prepared using similar steps as explained in example 74, step 8. During the process, 16 mg, 0.042 mmol of 1-propyl-3-(3-dimethyl amino propyl amino carbonyl)-5,10-dihydro-5,10-dioxo-1H-naphtho-[2,3-c]-pyran was used along with HCl in ether - 1 eq, to produce 15 mg of the title compound.

Dec. 175° C.: m.p. 185°–188° C.

EXAMPLE 76

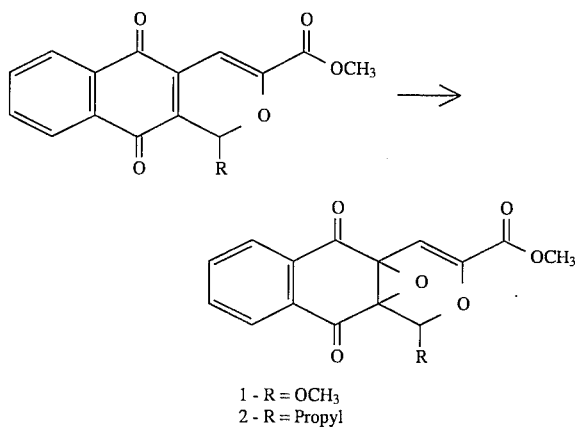

1 - R = OCH₃
2 - R = Propyl

1: (1,10ₐ-trans)-1-methoxy-3-methoxycarbonyl-5,10-dioxo-5,10-dihydro-4ₐ,10ₐ,epoxy-naphtho-[2,3-c]-pyran Methyl (1-methoxy-5,10-dioxo-5,10-dihydro-1H-naphtho[2,3-c]pyran-3-yl)formate (15.5 mg, 0.052 mmol) was dissolved in 2.2 ml of tetrahydrofuran, then coolLed to 0° C. Sodium bicarbonate (74 mg, 0.886 mmol) was added and this was followed by addition of hydrogen peroxide (30%, 42.3 µl, 0.373 mmol). The reaction proceeded as the yellow solution turned colorless. After two hours, the crude product was poured to NH₄Cl (sat) and extracted with dichloromethane. The organic layer was dried over sodium sulfate and then evaporated to give the titled product (15.4 mg, 95%).

$^1$H NMR (CDCl₃, 250 MHz, Bruker), δ: 3.60 (3H, s, OCH₃), 3.84 (3H, s, OCH₃), 5.90 (1H, s, 1-H), 7.20 (1H, s, 4-H), 7.78 (2H, m, 7, 8-ArH), 8.10 (2H, m, 6, 9-ArH).

2: (1,10ₐ- trans)-1-propyl-3-methoxycarbonyl-5,10-dihydro-5,10-dioxo-4ₐ,10ₐ-epoxy-naphtho-[2,3-c]-pyran 1-propyl-3-methoxycarbonyl-5,10-dioxo-5,10-dihydro-1H-naphtho-[2,3-c]-pyran (17 mg, 0.254 mmol) was dissolved in ice-cold THF-H₂O (3 ml–1 ml) medium. Sodium bicarbonate (77.8 mg, 0.926 mmol) was added. Then hydrogen peroxide (30%, 47.3 µl, 0.463 mmol) was added. After 45 minutes, the reaction mixture was poured to water and extracted with ethyl acetate. The titled compound was obtained in good purity (16.3 mg, 91.1%).

$^1$H NMR (CDCl₃, 250 MHz, Bruker), δ: 0.96 (3H, tr, J=7.3 Hz, CH₃), 1.50–1.77 (4H, m, CH₂CH₂), 3.84 (3H, s, OCH₃), 5.12 (1H, dd, J=7.9 Hz, 1.8 Hz, 1-H), 7.10 (1H, s, 4-H), 7.79 (2H, m, 7, 8-ArH), 8.05 (2H, m, 6, 9-ArH).

IR (Nicolet 205 FT film on NaCl): cm⁻¹, 2958.9, 2926.0, 2978.4, 1736.2 1699.6, 1644.7, 1589.8, 1432.4, 1297.0, 1267.7, 1238.4, 1120.1, 764.48, 711.07, 632.30.

EXAMPLE 77

3-methoxy carbonyl-5,10-dioxo-5,10-dihydro-1H-naphtho-[2,3-c]-pyran (BCH-2830)

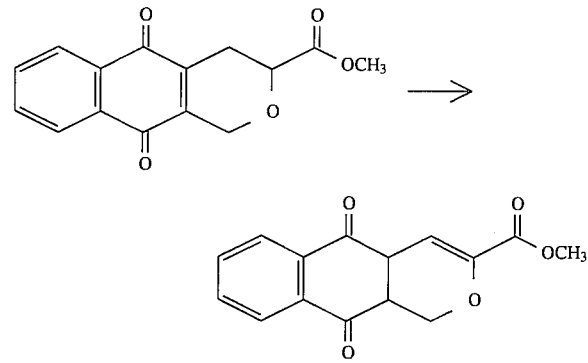

Preparative details: See example 75. I: 80 mg, 0.294 mmol Triethyl amine: 59.4 µl, 0.588 mmol triphenylphosphine: 308.4 mg, 1.176 mmol II: 12 mg $^1$H NMR (CDCl₃, 250 MHz, Bruker), δ: 3.90 (3H, s, OCH₃), 5.30 (2H, s, OCH₂), 7.13 (1H, s, 4-H), 7.75 (2H, m, 7, 8-ArH), 8.11 (2H, m, 6, 9-ArH). IR (Nicolet 205 FT, film on NaCl plate): cm⁻¹, 2962.7, 2924.6, 2851.5, 1736.0, 1669.3, 1653.4, 1589.8, 1437.3, 1395.9, 1338.7, 1287.9, 1268.8, 1237.0, 1125.8, 718.81.

EXAMPLE 78

2-hydrochloro-(N-pyrrolidinyl)ethyl-(1-propyl-5,10-dioxo-5,10-dihydro-1H-naphtho-[2,3-cl-pyran-3)-carboxamide (BCH-2875)

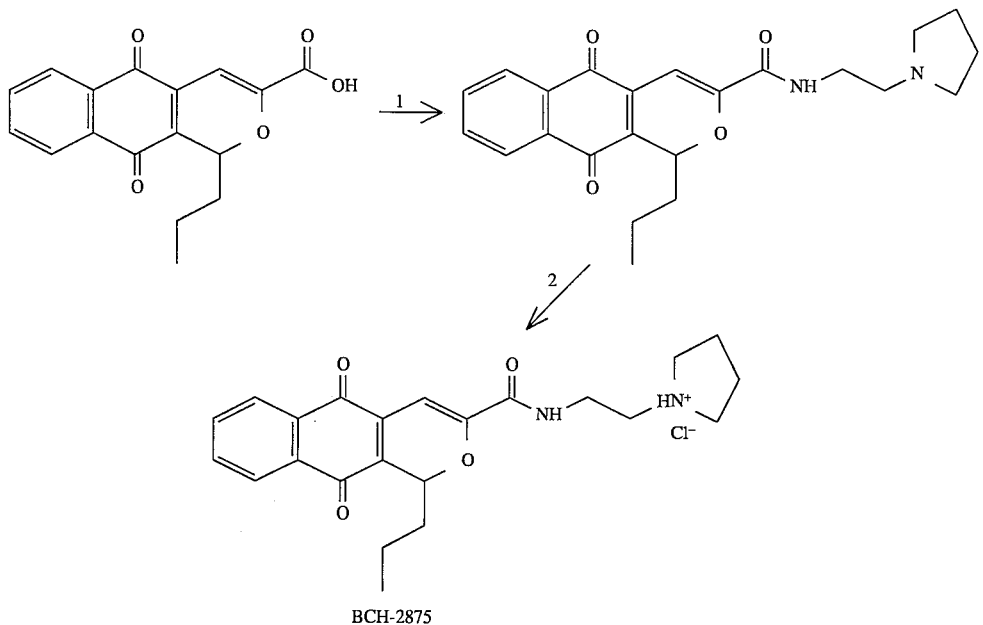

BCH-2875

Step 1: 2-(N-pyroolidinyl) ethyl-(1-propyl-5,10-dioxo-5,10-dihydro-1H-naphtho-[2,3-c]-pyran-3)-carboxamide Tricyclic carboxylic acid (25 mg, 0.084 mmol) in $CH_2Cl_2$ (2 ml) was converted into acid chloride by oxalyl chloride (0.1 ml of 2M solution in $CH_2Cl_2$). Excess reagent was pumped off and the acid chloride in $CH_2Cl_2$ (2 ml) was treated with 1-(2-amino ethyl)-pyrrolidine (9 mg, 0.079 mmol) in $CH_2Cl_2$ (0.75 ml) at −10° C. Reaction was almost complete in 5 minutes. 1-(2-amino ethyl)-pyrrolidine (1.2 mg) in $CH_2Cl_2$ (0.1 ml) was further added and the reaction was stirred for 10 minutes at −10° C. The mixture was poured into 0.05N HCl (10 ml), extracted with $CH_2Cl_2$ (50 ml). The aqueous part was basified with $NaHCO_3$ (2.5%), extracted with ethyl acetate (3×25 ml), washed with water (2×10 ml), dried and evaporated. Pure product was obtained by column chromatography over silica gel eluted with 5% and 10% MeOH in $CH_2Cl_2$ in 52% yield (17 mg).

NMR ($CDCl_3$, δ): 0.98 (3H, t, J=6.6 Hz, $CH_3$ of the propyl), 1.43–1.58 (4H, m, $CH_2$ of propyl group), 1.84 (4H, br signal, $CH_2$ of pyrrolidine), 2.63 (4H, br signal, $CH_2$ of pyrrolidine, next to nitrogen), 2.69–2.77 (2H, m, $CH_2$ of the side-chain next to pyrrolidine), 3.52 (2H, q, J=5.7 Hz, $CH_2NHCO$), 5.71 (1H, dd, J=1.8, 9.6 Hz, H-1), 7.13 (1H, s, olefinic proton), 7.39 (1H, br signal, —NHCO—), 7.73–7.78 (2H, m, Ar-H) , 8.06–8.15 (2H, m, Ar—H).

Step 2: 2-hydrochloro-(N-pyrrolidinyl) ethyl-(1-propyl-5,10-dioxo-5,10-dihydro-1H-naphtho-[2,3-c]-pyran-3)-carboxamide Amine (17 mg) was dissolved in $CH_2Cl_2$ (3 ml) and filtered. It was diluted with ether (10 ml). Hydrochloric acid in ether (1M) (1 equivalent) was added. The mixture was evaporated, and redissolved in $CH_2Cl_2$ (2 ml). Hydrochloride salt was precipitated from the solution by adding ether, separated, washed with ether and dried (8 mg) (yield=43%). Mother liquor contained some hydrochloride salt.

$^1$H NMR (acetone-$d_6$, δ): 0.96 (3H, t, J=6.4 Hz, $CH_3$ of the propyl) 1.47–1.63 (4H, m, $CH_2$ of the propyl side-chain), 3.07 (2H, m,) , 3.33–3.40 (2H, m), 3.68–3.82 (4H, m), 5.69 (1H, br d, J=10.7 Hz, H-1), 6.93 (1H, s, olefinic proton), 7.89 (2H, m, Ar—H), 8.05—8.09 (2H, m, Ar—H), 8.83–8.92 (1H, m,).

EXAMPLE 79

3-N-oxo-dimethylaminopropyl-(1-methoxy-5,10-dioxo-5,10-dihydro-1H-naphtho-[2,3-c]pyran-3)-carboxamide (BCH-2877)

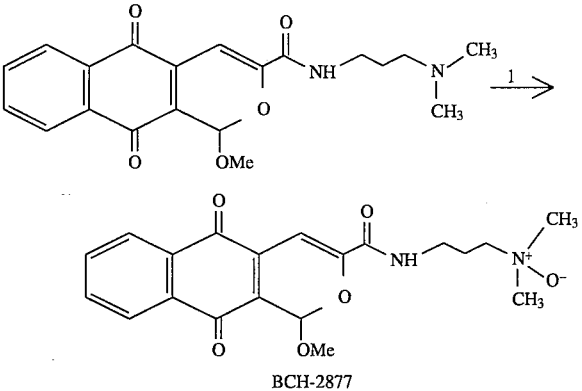

BCH-2877

To a solution of tricyclic amide (17 mg, 0.046 mmol) in $CH_2Cl_2$ (5 ml) at 0° C. was added a solution of m-chloroperbenzoic acid (8 mg, 0.046 mmol) in $CH_2Cl_2$ (1.1 ml) slowly. The mixture was stirred for 0.5 hour at 0° C.; 2.5% sodium bicarbonate (3 ml) was added. It was extracted with $CH_2Cl_2$ (3×50 ml), washed with water (10 ml), and with saturated NaCl (10 ml), dried and evaporated. NMR revealed that it contained some starting material (−33%). It was dissolved in $CH_2Cl_2$ (5 ml), cooled to 0° C.; m-choloperbenzoic acid (5 mg, 0.029 mmol) in $CH_2Cl_2$ (1 ml) was added and the mixture was stirred at 0 ° C. for 45 minutes. It was worked up in the same way as described before. NMR showed disappearance of starting material. Pure N-oxide was obtained by column chromatography over a small column of silica gel eluted with 20% methanol in $CH_2Cl_2$ (yield=5 mg, 28%).

NMR ($CDCL_3$, δ): 2.19–2.29 (2H, m, $CH_2$ of the side-chain), 3.26 (6H, s, —N(O) $(CH_3)_2$), 3.46–3.50 (2H, m, $CH_2$ of the side-chain), 3.59–3.67 (2H, m, $CH_2$ of the side-chain), 3.69 (3H, s, OCH₃), 6.42 (1H, s, H-1), 7.32 (1H, s, olefinic proton), 7.71–7.79 (2H, m, Ar—H), 8.10–8.16 (2H, m, Ar—H) , 9.47 (1H, br signal, —NHCO—).

EXAMPLE 80

2-(2-N-methyl pyrrolyl)-ethyl-(1-propyl-5,10-dioxo-5,10-dihydro-1H-naphtho-[2,3-c]-pyran-3)-carboxamide (BCG-2876)

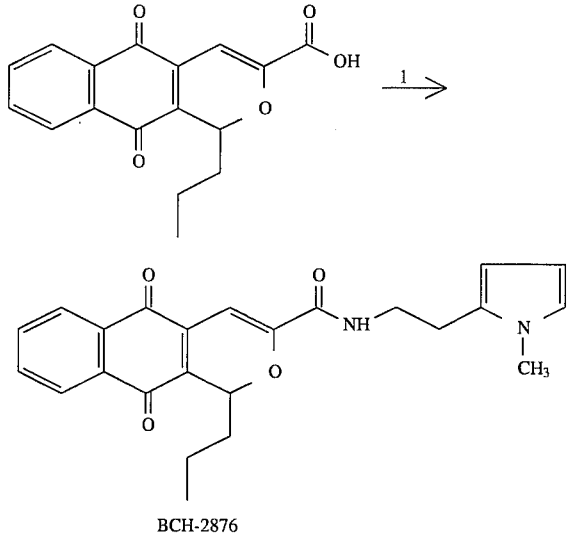

BCH-2876

To a cold solution of tricyclic carboxylic acid (25 mg, 0.084 mmol) in dry THF (1 ml) at −15° C. was added N-methyl morpholine (9.2 µl, 0.084 mmol) in THF (0.1 ml) followed by addition of isobutyl chloroformate (10.9 µl, 0.084 mmol) in THF (0.1 ml). The mixture was stirred at −15° C. for 15 minutes. 2-(2-Amino ethyl)-1-methyl pyrrole (10.41 mg, 0.084 mmol) in THF (0.6 ml) was added. After 10 minutes the mixture was diluted with ethyl acetate (50 ml), acidified with 0.1N HCl. Water was added and the organic layer was separated, washed with 2.5% NaHCO₃ (5 ml), water and saturated NaCl solution, dried and evaporated. Pure product was obtained by passing through a column of silica gel eluted with 2% and 5% methanol in CH₂Cl₂ (yield=29 mg, 85%).

NMR (CDCl₃, δ): 0.97 (3t, J=6.8 Hz, CH₃ of the propyl side-chain), 1.41–1.52 (4H, m, CH₂ of the propyl side-chain), 2.87 (2H, t, J=6.7 Hz, CH₂ of the side-chain), 3.57–3.67 (5H, a sharp singlet in the middle of a multiplet, N—CH₃ and CH₂ of the side-chain), 5.67 (1H, dd, J=2.6, 10.3 Hz, H-1), 5.96 (1H, br singlet, pyrrole-H), 6.08 (1H, t, J=2.9 Hz, pyrrole-H) , 6.60 (1H, br singlet, pyrrole-H) , 6.87 (1H, ill-resolved triplet, —NHCO—) , 7.14 (1H, s, olefinic proton), 7.73–7.78 (2H, m, Ar—H), 8.06–8.15 (2H, m, Ar—H).

EXAMPLE 81

1-methoxy-3-(2-trimethyl ammonium ethyl amino carbonyl)-5,10-dioxo-5,10-dihydro-1H-naphtho-[2,3-c]-pyran chloride salt (BCH-2837)

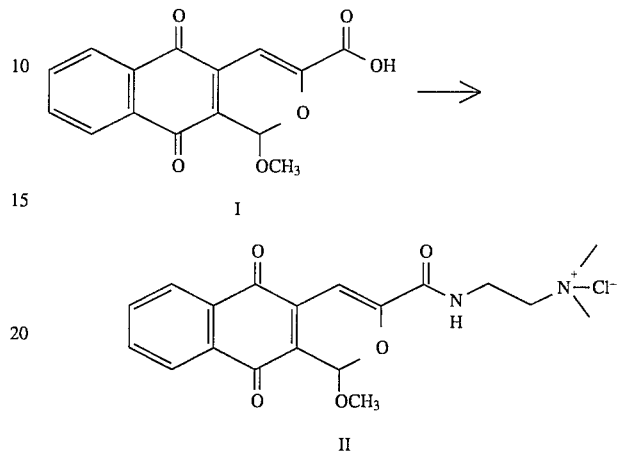

The acid I (20 mg, 0.07 mmol) in 2 ml of dichloromethane was treated with oxalyl chloride (9.2 µl, 0.105 mmol) and trace of DMF. After stirred at room temperature for 1 hour, all the solid was dissolved to give a yellow solution. The crude liquid was evaporated and the solid residue was subjected to vacuum until oxalyl chloride was entirely pumped out. The acid chloride thus obtained was redissolved in THF. After chilled to −10° C., (2-aminoethyl)-trimethyl ammonium chloride hydrochloride (12.3 mg, 0.07 mmol) was added. This was followed by addition of diisopropyl ethyl amine (24.4 µl, 0.14 mmol). After 20 minutes, the solvent was evaporated. The crude product wetted with dichloromethane was filtered. The filtrate was concentrated to give a product which can be further purified on RP-8 silica gel. Yield 70%.

¹H NMR (CDCl₃, 250 MHz, Bruker), δ: 1.39 (9H, br s, 3×CH₃), 3.14 [2H, m, CH₂N(CH₃)₃], 3.62 (3H, s, OCH₃), 3.74 (2H, m, NHCH₂), 6.40 (1H, s, 1-H), 7.20 (1H, s, 4-H), 7.71 (2H, m, 7, 8-ArH), 8.10 (2H, m, 6, 9-ArH). IR (Nicolet, 205 FT, film on NaCl plate): cm⁻¹, 3415.5, 2991.0, 2929.3, 2832.8, 2693.9, 2508.7, 1671.7, 1655.9, 1598.0, 1563.3, 1339.6, 1324.1, 1300.9, 1067.0, 989.6, 954.5, 864.4, 722.9.

EXAMPLE 82

1-methoxy-3-(3-S-methyl mercapto propyl amino carbonyl)-5,10-dihydro-5,10-dioxo-1H-naphtho-[2,3-c]-pyran (BCH-2831)

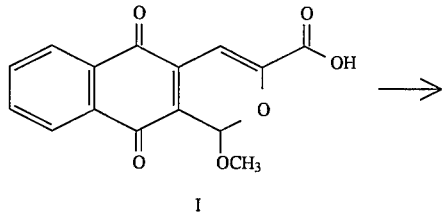

277
-continued

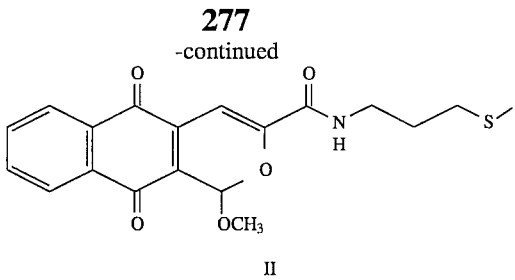

II

The compounds were prepared using a similar process as described in Example 79.

I: 40 mg, 0.140 mmol Oxalyl chloride: 18.4 μl, 0.205 mmol Diisopropyl ethylamine: 24.4 μl 3-methyl mercapto propyl amine trifluoroacetate: 25.75 mg, 0.140 mmol II: 34 mg, 65%

$^1$H NMR (CDCl$_3$, 250 MHz, Bruker), δ: 1.93 (2H, quin, J=6.7 Hz, CH$_2$—C—N), 2.11 (3H, s, SCH$_3$), 2.57 (2H, tr, J=6.1 Hz, CH$_2$S), 3.54 (2H, m, CONHCH$_2$), 3.62 (3H, s, OCH$_3$), 6.37 (1H, s, 1-H), 7.03 (1H, tr, J=6.1 Hz, 4-H), 7.75 (2H, m, 7, 8 -ArH), 8.12 (2H, m, 6, 9-ArH).

EXAMPLE 83

1-methoxy-3-(2-pyrrolidinoethylcarbonyl)-5,10-dioxo-5,10-dihydro-1H-naphtho-[2,3-c]pyran

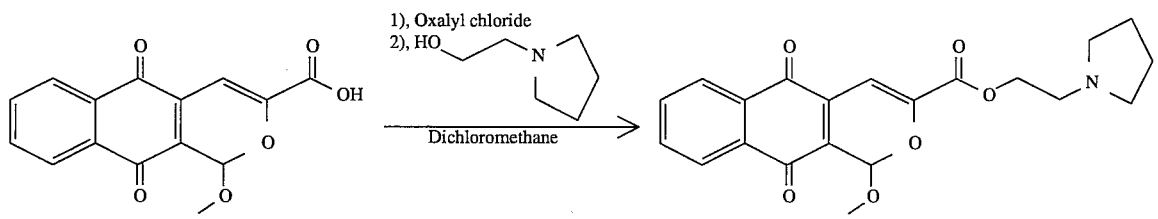

Using a similar procedure as described in EXAMPLE 16, step 7, the titled compound was prepared.

$^1$H NMR (CDCl$_3$, 300 MHz, Bruker), δ: 1.87 (4H, broad, pyrr-CH$_2$), 2.73 (4H, broad, pyrr-NCH$_2$), 2.95 (3H, t, J=5.9 Hz, CH$_2$N), 3.66 (3H, s, OCH$_3$), 4.52 (2H, t, J=5.9 Hz, OCH$_2$), 6.40 (1H, s, 1-H), 7.28 (1H, s, 4-H), 7.79 (2H, m, Ar-H), 8.15 (2H, m, Ar-H).

EXAMPLE 84

1-methoxy-3-(2-pyrrolidinoethylcarbonyl)-5,10-dioxo-5,10-dihydro-1H-naphtho-[2,3-c]pyran hydrochloride (BCH-2854)

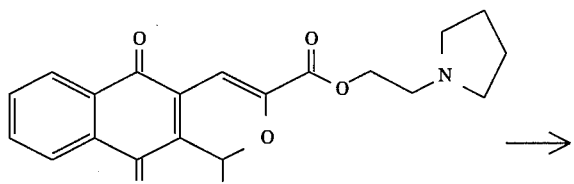

278
-continued

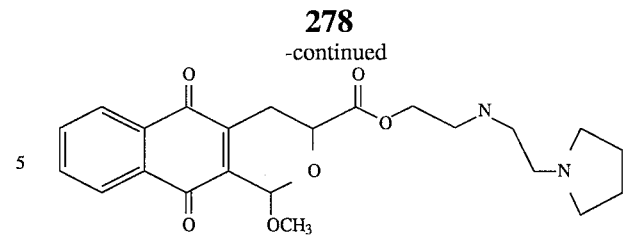

Preparative details: See EXAMPLE 16, step 8.

$^1$H NMR (DMSO-d$_6$, 300 MHz, Bruker), δ: 2.11 (2H, broad, pyrr-CH$_2$), 2.84 (2H, broad, pyrr-CH$_2$), 3.19 (2H, broad, pyrr-NCH$_2$), 3.61 (3H, s, OCH$_3$), 3.66 (2H, broad, CH$_2$N), 3.75 (2H, broad, pyrr-NCH$_2$), 4.87 (2H, broad, OCH$_2$), 6.40 (1H, s, 1-H), 7.28 (1H, s, 4-H), 7.94 (2H, m, Ar-H), 8.12 (2 m, Ar-H), 10.45 (1H, broad, NH$^+$).

IR (Nicolet 205 FT, film on NaCl plate) cm$^{-1}$: 2951, 2930, 2845, 2361, 2345, 1234, 1665, 1660, 1585, 1564, 1453, 1384, 1330, 1299, 1267, 1240, 1144, 1075, 953, 862.

EXAMPLE 85

1-methoxy-3-[N-(2-dimethyl amino) ethyl-N-methyl amino carbonyl]-5,10-dioxo-5,10-dihydro-1H-naphtho-[2,3-c]-pyran

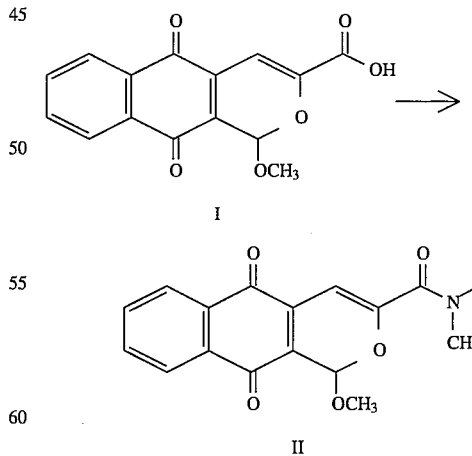

Preparative details: See EXAMPLE 16, step 7.

I: 20 mg, 0.070 mmol Oxalyl chloride: 9.2 μl, 0.105 mmol N,N,N'-trimethyl ethylene diamine: 10.1 μl, 0.077 mmol II: 27 mg ¹H NMR (CDCl₃, 250 MHz, Bruker), δ: 2.25 (6H, br s N(CH₃)₂), 2.52 [2H, br tr, J=5.9 Hz, CH₂N(Me)₂], 3.09 (3H, br s, CONCH₃), 3.54 (2H, br m, CONCH₂), 3.64 (3H, s, OCH₃), 6.36 (1H, s, 1-H) , 6.67 (1H, s, 4-H), 7.74 (2H, m, 7, 8 -ArH), 8.10 (2H, m, 6, 9-ArH).

IR (Nicolet, 205 FT, film on NaCl plate): cm⁻¹, 2937.0, 2771.1, 1676.7, 1648.2, 1595.6, 1565.9, 1300.8, 1108.7, 1054.6, 949.16, 839.44, 801.92, 722.25.

EXAMPLE 86

1-methoxy-3-[N-(2-dimethyl amino) ethyl-N-methyl amino carbonyl]-5,10-dioxo-5,10-dihydro-1H-naphtho-[2,3-c]-pyran (BCH-2847)

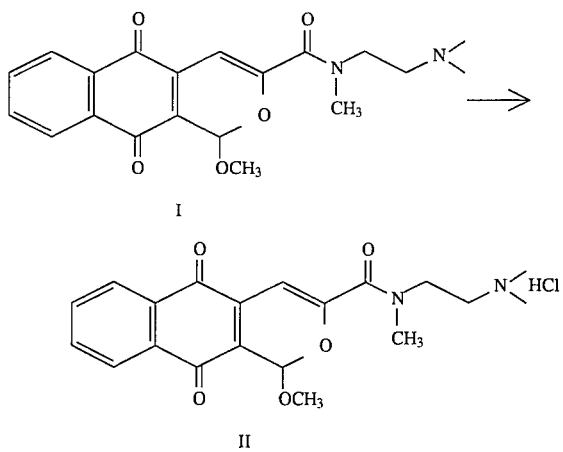

Preparative details: See EXAMPLE 16, step 8.
I: 22.9 mg, 0.062 mmol HCl in ether: 1 eq. II: 22.9 mg
¹H NMR (Acetone-d₆, 300 MHz, Bruker), δ: 2.23 (6H, br s, N(CH₃)₂), 2.56 (2H, tr, J=5.4 Hz, CH₂N(CH₃)₂), 3.07 (3H, br, CONCH₃), 3.58 (2H, m, CONCH₃CH₂), 3.65 (3H, s, OCH₃), 6.40 (1H, s, 1-H), 6.54 (1H, s, 4-H), 7.91 (2H, m, 7, 8-ArH), 8.11 (2H, m, 6, 9-ArH).

IR (Nicolet, 205 FT, film on NaCl plate): cm⁻¹, 2942.4, 2768.2, 1677.5 1643.2, 1597.5, 1571.8, 1297.7, 1109.3, 1057.9, 1080.7, 946.5, 861.9, 721.99.

EXAMPLE 87

1-Methoxy-3[2-(N-pyrrolidinylethoxylcarbonyl)]-5,10-dioxo-5,10-dihydro-1H-naphtho-[2,3-c]-pyran (BCH-2861)

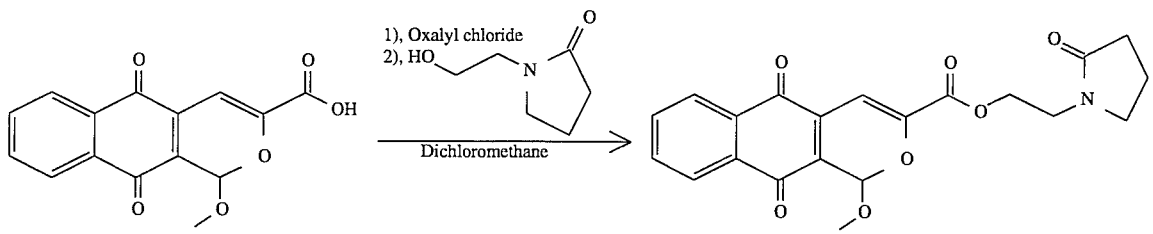

Using a similar procedure as described in step 7, example 2, the carboxylic acid from step 6, EXAMPLE 16, was converted to the titled compound.

¹HNMR (300MHz, Bruker, CDCl₃) δ: 2.08 (2H, m, pyrr-CH₂), 2.42 (2H, t, J=8.09 Hz, pyrr-COCH₂), 3.56 (2H, t, J=7.05 Hz, pyrr-NCH₂), 3.66 (3H, s, OCH₃), 3.68 (2H, m, CH₂N), 4.47 (2H, m, OCH₂), 6.40 (1H, s, 1-H), 7.34 (1H, s, 4-H), 7.79 (2H, m, Ar-H), 8.15 (2H, m, Ar-H).

IR (Nicolet 205 FT, film on NaCl plate) cm⁻¹: 2959, 2932, 2863, 1733, 1677, 1659, 1594, 1565, 1497, 1461, 1393, 1337, 1287, 1267, 1236, 1139, 1069, 990, 860, 798, 769, 743, 720.

EXAMPLE 88

1-methoxy-5,10-dioxo-5,10-dihydro-1H-naphtho [2,3-c] thiine-3-[N-(3-dimethylaminopropyl) carboxamide] (BCH-2878)

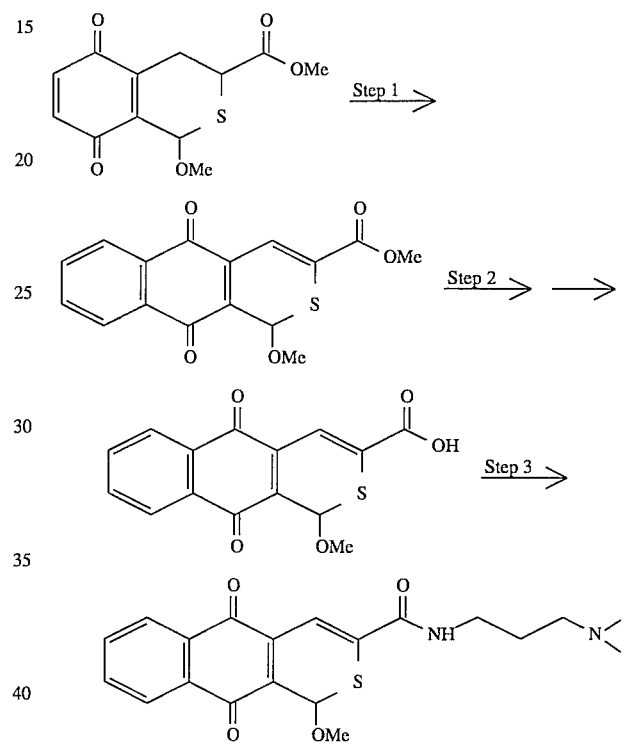

Step 1: Methyl-1-methoxy-5,10-dioxo-3,4,5,10-tetrahydro-1H-naphtho[2,3-c] thiine-3-carboxylate Methyl-1-methoxy-5,8-dioxo-5,8-dihydro-3-isothiocromane (1.14 g, 4.25 mmol), 1-acetoxybutadiene (lg, 8.92 mmol) and dry toluene (10 ml) was stirred for 14 hours at room temperature. The solvent was removed under reduced pressure, the residue was dissolved in CH₂Cl₂ (20 ml) and thiethylamine (1 ml, 7.22 mmol). The reaction mixture was stirred for 3 hours at room temperature. The solvents were removed under reduced pressure, the residue was dissolved in CH₂Cl₂ (20 ml), triphenylphosphine (1.1 g, 4.2 mmol) was added. The reaction mixture was stirred at room temperature for 14 hours. The product was isolated by flash chromatography (toluene:ethylacetate, 50:1), 0.77 g (56.6% of the product was obtained).

$^1$H NMR (300 MHz, Bruker, CDCl$_3$), δ: 3.40 (3H, s, 1-MeO), 3.95 (3H, s, COOMe), 6.12 (1H, s, 1-H), 7.28 (2H, m, Ar-H), 8.16 (2H, m, Ar-H), 8.27 (1H, s, 4H).

Step 2: 1-methoxy-5,10-dioxo-5,10-dihydro-1H-naphtho [2,3-c] thiine-3-carboxylic acid Methyl 1-methoxy-5,10-dioxo-5,10-dihydro-1H-naphtho [2,3-c] thiine-3-carboxylate (106 mg, 0.33 mmol) was dissolved in THF (2 ml). 1.75M solution of sodium hydroxide (0.32 mg, 0.55 mmol) was added dropwise at 0° C. followed by water (0.5 ml). The reaction mixture was stirred at 0° C. for 3 hours, then water (10 ml) was added, and the reaction mixture was acidified to pH=3 with 5% hydrochloric acid. After that, the reaction mixture was extracted with dichloromethane (5×5 ml). Organic fractions were evaporated to dryness. The residue 98 mg (crude) was used in the next step.

Step 3: 1-methoxy-5,10-dioxo-5,10-dihydro-1H-naphtho [2,3-c] thiine-3[N-(3-dimethylaminopropyl) carboxamide]

1-methoxy-5,6-dioxo-5,10-dihydro-1H-naphtho [2,3-c] thiine-3-carboxylic acid (55 mg, 0.18 mmol) was dissolved in THF (2 ml). DMF (1 drop) was added. The reaction mixture was cooled to 0° C. and 2M solution of oxalyl chloride in dichloromethane (0.18 ml, 0.36 mmol) was added dropwise. The reaction mixture was stirred at 0° C. for 0.5 hour, then evaporated to dryness at reduced pressure. The residue was dissolved in THF (2 ml), cooled to 0° C. and N,N-dimethylaminopropylamine (20 μl, 0.2 mmol) was added dropwise. The reaction mixture was stirred for 0.5 hour, then saturated solution of sodium carbonate (3 ml) was added, and organics were extracted by dichloromethane (3×5 ml). Dichloromethane solution was dried over MgSo$_4$, evaporated to dryness and the title product (25 mg, 35%) was isolated by thin layer chromatography (MeOH).

$^1$H NMR (300 MHz, Brucker, CD$_2$Cl$_2$), δ: 1.74 (2H, quint, CH$_2$), 2.36 (6H, s, NMe$_2$), 2.54 (2H, t, CH$_2$), 3.39 (s, 3H, OMe), 3.54 (2H, quint, CH$_2$), 6.14 (1H, s, 1-H), 7.75 (2H, m. Ar-H), 7.91 (1H, s, 4H), 8.14 (2H, m, Ar—H), 9.42 (1H, broad, NH).

EXAMPLE 89

(1'S) Methyl (5,10-dioxo-1-(2',3',4',6'-tetradeoxy-3',4'-diacetoxy-L-lyxohexopyranose-5,10-dihydro-1H-naphtho[2,3-c]thiopyran-3-yl) ketone (BCH-2879)

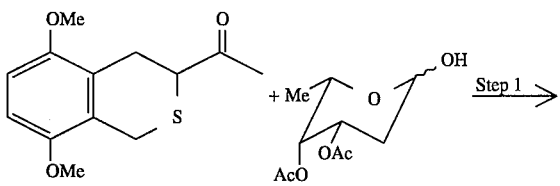

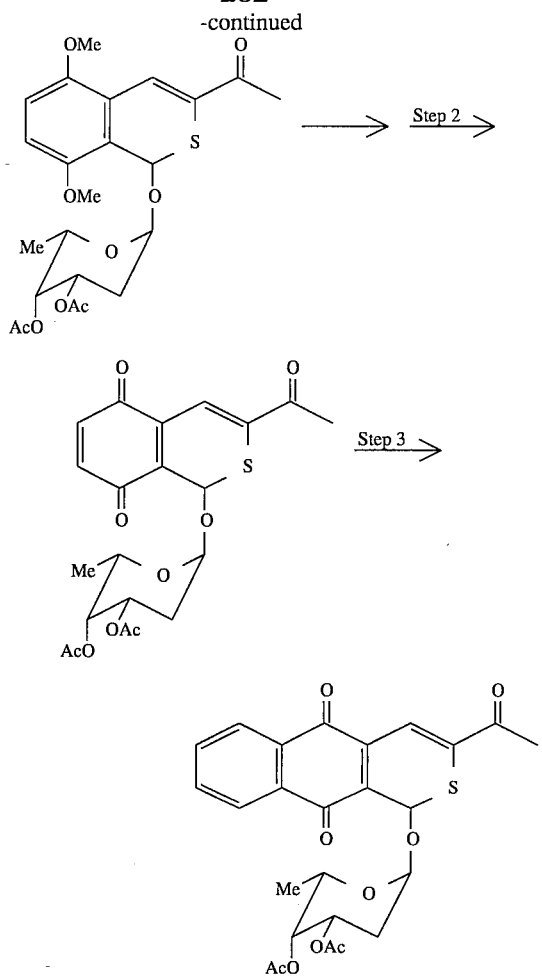

Step 1: (1'S) Methyl (5,8-dimethoxy-1-(2',3',4',6'-tetradeoxy-3',4'-diacetoxy-L-lyxohexopyranose)-1H-benzo[2,3-c]thiopyran-3-yl) ketone A mixture of 3-acetyl-5,8-dimetoxythioisochromane (2.52 g, 10.00 mmol), 3,4-di-O-acetyl-2,6-dideoxy-L-lyxohexopyranose (sugar) (2.79 g, 12.00 mmol) and diciano dichloro benzoquinone (DDQ) (2.72 g, 12.00 mmol) in dichloromethane (30 ml) was stirred for 4 hours at ambient temperature, then more sugar (1.00 g, 4.31 mmol) and DDQ (1.00 g, 4.41 mmol) were added.

The reaction mixture was stirred overnight, then saturated NaHCO$_3$ solution (10 ml) was added. The solids were filtered, the organic phase of the filtrate was washed with NaHCO$_3$ solution (10 ml), dried (MgSO$_4$) and evaporated to dryness. The residue was flash chromatographed on silica (hexane/CH$_2$Cl$_2$/EtOAc, 5/9/1) to give the title product (1.16 g, 21.1%).

$^1$H NMR (CDCl$_3$), δ: 1.20 (d, 3H, 6.5 Hz), 1.58 (dd, 1H, 4.9 Hz, 29.2 Hz), 1.91 (s, 3H), 2.03 (td, 1H, 3.3 Hz, 29.2 Hz), 2.16 (s, 3H), 2.59 (s, 3H), 3.87 (s, 3H), 3.91 (s, 3H), 4.17 (q, 1H, 6.5 Hz), 4.98 (m, 1H), 5.11 (s, 1H, broad), 5.60 (d, 1H, 2.0 Hz), 6.55 (s, 1H), 6.92 (d, 1H, 8.8 Hz), 7.04 (d, 1H, 8.8 Hz), 8.29 (s, 1H).

Step 2: (1'S) Methyl (5,8-dioxo-1-(2',3',4',6'-tetradeoxy-3',4'-diacetoxy-L-lyxohexopyranose)-5,8-dihydro-1H-benzo [2,3-c]thiopyran-3-yl) ketone To a stirred solution of the thioisochromane glycoside from Step 1 (0.50 g, 1.04 mmol) was added a solution of CAN (1.71 g, 3.12 mmol) and NaHCO$_3$ (0.17 g, 2.08 mmol) in water, dropwise at 0° C. The reaction mixture was stirred at 0° C. for 1 hour, then it was extracted with dichloromethane (4×5 ml). The combined organic layers were washed with saturated NaHCO₃ solution, dried (MgSO₄) and concentrated to dryness. The crude product (0.50 g, 100%) was used for the next step without purification.

¹H NMR (CDCl₃), δ: 1.27 (d,3 H, 6.4 Hz), 1.59 (dd, 1H, 5.1 Hz, 12.8 Hz), 1.94 (s, 3H), 2.05 (td, 1H, 4.1 Hz, 12.8 Hz), 2.16 (s, 3H), 2.62 (s, 3H), 3.92 (q, 1H, 6.4 Hz), 4.98 (m, 1H), 5.10 (s, 1H, broad), 5.54 (d, 1H, 3.3 Hz), 6.41 (s, 1H), 6.98 (s, 2H).

Step 3: (1'S) Methyl (5,10-dioxo-1-(2',3',4',6'-tetradeoxy-3',4'-diacetoxyl-L-lyxohexopyranose-5,10 -dihydro-1H-naphtho[2,3 -c]thiopyran-3-yl) ketone (BCH-2879)

The solution of benzo [2,3-c] thiopyrane glycoside from Step 2 (0.10 g, 0.22 mmol) and 1-acetoxy-1,3-butadiene (0.05 g, 0.44 mmol) in toluene (1 ml) was left to stand ovens 3 days at ambient temperature, then it was flash chromatographed on silica (hexane/EtOAc, 7/3) to give the title compound (0.073 g, 66.3%).

¹H NMR (CDCl₃), δ: 1.29 (d, 3H, 6.4 Hz), 1.61 (dd, 1H, 3.3 Hz, 12.8 Hz), 1.92 (s, 3H), 2.06 (td, 1H, 3.6 Hz, 12.8 Hz), 2.17 (s, 3H), 2.66 (s, 3H), 4.02 (q, 1H, 6.4 Hz), 5.00 (m, 1H), 5.09 (s, 1H, broad), 5.58 (d, 1H, 3.3 Hz), 6.65 (s, 1H), 7.81–7.88 (m, 2H), 8.20 (s, 1H), 8.20–8.27 (m, 2H).

EXAMPLE 90

N, N'-bis{1-Methoxy-5,10-dihydro-5,10-dioxo-1H-naphtho-[2,3-c]-pyran-3-carbonyl}-propyldiamine

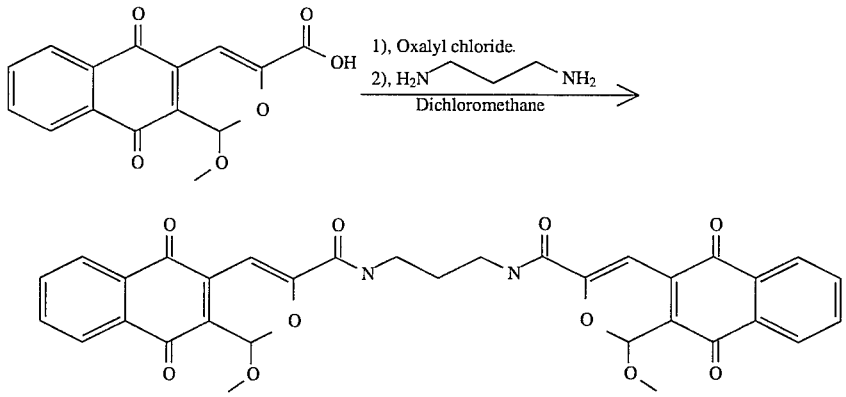

Using a similar procedure as described in EXAMPLE 16 step 7 the carboxylic acid from step 6, EXAMPLE 16, was converted to the titled compound. The title compound is a mixture of three isomers.

¹HNMR (300 MHz, Bruker, CDCl₃) δ: 1.85 (2H, m, —CH₂), 3.55 (4H, m, —NCH₂ and CH₂N), 3.69 (3H, s, OCH₃), 3.71 (3H, s, OCH₃), 6.42 (1H, s, 1-H), 6.44 (1H, s, 1-H), 7.36 (1H, s 4-H), 7.38 (1H, s, 4-H), 7.48 (2H, m, NH), 7.72 (4H, m, Ar—H and Ar—H'), 8.14 (4H, m, Ar—H and Ar—H').

IR (Nicolet 205 FT, film on NaCl plate) cm⁻¹: 3339, 2935, 2843, 1679, 1655, 1592, 1517, 1404, 1381, 1334, 1278, 1202, 1093, 954, 865, 796, 721.

EXAMPLE 91

N-Methyl-N, N'-bis{1-Methoxy-5,10-dihydro-5,10-dioxo-1H-naphtho-[2,3-c]-pyran-3-carbonyl}propyldiamine

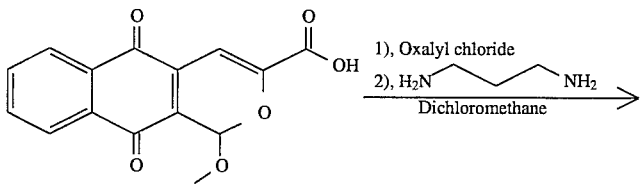

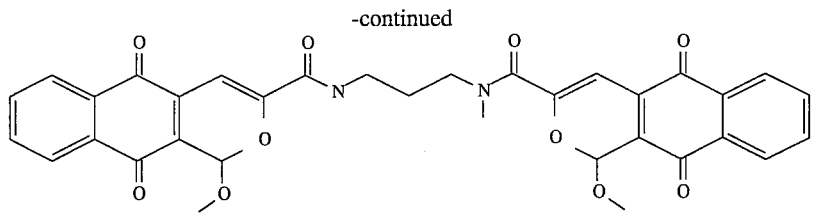
-continued

Using a similar procedure as described in step 7, EXAMPLE 16, the carboxylic acid from step 6, EXAMPLE 16, was converted to the titled compound. The title compound is a mixture of four isomers.

¹HNMR (300MHz, Bruker, CDCl₃) δ: 1.92 (2H, m, —CH₂—), 3.15 (3H, s, —NCH₃), 3.5 (4H, m, NCH₂ and CH₂N), 3.61 (3H, s, OCH₃), 3.72 (3H, s, OCH₃), 6.39 (1H, s, 1-H), 6.44 (1H, s, 1-H'), 6.71 (1H, s, 4-H), 7.36 (1H, s, 4-H'), 7.75 (4H, m, Ar—H and Ar—H'), 8.0 (1H, broad, NH), 8.25 (4H, m, Ar—H and Ar—H').

IR (Nicolet 205 FT, film on NaCl plate) cm⁻¹: 3341, 2936, 2833, 1675, 1656, 1597, 1570, 1520, 1450, 1411, 1383, 1330, 1276, 1199, 1121, 1083, 1057, 987, 946, 915, 863, 794, 722.

EXAMPLE 92

N-Boc-N-{1-methoxy-5,10-dihydro-5,10-dioxo-1H-naphtho-[2,3-c]-pyran-3-carbonyl}-propyldiamine (BCH-2881)

N-Boc-propyldiamine was prepared according to a procedure described by W. S. Saari, J. E. Schwering, P. A. Lyle, S. J. Smith and E. L. Engelhardt, J. Med. Chem. 1990, 33, 97–101.

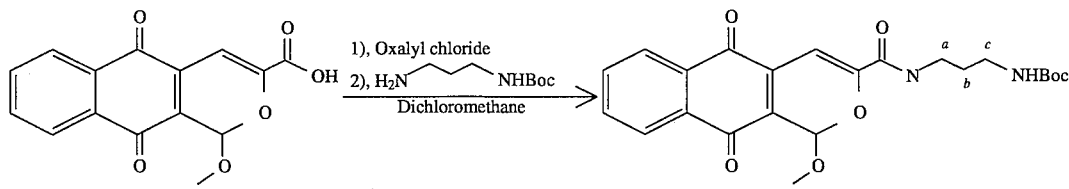

Using a similar procedure as described in step 7, EXAMPLE 16, the carboxylic acid from step 6, EXAMPLE 16, was converted to the titled compound.

¹HNMR (300 MHz, Bruker, CDCl₃) δ: 1.46 (9H, s, —Boc), 1.72 (2H, m, H_b), 3.28 (2H, m, H_c), 3.42 (1H, m, H_a), 3.52 (1H, m, H_a'), 3.69 (3H, s, OCH₃), 4.88 (1H, broad, NHBoc), 6.42 (1H, s, 1-H), 7.34 (1H, s, 4-H), 7.75 (2H, m, Ar—H), 7.84 (1H, broad, NH), 8.14 (2H, m, Ar—H).

IR (Nicolet 205 FT, film on NaCl plate) cm⁻¹: 3339, 2973, 2934, 1679, 1659, 1603, 1522, 1451, 1365, 1335, 1276, 1170, 1083, 950, 864, 796, 720.

EXAMPLE 93

2,5-Dimethoxybenzylbromide

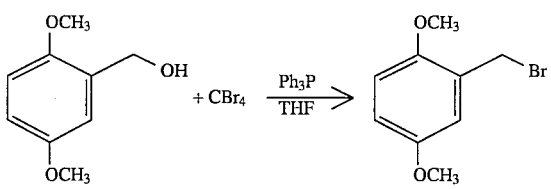

Carbon tetrabromide (0.47 g, 1.25 mmol) and triphenylphosphine (0.47 g, 1.25 mmol) were added to a solution of 2,5-dimethoxylbenzylalcohol (0.2 g, 1.19 mmol) in THF (10 ml) at room temperature. The mixture was stirred for two hours to form a precipitate which the preciptate was filtered off. The filtrate was evaprated and the crude product was chromatographed (ethyl acetate and hexane 7:3). The desired compound was isolated as a white solid (0.25 g, 93%).

¹HNMR (300 MHz, Bruker, CDCL₃) δ: 3.79 (3H, s, OCH₃), 3.87 (3H, s, OCH₃), 4.55 (2H, s, CH₂), 6.83 (2H, q, Ar—H), 6.90 (1H, s, Ar—H).

EXAMPLE 94

Methyl 3-(2' 5'-dimethoxy) phenyl-2-hydroxy propionate

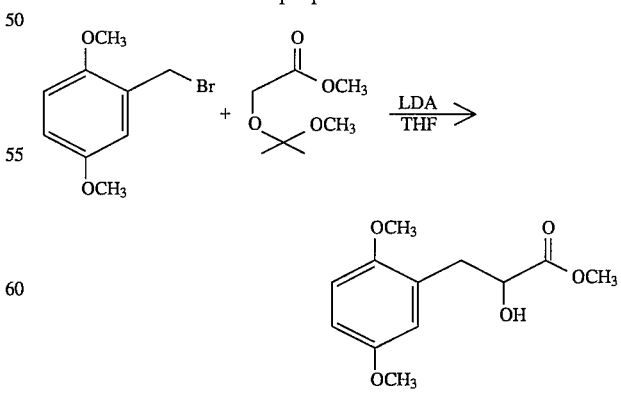

BuLi (1.96 mmol) was adde to a solution of diisopropylamine (1.96 mmol) in dry THF (15ml) at −78° C. The mixture was then warmed to 0° C. and stirred for 30 minutes. Then the mixture was recooled to −78° C., and methyl-2-methoxyisopropyloxy-acetate (0.3 g, 1.96 mmol) in THF (2 ml) was added. After 15 minutes, 2,5-dimethoxybenzylbromide (0.19 g, 0.83 mmol) was added dropwise, this was followed by addition of HMPA (0.2ml). The reaction mixture was stirred for another hour, then warmed to room temperature. Saturated NH₄Cl (5ml) was added, PH was adjusted to 2 using conc. HCl. After 1 hr, the mixture was extracted with ethyl acetate, the solvent was dried and evaporated. The pure titled compound was obtained as an oil (purification by chromatography with ethyl acetate and hexane 3:7).

¹HNMR (300 MHz, Bruker, CDCl₃) δ: 3.0 (2H, m, CH₂), 3.73 (6H, s, Ar—OCH₃), 3.77 (3H, s, OCH₃), 4.46 (1H, m, CH₂), 6.76 (3H, m, Ar—H).

EXAMPLE 95

3-methoxycarbonyl-3,4-didehydro-5,8-dimethoxy isochroman

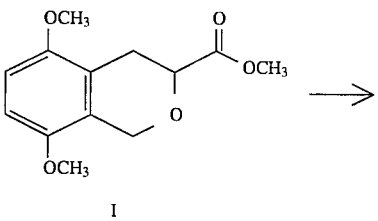

I

II

To a freshly prepared lithium diisopropylamide (diisopropylamine, 123.2 μl, 0.873 mmol, n-butyllithium, 2.5M in hexane 0.35 ml, 0.873 mmol) at −78° C. was added a solution of isochroman I (198 mg, 0.794 mmol). The mixture was stirred for 30 minutes. Hexamethyl phosphoramide (151.9 μl, 0.873 mmol) was added. It was followed by the addition of phenyl selenyl chloride in THF (167.2 mg, 0.873 mmol). The reaction mixture was stirred for 1 hour at −78° C. The reaction was quenched with NH₄Cl (sat). The organic layer was evaporated to give the selenyl product which was redissolved in dichloromethane. Following this, pyridine (148 μl) and 30% hydrogen peroxide (207.8 μl, 1.83 ml) was added in sequence. The mixture was vigorously stirred for 30 minutes at room temperature then washed with NaHSO₃ and extracted with dichloromethane. After evaporation of the solvent, the crude product was chromatographed to give desired product (impured with little amount of I) in 50% yield (97 mg).

¹H NMR (300 MHz, Bruker, CDCl₃), δ: 3.78 (3H, s, OCH₃), 3.81 (3H, s, OCH₃), 3.86 (3H, s, OCH₃), 5.24 (2H, s, 1-H), 6.71 (1H, d, J=6.9 Hz), 6.78 (1H, d, J=6.9 Hz), 7.22 (1H, s, 4-H).

EXAMPLE 96

1-methoxy-3-methoxycarbonyl-3,4-didehydro-5,8-dimethoxy isochroman

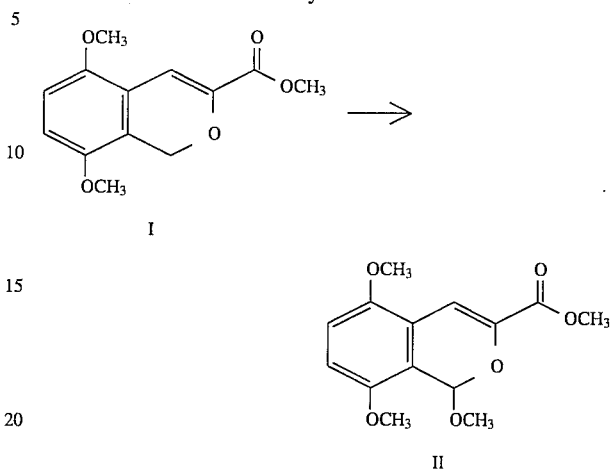

At room temperature, a mixture of isochroman I (48 mg, 0.192 mmol), as described in example 95, dichlorodicyanoquinone (56.7 mg, 0.249 mmol) and methanol (0.3 ml) was stirred in dichloromethane (5 ml) for 10 minutes. It was then poured to NaHCO₃ (sat.) and extracted with dichloromethane. The desired product was obtained in 68% yield (37 mg).

¹H NMR (300 MHz, Bruker, CDCl₃), δ: 3.59 (3H, s, 1-OCH₃), 3.83 (6H, s, 2×OCH₃), 3.89 (3H, s, OCH₃), 6.31 (1H, s, 1-H), 6.85 (2H, m, 6, 7-ArH), 7.45 (1H, s, 4-H).

EXAMPLE 97

1-methoxy-3-methoxycarbonyl-5,8-dioxo-1H-benzo-[2,3-c]-pyran

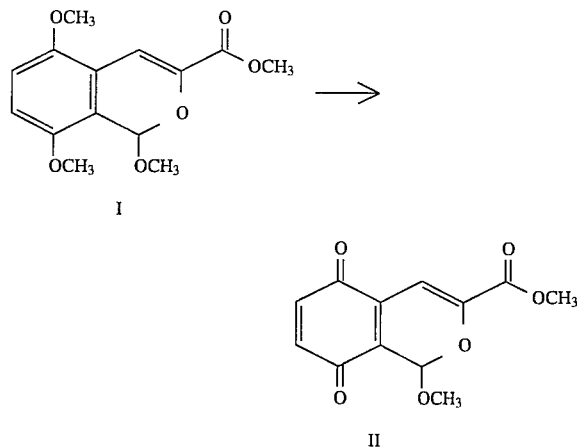

At room temperature, compound I (17 mg, 0.061 mmol) in acetonitrile (4 ml) as described in example 96, was oxidized by ammonium cerium nitrate (100 mg, 0.182 mmol) dissolved in 1 ml of water. After dichloromethane extraction and evaporation of the solvent, the desired compound was obtained (12 mg, 79%).

¹H NMR (300 MHz, Bruker, CDCl₃), δ: 3.62 (3H, s, OCH₃), 3.93 (3H, s, OCH₃), 6.21 (1H, s, 1-H), 6.85 (2H, br, s, 6, 7-ArH), 7.15 (1H, s, 4-H).

EXAMPLE 98

1-methoxy-3-methoxycarbonyl-5,8-dihydro-5,10-dioxo-naphtho-1H-[2,3-c]-pyran (BCH-2160)

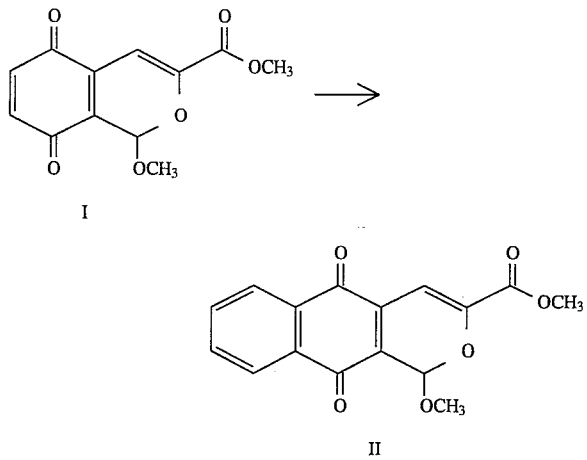

A sample of I (12 mg, 0.048 mmol), as described in example 97, dissolved in toluene (4 ml), was heated to 50° C. with 1-acetoxy-1,3-butadiene (34 µl, 0.288 mmol) for 18 hours. Solvent was evaporated and the crude product was chromatographed (v/v, Tol/EtOAc, 100/15) to give desired product (4 mg, 28%).

$^1$H NMR (300 MHz, Bruker, CDCl$_3$), δ: 3.67 (3H, s, OCH$_3$), 3.95 (3H, s, OCH$_3$), 6.41 (1H, s, 1-H), 7.37 (1H, s, 4-H), 7.81 (2H, m, 7, 8-ArH), 8.16 (2H, m, 6, 9-ArH).

EXAMPLE 99

1-hydroxy-3-methoxycarbonyl-3,4-didehydro-5,8-dimethoxy isochroman

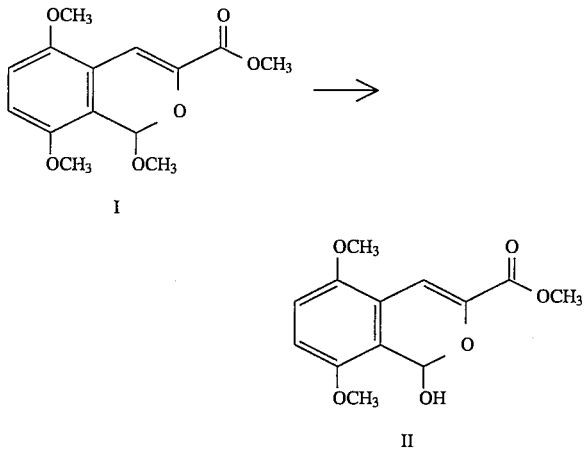

Compound I (8 mg, 0.028 mmol), as described in example 96, was stirred with para-toluene sulfonic acid (catalytic amount) in the solvent of water and acetone (1 ml/3 ml) for 17 hours at room temperature. After work-up (H$_2$O-EtOAc), the desired product was obtained (5 mg, 65%).

$^1$H NMR (300 MHz, Bruker, CDCl$_3$), δ: 3.40 (1H, bs, OH), 3.86 (6H, s, 2×OCH$_3$), 3.90 (3H, s, OCH$_3$), 6.79 (1H, s, 1-H), 6.87 (2H, m, ArH), 7.46 (1H, s, 4-H).

We claim:
1. A process for the preparation of a tricyclic compound of formula (1) and pharmaceutically acceptable acid addition salts thereof,

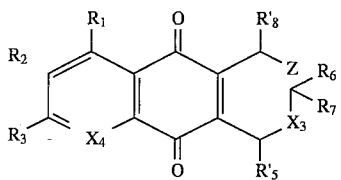

wherein;

$X_3$ is selected from the group consisting of O; S; and SO$_2$;

$X_4$ is selected from the group consisting of C—Q; nitrogen; and NO;

z is a single or a double bond with the proviso that if z is a double bond only one of $R_6$ or $R_7$ is present;

$R_1$, $R_2$, $R_3$ and Q are each independently selected from the group consisting of hydrogen; hydroxy; CN; NO$_2$; $C_{1-16}$alkyl; $C_{1-16}$alkenyl; $C_{1-16}$alkynyl; $C_{1-16}$alkoxy; $C_{6-16}$aryl; $C_{7-16}$aralkyl; $C_{6-16}$aryloxy; $C_{1-16}$alkoxyalkyl; $C_{1-16}$acyl; amine; amido; sulfono; $C_{2-16}$acyloxy; and halogen;

$R_6$ is selected from the group consisting of hydrogen; CN; NO$_2$; $C_{1-16}$alkyl; $C_{1-16}$ alkenyl; $C_{1-16}$alkynyl; $C_{1-16}$alkoxy; $C_{6-16}$aryl; $C_{7-16}$aralkyl; $C_{6-16}$aryloxy; $C_{1-16}$acyl; amine; sulfono; $C_{2-16}$ester; phosphono; and halogen;

$R_7$ is selected from the group consisting of hydrogen; hydroxy; CN; NO$_2$; $C_{1-16}$ alkyl; $C_{1-16}$alkoxy; $C_{1-16}$acyl; amine; sulfono; $C_{2-16}$ester; thiol; and halogen;

$R_5^{40}$ is selected from the group consisting of hydrogen; hydroxy; $C_{1-16}$alkyl; $C_{1-16}$ alkoxy; $C_{1-16}$acyl; amino; amido; sulfono; $C_{2-16}$ester; azole; phosphono; halogen; morpholino; and a saccharide W of formula (30):

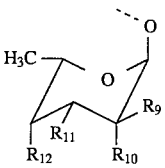

wherein:

$R_9$; $R_{10}$ are independently selected from the group consisting of hydrogen; hydroxy; —NH$_2$; $C_{1-16}$alkyl; $C_{1-16}$alkoxy; amino; amido; $C_{2-16}$ester; and halogen;

$R_{11}$ is selected from the group consisting of hydrogen; hydroxy; —NH$_2$; $C_{1-16}$ alkoxy; amino; amido; $C_{2-16}$ester sulfono;thiol; azido; and halogen; and $R_{12}$ selected from the group consisting of hydrogen; hydroxy; —NH$_2$; $C_{1-16}$alkoxy; amino; amido; $C_{1-16}$acyl;$C_{6-16}$aryl;$C_{2-16}$ester; sulfono; sahharide; and halogen;

$R_8'$ is selected from the group consisting of hydrogen; hydroxy; $C_{1-16}$alkyl; $C_{1-16}$ alkoxy; $C_{1-16}$acyl; amino; amido; sulfono; $C_{2-16}$ester; azole; phosphono; halogen; and morpholino.

said process comprising the step cycloadding a quinone of formula (2)

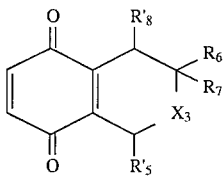

wherein $X_3$, $R_5'$, $R_6$, $R_7$ and $R_8'$ are as defined above; with a diene of formula (3a) or (3b)

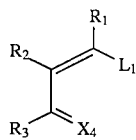

or

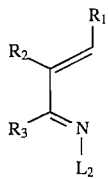

wherein $R_1$, $R_2$, $R_3$ and $X_4$ are as defined above;
 each one of $L_1$; and $L_2$ are independently a leaving group; with the proviso that z is a single bond;
 and, if z is a double bond, the compound obtained in step (1) is further air-oxidized with an organic or inorganic base or a fluoride salt (h) to yield to a tricyclic compound of formula (1).

2. A process for the preparation of an heteronaphthoquinone of formula (4) or a coupled heteronaphthoquinone of formula (8) and pharmaceutically acceptable acid addition salts thereof

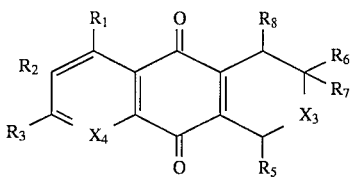

or

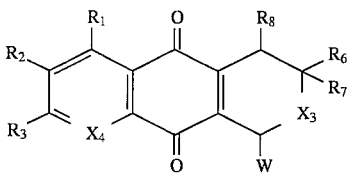

wherein;
 $X_3$ is selected from the group consisting of O; S; and $SO_2$
 $X_4$ is selected from the group consisting of C—Q; nitrogen; and NO;
 $R_1$, $R_2$, $R_3$ and Q are each independently selected from the group consisting of hydrogen; hydroxy; CN; $NO_2$; $C_{1-16}$alkyl; $C_{1-16}$alkenyl; $C_{1-16}$alkynyl; $C_{1-16}$alkoxy; $C_{6-16}$aryl; $C_{7-16}$aralkyl; $C_{6-16}$aryloxy; $C_{1-16}$alkoxyalkyl; $C_{1-16}$acyl; amino; amido; sulfono; $C_{2-16}$ester; and halogen;
 $R_6$ is selected from the group consisting of hydrogen; hydroxy; CN; $NO_2$; $C_{1-16}$alkyl; $C_{6-16}$alkenyl; $C_{1-16}$alkynyl; $C_{1-16}$alkoxy; $C_{1-16}$ aryl; $C_{7-16}$aralkyl; $C_{6-16}$aryloxy; $C_{1-16}$alkoxyalkyl; $C_{1-16}$acyl; amino; amido; sulfono; $C_{2-16}$ester; thiol; azole; phosphono; and halogen;
 $R_7$ is selected from the group consisting of hydrogen; hydroxy; CN; $NO_2$; $C_{1-16}$alkyl; $C_{1-16}$alkenyl; $C_{1-16}$alkynyl; $C_{1-16}$alkoxy; $C_{6-16}$aryl; $C_{7-16}$aralkyl; $C_{6-16}$aryloxy; $C_{1-16}$alkoxyalkyl; $C_{1-16}$acyl; amine; amido; sulfono; $C_{2-16}$ester; thiol; azole; phosphono; and halogen;
 $R_5$ is selected from the group consisting of hydrogen; hydroxy; CN; $NO_2$; $C_{1-16}$ alkyl; $C_{1-16}$alkenyl; $C_{1-16}$alkynyl; $C_{1-16}$alkoxy; $C_{6-16}$aryl; $C_{7-16}$aralkyl; $C_{7-16}$aryloxy; $C_{1-16}$alkoxyalkyl; $C_{1-16}$acyl; amino; amido; sulfono; $C_{2-16}$ester; thiol; azole; phosphono; morpholino; and halogen;
 $R_8$ is selected from the group consisting of hydrogen; hydroxy; $C_{1-16}$alkyl; $C_{1-16}$ alkenyl; $C_{1-16}$alkynyl; $C_{1-16}$alkoxy; $C_{1-16}$acyl; halogen; and $C_{2-16}$ester, and
 W is a saccharide of formula (30):

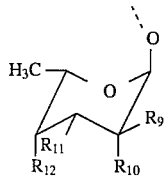

wherein;
 $R_9$; $R_{10}$ are independently selected from the group consisting of hydrogen; hydroxy; —$NH_2$; $C_{1-16}$alkyl; $C_{1-16}$alkoxy; amino; amido; $C_{2-16}$ester; and halogen;
 $R_{11}$ is selected from the group consisting of hydrogen; hydroxy; —$NH_2$; $C_{1-16}$ alkoxy; amino; amido; $C_{2-16}$ester; sulfono;thiol; azido; and halogen; and
 $R_{12}$ selected from the group consisting of hydrogen; hydroxy; —$NH_2$; $C_{1-16}$alkoxy; amino; amido; $C_{1-16}$acyl;$C_{6-16}$aryl; $C_{2-16}$ester; sulfono; sahharide; and halogen;
 said process comprising the steps of
 step 1) oxidizing a protected isochroman of formula (5) with an oxidant (a)

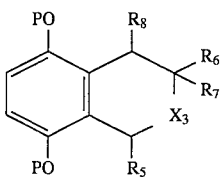

wherein;
 is an oxygen protecting group; and $R_5$, $R_6$, $R_7$, $R_8$, and $X_3$ are as defined above; to yield a dioxoisochroman compound of formula (6)

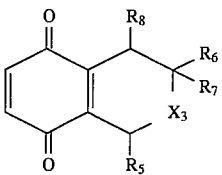

wherein $R_5$, $R_6$, $R_7$, $R_8$, and $X_3$ axe as defined above;
 step 2) cyclo-adding said dioxoisochroman of formula (6) with a diene of formula (3a) or (3b)

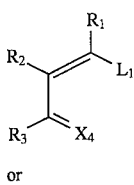
3a or

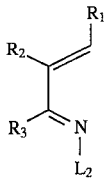
3b each one of $L_1$; and $L_2$ is independently a leaving group; to yield a heteronaphthoquinone of formula (4)

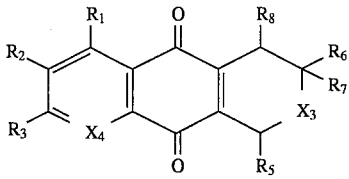
4 wherein $R_1, R_2, R_3, R_5, R_6, R_7, R_8, X_3$, and $X_4$ are as defined above;

step 3) coupling said heteronaphthoquinone of formula (4) at position $R_5$, wherein $R_5$ is —OH, with W' wherein W' is an activated precursor of W; and W is as defined above;

in the presence of a coupling agent (b) to yield a coupled heteronaphthoquinone of formula (8)

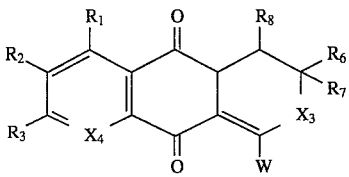
8 wherein; $R_1, R_2, R_3, R_6, R_7, R_8, X_3, X_4$, and W are as defined above;

wherein said coupled heteronaphthoquinone of formula (8) or the heteronaphthoquinone of formula (4) is air-oxidized with an organic or inorganic base or a fluoride salt (h) to yield to said insaturated coupled heteronaphthoquinone of formula (8a) or insaturated heteronaphthoquinone of formula (4a).

3. A process according to claim 1 or 2 wherein;
said organic or inorganic base (h) is sodium hydroxide or triethylamine.

4. A process according to claim 2 wherein;
$X_3$ is O or S;
$R_5$ is selected from the group consisting of hydrogen; hydroxy; amino; amido; and morpholino;
W is a saccharide of formula (30):

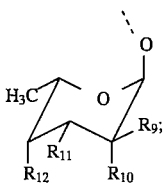
30

$R_6$ is selected from the group consisting of hydrogen; hydroxy; CN; $C_{1-16}$ alkyl; $C_{1-16}$ alkenyl; $C_{1-16}$ alky-nyl; $C_{1-16}$ alkoxy; $C_{6-16}$ aryl; $C_{7-16}$ aralkyl; $C_{6-16}$ aryloxy; $C_{1-16}$ acyl; amino; amido; $C_{2-16}$ ester; azole; and halogen;

$R_7$ is selected from the group consisting of hydrogen; hydroxy; $C_{1-16}$ alkyl; $C_{1-16}$ alkenyl; $C_{1-16}$ alkynyl; $C_{1-16}$ alkoxy; and $C_{2-16}$ ester;

$R_8$ is selected from the group consisting of hydrogen; hydroxy; $C_{1-16}$ alkyl; $C_{1-16}$ alkenyl; $C_{1-16}$ alkynyl; $C_{1-16}$ alkoxy; and halogen; and $R_9; R_{10}; R_{11}$; and $R_{12}$ are independently selected from the group consisting of hydrogen; hydroxy; CN; $C_{1-16}$ alkyl; $C_{1-16}$ alkenyl; $C_{1-16}$ alkynyl; $C_{1-16}$ alkoxy; $C_{1-16}$ acyl; amino; amido; $C_{2-16}$ ester; azido; saccharide, NH2; sulfono; morpholino; and halogen.

5. A process according to claim 2 wherein; $R_1, R_2, R_3$ and Q are each independently selected from the group consisting of hydrogen; hydroxy; $C_{1-16}$ alkyl; $C_{1-16}$ alkoxy; $C_{6-16}$ aryl; and halogen;

$X_3$ is O or S;

$R_5$ is selected from the group consisting of hydrogen; hydroxy; amino; amido; and morpholino; $R_6$ is selected from the group consisting of $C_{1-6}$ alkyl; $C_{1-6}$ alkenyl; $C_{1-6}$ alkynyl; $C_{1-6}$ alkoxy; $C_{1-6}$ acyl; amido; thiol; azole and $C_{2-6}$ ester;

$R_7$ is selected from the group consisting of hydrogen; hydroxy; $C_{1-6}$ alkyl; $C_{1-6}$ alkoxy; and $C_{2-6}$ ester; and $R_8$ is selected from the group consisting of hydrogen; hydroxy; $C_{1-6}$ alkyl; $C_{1-6}$ alkoxy; and halogen.

6. A process according to claim 2 wherein;

$X_4$ is CQ;

$R_1, R_2, R_3$ and Q are each independently selected from the group consisting of hydrogen; hydroxy; $C_{1-6}$ alkyl; $C_{1-6}$ alkoxy; $C_{6-12}$ aryl; and halogen;

$R_5$ is selected from the group consisting of hydrogen; hydroxy; prolyl; seryl; leucyl; serylleucine methyl ester;

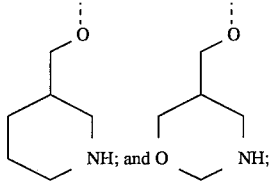

—NHCOCH$_3$;

$R_6$ is selected from the group consisting of $C_{1-6}$ acyl; amido; and $C_{2-6}$ ester;

$R_7$ is hydrogen; and $R_8$ is selected from the group consisting of hydrogen; hydroxy; and $C_{1-6}$ alkyl.

7. A process according to claim 6 wherein;

$R_1, R_2, R_3$ and Q are hydrogen;

$X_3$ is O;

$R_6$ is acetyl;

$R_7$ is hydrogen;

$R_8$ is hydrogen or hydroxy;

$L_1$ is a $C_{1-6}$ acyl; and $L_2$ is N($C_{1-6}$ alkyl)$_2$.

8. A process according to claim 2 comprising the steps of step 1) coupling the protected isochroman of formula (5), wherein $R_5$ is H, with W;

in the presence of a coupling agent (c) to yield a coupled protected isochroman of formula (11)

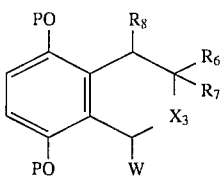

wherein P, $R_6$, $R_7$, $R_8$, W, and $X_3$ are as defined in claim 2, step 2) oxidizing the coupled protected isochroman of formula (11) with an oxidizing agent (a) to yield a coupled dioxoisochroman of formula (12)

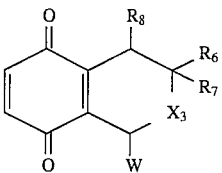

wherein; $R_6$, $R_7$, $R_8$, W, and $X_3$ are as defined in claim 2, step 3) cyclo-adding coupled dioxoisochroman of formula (12) with a diene of formula (3a) or (3b)

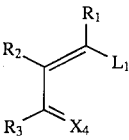

or

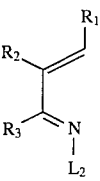

wherein $R_1$, $R_2$, $R_3$, $X_4$, $L_1$, and $L_2$ are as defined in claim 2, to yield the coupled naphthoquinone of formula (8)

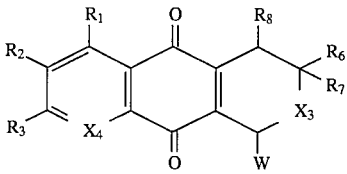

wherein; $R_1$, $R_2$, $R_3$, $R_6$, $R_7$, $R_8$, W, $X_3$, and $X_4$ are as defined in claim 2.

9. A process according to claim 8 wherein the protected isochroman of formula (5) is coupled with a saccharide precursor W' of formula (33)

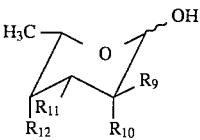

; and

W is a saccharide of formula (30):

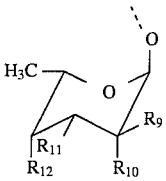

wherein;

$R_9$; $R_{10}$; $R_{11}$; and $R_{12}$ are independently selected from the group consisting of hydrogen; hydroxy; CN; $C_{1-16}$alkyl; $C_{1-16}$alkenyl; $C_{1-16}$alkynyl; $C_{1-16}$alkoxy; $C_{1-16}$acyl; amino; amido; $C_{2-16}$ester; and halogen.

10. A process according to claim 9 wherein;

$R_9$; $R_{10}$; $R_{11}$; and $R_{12}$ are independently selected from the group consisting of hydrogen; hydroxy; $C_{1-6}$ alkyl; $C_{1-6}$ alkenyl; $C_{1-6}$ alkynyl; $C_{1-6}$ alkoxy; $C_{1-6}$ acyl; $C_{2-6}$ ester; amino; amido; and halogen;

$R_6$ is selected from the group consisting of hydrogen; $C_{1-16}$ alkyl; $C_{1-16}$ alkenyl; $C_{1-16}$ alkynyl; $C_{1-16}$ alkoxy; $C_{1-16}$ acyl; $C_{1-16}$ acyl; $C_{6-16}$ aryl; $C_{6-16}$ aryloxy; amino; thiol; halogen; azole; phosphono; and $C_{2-6}$ ester;

$R_7$ is selected from the group consisting of hydrogen; $C_{1-16}$ alkyl; and $C_{1-16}$ alkoxy;

$R_8$ is selected from the group consisting of hydrogen; hydroxy; and $C_{1-16}$ alkyl.

11. A process according to claim 9 wherein;

$X_3$ is O or S;

$R_6$ is selected from the group consisting of hydrogen; $C_{1-6}$ alkyl; $C_{1-6}$ alkenyl; $C_{1-6}$ alkynyl; $C_{1-6}$ alkoxy; $C_{1-6}$ acyl; $C_{1-6}$ acyl; $C_{6-12}$ aryl; $C_{6-12}$ aryloxy; amino; halogen;azole; phosphono; and $C_{2-6}$ ester;

$R_7$ is selected from the group consisting of hydrogen; $C_{1-6}$ alkyl; and $C_{1-6}$ alkoxy;

$R_8$ is selected from the group consisting of hydrogen; hydroxy;and $C_{1-6}$ alkyl;

$R_9$ is selected from the group consisting of hydrogen; hydroxy;and $C_{1-6}$ alkyl;

$R_{10}$ is selected from the group consisting of hydrogen; $C_{1-6}$ alkyl; $C_{1-6}$ acyl; amino; halogen; and hydroxy;

$R_{11}$ and $R_{12}$ are independently selected from the group consisting of hydrogen; $C_{1-6}$ alkyl; $C_{1-6}$ acyl; $C_{2-6}$ ester; halogen; hydroxy; and amino.

12. A process according to claim 9 wherein;

$X_4$ is CQ;

$R_6$ is selected from the group consisting of hydrogen; $C_{1-6}$ acyl; amido; and $C_{2-6}$ ester;

$R_7$ is hydrogen;

$R_8$ is selected from the group consisting of hydrogen; hydroxy;and $C_{1-6}$ alkyl;

$R_9$ is selected from the group consisting of hydrogen; hydroxy; and $C_{1-6}$ alkyl;

$R_{10}$ is selected from the group consisting of hydrogen; $C_{1-6}$ alkyl; $C_{1-6}$ acyl; halogen; and hydroxy;

$R_{11}$ and $R_{12}$ are independently selected from the group consisting of hydrogen; $C_{1-6}$ alkyl; $C_{1-6}$ acyl; $C_{2-6}$ ester; halogen; hydroxy; and amino.

13. A process according to claim 9 wherein;

$X_4$ is CQ;

$R_1$, $R_2$, $R_3$ and Q are hydrogen;

$X_3$ is O;

$R_6$ is acetyl;

$R_7$ is hydrogen;

$R_8$ is hydrogen or hydroxy;

$R_9$ is hydrogen;

$R_{10}$ is selected from the group consisting of hydrogen; $C_{1-6}$ acyl; halogen; and hydroxy;

$R_{11}$ is selected from the group consisting of hydrogen; $C_{1-6}$ alkyl; $C_{1-6}$ acyl; hydroxy and amino;

$R_{12}$ is selected from the group consisting of $C_{1-6}$ acyl; $C_{2-6}$ ester; halogen; hydroxy; and amino;

each oxygen protecting group P is independently a $C_{1-6}$ alkyl; and said oxidizing agent (a) is ceric ammonium nitrate or silver oxide.

14. A process according to claim 8, 9, 10, 11, 12 or 13 wherein;

each oxygen protecting group P is —$CH_3$;

said coupling agent (c) is 2,3 dichloro-5,6-dicyano-1,4-benzoquinone; and said oxydating agent (a) is ceric ammonium nitrate.

15. A process according to claim 2 comprising the step of step 1) coupling the dioxoisochroman of formula (6),

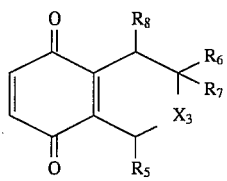

of process (I), step 1), wherein $R_5$ is —OH, with W' wherein W' is a saccharide precursor of formula (33)

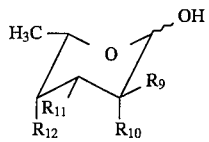

wherein;

$R_9$; $R_{10}$; $R_{11}$; and $R_{12}$ are independently selected from the group consisting of hydrogen; hydroxy; CN; $C_{1-16}$alkyl; $C_{1-16}$alkenyl; $C_{1-16}$alkynyl; $C_{1-16}$alkoxy; $C_{1-16}$ acyl; amino; amido; $C_{2-16}$ester; and halogen, in the presence of a coupling agent (b) to yield a coupled dioxoisochroman of the formula (12)

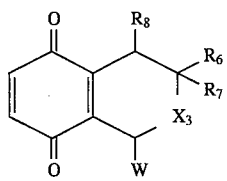

wherein $R_6$, $R_7$, $R_8$, W, and $X_3$ are as defined in claim 2 step 2) cycloadding said a coupled dioxoisochroman of formula (12) with a diene of formula (3a) or (3b) in a solvent (b)

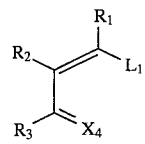

or

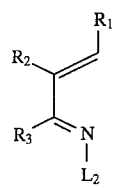

wherein $R_1$, $R_2$, $R_3$, $X_4$, $L_1$; and $L_2$ are as defined in claim 2, to yield a coupled naphthoquinone of formula (8)

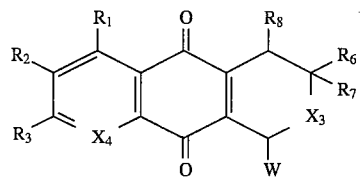

wherein; $R_1$, $R_2$, $R_3$, $R_6$, $R_7$, $R_8$, W, $X_3$, and $X_4$ as as defined in claim 2.

16. A process according to claim 15 wherein;

W' is a saccharide precursor of formula (34a) or (34b)

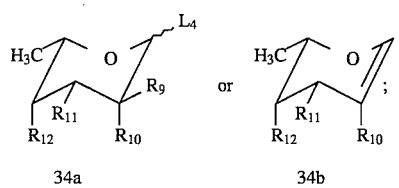

W is a saccharide of formula (30):

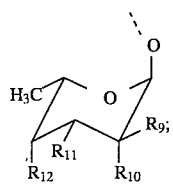

wherein;

$L_4$ is a leaving group;

$R_9$; $R_{10}$; $R_{11}$; and $R_{12}$ are independently selected from the group consisting of hydrogen; hydroxy; CN; $C_{1-16}$ alkyl; $C_{1-16}$ alkenyl; $C_{1-16}$ alkynyl; $C_{1-66}$ alkoxy; $C_{1-6}$ acyl; amino; amido; $C_{2-16}$ ester; and halogen.

17. A process according to claim 16 wherein;

$R_6$ is selected from the group consisting of hydrogen; $C_{1-16}$ alkyl; $C_{1-16}$ alkenyl; $C_{1-16}$ alkynyl; $C_{1-16}$ alkoxy; $C_{1-16}$ acyl; $C_{6-16}$ aryl; $C_{6-16}$ aryloxy; amino; halogen; thiol; azole; phosphono; and $C_{2-6}$ ester;

$R_7$ is selected from the group consisting of hydrogen; $C_{1-16}$ alkyl; and $C_{1-16}$ alkoxy;

$R_8$ is selected from the group consisting of hydrogen; hydroxy; and $C_{1-16}$ alkyl;

$L_4$ is selected from the group consisting of I; Cl; Br; tosyl; benzoyl; p-nitrobenzyl; O($C_{1-6}$ alkyl) and O($C_{1-6}$ acyl);

$R_9$; $R_{10}$; $R_{11}$; and $R_{12}$ are independently selected from the group consisting of hydrogen; hydroxy; $C_{1-6}$ alkyl;

$C_{1-6}$ alkenyl; $C_{1-6}$ alkynyl; $C_{1-6}$ alkoxy; $C_{1-6}$ acyl; $C_{2-6}$ ester; amino; amido; and halogen.

18. A process according to claim 16 wherein;

$R_6$ is selected from the group consisting of hydrogen; $C_{1-6}$ alkyl; $C_{1-6}$ alkenyl; $C_{1-6}$ alkynyl; $C_{1-6}$ alkoxy; $C_{1-6}$ acyl; $C_{6-12}$ aryl; $C_{6-12}$ aryloxy; amido; halogen;azole; phosphono; and $C_{2-6}$ ester;

$R_7$ is selected from the group consisting of hydrogen; $C_{1-6}$ alkyl; and $C_{1-6}$ alkoxy;

$R_8$ is selected from the group consisting of hydrogen; hydroxy;and $C_{1-6}$ alkyl;

$R_9$ is selected from the group consisting of hydrogen; hydroxy;and $C_{1-6}$ alkyl;

$R_{10}$ is selected from the group consisting of hydrogen; $C_{1-6}$ alkyl; $C_{1-6}$ acyl; halogen; amino; and hydroxy;

$R_{11}$ and $R_{12}$ are independently selected from the group consisting of hydrogen; $C_{1-6}$ alkyl; $C_{1-6}$ acyl; $C_{2-6}$ ester; halogen; hydroxy and amino.

19. A process according to claim 16 wherein;

$X_3$ is O or S;

$X_4$ is CQ;

$R_6$ is selected from the group consisting of hydrogen; $C_{1-6}$ acyl; amido; and $C_{2-6}$ ester;

$R_7$ is hydrogen;

$R_8$ is selected from the group consisting of hydrogen; hydroxy;and $C_{1-6}$ alkyl;

$R_9$ is selected from the group consisting of hydrogen; hydroxy;and $C_{1-6}$ alkyl;

$R_{10}$ is selected from the group consisting of hydrogen; $C_{1-6}$ acyl; halogen; and hydroxy;

$R_{11}$ and $R_{12}$ are independently selected from the group consisting of hydrogen; $C_{1-6}$ alkyl; $C_{1-6}$ acyl; $C_{2-6}$ ester; halogen; hydroxy; and; amino; and $L_4$ is selected from the group consisting of I; Cl; Br; tosyl; benzoyl; p-nitrobenzyl; O($C_{1-6}$ alkyl); and O($C_{1-6}$ acyl).

20. A process according to claim 16 wherein;

$X_4$ is CQ;

$R_1, R_2, R_3$ and Q are hydrogen;

$X_3$ is O;

$R_6$ is acetyl;

$R_7$ is hydrogen;

$R_8$ is hydrogen or hydroxy;

$R_9$ is hydrogen;

$R_{10}$ is selected from the group consisting of hydrogen; $C_{1-6}$ acyl; halogen; and hydroxy;

$R_{11}$ is selected from the group consisting of hydrogen; $C_{1-6}$ alkyl; $C_{1-6}$ acyl; hydroxy; and amino;

$R_{12}$ is selected from the group consisting of $C_{1-6}$ acyl; $C_{2-6}$ ester; halogen; hydroxy; and amino; and $L_4$ is selected from the group consisting of I; Cl; and Br.

21. A process according to claim 16, 17, 18, 19 or 20 wherein said coupling agent (b) is a Lewis acid.

22. A process according to claim 21 wherein said coupling agent (b) is trimethyl silyl triflate.

23. A process according to claim 2 wherein said protected isochroman of formula (5) or said dioxoisochroman of formula (6) is produced by: step 1) condensing a precursor compound of formula (13)

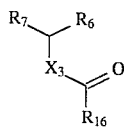

wherein:

$R_6$ is selected from the group consisting of $C_{1-16}$ acyl; $C_{2-16}$ ester; and —CN;

$R_7$ is a $C_{2-16}$ ester or a $C_{1-16}$ alkyl;

$X_3$ is O or S;

$R_{16}$ is a $C_{6-12}$ aryl;

with a protected aromatic compound of formula (14);

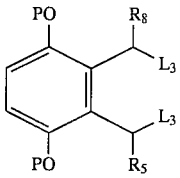

wherein:

P, $R_5$ and $R_8$ are as defined in claim 2; with the proviso that $R_5$ and $R_8$ are not OH; CN or $NO_2$; and each one of $L_3$ is indepently a leaving group;

to yield a protected isochroman of formula (5)

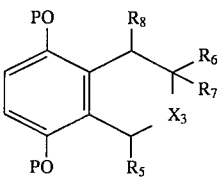

wherein:

$R_5, R_6, R_7, R_8$, and $X_3$ are as defined above;

step 2) oxidizing the protected isochroman of formula (5) in the presence of an oxydating agent (a) to yield to a dioxoisochroman of formula (6)

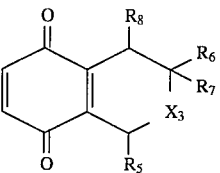

wherein $X_3, R_5, R_6, R_7$, and $R_8$ are as defined above.

24. A process according to claim 23 wherein;

$R_6$ is selected from the group consisting of $C_{1-6}$ acyl; $C_{2-6}$ ester; and —CN;

$R_7$ is a $C_{2-6}$ ester or a $C_{1-6}$ alkyl; and $X_3$ is O.

25. A process according to claim 24 wherein;

$R_5$ is selected from the group consisting of hydrogen; $C_{1-16}$ alkyl; $C_{6-16}$ aryl; amino; and amido;

$R_8$ is selected from the group consisting of of hydrogen; $C_{1-16}$ alkyl; $C_{6-16}$ aryl; and halogen;

P is a $C_{1-6}$ alkyl; and said oxidizing agent (a) is ceric ammonium nitrate or silver oxide.

26. A process according to anyone of claim 23 to 25 wherein;

$R_5$ is selected from the group consisting of hydrogen; $C_{1-6}$ alkyl; $C_{6-12}$ aryl; amino; and amido;

P is —CH$_3$;

each of L$_3$ is independently selected from the group consisting of I; Br; and Cl; and said oxidizing agent (a) is ceric ammonium nitrate.

27. A process according to claim 2 wherein said protected isochroman of formula (5) or said dioxoisochroman of formula (6) is produced by: step 1) reacting an intermediate of formula (15)

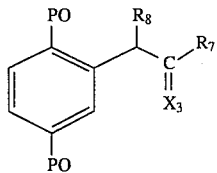  15 wherein:

X$_3$ is O; and

P is as defined in claim 2;

R$_7$ is hydrogen; and R$_8$ is hydrogen or a C$_{1-16}$alkyl; with a magnesium halide of formula (16)

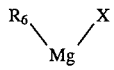  16 wherein:

R$_6$ is selected from the group consisting of C$_{1-16}$alkyl; C$_{1-16}$alkenyl; C$_{1-16}$alkynyl; and C$_{6-16}$aryl; and X is an halogen; to yield product of formula (17)

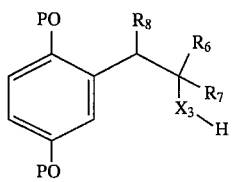  17 wherein:

X$_3$ is oxygen; and

R$_6$, R$_7$, and R$_8$ are as defined above; and step 2) further reacting said product: with a compound of formula (18a) or (18b) in the presence of an coupling agent

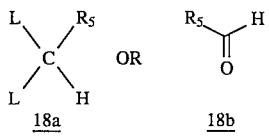

wherein:

R$_5$, is as defined in claim 2, with the proviso that R$_5$ is not alkoxy, and each L is independently a leaving group to yield a protected isochroman of formula (5)

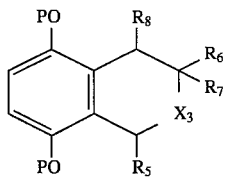  5 wherein:

X$_3$ is O, and P, R$_5$, R$_6$, R$_7$, and R$_8$ are as defined above.

28. A process according to claim 27 wherein;

R$_5$ is selected from the group consisting of C$_{1-16}$ alkyl; and C$_{6-16}$ aryl;

R$_6$ is selected from the group consisting of hydrogen; C$_{1-16}$ alkyl; and C$_{6-16}$ aryl; and P is a C$_{1-6}$ alkyl.

29. A process according to claim 27 wherein;

R$_5$ is selected from the group consisting of C$_{1-6}$ alkyl; and C$_{6-12}$ aryl;

R$_6$ is selected from the group consisting of hydrogen; C$_{1-6}$ alkyl; and C$_{6-12}$ aryl; and P is a C$_{1-6}$ alkyl.

30. A process according to claim 27 or 29 wherein;

P is —CH$_3$;

said coupling agent (d) is a Lewis acid; and each of the leaving group L is independently —O.

31. A process according to claim 30 wherein;

said coupling agent (d) is boron trifluoroetherate; and each of the leaving group L is —OCH$_3$.

32. A process according to claim 2 wherein said protected isochroman of formula (5) or said dioxoisochroman of formula (6) is produced by:

step 1) reacting a protected benzene of formula (19)

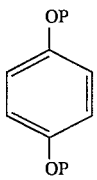  19 wherein:

P is as defined in claim 2; in the presence of a coupling agent (e) with an epoxide of formula (20)

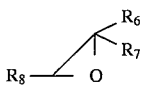  20 wherein:

R$_7$ and R$_8$ are hydrogen; and

R$_6$ is selected from the group consisting of C$_{1-16}$alkyl; C$_{6-16}$aryl; silyloxy; and hydrogen; to yield to an intermediate of formula (17)

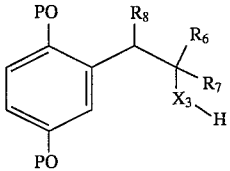  17 wherein:

X$_3$ is O; R$_7$ and R$_8$ are hydrogen; and

P and R$_6$ are as defined above;

step 2) further reacting said intermediate of formula (17) with a compound of formula (18a) or (18b) in the presence of a coupling agent (d);

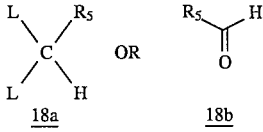

wherein:

R$_5$ is as defined in claim 2, with the proviso that R$_5$ is not alkoxy, and each L is independently a leaving group;

to yield a protected isochroman of formula (5)

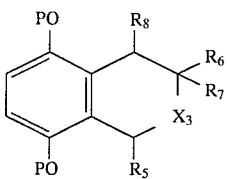

wherein:

$X_3$, $R_7$, $R_8$, P, $R_5$, and $R_6$ are as defined above;

step 3) oxidizing the protected isochroman of formula (5) in the presence of an oxydating agent (a) to yield to a dioxoisochroman of formula (6)

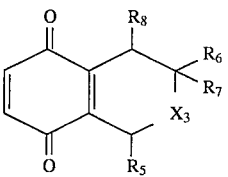

wherein:

$X_3$, $R_7$, $R_8$, P, $R_5$, and $R_6$ are as defined above.

33. A process according to claim 32 wherein;

$R_5$ is selected from the group consisting of hydrogen; $C_{1-16}$ alkyl; and $C_{6-16}$ aryl; and $R_4$ is a $C_{1-16}$ alkyl or hydrogen.

34. A process according to claim 32 wherein;

$R_5$ is selected from the group consisting of hydrogen; $C_{1-6}$ alkyl; and $C_{6-16}$ aryl;

$R_6$ is a $C_{1-6}$ alkyl or an hydrogen;

P is a $C_{1-6}$ alkyl; and said oxidizing agent (a) is ceric ammonium nitrate or silver oxide.

35. A process according to anyone of claim 32 to 34 wherein;

P is —$CH_3$;

each of L is independently —O;

said oxidizing agent (a) is ceric ammonium nitrate; and said coupling agents (d) and (e) are independently Lewis acids.

36. A process according to claim 2 wherein said coupling agents (d) and (e) are boron trifloroetherate.

37. A process according to claim 2 wherein said protected isochroman of formula (5) or said dioxoisochroman of formula (6) is produced by:

step 1) reacting a protected intermediate of formula (21);

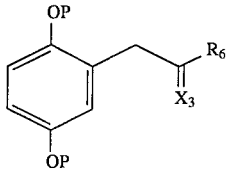

wherein:

$X_3$ is O; and

P is as defined in claim 2; and $R_6$ is hydrogen or a $C_{1-16}$ alkyl; with an haloalkyl of formula (22)

$$R_8-X \quad 22$$

wherein:

$R_8$ is a $C_{1-16}$ alkyl; a $C_{1-16}$ acyl or an ester; and X is halogen; to yield to a compound of fomula (23):

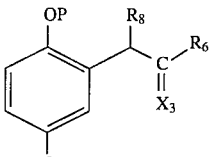

wherein:

$X_3$, P, $R_6$ and $R_8$ are as defined above;

step 2) reducing said compound of formula (23) with a reducing agent (f) to yield to a compound of formula (24)

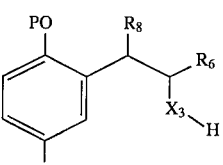

wherein:

$X_3$, $R_6$, P, and $R_8$ are as defined above;

step 3) further reacting said compound of formula (24) with a compound of formula (18a) or (18b) in the presence of an coupling agent (d);

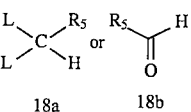

wherein:

L and $R_5$ are as defined in claim 2, with the proviso that $R_5$ is not alkoxy, to yield a protected isochroman of formula (5)

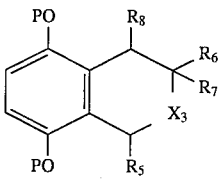

wherein:

$X_3$, $R_7$, P, $R_5$, $R_6$ are as defined above;

step 4) oxidizing the protected isochroman of formula (5) in the presence of an oxidizing agent (a) to yield to a dioxoisochroman of formula (6)

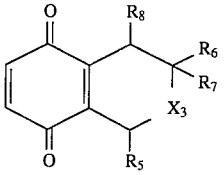

wherein:

$X_3$, $R_7$, $R_5$, $R_6$, and $R_8$ are as defined above.

38. A process according to claim 37 wherein;

$R_5$ is selected from the group consisting of hydrogen; $C_{1-16}$ alkyl; and $C_{6-16}$ aryl;

$R_6$ is a $C_{1-16}$ alkyl $C_{1-16}$ alkoxy;

$R_8$ is selected from the group consisting of $C_{1-16}$ alkyl; and $C_{1-16}$ acyl; and $C_{1-16}$ alkoxy; and X is I.

39. A process according to claim 38 wherein;

$R_5$ is selected from the group consisting of hydrogen; $C_{1-6}$ alkyl; and $C_{6-12}$ aryl;

$R_6$ is a $C_{1-6}$ alkyl or a $C_{1-6}$ alkoxy;

$R_8$ is selected from the group consisting of $C_{1-6}$ alkyl; and $C_{1-6}$ acyl; and $C_{1-6}$ alkoxy;

X is I; and

P is a $C_{1-6}$ alkyl; and said oxidizing agent (a) is ceric ammonium nitrate or silver oxide.

40. A process according to claim 30 or 39 wherein;

P is —$CH_3$;

each of L is independently —O;

said oxydating agent (a) is ceric ammonium nitrate;

said reducing agent (f) is diisobutylaluminium hydride; and said coupling agent (d) is a Lewis acid.

41. A process according to claim 40 wherein said coupling agent (d) is boron trifloroetherate; and wherein each L is —$OCH_3$.

42. A process according to claim 2 wherein said a coupled heteronaphthoquinone of formula (8):

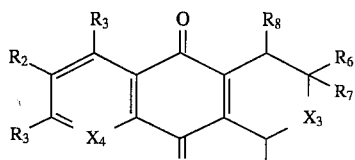

wherein; $R_1$, $R_2$, $R_3$, $R_6$, $R_7$, $R_8$, $X_3$, and $X_4$ are as defined in claim 2 and W is defined by formula (50):

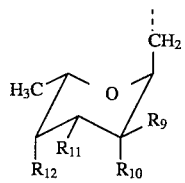

wherein;

$R_9$; $R_{10}$; $R_{11}$; and $R_{12}$ are independently selected from the group consisting of hydrogen; hydroxy; CN; $C_{1-16}$alkyl; $C_{1-16}$alkenyl; $C_{1-16}$alkynyl; $C_{1-16}$alkoxy; $C_{1-16}$acyl; amino; amido; $C_{2-16}$ester; and halogen; is produced by:

step 1) coupling a coupled saccharide dioxoisochroman of formula (51);

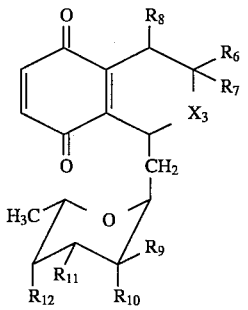

wherein; $R_1$, $R_2$, $R_3$, $R_6$, $R_7$, $R_8$, $X_3$, $X_4$, $R_9$, $R_{10}$, $R_{11}$, and $R_{12}$ are as defined above; with a diene of formula (3 a) or (3b)

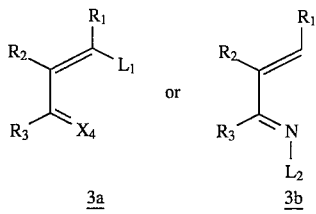

wherein $R_1$, $R_2$, $R_3$ and $X_4$ are as defined above; and each one of $L_1$ and $L_2$ are independently a leaving group to yield to a coupled heteronaphthoquinone of formula (8).

43. A process according to claim 42 wherein said coupled saccharide dioxoisochroman of formula (51);

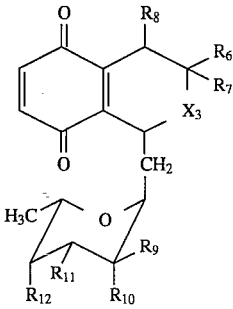

wherein;

$X_3$ is O;

$R_6$ is selected from the group consisting of $C_{1-16}$alkyl; $C_{1-16}$alkenyl; $C_{1-16}$alkynyl; and $C_{6-16}$aryl;

$R_7$ is hydrogen;

$R_8$ is hydrogen or a $C_{1-16}$alkyl; and $R_9$, $R_{10}$, $R_{11}$, and $R_{12}$ are as defined in claim 42; is produced by:

step 1) reacting a compound of formula (17);

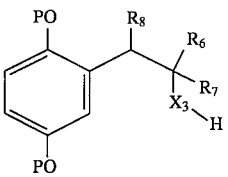

wherein:

$X_3$, $R_6$, $R_7$, and $R_8$ are as defined above; and each P is independently a protecting group; with a saccharide precursor of formula (52a) or (52b) in the presence of a coupling agent (d);

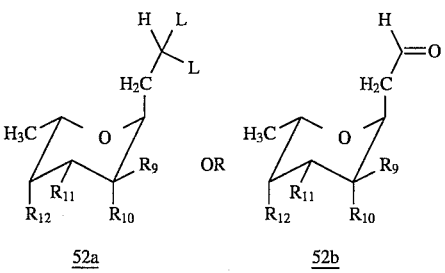

wherein;

$R_9$, $R_{10}$, $R_{11}$, and $R_{12}$ are as defined above; and each L is independently a leaving group; to yield to a coupled saccharide protected isochroman of formula (53);

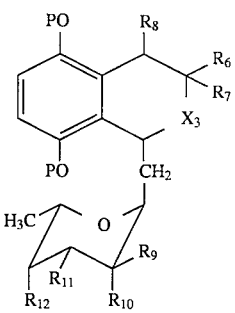

wherein; $R_6$, $R_7$, $R_8$, $X_3$, $R_9$, $R_{10}$, $R_{11}$, and $R_{12}$ are as defined above;

step 2) oxidizing said coupled saccharide protected isochroman of formula (53) in the presence of an oxidizing agent (a) to yield to a coupled saccharide dioxoisochroman of formula (51).

44. A process according to claim 43 wherein;

$R_6$ is selected from the group consisting of hydrogen; $C_{1-16}$ alkyl; and $C_{6-16}$ aryl;

P is a $C_{1-6}$ alkyl;

$R_9$; $R_{10}$; $R_{11}$; and $R_{12}$ are independently selected from the group consisting of hydrogen; hydroxy; $C_{1-6}$ alkyl; $C_{1-6}$ alkenyl; $C_{1-6}$ alkynyl; $C_{1-6}$ alkoxy; $C_{1-6}$ acyl; $C_{2-6}$ ester; amino; amido; and halogen.

45. A process according to claim 43 wherein;

$R_6$ is selected from the group consisting of hydrogen; $C_{1-6}$ alkyl; and $C_{6-12}$ aryl; and P is a $C_{1-6}$ alkyl;

$R_9$ is selected from the group consisting of hydrogen; hydroxy; and $C_{1-6}$ alkyl;

$R_{10}$ is selected from the group consisting of hydrogen; $C_{1-6}$ alkyl; $C_{1-6}$ acyl; amino; halogen; and hydroxy;

$R_{11}$ and $R_{12}$ are independently selected from the group consisting of hydrogen; $C_{1-6}$ alkyl; $C_{1-6}$ acyl; $C_{2-6}$ ester; halogen; hydroxy; and amino.

46. A process according to claim 43 wherein;

$R_9$ is hydrogen;

$R_{10}$ is selected from the group consisting of hydrogen; $C_{1-6}$ acyl; halogen; and hydroxy;

$R_{11}$ is selected from the group consisting of hydrogen; $C_{1-6}$ alkyl; $C_{1-6}$ acyl; hydroxy; and amino; and $R_{12}$ is selected from the group consisting of $C_{1-6}$ acyl; ester; halogen; hydroxy; and amino.

47. A process according to anyone of claims 43 to 46 wherein;

P is —$CH_3$;

said oxydizing agent (a) is ceric ammonium nitrate or silver oxide;

said coupling agent (d) is a Lewis acid; and each of the leaving group L is independently —O.

48. A process according to claim 47 wherein;

said oxydating agent (a) is ceric ammonium nitrate;

said coupling agent (d) is boron trifluoroetherate; and each of the leaving group L is —$OCH_3$.

49. A process according to claim 1 or 2 wherein said tricyclic compound of formula (1); said coupled heteronaphthoquinone of formula (8); heteronaphthoquinone of formula (4); insaturated coupled heteronaphtoquinone of formula (8a); and insaturated heteronaphthoquinone of formula (4a) are selected from the group consisting of Monofluoromethyl (5,10-dioxo-3,4,5,10-tetrahydronaphtho [2,3-C] pyran-3-yl) ketone;

(1'S, 1S, 3R) -Methyl (5,10-dioxo-1-(2',3',6'-trideoxy-3'-trifluoroacetamido-4'-O-p-nitrobenzoyl-L-lyxohexopyranose) -3,4,5,10-tetrahydronaphtho [2,3 -C]pyran-3-yl) ketone;

(1'S,1R,3S) -Methyl (5,10-dioxo-1-(2',3',6'-trideoxy-3'-trifluoroacetamido-4'-O-p-nitrobenzoyl-L-lyxohexopyranose)-7-hydroxy-3,4,5,10-tetrahydronaphtho [2,3-C] pyran-3-yl) ketone;

(1'S,1S,3R) -Methyl (5,10-dioxo-1-(2',3',6'-trideoxy-3'-trifluoroacetamido-4'-O-p-nitrobenzoyl-L-lyxohexopyranose)-7-hydroxy-3,4,5,10-tetrahydronaphtho [2,3-C] pyran-3-yl) ketone;

2-[4,-Hydroxy-1',2'-dioxo-3'-cyclobutenoxy] methyl-(5,10-dioxo-3,4,5,10-tetrhydronaphtho [2,3-C] pyran-3-yl) ketone;

Bromomethyl (5,10-dioxo-5,10-dihydronaphtho [2,3-C] pyran-3-yl) Ketone;

2-[4'-Hydroxy-1',2'-dioxo-3'-cyclobutenoxy] methyl (5,10-dioxo-3,4,5,10-tetrahydro [2,3-C] pyran-3-yl) ketone;

(1'S,1R,3S) and (1'S,1S,3R) -Bromomethyl (5,10-dioxo-1-(2',3',6'trideoxy-4'-O-P-nitrobenzoyl-3'-trifluoro acetamido-L-lyxohexopyranose)-(3,4,5,10-tetrahydronaphtho [2,3-C] pyran-3-yl) ketone;

(1'S,1R,3S) and (1'S,1S,3R)-2-[4'-hydroxy-1',2'-dioxo-3'-cyclobutenoxy] methyl (5,10-dioxo-1-[2", 3",6"-trideoxy-4"-O-p-nitrobenzoyl-3"-trifluoroacetamido-L-lyxohexopyranose]-3,4,5,10-tetrahydronaphtho [2,3,c] pyran-3-yl) ketone;

(1'-S, 1-R, 3-S)-1-(2'-3'-6'-trideoxy-4'-p-nitrobenzoyl-3'-trifluoroacetamido-L-lyxohexopyranose)3-(2-bromoacetyl)-5,10-dioxo-3,4,5,10-tetrahydro-1H-naphtho-(2,3-c)-pyran;

(1'S,1-R,3-S)-1-(2',3',6'-trideoxy-4'-p-nitrobenzoyl-3'-trifluoroacetamido-L-lyxophexopyranose)-3-(2-aza-3-aminothiazolyl)-5,10-dioxo-3,4,5,10-tetrahydro-1H-naphtho-(2,3-c)pyran;

(1'S,1-R,3-S)-1-(2',3',6'-trideoxy-3'-trifluoroacetamido-4'-p-nitrobenzoyl-L-lyxohexopyranose)-3-(2-aza-3-acetamidothiazolyl)-5,10-dioxo-3,4,5,10-tetrahydro-1H-naphtho-[2,3-c]-pyran;

(1'-S, 1-R, 3-S)-1-(2',3',6'-trideoxy-3'-trifluoro acetamido-L-lyxohexopyranose)-3-(2-aza-3-acetamido thiazolyl)-5,10-dioxo-3,4,5,10-tetrahydro-1H-naphtho-[2,3-c]-pyran;

(1'-S, 1-R, 3-S)-1-(2',3',6'-trideoxy-3'-trifluoro acetamido-L-lyxohexopyranose)-3-(2 -aza -3-aminothiazolyl)-5,0-dioxo-3,4,5,10-tetrahydro-1H-naphtho-[2,3-C] pyran;

(1'-S,1-S,3-R)-1-(2',3'-6'-trideoxy-4'-p-nitrobenzoyl-3'-trifluoroacetamido-L-lyxohexopyranose)-3-(2-bromoacetyl)-5,10-dioxo-3,4,5,10-tetrahydro-1H-naphtho-[2,3 -c]-pyran;

(1'-S,1-S,3-R)-1-(2',3'-6'-trideoxy-4'O-p-nitrobenzoyl-3'trifluoroacetamido-L-lyxohexopyranose)-3-(2-aza-3-acetamido)-5,10-dioxo-3,4,5,10-tetrahydro-1H-naphtho-[2,3-c]-pyran;

(1'S,1S,3R) and (1'S,1R,3S) methyl (1-[2',3',6'-trideoxy-3'-trifluoroacetamido-4'-O-p-nitrobenzoyl-L-lyxohexo-pyranose)-5,10-dioxo-3,4,5,10-tetrahydro-7-methyl-9-aza naphtho [2,3-c] pyran-3-yl ketone;

(1S,1S,3R) and (1'S,1R,3S) methyl-1-(2',3',6'-trideoxy-3'-trifluoroacetamido-4'-hydroxy-L-lyxohexopyranose)-5,10-dioxo-3,4,5,10-tetrahydro-7-methyl-O-azanaphtho [2,3-c] pyran-3-yl ketone;

Trans-3-aceto-1-methoxy-1,2,3,4-tetrahydro-(2-sulfur)anthracene -5,10-dione and cis-3-aceto-1-methoxy-1,2,3,4-tetrahydro-(2-sulfur)anthracene-5,10-dione;

cis-3-aceto-1-methoxy-1,2,3,4-tetrahydro-(2-sulfur)anthracene-5,10-dione and trans-3-aceto-1-methoxy-1,2,3,4-tetrahydro-(2-sulfur) anthracene-5,10-dione;

Methyl (1-methoxy-5,10-dioxo-3,4,5,10-tetrahydro-1H-naphtho [2,3-c]pyran-3-yl) formate;

Methyl (1-methoxy-5,10-dioxo-5,10-dihydro-1H-naphtho[2,3-c]pyran-3 -yl) formate;

Methyl (1-methoxy-5,10-dioxo-5,10-dihydro-1H-naphtho[2,3-c]pyran-3-yl) formate;

1-Methoxy-5,10-dioxo-5,10-dihydro-1H-naphtho[2,3-c]pyran-3-carboxylic acid;

1-Methoxy-5,10-dioxo-5,10-dihydro-1H-naphtho[2,3-c]pyran-3-[N-(3-dimethylamino-propyl)carboxamide];

(1S, 2'S, 3R) and (1R, 2'S, 3S)-methyl-(1-[O-N-BOC-serine methyl ester]-5,10 -dioxo-3,4,5,10-tetrahydro-1H-naphtho [2,3-C] pyran-3-yl) ketone;

(1'S, 1S, 3R) and (1'S, 1R, 3S)-5,10-dioxo-3-cyano-1-(2',3',6',-trideoxy-3'-trifluoroacetamido-4'-O-p-nitrobenzoyl-L-lyxohexopyranose)-3,4,5,10-tetrahydro-1H-naphtho-[2,3-c] pyran;

5,10-Dioxo-3-(propane-2-one)-1-(2',3',6'-trideoxy-3'-trifluoroacetamido-4'-O-p-nitrobenzoyl-L-lyxohexopyranose)-3,4,5,10-tetrahydro-1H-naphtho-[2,3-c] pyran;

(1'S, 1R, 3S)-5,10-dioxo-3-methoxymethyl-1-(2',3',6'-trideoxy-3'-trifluoroacetamido-4'-O-p-nitrobenzoyl-L-lyxohexo-pyranose)-3,4,5,10-tetrahydro-1H-naphtho-[2,3c]-pyran;

(1'S, 1R, 3R)-5,10-dioxo-3-ethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-] pyran;

(1'S, 1S, 3S)-5,10-dioxo-3-ethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c]-pyran;

(1'S, 1S, 3R)-5,10-dioxo-3-isopropyl-1-(2',3',6'-trideoxy-3'-trifluoroacetamido-4'-O-p-nitrobenzoyl-L-lyxohexo-pyranose)-3,4,5,10-tetrahydro-1H-naphtho-[2,3-c]-pyran;

(1'S, 1R, 3S)-5,10-dioxo-3-isopropenyl-1-(2',3',6'-trideoxy-3'-trifluoroacetamido-4'-O-p-nitrobenzoyl-L-lyxohexo-pyranose) 3,4,5,10-tetrahydro-1H-naphtho-[2,3-c]-pyran;

(1'S, 1S, 3R)-5,10-dioxo-3-isopropenyl-1-(2',3',6'-trideoxy-3'-trifluoroacetamido-4'-O-p-nitrobenzoyl-L-lyxohexo-pyranose) 3,4,5,10-tetrahydro-1H-naphtho-[2,3-c]-pyran;

(1'S, 1R, 3S)-5,10-dioxo-3-methoxycarbonyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c]-pyran;

(1'S, 1R, 3S)-isopropyl-[1-(2',3',6'-trideoxy-3'-trifluoroacetamido-4'-O-p-nitrobenzoyl-L-lyxohexopyranose)-5,10-dioxo-3,4,5,10-tetrahydro-1H-naphtho-[2,3-c]-pyranyl]-ketone;

(1'S, 1R, 3S), and (1'S, 1S, 3R)-5,10-dioxo-3-isopropoxycarbonyl-1-(2',3',6'-trideoxy-3',trifluoroacetamido-4'-O-p-nitrobenzoyl-L-lyxohexopyranose)-3,4,5,10-tetrahydro-1H-naphtho-[2,3-c]-pyran;

(1'S, 1S)-5,10-dioxo-3,3-dimethoxymethyl-1-(2',3',6'-trideoxy-3' -trifluoroacetamido-4'-O-p-nitrobenzoyl-L-lyxohexopyranose)-3,4,5,10-tetrahydro-1H-naphtho-[2,3-c] pyran;

(1'S, 1R, 4R)-5,10-dioxo-4-ethyl-1-(2',3',6'-trideoxy-3'-trifluoroacetamido-4'-O-p-nitrobenzoyl-L-lyxohexopyranose)-3,4,5,10-tetrahydro-1H-naphtho-[2,3-c]-pyran;

(1'S, 1R, 3S)-5,10-dioxo-3-phenyloxymethyl-1-(2',3',6'-trideoxy-3' -trifluoroacetamido-4'-O-p-nitrobenzoyl-L-lyxohexopyranose)-3,4,5,10-tetrahydro-1H-naphtho-[2,3-c] pyran;

(1'S,1S,3S) and (1'-S,1-R,3-R)-3-([2',3',6'-trideoxy-3-trifluoroacetamidoo-4'-paramitrobenzoyl-L-lyxohexopyranose)-5,10-dioxo-3,4,5,10-tetrahydronaphtho-[2,3-c] -pyran-3-yl)-propene;

(1'R, 1R, 3S)-3-aceto-5,10-dioxo-1-(2-deoxy-2-chloroethylureido-4,6-benzylidene-D-glucopyranose)-3,4,5,10-tetrahydro-1H-naphtho-[2,3-C] pyran;

(1R,3S) and (1S,3R)-3-Aceto-5,10-dioxo-1 (4-chloroethylureido cyclohexyl-oxy)-3,4,5,10-tetrahydro-1H-naphtho-(2,3-c)-pyran;

(3-N-imidazolylpropyl)-1-methoxy-5,10-dioxo-5,10-dihydro-1H-naphtho-[2,3-c]-pyran-3-carboxamide;

(1'S, 1S, 3R)-1-(4'-p-nitrobenzoyl-3'-trifluoroacetamido-2',3',6'-trideoxy-lyxohexopyranose)-3-methoxy-carbonyl-3-methyl-5,10-dioxo-4,5,10-trihydro-1H-naphtho-[2,3-c]-pyran;

(1'S, 1R, 3S)-1-(4'-p-nitrobenzoyl-3'-trifluoroacetamido-2',3',6'-trideoxy-L-lyxohexopyranose)-3-(5"-tosyl-oxazolyl)-5,10-dioxo-3,4,5,10-tetrahydro-1H-naphtho-[2,3-c]-pyran;

(1'S, 1S, 3R)-1-(4'-p-nitrobenzoyl-3'-trifluoroacetamido-2',3',6'-trideoxy-L-lyxohexopyranose)-3-(5"-tosyl-oxazolyl)-5,10-dioxo-3,4,5,10-tetrahydro-1H-naphtho-[2,3-c]-pyran;

1-methoxy-3-acetyl-5,10-dioxo-3,4,5,10-tetrahydro-1H-naphtho-[2,3-c]-pyran;

3-bromoacethyl-1-methoxy-5,10-dioxo-3,4,5,10-tetrahydro-1H-naphtho-[2,3-c]-pyran;

(1'S, 1R, 3S)-1-(4'-p-nitrobenzoyl-3'-trifluoroacetamido-2',3',6'-trideoxy-lyxohexopyranose)-3-methoxy-carbonyl-3-methyl-5,10-dioxo-4,5,10-trihydro-1H-naphtho-[2,3-c]-pyran;

(1'S, 1S, 3S)-1-(4'-p-nitrobenzoyl-3'-trifluoroacetamido-2',3',6'-trideoxy-lyxohexopyranose)3-methoxy-carbonyl-3-methyl-5,10-dioxo-4,5,10-trihydro-1H-naphtho-[2,3-c]-pyran;

(1'S,1S,3S)-1-(4'-p-nitrobenzoyl-3'-trifluoroacetamido-2',3',6'-trideoxy-L-lyxohexopyranose)-3-acetyl-5,10-dioxo-3,4,5,10-tetrahydro-1H-naphtho-[2,3-c]-thiopyran;

(1'S,1S,3S) and (1'S, 1S, 3R)-1-(4'-p-nitrobenzoyl-3'-trifluoroacetamido-2',3',6'-trideoxy-lyxohexopyranose)-3-acetyl-3-methyl-5,10-dioxo-4,5,10-trihydro-1H-naphtho-[2,3-c]-pyran;

(1'S,1R,3S)-1-(2',3',6'-trideoxy-4'-p-niprobenzoyl-3'-trifluoroacetamido-L-lyxohexo pyranose)-3-dimethyl phosphonoacetyl-5,10-dioxo-3,4,5,10-tetrahydro-1H-naphtho[2,3-c]-pyran;

(1'S,1S,3R)-methyl-(6 and 9-hydroxy-1-(2',3',6'-trideoxy-3'-trifluoroacetamido-4'-O-p -nitrobenzoyl-L-lyxohexopyranose)-5,10-dioxo-3,4,5,10-tetrahydro-1H-naphtho-[2,3-c]-pyran-3yl) ketone;

3 -aceto-5,10-dioxo-3,4,5,10-tetrahydro-1H-naphtho-[2, 3-c]-pyran;

3-bromoacetyl-5,10-dioxo-3,4,5,10-tetrahydro-1H-naphtho-[2,3 -c]-pyran;

Methyl (1-methoxy-5,10-dioxo-3,4,5,10-tetrahydro-1H-naphtho [2,3-c]pyran-3-yl) formate;

Methyl (1-methoxy-5,10-dioxo-5,10-dihydro-1H-naphtho[2,3-c]pyran-3-yl) formate;

Methyl (1-methoxy-5,10-dioxo-5,10-dihydro-1H-naphtho[2,3-c]pyran-3-yl)formate;

1-Methoxy-5,10-dioxo-5,10-dihydro-1H-naphtho[2,3-c] pyran-3-carboxylic acid;

1-Methoxy-5,10-dioxo-5,10-dihydro-1H-naphtho[2,3-c] pyran-3-[N-(3-dimethylamino-propyl) carboxamide];

1-methoxy-3-methoxy carbonyl-5,10-dioxo-5,10-dihydro-1H-naphtho-[2,3-c]-pyran;

(3-N-imidazolylpropyl)-1-methoxy-5,10-dioxo-5,10-dihydro-1H-naphtho-[2,3 -c]-pyran-3-carboxamide;

1-methoxy-3-[2-(N-morpholino) ethyl amino carbonyl]-5,10-dioxo-5,10-dihydro-1H-naphtho-[2,3c]-pyran;

1-methoxy-3-[2-(N-morpholine) ethyl amino carbonyl]-5,10-dioxo-5,10-dihydro-1H-naphtho-[2,3-c]-pyran;

1-methoxy-3-[2-(2-pyridinyl) ethyl amino carbonyl]-5,10-dioxo-5,10-dihydro-1H-naphtho-[2,3-c)-pyran;

1-methoxy-3-[2-(2-pyridinyl) ethyl amino carbonyl]-5,10 -dioxo-5,10-dihydro-1H-naphtho-[2,3-c]-pyran hydrochloride;

1-methoxy-3-[(2-pyridinyl) methyl amino carbonyl]-3-methoxy-5,10-dioxo-5,10-dihydro-1H-naphtho-[2,3-c]-pyran hydrochloride salt;

1-methoxy-3-[2-(N-pyrrolidinyl) ethyl amino carbonyl]-5,10-dioxo-5,10-dihydro-1H-naphtho-[2,3-c]-pyran;

1-methoxy-3-[2-(N-pyrrolidinyl) ethyl amino carbonyl]-5,10-dioxo-5,10-dihydro-1H-naphtho-[2,3-c]-pyran hydrochloride salt;

1methoxy-3-[(4-diethoxy) butyl amino carbonyl]-5,10-dioxo-5,10-dihydro-1H-naphtho-[2,3-c]-pyran;

1-methoxy-3-(3-hydroxy) propyl amino carbonyl-5,10-dioxo-5,10-dihydro-1H-naphtho-[2,3-c]-pyran;

1-propyl-3-methoxycarbonyl-5,10-dioxo-5,10-dihydro-1H-naphtho-[2,3 -c]-pyran;

1-propyl-3-carboxyl-5,10-dihydro-5,10-dioxo-1H-naphtho-[2,3-c]-pyran;

1-propyl-3-(3-dimethyl amino propyl amino carbonyl)-5,10-dihydro-5,10-dioxo-1H-naphtho-[2,3-c]-pyran;

2-(N-pyrrolidinyl) ethyl-(1-propyl-5,10-dioxo-5,10-dihydro-1H-naphtho-[2,3-c]-pyran-3 )-carboxamide;

Methyl-1-methoxy-5,10-dioxo-3,4,5,10-tetrahydro-1H-naphtho [2,3 -c] thiine-3carboxylate;

1-methoxy-5,10-dioxo-5,10-dihydro-1H-naphtho [2,3-c] thiine-3-carboxylic acid;

Methyl (5,10-dioxo-3,4,5,10-tetrahydronaphtho [2,3-C] pyran-3-yl) ketone;

Methyl (5,10-dioxo-3,4,5,10-tetrahydronaphtho [2,3-C] pyran-3-yl) ketone BCH-1125;

Methyl (7-hydroxy-5,10-dioxo-3,4,5,10-tetrahydronaphtho [2,3-C]pyran-3-yl) ketone BCH-1129;

Methyl (1-hydroxy-5,10-dioxo-3,4,5,10-tetrahydronaphtho [2,3-C] pyran-3-yl) ketone BCH-1148;

(trans)-5,10-dioxo-3-isopropenyl-1-methoxy-3,4,5,10-tetrahydro-1H-naphtho-[2,3-c]-pyran (BCh-2148);

3-ethylthiocarbonyl-1,3,4,5,10-pentahydro-5,10-dioxo-naphtho-[2,3-c] pyran (BCH-2003);

3 -(5'-tosyloxazolyl)-1,3,4,5,10-pentahydro-5,10-dioxo-naphtho-[2,3-c]-pyran (BCH-2155);

(1,3-trans)-anline-(1-methoxy-5,10-dioxo-3,4,5,10-tetrahydro-1H-naphtho-[2,3-c]-pyran)-3-carboxamide (BCH-2041);

(1,3-cis)-anline-(1-methoxy-5,10-dioxo-3,4,5,10-tetrahydro-1H-naphtho-[2,3-c]-pyran)3-carboxamide (BCH-2042);

(1,3 -trans)-1-methoxy-3-(3'-aminothiazolyl)-5,10-dioxo-3,4,5,10 -tetrahydro-1H-naphtho [2,3-c] pyran (BCH-1616);

1-methoxy-3-dimethyl phosphonoacetyl-5,10-dioxo-3,4,5,10-tetrahydro-1H-naphtho-[2,3-c]-pyran (BCH-1674);

3-(3'-aminothiazolyl)-5,10-dioxo-1,3,4,5,10-pentahydro-naphtho-[2,3-c]-pyran (BCH);

(1S,2'S,3S,5'S) -Methyl-(1-O[N-BOC-Serine-Leucine-Me ester]-5,10-dioxo-3,4,5,10-tetrahydro-1-H-naphtho [2,3-c] pyran-3-yl) ketone (BCH-1998);

(1S, 2'S, 3R) and (1R, 2'S, 3S)-methyl-(1-[O-serine methyl ester]-5,10-dioxo-3,4,5,10-tetrahydronaphtaleno [2,3-C] pyran-3-yl) ketone hydrochloride (BCH-1654);

Trans-5,10-dioxo-1-acetamido-3-ethyl-3,4,5,10-tetrahydro-1H-naphtho-[2,3-c]-pyran (BCH-2027);

3-ethyl-5,10-dioxo-3,4,5,10-tetrahydro-1H-naphtho-[2,3-c] pyran (BCH-2154);

(1,3-trans)-1-methoxy-3-carboxyl-5,10-dioxo-3,4,5,10-tetrahydro-1H-naphtho-[2,3-c]-pyran, (BCH-2045);

(1S,2'S,3S,5'S) -Methyl-(1-O-[Serine-Leucine-Me ester]-5,10-dioxo-3,4,5,10-tetrahydro-1-H-naphtho [2,3-c] pyran-3-yl) ketone hydrochloride BCH-2000;

(1S, 2'S, 3R) and (1R, 2'S, 3S)-methyl-(1-[O-N-BOC-prolinol]-5,10-dioxo- 3,4,5,10-tetrahydro-1-H-naphtho [2,3-C] pyran-3-yl) ketone BCH-2067;

Methyl-(1-O-[2'-piperidinemethanol]-5,10-dioxo-3,4,5,10-tetrahydronaphthaleno-[2,3-c] pyran-3-yl) ketone, racemic, hydrochloride (BCH-2069);

Methyl-(1-O-[N-BOC-4-piperidine-methanol]-5,10-dioxo-3,4,5,10-tetrahydronaphthaleno-[2,3-c] pyran-3-yl) ketone, racemic, hydrochloride (BCH-2068);

Methyl-(1-O-[N-BOC-3-piperidinemethanol]-5,6-dioxo-3,4,5,10-tetrahydronaphthaleno-[2,3-c] pyran-3-yl) ketone, mixture of isomers (BCH-2060);

Methyl-(1-O-[3 -piperidinemethanol]-5,10-dioxo-3,4,5,10-tetrahydronaphthaleno-[2,3-c] pyran-3-yl) ketone hydrochloride salt, mixture of isomers (BCH-2061);

(1S, 2'S, 3R) and (1R, 2'S, 3S)-methyl-(1-[O-prolinol]-3,4,5,12-tetrahydronaphtho-[2,3-C] pyran-3-yl) ketone hydrochloride salt (BCH-1658);

(1'S,1R,3S)-Methyl (5,10-dioxo-1-(2',3',6'-trideoxy-3'-trifluoroacetamido-4'-hydroxy-L-lyxohexopyranose) -3,4,5,10-tetrahydronaphtho [2,3-C] pyran-3-yl) ketone BCH-1184;

(1'S,1S,3R)-Methyl (5,10-dioxo-1-(2',3',6'-trideoxy-3'-trifluoroacetamido-4'-hydroxy-L-lyxohexopyranose)-3,4,5, 10-tetrahydronaphtho [2,3 -C] pyran-3-yl) ketone BCH-1146;

(1'S,1R,3S)-Methyl (5,10-dioxo-1-(2',3',6'-trideoxy-3'-trifluoroacetamido-L-lyxohexopyranose)-7-hydroxy-3,4,5, 10-tetrahydro [2,3 -C] pyran-3-yl) ketone BCH-1181;

(1'S,1S,3R)-Methyl (5,10-dioxo-1-(2',3',6'-trideoxy-3'-trifluoroacetamido-L-lyxohexopyranose)-7-hydroxy-3,4,5, 10-tetrahydro [2,3-C] pyran-3-yl) ketone BCH-1180;

(1'-S, 1-R, 3-S) and (1'-S, 1-S, 3-R)-3-cyano-1-[2',3',6'-trideoxy-3'-trifluoroacetamido-4'-hydroxy-L-lyxohexopyranose)-5,10-dioxo-3,4,5,10-tetrahydronaphtho-[2,3-C] pyran-3-yl BCH-1688;

(1'-S, 1-S, 3-R) and (1'-S, 1-R, 3-S)-methyl-(1-[2',3',4',6'tetradeoxy-3'-trifluoroacetamido-4'-O-methane-sulfonyl-L-lyxohexopyranose)-5,10 -dioxo-3,4,5,10 tetrahydronaphtho-[2,3-c] pyran-3 -yl) ketone BCH-2095;

(1'-S, 1-S, 3-R) -methyl-(1-[2',3',4',6' tetradeoxy-3'-trifluoroacetamideo-4'-O-(2 -bromo-acetyl)-L-lyxopyranose]-5, 10 -dioxo-3,4,5,10 tetrahydronaphtho-[2,3-c] pyran-3-yl) ketone BCH-2105;

(1'-S, 1-R, 3-S)-methyl-(1-[2',3',4',6' tetradeoxy-3'-methoxy-4'-O-methanesulfonyl-L-lyxohexopyranose)-5,10-dioxo-3,4,5,10 tetrahydronaphtho-[2,3-c] pyran-3-yl) ketone BCH-2070;

(1'-S, 1'S, 3-R) -methyl-(1-[2',3',4',6' tetradeoxy-3'-methoxy-4'-O-methanesulfonyl-L-lyxohexopyranose)-5,10-dioxo-3,4,5,10 tetrahydronaphtho-[2,3 -c] pyran-3 -yl) ketone BCH-2072;

(1-S, 3-R) and (1-R, 3-S)-methyl-(1-(1-methoxy-4-oxo-cyclohexyloxy)-5,10-dioxo-3,4,5,10tetrahydronaphtho-[2,3-c] pyran-3-yl) ketone BCH-2096;

(1'-S, 1-S, 3-R) and (1'-S, 1-R, 3-S)-1-(6-hydroxy-1-(2',3',6'-trideoxy-3'-trifluoracetamido, 4-hydroxy-L-lyxopyranose)-5,10 -dioxo-3,4,5,10 tetrahydronaphtho-[2,3-c] pyran-3-yl) propane-2-one BCH-2098;

3,3-bis-(methoxycarbonyl)-5,10-dioxo-3,4,5,10-tetrahydro-1H-naphtho-[2,3-c]-pyran (BCH-1665);

(1'S, 1R, 3S)-5,10-dioxo-3-methoxymethyl-1-(2',3',6'-trideoxy-3'-trifluoroacetamideo-L-lyxohexopyranose)-3,4,5,10-tetrahydro-1H-naphtho-[2,3-c]-pyran (BCH-1691);

(1'S, 1S, 3R)-5,10-dioxo-3-methoxymethyl-1-(2',3',6'-trideoxy-3'-trifluoroacetamido-L-lyxohexopyranose)-3,4,5,10-tetrahydro-1H-naphtho [2,3-c]pyran (BCH-1693);

(1'S, 1R, 3R)-5,10-dioxo-3-ethyl-1-(2',3',6'-trideoxy-3'-trifluoroacetamido-L-lyxohexopyranose)-3,4,5,10 -tetrahydro-1H-naphtho-[2,3-c]-pyran (BCH-2026 );

(1'S, 1S, 3S)-5,10-dioxo-3-ethyl-1-(2',3',6'-trideoxy-3'-trifluoroacetamido-L-lyxohexopyranose) -3,4,5,10-tetrahydro-1H-naphtho-[2,3-c]-pyran (BCH-2020);

(1'S, 1S, 3S)-5,10-dioxo-3-ethyl-1-(2',3',6'-trideoxy-3'-amino-L-lyxohexopyranose)-3,4,5,10-tetrahydro-1H-naphtho-[2,3-c]-pyran (BCH-2021);

(1'S, 1R, 3S)-5,10-dioxo-3-isopropyl-1-(2',3',6'-trideoxy-3'-trifluoroacetamido-L-lyxohexopyranose)-3,4,5,10-tetrahydro-1H-naphtho-[2,3-c]-pyran (BCH-2053);

(1'S, 1S, 3R)-5,10-dioxo-3-isopropyl-1-(2',3',6'-trideoxy-3'-trifluoroacetamido-L-lyxohexopyranose)-3,4,5,10-tetrahydro-1H-naphtho-[2,3-c]-pyran (BCH-2052);

(1'S, 1R, 3S) -5,10-dioxo-3-isopropenyl-1-(2',3',6'-trideoxy-3'-trifluoroacetamido-L-lyxohexopyranose)-3,4,5,10-tetrahydro-1H-naphtho-[2,3-c]-pyran (BCH-2153);

(1'S, 1S, 3R)-5,10-dioxo-3-isopropenyl-1-(2',3',6'-trideoxy-3'-trifluoroacetamido-L-lyxohexopyranose)-3,4,5,10-tetrahydro-1H-naphtho-[2,3-c]-pyran (BCH-21-52);

(1'S, 1R, 3S)-5,10-dioxo-3-methoxycarbonyl-1-(2',3',6'-trideoxy-3'-trifluoroacetamido-L-lyxohexopyranose)-3,4,5,10-tetrahydro-1H-naphtho-[2,3-c]-pyrano (BCH-2128);

(1'S, 1R, 3S)-isopropyl-[1-(2',3',6'-trideoxy-3'-trifluoroacetamido-L-lyxohexopyranose)-5,10-dioxo-3,4,5,10-tetrahydro-1H-naphto-[2,3-c]-pyranyl]-ketone (BCH-2112);

(1'S, 1R, 3S)-5,10-dioxo-3-isopropoxycarbonyl-1-(2',3',6'-trideoxy-3'-trifluoroacetamido -L-lyxohexopyranose)-3,4,5,10-tetrahydro-1H-naphtho-[2,3-c]-pyran (BCH-2122);

(1'S, 1S)-5,10-dioxo-3,3-dimethoxymethyl-1-(2',3',6'-trideoxy-3'-trifluoroacetamido-4'-O-p-nitrobenzoyl-L-lyxohexo-pyranose)-isochroman (BCH-1697);

(1'S, 1R, 4R)-5,10-dioxo-4-ethyl-1-(2',3',6'-trideoxy-3'-trifluoroacetamido-L-lyxohexopyranose)-3,4,5,10-tetrahydro-1H-naphtho-[2,3-c] pyran (BCH-2091);

(1'S, 1R, 3S)-5,10-dioxo-3-phenyloxymethyl-1-(2',3',6'-trideoxy-3'-trifluoroacetamido-L-lyxohexopyranose)-3,4,5,10-tetrahydro-1H-naphtho-[2,3-c] pyran (BCH-2032);

(1'S, 1S, 3S) and (1'S,1-R,3-R)-3-([2',3',6'-trideoxy-3'-trifluoroacetamido-4'-hydroxy-L-lyhohexopyranose]-5,10-dioxo-3,4,5,10-tetrahydronaphtho-[2,3-c]-pyran-3-yl)-propene (BCH-2031);

(1'-S,1-R,3-S)-methyl-(1-[2',3',6'-trideoxy-3'-trifluoroacetamido-4'-iodo-L-lyxohexopyranose]-5,10-dioxo-3,4,5,10-tetrahydronaphtho-[2,3-c]-pyran-3-yl)-ketone (BCH-1620);

(1'-S,1-R,3-S)-3-([2',3',6'-trideoxy-3'-trifluoroacetamido-4'-hydroxy-L-lyhohexopyranose]-5,10-dioxo-3,4,5,10-tetrahydronaphtho-[2,3-c]-pyran-3-yl)-propene (BCH-1649);

(1'-S,1-R,3-S,4a-S,10a-S)-methyl-(1-[2',3',4',6'-tetradeoxy-3'-methoxy-4'O-methanesulfonyl-L-lyxohexopyranose)-4a,10a-epoxy-5,10-dioxo-3,4,5,10 -tetrahydronaphtho-[2,3-c] pyran-3-yl) ketone (BCH-2141);

(1S,3R,1'S,5'S,6'S) and (1R,3S,1'S,5'S,6'S)-methyl-(1-[4'trifluoroacetamido-5'-methyltetrahydropyranyl]-5,10-dioxo-3,4,5,10-tetrahydronaphthaleno-[2,3-c] pyran-3-yl) ketone (BCH-1673);

(1'S,1S,3R)-3 (oximoethyl)-5,10-dioxo-1 (2,3,6-trideoxy-3-trifluoroacetamido-L-lyxohexopyranose)-3,4,5,10-tetrahydro-1H-naphtho-[2,3-c] pyran (BCH-2101);

(1'S, 1R, 3S)-3 (oximoethyl)-5,10-dioxo-1 (2,3,6-trideoxy-3-trifluoroacetamido-L-lyxohexopyranose)-3,4,5,10 -tetrahydro-1H-naphtho-(2,3-c)-pyran (BCH-2115);

(1'S,1S,3R)-3-(trifluoroacetamidoethyl)-5,10-dioxo-1-(2',3',6'-trideoxy-3',4 '-dihydroxy-L-lyxohexopyranose)-3,4,5,10-tetrahydro-1H-naphtho-[2,3-c]-pyran (BCH-2018);

(1'R, 1R, 3S)-3-aceto-5,10-dioxo-1-(2-deoxy-2-chloroethyl-nitrosoureido-D-glucopyranose)-3,4,5,10-tetrahydro-1H-naphtho-[2,3-C] pyran (BCH-2038);

(1R,3S) and (1S,3R)-3-aceto-5,10-dioxo-1 (4-chloroethylnitrosoureido cyclohexyl-oxy)-3,4,5,10-tetrahydro-1H-naphtho-(2,3-c)-pyran (BCH-2114);

(1'S,1S,3R)-1-(3'-trifluoroacetamido-2',3',6'-trideoxy-lyxo-L-hexopyranose)-3-methoxycarbonyl-3-methyl-3,4,5,10-tetrahydro-5,10-dioxo-naphtho-[2,3-c] pyran (BCH-2076);

(1'S, 1R, 3S)-2',3',6'-trideoxy-3'-trifluoroacetamido-L-lyxohexopyranose-3-[5'-tosyloxazolyl]-5,10-dioxo-3,4,5,10-tetrahydro-1H-naphtho-[2,3-c]-pyran (BCH-2150);

(1'S, 1S, 3R)-2',3',6'-trideoxy-3'-trifluoroacetamido-L-lyxohexopyranose-3-[5'-tosyloxazolyl)]-5,10-dioxo-3,4,5,10-tetrahydro-1H-naphtho-[2,3-C]-pyran (BCH-2151);

(1'S, 1R, 3S)-1-(3'-trifluoroacetamido-2',3',6'-trideoxy-L-lyxohexopyranose)-5,10-dioxo-4,5,10-trihydro-1H-naphtho-[2,3-c]-pyran (BCH-2077);

(1'S, 1S, 3R)-1-(3'-trifluoroacetamido-2',3',6'-trideoxy-L-lyxohexopyranose)-3-acetyl-3-methyl-5,10-dioxo-4,5,10-trihydro-1H-naphtho-[2,3-c]-pyran (BCH-2082);

(1'S,1S,3R)-1-(2',3',6'-trideoxy-3'-trifluoroacetamido-L-lyxohexopyranose)-3-dimethylphosphonoacetyl-5,10-dioxo-3,4,5-10-tetrahydro-1H-naphtho-[2,3-c]-pyran (BCH-1690);

(1'S, 1S, 3S)-1-(3'-trifluoroacetamido-2',3',6'-trideoxy-lyxohexopyranose)-3-methoxycarbonyl-3-methyl-5,10-dioxo-4,5,10-trihydro-1H-naphtho-[2,3-c]-pyran (BCH-2081);

(1'S,1S,3S)-1-(3'-trifluoroacetamido-2',3',6'-trideoxy-L-lyxohexopyranose)-5,10-dioxo-3,4,5,10-tetrahydro-1H-naphtho-[2,3-c]-thiopyran (BCH-2037.001);

(1'S,1R,3R)-1-(3'trifluoroacetamido-2',3',6'-trideoxy-lyxo-L-hexopyranose)-3-dimethoxyphosphonoacetyl-3,4,5,10-tetrahydro-5,10-dioxo-naphtho-[2,3-c]pyran (BCH-2127);

(1'S,1S,3S)-1-(3'-trifluoroacetamido-2',3',6'-trideoxy-lyxo-L-hexopyranose)-3-acetyl-3-methyl-3,4,5,10-tetrahydro-5,10-dioxo-1H-naphtho-[2,3-c] pyran (BCH-2090);

(1'S,1R,3S)-1-(3'-trifluoroacetamido-2',3',6'-trideoxy-lyxo-L-hexopyranose)-3-dimethoxyphosphonoacetyl-3,4,5,10-tetrahydro-5,10-dioxo-naphtho-[2,3-c] pyran (BCH-1689);

(1'S,1R,3S)-methyl-(1-[2',6'-dideoxy-3', 4'-dihydroxy-2'-iodo-L-lyxohexopyranose]-5,10-dioxo-3,4,5,10-tetrahydronaphtho [2,3-c]-pyran-3-yl) ketone (BCH-2015);

(1'S,1R,3S)-methyl-(1-[2',6'-dideoxy-3'-4'-diacetoxy-2'-iodo-L-lyxohexopyranose]-5,10-dioxo-3,4,5,10-tetrahydronaphtho[2,3-c]-pyran-3-yl) ketone (BCH-1666);

(1'S,1S,3R)-methyl-(1-[2',6'-dideoxy-3',4'-diacetoxy-2'-iodo-L-lyxohexopyranose]-5,10-dioxo-3,4,5,10-tetrahydronaphtho [2,3-c]-pyran-3-yl) ketone (BCH-1667);

(1'S,1S,3R)-methyl-(1-[2',6'-dideoxy-3',4'-dihydroxy-2'-iodo-L-lyxohexopyranose]-5,10-dioxo-3,4,5,10-tetrahydronaphtho [2,3-c]-pyran-3-yl)-ketone (BCH-2014);

(1S,1R,3S)-methyl-(1-[2',6'-dideoxy-3',4'-diacetoxy-2'-bromo-L-lyxohexopyranose]-5,10-dioxo-3,4,5,10-tetrahydronaphtho-[2,3-c ]-pyran-3 -yl) ketone (BCH-2100);

(1'S,1R,3S)-methyl-(1-[2',3',6'-trideoxy-2'-iodo-3'-trifluoroacetamido-4'-hydroxy-L-lyxohexopyranose]-5,10-dioxo-3,4,5,10-tetrahydronaphtho-[2,3-c]-pyran-3-yl) ketone (BCH-2023);

(1'S,1S,3R)-methyl-(1-[2',3',6'-trideoxy-2'-iodo-3'-trifluoroacetamido-4'-hydroxy-L-lyxohexopyranose]-5,10-dioxo-3,4,5,10-tetrahydronaphtho-[2,3-c]-pyran-3-yl) ketone (BCH-2022);

(1'S,1R,1S) and (1'S,1S,3R)-methyl-(1-[2',6'-dideoxy-3',4'diacetoxy-2'-iodo-L-arabino-hexopyranose]-5,10-dioxo-3,4,5,10-tetrahydronaphtho-[2,3-c ]-pyran 3-yl) ketone (BCH-2065);

(1'S,1S,3R) and (1'S,1R,3S)-methyl-(1-[dideoxy-2',6'-dihydroxy-3',4'-L-lyxohexopyranose]-5,10-dioxo-3,4,5, 10-tetrahydronaphtho-[2,3-c]-pyran-3 -yl) ketone (BCH-2117);

(1'S,1S,3R) and (1'S,1R,3S)-methyl-(1-[dideoxy-2',6'-diacetoxy-3',4'-L-lyxohexopyranose]-5,10 -dioxo-3,4,5, 10-tetrahydronaphtho-[2,3-c]-pyran-3-yl) ketone (BCH-2118);

Methyl-(6-hydroxy-5,10-dioxo-3,4,5,10-tetrahydronaphtho-[2,3-c]-pyran-3-yl) ketone and methyl-(9-hydroxy-5,10-dioxo-3,4,5,10-tetrahydronaphtho-[2,3-c]-pyran-3-yl) ketone (BCH-2062);

(1'S,1S,3R)-methyl-(6 and 9 -hydroxy-1-[2',3',6'-trideoxy-3'-trifluoroacetamido-4'-hydroxy-L-lyxohexopyranose]-5,10-dioxo-3,4,5,10-tetrahydronaphtho-[2,3-c]-pyran-3-yl-ketone (BCH-2078);

(1R,3S,1'S) and (1S,3R,1'S)-Methyl-(1-[2',3',4',6'-tetradeoxy-3',4'-bis-trifluoroacetamido-L-arabinohexopyranose]-5,10-dioxo-3,4,5,10-tetrahydronaphthaleno-[2,3-c] pyran-3-yl) ketone (BCH-2104 and BCH-2102);

(1S,3R,1'S)-Methyl-(1-[2',3',4',6'-tetradeoxy-3'-trifluoroacetamido-4'-bromo-L-lyxohexopyranose]-5,10-dioxo-3,4,5,10-tetrahydronaphthaleno-[2,3-c] pyran-3-yl) ketone (BCH-2047);

(1'-S,1-S,3-R)-1-(2',3',6'-trideoxy-3'-trifluoro acetamido-L-lyxohexopyranose)-3-(2-aza-3-acetamido-thiazolyl)-5,10-dioxo-3,4,5,10-tetrahydro-1H-naphtho-[2,3-c]-pyran (BCH-1198);

(1'S, 1S, 3S) and (1'S, 1R, 3R)-5,10-dioxo-3-ethyl-1-(2',3',4',6'-tetradeoxy-3',4'-diacetoxy-L-lyxohexo-pyranose) 3,4,5,10-tetrahydro-1H-naphtho [2,3-C] pyran (BCH-1607);

(1'S, 1S, 3R) -methyl-(1-[2',6'-dideoxy-3',4'-diacetoxy-2'-bromo-L-lyxohexopyranose]-5,10-dioxo-3,4,5,10-tetrahydronaphtho-[2,3 -c]-pyran-3-yl) ketone (BC-2099);

(1'S, 2'R, 3'S, 5'R, 1S, 3R)-1-(3-trifluoroacetamido-2-hydroxy-1 -methyl tetrahydropyran-5-yl)-methyl-3-ethyl-5, 10-dioxo-3,4,5,10-tetrahydro-1H-naphtho[2,3-C]pyran (BCH-2818);

(1'S, 2'R, 3'S, 5'R, 1R, 3S)-1-(3-trifluoroacetamido-2-hydroxy-1-methyl tetrahydropyran-5-yl)-methyl-3-ethyl-5, 10-dioxo-3,4,5,10-tetrahydro-1H-naphtho[2,3-C]pyran (BCH-2819);

(1'S,2'R, 3'S,5'R,1R, 3R)-1-(3-trifluoroacetamido-2-hydroxy-1methyl tetrahydropyran-5-yl) methyl-3-methylketone-5,10-dioxo-3,4,5,10-tetrahydro-1H-naphtho [2,3-C] pyran (BCH-2821);

(1'S,2'R,3'S,5'R,1S, 3S)-1-(3-trifluoroacetamido-2-hydroxy-1methyl tetrahydropyran-5 -yl)methyl-3-methylketone-5,10-dioxo-3,4,5,10-tetrahydro-1H-naphtho [2,3-C] pyran (BCH-2820);

1-Methoxy-5,10-dioxo-5,10-dihydro-1H-naphtho[2,3-c] pyran-3-[N-(3-dimethylamino-propyl)carboxamide] hydrochloride monohydrate (BCH-2051);

3-Aceto-5,10-dioxo-1-methoxy-5,10-dihydro-1H-naphtho-(2,3-c)-pyran (BCH-2129); 1-methoxy-3-N-anilinylcarbonyl-5,10-dioxo-5,10-dihydro-1H-naphtho-[2,3-c]-pyran (BCH-2044);

1-methoxy-3-(3-N-pyrrolidinomylpropylaminocarbonyl)-5,10-dioxo-5,10-dihydro-1H-naphtho-[2,3-c]-pyran (BCH-2166);

(3-N-hydrochloroimidazolylpropyl)-1-methoxy-5,10-dioxo-5,10-dihydro-1H-naphtho-[2,3-c]-pyran-3-carboxamide (BCH-2157);

2-hydrochloro-(N-pyrrolidinyl) ethyl-(1-propyl-5,10-dioxo-5,10-dihydro-1H-naphtho-[2,3-c]-pyran-3)-carboxamide (BCH-2875);

3-N-oxo-dimethylaminopropyl-(1-methoxy-5,10-dioxo-5,10-dihydro-1H-naphtho-[2,3-c]-pyran-3)-carboxamide (BCH-2877);

2-(2-N-methyl pyrrolyl)-ethyl-(1-propyl-5,10-dioxo-5,10-dihydro-1H-naphtho-[2,3-c]-pyran-3)-carboxamide (BCH-2876);

1-methoxy-3-[2-(N-morpholino) ethyl amino carbonyl]-5,10-dioxo-5,10-dihydro-1H-naphtho-[2,3-c]-pyran (BCH-2170);

1-methoxy-3-[2-(N-morpholine) ethyl amino carbonyl]-5,10-dioxo-5,10-dihydro-1H-naphtho-[2,3-c]-pyran (BCH-2171);

1-methoxy-3-[2-(2 -pyridinyl) ethyl amino carbonyl]-5,10-dioxo-5,10-dihydro-1H-naphtho-[2,3-c]-pyran hydrochloride (BCH-2835);

1-methoxy-3-[(2-pyridinyl) methyl amino carbonyl]-3-methoxy-5,10-dioxo-5,10-dihydro-1H-naphtho-[2,3-c]-pyran (BCH-2840);

1-methoxy-3-[(2-pyridinyl) methyl amino carbonyl]-3-methoxy-5,10-dioxo-5,10-dihydro-1H-naphtho-[2,3-c]-pyran hydrochloride salt (BCH-2841);

1-methoxy-3-[2-(N-pyrrolidinyl) ethyl amino carbonyl]-5,10-dioxo-5,10-dihydro-1H-naphtho-[2,3-c]-pyran hydrochloride salt (BCH-2839);

1-methoxy-3-[(4-diethoxy) butyl amino carbonyl]-5,10dioxo-5,10-dihydro-1H-naphtho-[2,3-c]-pyran (BCH-2848);

1-methoxy-3-(3-hydroxy) propyl amino carbonyl-5,10-dioxo-5,10-dihydro-1H-naphtho-[2,3-c]-pyran (BCH-2849);

1-methoxy-3-methoxy carbonyl-5,10-dioxo-5,10-dihydro-1H-naphtho-[2,3-c]-pyran (BCH-2160);

1-propyl-3-(3-dimethyl amino propyl amino carbonyl)-5,10-dihydro-5,10-dioxo-1H-naphtho-[2,3-c]-pyran (BCH-2168);

3-methoxy carbonyl-5,10-dioxo-5,10-dihydro-1H-naphtho-[2,3-c]-pyran (BCH-2830);

1-methoxy-3-(2-trimethyl ammonium ethyl amino carbonyl)-5,10-dioxo-5,10-dihydro-1H-naphtho-[2,3-c]-pyran chloride salt (BCH-2837);

1-methoxy-3 -(2-pyrrolidinoethylcarbonyl)-5,10-dioxo-5,10-dihydro-1H-naphtho-[2,3-c] pyran hydrochloride (BCH-2854);

1-Methoxy-3[2-(N-pyrrolidinylethoxylcarbonyl)]-5,10-dioxo-5,10-dihydro-1H-naphtho-[2,3-c]-pyran (BCH-2861);

1-methoxy-5,10-dioxo-5,10-dihydro-1H-naphtho [2,3-c] thiine-3-[N-(3-dimethylaminopropyl) carboxamide] (BCH-2878);

(1'S) Methyl (5,10-dioxo-1-(2',3',4',6'-tetradeoxy-3',4'-diacetoxyl-L-lyxohexopyranose-5,10-dihydro-1H-naphtho[2,3-c]thiopyran-3-yl) ketone (BCH-2879); and N-Boc-N-{1-methoxy-5,10-dihydro-5,10-dioxo-1H-naphtho-[2,3-c]-pyran-3-carbonyl}-propyldiamine (BCH-2881).

50. A process according to claim 1, 8 or 15 wherein said quinoid of formula (2); and coupled dioxoisochroman of formula (12) are selected from the group consisting of (1'S,1R,3S) and (1'S,1S,3R)-Methyl (5,8-dioxo-1-(2',3',6'-trideoxy-3'-trifluoroacetamido-4'-0-p-nitrobenzoyl-L-lyxohexopyranose)-3,4,5,8-tetrahydrobenzo [2,3-C] pyran-3-yl) ketone;

(1'S,1R,3S)-Methyl (5,10-dioxo-1-(2',3',6'-trideoxy-3'-trifluoroacetamido-4'-O-p-nitrobenzoyl-L-lyxohexopyranose)-3,4,5,10-tetrahydronaphtho [2,3-C]pyran-3-yl) ketone;

(1'S,1S,3R) and 1'S,1R,3S)-methyl-1-(2',6'-dideoxy-3',4'-di-O-p-nitrobenzoyl-L-lyxohexopyranose)-5,10-dioxo-3,4,5,10-tetrahydronaphtho [2,3-C] pyran-3-yl) ketone;

(1'S,1R,3S) and (1'S,1S,3R) methyl (5,8-dioxo-1-(2',3',4',6'-tetradeoxy-3',4'-diacetoxy-L-lyxohexo-pyranose)-3,4,5,8-tetrahydrobenzo [2,3-c]thiopyran-3-yl) ketone;

5,8-Dioxo-3-(propane-2-one)-1-(2',3',6'-trideoxy-3'-trifluoroacetamido-4'-O-p-nitrobenzoyl-L-lyxohexopyranose)-isochroman;

(1'S, 1R, 3S)-5,8-dioxo-3-methoxymethyl-1-(2',3',6'-trideoxy-3'-trifluoroacetamido-4'-O-p-nitrobenzoyl-L-lyxohexo-pyranose)-5,8-dihydroisochroman and its (1'S, 1S, 3R) diastereomer;

(1'S, 1R, 3R)-5,8-dioxo-3-ethyl-1-(2',3',6'-trideoxy-3'-trifluoroacetamido-4'-O-p-nitrobenzoyl-L-lyxohexopyranose)-isochroman;

(1'S, 1S, 3S)-5,8-dioxo-3-ethyl-1-(2',3',6'-trideoxy-3'-trifluoroacetamido-4'-O-p-nitrobenzoyl-L-lyxohexo-pyranose)-5,8-dihydro-isochroman; (1'S, 1R, 3S);

(1'S, 1S, 3R)-5,8-dioxo-3-isopropyl-1-(2',3',6'-trideoxy-3'-trifluoroacetamido-4'-O-p-nitrobenzoyl-L-lyxohexopyranose)-5,8-dihydro-isochroman;

(1'S, 1R, 3S) and (1'S, 1S, 3R)-5,8 dioxo-3-methoxycarbonyl-1-(2',3',6'-trideoxy-3'-trifluoroacetamido-4'-O-p-nitrobenzoyl-L-lyxohexopyranose)-5,8-dihydro-isochroman;

(1'S, 1S)-5,8-dioxo-3,3-dimethoxymethyl-1-(2',3',6'-trideoxy-3'-trifluoroacetamido-4'-O-p-nitrobenzoyl-L-lyxohexopyranose)-isochroman;

(1'S, 1R, 4R)-5,8-dioxo-4-ethyl-1-(2',3',6'-trideoxy-3'-trifluoroacetamido-4'-O-p-nitrobenzoyl-L-lyxohexopyranose)-isochroman;

(1'S, 1R, 3S)-5,8-dioxo-3-phenyloxymethyl-1-(2',3',6'-trideoxy-3'-trifluoroacetamido-4'-O-p-nitrobenzoyl-L-lyxohexopyranose)-isochroman;

(±)-Methyl ketone hydroxy-1-isochroman quinone;

(1'S, 1S, 3R)-1-(4'-p-nitrobenzoyl-3'-trifluoroacetamido-2',3',6'-trideoxy-lyxohexopyranose)-3-methoxy-carbonyl-3-methyl-5,8-dioxo-4,5,8-trihydro-1H-benzo-[2,3-c]-pyran;

(1'S, 3R)-1-(4'-p-nitrobenzoyl-2',3',6'-trideoxy-3'-trifluoroacetamido-L-lyxohexopyranose)-3-(5"-tosyloxazolyl)-5,8-dioxo-3,4,5,8-tetrahydrobenzo-[2,3-c]-pyran;

(1'S, 1S, 3R)-1-(4'-p-nitrobenzoyl-2',3',6'-trideoxy-3'-trifluoroacetamido-L-lyxohexopyranose)-3-(5"-tosyloxazolyl)-5,8-dioxo-3,4,5,8-tetrahydrobenzo-[2,3-c]-pyran;

(1'S, 1R, 3S)-1-(4'-p-nitrobenzoyl-3'-trifluoroacetamido-2',3',6'-trideoxy-lyxohexopyranose)-3-methoxycarbonyl-3-methyl-5,8-dioxo-4,5,8-trihydro-1H-benzo-[2,3-c]-pyran;

(1'S, 1S, 3S)-1-(4'-p-nitrobenzoyl-3'-trifluoroacetamido-2',3',6'-trideoxy-lyxohexopyranose)-3-methoxy-carbonyl-3-methyl-5,8-dioxo-4,5,8-trihydro-1H-benzo-[2,3-c]-pyran;

(1'S,1S,3S) and (1'S,1R,3R)-1-(4'-p-nitrobenzoyl-3'-trifluoroacetamido-2',3',6'-trideoxy-L-lyxohexopyranose)-3-acetyl-5,8-dioxo-4,5,8-trihydro-1H-benzo-[2, 3-c]-pyran;

(1'S,1S,3S) and (1'S, 1S, 3R)-1-(4'-p-nitrobenzoyl-3'-trifluoroacetamido-2',3',6'-trideoxy-lyxohexopyranose)-3-acetyl-3-methyl-5,8-dioxo-4,5,8-trihydro-1 H-benzo-[2,3-c]-pyran;

(1'S,1S,3R) and (1'S,1R,3S)-1-(2',3,6'-trideoxy-3'-trifluoroacetamido-4'-p-nitrobenzoyl-L-lyxohexopyanose)-3-dimethylphosphonoacethyl-3,4,5,8-tetrahydronaphthaleno-[2,3-c]-pyran;

(1'S,1R,3S)-3-aceto-1-(2',6'-dideoxy-2'-iodo-L-lyxohexopyranose)-5,8-dioxo-5,8-dihydroisochroman;

(1'S,1R,3S)-5,8-Dioxo-3-aceto-1-(2',6'-dideoxy-3',4'-diacetoxy-2'-iodo-L-lyxohexopyranose)-5,8-dihydroisochroman;

(1'S,1S,3R)-3-aceto-1-(2',6'-dideoxy-2'-iodo-L-lyxohexopyranose)-5,8-dioxo-5,8-dihydroisochroman;

(1'S,1R,3S)-5,8-dioxo-1-(2',6'-dideoxy-3',4'-diacetoxy-2'-bromo-L-lyxohexopyranose)-5,8-dihydroisochroman;

(1'S,1R,3S)-5,8-dioxo-3-aceto-1-(2',6'-dideoxy-3',4'-diacetoxy-2'-bromo-L-lyxohexopyranose)-5,8-dihydroisochroman;

(1'S,1R,3S)-5,8-Dimethoxy-3-aceto-1-(2',3',6'-trideoxy-3'-trifluoroacetamido-2'-iodo-L-lyxohexopyranose)-isochroman;

(1S,1R,3S)-3-aceto-1-(2',3',6'-trideoxy -2'-iodo-3'-trifluoroacetamido-L-lyxohexopyranose)-5,8-dioxo-5,8-dihydroisochroman;

(1'S,1S,3R)-3-aceto-1-(2',3',6'-trideoxy-2'-iodo-3'-trifluoroacetamido-L-lyxohexopyranose)-5,8-dioxo-5,8-dihydroisochroman;

(1'S,1R,3S) and (1'S,1S,3R)-3-aceto-1-(2',6'-dideoxy-2'-iodo-L-arabinohexopyranose)-5,8-dioxo-5,8-dihydroisochroman;

(1'S,1S,3R) and (1'S,1R,3S)-5,8-dioxo-3-aceto-1-(2',6'-dideoxy-L-lyxohexopyranose)-5,8-dihydroisochroman;

(1'S,1S,3R) and (1'S,1R,3S)-5,8-dioxo-3-aceto-1-(2',6'-dideoxy-3',4'-diacetoxy-L-lyxohexopyranose) isochroman;

(1R,3S,1'S)-Methyl-(1-[2',3',4',6'-tetradeoxy-3'-trifluoroacetamido-4'-bromo-L-lyxohexopyranose]-5,10-dioxo-3,4,5,10-tetrahydronaphthaleno-[2,3-c]pyran-3 -yl) ketone; and (1'S) Methyl (5,8-dioxo-1-(2',3',4',6'-tetradeoxy-3',4' -diacetoxy-L-lyxohexopyranose)-5,8 -dihydro-1H-benzo [2,3-c]thiopyran-3-yl) ketone. ketone.

51. A process according to claim 1, 2, or 15 wherein said quinoid of formula (2); and said dioxoisochroman of formula (6) are selected from the group consisting of Monofluoromethyl (5,8-dioxo-3,4,5,8-tetrahydrobenzo [2,3-C] pyran-3-yl) ketone;

Bromomethyl (5,8-dioxo-5,8-dihydrobenzo [2,3-C] pyran-3-yl) ketone;

3-Ethyl-1-hydroxy-isochroman-5,8-dione;

cis-3-aceto-1-methoxy-5,8-dioxoisothiochroman;

Methyl (1-Methoxy-5,8-dioxo-5,8-dihydro-isochroman-3-yl) formate;

(1S,2'S,3R,5'S) and (1R,2'S,3S,5'S)-1-[O-N-BOC-Serine-Leucine-Me ester]-3-aceto-5,8-dimethoxy-isochroman;

1-hydroxy-3-cyano-5,8-dioxo-5,8-dihydroisochroman;
5,8-dioxo-3,3 bis (methoxycarbonyl)-5,8-dihydro-isochroman;

(trans)-1-acetamido-5,8-dioxo-3-ethyl-5,8-dihydro-isochroman;

5,8-dioxo-3-ethyl-5,8-dihydro-isochroman;

3 -ethylthiocarbonyl-5,8 -dioxo-1,3,4,5,8-penta-1H-benzo-[2,3-c]-pyran;

3-(5'-tosyloxazolyl)-5,8-dioxo-1,3,4,5,8-pentahydrobenzo-[2,3-c]-pyran;

1-methoxy-3-acetyl-5,8-dioxo-3,4,5,8-tetrahydrobenzo-[2,3-c]-pyran;

3-aceto-5,8-dioxo-3,4,5,8-tetrahydro-1H-benzo-[2,3-c]-pyran;

Methyl (1-Methoxy-5,8-dioxo-5,8-dihydro-isochroman-3-yl) formate;

1-propyl-3-methoxycarbonyl-3,4,5,8-tetrahydro-5,8-dioxo-1H-benzo-[2,3-c]-pyran;

1-methoxy-3 -methoxycarbonyl-5,8 -dioxo-1H-benzo-[2, 3-c]-pyran.

52. A process according to claim 8 wherein said coupled protected isochroman of formula (11) is selected from the group consisting of (1'S,1R,3S) and (1'S,1S,3R) methyl (5,8-dimethoxy-1-(2',3',4',6'-tetradeoxy-3',4'-diacetoxy-L-lyxohexo-pyranose)-3,4,-dihydrobenzo [2,3-c] thiopyran-3-yl) ketone;

5,8-Dimethoxy-3-(propane-2-one)-1-(2',3',6'-trideoxy-3'-trifluoroacetamido-4'-O-p-nitrobenzoyl-L-lyxohexopyranose)-isochroman;

(1'S, 1R, 3R)-5,8-dimethoxy-3-ethyl-1-(2',3',6'-trideoxy-3'-trifluoroacetamido-4'-O-p-nitrobenzoyl-L-lyxohexopyranose)-isochroman;

(1'S, 1S, 3R)-5,8-dimethoxy-3-isopropenyl-1-(2',3',6'-trideoxy-3'-trifluoroacetamido-4'-O-p-nitrobenzoyl-L-lyxohexo-pyranose) isochroman;

(1'S, 1R, 3S) and (1'S, 1S, 3R)-5,8 dimethoxy-3-methoxycarbonyl-1-(2',3',6'-trideoxy-3'-trifluoroacetamido-4'-O-p-nitrobenzoyl-L-lyxohexopyranose)-isochroman;

(1'S, 1S)-5,8-dimethoxy-3,3-dimethoxymethyl-1-(2',3',6'-trideoxy-3'-trifluoroacetamido-4'-O-p-nitrobenzoyl-L-lyxohexopyranose)-isochroman;

(1'S, 1R, 4R)-5,8-dimethoxy-4-ethyl-1-(2',3',6'-trideoxy-3'-trifluoroacetamido-4'-O-p-nitrobenzoyl-L-lyxo-hexo-pyranose)-isochroman;

(1'S, 1R, 3S)-5,8-dimethoxy-3-phenyloxymethyl-1-(2',3', 6'-trideoxy-3' -trifluoroacetamido-4'-O-p-nitrobenzoyl-L-lyxohexopyranose)-isochroman;

(1'S,1S,3S) and (1'S,1-R,3-R)-1-(2',3',6',-trideoxy-3'-trifluoroacetamido-4'-O-paranitrobenzoyl-L-lyxohexopyranose)-5,8-dimethoxy-3-(2-propenyl)-isochroman;

(1S,3R)-3 (oximoethyl)-1 (2,3,6-trideoxy-3-trifluoroacetamido-4-p-nitrobenzoyl-L-lyxohexopyranose)-5,8-dimethoxy-isochroman;

(1R,3S)-3-(oximoethyl)-1 (2,3,6-trideoxy-3-trifluoroacetamido-4-p-nitrobenzoyl-L-lyxohexopyranose)-5,8-dimethoxy-isochroman;

(1S',1S,3R)-3-(trifluoroacetamidoethyl)-5,8-dimethoxy-1-(2',3',6'-trideoxy-3',4'-dihydroxy-L-lyxohexopyranose)-isochroman;

(1R', 1R, 3S)-3-aceto-5,8-dimethoxy-1(2-deoxy-2-chloroethylureido-3,4,6-triacetyl-D-glucopyranose)-isochroman;

(1'R, 1R, 3S)-3-aceto-5,8-dimethoxy-1(2-deoxy-2-chloroethylureido-4,6-benzylidene-D-glucopyranose)-isochroman;

(1'S, 1S, 3R)-1-(4'-p-nitrobenzoyl-2',3',6'-trideoxy-3'-trifluoroacetamido-L-lyxohexopyranose)-3-(5"-tosyloxazolyl)-5,8-dimethoxy isochroman;

(1S, 1R, 3S)-1-(4'-p-nitrobenzoyl-3'-trifluoroacetamido-2',3',6'-trideoxy-Llyxohexopyranose)-3-methoxy-carbonhyl-3-methyl-5,8-dimethoxy-isochroman;

(1'S,1S,3S) and (1'S,1R,3R)-1-(3'-trifluoroacetamido-2',3',6'-trideoxy-L-lyxohexopyranose)-3-acetyl-5,8-dimethoxy-thioisochroman;

(1'S,1S,3S) and (1'S,1S,3R)-1-(4'-p-nitrobenzoyl-3'-trifluoroacetamido-2',3',6'-trideoxy-L-lyxohexopyranose)-3-acetyl-3-methyl-5,8-dimethoxy-isochroman;

(1'S,1S,3R) (1'S,1R,3S)-5,8-dimethoxyl(2',3',6'-trideoxy-3'-trifluoroacetamido-4'-p-nitrobenzoyl-L-lyxohexopyranose)-3-dimethylphosphonoacetyl isochroman;

(1'S,1R,3S) and (1'S,1S,3R)-2,5-Dimethoxy-1-(2',6'-dideoxy-3',4'-diacetoxy-2'-iodo-L-lyxohexopyranose)-3-acetoisochroman;

(1'S,1R,3S)-5,8-Dimethoxy-3-aceto-1-(2',6'-dideoxy-2'-iodo-L-lyxohexopyranose)-isochroman;

(1'S,1R,3S) and (1'S,1S,3R)-2,5-Dimethoxy-1-(2',6'-dideoxy-3',4'-diacetoxy-2'-bromo-L-lyxohexopyranose)-3-acetoisochroman;

(1'S,1R,3S) and (1'S,1S,3R)-2,5-Dimethoxy-3-aceto-1-(2',3',6'-trideoxy-2'iodo-3'-trifluoroacetamido-4'-O-acetyl-L-lyxohexopyranose)-isochroman;

(1'S,1S,3R)-5,8-dimethoxy-3-aceto-1-(2',3',6'-trideoxy-3'-trifluoroacetamido-2'-iodo-L-lyxohexopyranose) isochroman;

(1'S,1S,3R) and (1'S,1R,3S)-5,8-Dimethoxy-3-aceto-1-(2',6'-dideoxy-3',4'-diacetoxy-2'-iodo-L-arabinohexopyranose) isochroman;

(1'S,1S,3R) and (1'S,1R,3S)-5,8-dimethoxy-3-aceto-1-(2',6'-dideoxy-3',4'-diacetoxy-L-lyxohexopyranose) isochroman;

(1'S,1S,3R) and (1'S,1R,3S)-5,8-dimethoxy-3-aceto-1-(2',6'-dideoxy-L-lyxohexopyranose) isochroman; and (1'S) Methyl (5,8-dimethoxy-1-(2',3',4',6'-tetradeoxy-3',4'-diacetoxy-L-lyxohexopyranose)-1H-benzo[2,3-c]thiopyran-3-yl) ketone.

53. A process according to claim 2 wherein said protected isochroman of formula (5) is selected from the group consisting of 5,8-Dimethoxy-3-ethyl-1hydroxy-isochroman;

3-Aceto-5,8-dimethoxythioisochroman;

Trans-3-aceto-1,5,8-trimethoxythioisochroman and cis-3-aceto-1,5,8-trimethoxythioisochroman;

Trans-3-aceto-1-methoxy-5,8-dioxoisothiochroman;

Methyl (1,5,8-trimethoxyisochroman-3-yl) formate;

(1S, 2'S, 3R) and (1R, 2'S, 3S)-1-[O-serine methyl ester]-3-aceto-5,8-dimethoxy isochroman;

(1S, 2'S, 3R) and (1R, 2'S, 3S)-1-[O-N-BOC-prolinol]-3-acetyl-5,8-dimethoxy isochroman;

5,8-dimethoxy-3-phenylsulphone isochroman;

5,8-dimethoxy-3-cyano isochroman;

1-hydroxy-3-cyano-5,8-dimethoxy isochroman;

5,8-Dimethoxy-3-(t-butyl acetoacetato) isochroman;

5,8-Dimethoxy-3-(propane-2-one) isochroman;

5,8-dimethoxy-3,3 bis (methoxycarbonyl)-isochroman;

5,8-dimethoxy-3-hydroxymethyl-isochroman;

5,8-dimethoxy-3-methoxymethylisochroman;

5,8-dimethoxy-3-ethyl-isochroman;

3-isopropyl-5,8-dimethoxy-isochroman;

5,8-dimethoxy-3-isopropenyl-isochroman;

isopropyl-(5,8-dimethoxy-isochroman-3-yl)-ketone;

5,8-dimethoxy-3,3 bis (dihydroxymethyl)-isochroman;

5,8-dimethoxy-3,3 bis (dimethoxymethyl)-isochroman;

5,8-dimethoxy-4-ethyl-isochroman;

5,8-dimethoxy-3-phenoxymethyl-isochroman;

5,8-dimethoxy-3-(2-propenyl)-isochroman;

3-(Trifluoroacetamido-ethyl)-5,8-dimethoxy isochroman;

(1R,3S) and (1S,3R)-3-Aceto-1 (4-chloroethylureido-cyclohexyloxy)-5,8-dimethoxy-isochroman;

3-ethylthiocarbonyl-5,8-dimethoxy-isochroman;

3-(5'-tosyloxazolyl)-5,8-dimethoxy isochroman;

3-methoxycarbonyl-3-methyl-5,8-dimethoxy isochroman;

3-acetyl-3-methyl-5,8-dimethoxy isochroman;

3-bromoacetyl-5,8-dimethoxy-isochroman;

3-dimethoxy phosphinoacetyl-5,8-dimethoxy-isochroman;

1-O-[N-BOC-4-piperidinemethanol]-3-acetyl-5,8-dimethoxy isochroman racemic;

1-O-[N-BOC-3-piperidinemethanol]-3-acetyl-5,8-dimethoxy isochroman;

Methyl (1,5,8-trimethoxyisochroman-3-yl) formate;

(1,3-trans)-1-allyl-3-methoxy carbonyl-5,8-dimethoxy-isochroman;

1-propyl-3-methoxy carbonyl-5,8-dimethoxy-isochroman;

3-methoxycarbonyl-3,4-didehydro-5,8-dimethoxy isochroman;

1-methoxy-3-methoxycarbonyl-3,4-didehydro-5,8-dimethoxy isochroman; and 1-hydroxy-3-methoxycarbonyl-3,4-didehydro-5,8-dimethoxy isochroman.

* * * * *